(12) United States Patent
Seo et al.

(10) Patent No.: US 12,139,446 B2
(45) Date of Patent: Nov. 12, 2024

(54) ARYLAMINE COMPOUND, HOLE-TRANSPORT LAYER MATERIAL, HOLE-INJECTION LAYER MATERIAL, LIGHT-EMITTING DEVICE, LIGHT-EMITTING APPARATUS, ELECTRONIC APPARATUS, AND LIGHTING DEVICE

(71) Applicant: SEMICONDUCTOR ENERGY LABORATORY CO., LTD., Atsugi (JP)

(72) Inventors: Satoshi Seo, Kanagawa (JP); Nobuharu Ohsawa, Kanagawa (JP); Tomohiro Kubota, Kanagawa (JP); Takeyoshi Watabe, Kanagawa (JP); Airi Ueda, Kanagawa (JP); Yasushi Kitano, Kanagawa (JP); Takao Tosu, Kanagawa (JP)

(73) Assignee: Semiconductor Energy Laboratory Co., Ltd., Atsugi (JP)

( * ) Notice: Subject to any disclaimer, the term of this patent is extended or adjusted under 35 U.S.C. 154(b) by 695 days.

(21) Appl. No.: 17/213,709

(22) Filed: Mar. 26, 2021

(65) Prior Publication Data

US 2021/0317069 A1    Oct. 14, 2021

(30) Foreign Application Priority Data

Apr. 3, 2020   (JP) .................................. 2020-067217
Apr. 28, 2020  (JP) .................................. 2020-078772
Jul. 30, 2020  (JP) .................................. 2020-129665

(51) Int. Cl.
  *C07C 211/56*    (2006.01)
  *H10K 50/15*     (2023.01)
  (Continued)

(52) U.S. Cl.
  CPC .......... *C07C 211/56* (2013.01); *H10K 85/615* (2023.02); *H10K 85/633* (2023.02); *H10K 50/15* (2023.02); *H10K 50/17* (2023.02)

(58) Field of Classification Search
  CPC .... C07C 211/54; H10K 85/633; H10K 50/15; H10K 50/17
  See application file for complete search history.

(56) References Cited

U.S. PATENT DOCUMENTS

| 8,642,190 B2 | 2/2014 | Ogita et al. |
| 9,051,239 B2 | 6/2015 | Osaka et al. |

(Continued)

FOREIGN PATENT DOCUMENTS

| CN | 104488359 A | 4/2015 |
| CN | 105111143 A | 12/2015 |

(Continued)

OTHER PUBLICATIONS

Lee.J et al., "Synergetic electrode architecture for efficient graphene-based flexible organic light-emitting diodes", Nature Communications, Jun. 2, 2016, vol. 7, pp. 11791-1-11791-9.

(Continued)

*Primary Examiner* — Vu A Nguyen
(74) *Attorney, Agent, or Firm* — Fish & Richardson P.C.

(57) ABSTRACT

To provide a novel arylamine compound with a low refractive index. The provided arylamine compound includes at least one aromatic group. The aromatic group includes a first benzene ring, a second benzene ring, a third benzene ring, and at least three alkyl groups. The first benzene ring, the second benzene ring, and the third benzene ring are directly bonded in this order. The first benzene ring is bonded to nitrogen of amine. The first benzene ring may further include a substituted or unsubstituted phenyl group. The second benzene ring or the third benzene ring may further (Continued)

include an alkylated phenyl group. Each of first positions and third positions of two or more of the first to third benzene rings is independently bonded to another benzene ring, a benzene ring of the alkylated phenyl group, any of the at least three alkyl groups, or the nitrogen of the amine.

23 Claims, 73 Drawing Sheets

(51) Int. Cl.
  *H10K 50/17* (2023.01)
  *H10K 85/60* (2023.01)

(56) References Cited

U.S. PATENT DOCUMENTS

| | | | |
|---|---|---|---|
| 9,496,503 | B2 | 11/2016 | Takeda et al. |
| 9,634,263 | B2 | 4/2017 | Ogita et al. |
| 9,768,391 | B2 | 9/2017 | Mujica-fernaud et al. |
| 9,818,984 | B2 | 11/2017 | Mizuno |
| 10,497,877 | B2 | 12/2019 | Mujica-fernaud et al. |
| 10,505,119 | B2 | 12/2019 | Yokoyama et al. |
| 10,556,864 | B2 | 2/2020 | Nomura et al. |
| 11,258,018 | B2 | 2/2022 | Mujica-fernaud et al. |
| 11,925,108 | B2 | 3/2024 | Uehara et al. |
| 2009/0066227 | A1 | 3/2009 | Okinaka et al. |
| 2009/0160323 | A1 | 6/2009 | Nomura et al. |
| 2010/0104969 | A1 | 4/2010 | Mochizuki et al. |
| 2013/0207046 | A1 | 8/2013 | Pflumm et al. |
| 2018/0009751 | A1 | 1/2018 | Nomura et al. |
| 2019/0016666 | A1 | 1/2019 | Jeong et al. |
| 2021/0005814 | A1* | 1/2021 | Watabe ............... C09K 11/06 |
| 2022/0216445 | A1 | 7/2022 | Seo et al. |
| 2023/0225149 | A1 | 7/2023 | Watabe et al. |
| 2023/0276647 | A1 | 8/2023 | Kawano et al. |
| 2023/0320130 | A1 | 10/2023 | Watabe et al. |
| 2023/0337462 | A1 | 10/2023 | Ueda et al. |

FOREIGN PATENT DOCUMENTS

| | | | | |
|---|---|---|---|---|
| CN | 107408636 | A | | 11/2017 |
| CN | 109206324 | A * | 1/2019 | ........... C07C 211/60 |
| CN | 109206327 | A | | 1/2019 |
| CN | 109485577 | A | | 3/2019 |
| CN | 112186112 | A | | 1/2021 |
| EP | 3244465 | A | | 11/2017 |
| EP | 3812367 | A | | 4/2021 |
| JP | 11-162649 | A | | 6/1999 |
| JP | 11-282181 | A | | 10/1999 |
| JP | 2005-120030 | A | | 5/2005 |
| JP | 2009-091304 | A | | 4/2009 |
| JP | 2014-207356 | A | | 10/2014 |
| JP | 2018-181916 | A | | 11/2018 |
| JP | 2019-505566 | | | 2/2019 |
| JP | 2021-176185 | A | | 11/2021 |
| KR | 2017-0080432 | A | | 7/2017 |
| KR | 2018-0137315 | A | | 12/2018 |
| KR | 2019-0035567 | A | | 4/2019 |
| WO | WO-2017/116167 | | | 7/2017 |
| WO | WO-2017/116168 | | | 7/2017 |
| WO | WO-2020/004235 | | | 1/2020 |

OTHER PUBLICATIONS

Chinese Office Action (Application No. 202110362077.3) Dated Apr. 8, 2024.

Kim.S et al., "Diarylamino-Substituted Stilbene Derivatives for Blue Organic Light-Emitting Diodes", INEC 2010 (3rd International Nanoelectronics Conference), 2010, pp. 678-679, IEEE.

Compendium of Chemical Terminology, Gold Book, Aug. 19, 2012, pp. 73, 499, 694-695 of 1622, International Union of Pure and Applied Chemistry.

* cited by examiner

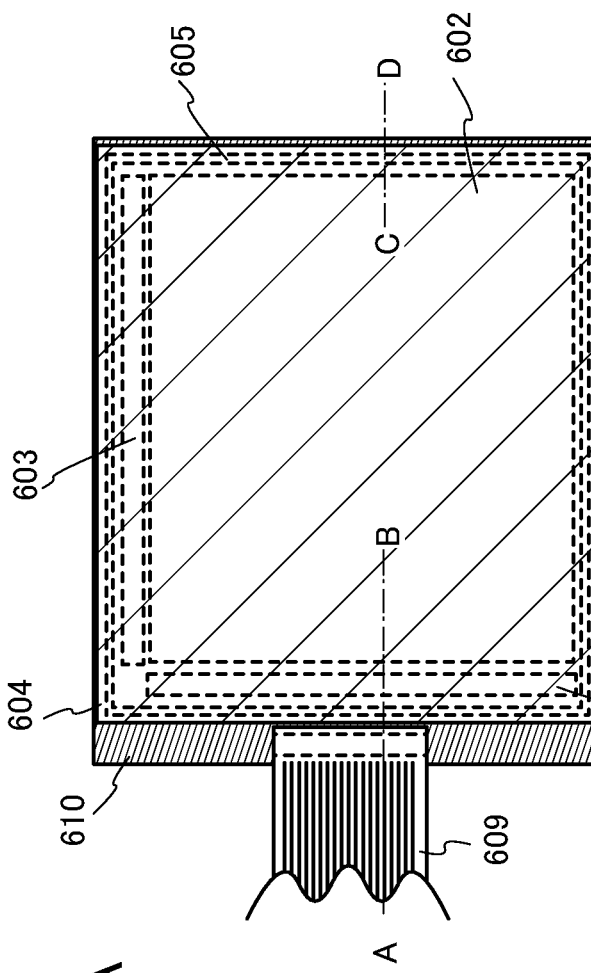
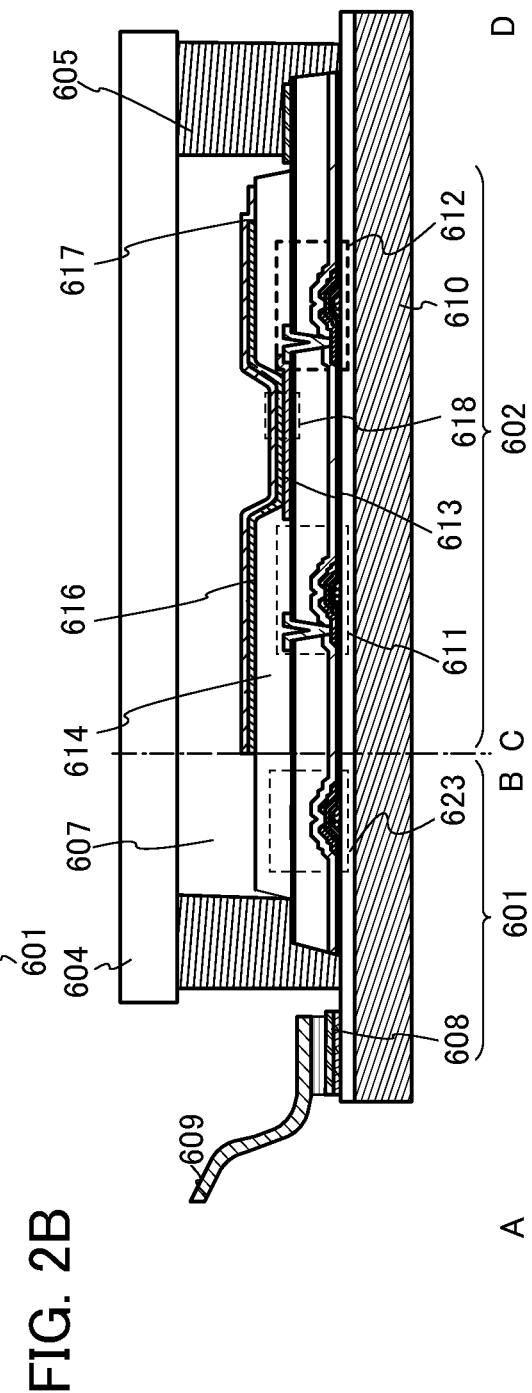
FIG. 2A
FIG. 2B

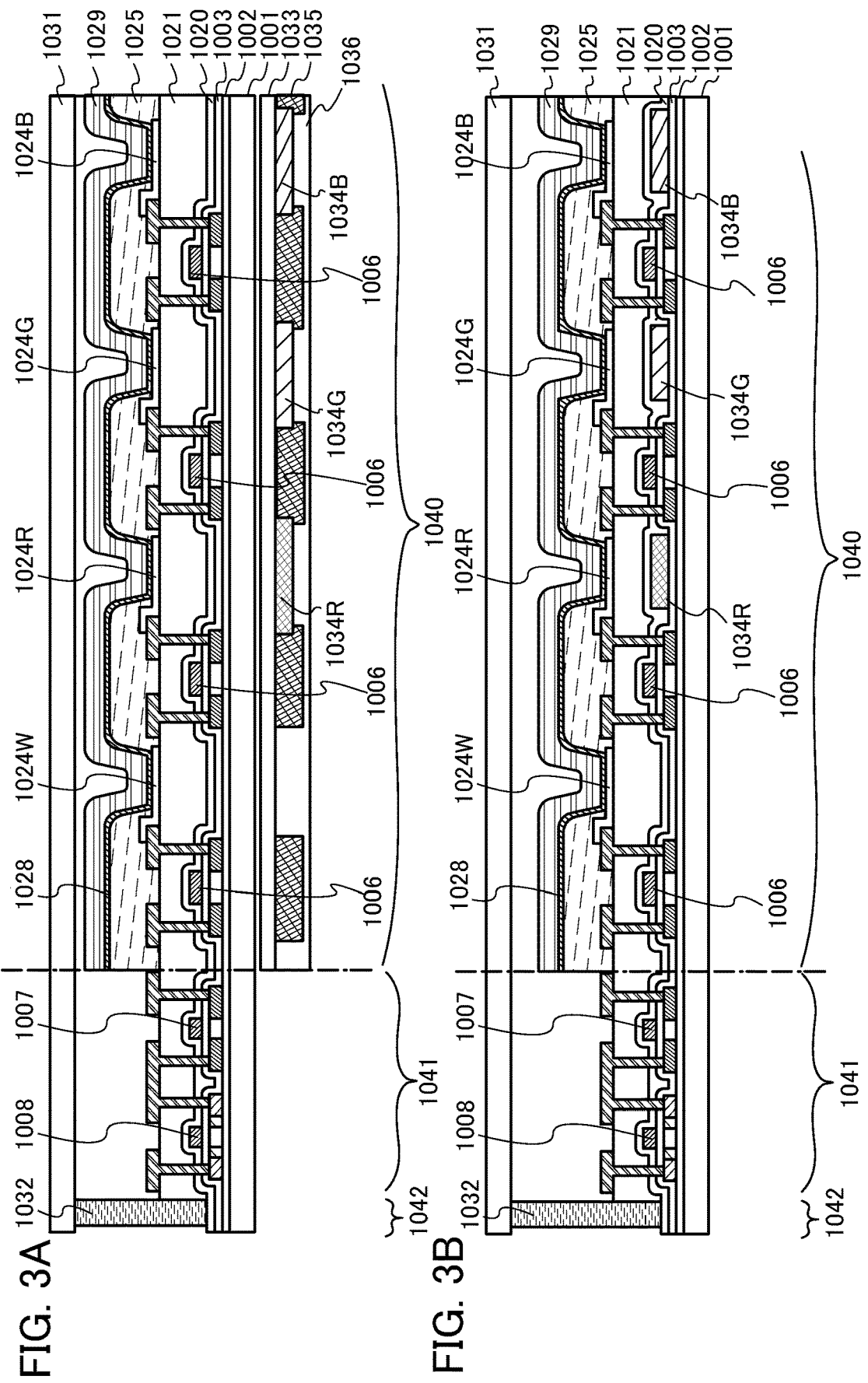

FIG. 7A
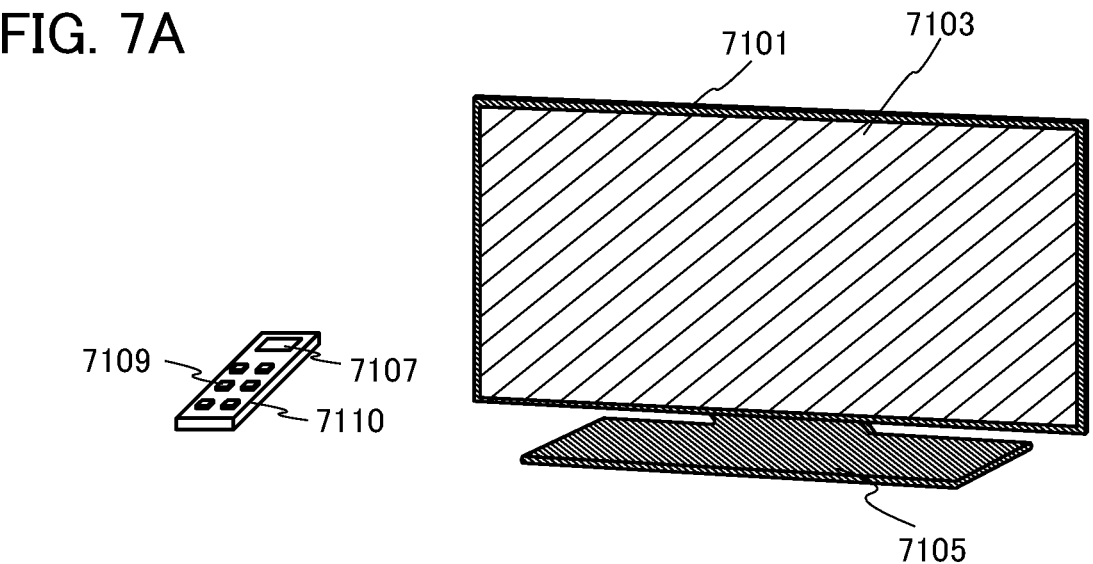
FIG. 7B1
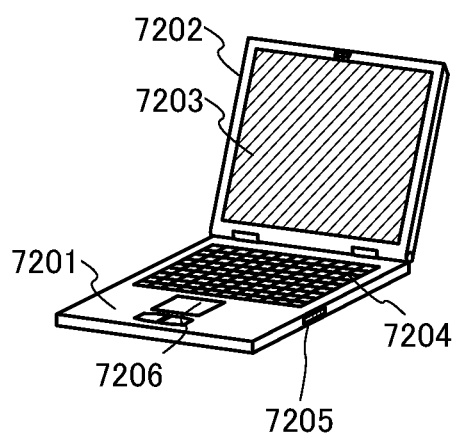
FIG. 7B2
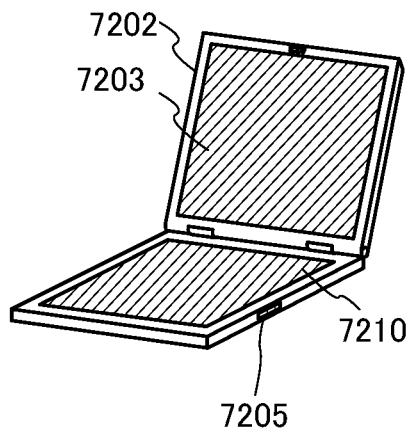
FIG. 7C
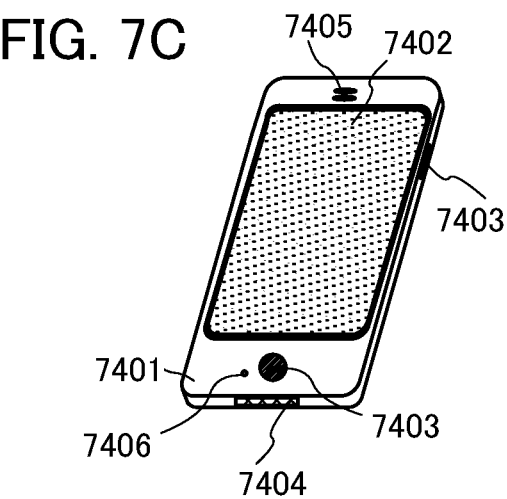

FIG. 38
mmtBumTPChPAF-02
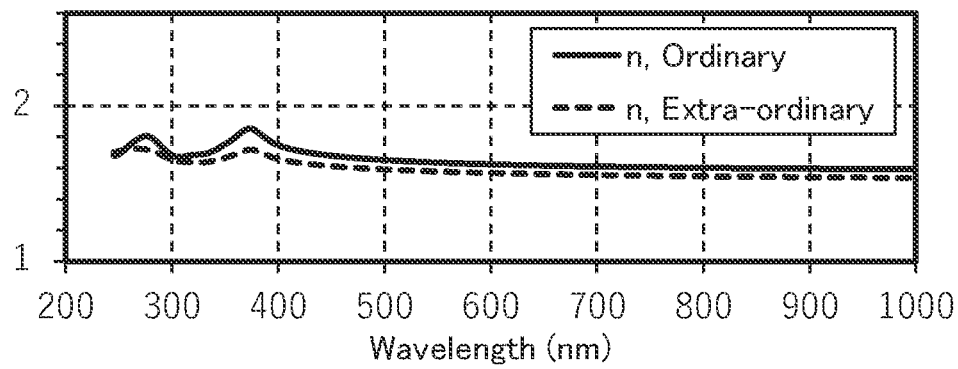
mmtBumTPoFBi-02
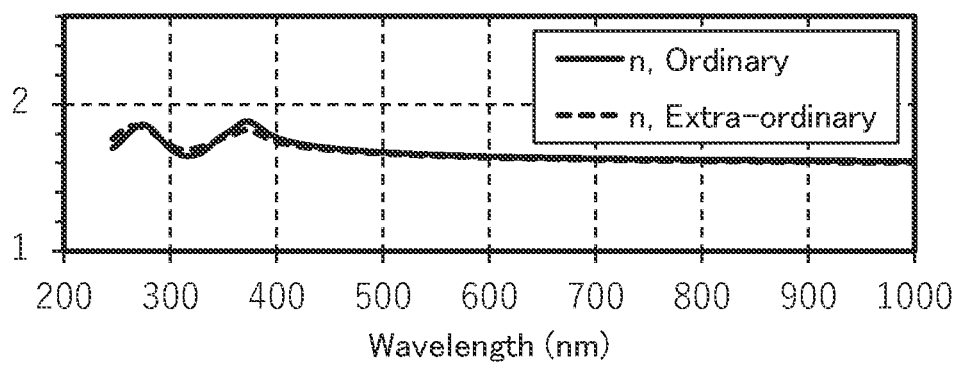
PCBBiF
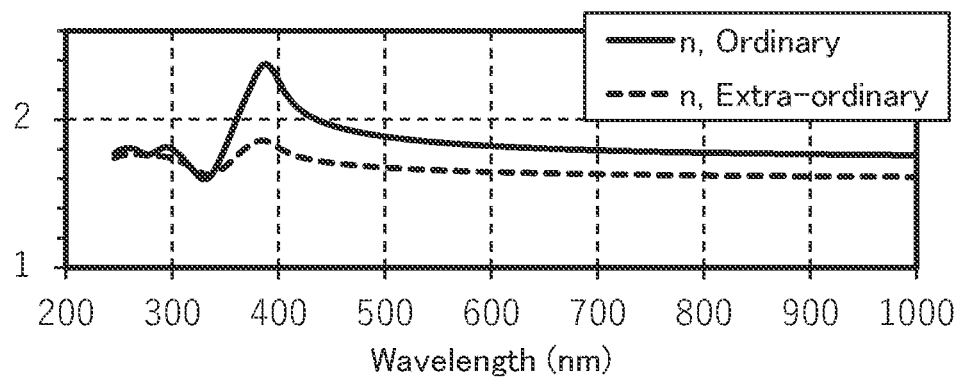

FIG. 45
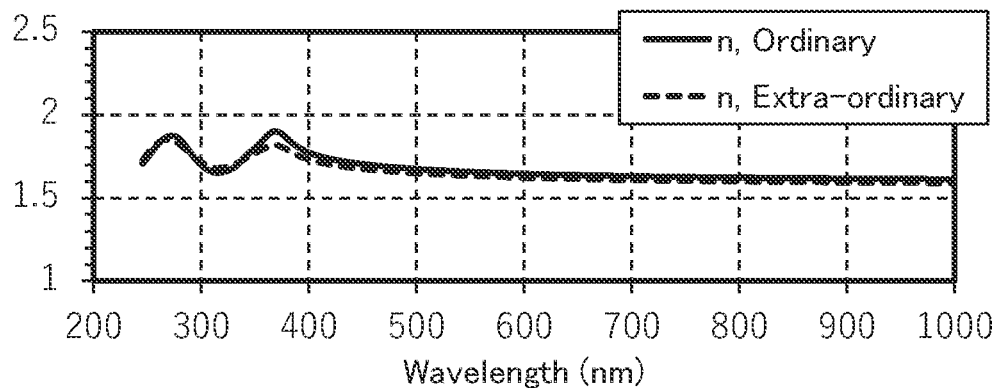
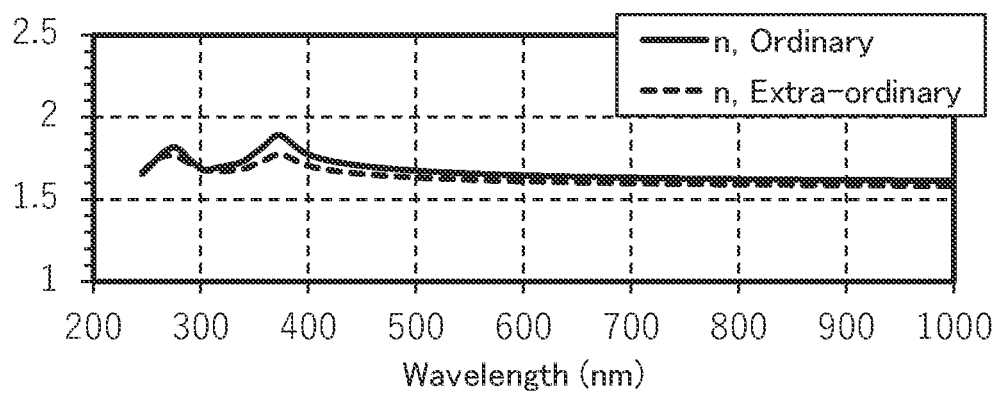
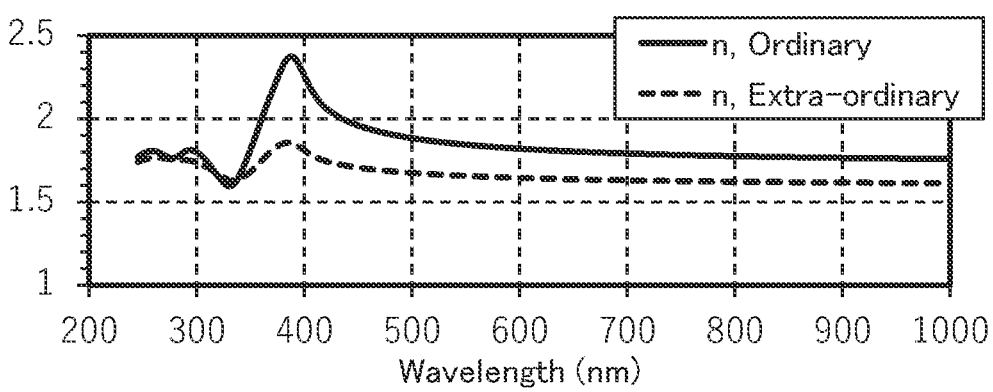

FIG. 52
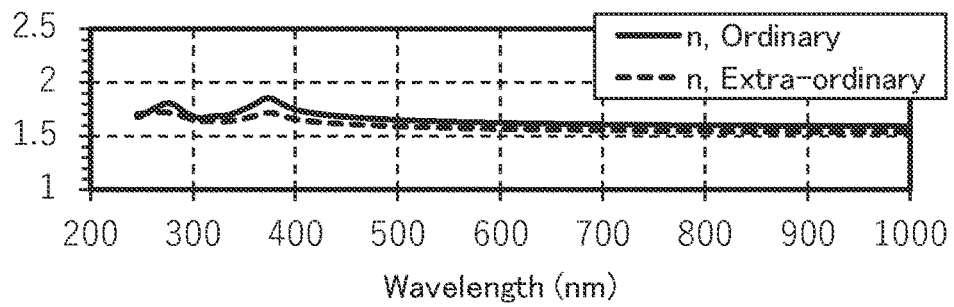
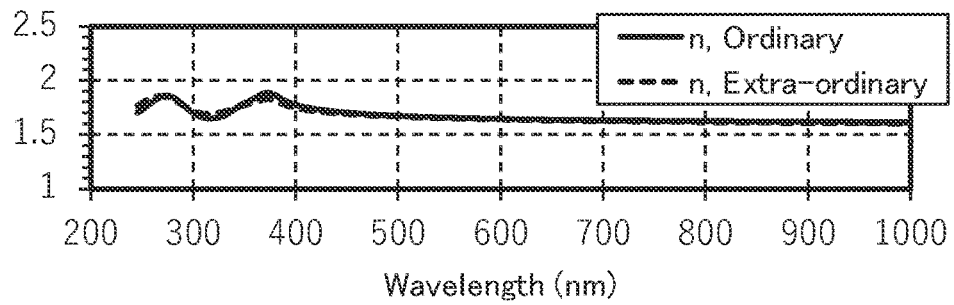
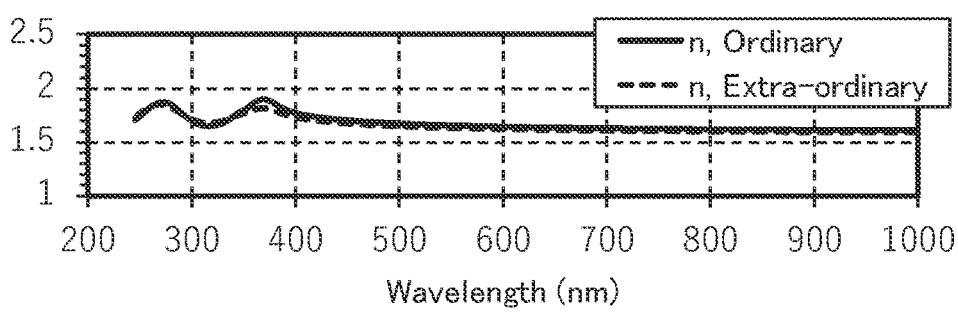
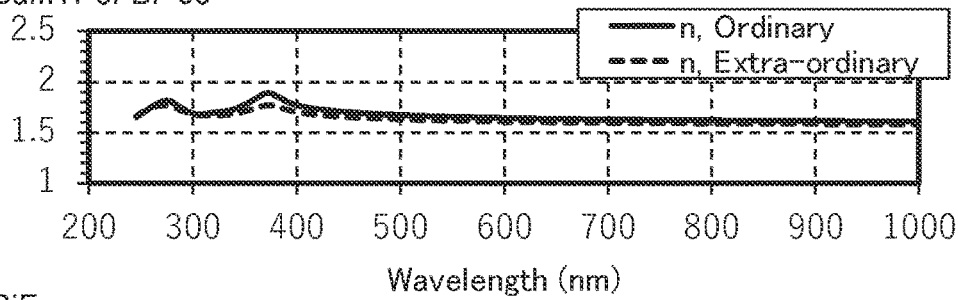
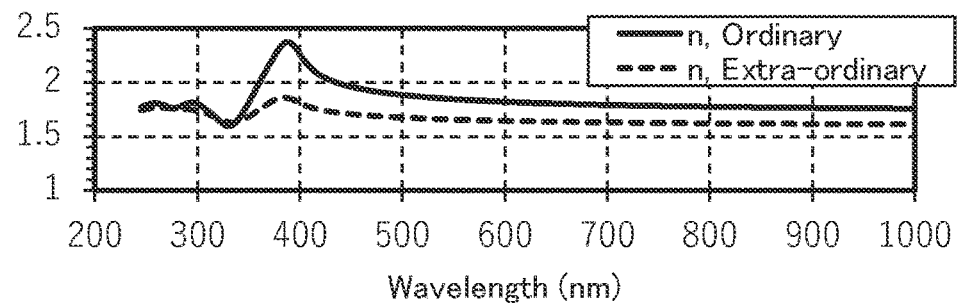

FIG. 59
mmtBumTPChPAF-02
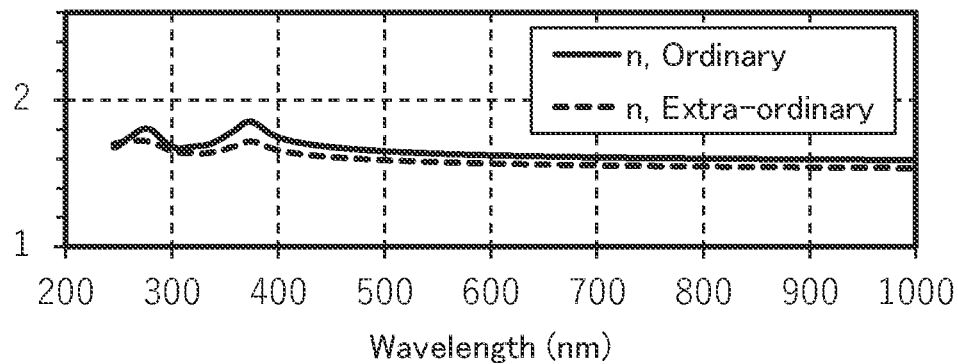
mmtBumTPoFBi-02
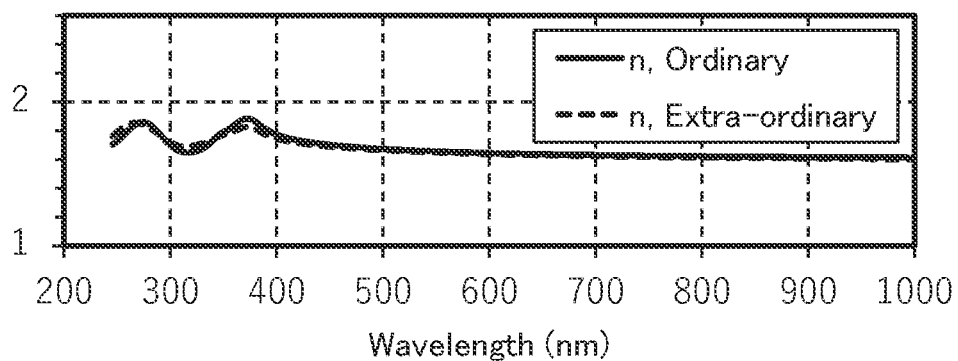
PCBBiF
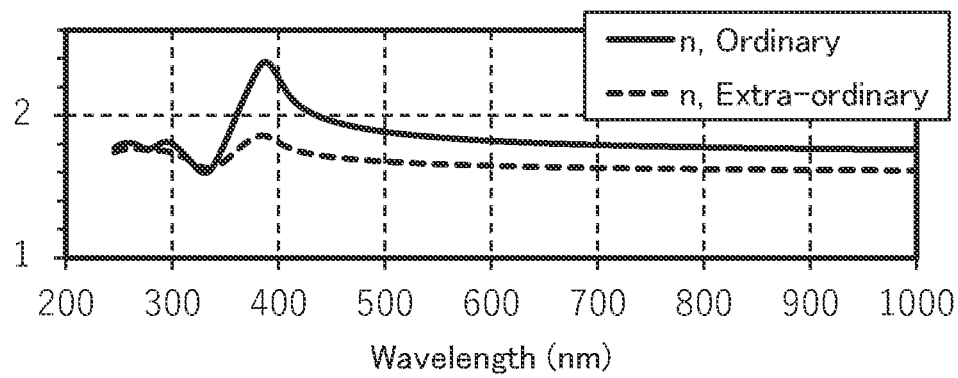

FIG. 68
mmtBumTPChPAF-02
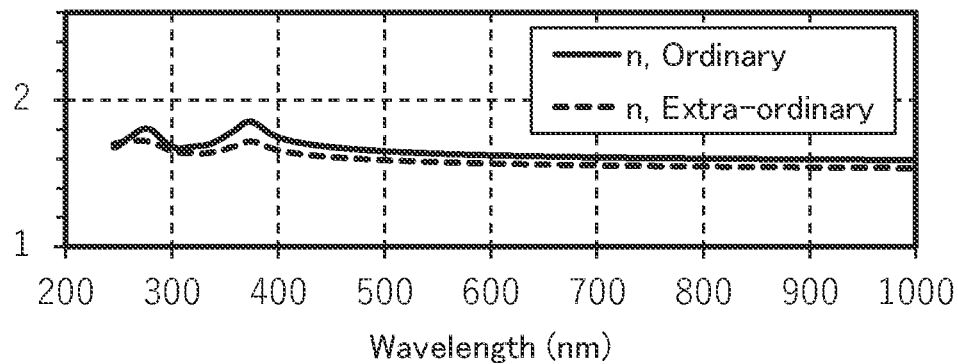
mmtBumTPoFBi-02
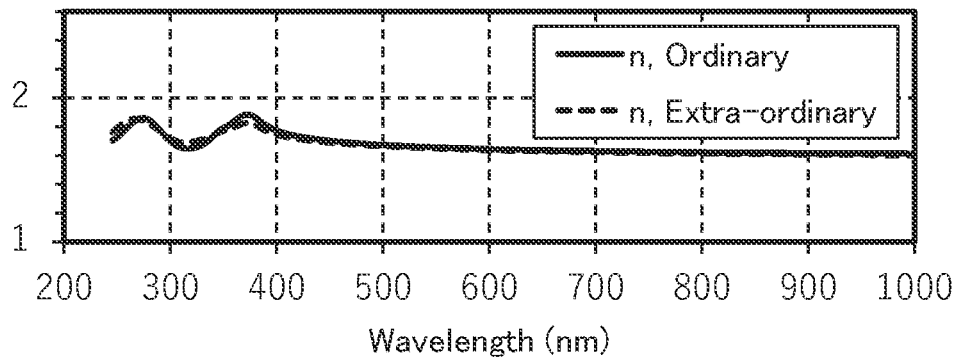
PCBBiF
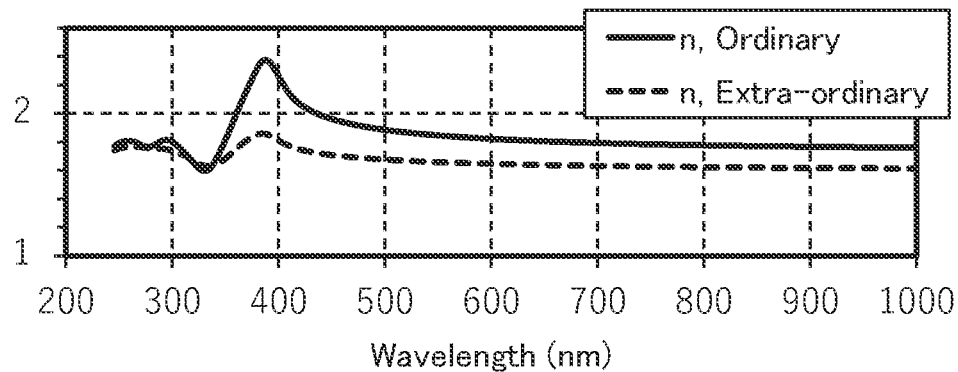

ARYLAMINE COMPOUND, HOLE-TRANSPORT LAYER MATERIAL, HOLE-INJECTION LAYER MATERIAL, LIGHT-EMITTING DEVICE, LIGHT-EMITTING APPARATUS, ELECTRONIC APPARATUS, AND LIGHTING DEVICE

BACKGROUND OF THE INVENTION

1. Field of the Invention

One embodiment of the present invention relates to an organic compound, a light-emitting element, a light-emitting device, a display module, a lighting module, a display device, a light-emitting apparatus, an electronic apparatus, a lighting device, and an electronic device. Note that one embodiment of the present invention is not limited to the above technical field. The technical field of one embodiment of the invention disclosed in this specification and the like relates to an object, a method, or a manufacturing method. One embodiment of the present invention relates to a process, a machine, manufacture, or a composition of matter. Specifically, examples of the technical field of one embodiment of the present invention disclosed in this specification include a semiconductor device, a display device, a liquid crystal display device, a light-emitting apparatus, a lighting device, a power storage device, a memory device, an imaging device, a driving method thereof, and a manufacturing method thereof.

2. Description of the Related Art

Light-emitting devices (organic EL devices) including organic compounds and utilizing electroluminescence (EL) have been put to more practical use. In the basic structure of such light-emitting devices, an organic compound layer containing a light-emitting material (an EL layer) is interposed between a pair of electrodes. Carriers (holes and electrons) are injected by application of voltage to the element, and recombination energy of the carriers is used, whereby light emission can be obtained from the light-emitting material.

Such light-emitting devices are of self-light-emitting type and thus have advantages over liquid crystal displays, such as high visibility and no need for backlight when used as pixels of a display, and are suitable as flat panel display devices. Displays including such light-emitting devices are also highly advantageous in that they can be thin and lightweight. Moreover, such light-emitting devices also have a feature that response speed is extremely fast.

Since light-emitting layers of such light-emitting devices can be successively formed two-dimensionally, planar light emission can be achieved. This feature is difficult to realize with point light sources typified by incandescent lamps and LEDs or linear light sources typified by fluorescent lamps; thus, the light-emitting devices also have great potential as planar light sources, which can be applied to lighting devices and the like.

Displays or lighting devices including light-emitting devices are suitable for a variety of electronic apparatuses as described above, and research and development of light-emitting devices have progressed for more favorable characteristics.

Low outcoupling efficiency is often a problem in an organic EL device. In particular, the attenuation due to reflection which is caused by a difference in refractive index between adjacent layers is a main cause of a reduction in device efficiency. In order to reduce this effect, a structure including a layer formed using a low refractive index material in an EL layer (see Non-Patent Document 1, for example) has been proposed.

A light-emitting device having this structure can have higher outcoupling efficiency and higher external quantum efficiency than a light-emitting device having a conventional structure; however, it is not easy to form such a layer with a low refractive index in an EL layer without adversely affecting other critical characteristics of the light-emitting device. This is because a low refractive index is in a trade-off relationship with a high carrier-transport property or high reliability of a light-emitting device including a layer with a low refractive index. This problem is caused because the carrier-transport property and reliability of an organic compound largely depend on an unsaturated bond, and an organic compound having many unsaturated bonds tends to have a high refractive index.

REFERENCE

Patent Document 1

Japanese Published Patent Application No. H11-282181

Patent Document 2

Japanese Published Patent Application No. 2009-91304

Patent Document 3

United States Patent Application Publication No. 2010/104969

Non-Patent Document 1

Jaeho Lee et al., "Synergetic electrode architecture for efficient graphene-based flexible organic light-emitting diodes", nature COMMUNICATIONS, Jun. 2, 2016, DOI: 10.1038/ncomms 11791.

SUMMARY OF THE INVENTION

An object of one embodiment of the present invention is to provide a novel material for a hole-transport layer. Another object of one embodiment of the present invention is to provide a low-refractive-index material for a hole-transport layer. Another object of one embodiment of the present invention is to provide a low-refractive-index material for a hole-transport layer and an adequate carrier-transport property. Another object of one embodiment of the present invention is to provide a low-refractive-index material for a hole-transport layer and an adequate hole-transport property.

An object of one embodiment of the present invention is to provide a novel arylamine compound. Another object of one embodiment of the present invention is to provide a novel arylamine compound having an adequate hole-transport property. Another object of one embodiment of the present invention is to provide a novel arylamine compound having a low refractive index. Another object of one embodiment of the present invention is to provide a novel arylamine compound having a low refractive index and an adequate hole-transport property.

Another object of one embodiment of the present invention is to provide a light-emitting device having high emission efficiency. Another object of one embodiment of the present invention is to provide a light-emitting device, a light-emitting apparatus, an electronic apparatus, a display device, and an electronic device each having low power consumption.

Note that the description of these objects does not preclude the existence of other objects. One embodiment of the present invention does not necessarily achieve all the objects listed above. Other objects will be apparent from and can be derived from the description of the specification, the drawings, the claims, and the like.

It is only necessary that at least one of the above-described objects be achieved in the present invention.

One embodiment of the present invention is an arylamine compound including at least one aromatic group. The aromatic group includes a first benzene ring, a second benzene ring, a third benzene ring, and at least three alkyl groups. The first benzene ring, the second benzene ring, and the third benzene ring are directly bonded in this order. The first benzene ring is bonded to nitrogen of amine in the arylamine compound. The first benzene ring may further include a substituted or unsubstituted phenyl group. The second benzene ring or the third benzene ring may further include an alkylated phenyl group. Each of first positions and third positions of two or more of the first benzene ring, the second benzene ring, and the third benzene ring is independently bonded to another benzene ring, a benzene ring of the alkylated phenyl group, any of the at least three alkyl groups, or the nitrogen of the amine.

Another embodiment of the present invention is the arylamine compound with the above structure in which the second benzene ring or the third benzene ring includes an alkylated phenyl group.

Another embodiment of the present invention is the arylamine compound with the above structure in which the first benzene ring includes an unsubstituted phenyl group.

Another embodiment of the present invention is the arylamine compound with the above structure in which each of first positions and third positions of all of the first benzene ring, the second benzene ring, the third benzene ring, and the benzene ring of the alkylated phenyl group is independently bonded to another benzene ring, any of the at least three alkyl groups, or the nitrogen of the amine.

Another embodiment of the present invention is the arylamine compound with the above structure in which each of first positions, third positions, and the fifth positions of all of the first benzene ring, the second benzene ring, the third benzene ring, and the benzene ring of the alkylated phenyl group is independently bonded to another benzene ring, any of the at least three alkyl groups, or the nitrogen of the amine, and the other bonding positions are unsubstituted.

Another embodiment of the present invention is the arylamine compound with the above structure, further including a second aromatic group, in which the second aromatic group is a substituted or unsubstituted monocyclic ring or a substituted or unsubstituted condensed ring skeleton composed of three or less rings.

Another embodiment of the present invention is the arylamine compound with the above structure in which the second aromatic group is a substituted or unsubstituted condensed ring skeleton composed of three or less rings, and the number of carbon atoms forming the condensed ring skeleton is 6 to 13.

Another embodiment of the present invention is the arylamine compound with the above structure in which the condensed ring skeleton is a fluorene ring.

Another embodiment of the present invention is the arylamine compound with the above structure in which the second aromatic group is a dimethylfluorenyl group.

Another embodiment of the present invention is the arylamine compound with the above structure, further including a third aromatic group, in which the third aromatic group includes 1 to 3 substituted or unsubstituted benzene rings.

Another embodiment of the present invention is the arylamine compound with the above structure in which the alkyl group is a chain alkyl group having 2 to 5 carbon atoms.

Another embodiment of the present invention is the arylamine compound with the above structure in which the alkyl group is a chain alkyl group having a branch formed of 3 to 5 carbon atoms.

Another embodiment of the present invention is the arylamine compound with the above structure in which the alkyl group is a tert-butyl group.

Another embodiment of the present invention is the arylamine compound with the above structure in which the arylamine compound is a triarylamine compound.

Another embodiment of the present invention is the arylamine compound with the above structure in which the refractive index of a layer formed of the arylamine compound with respect to an ordinary light with a wavelength greater than or equal to 455 nm and less than or equal to 465 nm is greater than or equal to 1.5 and less than or equal to 1.75.

Another embodiment of the present invention is the arylamine compound with the above structure in which the refractive index of a layer formed of the arylamine compound with respect to an ordinary light with a wavelength of 633 nm is greater than or equal to 1.45 and less than or equal to 1.70.

Another embodiment of the present invention is the arylamine compound with the above structure, having a molecular weight greater than or equal to 400 and less than or equal to 1100.

Another embodiment of the present invention is the arylamine compound with the above structure in which the glass transition temperature is higher than or equal to 100° C., preferably higher than or equal to 110° C., further preferably higher than or equal to 120° C.

Another embodiment of the present invention is the arylamine compound with the above structure in which the arylamine compound is a monoamine compound.

Another embodiment of the present invention is an arylamine compound represented by General Formula (G1) below.

[Chemical Formula 1]

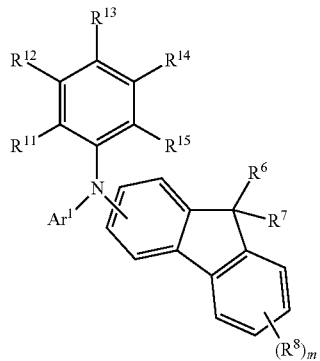

(G1)

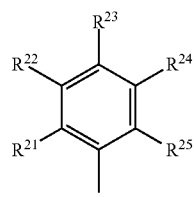

(g1)

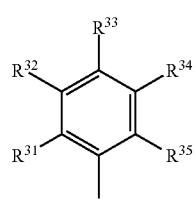

(g2)

[Chemical Formula 2]

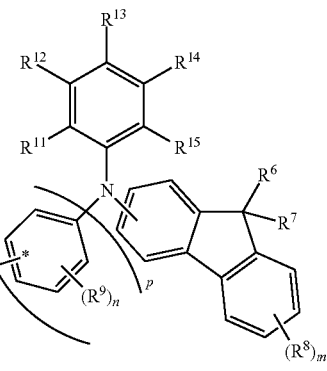

(G2)

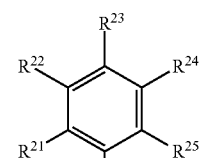

(g1)

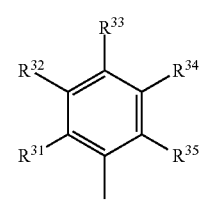

(g2)

In General Formula (G1), $Ar^1$ represents a substituted or unsubstituted benzene ring or a substituent in which two or three substituted or unsubstituted benzene rings are bonded to one another; each of $R^6$, $R^7$, and $R^8$ independently represents an alkyl group having 1 to 4 carbon atoms; m represents an integer of 0 to 4; when m is greater than or equal to 2, a plurality of $R^8$ may be the same or different; and one of $R^{11}$ to $R^{15}$ represents a substituent represented by General Formula (g1), and each of the others independently represents any one of hydrogen, an alkyl group having 1 to 6 carbon atoms, and a substituted or unsubstituted phenyl group. In General Formula (g1), one of $R^{21}$ to $R^{25}$ represents a substituent represented by General Formula (g2), and each of the others independently represents any one of hydrogen, an alkyl group having 1 to 6 carbon atoms, and a phenyl group substituted with an alkyl group having 1 to 6 carbon atoms. In General Formula (g2), each of $R^{31}$ to $R^{35}$ independently represents any one of hydrogen, an alkyl group having 1 to 6 carbon atoms, and a phenyl group substituted with an alkyl group having 1 to 6 carbon atoms; at least three of $R^{11}$ to $R^{15}$, $R^{21}$ to $R^{25}$, and $R^{31}$ to $R^{35}$ represent an alkyl group having 1 to 6 carbon atoms; none or one of $R^{11}$ to $R^{15}$ represents the substituted or unsubstituted phenyl group; none or one of $R^{21}$ to $R^{25}$ and $R^{31}$ to $R^{35}$ represents the phenyl group substituted with an alkyl group having 1 to 6 carbon atoms; and in at least two combinations of the three combinations $R^{12}$ and $R^{14}$, $R^{22}$ and $R^{24}$, and $R^{32}$ and $R^{34}$, at least one R represents any of the substituents other than hydrogen.

Another embodiment of the present invention is an arylamine compound represented by General Formula (G2) below.

In General Formula (G2), each of p and r independently represents 1 or 2 and p+r represents 2 or 3; each of $R^6$ to $R^9$ independently represents an alkyl group having 1 to 4 carbon atoms; each of m and n independently represents an integer of 0 to 4; each of $R^{41}$ to $R^{45}$ independently represents any one of hydrogen, an alkyl group having 1 to 6 carbon atoms, and a cycloalkyl group having 5 to 12 carbon atoms; when m is 2 or larger, a plurality of $R^8$ may be the same or different; when n is 2 or larger, a plurality of $R^9$ may be the same or different; when p is 2, kinds and numbers of substituents and positions of bonds included in two phenylene groups may be the same or different; when r is 2, kinds and numbers of substituents and positions of bonds included in two phenyl groups may be the same or different; and one of $R^{11}$ to $R^{15}$ is a substituent represented by General Formula (g1), and each of the others independently represents any one of hydrogen, an alkyl group having 1 to 6 carbon atoms, and a substituted or unsubstituted phenyl group. In General Formula (g1), one of $R^{21}$ to $R^{25}$ represents a substituent represented by General Formula (g2), and each of the others independently represents any one of hydrogen, an alkyl group having 1 to 6 carbon atoms, and a phenyl group substituted with an alkyl group having 1 to 6 carbon atoms. In General Formula (g2), each of $R^{31}$ to $R^{35}$ independently represents any one of hydrogen, an alkyl group having 1 to 6 carbon atoms, and a phenyl group substituted with an alkyl group having 1 to 6 carbon atoms; at least three of $R^{11}$ to $R^{15}$, $R^{21}$ to $R^{25}$, and $R^{31}$ to $R^{35}$ represent the alkyl group having 1 to 6 carbon atoms; none or one of $R^{11}$ to $R^{15}$ represents the substituted or unsubstituted phenyl group; and none or one of $R^{21}$ to $R^{25}$ and $R^{31}$ to $R^{35}$ represents the phenyl group substituted with an alkyl group having 1 to 6 carbon atoms; and in at least two combinations of the three combinations $R^{12}$ and $R^{14}$, $R^{22}$ and $R^{24}$, and $R^{32}$ and $R^{34}$, at least one R represents any of the substituents other than hydrogen.

Another embodiment of the present invention is the arylamine compound with the above structure in which n represents 0.

Another embodiment of the present invention is the arylamine compound with the above structure in which p represents 1 and r represents 1.

Another embodiment of the present invention is an arylamine compound represented by General Formula (G3) below.

[Chemical Formula 3]

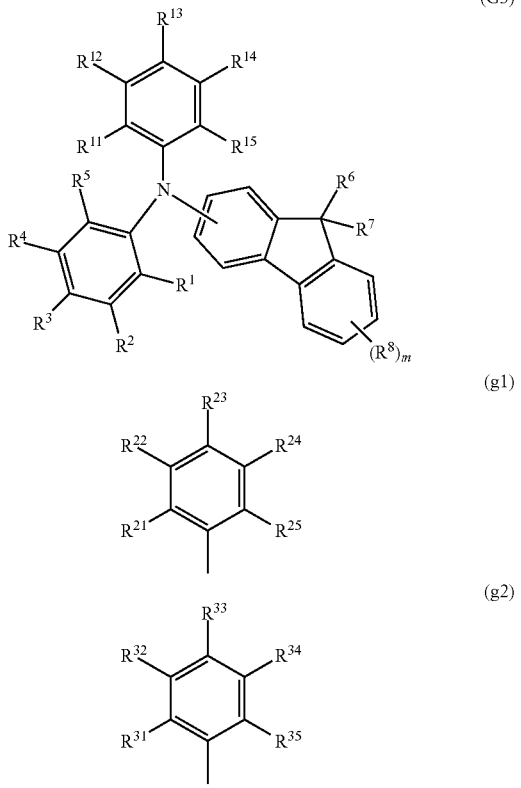

In General Formula (G3), each of $R^1$ to $R^5$ independently represents any one of hydrogen, an alkyl group having 1 to 6 carbon atoms, a cycloalkyl group having 5 to 12 carbon atoms, and a substituted or unsubstituted phenyl group; each of $R^6$, $R^7$, and $R^8$ independently represents an alkyl group having 1 to 4 carbon atoms; m represents an integer of 0 to 4; when m is greater than or equal to 2, a plurality of $R^8$ may be the same or different; and one of $R^{11}$ to $R^{15}$ represents a substituent represented by General Formula (g1), and each of the others independently represents any one of hydrogen, an alkyl group having 1 to 6 carbon atoms, and a substituted or unsubstituted phenyl group. In General Formula (g1), one of $R^{21}$ to $R^{25}$ represents a substituent represented by General Formula (g2), and each of the others independently represents any one of hydrogen, an alkyl group having 1 to 6 carbon atoms, and a phenyl group substituted with an alkyl group having 1 to 6 carbon atoms. In General Formula (g2), each of $R^{31}$ to $R^{35}$ independently represents any one of hydrogen, an alkyl group having 1 to 6 carbon atoms, and a phenyl group substituted with an alkyl group having 1 to 6 carbon atoms; at least three of $R^{11}$ to $R^{15}$, $R^{21}$ to $R^{25}$, and $R^{31}$ to $R^{35}$ represent an alkyl group having 1 to 6 carbon atoms; none or one of $R^{11}$ to $R^{15}$ represents the substituted or unsubstituted phenyl group; none or one of $R^{21}$ to $R^{25}$ and $R^{31}$ to $R^{35}$ represents the phenyl group substituted with an alkyl group having 1 to 6 carbon atoms; and in at least two combinations of the three combinations $R^{12}$ and $R^{14}$, $R^{22}$ and $R^{24}$, and $R^{32}$ and $R^{34}$, at least one R represents any of the substituents other than hydrogen.

Another embodiment of the present invention is the arylamine compound with the above structure in which $R^3$ represents a cyclohexyl group and each of $R^1$, $R^2$, $R^4$, and $R^5$ represents hydrogen.

Another embodiment of the present invention is the arylamine compound with the above structure in which $R^1$ represents an unsubstituted phenyl group and each of $R^2$ to $R^5$ represents hydrogen.

Another embodiment of the present invention is the arylamine compound with the above structure in which at least one of $R^{12}$, $R^{14}$, $R^{22}$, and $R^{24}$ represents any of the substituents other than hydrogen, and at least one of $R^{32}$ and $R^{34}$ represents any of the substituents other than hydrogen.

Another embodiment of the present invention is the arylamine compound with the above structure in which m represents 0.

Another embodiment of the present invention is the arylamine compound with the above structure in which the alkyl group having 1 to 6 carbon atoms is a chain alkyl group having 2 to 5 carbon atoms.

Another embodiment of the present invention is the arylamine compound with the above structure in which the alkyl group having 1 to 6 carbon atoms is a chain alkyl group having a branch formed of 3 to 5 carbon atoms.

Another embodiment of the present invention is the arylamine compound with the above structure in which the alkyl group having 1 to 6 carbon atoms is a tert-butyl group.

Another embodiment of the present invention is the arylamine compound with the above structure in which each of $R^{12}$, $R^{14}$, $R^{22}$, $R^{32}$, and $R^{34}$ among $R^{11}$ to $R^{15}$, $R^{21}$ to $R^{25}$, and $R^{31}$ to $R^{35}$ represents any of the substituents other than hydrogen, and each of the others represents hydrogen.

Another embodiment of the present invention is the arylamine compound with the above structure in which $R^{12}$ represents a substituent represented by General Formula (g1) and $R^{22}$ represents a substituent represented by General Formula (g2).

Another embodiment of the present invention is the arylamine compound with the above structure in which each of $R^{14}$, $R^{32}$, and $R^{34}$ represents a tert-butyl group.

Another embodiment of the present invention is the arylamine compound with the above structure in which each of $R^5$ and $R^6$ represents a methyl group.

Another embodiment of the present invention is the arylamine compound with the above structure in which the refractive index of a layer formed of the arylamine compound with respect to an ordinary light with a wavelength greater than or equal to 455 nm and less than or equal to 465 nm is greater than or equal to 1.50 and less than or equal to 1.75.

Another embodiment of the present invention is the arylamine compound with the above structure in which the refractive index of a layer formed of the arylamine compound with respect to an ordinary light with a wavelength of 633 nm is greater than or equal to 1.45 and less than or equal to 1.70.

Another embodiment of the present invention is the arylamine compound with the above structure in which the glass transition temperature is higher than or equal to 100° C., preferably higher than or equal to 110° C., further preferably higher than or equal to 120° C.

Another embodiment of the present invention is a material for a hole-transport layer, including the arylamine compound.

Another embodiment of the present invention is a material for a hole-injection layer, including the arylamine compound.

Another embodiment of the present invention is a material for a hole-injection layer, including the arylamine compound and an organic compound including a cyano group or a fluorine atom.

Another embodiment of the present invention is a light-emitting device using any of the above organic compounds.

Another embodiment of the present invention is an electronic apparatus including any of the above light-emitting devices, and at least one of a sensor, an operation button, a speaker, and a microphone.

Another embodiment of the present invention is a light-emitting apparatus including any of the above light-emitting devices, and at least one of a transistor and a substrate.

Another embodiment of the present invention is a lighting device including any of the above light-emitting devices and a housing.

Note that the light-emitting apparatus in this specification includes, in its category, an image display device that uses a light-emitting device. The light-emitting apparatus may include a module in which a light-emitting device is provided with a connector such as an anisotropic conductive film or a tape carrier package (TCP), a module in which a printed wiring board is provided at the end of a TCP, and a module in which an integrated circuit (IC) is directly mounted on a light-emitting device by a chip on glass (COG) method. Furthermore, a lighting device or the like may include the light-emitting apparatus.

According to one embodiment of the present invention, a novel material for a hole-transport layer can be provided. According to one embodiment of the present invention, a material for a hole-transport layer with a low refractive index can be provided. According to another embodiment of the present invention, a material for a hole-transport layer with a low refractive index and an adequate hole-transport property can be provided.

According to one embodiment of the present invention, a novel material for a hole-injection layer can be provided. According to one embodiment of the present invention, a material for a hole-injection layer with a low refractive index can be provided. According to another embodiment of the present invention, a material for a hole-injection layer with a low refractive index and an adequate hole-transport property can be provided.

According to one embodiment of the present invention, a novel arylamine compound can be provided. According to one embodiment of the present invention, a novel arylamine compound having an adequate hole-transport property can be provided. According to one embodiment of the present invention, a novel arylamine compound having a low refractive index can be provided. According to one embodiment of the present invention, a novel arylamine compound having a low refractive index and an adequate hole-transport property can be provided.

According to one embodiment of the present invention, a light-emitting device having high emission efficiency can be provided. According to one embodiment of the present invention, a light-emitting device, a light-emitting apparatus, an electronic apparatus, a display device, and an electronic device each having low power consumption can be provided.

Note that the description of these effects does not preclude the existence of other effects. One embodiment of the present invention does not necessarily achieve all the effects listed above. Other effects will be apparent from and can be derived from the description of the specification, the drawings, the claims, and the like.

BRIEF DESCRIPTION OF THE DRAWINGS

In the accompanying drawings:

FIGS. 2A and 2B are conceptual views of an active matrix light-emitting apparatus;

FIGS. 3A and 3B are conceptual views of active matrix light-emitting apparatuses;

FIGS. 7A, 7B1, 7B2, and 7C illustrate electronic apparatuses;

FIG. 38 shows measurement results of the refractive indices of mmtBumTPchPAF-02, mmtBumTPoFBi-02, and PCBBiF;

FIG. 45 shows measurement results of the refractive indices of mmtBumTPchPAF-03, mmtBumTPoFBi-03, and PCBBiF;

FIG. 52 shows measurement results of the refractive indices of mmtBumTPchPAF-02, mmtBumTPoFBi-02, mmtBumTPchPAF-03, mmtBumTPoFBi-03, and PCBBiF;

FIG. 59 shows measurement results of the refractive indices of mmtBumTPchPAF-02, mmtBumTPoFBi-02, and PCBBiF;

FIG. 68 shows measurement results of the refractive indices of mmtBumTPchPAF-02, mmtBumTPoFBi-02, and PCBBiF;

DETAILED DESCRIPTION OF THE INVENTION

Figure 1A:
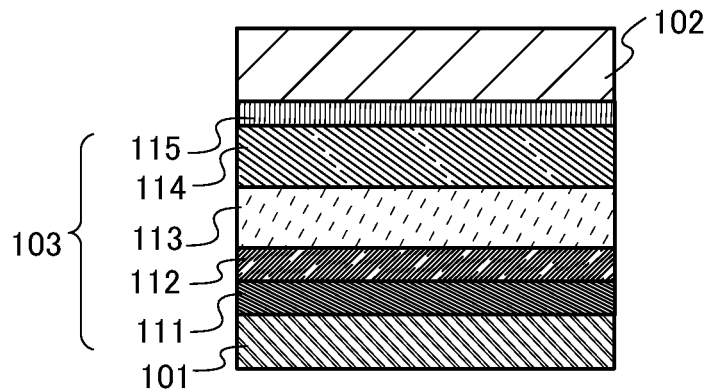
FIGS. 1A to 1C are schematic views of light-emitting devices.

Embodiments of the present invention will be described in detail below with reference to the drawings. Note that the present invention is not limited to the following description, and it will be readily appreciated by those skilled in the art that modes and details of the present invention can be modified in various ways without departing from the spirit and scope of the present invention. Therefore, the present invention should not be construed as being limited to the description in the following embodiments.

Embodiment 1

Among organic compounds that have a carrier-transport property and can be used for an organic EL device, 1,1-bis-(4-bis(4-methyl-phenyl)-amino-phenyl)-cyclohexane (abbreviation: TAPC), which is a material with a low refractive index, is known. The use of such a material with a low refractive index for the EL layer enables a light-emitting device to have high external quantum efficiency; therefore, with TAPC, high external quantum efficiency of a light-emitting device can be expected.

In general, a high carrier-transport property and a low refractive index have a trade-off relationship. This is because the carrier-transport property of an organic compound largely depend on an unsaturated bond, and an organic compound having many unsaturated bonds tends to have a high refractive index. TAPC has both a hole-transport property and a low refractive index in an exquisite balance; however, in a compound including 1,1-disubstituted cyclohexane such as TAPC, two bulky substituents are bonded to a carbon atom of cyclohexane, which causes larger steric repulsion and unstability of the molecule itself, leading to disadvantage in reliability. In addition, TAPC has a skeleton structure including cyclohexane and simple benzene rings, and thus has a low glass transition temperature (Tg) and a heat resistance problem.

One of the possible methods for obtaining a hole-transport material with high heat resistance and high reliability is introducing an unsaturated hydrocarbon group, particularly a cyclic unsaturated hydrocarbon group, into a molecule. Meanwhile, in order to obtain a material with a low refractive index, a substituent with low molecular refraction is preferably introduced into the molecule. Examples of the substituent include a saturated hydrocarbon group and a cyclic saturated hydrocarbon group.

A material used as a carrier-transport material for an organic EL device preferably has a skeleton with a high carrier-transport property, and an aromatic amine skeleton is particularly preferable because of its high hole-transport property. For a higher hole-transport property, two amine skeletons can be introduced as another method. However, as in the above-described TAPC, the diamine structure sometimes adversely affects the reliability depending on the substituents arranged around the amine skeletons.

As a compound that overcomes the trade-off and has a carrier-transport property, a low refractive index, and high reliability, the present inventors have found an arylamine compound in which the proportion of carbon atoms each forming a bond by the sp$^3$ hybrid orbitals, which form a saturated hydrocarbon group, is within a certain range. In particular, the arylamine compound has high reliability equivalent to those of conventional materials for a hole-transport layer with a normal refractive index. Furthermore, the arylamine compound can have more favorable characteristics when the number or position of substituents (i.e., an alkyl group or a cycloalkyl group) containing the carbon atoms each forming a bond by the sp$^3$ hybrid orbitals is adjusted.

An organic compound of one embodiment of the present invention is an arylamine compound including at least one aromatic group. In the aromatic group, a first benzene ring, a second benzene ring, and a third benzene ring are directly bonded in this order. The aromatic group includes at least three alkyl groups. The aromatic group including at least three alkyl groups can achieve a low-refractive-index material for a hole-transport layer. Note that the alkyl group preferably has 1 to 6 carbon atoms. In view of decreasing the refractive index, a chain alkyl group having 2 or more carbon atoms is preferred, and in view of ensuring the carrier-transport property, a chain alkyl group having 5 or less carbon atoms is preferred. Since a chain alkyl group having 3 or more carbon atoms is significantly effective in reducing the refractive index, a chain alkyl group having 2 to 5 carbon atoms is particularly preferred, and a chain alkyl group having 3 to 5 carbon atoms is further preferred. Note that a tert-butyl group is still further preferred.

Note that the first benzene ring may further include a substituted or unsubstituted phenyl group, and the second benzene ring or the third benzene ring may further include an alkylated phenyl group.

In the aromatic group, the first benzene ring is bonded to nitrogen of amine; carbon atoms at the first positions and the third positions of two or more of the first to third benzene rings are bonded to a substituent other than hydrogen. These first and third positions are preferably bonded to an alkyl group, a benzene ring, or nitrogen of amine. In other words, it is preferable that each of the first positions and the third positions of two or more of the first to third benzene rings be independently bonded to another benzene ring (e.g., any of the first to third benzene rings or a benzene ring of the alkylated phenyl group), an alkyl group (e.g., any of the above at least three alkyl groups), or the nitrogen of the amine. As the arylamine compound of one embodiment of the present invention, a triarylamine compound is preferred in terms of electrical stability of a light-emitting device. The triarylamine compound is preferably a monoamine compound (i.e., there is only one nitrogen of amine to which three aryl groups are bonded in the compound) in terms of low refractive index and sublimability.

In the first benzene ring, when a carbon atom located at the meta position with respect to carbon bonded to nitrogen of amine has a substituent, the substituent is preferably the second benzene ring; when the carbon atoms at the two meta positions each have a substituent, one of the substituents is preferably the second benzene ring and the other is preferably an alkyl group or a benzene ring including an alkyl group. In the second benzene ring, when a carbon atom located at the meta position with respect to a carbon atom bonded to the first benzene ring has a substituent, the substituent is preferably the third benzene ring; when the carbon atoms at the two meta positions each have a substituent, one of the substituents is preferably the third benzene ring and the other is preferably an alkyl group or an alkylated phenyl group. In the third benzene ring, when a carbon atom located at the meta position with respect to a carbon atom bonded to the second benzene ring has a substituent, the substituent is preferably an alkyl group or an alkylated phenyl group.

In the phenyl group substituted with an alkyl group that can be used as a substituent of the second benzene ring and a substituent of the third benzene ring, at least one of the carbon atoms at the meta positions is preferably substituted with an alkyl group, and further preferably each of the carbon atoms at the two meta positions are substituted with an alkyl group. Bonding of two or more alkylated phenyl groups to the arylamine compound hardly contributes to a reduction in refractive index, but might cause a reduction in sublimability due to an increase in molecular weight; therefore, the alkylated phenyl group is preferably bonded to only one of the second and third benzene rings.

When the second benzene ring and/or the third benzene ring include an alkylated phenyl group, the number of alkyl groups in the aromatic group includes the number of alkyl groups bonded to the phenyl group.

As long as a benzene ring, an alkyl group, or nitrogen of amine is bonded to each of the first and third positions of at least two of the first to third benzene rings, the other benzene ring may have a substituent at a carbon atom of any position.

In this manner, the first positions and the third positions of at least two of the first to third benzene rings are preferably bonded to another benzene ring, a benzene ring of an alkylated phenyl group, an alkyl group, or nitrogen of amine, in which case the refractive index is lowered.

In order to lower the refractive index, the first positions and the third positions of all of the first to third benzene rings and the benzene ring of the alkylated phenyl group are preferably bonded to another benzene ring, an alkyl group (e.g., any of the above at least three alkyl groups), or nitrogen of amine. In order to shorten the conjugation, it is preferable that carbon atoms in the first positions, the third positions, and the fifth positions of all of the first to third benzene rings and the benzene ring of the alkylated phenyl group be bonded to another benzene ring, an alkyl group (e.g., any of the above at least three alkyl groups), or nitrogen of amine and the other carbon atoms be unsubstituted. Extension of the conjugation of the benzene rings might cause a harmful effect on a light-emitting device, such as absorption of light in the visible region.

In the case where the second benzene ring and/or the third benzene ring have (has) an alkylated phenyl group, it is preferable that the phenyl group have an alkyl group at each of the two meta positions, and it is further preferable that the phenyl group have an alkyl group at each of the two meta positions and the ortho and para positions be unsubstituted.

The first benzene ring preferably further includes a substituted or unsubstituted phenyl group, and further preferably includes an unsubstituted phenyl group, in which case shielding of nitrogen of amine can be prevented. In that case, the substituted or unsubstituted phenyl group is preferably bonded to the ortho position of the first benzene ring, in which case the carrier-transport property is improved. In the case where the substituted or unsubstituted phenyl group has a substituent, the substituent is an alkyl group.

The arylamine compound preferably includes a second aromatic group in order to improve the hole-transport property. The second aromatic group is preferably a substituted or unsubstituted monocyclic ring or a substituted or unsubstituted condensed ring skeleton composed of three or less rings in order to improve the hole-transport property. This enables the refractive index to be kept low because the refractive index tends to increase with an increase in the number of rings of the condensed ring skeleton. In addition, the substituted or unsubstituted monocyclic ring or the substituted or unsubstituted condensed ring skeleton composed of three or less rings can reduce the influence of absorption and emission of light because an increase in the number of rings of the condensed ring skeleton makes absorption and emission of light in the visible region observable. Note that the number of carbon atoms forming the condensed ring skeleton as the second aromatic group is preferably 6 to 13 in order to keep the refractive index low. Specific examples of the aromatic group that can be used as the second aromatic group include a benzene ring, a naphthalene ring, a fluorene ring, and an acenaphthylene ring. In particular, the second aromatic group preferably includes a fluorene ring and further preferably is a fluorene ring, in which case favorable hole-transport property can be obtained. Note that the second aromatic group is further preferably a dimethylfluorenyl group, in which case the durability of the material can be increased. In particular, it is preferable that the dimethyl fluorenyl group do not have any other substituents, in which case the hole-transport property can be maintained. It is preferable that the second aromatic group be directly bonded to nitrogen of amine in the arylamine compound, which contributes to a shallower HOMO level of the molecule and thus facilitates hole transfer.

The above-described alkyl group preferably has 1 to 6 carbon atoms. In terms of lowering the refractive index, a chain alkyl group having two or more carbon atoms is preferred; in terms of ensuring the carrier-transport property, a chain alkyl group having or less carbon atoms is preferred. A chain alkyl group having a branch formed of 3 or more carbon atoms is significantly effective in lowering the refractive index. That is, the alkyl group having 1 to 6 carbon atoms is preferably a chain alkyl group having 2 to carbon atoms, and further preferably a chain alkyl group having a branch formed of 3 to 5 carbon atoms. Examples of the alkyl group having 1 to 6 carbon atoms include a methyl group, an ethyl group, a propyl group, an isopropyl group, a butyl group a sec-butyl group, an isobutyl group, a tert-butyl group, a pentyl group, and a hexyl group. In particular, a tert-butyl group is preferred.

The arylamine compound preferably includes a third aromatic group. A group having 1 to 3 substituted or unsubstituted benzene rings is preferred as the third aromatic group. In the case where the third aromatic group includes two or three benzene rings, the two or three benzene rings are preferably bonded to each other to form a substituent. In other words, the third aromatic group is preferably a phenyl group, a biphenyl group, a terphenyl group, or a naphthylphenyl group. The third aromatic group is preferably a biphenyl group bonded at the ortho position to obtain a favorable hole-transport property. In the case where one or more of the 1 to 3 benzene rings have a substituent, the substituent can be an alkyl group having 1 to 6 carbon atoms or a cycloalkyl group having to 12 carbon atoms, for example. In terms of lowering the refractive index, the alkyl group having 1 to 6 carbon atoms is preferably a chain alkyl group having two or more carbon atoms; in terms of ensuring the carrier-transport property, the alkyl group having 1 to 6 carbon atoms is preferably a chain alkyl group having 5 or less carbon atoms. A chain alkyl group having a branch formed of 3 or more carbon atoms is significantly effective in lowering the refractive index. That is, the alkyl group having 1 to 6 carbon atoms is preferably a chain alkyl group having 2 to 5 carbon atoms, and further preferably a chain alkyl group having a branch formed of 3 to 5 carbon atoms. Examples of the alkyl group having 1 to 6 carbon atoms include a methyl group, an ethyl group, a propyl group, an isopropyl group, a butyl group a sec-butyl group, an isobutyl group, a tert-butyl group, and a pentyl group. In particular, a tert-butyl group is preferred. Note that as the cycloalkyl group having 5 to 12 carbon atoms, a cyclohexyl group, a 4-methylcyclohexyl group, a cycloheptyl group, a cyclooctyl group, a cyclononyl group, a cyclodecyl group, a decahydronaphthyl group, a cycloundecyl group, a cyclododecyl group, or the like can be used. In terms of lowering the refractive index, a cycloalkyl group having 6 or more carbon atoms is preferred, and in particular, a cyclohexyl group or a cyclododecyl group is preferred.

Note that the arylamine compound of one embodiment of the present invention is preferably a monoamine compound. The arylamine compound of one embodiment of the present invention is preferably a triarylamine compound in view of the hole-transport property.

The arylamine compound of one embodiment of the present invention with the above-described structure can have a significantly low refractive index. The refractive index with respect to ordinary light in the entire wavelength region from 455 nm to 465 nm is greater than or equal to 1.5 and less than or equal to 1.75, and the refractive index with respect to ordinary light with a wavelength of 633 nm is greater than or equal to 1.45 and less than or equal to 1.70. In the case where the material has an anisotropy, the ordinary refractive index and the extraordinary refractive index are different from each other in some cases. When a thin film to be measured is in such a state, anisotropy analysis can be performed to separately calculate the ordinary refractive index and the extraordinary refractive index. In this specification, when the measured material has both the ordinary refractive index and the extraordinary refractive index, the ordinary refractive index is used as an indicator.

The arylamine compound of one embodiment of the present invention with the above-described structure can achieve high heat resistance at a glass transition temperature of 100° C. or higher. In a further preferable embodiment of the present invention, the glass transition temperature can be 110° C. or higher, further preferably 120° C. or higher.

Since film formation by an evaporation method easily enables a low refractive index and high heat resistance as described above, the molecular weight is preferably greater than or equal to 400 and less than or equal to 1100.

The arylamine compound having the above-described structure is an organic compound with a hole-transport property and a low refractive index, and thus can be suitably used as a material for a hole-transport layer or a hole-injection layer of an organic EL device. Furthermore, an organic EL device using the material for a hole-transport layer or a hole-injection layer has a hole-transport layer or a hole-injection layer with a low refractive index, and thus can be a light-emitting device having high emission efficiency, i.e., high external quantum efficiency, high current efficiency, and a high blue index. Furthermore, the organic EL device using the material for a hole-transport layer or a hole-injection layer preferably uses the arylamine compound as the material for the hole-transport layer or the hole-injection layer. The number of aromatic groups bonded to the saturated hydrocarbon group is limited, the steric repulsion can be reduced to improve the stability of the molecule, so that the organic EL device can be a light-emitting device having a long lifetime.

It is particularly preferable that the arylamine compound be an organic compound represented by the following General Formula (G1).

[Chemical Formula 4]

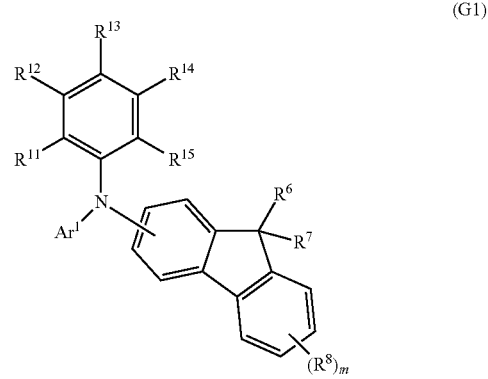

(G1)

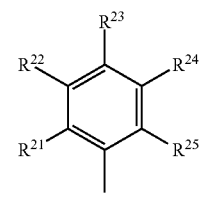

(g1)

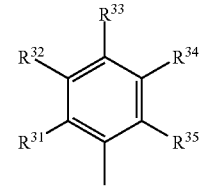

(g2)

In General Formula (G1), $Ar^1$ represents a substituted or unsubstituted benzene ring or a substituent in which two or three substituted or unsubstituted benzene rings are bonded to one another. Specific examples of $Ar^1$ include a phenyl group, a biphenyl group, a terphenyl group, and a naphthylphenyl group. A phenyl group is particularly preferable in order to lower the refractive index and maintain the hole-transport property of the nitrogen atom.

One of $R^{11}$ to $R^{15}$ represents a substituent represented by General Formula (g1), and each of the others independently represents any one of hydrogen, an alkyl group having 1 to 6 carbon atoms, and a substituted or unsubstituted phenyl group. The substituted or unsubstituted phenyl group is preferably an unsubstituted phenyl group, and, when being a substituted phenyl group, has 1 to 6 carbon atoms.

In General Formula (g1), one of $R^{21}$ to $R^{25}$ represents a substituent represented by General Formula (g2), and each of the others independently represents any one of hydrogen, an alkyl group having 1 to 6 carbon atoms, and a phenyl group substituted with an alkyl group having 1 to 6 carbon atoms.

In General Formula (g2), each of $R^{31}$ to $R^{35}$ independently represents any one of hydrogen, an alkyl group having 1 to 6 carbon atoms, and a phenyl group substituted with an alkyl group having 1 to 6 carbon atoms.

At least three of $R^{11}$ to $R^{15}$, $R^{21}$ to $R^{25}$, and $R^{31}$ to $R^{35}$ each represent an alkyl group having 1 to 6 carbon atoms. Thus, the arylamine compound represented by General Formula (G1) can have a low refractive index.

The number of substituted or unsubstituted phenyl groups in $R^{11}$ to $R^{15}$ is less than or equal to 1.

The number of phenyl groups substituted with an alkyl group having 1 to 6 carbon atoms in $R^{21}$ to $R^{25}$ and $R^{31}$ to $R^{35}$ is less than or equal to 1, that is, 1 or 0.

In at least two combinations of the three combinations $R^{12}$ and $R^{14}$, $R^{22}$ and $R^{24}$, and $R^{32}$ and $R^{34}$, at least one R represents any of the substituents other than hydrogen. In other words, in each of two or more benzene rings selected from a benzene ring including $R^{12}$ and $R^{14}$, a benzene ring including $R^{22}$ and $R^{24}$, and a benzene ring including $R^{32}$ and $R^{34}$, at least one of the carbon atoms at the meta positions is not hydrogen, that is, has a substituent. At this time, it is preferable that at least one of $R^{12}$, $R^{14}$, $R^{22}$, and $R^{24}$ be any of the substituents other than hydrogen and at least one of $R^{32}$ and $R^{34}$ be any of the substituents other than hydrogen.

Each of $R^6$, $R^7$, and $R^8$ independently represents an alkyl group having 1 to 4 carbon atoms, and in represents an integer of 0 to 4. Note that in the case where in is an integer of 2 or more, a plurality of $R^8$ may be the same or different.

Specifically, as examples of the alkyl group having 1 to 4 carbon atoms, a methyl group, an ethyl group, a propyl group, an isopropyl group, a butyl group, a sec-butyl group, and an isobutyl group are given, and particularly, a tert-butyl group is preferred.

In the case where the substituted or unsubstituted benzene ring or the substituted or unsubstituted phenyl group have a substituent, the substituent can be an alkyl group having 1 to 6 carbon atoms or a cycloalkyl group having 5 to 12 carbon atoms.

In terms of lowering the refractive index, the alkyl group having 1 to 6 carbon atoms is preferably a chain alkyl group having 2 or more carbon atoms; in terms of ensuring the carrier-transport property, the alkyl group having 1 to 6 carbon atoms is preferably a chain alkyl group having 5 or less carbon atoms. A chain alkyl group having a branch formed of 3 or more carbon atoms is significantly effective in lowering the refractive index. That is, the alkyl group having 1 to 6 carbon atoms is preferably a chain alkyl group having 2 to 5 carbon atoms, and further preferably a chain alkyl group having a branch formed of 3 to 5 carbon atoms. Specific examples of the alkyl group having 1 to 6 carbon atoms include a methyl group, an ethyl group, a propyl group, an isopropyl group, a butyl group a sec-butyl group, an isobutyl group, a tert-butyl group, a pentyl group, and a hexyl group. In particular, a tert-butyl group is preferred.

Note that as the cycloalkyl group having 5 to 12 carbon atoms, specifically, a cyclohexyl group, a 4-methylcyclohexyl group, a cycloheptyl group, a cyclooctyl group, a cyclononyl group, a cyclodecyl group, a decahydronaphthyl group, a cycloundecyl group, a cyclododecyl group, or the like can be used. In terms of lowering the refractive index, a cycloalkyl group having 6 or more carbon atoms is preferred, and in particular, a cyclohexyl group or a cyclododecyl group is preferred.

In General Formula (G1), $Ar^1$ is preferably a substituent in which two or three substituted or unsubstituted benzene rings are bonded to one another. In other words, an arylamine compound represented by General Formula (G2) is preferred.

[Chemical Formula 5]

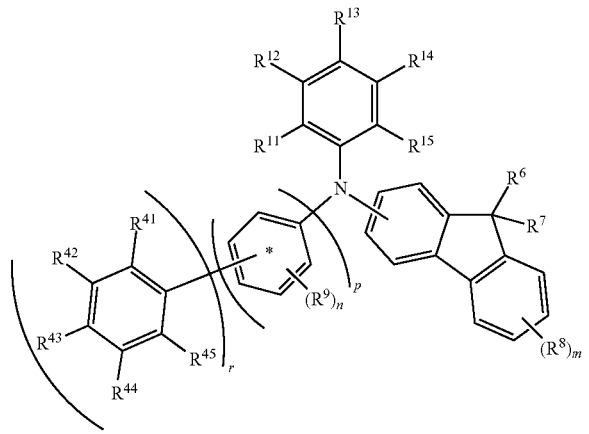

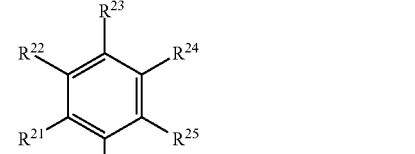

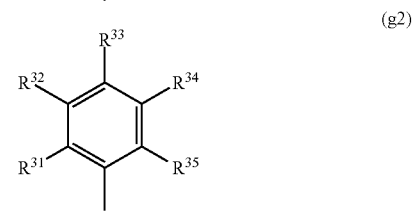

In General Formula (G2), each of p and r independently represents 1 or 2 and p+r represents 2 or 3. When p is 2, kinds and numbers of substituents and positions of bonds included in two phenylene groups may be the same or different; when r is 2, kinds and numbers of substituents and positions of bonds included in two phenyl groups may be the same or different. It is preferable that p represent 1 and r represent 1.

Each of $R^{41}$ to $R^{45}$ independently represents any one of hydrogen, an alkyl group having 1 to 6 carbon atoms, and a cycloalkyl group having 5 to 12 carbon atoms.

Furthermore, $R^9$ represents an alkyl group having 1 to 4 carbon atoms, and n represents an integer of 0 to 4. When n is 2 or larger, a plurality of $R^9$ may be the same or different. Note that n preferably represents 0.

Specifically, as examples of the alkyl group having 1 to 4 carbon atoms, a methyl group, an ethyl group, a propyl group, an isopropyl group, a butyl group, a sec-butyl group, an isobutyl group, and a tert-butyl group are given, and particularly, a tert-butyl group is preferred.

In terms of lowering the refractive index, the alkyl group having 1 to 6 carbon atoms is preferably a chain alkyl group having 2 or more carbon atoms; in terms of ensuring the carrier-transport property, the alkyl group having 1 to 6 carbon atoms is preferably a chain alkyl group having 5 or less carbon atoms. A chain alkyl group having a branch formed of 3 or more carbon atoms is significantly effective in lowering the refractive index. That is, the alkyl group having 1 to 6 carbon atoms is preferably a chain alkyl group having 2 to 5 carbon atoms, and further preferably a chain alkyl group having a branch formed of 3 to 5 carbon atoms. Specific examples of the alkyl group having 1 to 6 carbon atoms include a methyl group, an ethyl group, a propyl group, an isopropyl group, a butyl group a sec-butyl group, an isobutyl group, a tert-butyl group, a pentyl group, and a hexyl group. In particular, a tert-butyl group is preferred.

Note that as the cycloalkyl group having 5 to 12 carbon atoms, specifically, a cyclohexyl group, a 4-methylcyclohexyl group, a cycloheptyl group, a cyclooctyl group, a cyclononyl group, a cyclodecyl group, a decahydronaphthyl group, a cycloundecyl group, a cyclododecyl group, or the like can be used. In terms of lowering the refractive index, a cycloalkyl group having 6 or more carbon atoms is preferred, and in particular, a cyclohexyl group or a cyclododecyl group is preferred.

Note that description of $R^6$, $R^7$, $R^{11}$ to $R^{15}$, $R^{21}$ to $R^{25}$, $R^{31}$ to $R^{35}$, and m is the same as that in General Formula (G1) and thus omitted.

In General Formula (G1), $Ar^1$ is preferably a substituted or unsubstituted benzene ring. In other words, an arylamine compound represented by General Formula (G3) is preferred.

[Chemical Formula 6]

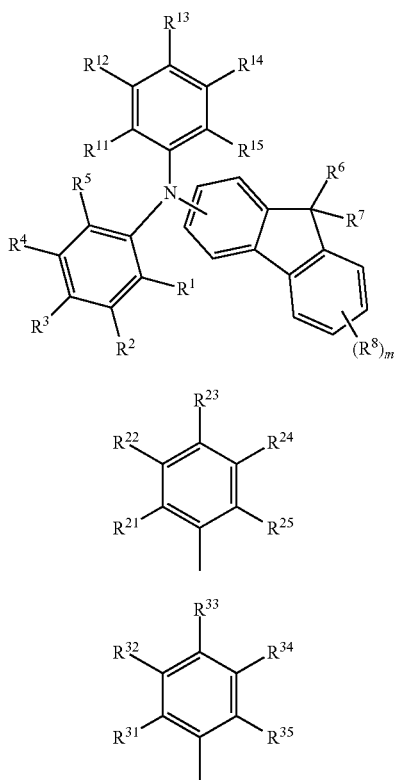

(G3)

(g1)

(g2)

In General Formula (G3), each of $R^1$ to $R^5$ independently represents any one of hydrogen, an alkyl group having 1 to 6 carbon atoms, a cycloalkyl group having 5 to 12 carbon atoms, and a substituted or unsubstituted phenyl group.

In General Formula (G3), it is preferable that $R^3$ represent a cyclohexyl group and each of $R^1$, $R^2$, $R^4$, and $R^5$ represent hydrogen. Alternatively, it is preferable that $R^1$ represent an unsubstituted phenyl group and each of $R^2$, $R^3$, $R^4$, and $R^5$ represent hydrogen, in which case the hole-transport property is improved.

In the case where the substituted or unsubstituted phenyl group has a substituent, the substituent can be an alkyl group having 1 to 6 carbon atoms or a cycloalkyl group having 5 to 12 carbon atoms.

In terms of lowering the refractive index, the alkyl group having 1 to 6 carbon atoms is preferably a chain alkyl group having 2 or more carbon atoms; in terms of ensuring the carrier-transport property, the alkyl group having 1 to 6 carbon atoms is preferably a chain alkyl group having 5 or less carbon atoms. A chain alkyl group having a branch formed of 3 or more carbon atoms is significantly effective in lowering the refractive index. That is, the alkyl group having 1 to 6 carbon atoms is preferably a chain alkyl group having 2 to 5 carbon atoms, and further preferably a chain alkyl group having a branch formed of 3 to 5 carbon atoms. Specific examples of the alkyl group having 1 to 6 carbon atoms include a methyl group, an ethyl group, a propyl group, an isopropyl group, a butyl group a sec-butyl group, an isobutyl group, a tert-butyl group, a pentyl group, and a hexyl group. In particular, a tert-butyl group is preferred.

Note that as the cycloalkyl group having 5 to 12 carbon atoms, specifically, a cyclohexyl group, a 4-methylcyclohexyl group, a cycloheptyl group, a cyclooctyl group, a cyclononyl group, a cyclodecyl group, a decahydronaphthyl group, a cycloundecyl group, a cyclododecyl group, or the like can be used. In terms of lowering the refractive index, a cycloalkyl group having 6 or more carbon atoms is preferred, and in particular, a cyclohexyl group or a cyclododecyl group is preferred.

Note that description of $R^6$, $R^7$, $R^{11}$ to $R^{15}$, $R^{21}$ to $R^{25}$, $R^{31}$ to $R^{35}$, and m is the same as that in General Formula (G1) and thus omitted.

In the arylamine compounds represented above by General Formulae (G1) to (G3), m preferably represents 0.

In the arylamine compounds represented above by General Formulae (G1) to (G3), it is preferable that each of $R^{12}$, $R^{14}$, $R^{22}$, $R^{32}$, and $R^{34}$ among $R^{11}$ to $R^{15}$, $R^{21}$ to $R^{25}$, and $R^{31}$ to $R^{35}$ represent any of the substituents other than hydrogen and each of the others among $R^{11}$ to $R^{15}$, $R^{21}$ to $R^{25}$, and $R^{31}$ to $R^{35}$ represent hydrogen. Furthermore, it is preferable that $R^{12}$ represent a substituent represented by General Formula (g1) and $R^{22}$ represent a substituent represented by General Formula (g2). Furthermore, each of $R^{14}$, $R^{32}$, and $R^{34}$ preferably represents a tert-butyl group.

The arylamine compound of one embodiment of the present invention with the above-described structure can have a significantly low refractive index. The refractive index with respect to ordinary light in the entire wavelength region from 455 nm to 465 nm is greater than or equal to 1.5 and less than or equal to 1.75, and the refractive index with respect to ordinary light with a wavelength of 633 nm is greater than or equal to 1.45 and less than or equal to 1.70.

The organic compound of one embodiment of the present invention having the above-described structure is an organic compound with a favorable hole-transport property and a low refractive index, and thus can be suitably used as a material for a hole-transport layer or a hole-injection layer of an organic EL device. Furthermore, an organic EL device using the material for a hole-transport layer or a hole-injection layer has a hole-transport layer or a hole-injection layer with a low refractive index, and thus can be a light-emitting device having high emission efficiency, i.e., high external quantum efficiency, high current efficiency, and a high blue index.

Specific examples of the organic compound having the above-described structure are shown below.

[Chemical Formula 7]

(100)

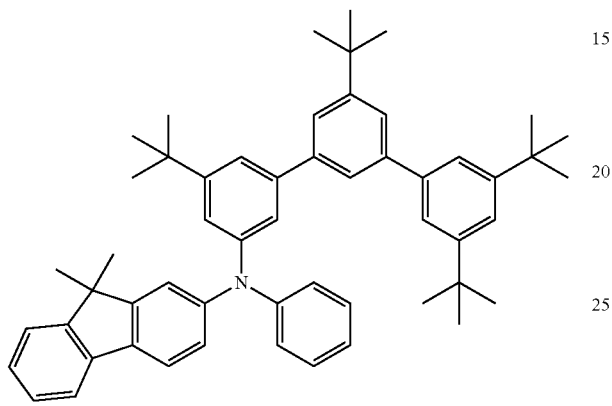

(101)

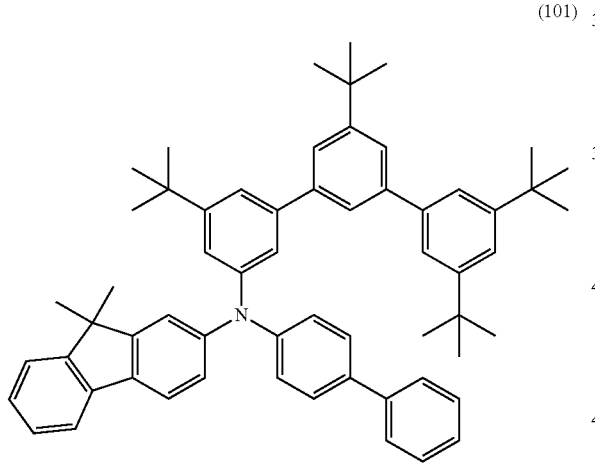

(102)

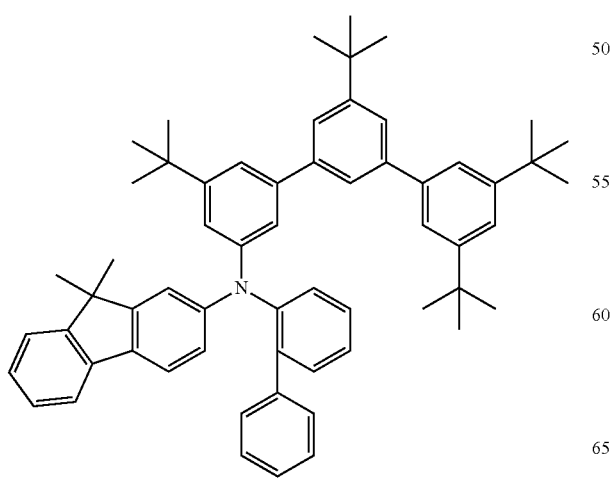

(103)

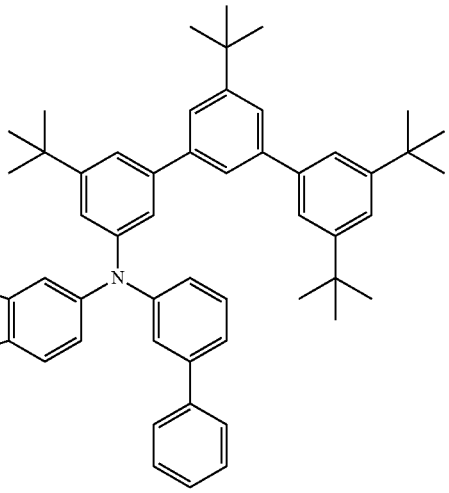

(104)

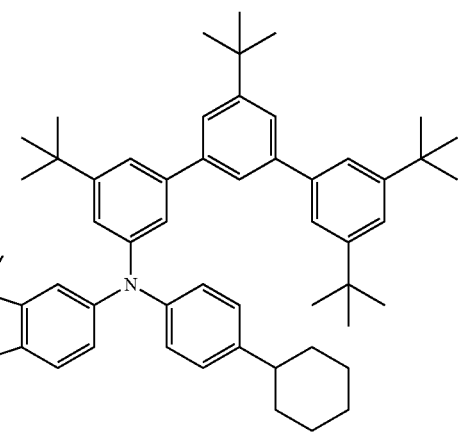

(105)

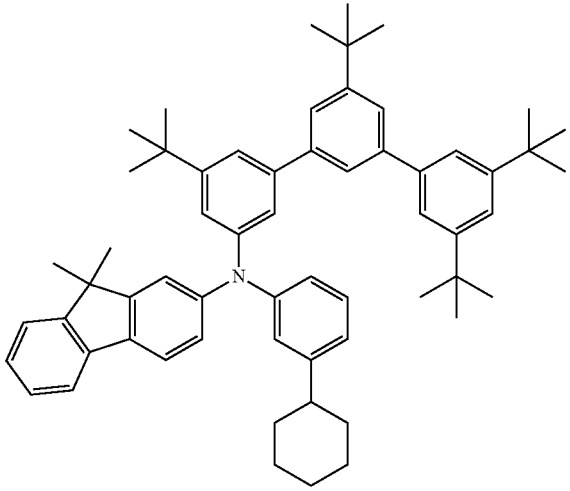

(106)
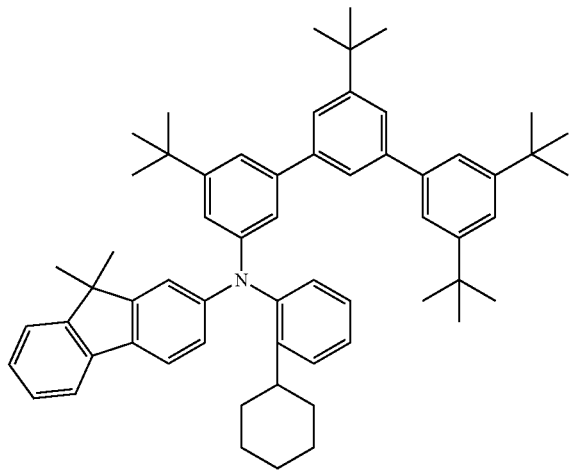
(107)
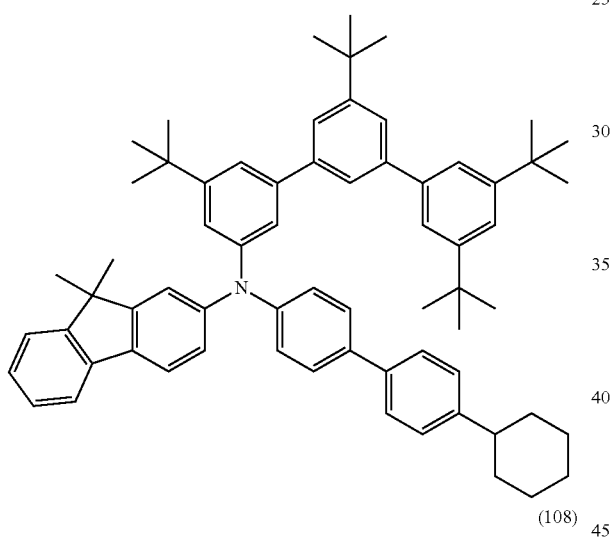
(108)
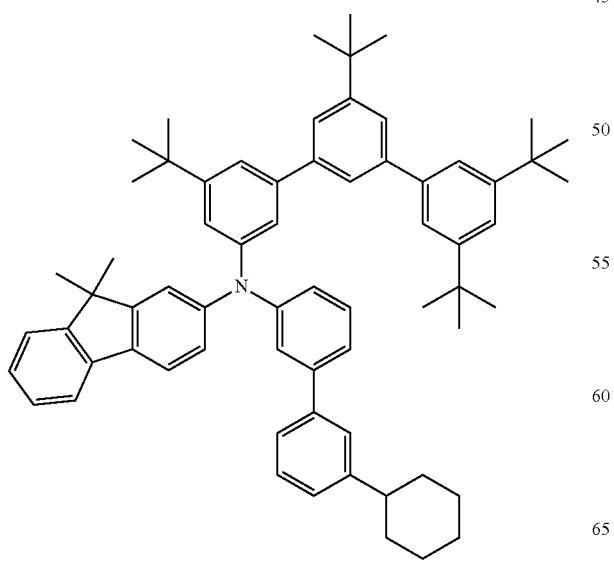
(109)
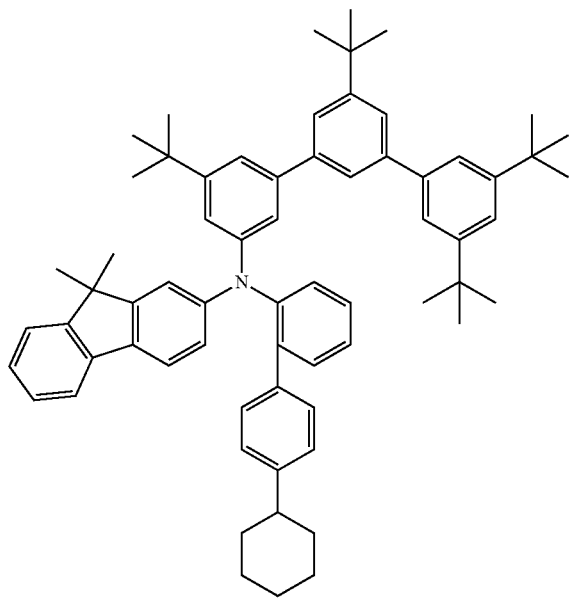
(110)
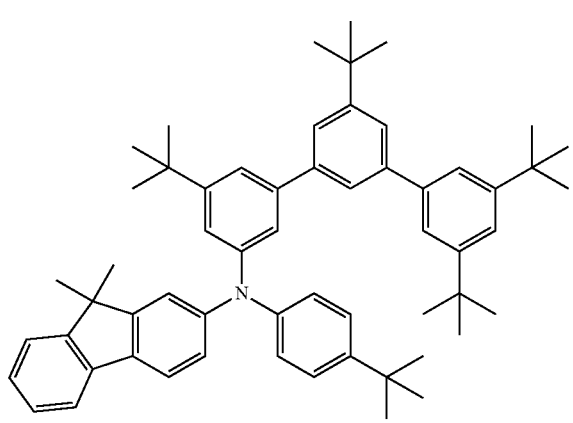
(111)
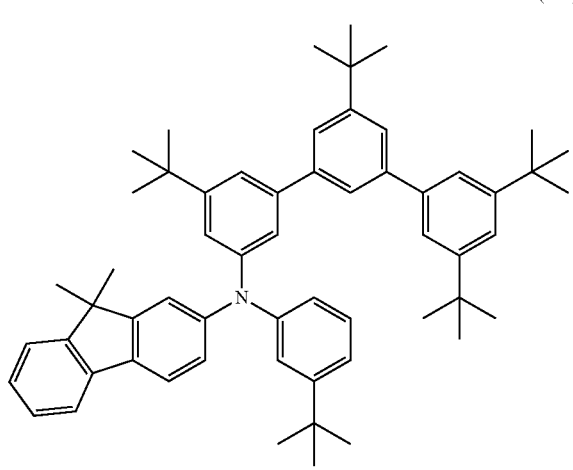

[Chemical Formula 8]
(112)
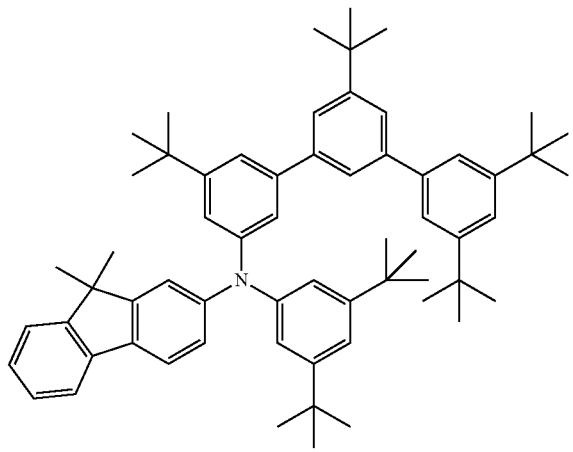
(113)
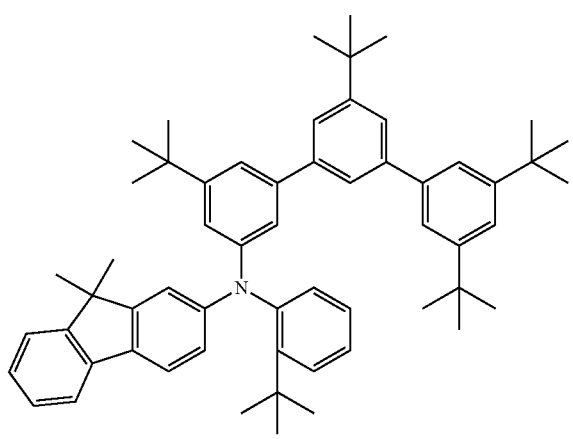
(114)
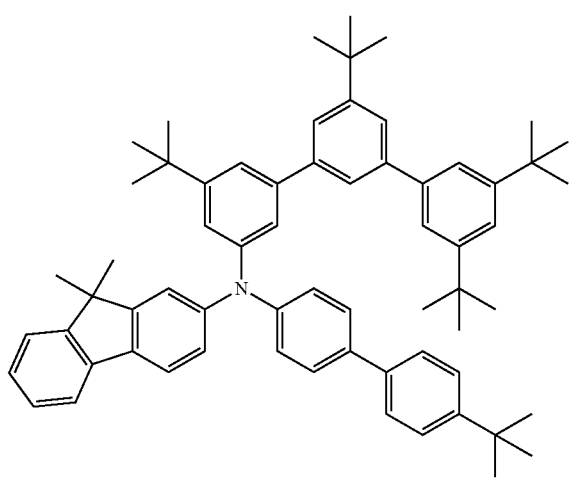
(115)
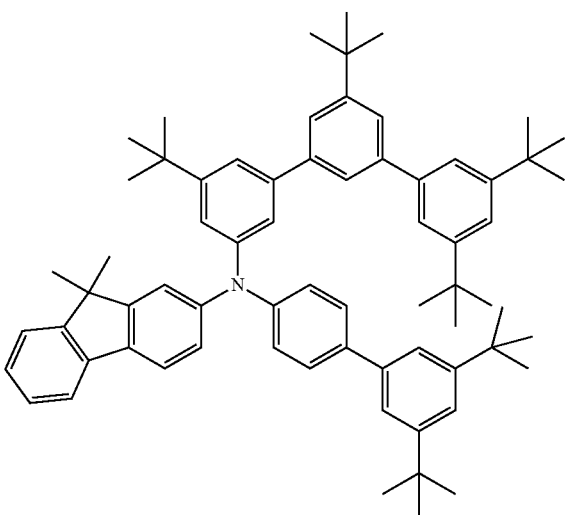
(116)
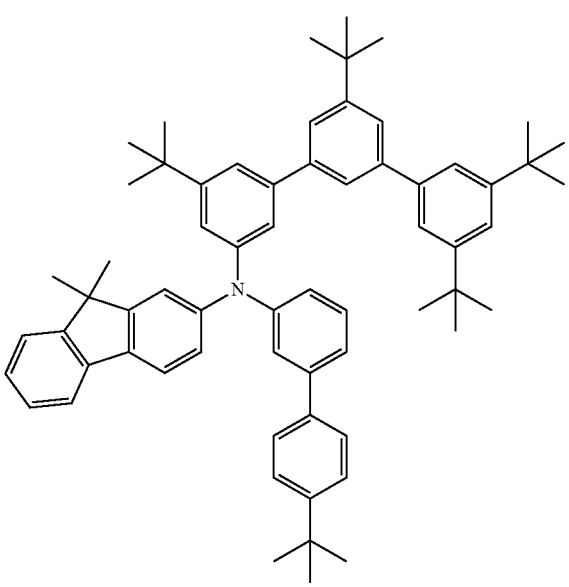
(117)
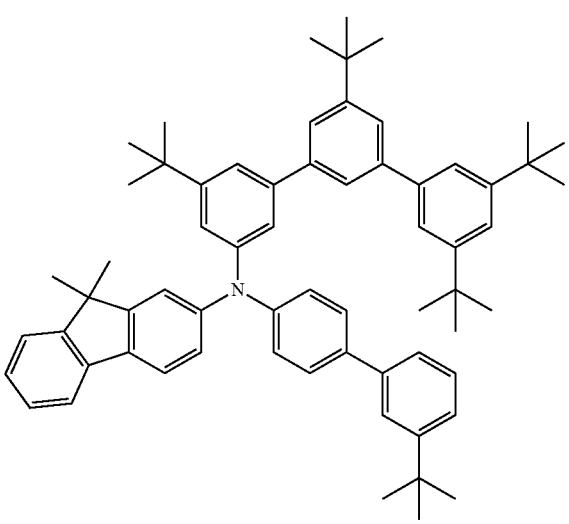

(118)
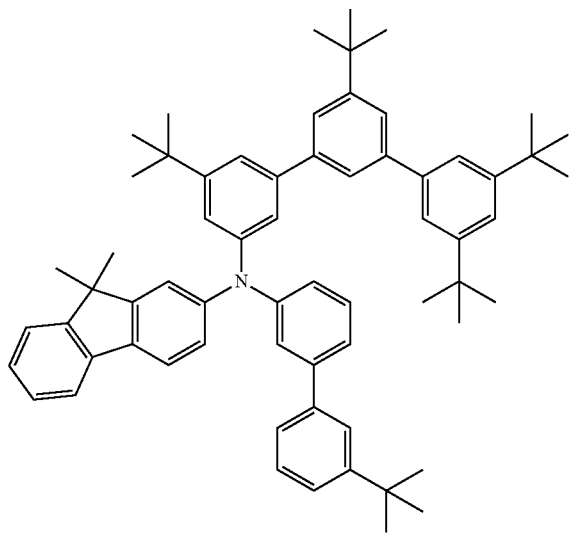
(119)
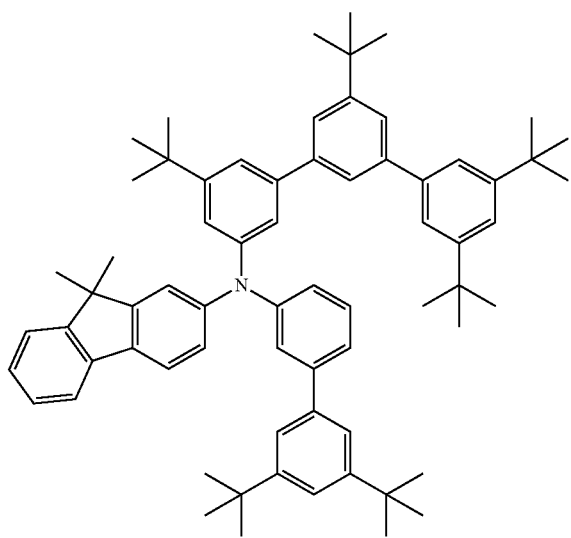
(120)
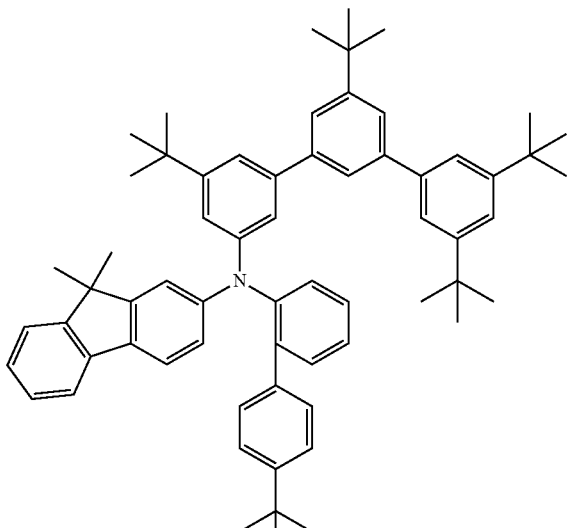
(121)
(122)
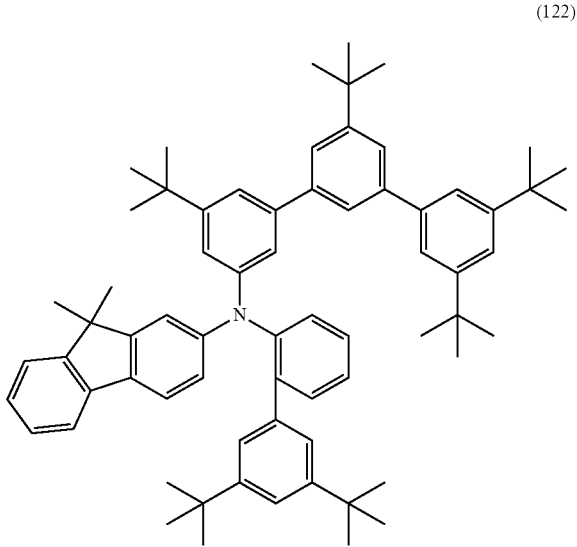

[Chemical Formula 9]
(123) 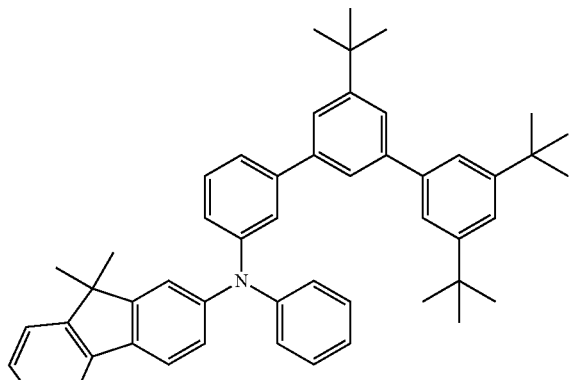
(124) 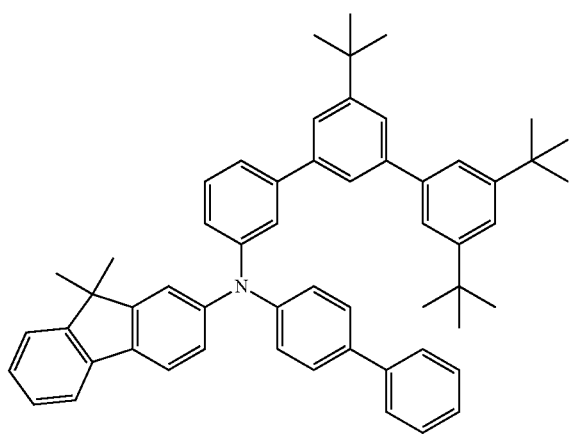
(125) 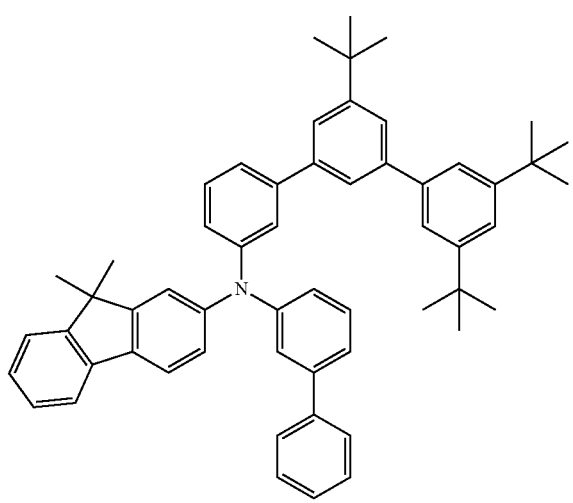
(126) 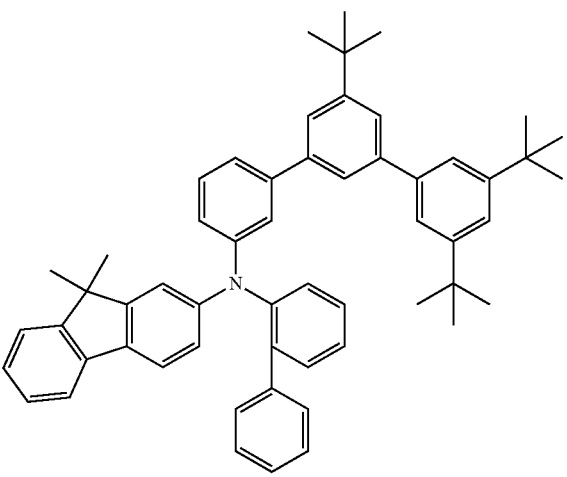
(127) 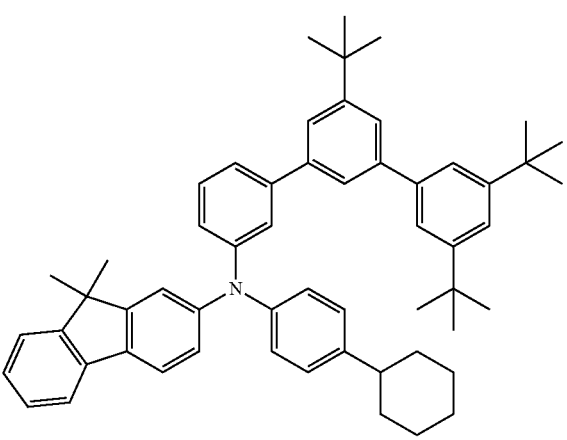
(128) 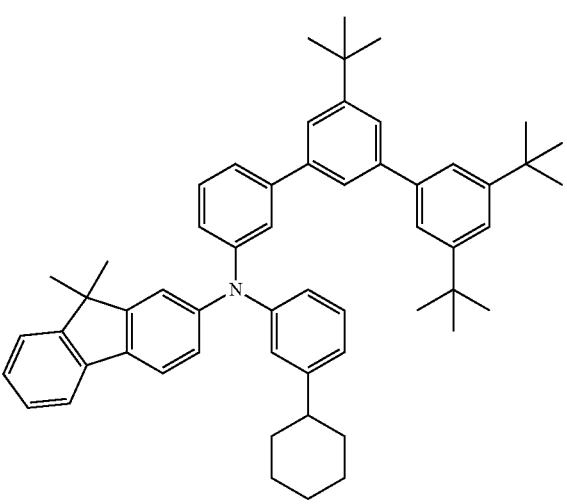

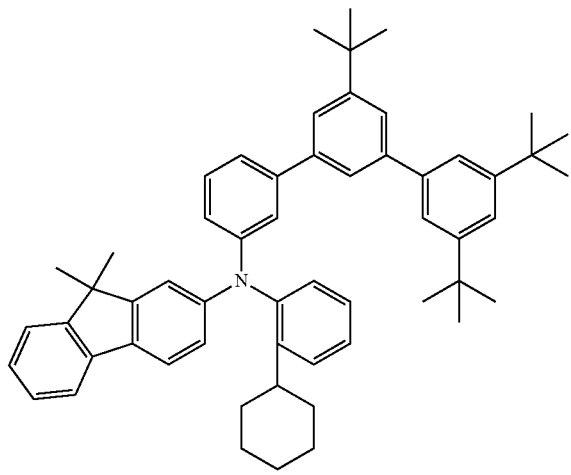
(129)
(130)
(131)
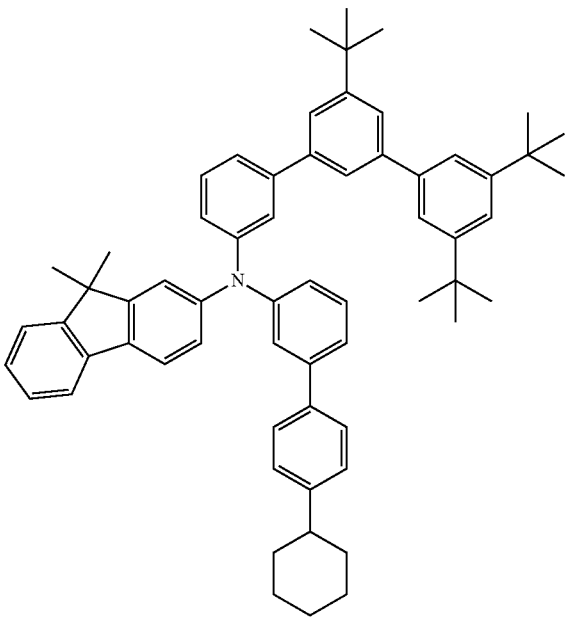
(132)
(133)

(134)
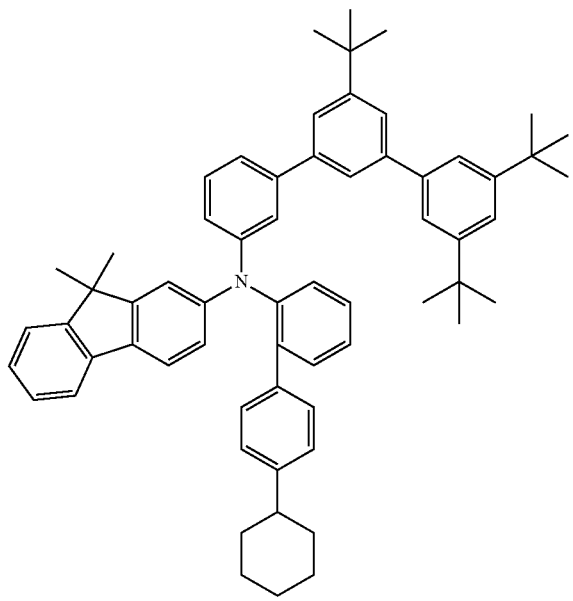
[Chemical Formula 10]
(135)
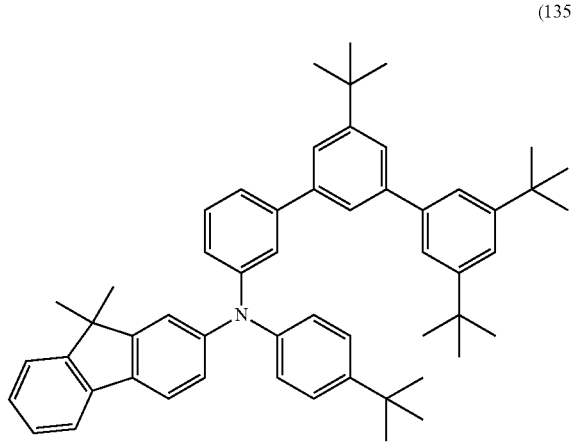
(136)
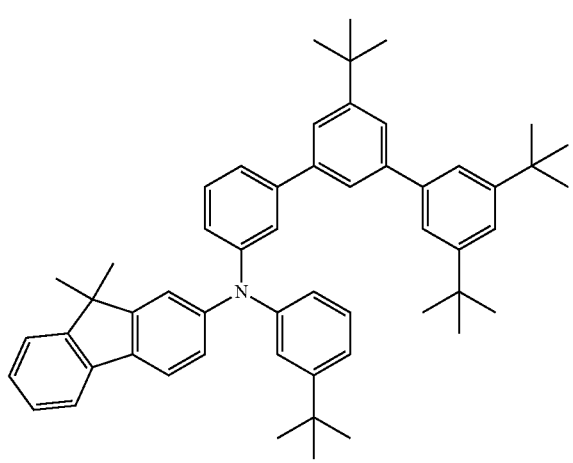
(137)
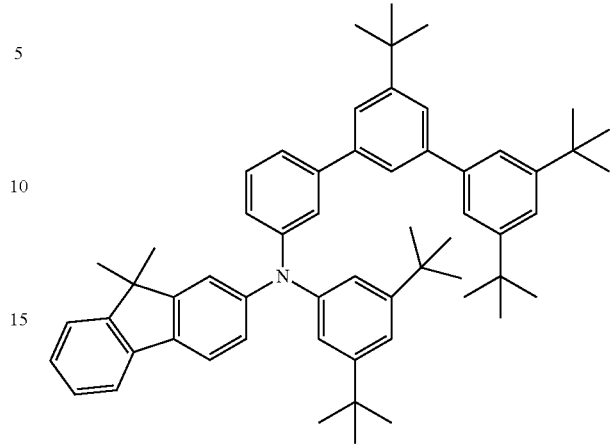
(138)
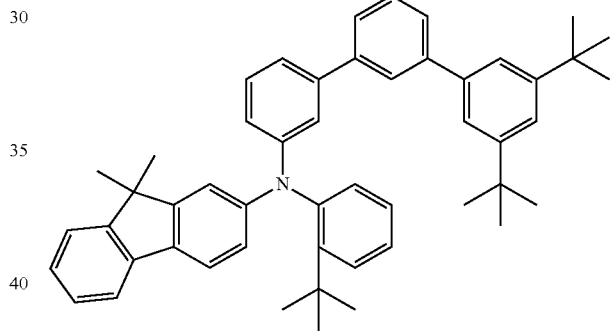
(139)
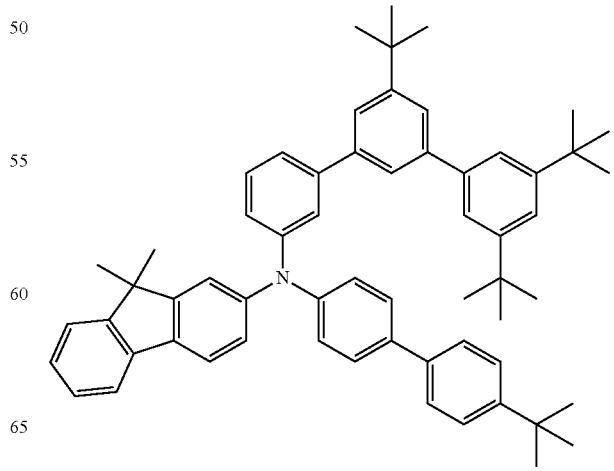

(140)
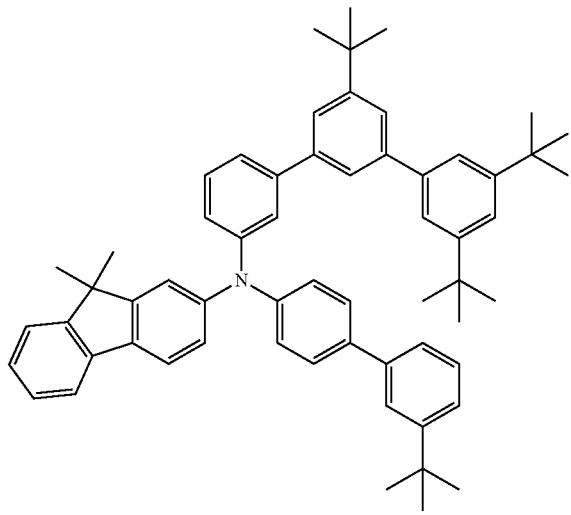
(141)
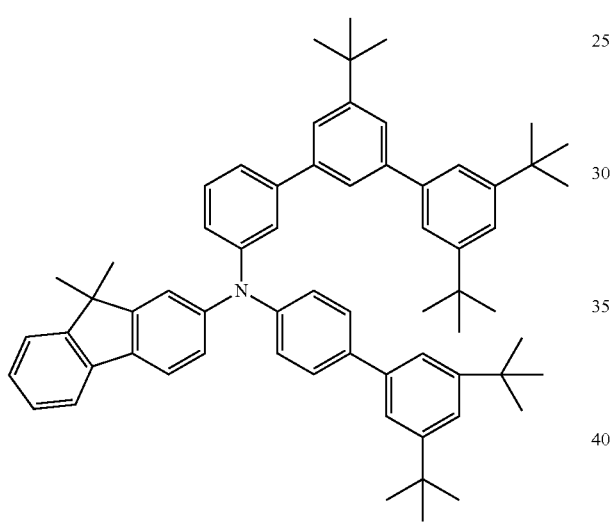
(142)
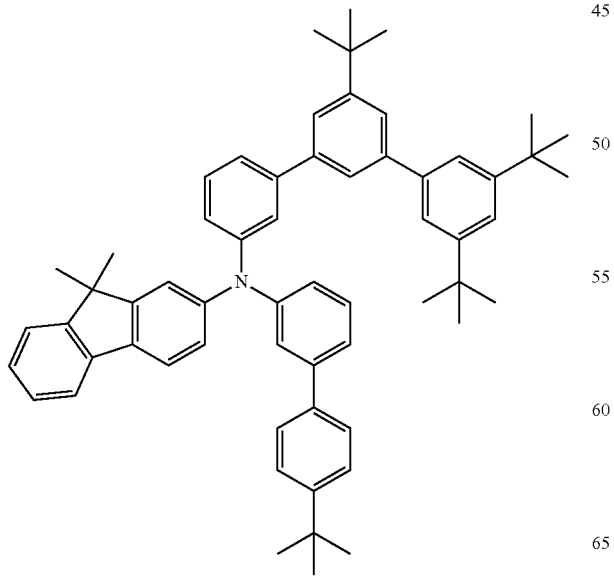
(143)
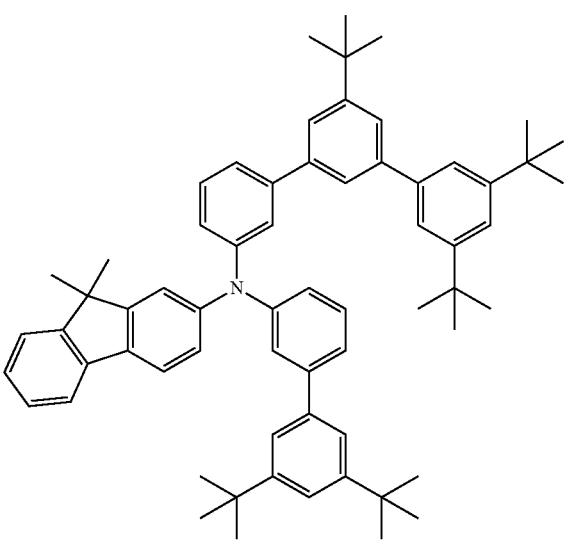
(144)
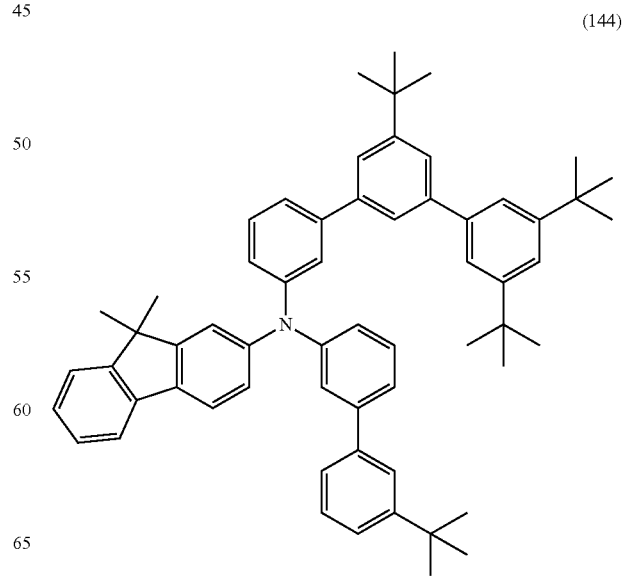

(145)
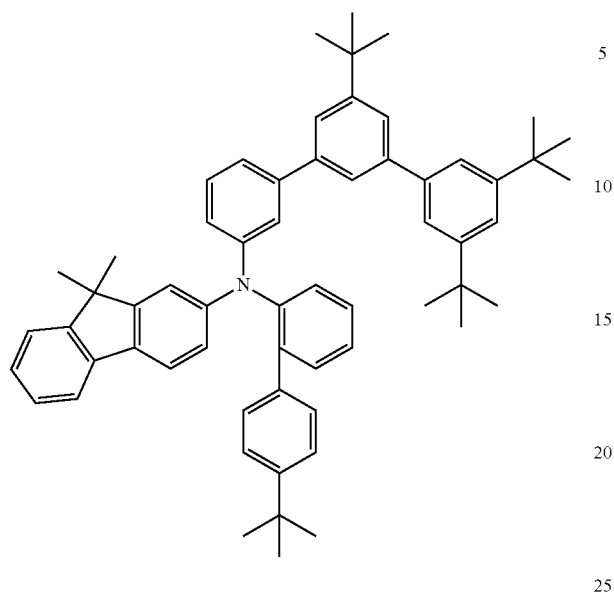
(147)
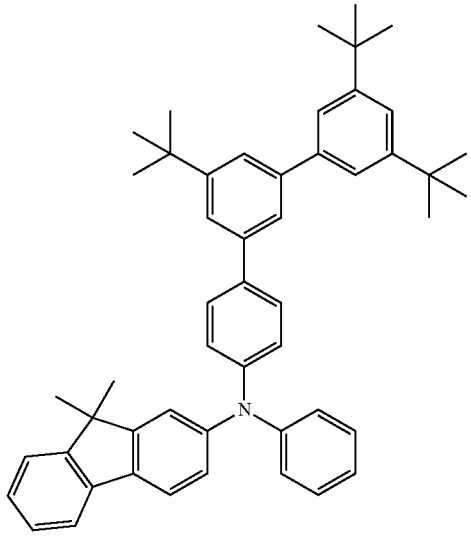
[Chemical Formula 11]
(146)
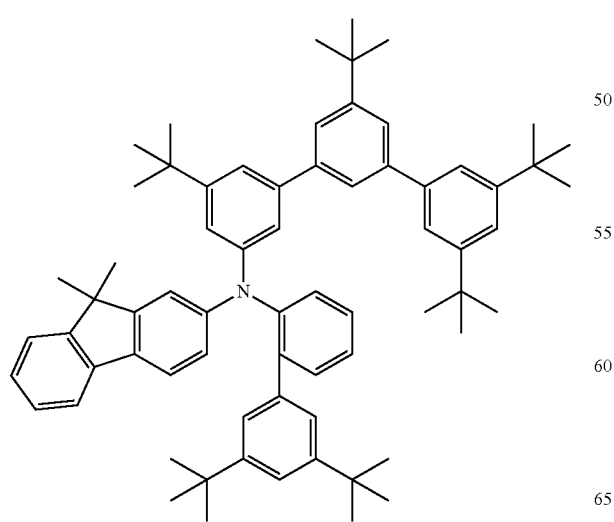
(148)
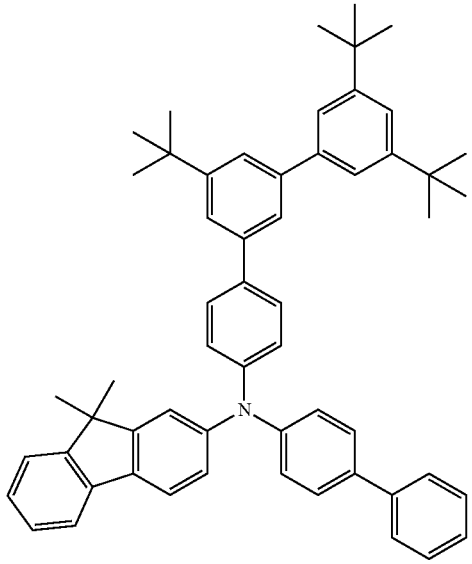

(149)
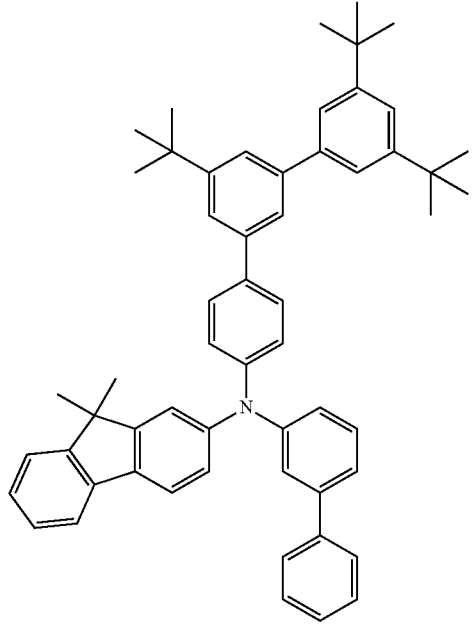
(150)
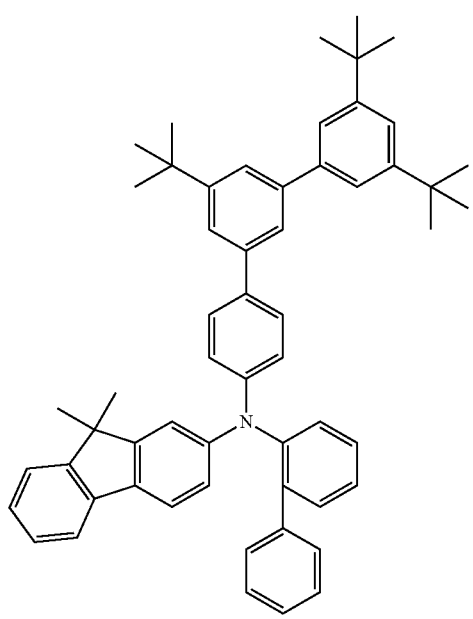
(151)
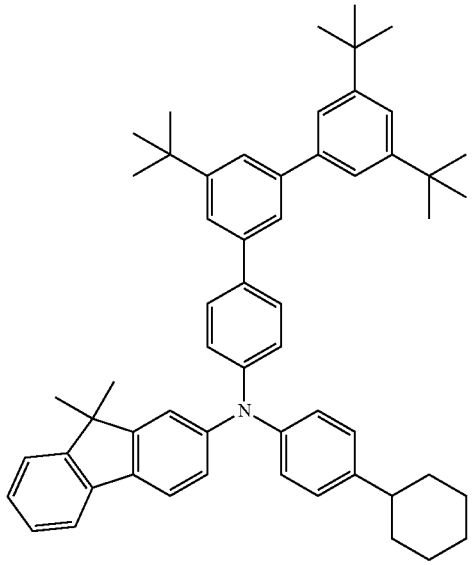
(152)
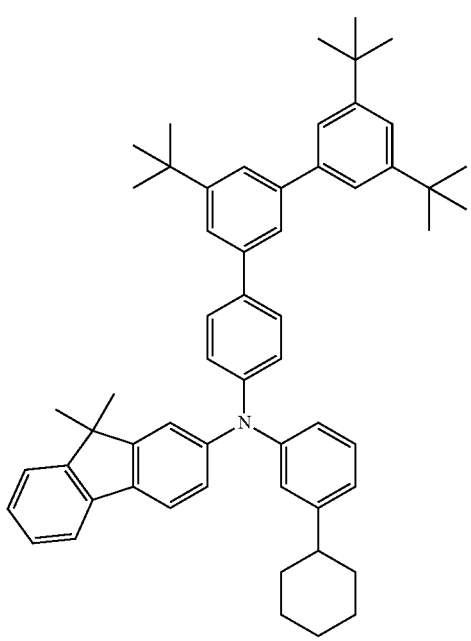

[Chemical Formula 12]
(153)
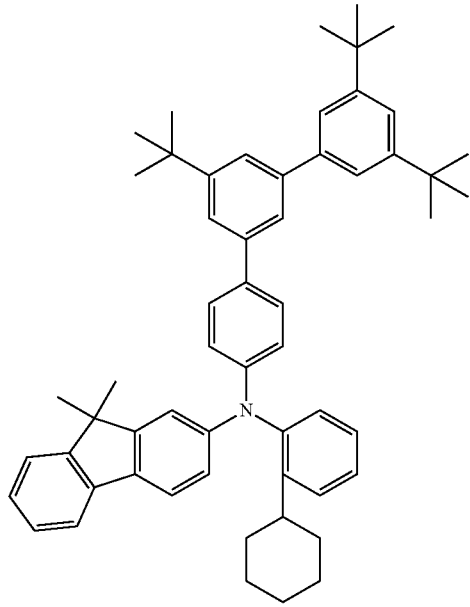
(154)
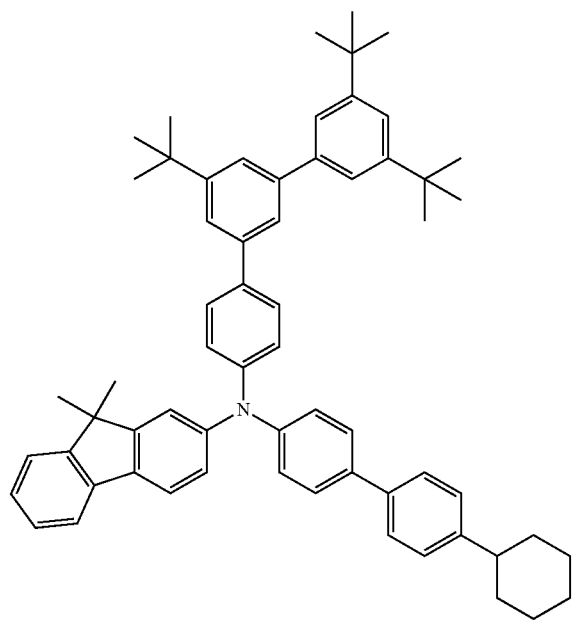
(155)
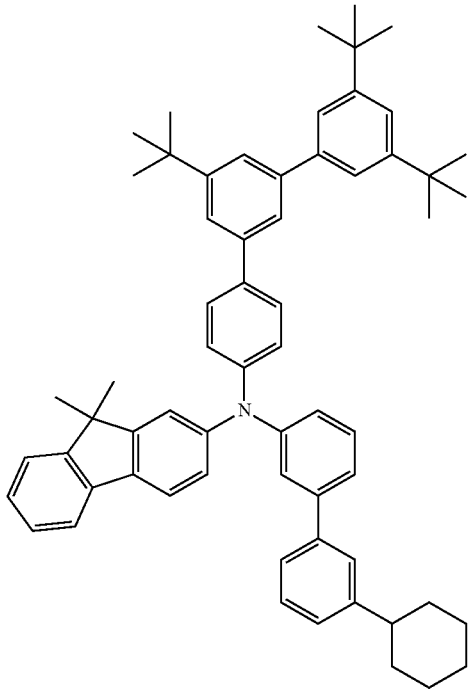
(156)
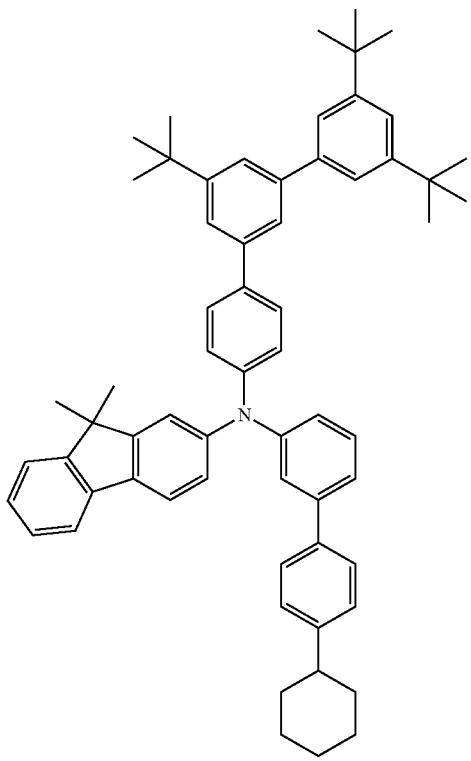

(157)
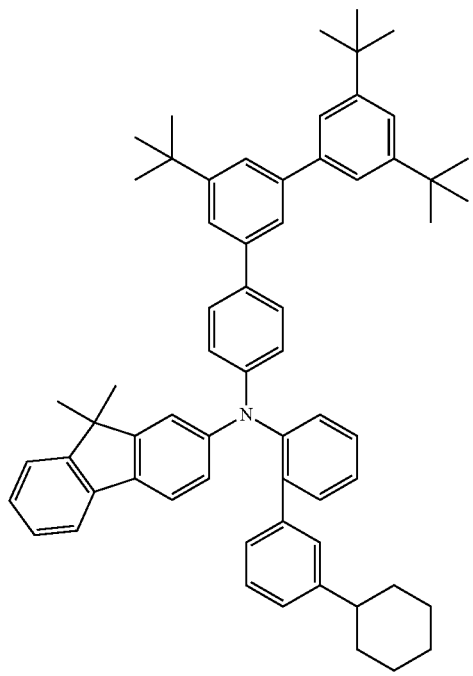
(158)
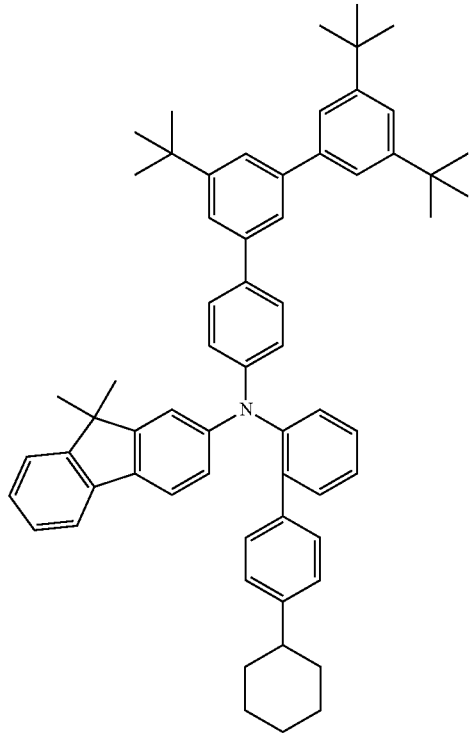
(159)
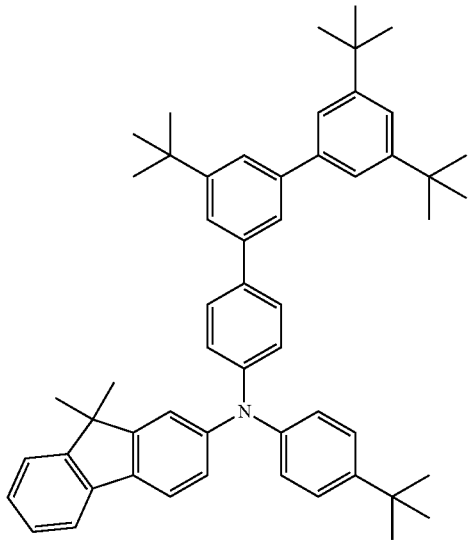
(160)
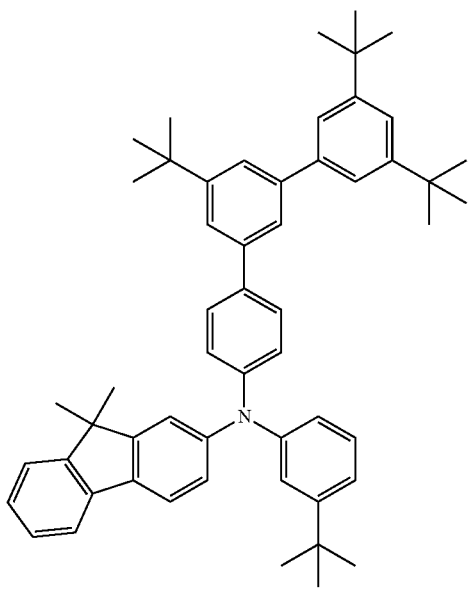

(161)
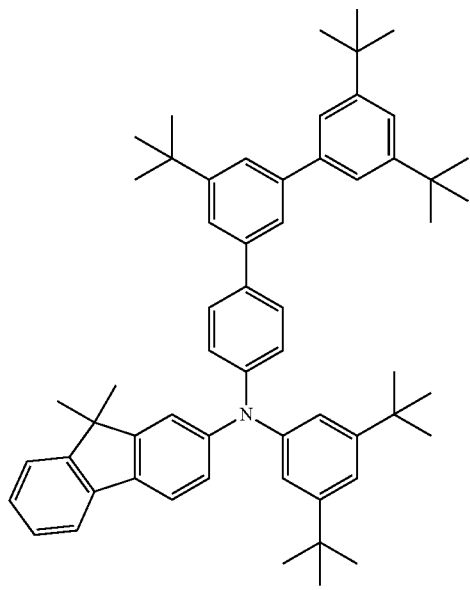
(162)
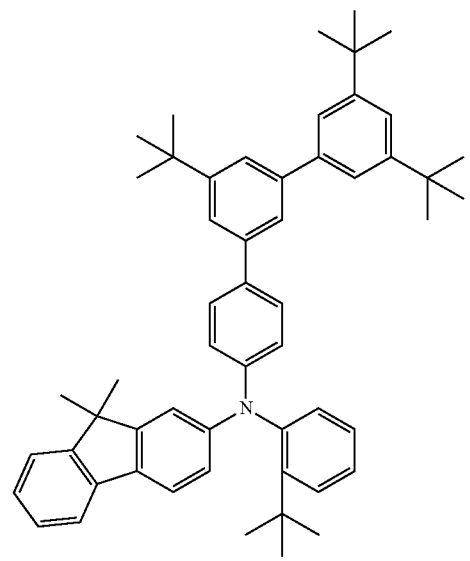
(163)
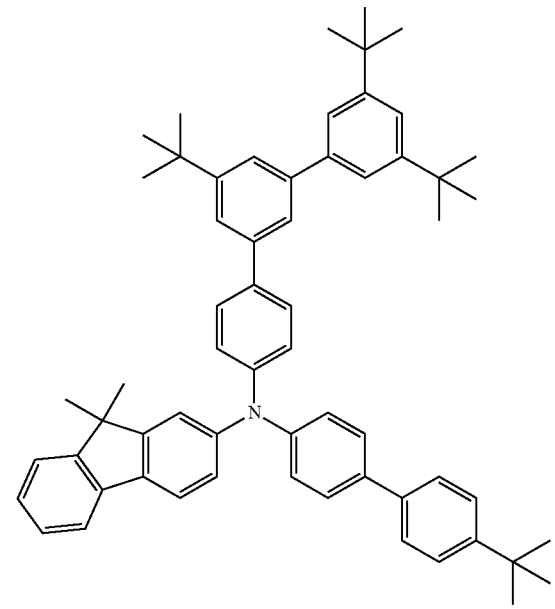
[Chemical Formula 13]
(164)
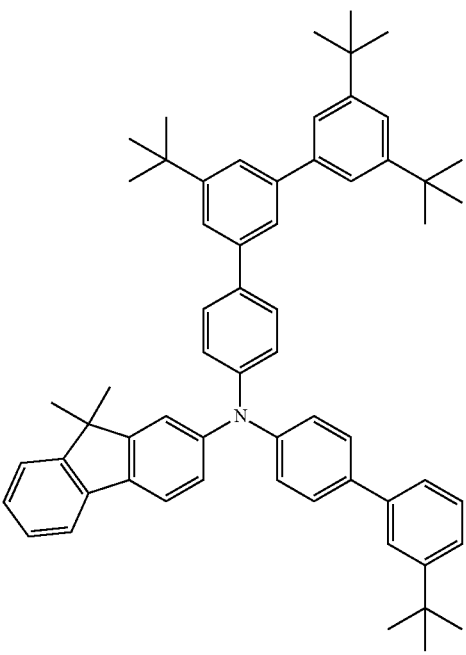

(165)
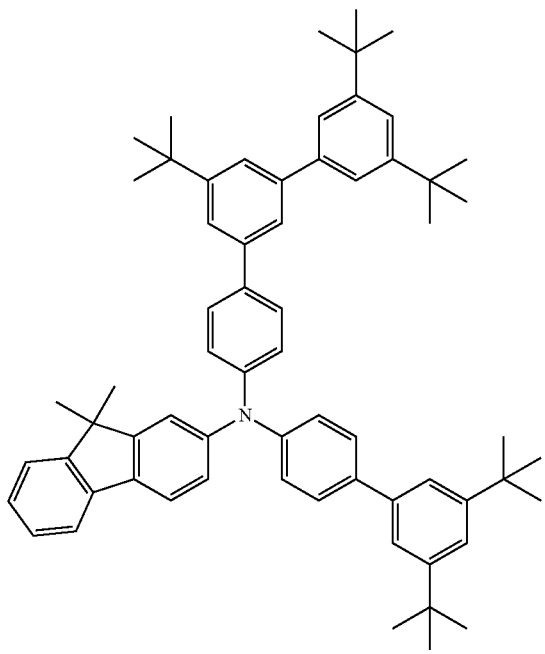
(166)
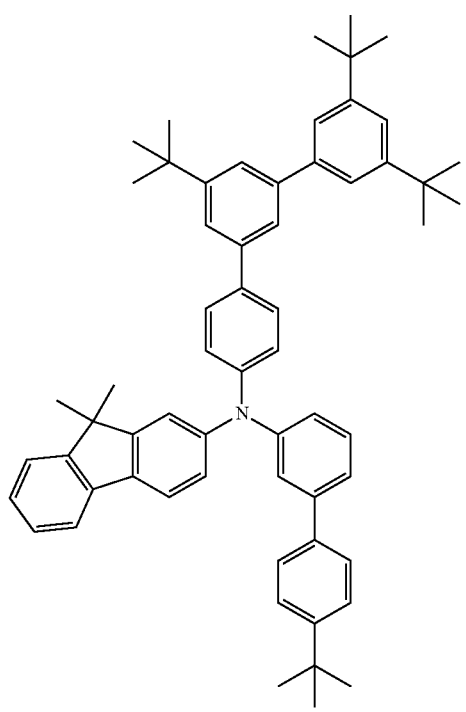
(167)
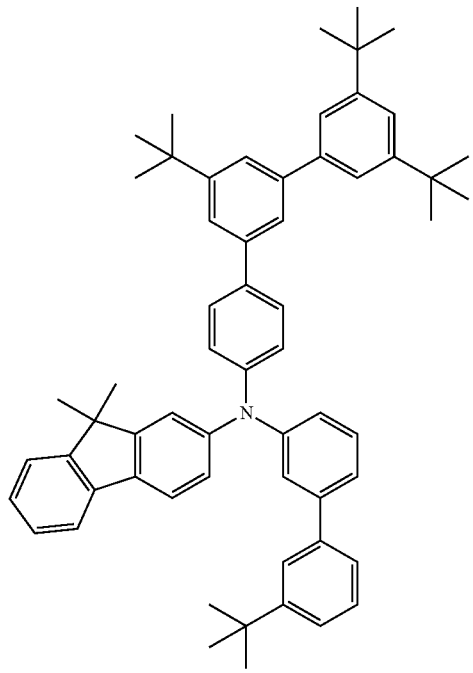
(168)
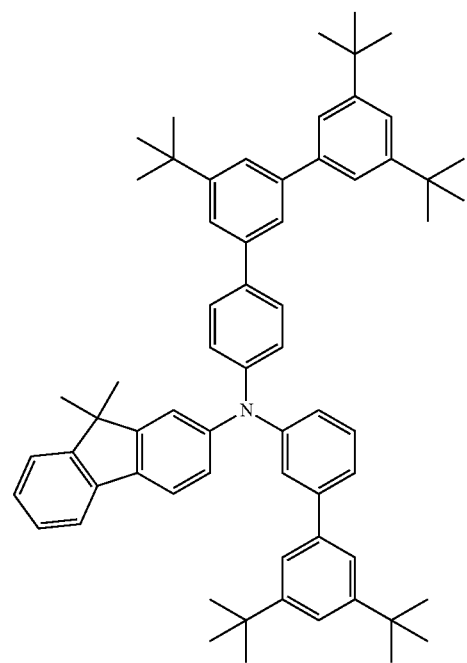

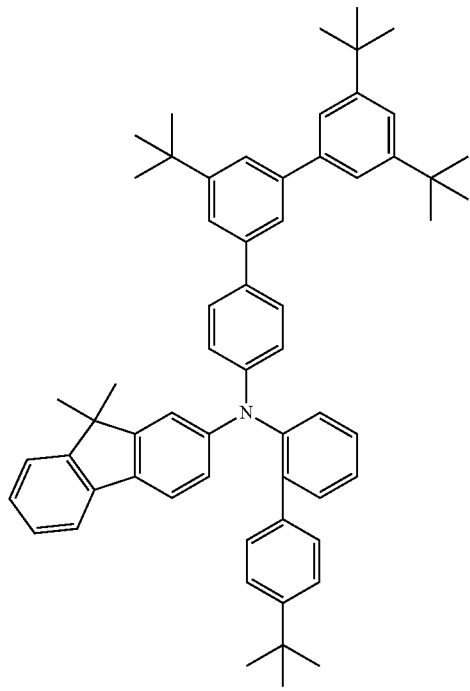
(169)
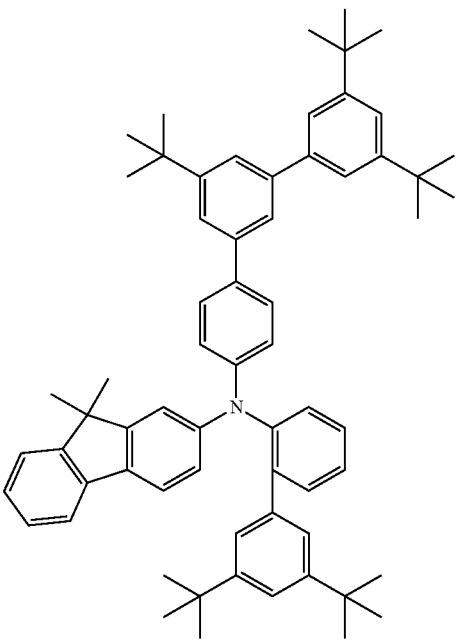
(171)
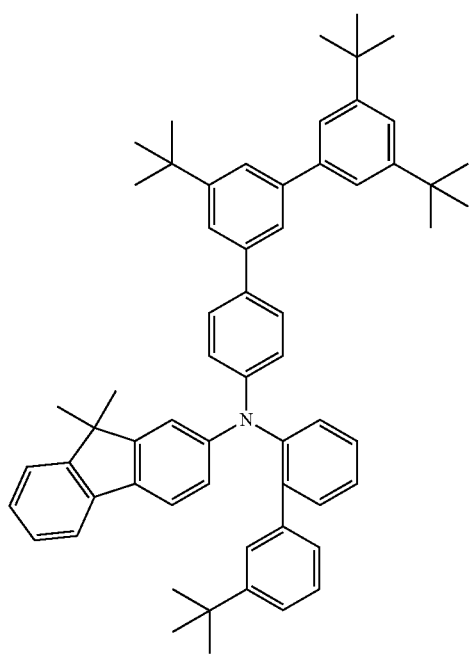
(170)
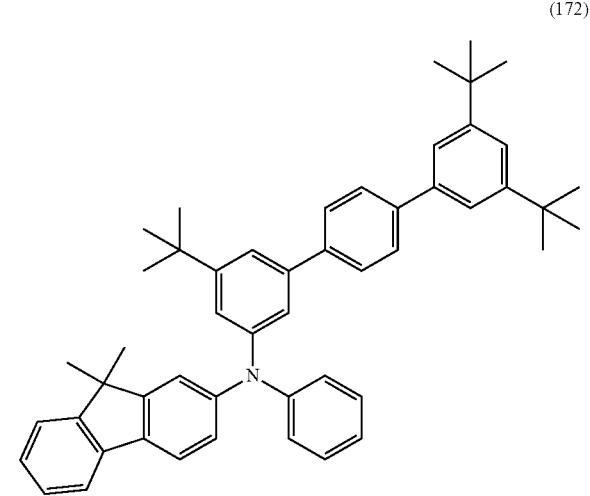
(172)

[Chemical Formula 14]
(173)
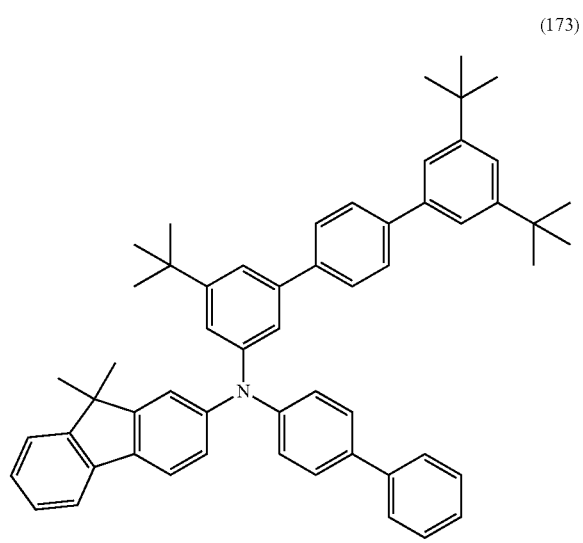
(174)
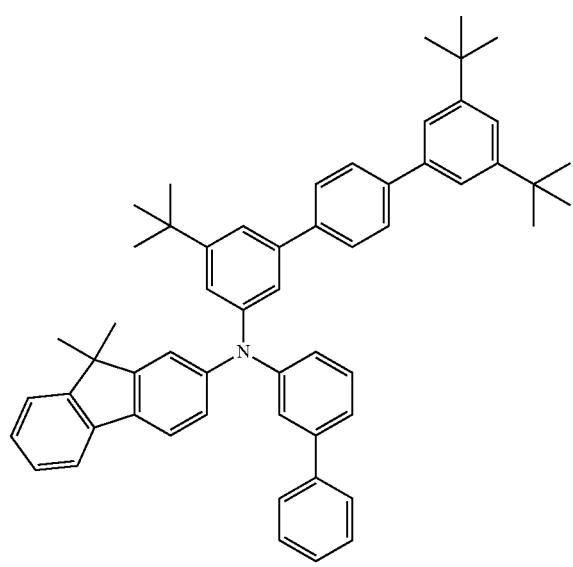
(175)
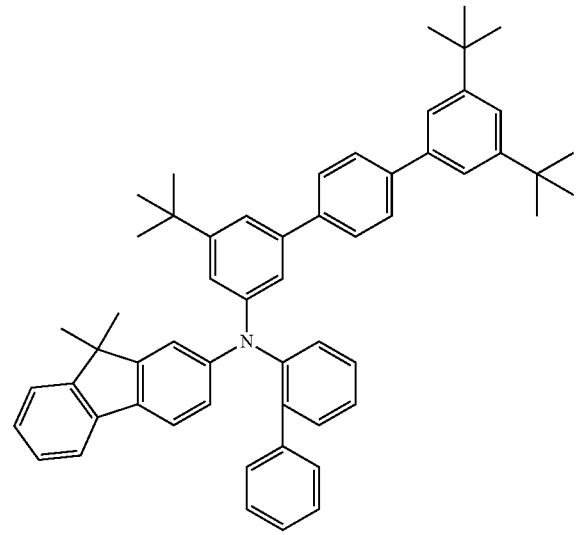
(176)
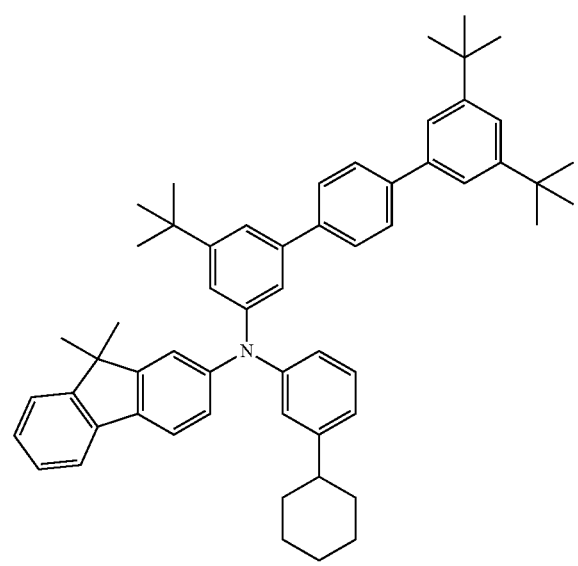
(177)

(178)
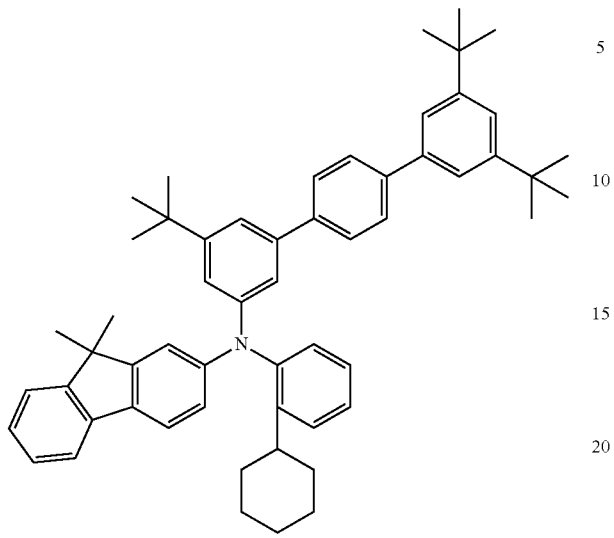
(180)
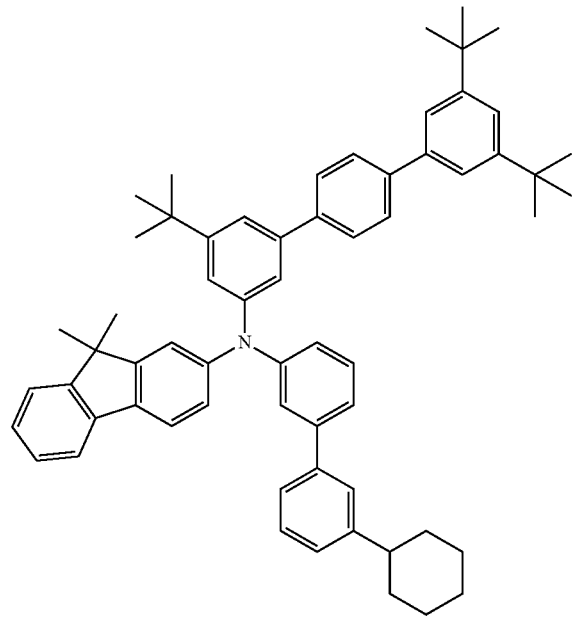
(179)
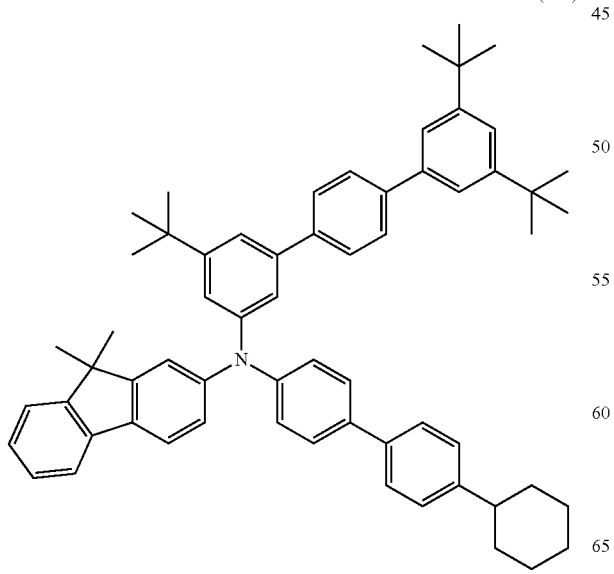
(181)
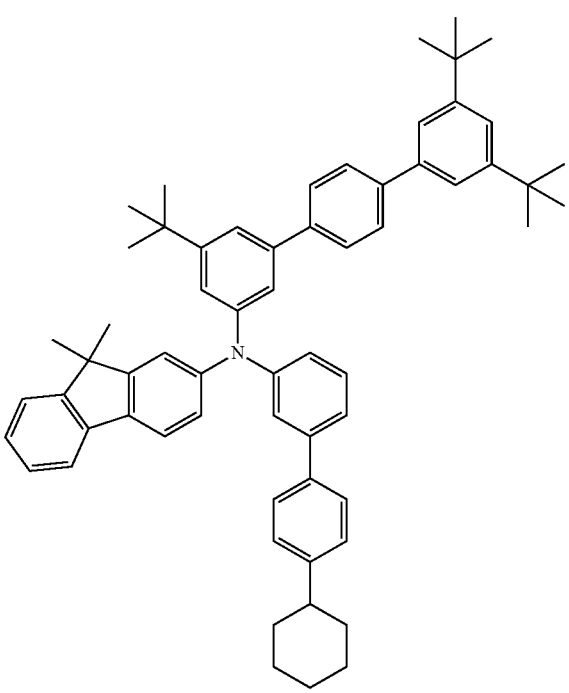

[Chemical Formula 15]
(182) 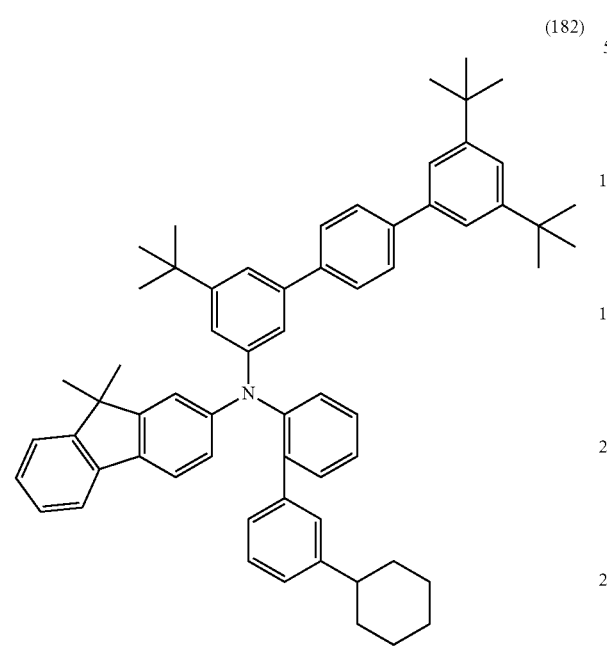
(183) 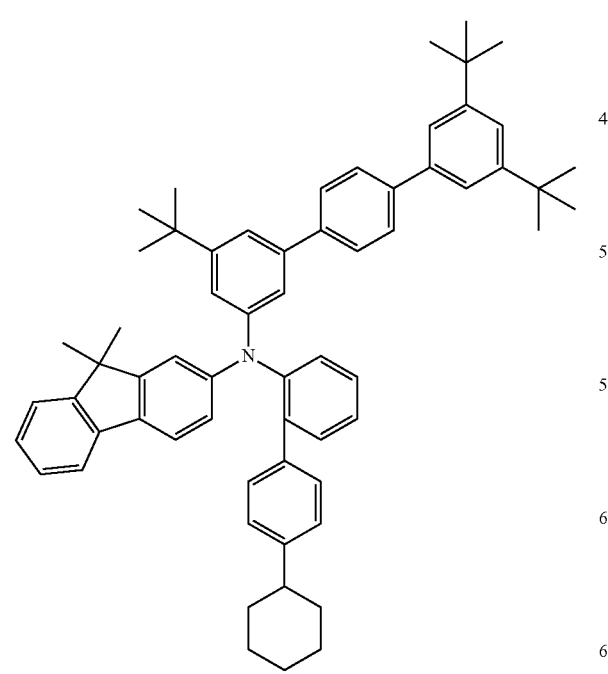
(184) 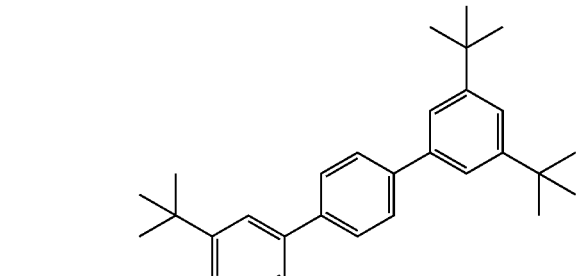
(185) 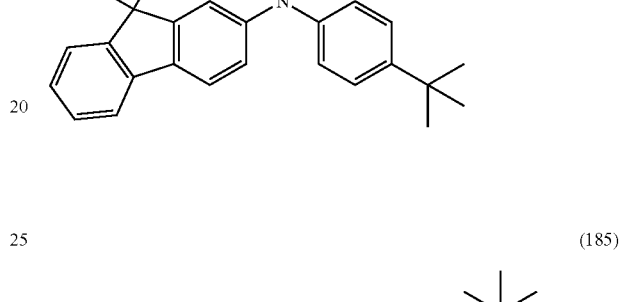
(186) 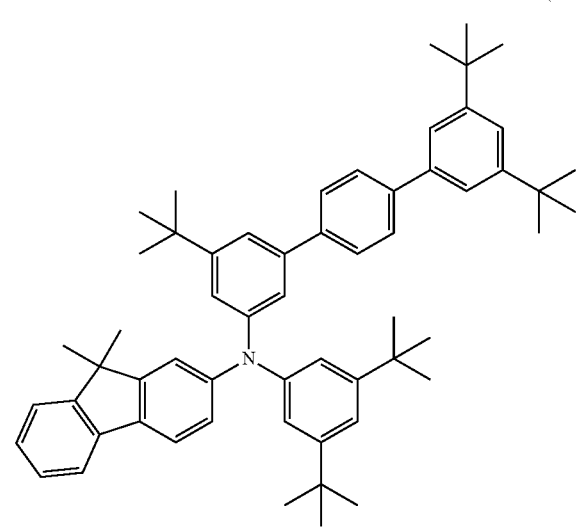

(187)
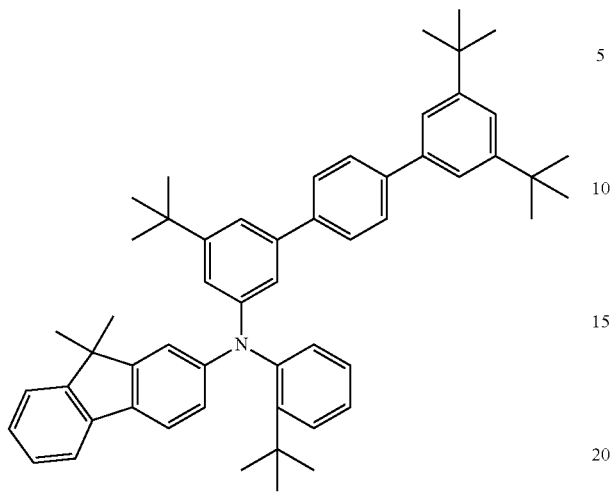
(188)
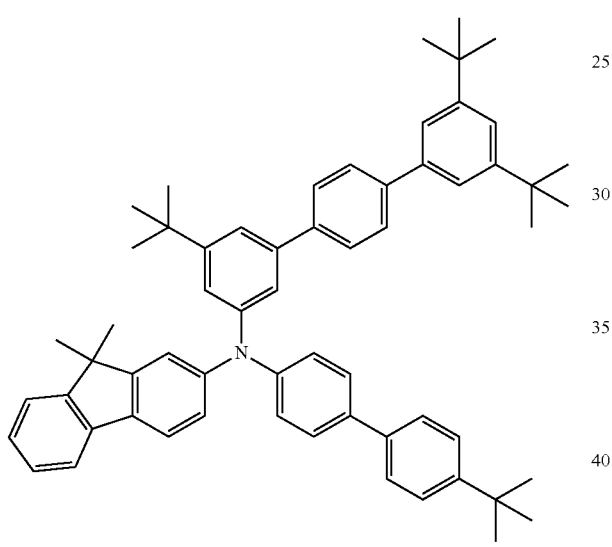
(189)
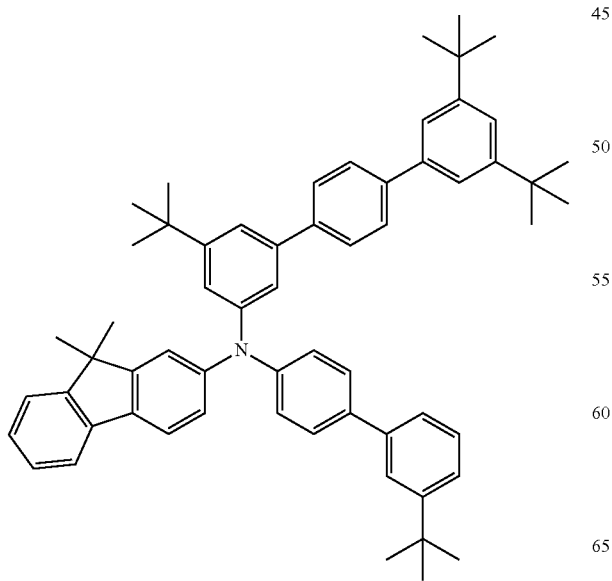
(190)
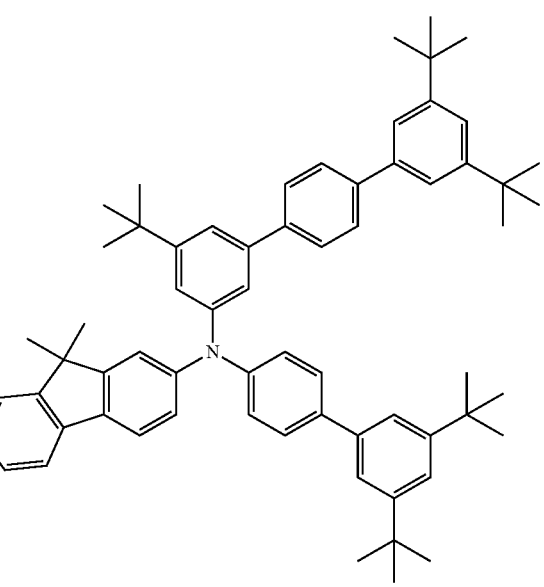
[Chemical Formula 16]
(191)
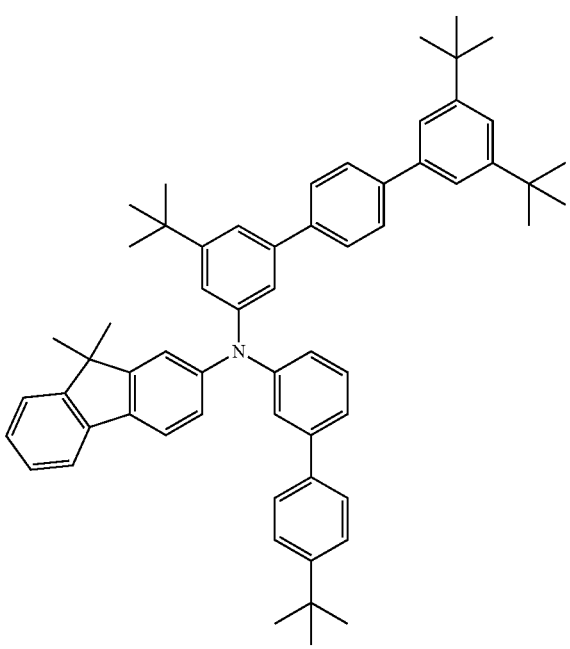

(192)
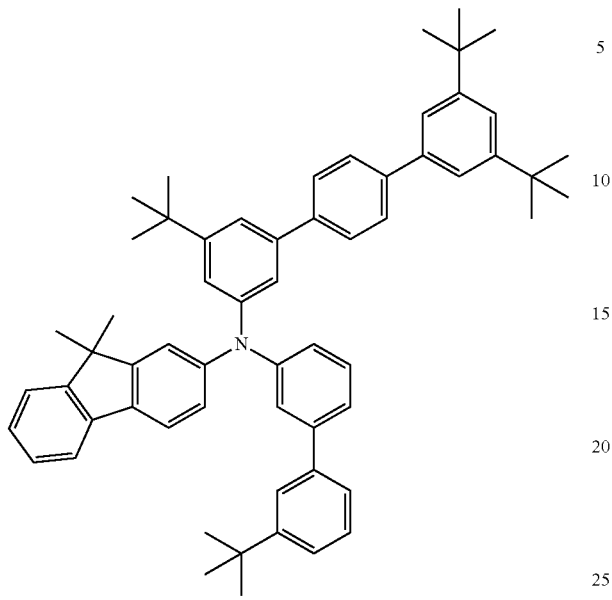
(194)
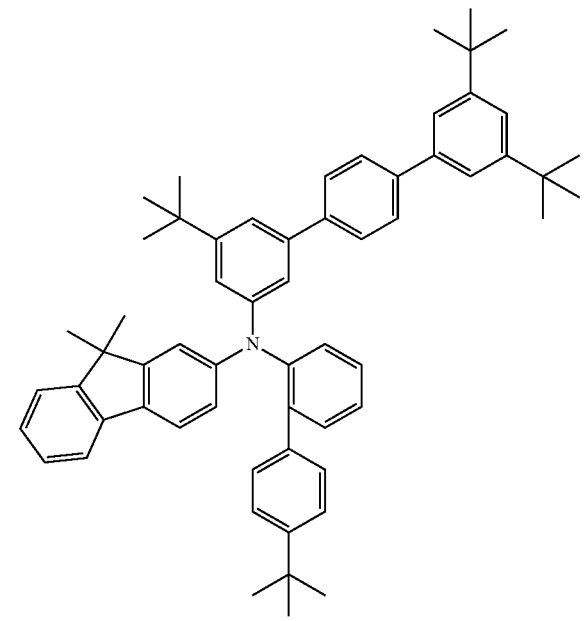
(193)
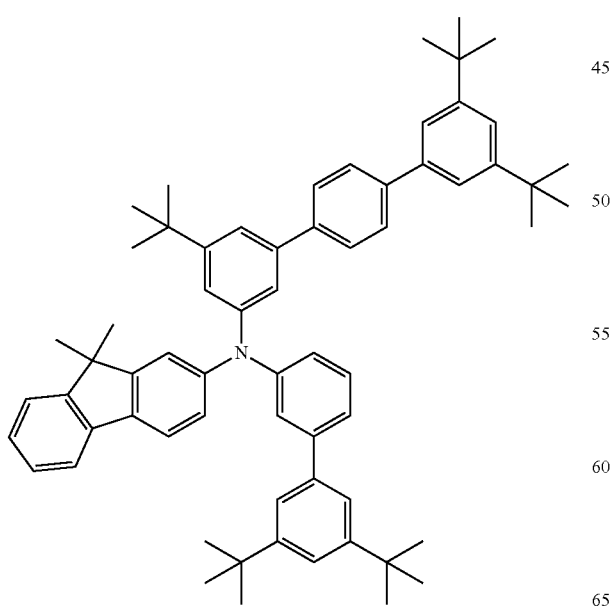
(195)
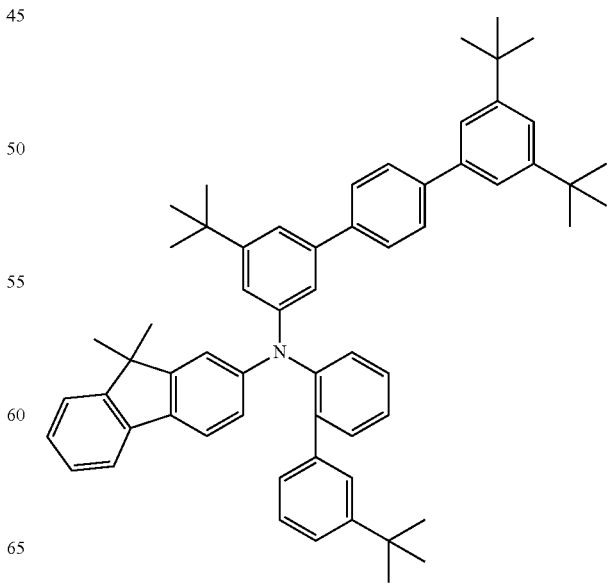

(196)
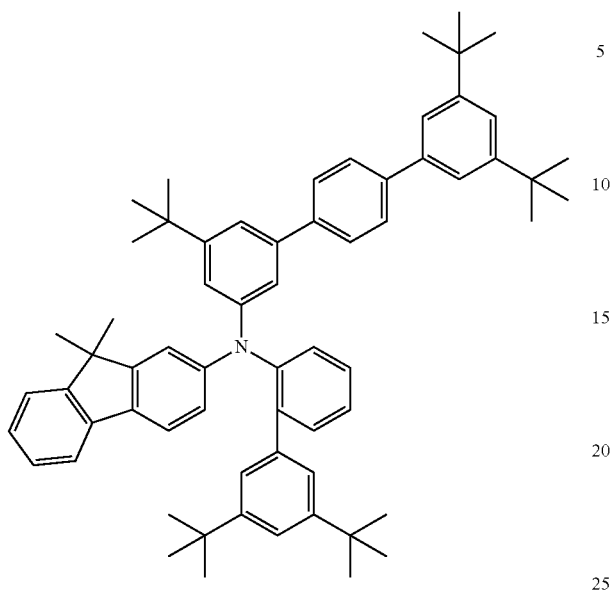
(198)
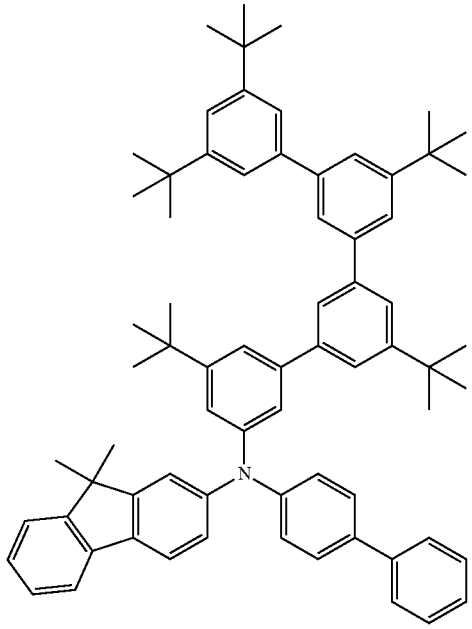
(197)
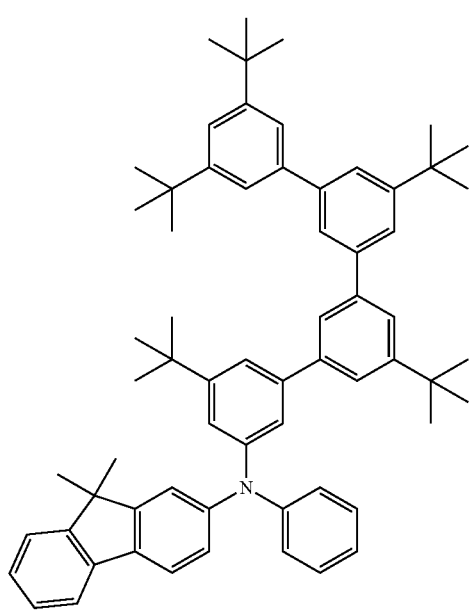
(199)
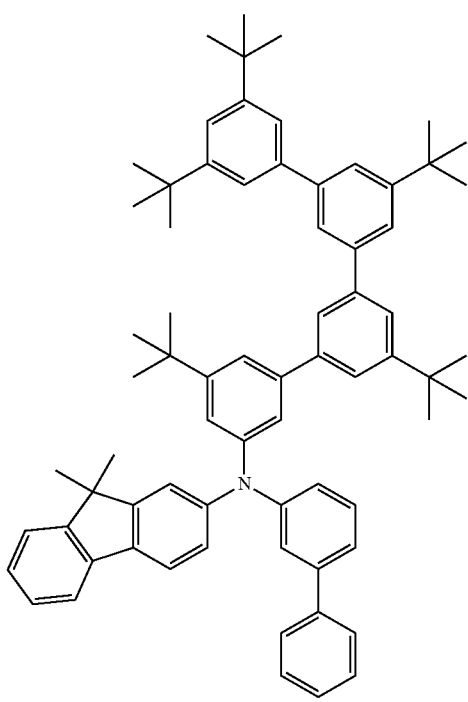

[Chemical Formula 17]
(200)
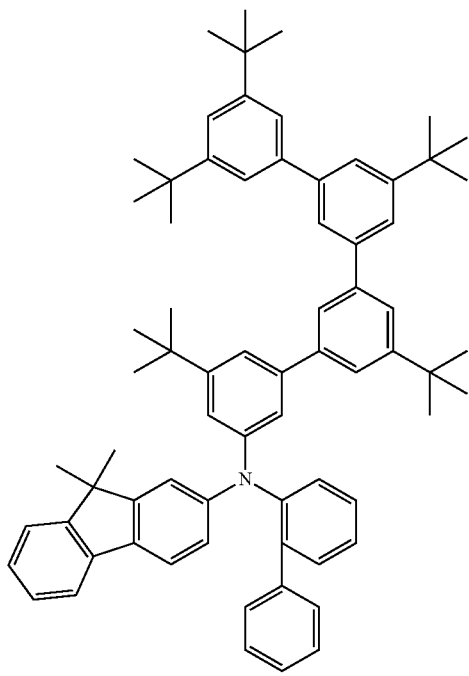
(201)
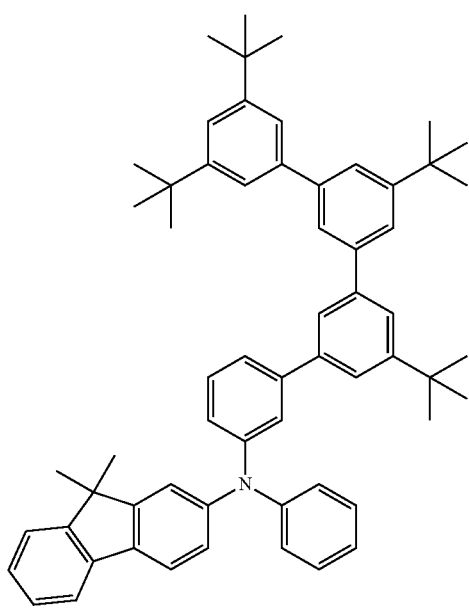
(202)
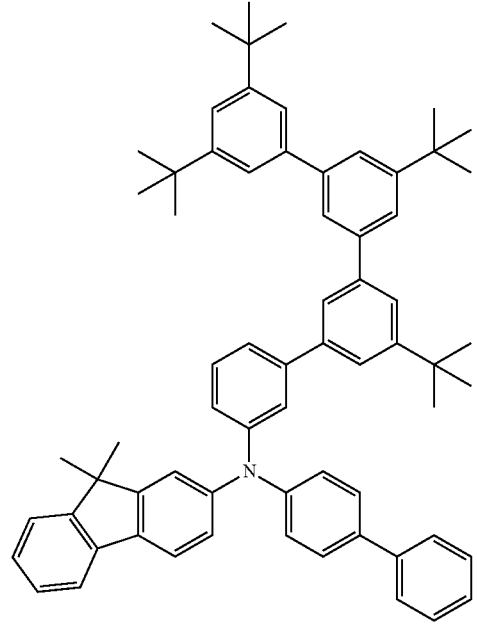
(203)
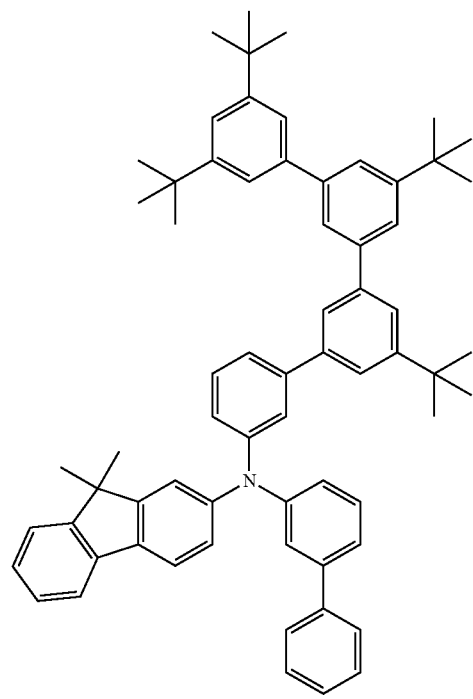

(204)
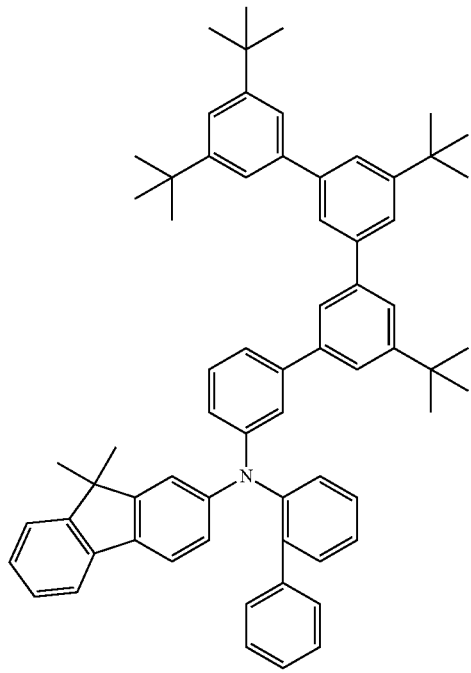
(205)
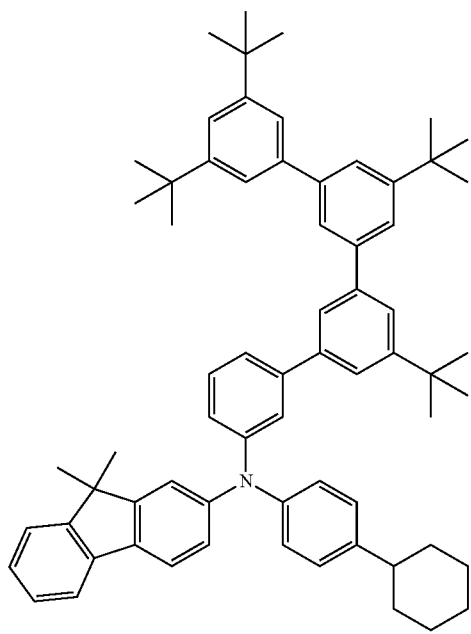
(206)
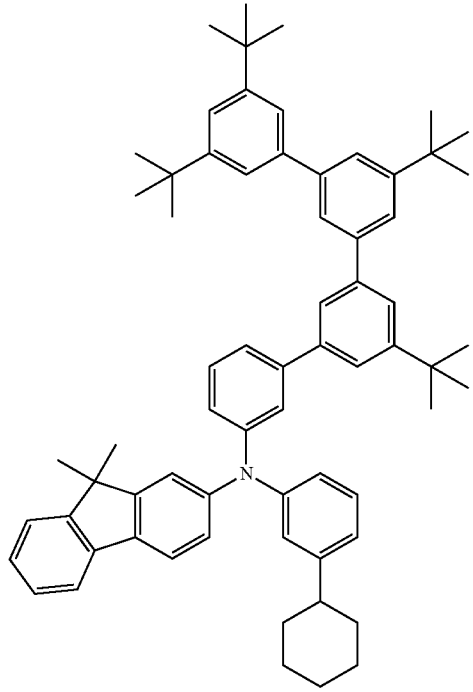
(207)
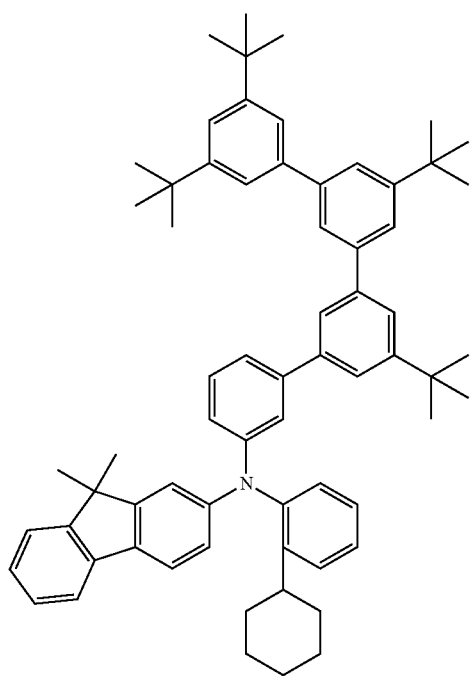

(208)
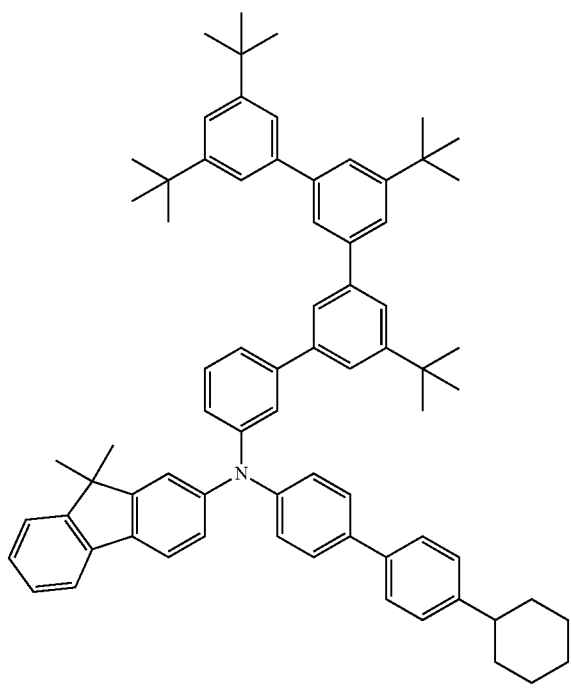
(210)
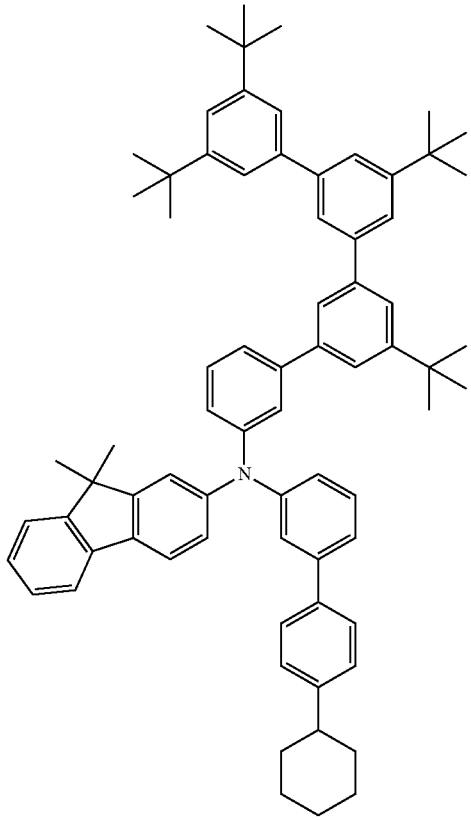
[Chemical Formula 18]
(209)
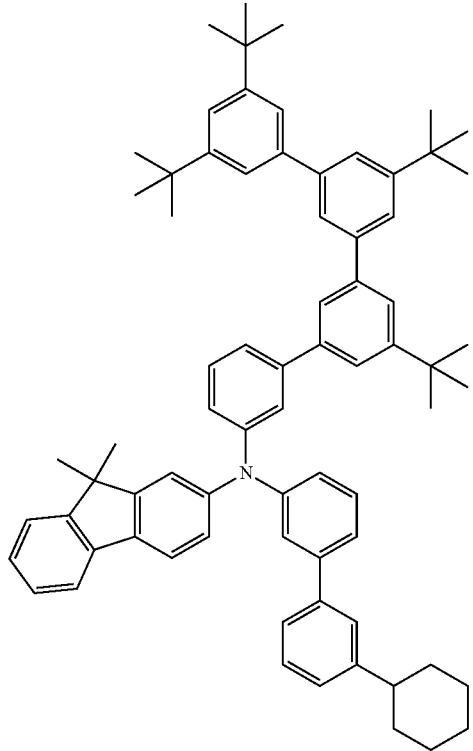
(211)
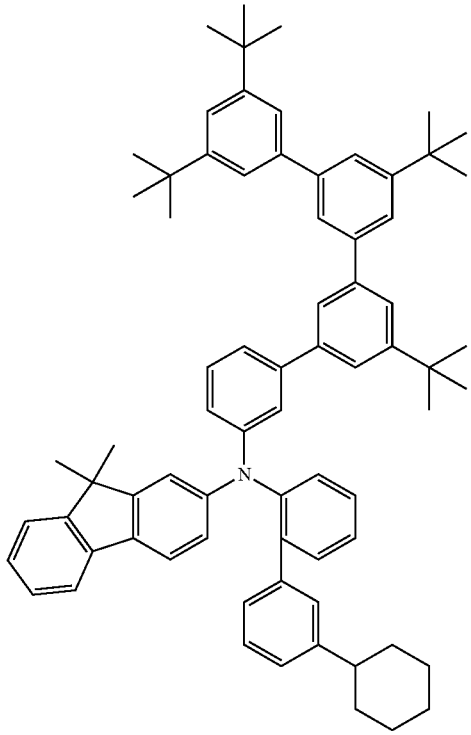

(212)
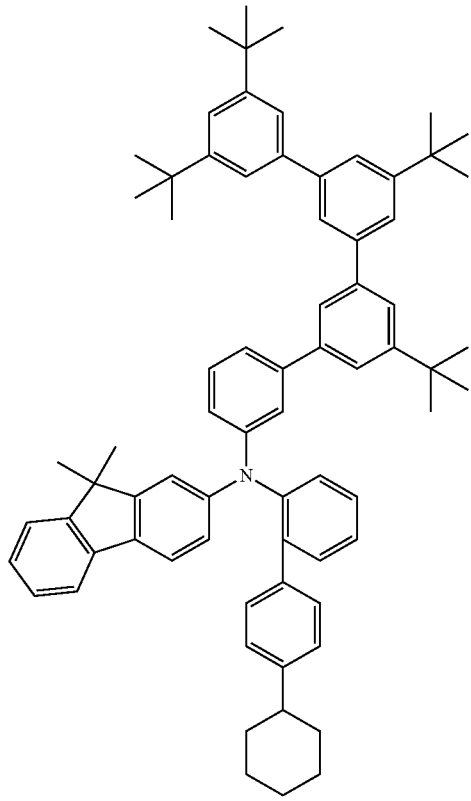
(214)
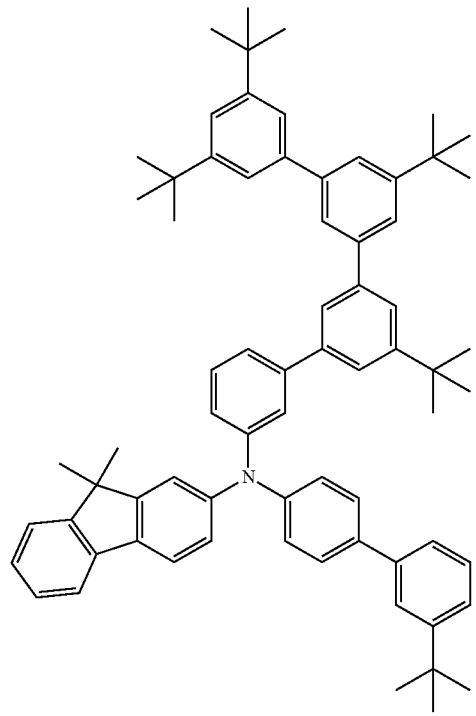
(213)
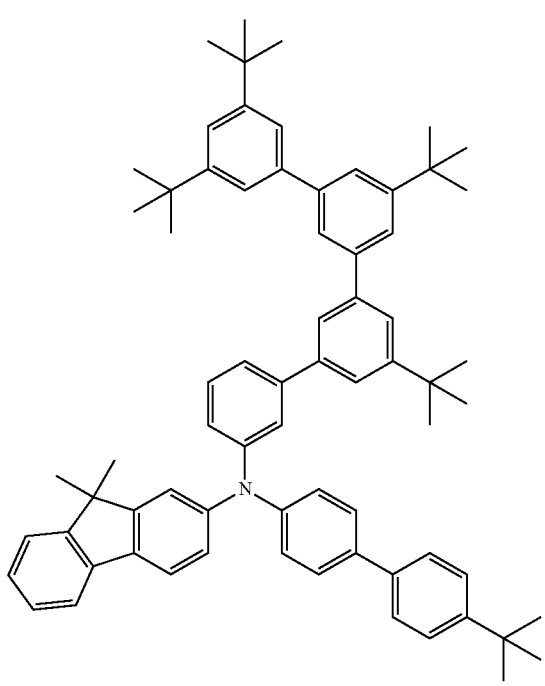
(215)
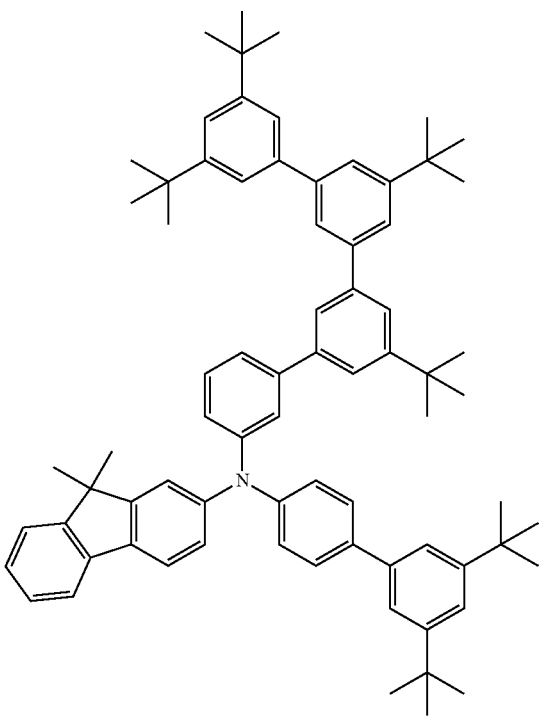

(216)
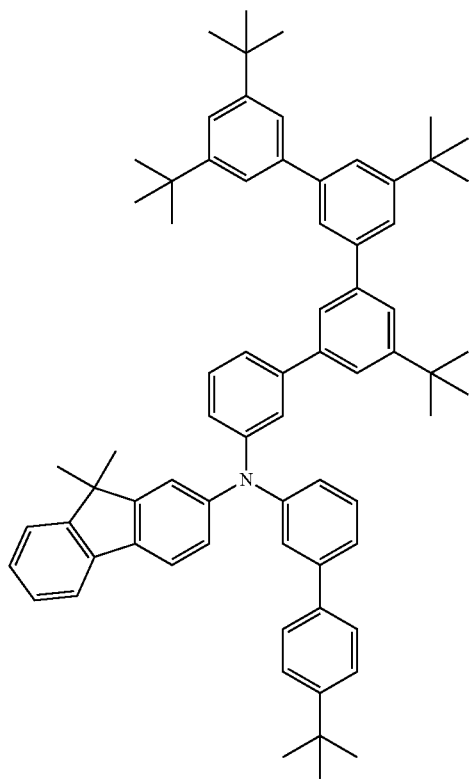
(218)
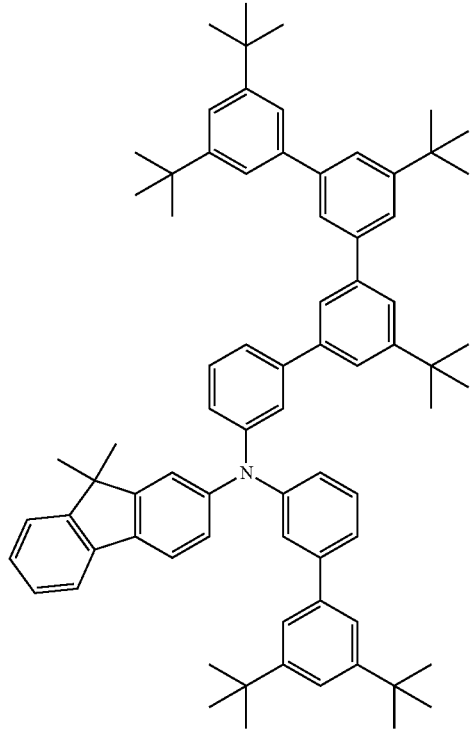
[Chemical Formula 19]
(217)
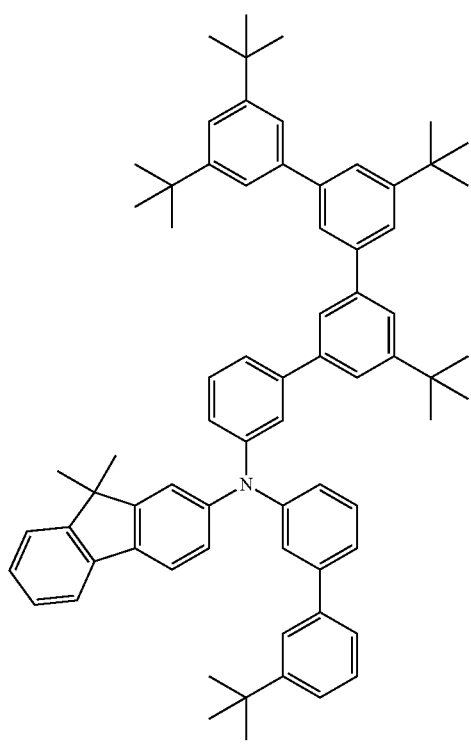
(219)
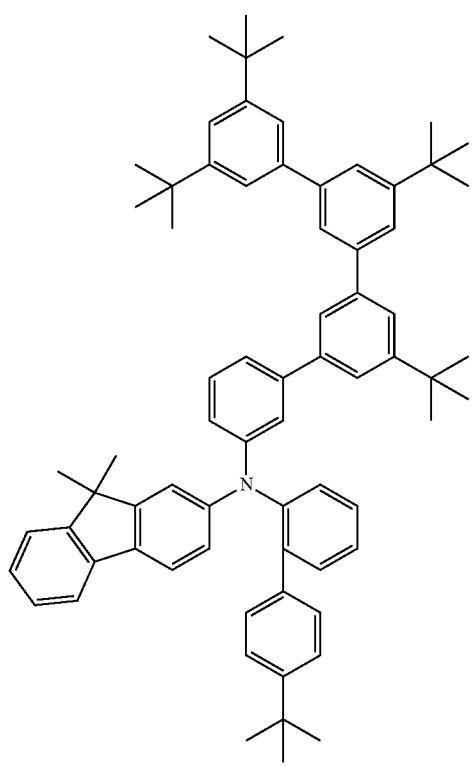

-continued
(220)
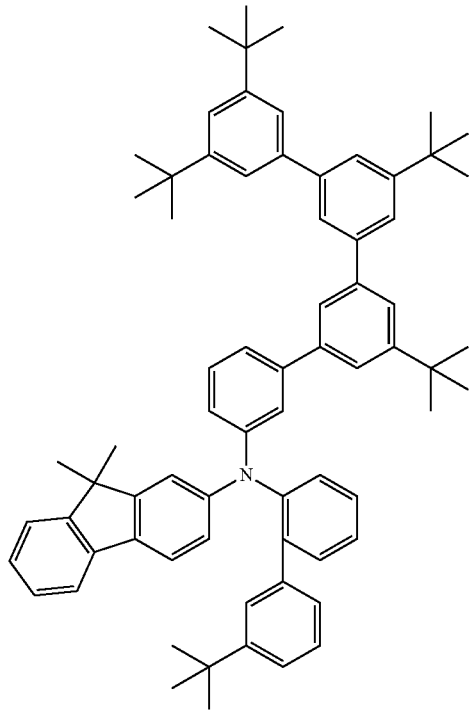
(221)
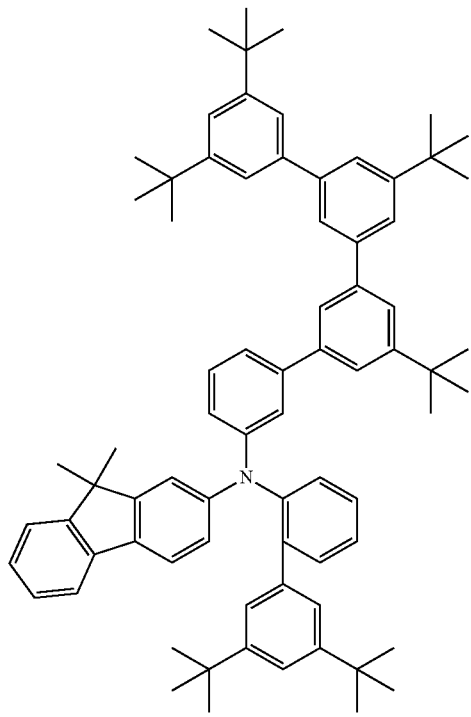
(222)
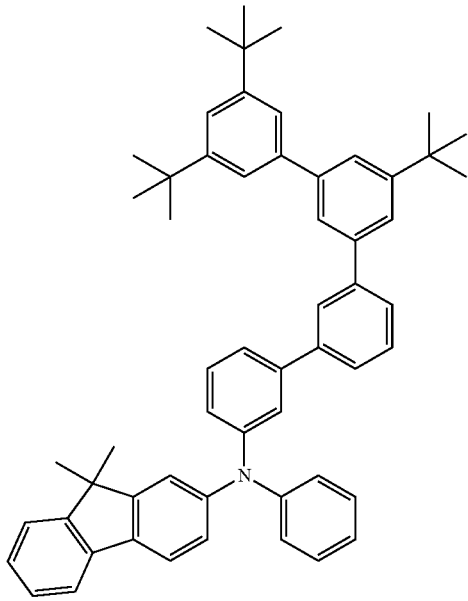
(223)
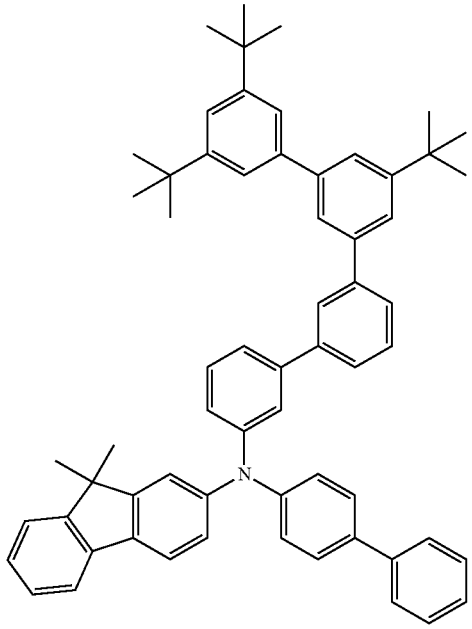

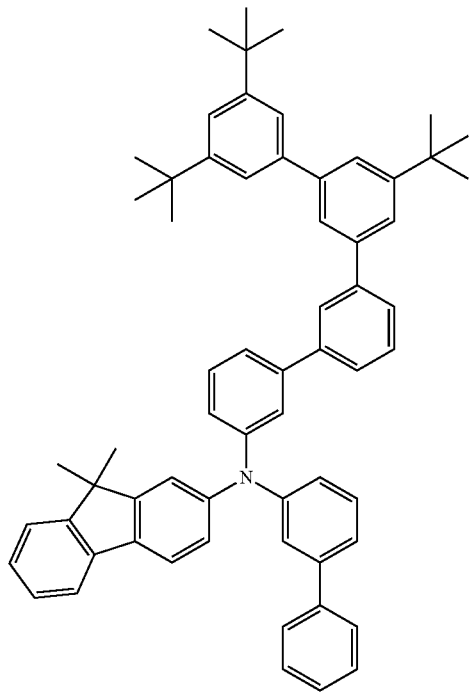
(224)
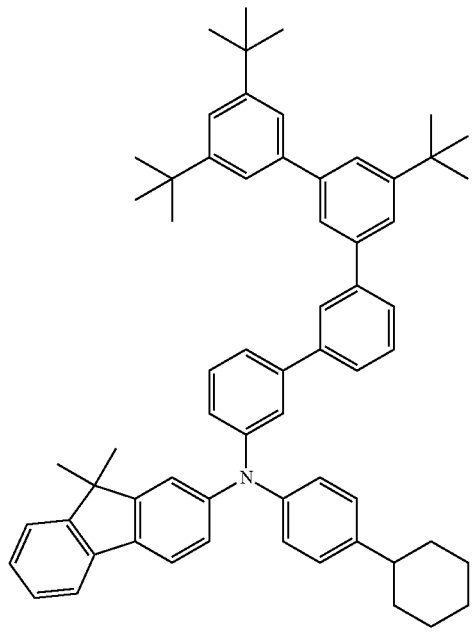
(226)
[Chemical Formula 20]
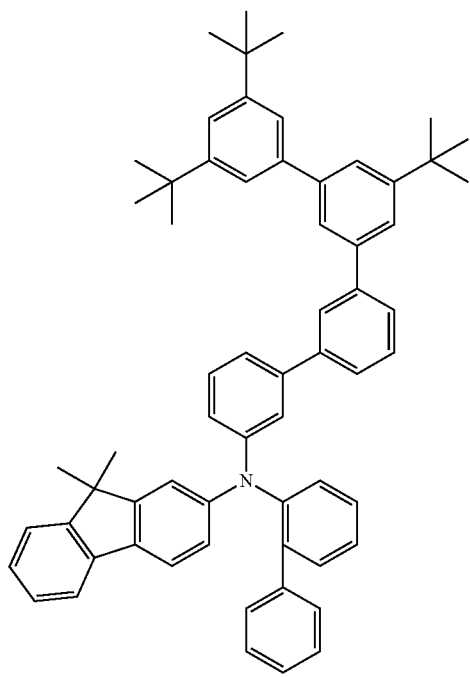
(225)
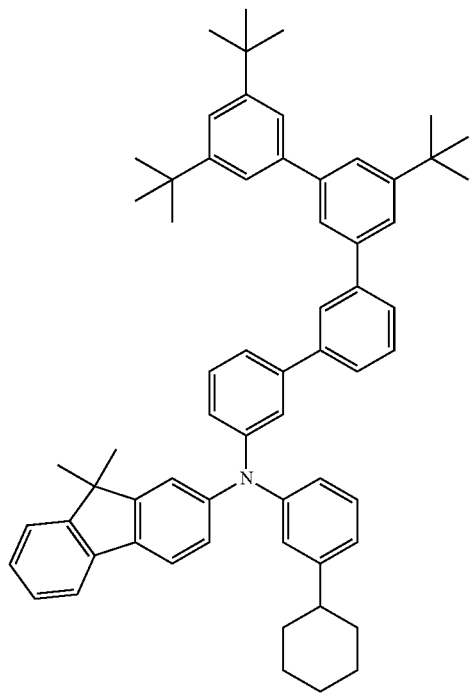
(227)

(228)
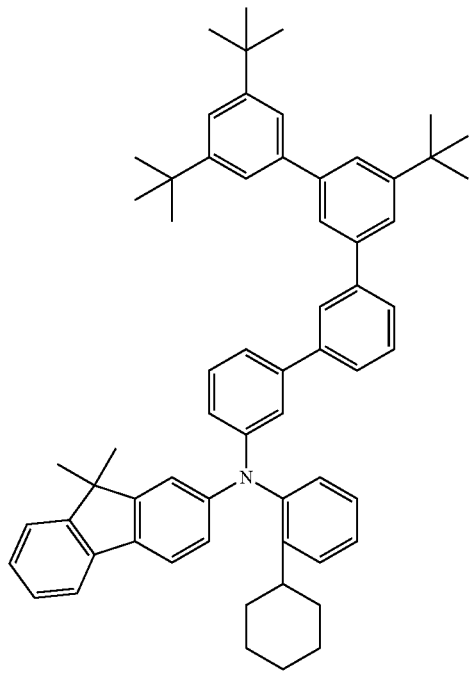
(230)
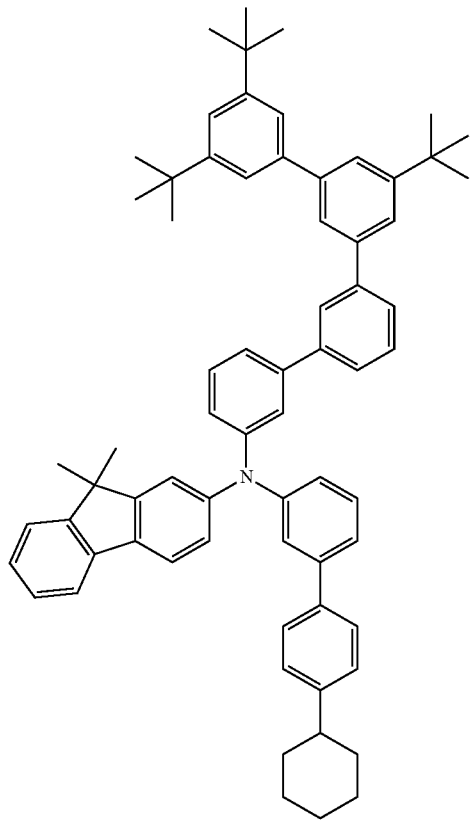
(229)
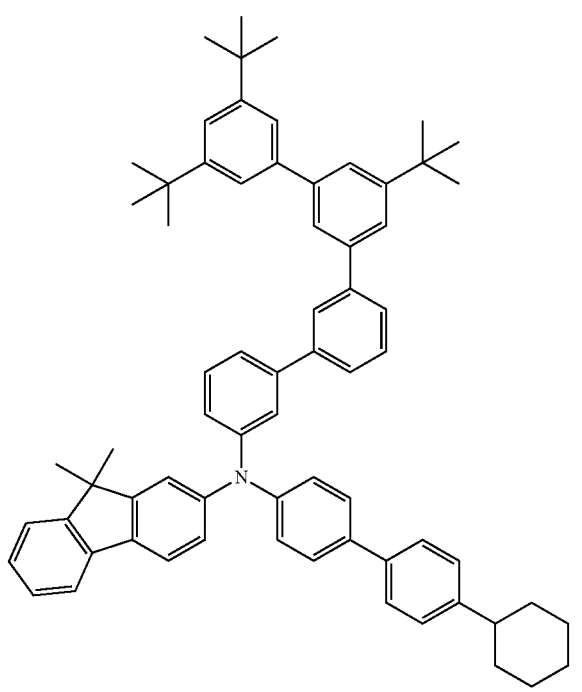
(231)
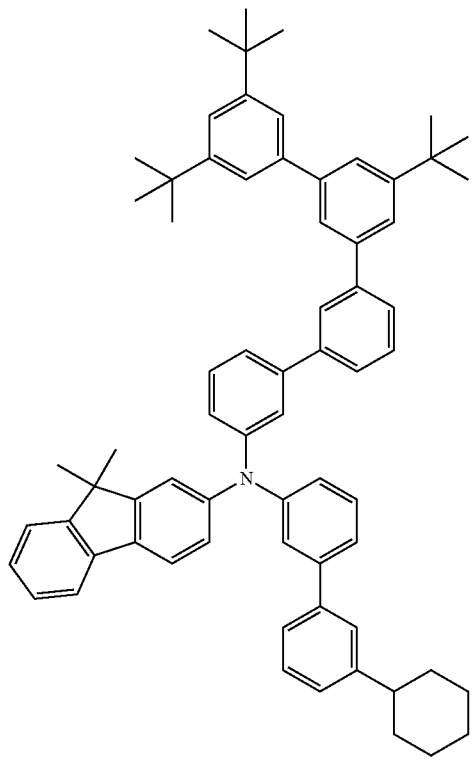

(232)
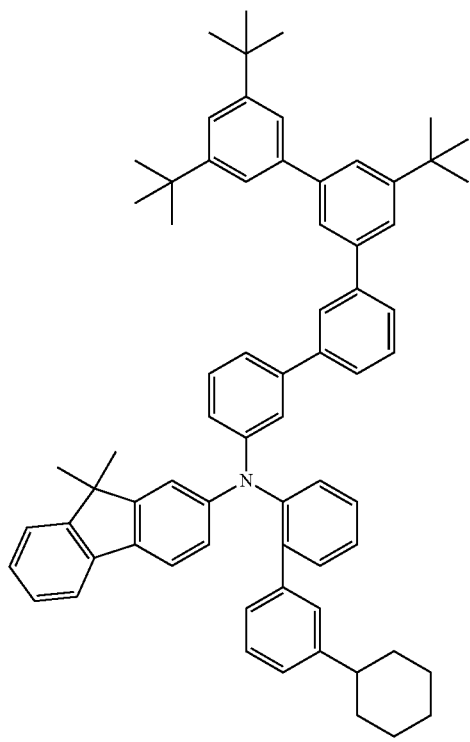
[Chemical Formula 21]
(234)
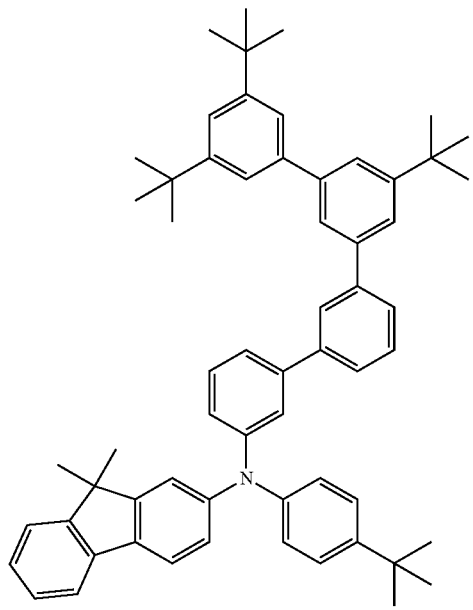
(233)
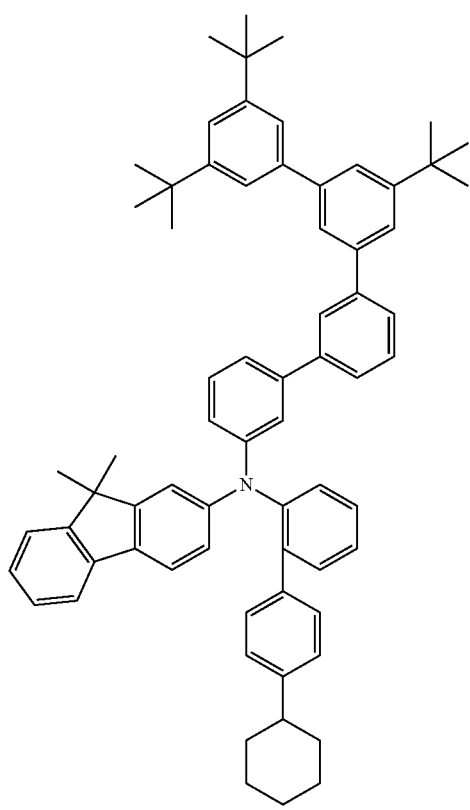
(235)
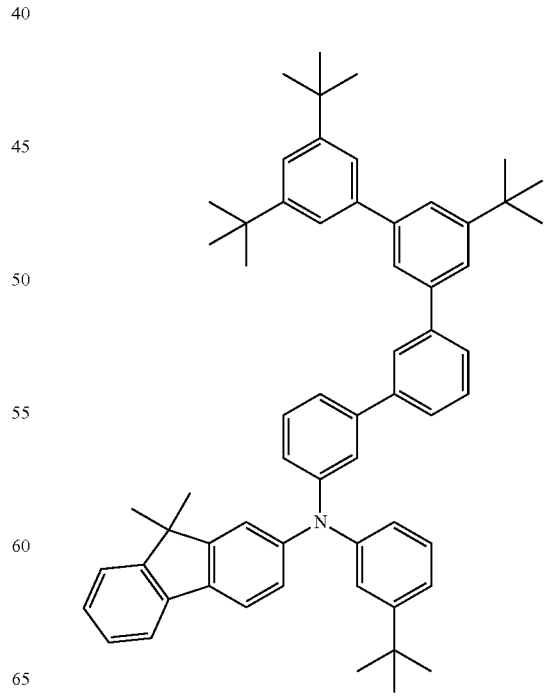

(236)
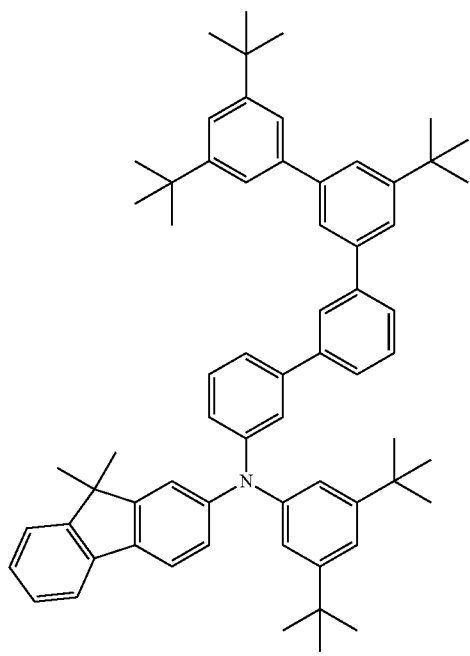
(237)
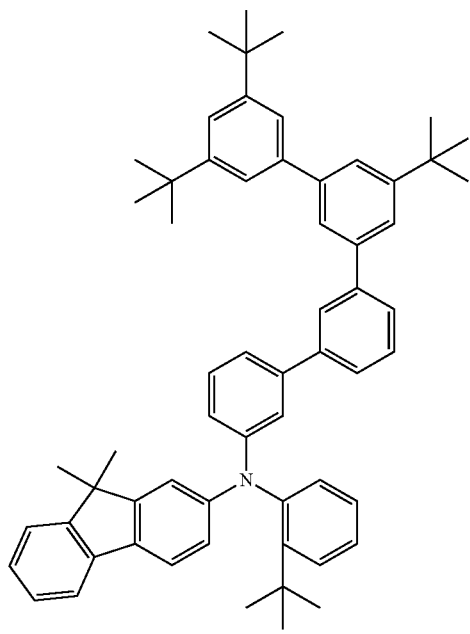
(238)
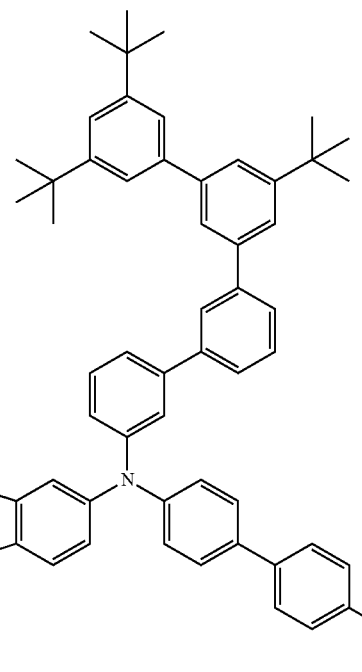
(239)
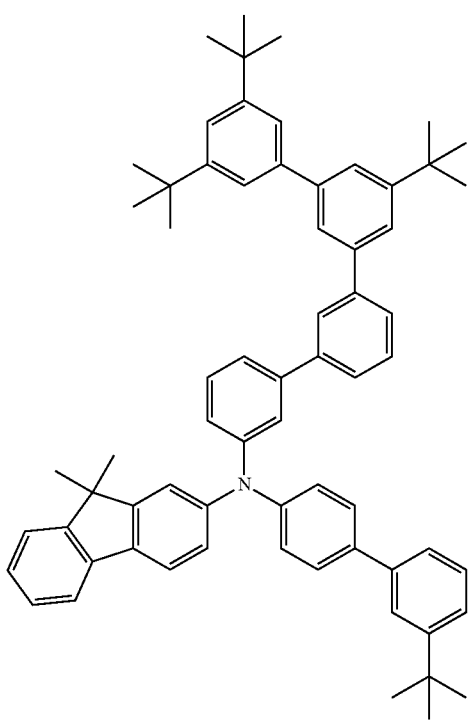

(240)
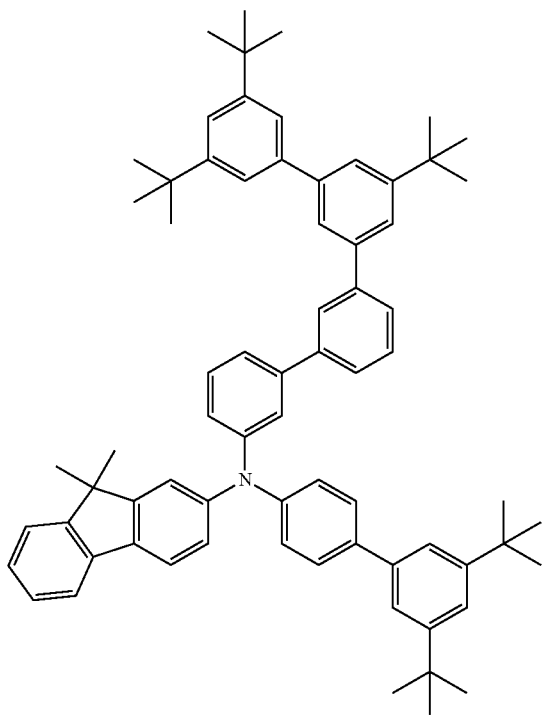
(241)
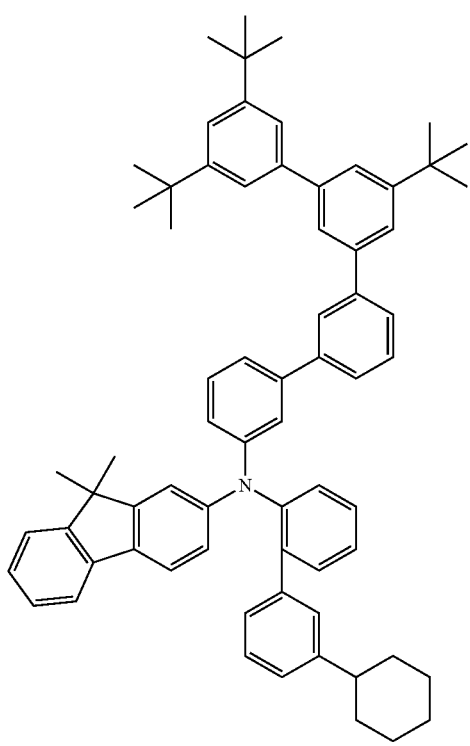
(242)
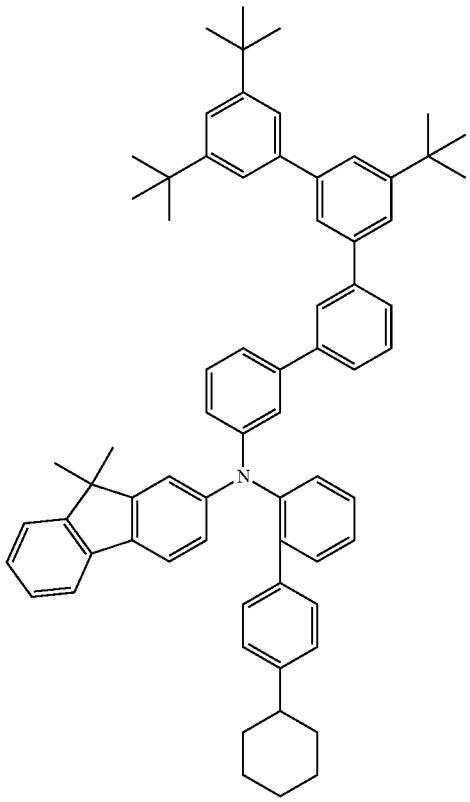
[Chemical Formula 22]
(243)
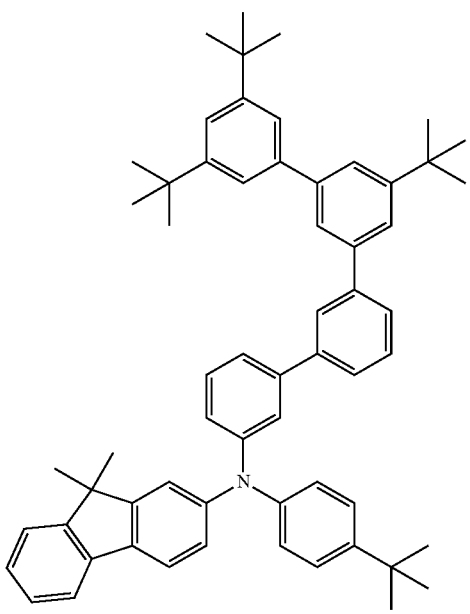

(244) 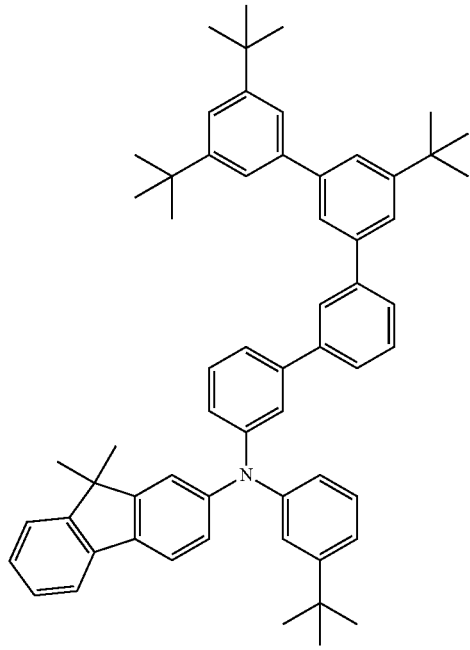
(245) 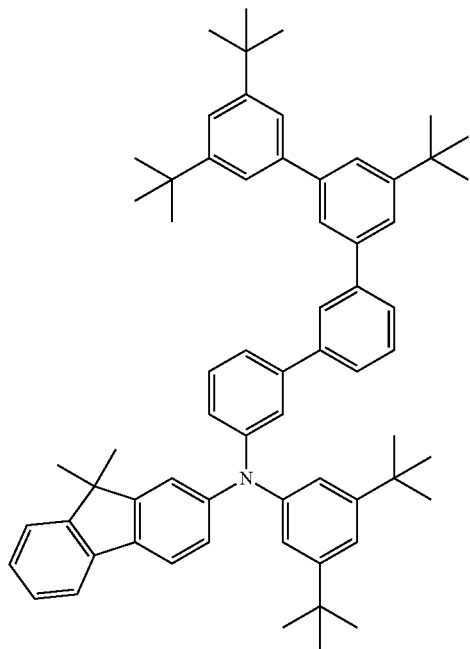
(246) 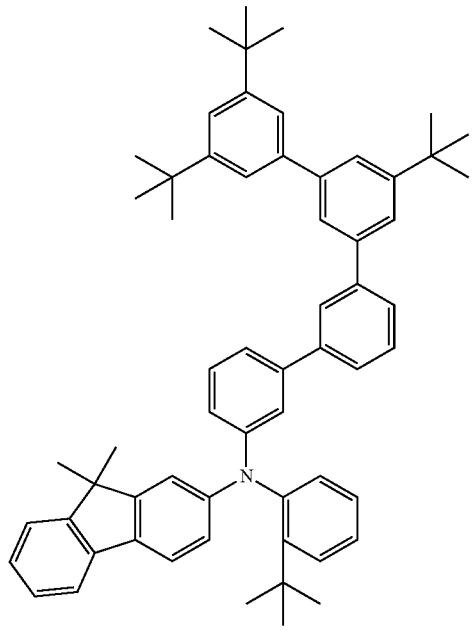
(247) 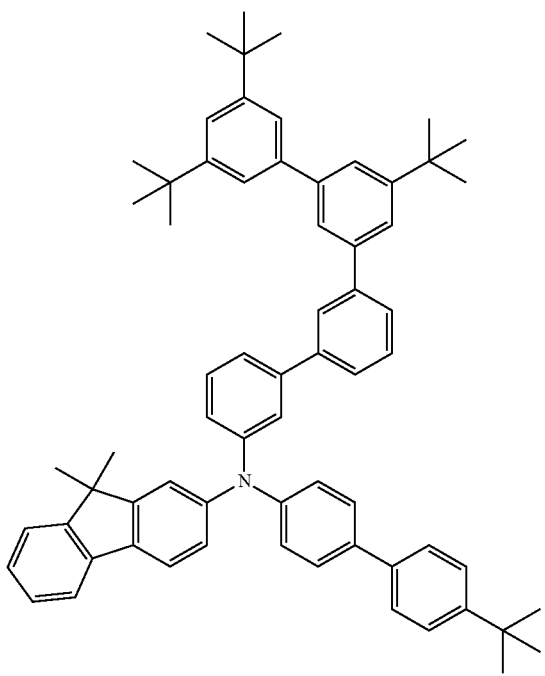

(248)
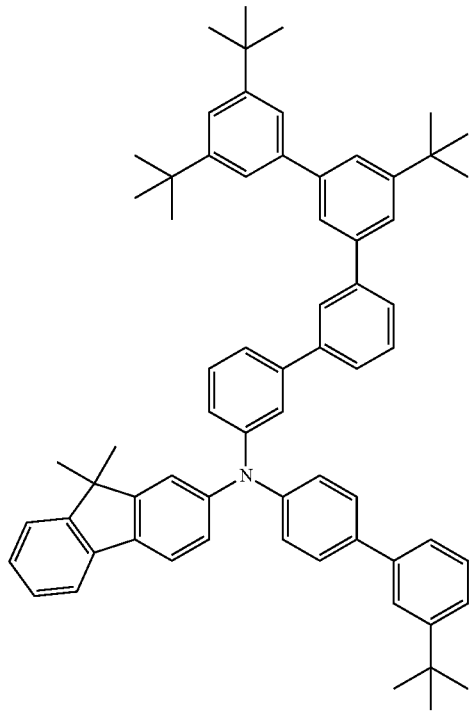
(250)
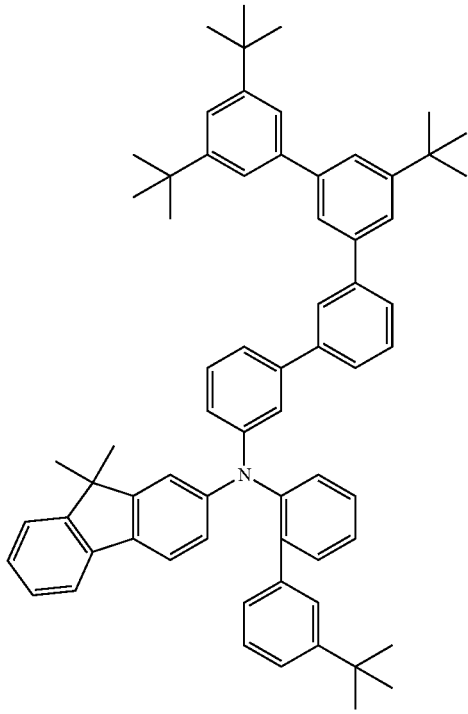
(249)
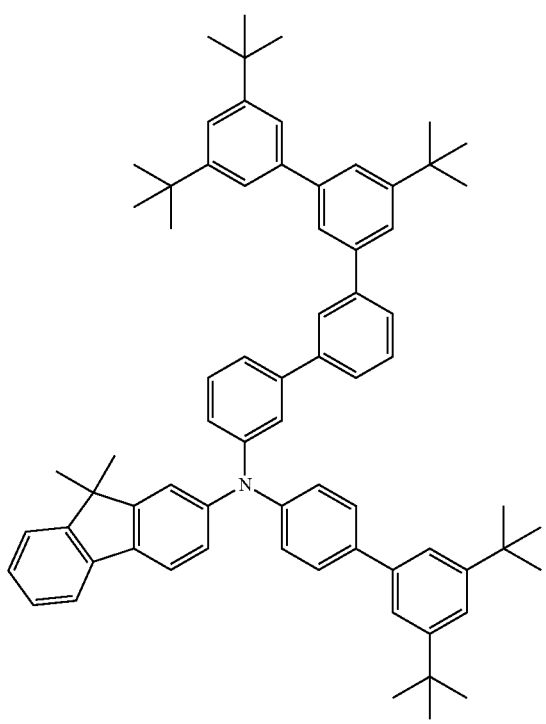
(251)
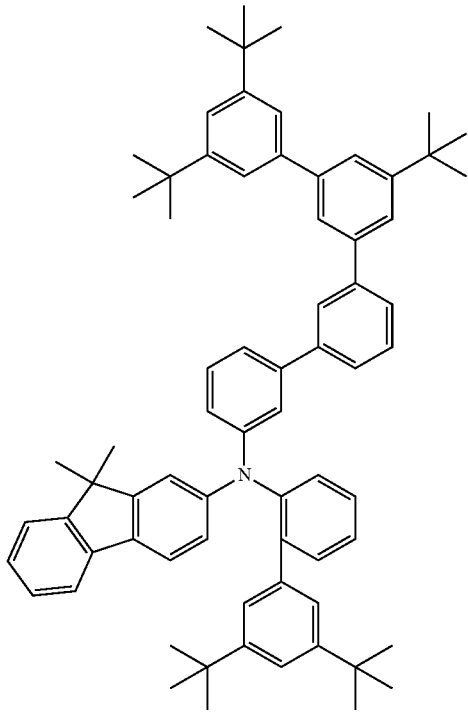

[Chemical Formula 23]
(252)
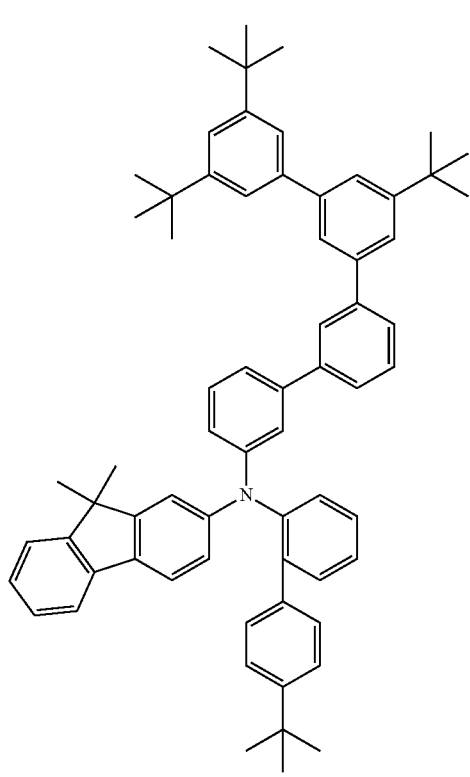
(254)
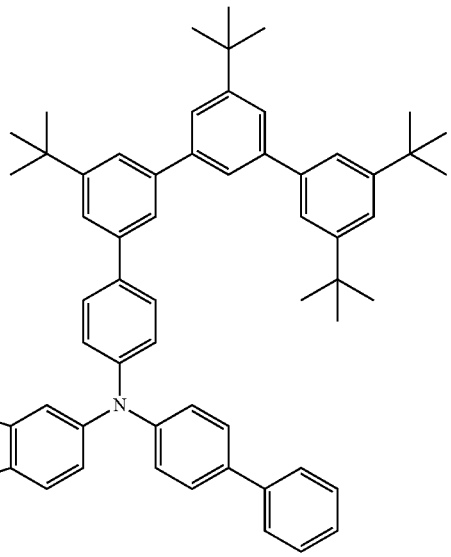
(253)
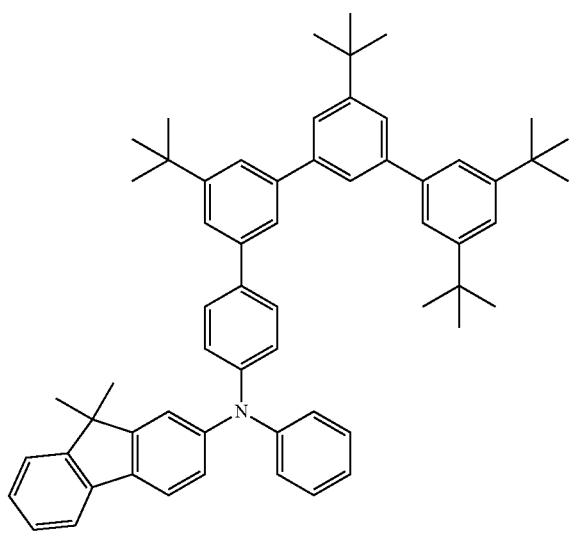
(255)
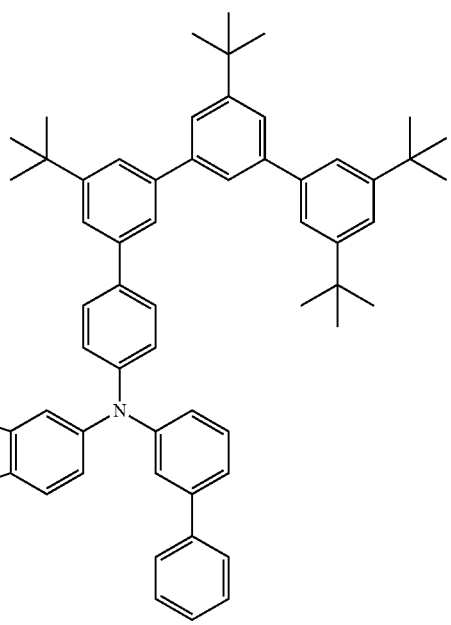

(256)
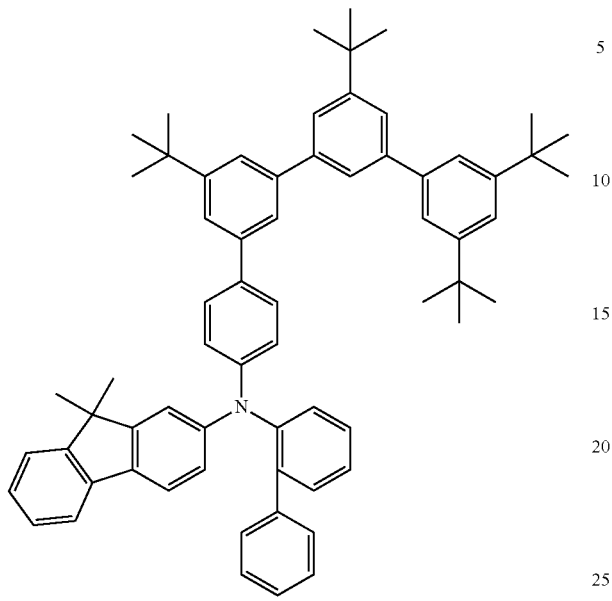
(258)
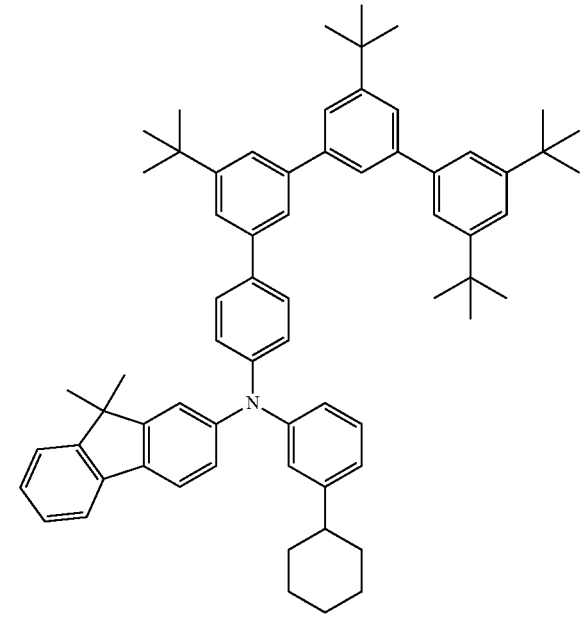
(257)
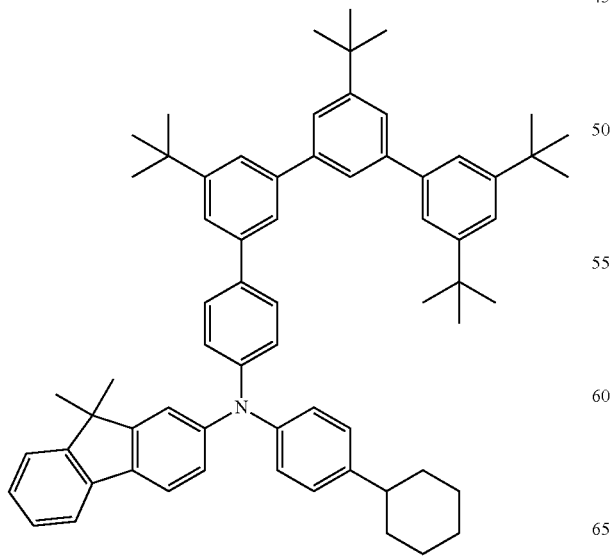
(259)
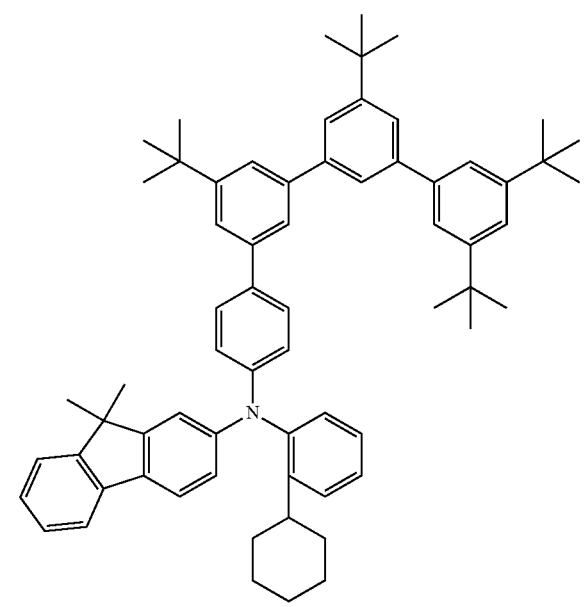

(260)
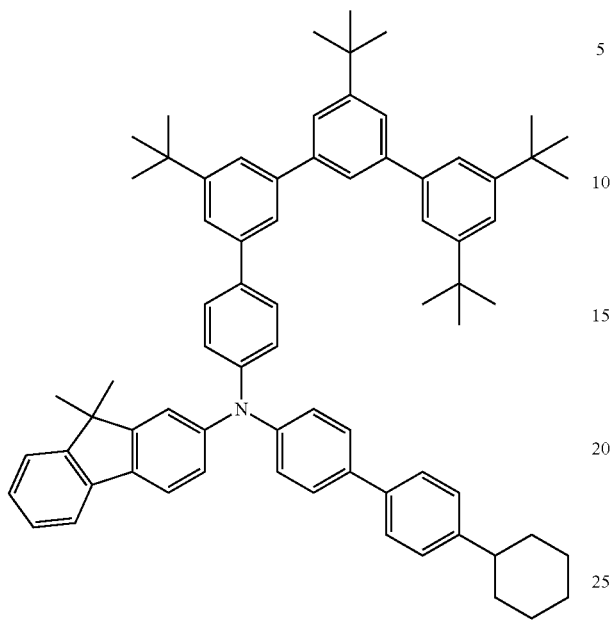
(262)
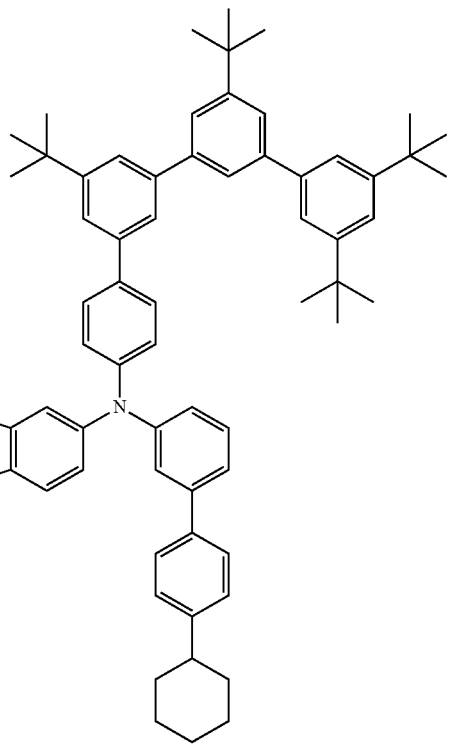
[Chemical Formula 24]
(261)
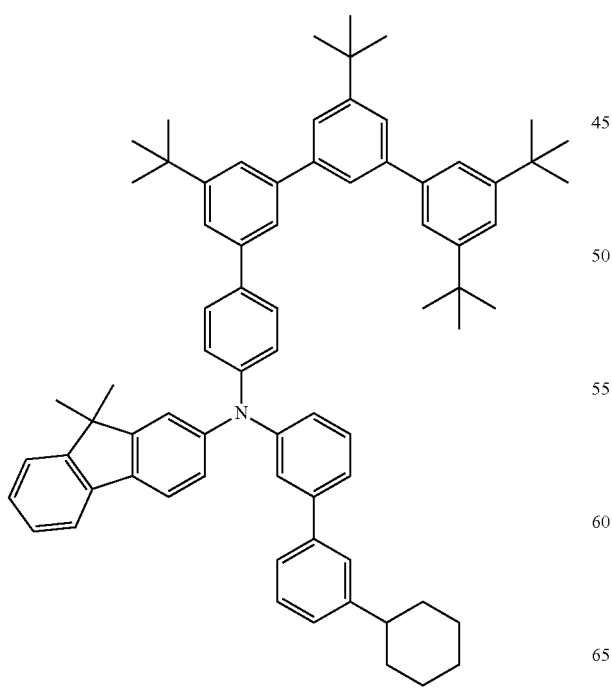
(263)

(264)
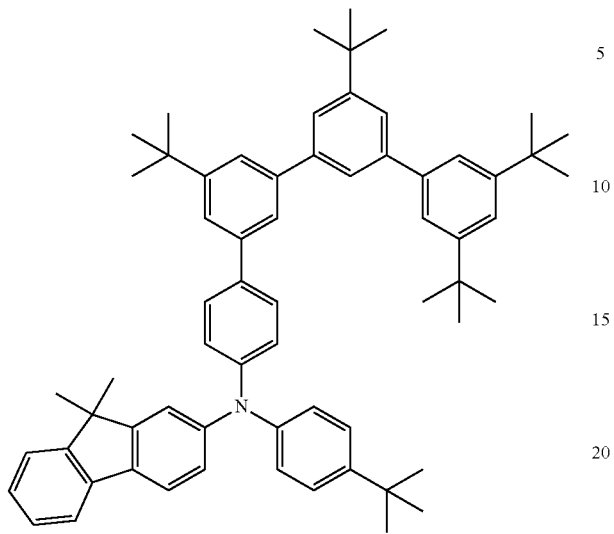
(266)
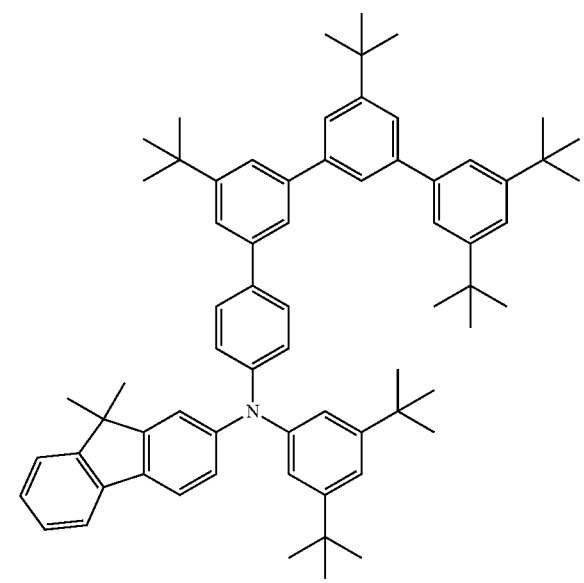
(265)
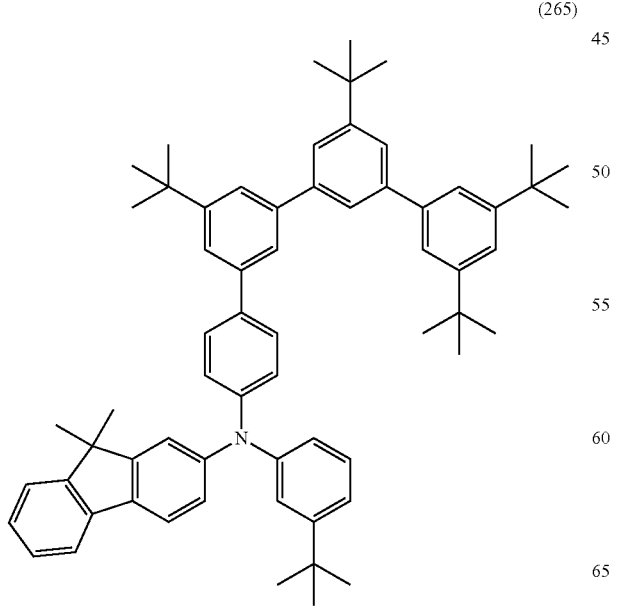
(267)
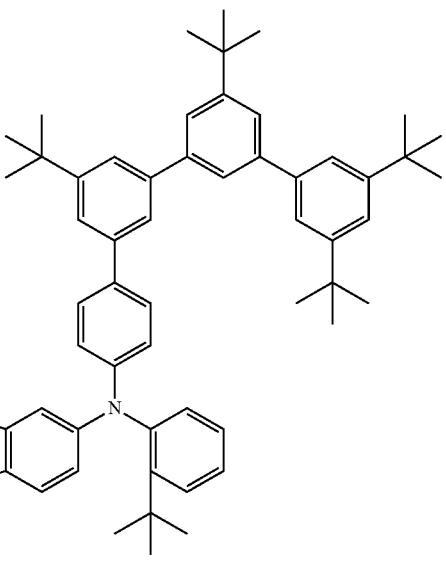

[Chemical Formula 25]
(268)
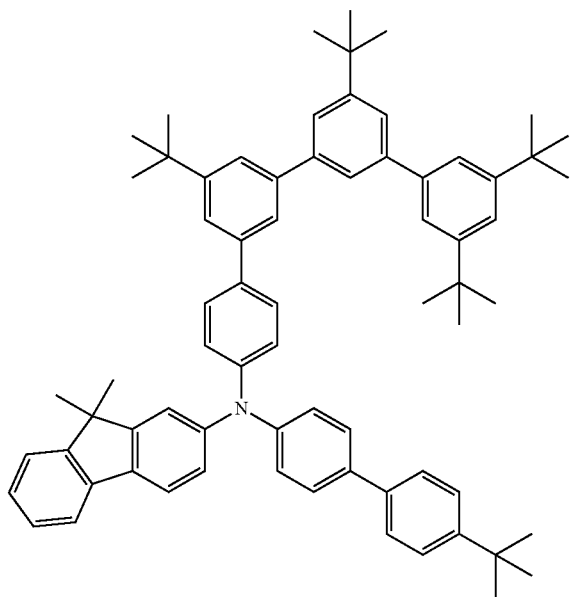
(269)
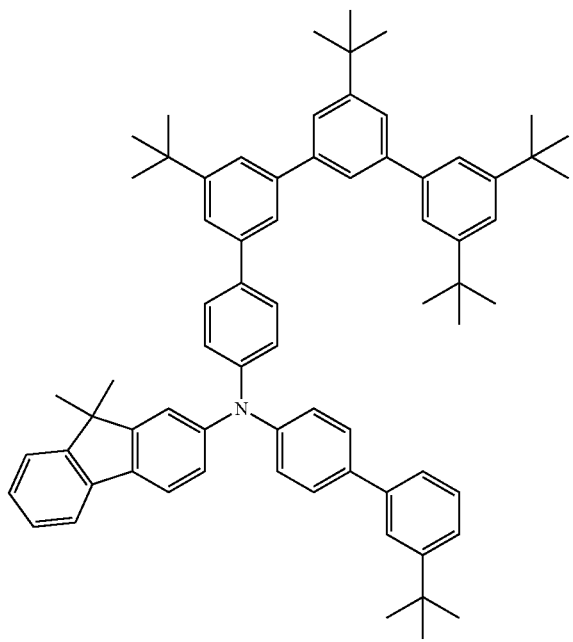
(270)
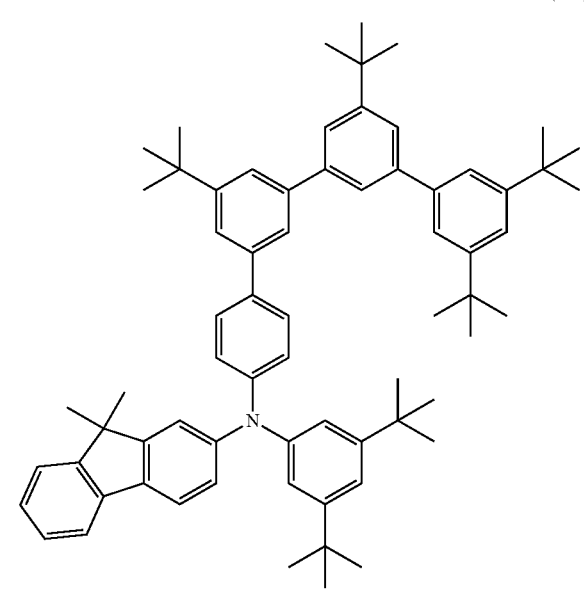
(271)
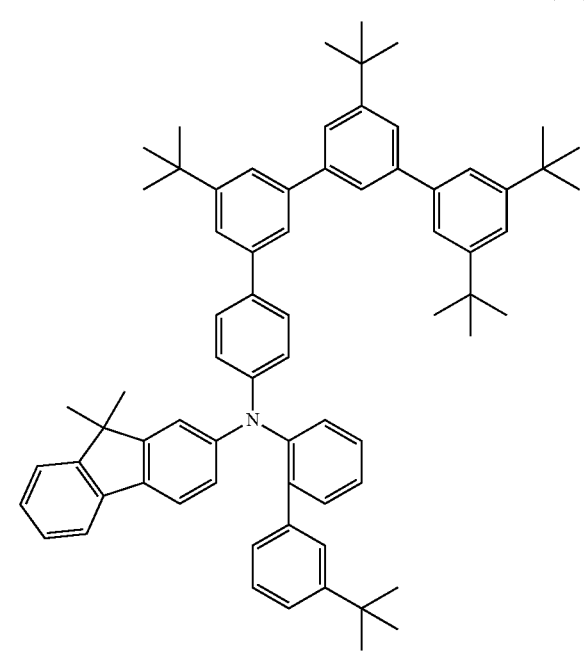

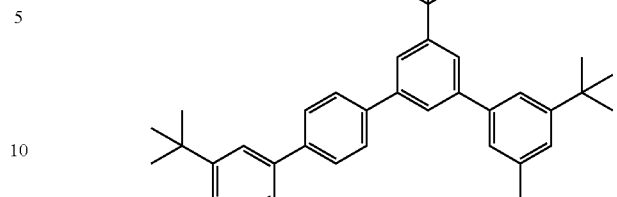
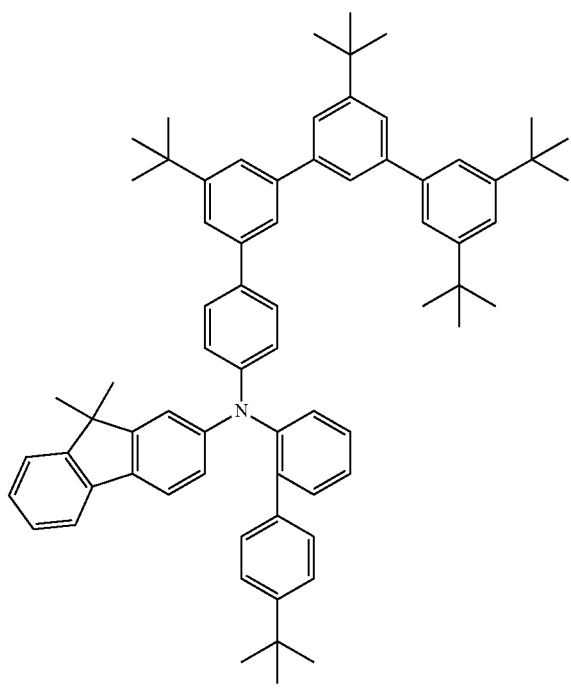
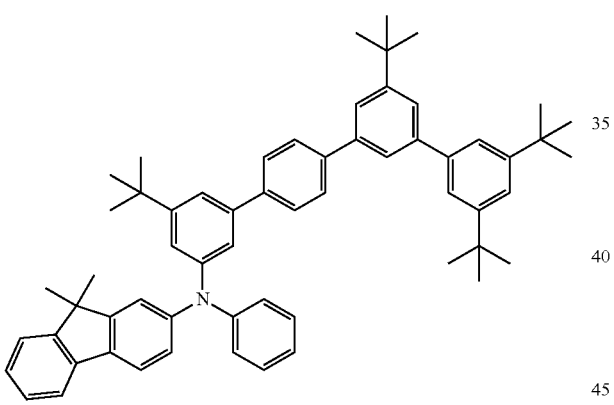
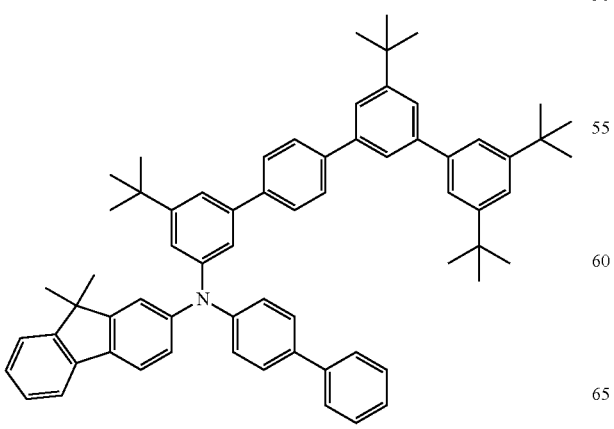
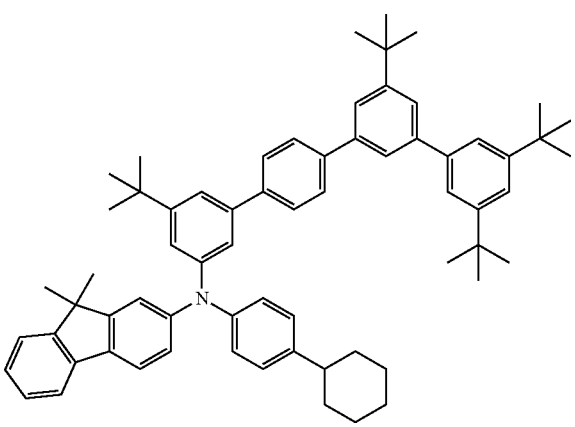

[Chemical Formula 26]
(278)
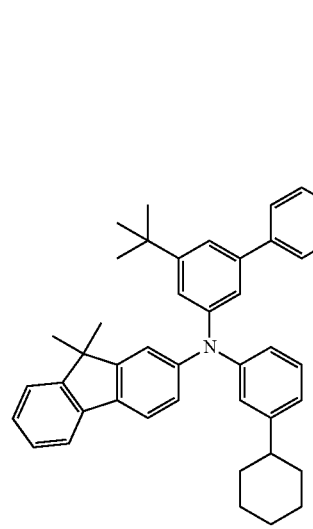
(279)
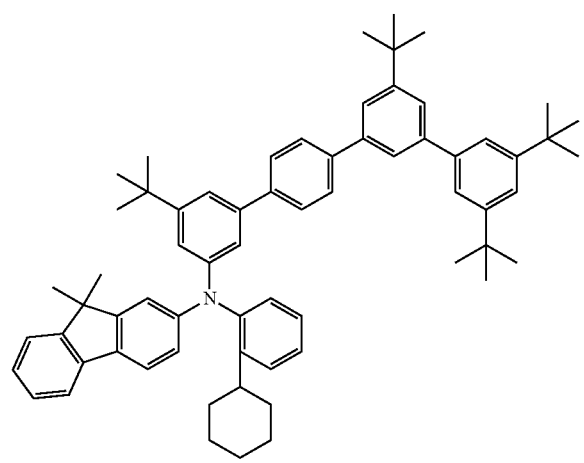
(280)
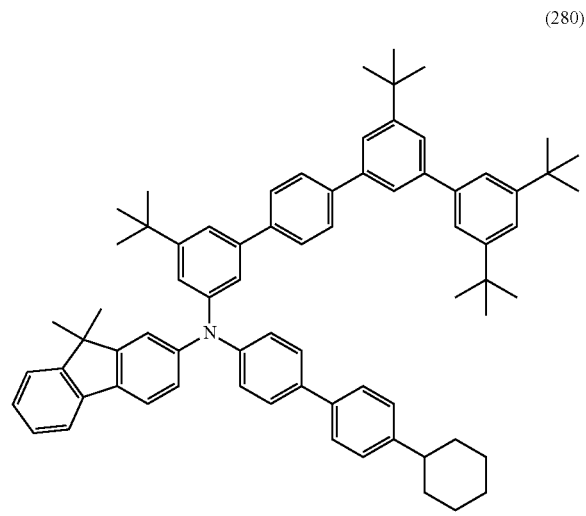
(281)
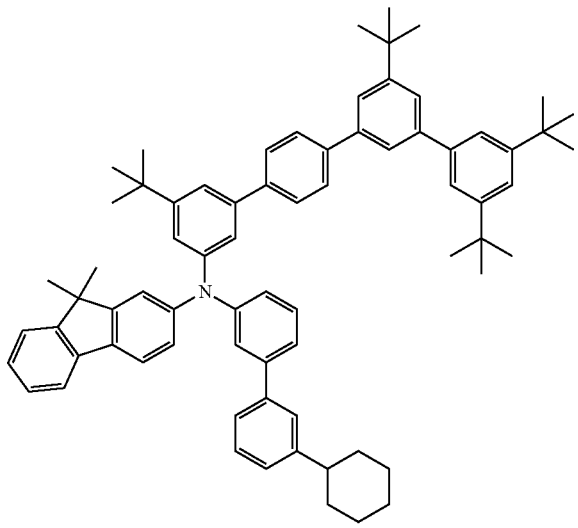
(282)
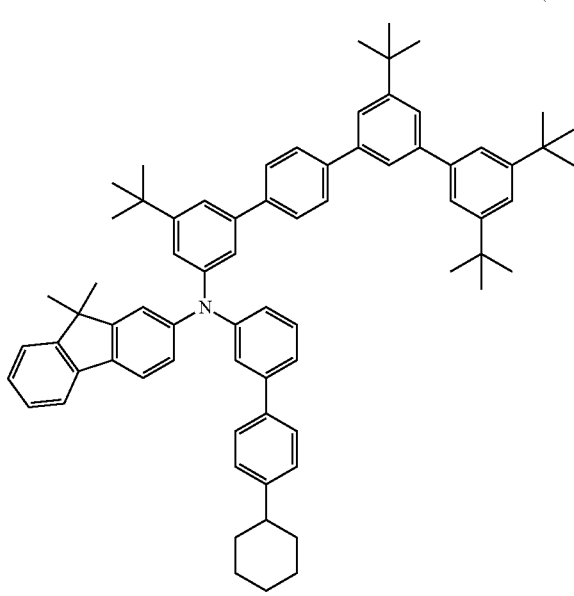
(283)
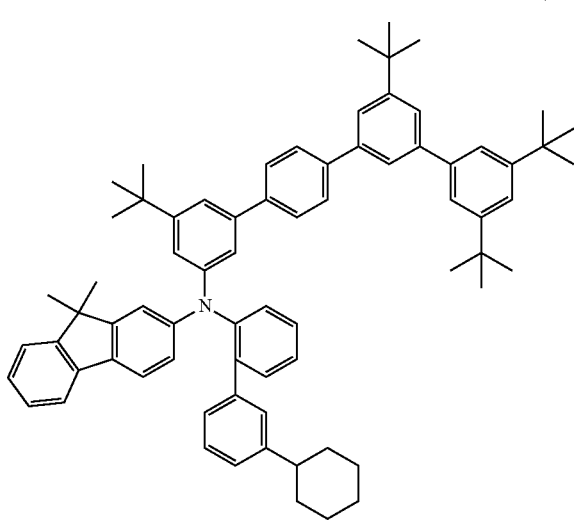

(284)
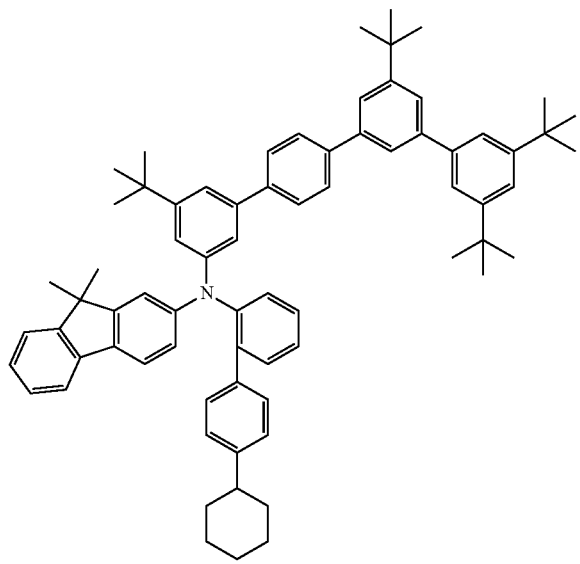
(285)
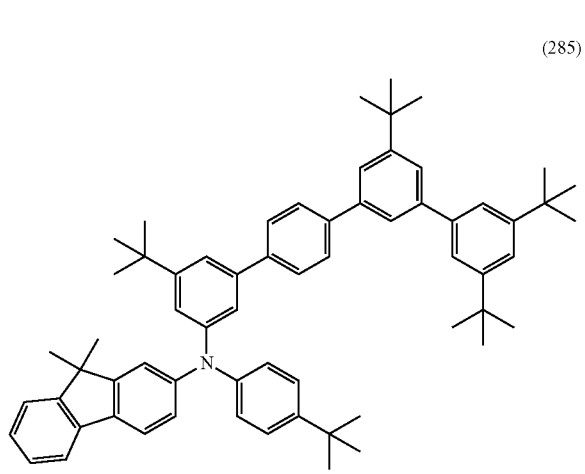
[Chemical Formula 27]
(286)
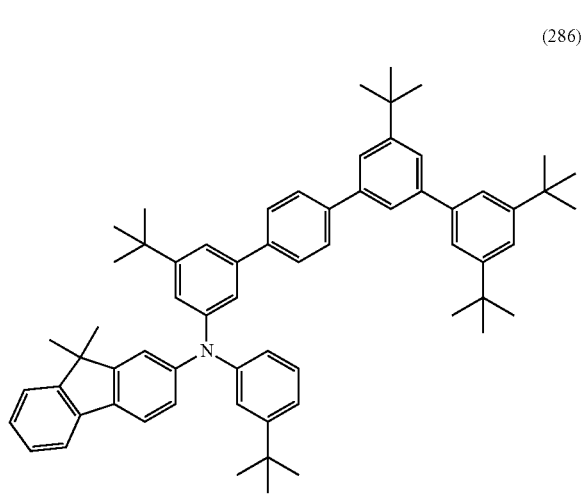
(287)
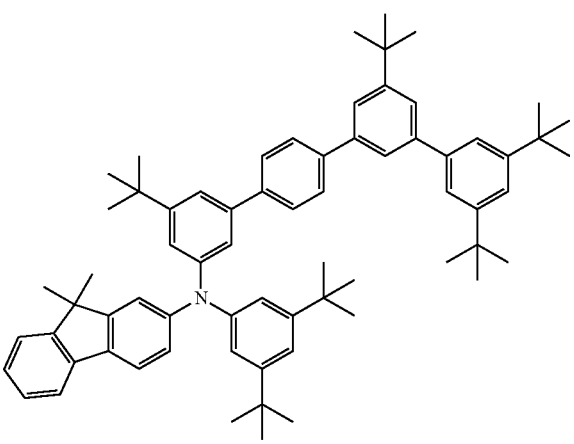
(288)
(289)
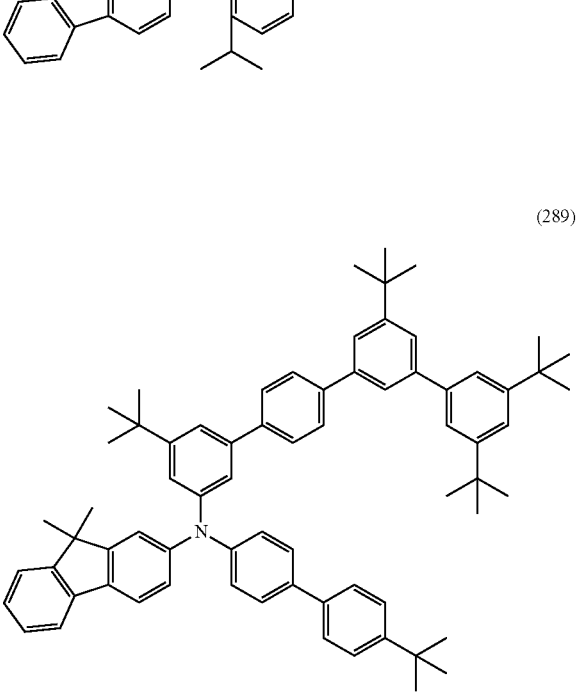

(290)
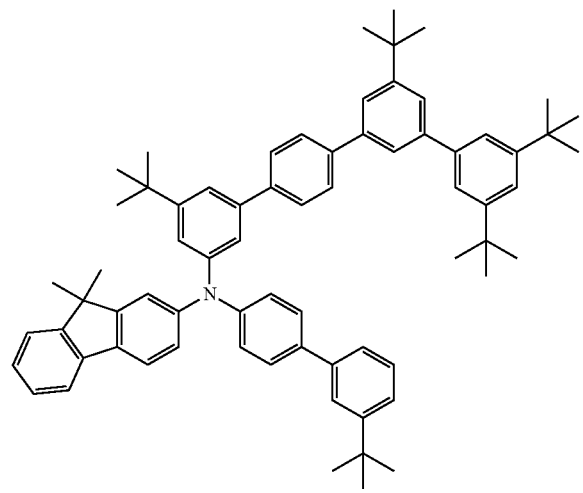
(293)
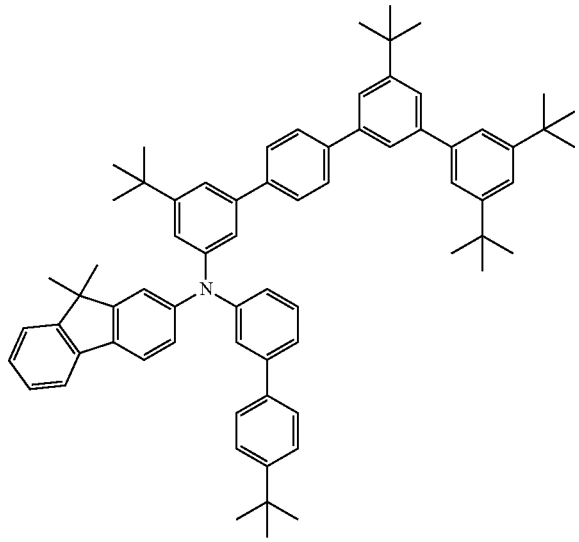
[Chemical Formula 28]
(291)
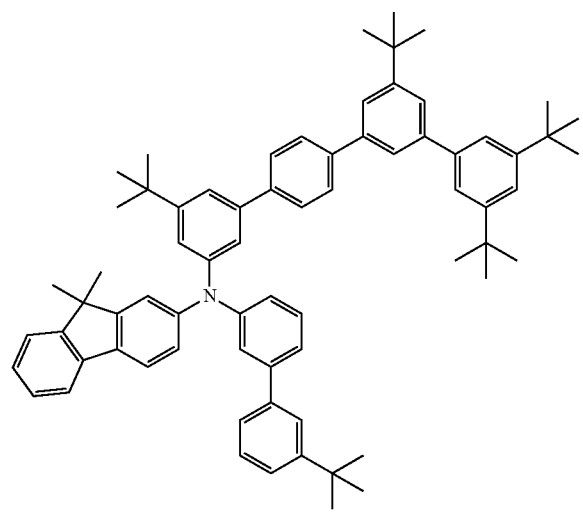
(294)
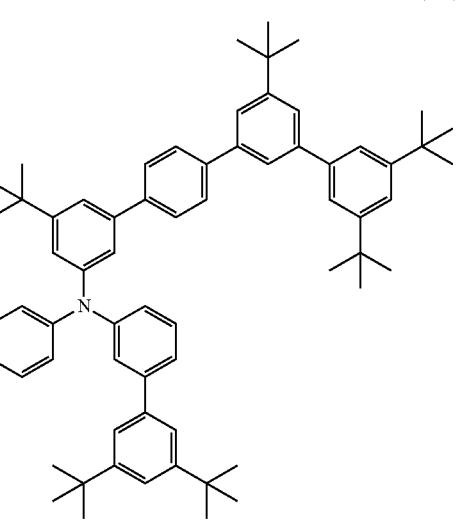
(292)
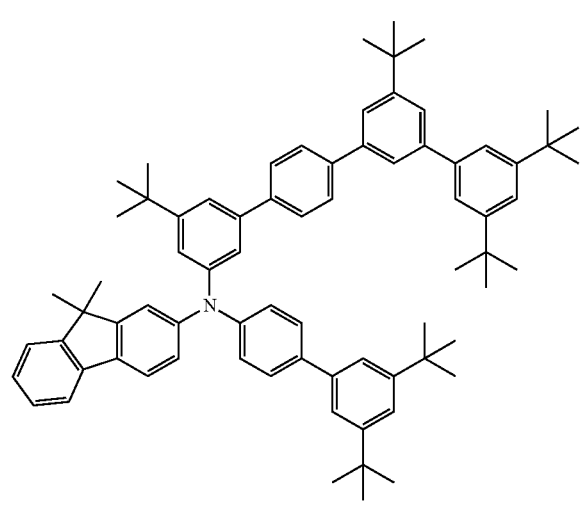
(295)
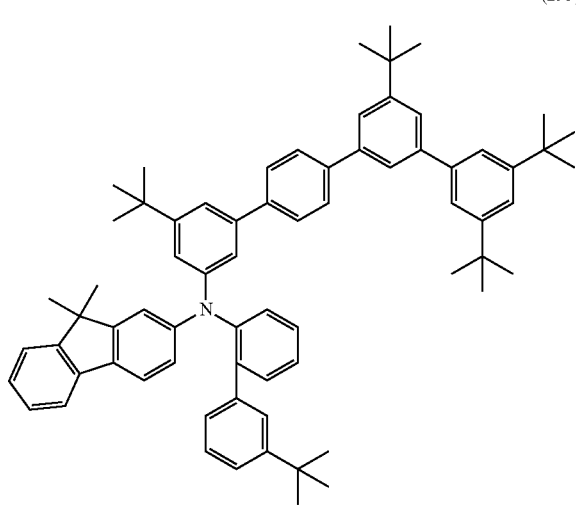

(296)
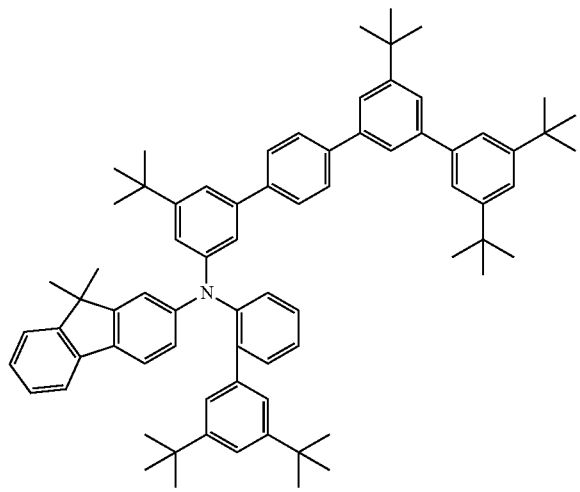
(297)
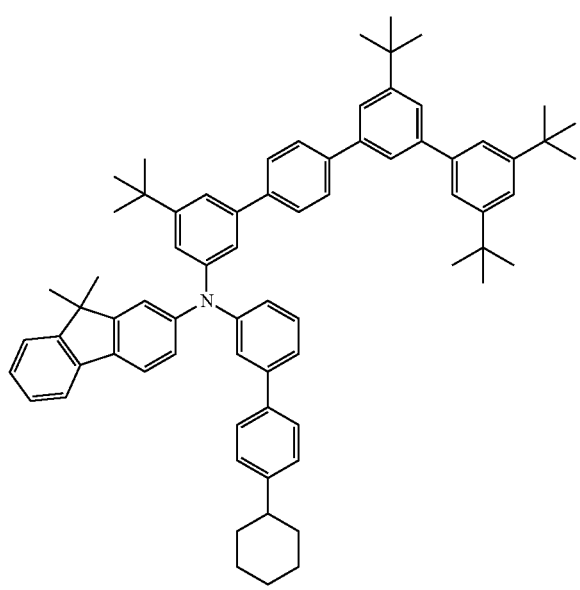
(298)
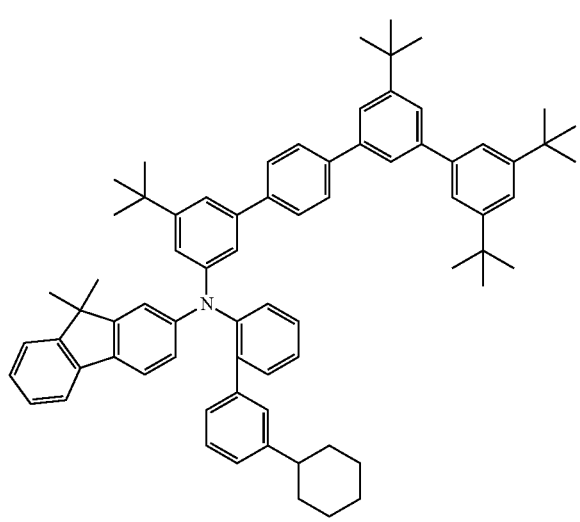
(299)
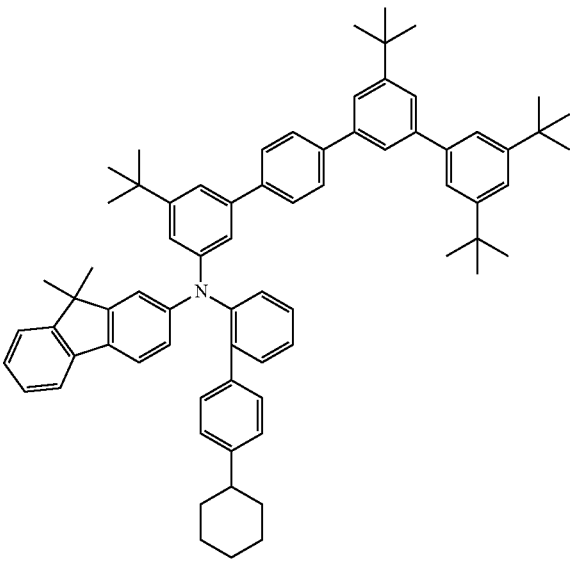
(300)
(301)
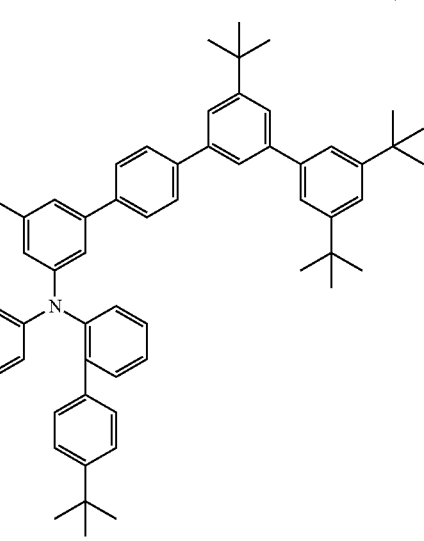

[Chemical Formula 29]
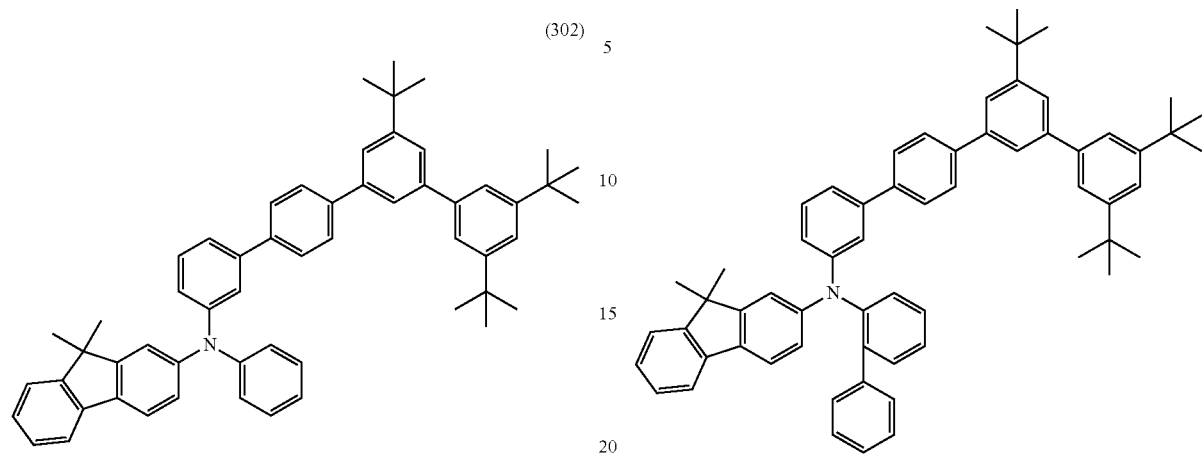
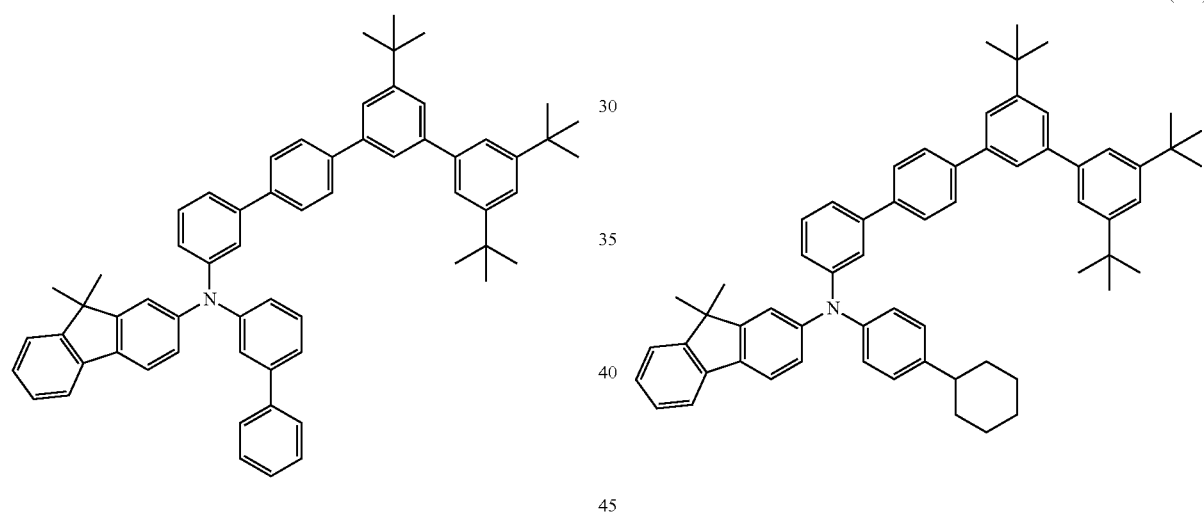

(308)
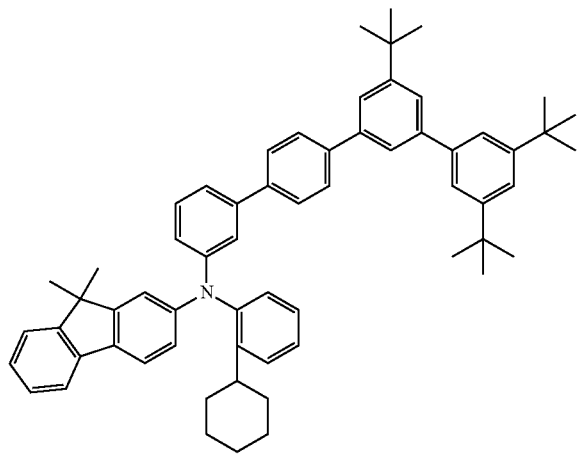
(309)
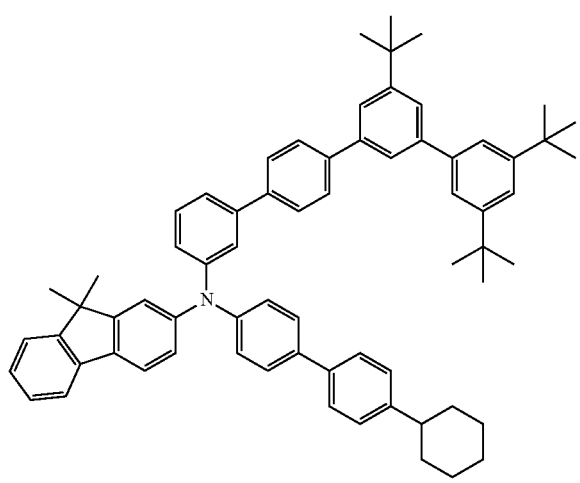
[Chemical Formula 30]
(310)
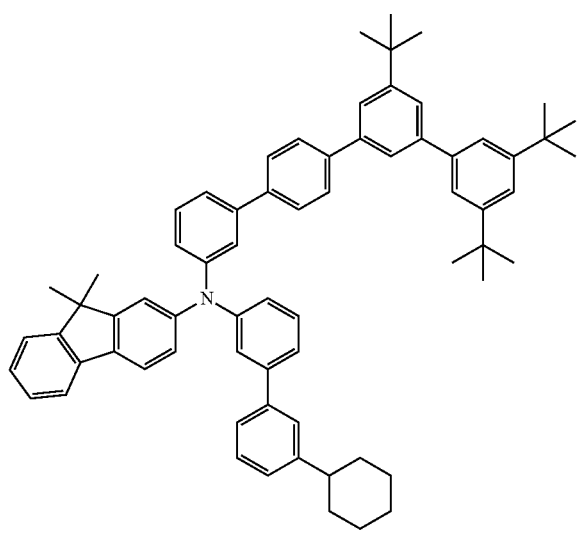
(311)
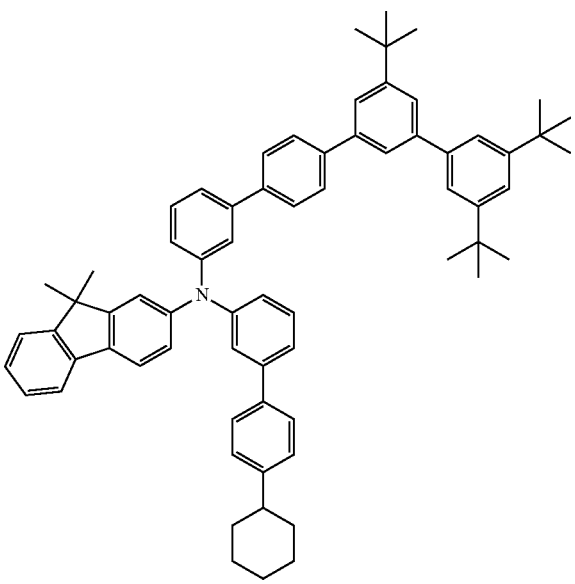
(312)
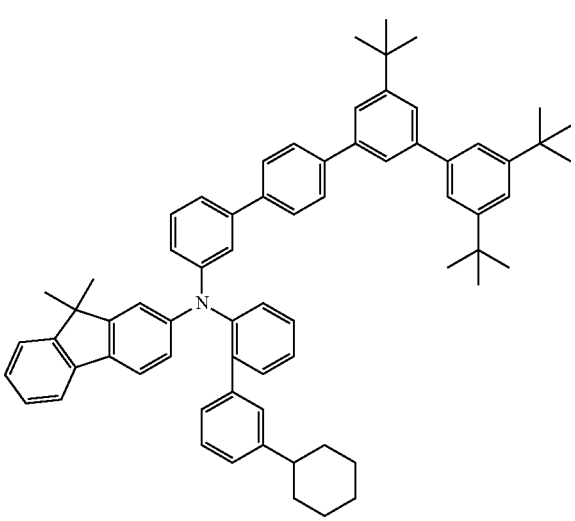

(313)
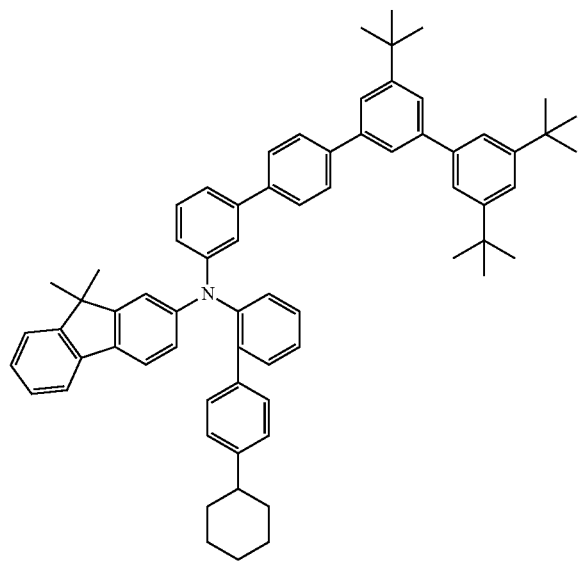
(314)
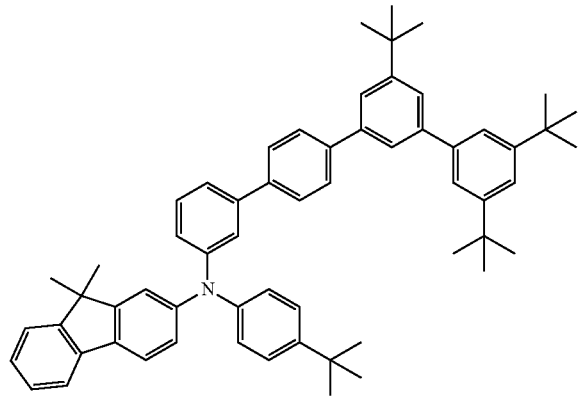
(315)
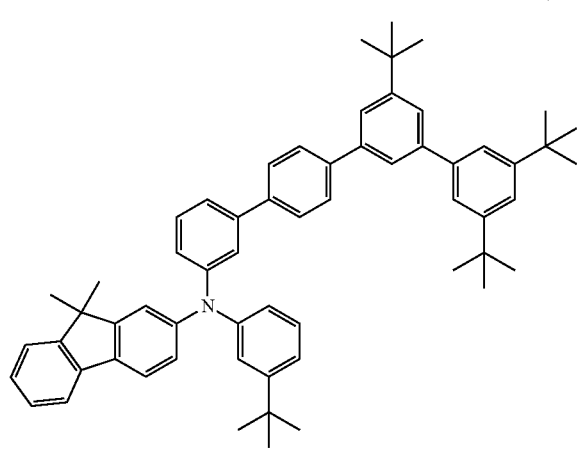
(316)
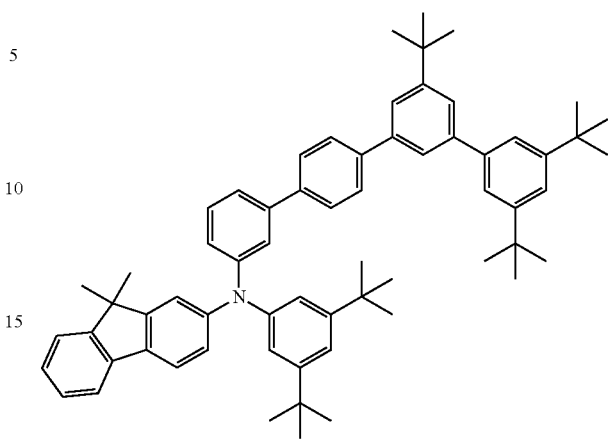
(317)
[Chemical Formula 31]
(318)
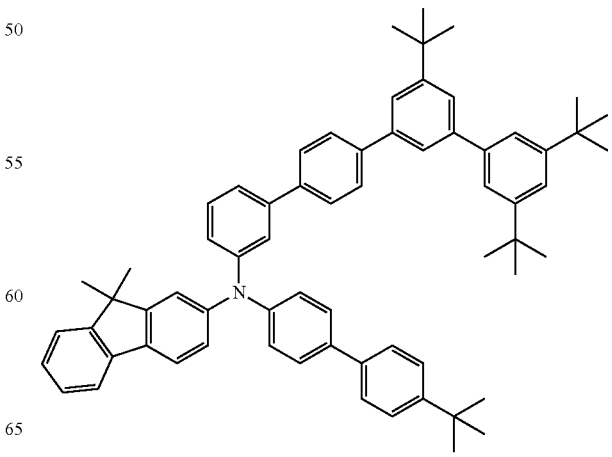

(319)
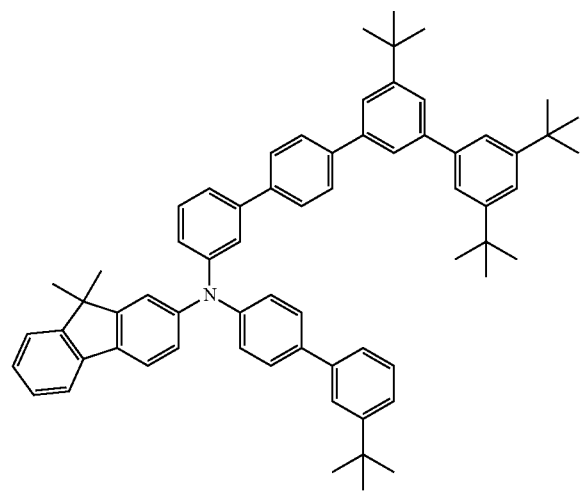
(320)
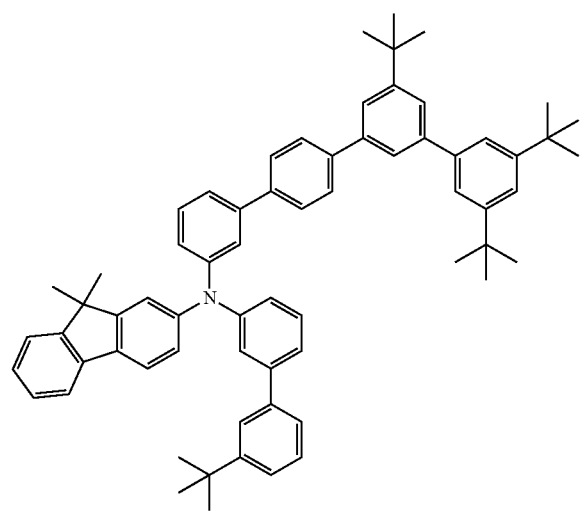
(321)
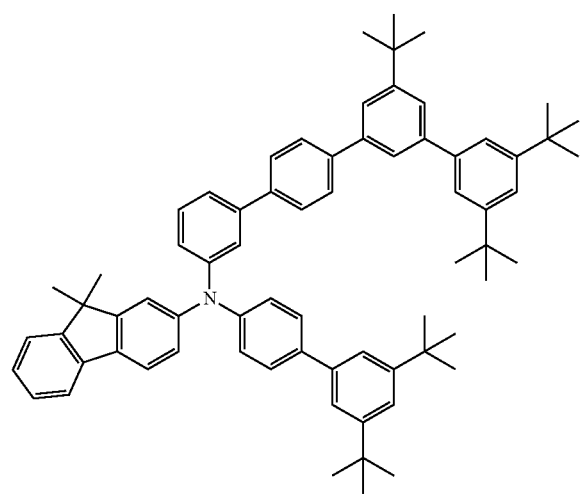
(322)
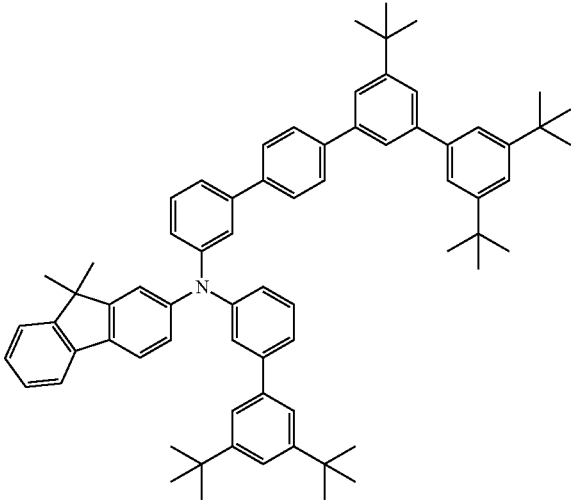
(323)

(324)
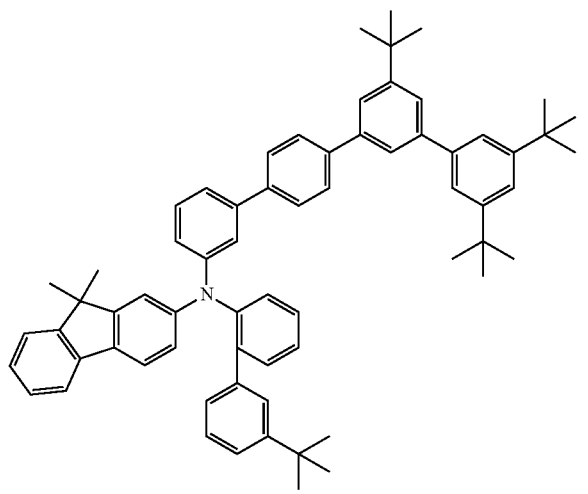
(326)
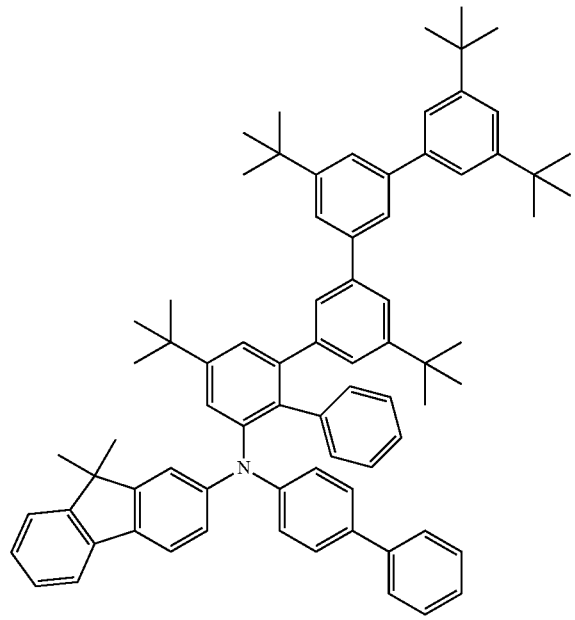
[Chemical Formula 32]
(325)
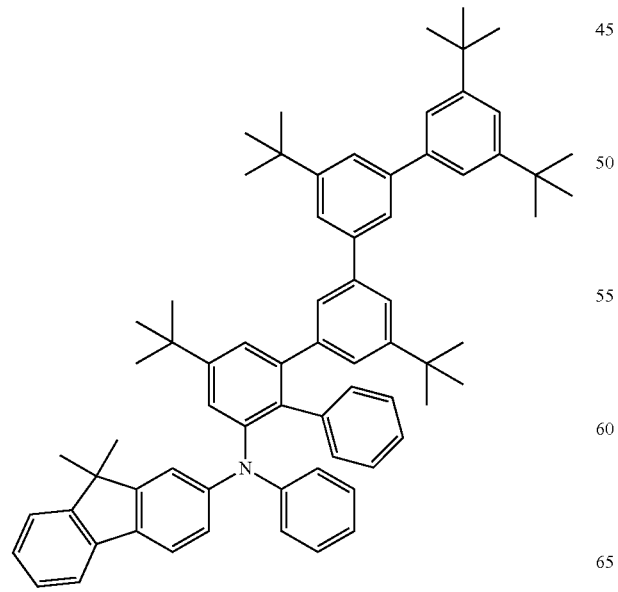
(327)

-continued
(328)
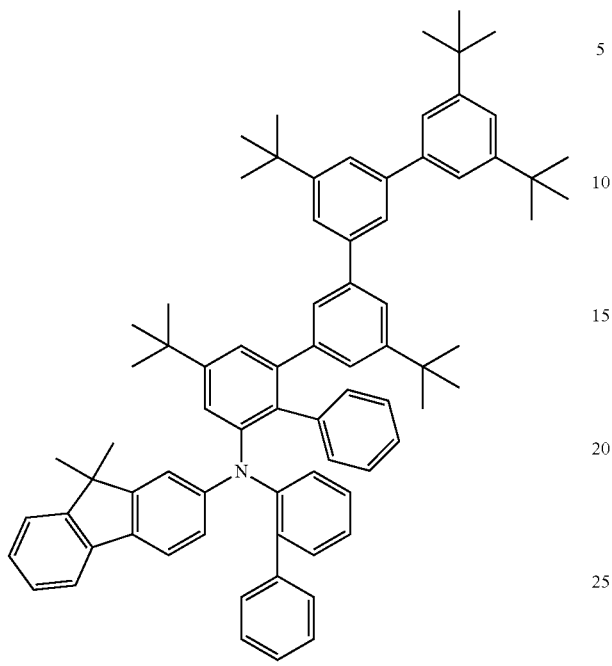
(329)
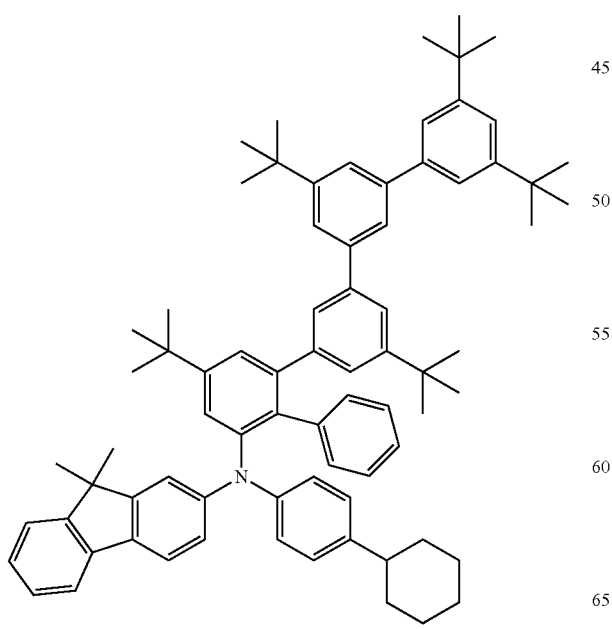
(330)
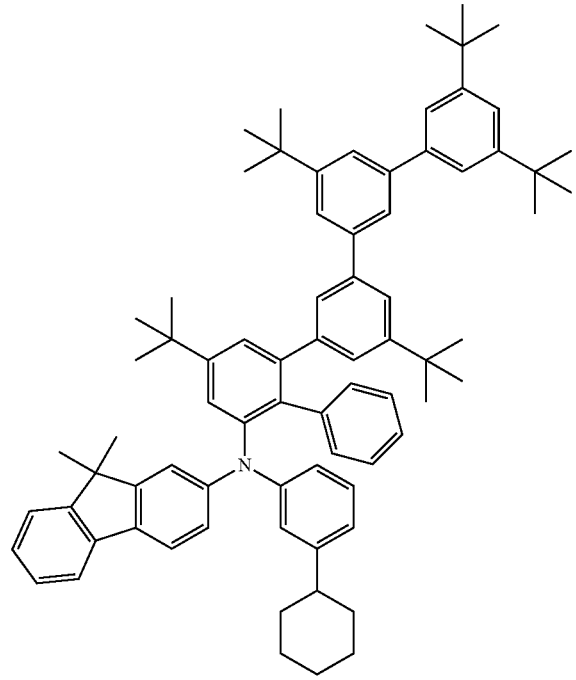
(331)
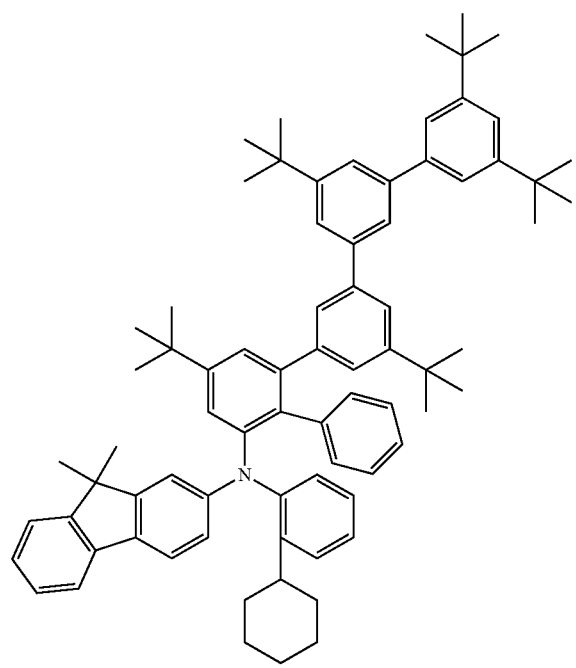

[Chemical Formula 33]
(332)
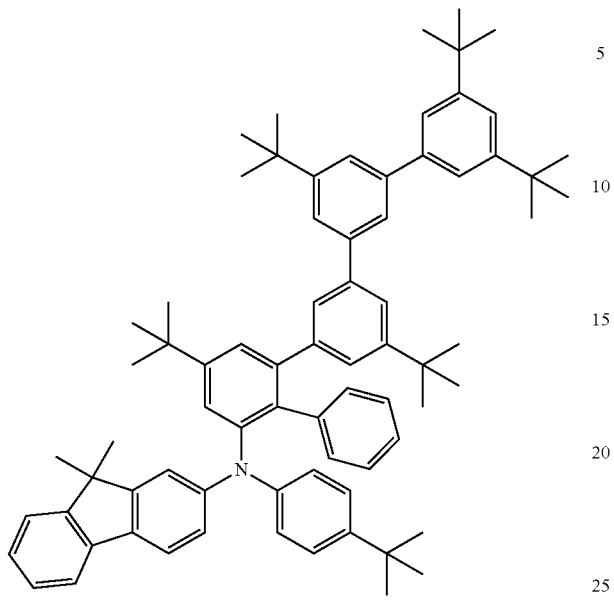
(334)
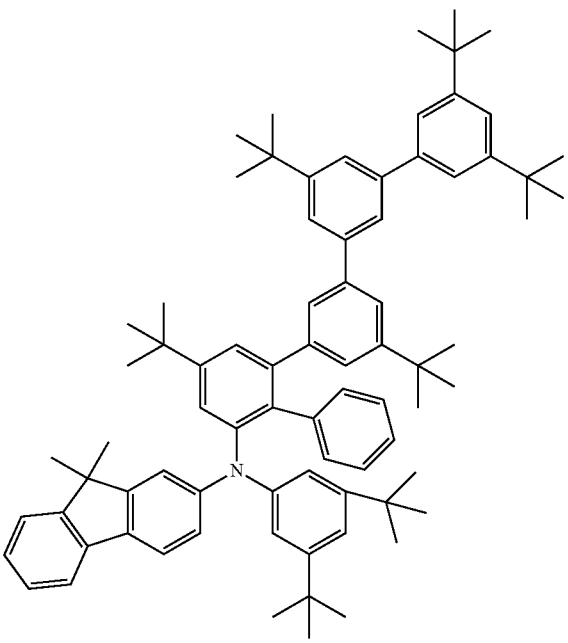
(333)
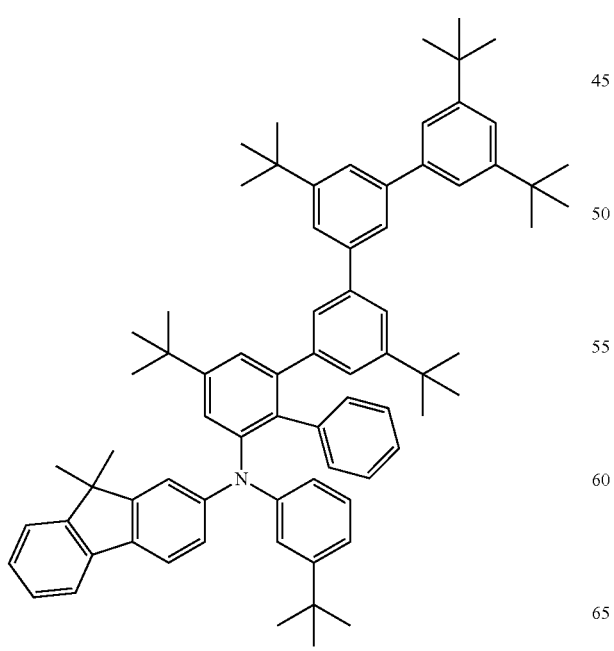
(335)
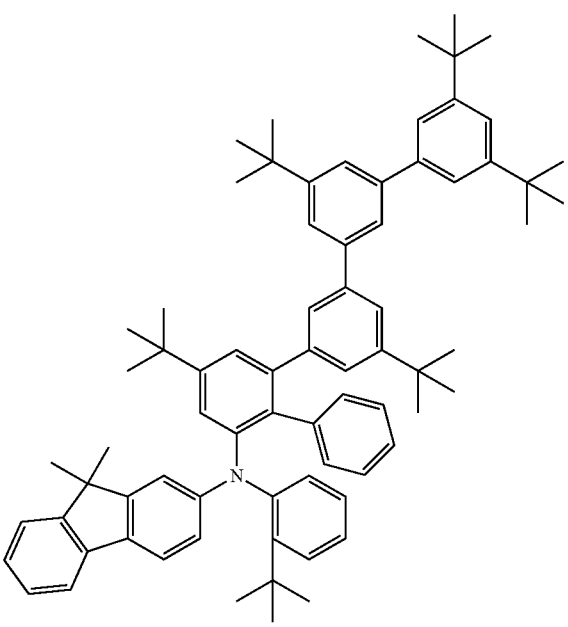

(336)
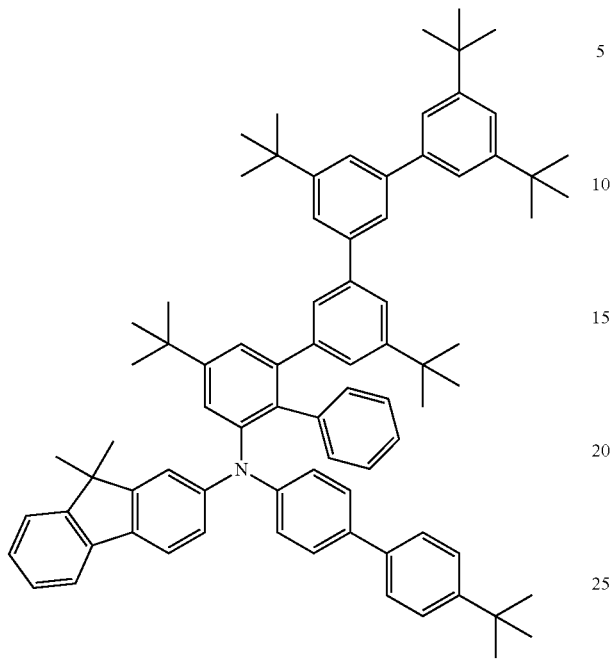
(338)
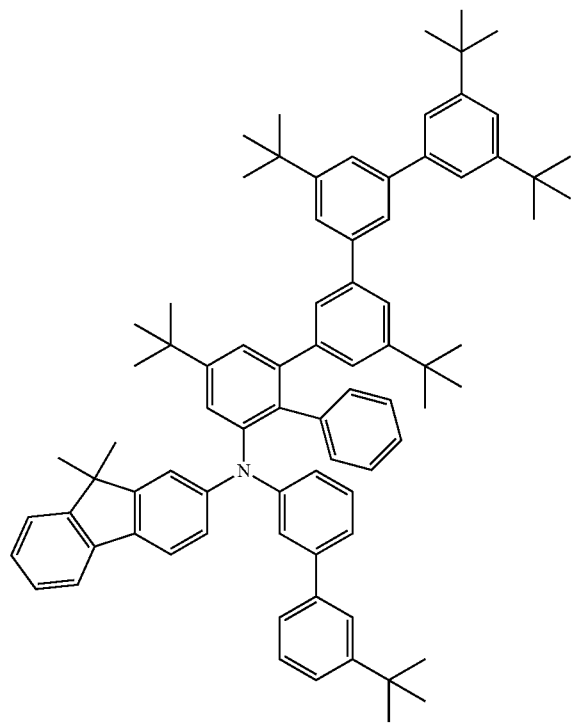
(337)
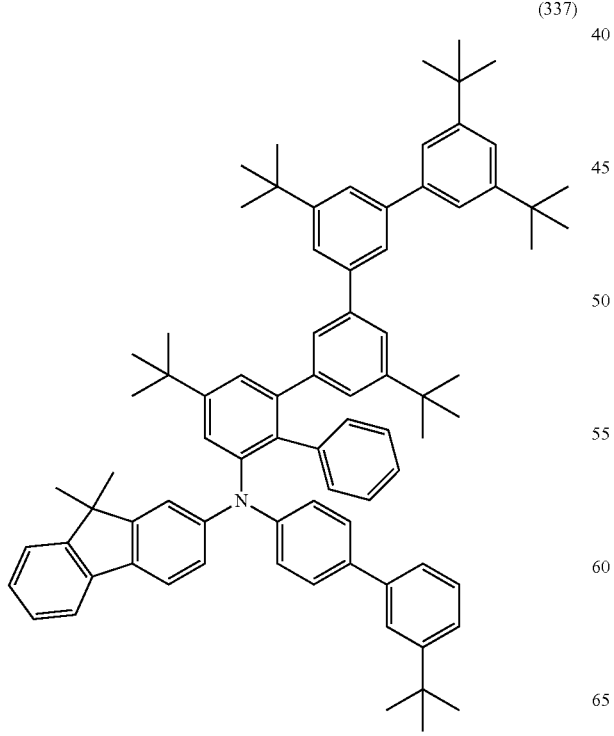
(339)
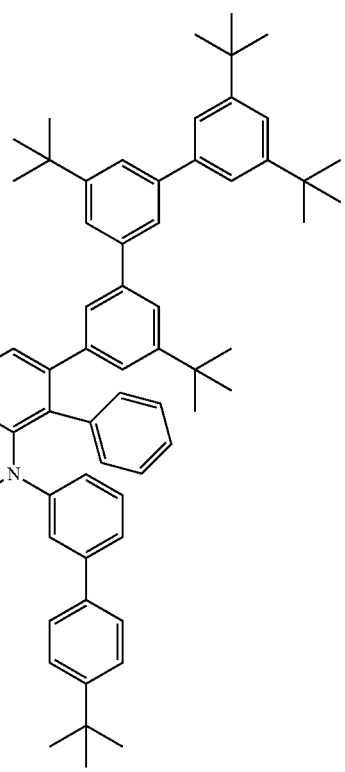

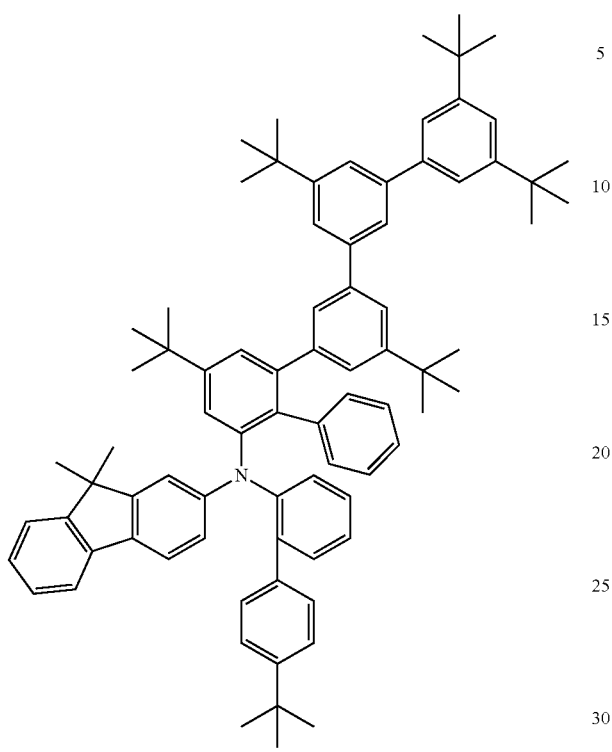
(340)
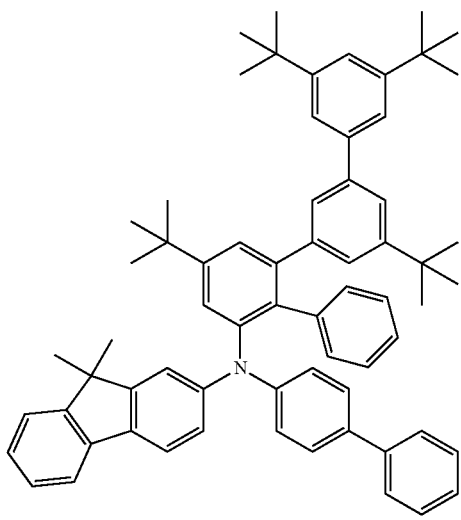
(342)
[Chemical Formula 34]
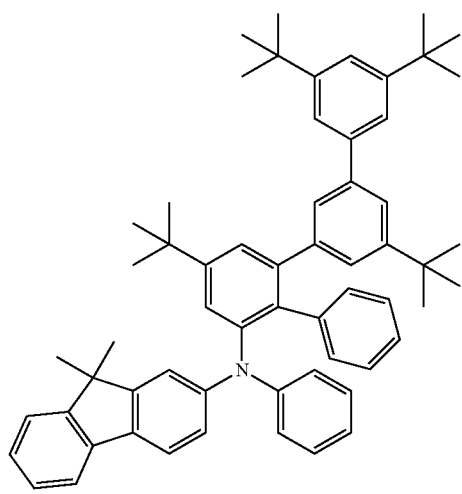
(341)
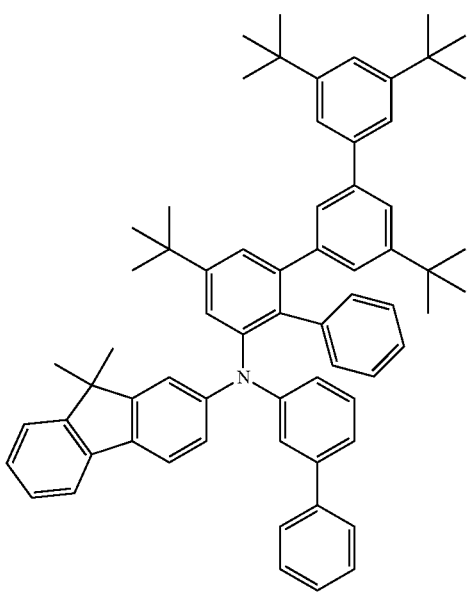
(343)

(344)
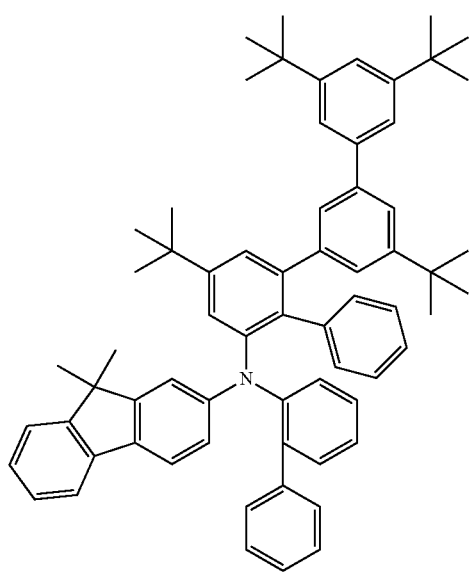
(345)
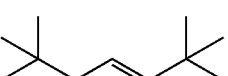
(346)
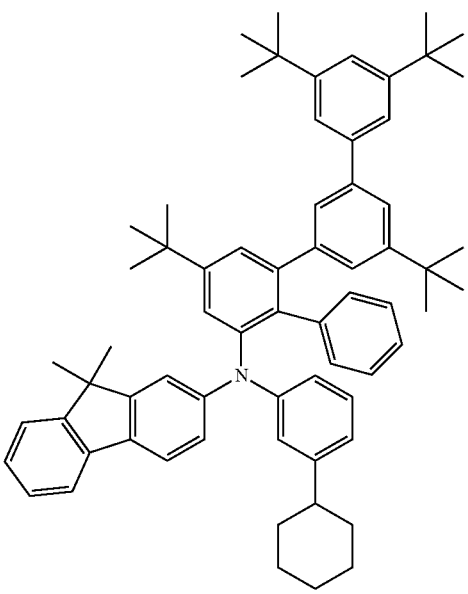
(347)
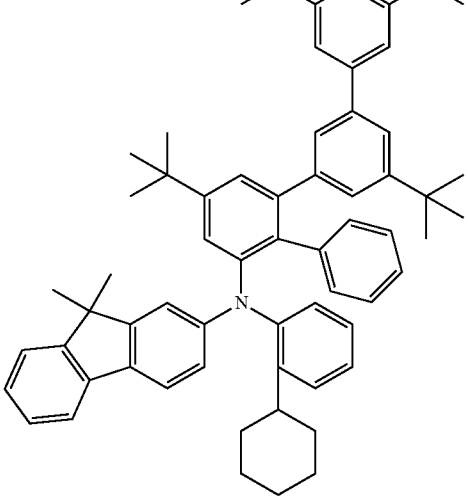
(348)
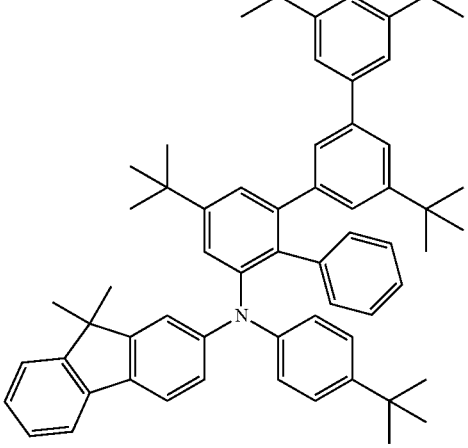

[Chemical Formula 35]
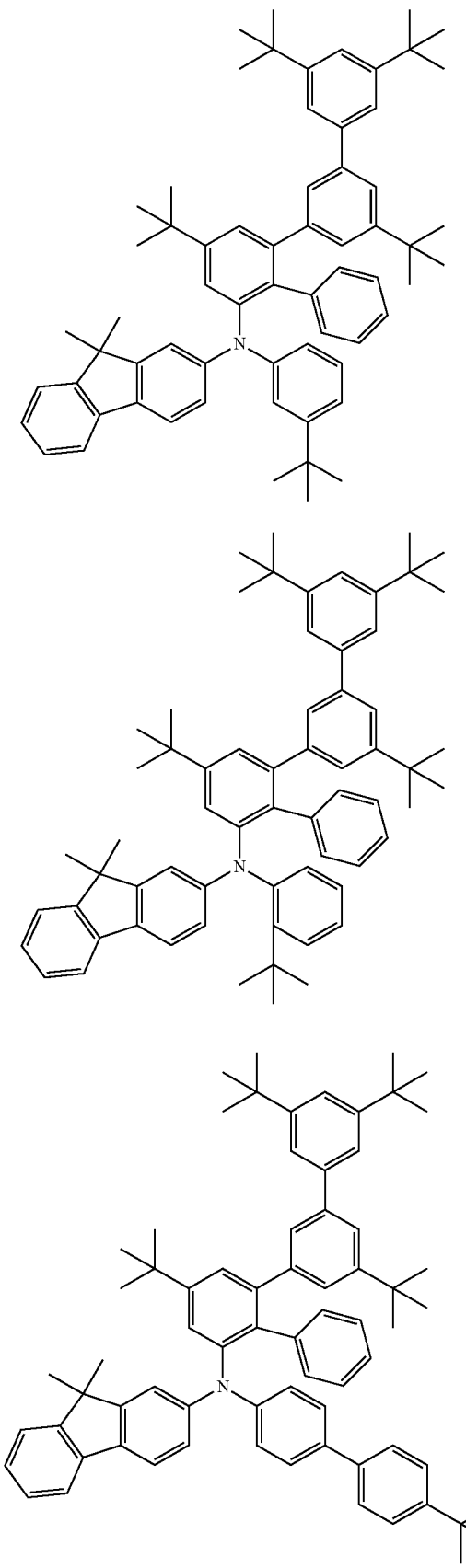
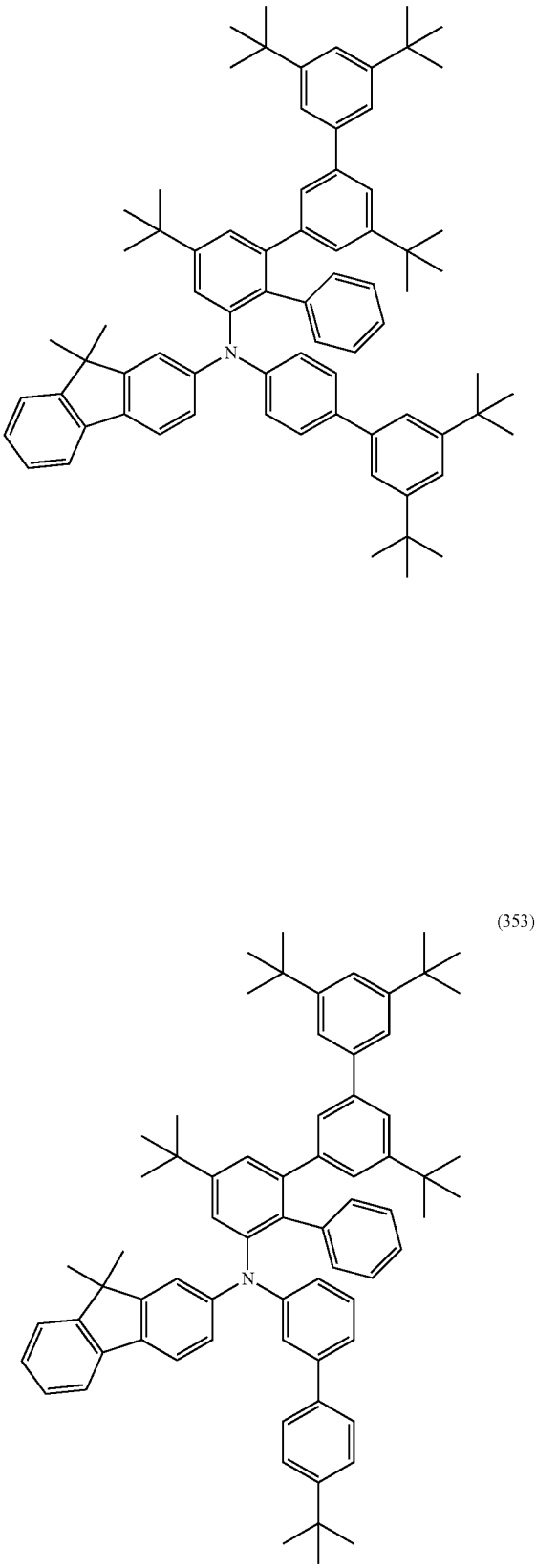

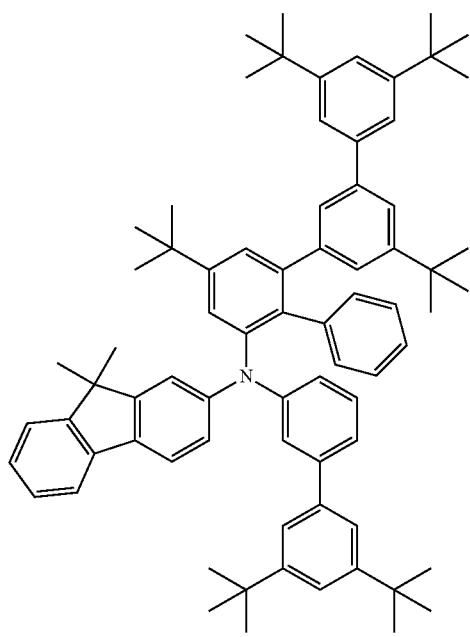
(354)
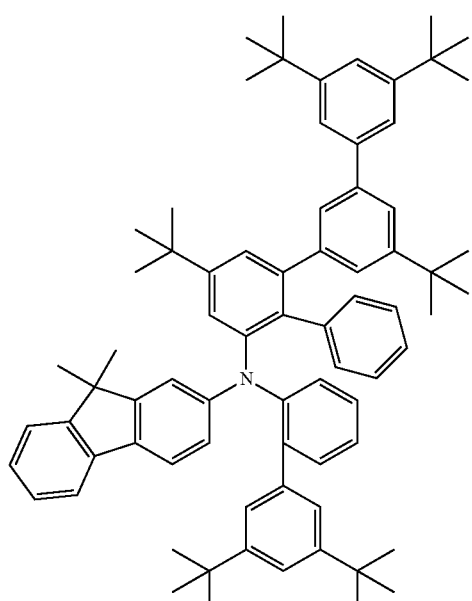
(356)
[Chemical Formula 36]
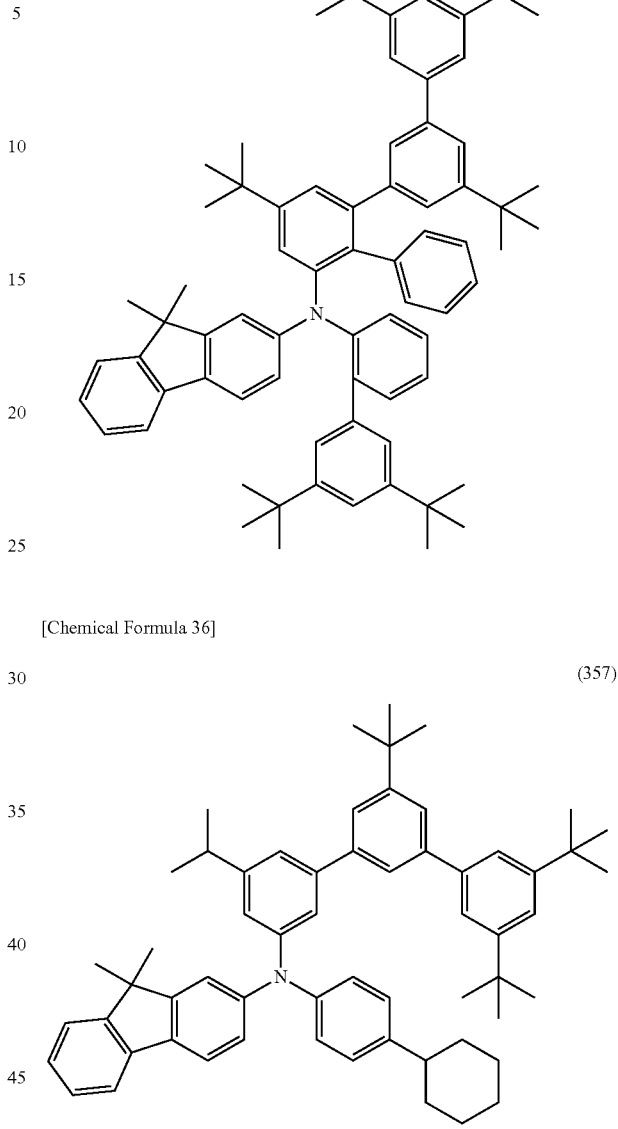
(357)
(358)
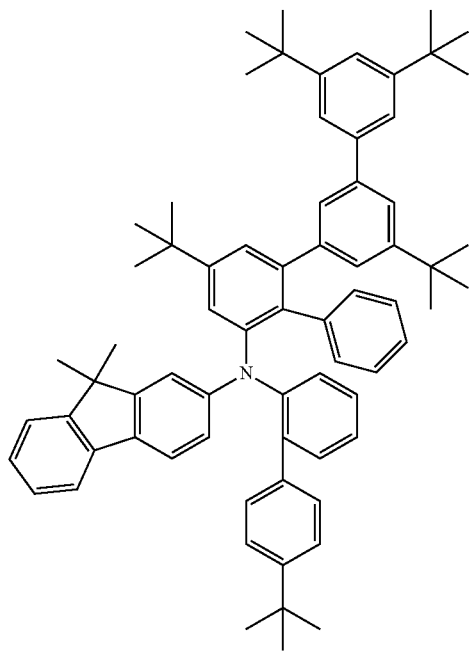
(355)

(359)
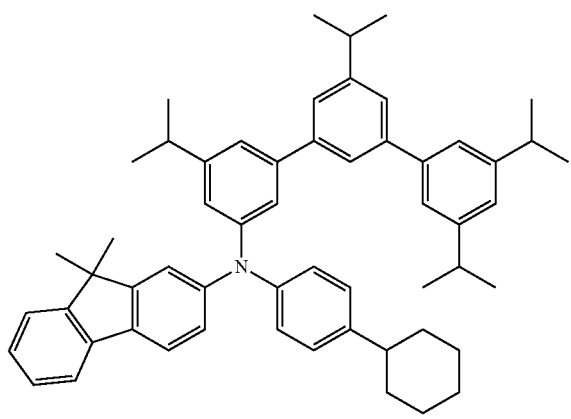

(340)
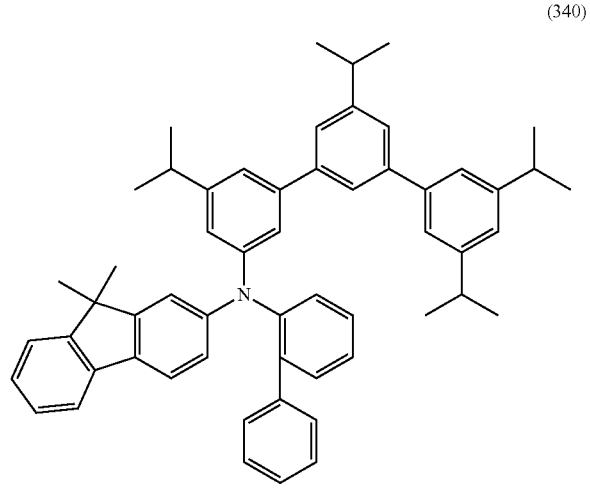

(341)
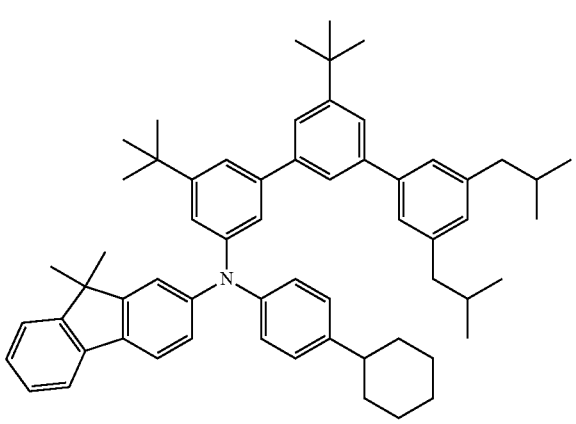

(342)
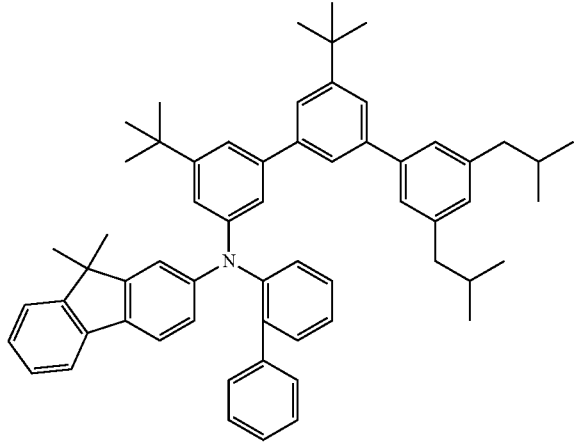

(343)
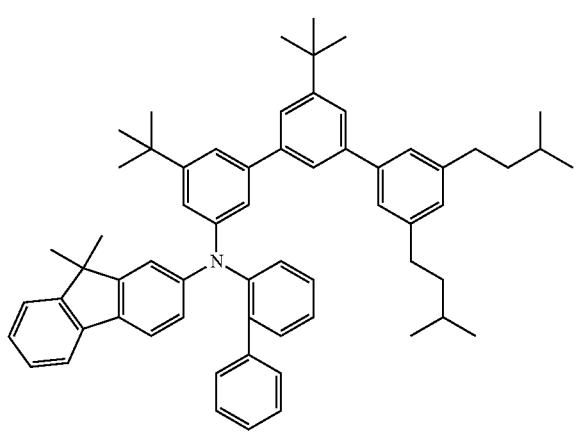

(344)

Embodiment 2

FIG. 1A illustrates a light-emitting device of one embodiment of the present invention. The light-emitting device of one embodiment of the present invention includes a first electrode 101, a second electrode 102, and an EL layer 103, and the organic compound described in Embodiment 1 is used for the EL layer.

The EL layer 103 includes a light-emitting layer 113 and may also include a hole-injection layer 111 and/or a hole-transport layer 112. The light-emitting layer 113 includes a light-emitting material, and light is emitted from the light-emitting material in the light-emitting device of one embodiment of the present invention. The light-emitting layer 113 may include a host material and other materials. The organic compound of one embodiment of the present invention described in Embodiment 1 may be included in any of the light-emitting layer 113, the hole-transport layer 112, and the hole-injection layer 111; alternatively, the organic compound may be included in all of them.

Note that FIG. 1A additionally illustrates an electron-transport layer 114 and an electron-injection layer 115; however, the structure of the light-emitting device is not limited thereto.

The organic compound exhibits a good hole-transport property and thus is effectively used for the hole-transport layer 112. Furthermore, a mixed film of the organic compound of one embodiment of the present invention and an acceptor substance can be used as the hole-injection layer 111.

In addition, the organic compound of one embodiment of the present invention can be used as a host material. Furthermore, the hole-transport material and an electron-transport material may be deposited by co-evaporation so that an exciplex is formed of the electron-transport material and the hole-transport material. The exciplex having an appropriate emission wavelength allows efficient energy transfer to the light-emitting material, achieving a light-emitting device with a high efficiency and a long lifetime.

Since the organic compound of one embodiment of the present invention has a low refractive index, the light-emitting device using the organic compound in its EL layer can have high external quantum efficiency.

Next, examples of specific structures and materials of the above-described light-emitting device will be described. As described above, the light-emitting device of one embodiment of the present invention includes, between the pair of electrodes of the first electrode 101 and the second electrode 102, the EL layer 103 including a plurality of layers; the EL layer 103 includes the organic compound disclosed in Embodiment 1 in any of the layers.

The first electrode 101 is preferably formed using any of metals, alloys, and conductive compounds with a high work function (specifically, higher than or equal to 4.0 eV), mixtures thereof, and the like. Specific examples include indium oxide-tin oxide (ITO: indium tin oxide), indium oxide-tin oxide containing silicon or silicon oxide, indium oxide-zinc oxide, and indium oxide containing tungsten oxide and zinc oxide (IWZO). Such conductive metal oxide films are usually formed by a sputtering method, but may be formed by application of a sol-gel method or the like. In an example of the formation method, indium oxide-zinc oxide is deposited by a sputtering method using a target obtained by adding 1 wt % to 20 wt % of zinc oxide to indium oxide. Furthermore, a film of indium oxide containing tungsten oxide and zinc oxide (IWZO) can be formed by a sputtering method using a target in which tungsten oxide and zinc oxide are added to indium oxide at 0.5 wt % to 5 wt % and 0.1 wt % to 1 wt %, respectively. Alternatively, gold (Au), platinum (Pt), nickel (Ni), tungsten (W), chromium (Cr), molybdenum (Mo), iron (Fe), cobalt (Co), copper (Cu), palladium (Pd), nitride of a metal material (e.g., titanium nitride), or the like can be used. Graphene can also be used. Note that when a composite material described later is used for a layer that is in contact with the first electrode 101 in the EL layer 103, an electrode material can be selected regardless of its work function.

Although the EL layer 103 preferably has a stacked-layer structure, there is no particular limitation on the stacked-layer structure, and various layers such as a hole-injection layer, a hole-transport layer, an electron-transport layer, an electron-injection layer, a carrier-blocking layer, an exciton-blocking layer, and a charge-generation layer can be employed. Two kinds of stacked-layer structure of the EL layer 103 are described: the structure illustrated in FIG. 1A, which includes the electron-transport layer 114 and the electron-injection layer 115 in addition to the hole-injection layer 111, the hole-transport layer 112, and the light-emitting layer 113; and the structure illustrated in FIG. 1B, which includes the electron-transport layer 114, the electron-injection layer 115, and a charge-generation layer 116 in addition to the hole-injection layer 111, the hole-transport layer 112, and the light-emitting layer 113. Materials for forming each layer will be specifically described below.

The hole-injection layer 111 contains a substance having an acceptor property. Either an organic compound or an inorganic compound can be used as the substance having an acceptor property.

As the substance having an acceptor property, it is possible to use a compound having an electron-withdrawing group (a halogen group or a cyano group); for example, 7,7,8,8-tetracyano-2,3,5,6-tetrafluoroquinodimethane (abbreviation: $F_4$-TCNQ), chloranil, 2,3,6,7,10,11-hexacyano-1,4,5,8,9,12-hexaazatriphenylene (abbreviation: HAT-CN), 1,3,4,5,7,8-hexafluorotetracyano-naphthoquinodimethane (abbreviation: F6-TCNNQ), or 2-(7-dicyanomethylene-1,3,4,5,6,8,9,10-octafluoro-7F7-pyren-2-ylidene)malononitrile can be used. A compound in which electron-withdrawing groups are bonded to a condensed aromatic ring having a plurality of heteroatoms, such as HAT-CN, is particularly preferable because it is thermally stable. A [3]radialene derivative having an electron-withdrawing group (in particular, a cyano group or a halogen group such as a fluoro group) has a very high electron-accepting property and thus is preferable. Specific examples include $\alpha,\alpha',\alpha''$-1,2,3-cyclopropanetriylidenetris[4-cyano-2,3,5,6-tetrafluorobenzeneacetonitrile], $\alpha,\alpha',\alpha''$-1,2,3-cyclopropanetriylidenetris[2,6-dichloro-3,5-difluoro-4-(trifluoromethyl)benzeneacetonitrile], and $\alpha,\alpha',\alpha''$-1,2,3-cyclopropanetriylidenetris[2,3,4,5,6-pentafluorobenzeneacetonitrile]. As the substance having an acceptor property, molybdenum oxide, vanadium oxide, ruthenium oxide, tungsten oxide, manganese oxide, or the like can be used, other than the above-described organic compounds. Alternatively, the hole-injection layer 111 can be formed using a phthalocyanine-based complex compound such as phthalocyanine (abbreviation: $H_2Pc$) and copper phthalocyanine (CuPc), an aromatic amine compound such as 4,4'-bis[N-(4-diphenylaminophenyl)-N-phenylamino]biphenyl (abbreviation: DPAB) and N,N'-bis{4-[bis(3-methylphenyl)amino]phenyl}-N,N-diphenyl-(1,1'-biphenyl)-4,4'-diamine (abbreviation: DNTPD), or a high molecular compound such as poly(3,4-ethylenedioxythiophene)/poly(styrenesulfonic acid) (PEDOT/PSS). The substance having an acceptor property can extract electrons from an adjacent hole-transport layer (or hole-transport material) by the application of an electric field.

Alternatively, a composite material in which a material having a hole-transport property contains any of the aforementioned substances having an acceptor property can be used for the hole-injection layer 111. By using a composite material in which a material having a hole-transport property contains an acceptor substance, a material used to form an electrode can be selected regardless of its work function. In other words, besides a material having a high work function, a material having a low work function can be used for the first electrode 101.

As the material having a hole-transport property used for the composite material, any of a variety of organic compounds such as aromatic amine compounds, carbazole derivatives, aromatic hydrocarbons, and high molecular compounds (e.g., oligomers, dendrimers, or polymers) can be used. Note that the material having a hole-transport property used for the composite material preferably has a hole mobility of $1 \times 10^{-6}$ cm$^2$/Vs or higher. Organic compounds which can be used as the material having a hole-transport property in the composite material are specifically given below.

Examples of the aromatic amine compounds that can be used for the composite material include N,N-di(p-tolyl)-N,N-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-diphenyl-(1,1'-biphenyl)-4,4'-diamine (abbreviation: DNTPD), and 1,3,5-tris[N-(4-diphenylaminophenyl)-N-phenylamino]benzene (abbreviation: DPA3B). Specific examples of the carbazole derivative include 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), 4,4'-di(N-carbazolyl)biphenyl (abbreviation: CBP), 1,3,5-tris[4-(N-carbazolyl)phenyl]benzene (abbreviation: TCPB), 9-[4-(10-phenylanthracen-9-yl)phenyl]-9H-carbazole (abbreviation: CzPA), and 1,4-bis[4-(N-carbazolyl)phenyl]-2,3,5,6-tetraphenylbenzene.
Examples of the aromatic hydrocarbon include 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, and 2,5,8,11-tetra(tert-butyl)perylene. Other examples include pentacene and coronene. The aromatic hydrocarbon may have a vinyl skeleton. Examples of the aromatic hydrocarbon having a vinyl group include 4,4'-bis(2,2-diphenylvinyl)biphenyl (abbreviation: DPVBi) and 9,10-bis[4-(2,2-diphenylvinyl)phenyl]anthracene (abbreviation: DPVPA). Note that the organic compound of one embodiment of the present invention can also be used.

Other examples include high molecular compounds such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine] (abbreviation: poly-TPD).

The material having a hole-transport property that is used in the composite material further preferably has any of a carbazole skeleton, a dibenzofuran skeleton, a dibenzothiophene skeleton, and an anthracene skeleton. In particular, an aromatic amine having a substituent that includes a dibenzofuran ring or a dibenzothiophene ring, an aromatic monoamine that includes a naphthalene ring, or an aromatic monoamine in which a 9-fluorenyl group is bonded to nitrogen of amine through an arylene group may be used. Note that the second organic compound having an N,N-bis(4-biphenyl)amino group is preferable because a light-emitting device having a long lifetime can be fabricated. Specific examples of the second organic compound include N-(4-biphenyl)-6,N-diphenylbenzo[b]naphtho[1,2-d]furan-8-amine (abbreviation: BnfABP), N,N-bis(4-biphenyl)-6-phenylbenzo[b]naphtho[1,2-d]furan-8-amine (abbreviation: BBABnf), 4,4'-bis(6-phenylbenzo[b]naphtho[1,2-d]furan-8-yl)-4"-phenyltriphenylamine (abbreviation: BnfBB1BP), N,N-bis(4-biphenyl)benzo[b]naphtho[1,2-d]furan-6-amine (abbreviation: BBABnf(6)), N,N-bis(4-biphenyl)benzo[b]naphtho[1,2-d]furan-8-amine (abbreviation: BBABnf(8)), N,N-bis(4-biphenyl)benzo[b]naphtho[2,3-d]furan-4-amine (abbreviation: BBABnf(II) (4)), N,N-bis[4-(dibenzofuran-4-yl)phenyl]-4-amino-p-terphenyl (abbreviation: DBfBB1TP), N-[4-(dibenzothiophen-4-yl)phenyl]-N-phenyl-4-biphenylamine (abbreviation: ThBA1BP), 4-(2-naphthyl)-4',4"-diphenyltriphenylamine (abbreviation: BBAβNB), 4-[4-(2-naphthyl)phenyl]-4',4"-diphenyltriphenylamine (abbreviation: BBAβNBi), 4,4'-diphenyl-4"-(6;1'-binaphthyl-2-yl)triphenylamine (abbreviation: BBAαNβNB), 4,4'-diphenyl-4"-(7;1'-binaphthyl-2-yl)triphenylamine (abbreviation: BBAαNβNB-03), 4,4'-diphenyl-4"-(7-phenyl)naphthyl-2-yltriphenylamine (abbreviation: BBAPβNB-03), 4,4'-diphenyl-4"-(6;2-binaphthyl-2-yl)triphenylamine (abbreviation: BBA(βN2)B), 4,4'-diphenyl-4"-(7;2'-binaphthyl-2-yl)triphenylamine (abbreviation: BBA(βN2)B-03), 4,4'-diphenyl-4"-(4;2'-binaphthyl-1-yl)triphenylamine (abbreviation: BBAβNαNB), 4,4'-diphenyl-4"-(5;2'-binaphthyl-1-yl)triphenylamine (abbreviation: BBAβNαNB-02), 4-(4-biphenylyl)-4'-(2-naphthyl)-4"-phenyltriphenylamine (abbreviation: TPBiAβNB), 4-(3-biphenylyl)-4'-[4-(2-naphthyl)phenyl]-4"-phenyltriphenylamine (abbreviation: mTPBiAβNBi), 4-(4-biphenylyl)-4'-[4-(2-naphthyl)phenyl]-4"-phenyltriphenylamine (abbreviation: TPBiAβNBi), 4-phenyl-4'-(1-naphthyl)triphenylamine (abbreviation: αNBA1BP), 4,4'-bis(1-naphthyl)triphenylamine (abbreviation: αNBB1BP), 4,4'-diphenyl-4"-[4'-(carbazol-9-yl)biphenyl-4-yl]triphenylamine (abbreviation: YGTBi1BP), 4'-[4-(3-phenyl-9H-carbazol-9-yl)phenyl]tris(1,1'-biphenyl-4-yl)amine (abbreviation: YGTBi1BP-02), 4-[4'-(carbazol-9-yl)biphenyl-4-yl]-4'-(2-naphthyl)-4"-phenyltriphenylamine (abbreviation: YGTBiβNB), N-[4-(9-phenyl-9H-carbazol-3-yl)phenyl]-N-[4-(1-naphthyl)phenyl]-9,9'-spirobi[9H-fluoren]-2-amine (abbreviation: PCBNBSF), N,N-bis([1,1'-biphenyl]-4-yl)-9,9'-spirobi[9H-fluoren]-2-amine (abbreviation: BBASF), N,N-bis([1,1'-biphenyl]-4-yl)-9,9'-spirobi[9H-fluoren]-4-amine (abbreviation: BBASF(4)), N-(1,1'-biphenyl-2-yl)-N-(9,9-dimethyl-9H-fluoren-2-yl)-9,9'-spirobi[9H-fluoren]-4-amine (abbreviation: oFBiSF), N-(4-biphenyl)-N-(9,9-dimethyl-9H-fluoren-2-yl)dibenzofuran-4-amine (abbreviation: FrBiF), N-[4-(1-naphthyl)phenyl]-N-[3-(6-phenyldibenzofuran-4-yl)phenyl]-1-naphthylamine (abbreviation: mPDBfBNBN), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-[4-(9-phenylfluoren-9-yl)phenyl]triphenylamine (abbreviation: BPAFLBi), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), N-phenyl-N-[4-(9-phenyl-9H-carbazol-3-yl)phenyl]-9,9'-spirobi[9H-fluoren]-2-amine (abbreviation: PCBASF), N-(1,1'-biphenyl-4-yl)-9,9-dimethyl-N-[4-(9-phenyl-9H-carbazol-3-yl)phenyl]-9H-fluoren-2-amine (abbreviation: PCBBiF), N,N-bis(9,9-dimethyl-9H-fluoren-2-yl)-9,9'-spirobi-9H-fluoren-4-amine, N,N-bis(9,9-dimethyl-9H-fluoren-2-yl)-9,9'-spirobi-9H-fluoren-3-amine, N,N-bis(9,9-dimethyl-9H-fluoren-2-yl)9,9'-spirobi-9H-fluoren-2-amine, and N,N-bis(9,9-dimethyl-9H-fluoren-2-yl)-9,9'-spirobi-9H-fluoren-1-amine.

Note that it is further preferable that the material having a hole-transport property to be used in the composite material have a relatively deep HOMO level of greater than or equal to −5.7 eV and lower than or equal to −5.4 eV. Using the material with a hole-transport property which has a relatively deep HOMO level in the composite material makes it easy to inject holes into the hole-transport layer 112 and to obtain a light-emitting device having a long lifetime.

Note that the monoamine compound described in Embodiment 1 also has a hole-transport property, and thus can be suitably used as the material for a hole-injection layer used in the composite material. A layer with a low refractive index can be formed in the EL layer 103 with the use of the monoamine compound described in Embodiment 1, leading to higher external quantum efficiency of the light-emitting device.

Note that mixing the above composite material with a fluoride of an alkali metal or an alkaline earth metal (the proportion of fluorine atoms in a layer using the mixed material is preferably greater than or equal to 20%) can lower the refractive index of the layer. This also enables a layer with a low refractive index to be formed in the EL layer 103, leading to higher external quantum efficiency of the light-emitting device.

The formation of the hole-injection layer 111 can improve the hole-injection property, which allows the light-emitting device to be driven at a low voltage. In addition, the organic compound having an acceptor property is easy to use because it is easily deposited by vapor deposition.

The hole-transport layer 112 is formed using a material having a hole-transport property. The material having a hole-transport material preferably has a hole mobility higher than or equal to $1×10^{-6}$ cm$^2$/Vs. The monoamine compound described in Embodiment 1 has a hole-transport property, and thus can be suitably used as a material for a hole-transport layer. Thus, the hole-transport layer 112 preferably includes the monoamine compound described in Embodiment 1, further preferably is formed using only the monoamine compound described in Embodiment 1. The hole-transport layer 112 including the monoamine compound described in Embodiment 1 can be a layer with a low refractive index in the EL layer 103, leading to higher external quantum efficiency of the light-emitting device.

Examples of the material having a hole-transport property, in the case of using a material other than the monoamine compound described in Embodiment 1 for the hole-transport layer 112, include compounds having an aromatic amine skeleton such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4'-(9-phenyl-9H-carbazol-3-yl)triphenylamine (abbreviation: PCBBi1BP), 4-(1-naphthyl)-4"-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), and N-phenyl-N-[4-(9-phenyl-9H-carbazol-3-yl)phenyl]-9,9'-spirobi[9H-fluoren]-2-amine (abbreviation: PCBASF); compounds having a carbazole skeleton such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), and 3,3'-bis(9-phenyl-9H-carbazole) (abbreviation: PCCP); compounds having a thiophene skeleton such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV); and compounds having a furan skeleton such as 4,4',4"-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II). Among the above materials, the compound having an aromatic amine skeleton and the compound having a carbazole skeleton are preferable because these compounds are highly reliable and have high hole-transport properties to contribute to a reduction in driving voltage. Note that any of the substances given as examples of the material having a hole-transport property which is used in the composite material for the hole-injection layer 111 can also be suitably used as the material included in the hole-transport layer 112.

The light-emitting layer 113 includes a light-emitting substance and a host material. The light-emitting layer 113 may additionally include other materials. Alternatively, the light-emitting layer 113 may be a stack of two layers with different compositions.

As the light-emitting substance, fluorescent substances, phosphorescent substances, substances exhibiting thermally activated delayed fluorescence (TADF), or other light-emitting substances may be used. Note that one embodiment of the present invention is more suitably used in the case where the light-emitting layer 113 emits fluorescence, specifically, blue fluorescence.

Examples of the material that can be used as a fluorescent substance in the light-emitting layer 113 are as follows. Other fluorescent substances can also be used.

The examples include 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N-diphenyl-N,N-bis[4-(9-phenyl-9H-fluoren-9-yl)phenyl]pyrene-1,6-diamine (abbreviation: 1,6FLPAPm), N,N'-bis(3-methylphenyl)-N,N'-bis[3-(9-phenyl-9H-fluoren-9-yl)phenyl]pyrene-1,6-diamine (abbreviation: 1,6mMemFLPAPm), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-

(9-phenyl-9H-carbazol-3-yl)triphenylamine (abbreviation: PCBAPA), N,N''-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N'',N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI, 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM), N,N'-diphenyl-N,N'-(1,6-pyrene-diyl)bis[(6-phenylbenzo[b]naphtho[1,2-d]furan)-8-amine] (abbreviation: 1,6BnfAPm-03), 3,10-bis[N-(9-phenyl-9H-carbazol-2-yl)-N-phenylamino]naphtho[2,3-b;6,7-b']bisbenzofuran (abbreviation: 3,10PCA2Nbf(IV)-02), and 3,10-bis[N-(dibenzofuran-3-yl)-N-phenylamino]naphtho[2,3-b;6,7-b']bisbenzofuran (abbreviation: 3,10FrA2Nbf(IV)-02). Condensed aromatic diamine compounds typified by pyrenediamine compounds such as 1,6FLPAPm, 1,6mMemFLPAPm, and 1,6BnfAPm-03 are particularly preferable because of their high hole-trapping properties, high emission efficiency, and high reliability. Furthermore, an organic compound having a naphthobisbenzofuran skeleton or a naphthobisbenzothiophene skeleton is preferable because it exhibits deep blue fluorescence and enables a favorable blue light-emitting device to be provided.

Examples of the material that can be used when a phosphorescent substance is used as the light-emitting substance in the light-emitting layer 113 are as follows.

The examples are as follows: an organometallic iridium complex having a 4H-triazole skeleton, such as tris{2-[5-(2-methylphenyl)-4-(2,6-dimethylphenyl)-4H-1,2,4-triazol-3-yl-κN2]phenyl-κC}iridium(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), and tris[4-(3-biphenyl)-5-isopropyl-3-phenyl-4H-1,2,4-triazolato]iridium(III) (abbreviation: [Ir(iPrptz-3b)$_3$]); an organometallic iridium complex having a 1H-triazole skeleton, such as tris 3-methyl-1-(2-methylphenyl)-5-phenyl-1H-1,2,4-triazolato iridium(III) (abbreviation: [Ir(Mptz1-mp)$_3$]) and tris(1-methyl-5-phenyl-3-propyl-1H-1,2,4-triazolato)iridium(III) (abbreviation: [Ir(Prptz1-Me)$_3$]); an organometallic iridium complex having an imidazole skeleton, such as fac-tris[1-(2,6-diisopropylphenyl)-2-phenyl-1H-imidazole]iridium (III) (abbreviation: [Ir(iPrpmi)$_3$]) and tris[3-(2,6-dimethylphenyl)-7-methylimidazo[1,2-f]phenanthridinato]iridium (III) (abbreviation: [Ir(dmpimpt-Me)$_3$]); and an organometallic iridium complex in which a phenylpyridine derivative having an electron-withdrawing group is a ligand, such as bis[2-(4',6'-difluorophenyl)pyridinato-N,C$^{2'}$]iridium (III) tetrakis(1-pyrazolyl)borate (abbreviation: FIr6), bis[2-(4',6'-difluorophenyl)pyridinato-N,C$^{2'}$]iridium(III) picolinate (abbreviation: FIrpic), bis{2-[3',5'-bis(trifluoromethyl)phenyl]pyridinato-N,C$^{2'}$}iridium(III) picolinate (abbreviation: [Ir(CF$_3$ppy)$_2$(pic)]), and bis[2-(4',6'-difluorophenyl)pyridinato-N,C$^{2'}$]iridium(III) acetyl acetonate (abbreviation: FIr(acac)). These compounds emit blue phosphorescence and have an emission peak at 440 nm to 520 nm.

Other examples include organometallic iridium complexes having a pyrimidine skeleton, such as tris(4-methyl-6-phenylpyrimidinato)iridium(III) (abbreviation: [Ir(mppm)$_3$]), tris(4-t-butyl-6-phenylpyrimidinato)iridium (III) (abbreviation: [Ir(tBuppm)$_3$]), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$(acac)]), (acetylacetonato)bis[6-(2-norbornyl)-4-phenylpyrimidinato]iridium(III) (abbreviation: [Ir(nbppm)$_2$(acac)]), (acetylacetonato)bis[5-methyl-6-(2-methylphenyl)-4-phenylpyrimidinato]iridium(III) (abbreviation: [Ir(mpmppm)$_2$(acac)]), and (acetylacetonato)bis(4,6-diphenylpyrimidinato)iridium(III) (abbreviation: [Ir(dppm)$_2$(acac)]); organometallic iridium complexes having a pyrazine skeleton, such as (acetylacetonato)bis(3,5-dimethyl-2-phenylpyrazinato)iridium(III) (abbreviation: [Ir(mppr-Me)$_2$(acac)]) and (acetylacetonato)bis(5-isopropyl-3-methyl-2-phenylpyrazinato)iridium(III) (abbreviation: [Ir(mppr-iPr)$_2$(acac)]); organometallic iridium complexes having a pyridine skeleton, such as tris(2-phenylpyridinato-N,C$^{2'}$)iridium(III) (abbreviation: [Ir(ppy)$_3$]), bis(2-phenylpyridinato-N,C$^{2'}$)iridium(III) acetylacetonate (abbreviation: [Ir(ppy)$_2$(acac)]), bis(benzo[h]quinolinato)iridium(III) acetylacetonate (abbreviation: [Ir(bzq)$_2$(acac)]), tris(benzo[h]quinolinato)iridium(III) (abbreviation: [Ir(bzq)$_3$]), tris(2-phenylquinolinato-N,C$^{2'}$)iridium(III) (abbreviation: [Ir(pq)$_3$]), and bis(2-phenylquinolinato-N,C$^{2'}$)iridium(III) acetylacetonate (abbreviation: [Ir(pq)$_2$(acac)]); and a rare earth metal complex such as tris(acetylacetonato) (monophenanthroline)terbium(III) (abbreviation: [Tb(acac)$_3$(Phen)]). These are mainly compounds that emit green phosphorescence and have an emission peak at 500 nm to 600 nm. Note that organometallic iridium complexes having a pyrimidine skeleton have distinctively high reliability and emission efficiency and thus are particularly preferable.

Other examples include organometallic iridium complexes having a pyrimidine skeleton, such as (diisobutyrylmethanato)bis[4,6-bis(3-methylphenyl)pyrimidinato] iridium(III) (abbreviation: [Ir(5mdppm)$_2$(dibm)]), bis[4,6-bis(3-methylphenyl)pyrimidinato](dipivaloylmethanato) iridium(III) (abbreviation: [Ir(5mdppm)$_2$(dpm)]), and bis[4,6-di(naphthalen-1-yl)pyrimidinato(dipivaloylmethanato)

iridium(III) (abbreviation: [Ir(dlnpm)₂(dpm)]); organometallic iridium complexes having a pyrazine skeleton, such as (acetylacetonato)bis(2,3,5-triphenylpyrazinato)iridium(III) (abbreviation: [Ir(tppr)₂(acac)]), bis(2,3,5-triphenylpyrazinato)(dipivaloylmethanato)iridium(III) (abbreviation: [Ir(tppr)₂(dpm)]), and (acetylacetonato)bis[2,3-bis(4-fluorophenyl)quinoxalinato]iridium(III) (abbreviation: [Ir(Fdpq)₂(acac)]); organometallic iridium complexes having a pyridine skeleton, such as tris(1-phenylisoquinolinato-N,C²')iridium(III) (abbreviation: [Ir(piq)₃]) and bis(1-phenylisoquinolinato-N,C²')iridium(III) acetylacetonate (abbreviation: [Ir(piq)₂(acac)]); platinum complexes such as 2,3,7,8,12,13,17,18-octaethyl-21H,22H-porphyrinplatinum (II) (abbreviation: [PtOEP]); and rare earth metal complexes such as tris(1,3-diphenyl-1,3-propanedionato) (monophenanthroline)europium(III) (abbreviation: [Eu(DBM)₃(Phen)]) and tris[1-(2-thenoyl)-3,3,3-trifluoroacetonato (monophenanthroline)europium(III) (abbreviation: [Eu(TTA)₃(Phen)]). These compounds emit red phosphorescence having an emission peak at 600 nm to 700 nm. Furthermore, the organometallic iridium complexes having a pyrazine skeleton can provide red light emission with favorable chromaticity.

Besides the above phosphorescent compounds, known phosphorescent substances may be selected and used.

Examples of the TADF material include a fullerene, a derivative thereof, an acridine, a derivative thereof, and an eosin derivative. Furthermore, a metal-containing porphyrin, such as a porphyrin containing magnesium (Mg), zinc (Zn), cadmium (Cd), tin (Sn), platinum (Pt), indium (In), or palladium (Pd), can be given. Examples of the metal-containing porphyrin include a protoporphyrin-tin fluoride complex (SnF₂(Proto IX)), a mesoporphyrin-tin fluoride complex (SnF₂(Meso IX)), a hematoporphyrin-tin fluoride complex (SnF₂(Hemato IX)), a coproporphyrin tetramethyl ester-tin fluoride complex (SnF₂(Copro III-4Me)), an octaethylporphyrin-tin fluoride complex (SnF₂(OEP)), an etioporphyrin-tin fluoride complex (SnF₂(Etio I)), and an octaethylporphyrin-platinum chloride complex (PtCbOEP), which are represented by the following structural formulae.

[Chemical Formula 37]

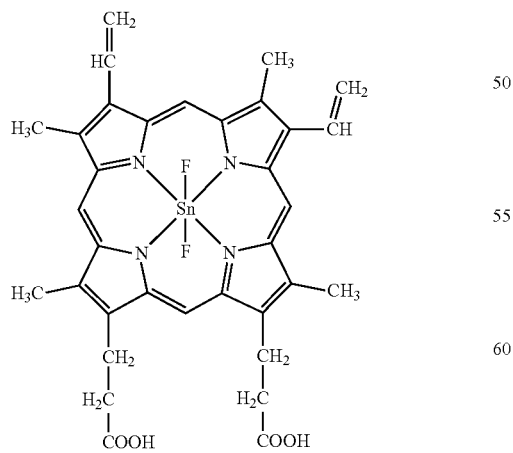

SnF₂(Proto IX)

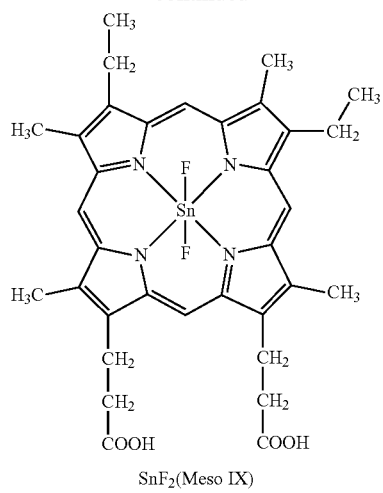

SnF₂(Meso IX)

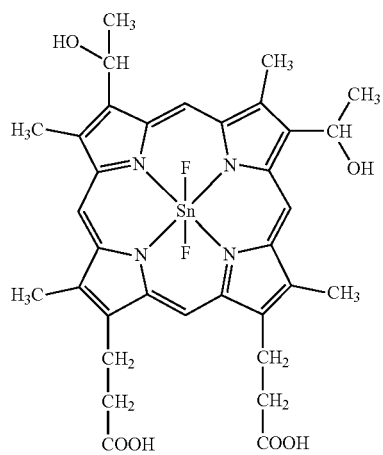

SnF₂(Hemato IX)

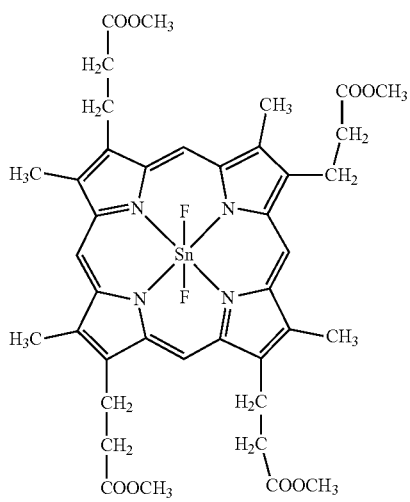

SnF₂(Copro III-4Me)

-continued

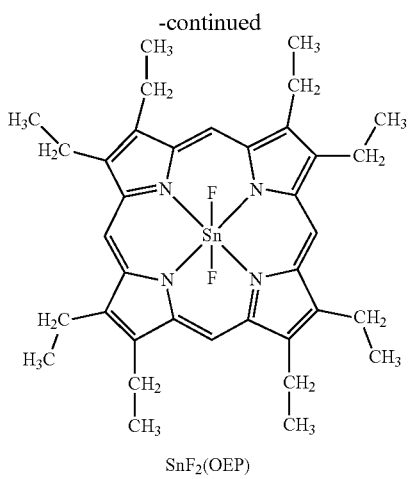

SnF₂(OEP)

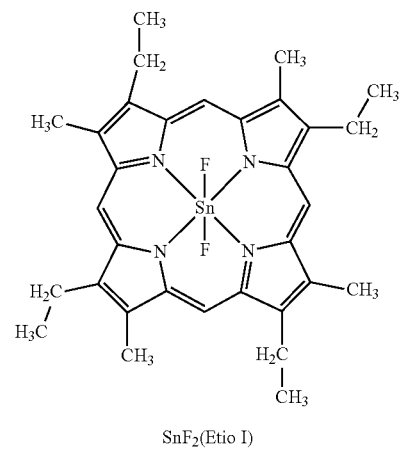

SnF₂(Etio I)

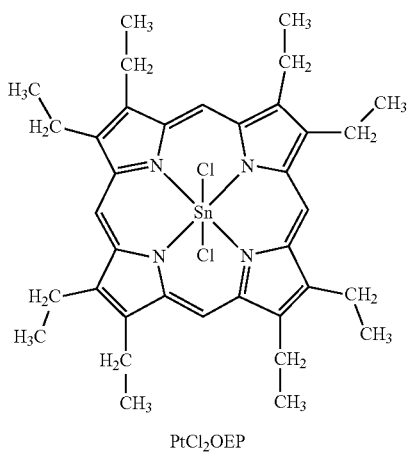

PtCl₂OEP

Alternatively, a heterocyclic compound having one or both of a π-electron rich heteroaromatic ring and a π-electron deficient heteroaromatic ring that is represented by the following structural formulae, such as 2-(biphenyl-4-yl)-4,6-bis(12-phenylindolo[2,3-a]carbazol-11-yl)-1,3,5-triazine (abbreviation: PIC-TRZ), 9-(4,6-diphenyl-1,3,5-triazin-2-yl)-9'-phenyl-9H,9'H-3,3'-bicarbazole (abbreviation: PCCzTzn), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10H-phenoxazine-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), or 10-phenyl-10H,10'H-spiro[acridin-9,9'-anthracen]-10'-one (abbreviation: ACRSA) can be used. Such a heterocyclic compound is preferable because of having excellent electron-transport and hole-transport properties owing to a π-electron rich heteroaromatic ring and a π-electron deficient heteroaromatic ring. Among skeletons having the π-electron deficient heteroaromatic ring, a pyridine skeleton, a diazine skeleton (a pyrimidine skeleton, a pyrazine skeleton, and a pyridazine skeleton), and a triazine skeleton are preferred because of their high stability and reliability. In particular, a benzofuropyrimidine skeleton, a benzothienopyrimidine skeleton, a benzofuropyrazine skeleton, and a benzothienopyrazine skeleton are preferred because of their high accepting properties and high reliability. Among skeletons having the π-electron rich heteroaromatic ring, an acridine skeleton, a phenoxazine skeleton, a phenothiazine skeleton, a furan skeleton, a thiophene skeleton, and a pyrrole skeleton have high stability and reliability; therefore, at least one of these skeletons is preferably included. A dibenzofuran skeleton is preferable as a furan skeleton, and a dibenzothiophene skeleton is preferable as a thiophene skeleton. As a pyrrole skeleton, an indole skeleton, a carbazole skeleton, an indolocarbazole skeleton, a bicarbazole skeleton, and a 3-(9-phenyl-9H-carbazol-3-yl)-9H-carbazole skeleton are particularly preferable. Note that a substance in which the π-electron rich heteroaromatic ring is directly bonded to the π-electron deficient heteroaromatic ring is particularly preferred because the electron-donating property of the π-electron rich heteroaromatic ring and the electron-accepting property of the π-electron deficient heteroaromatic ring are both improved, the energy difference between the S1 level and the T1 level becomes small, and thus thermally activated delayed fluorescence can be obtained with high efficiency. Note that an aromatic ring to which an electron-withdrawing group such as a cyano group is bonded may be used instead of the π-electron deficient heteroaromatic ring. As a π-electron rich skeleton, an aromatic amine skeleton, a phenazine skeleton, or the like can be used. As a π-electron deficient skeleton, a xanthene skeleton, a thioxanthene dioxide skeleton, an oxadiazole skeleton, a triazole skeleton, an imidazole skeleton, an anthraquinone skeleton, a skeleton containing boron such as phenylborane or boranthrene, an aromatic ring or a heteroaromatic ring having a cyano group or a nitrile group such as benzonitrile or cyanobenzene, a carbonyl skeleton such as benzophenone, a phosphine oxide skeleton, a sulfone skeleton, or the like can be used. As described above, a π-electron deficient skeleton and a π-electron rich skeleton can be used instead of at least one of the π-electron deficient heteroaromatic ring and the π-electron rich heteroaromatic ring.

[Chemical Formula 38]
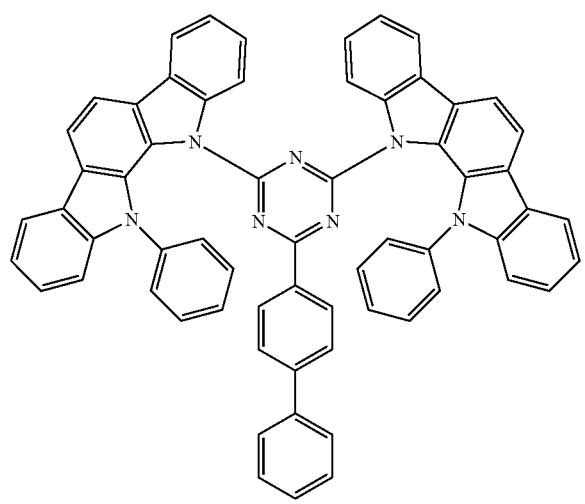
PIC-TRZ
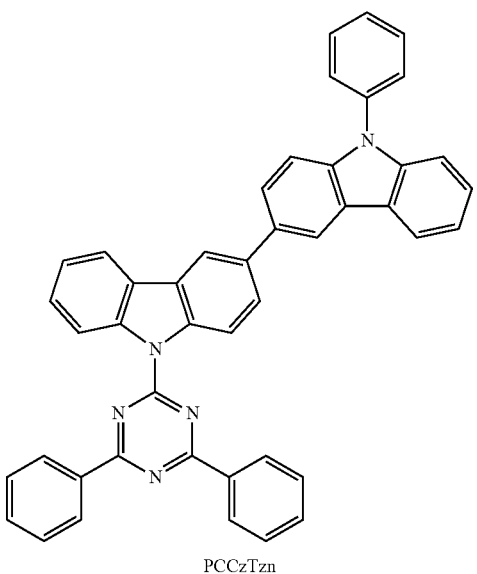
PCCzTzn
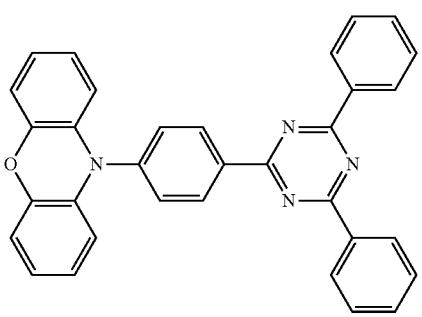
PXZ-TRZ
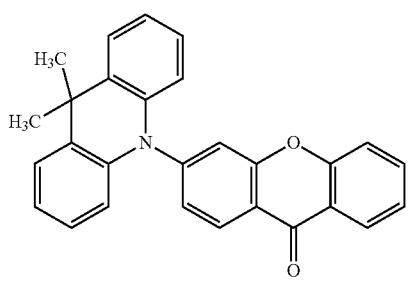
ACRXTN
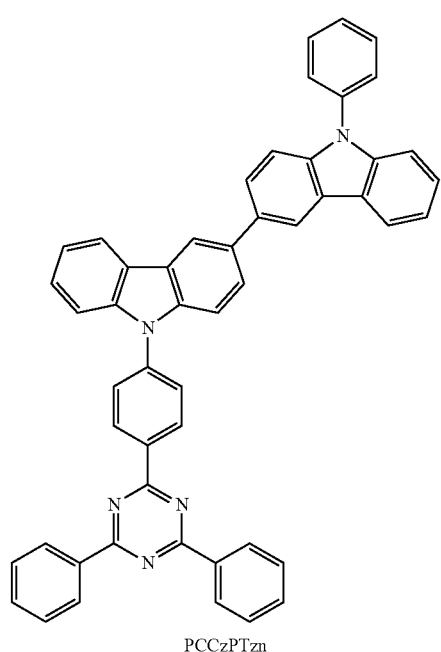
PCCzPTzn
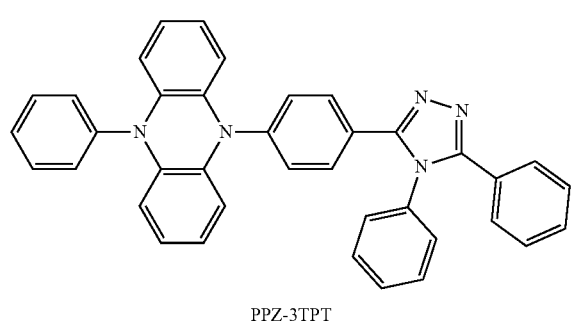
PPZ-3TPT

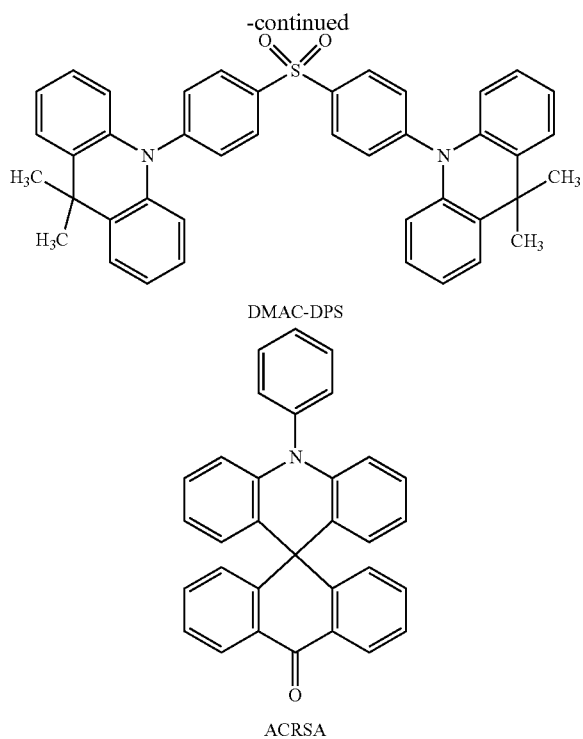

DMAC-DPS

ACRSA

Note that a TADF material is a material having a small difference between the S1 level and the T1 level and a function of converting triplet excitation energy into singlet excitation energy by reverse intersystem crossing. Thus, a TADF material can upconvert triplet excitation energy into singlet excitation energy (i.e., reverse intersystem crossing) using a small amount of thermal energy and efficiently generate a singlet excited state. In addition, the triplet excitation energy can be converted into luminescence.

An exciplex whose excited state is formed of two kinds of substances has an extremely small difference between the S1 level and the T1 level and functions as a TADF material capable of converting triplet excitation energy into singlet excitation energy.

A phosphorescent spectrum observed at a low temperature (e.g., 77 K to 10 K) is used for an index of the T1 level. When the level of energy with a wavelength of the line obtained by extrapolating a tangent to the fluorescent spectrum at a tail on the short wavelength side is the S1 level and the level of energy with a wavelength of the line obtained by extrapolating a tangent to the phosphorescent spectrum at a tail on the short wavelength side is the T1 level, the difference between the S1 level and the T1 level of the TADF material is preferably smaller than or equal to 0.3 eV, further preferably smaller than or equal to 0.2 eV.

When a TADF material is used as the light-emitting substance, the S1 level of the host material is preferably higher than that of the TADF material. In addition, the T1 level of the host material is preferably higher than that of the TADF material.

As the host material in the light-emitting layer, various carrier-transport materials such as materials having an electron-transport property, materials having a hole-transport property, and the TADF materials can be used.

The material having a hole-transport property is preferably an organic compound having an aromatic amine skeleton or a π-electron rich heteroaromatic ring skeleton. Examples of the substance include compounds having an aromatic amine skeleton such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4''-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4''-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), and N-phenyl-N-[4-(9-phenyl-9H-carbazol-3-yl)phenyl]spiro-9,9'-bifluoren-2-amine (abbreviation: PCBASF); compounds having a carbazole skeleton such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), and 3,3'-bis(9-phenyl-9H-carbazole) (abbreviation: PCCP); compounds having a thiophene skeleton such as 4,4',4''-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV); and compounds having a furan skeleton such as 4,4',4''-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II). Among the above materials, the compound having an aromatic amine skeleton and the compound having a carbazole skeleton are preferable because these compounds are highly reliable and have high hole-transport properties to contribute to a reduction in driving voltage. In addition, the organic compounds given as examples of the material having a hole-transport property can also be used.

As the material having an electron-transport property, metal complexes such as bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc (II) (abbreviation: ZnBTZ); or an organic compound having a π-electron deficient heteroaromatic ring skeleton is preferable. Examples of the organic compound having a π-electron deficient heteroaromatic ring skeleton include 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2''-(1,3,5-benzenetriyl)tris(1-phenyl-1H-benzimidazole) (abbreviation: TPBI), and 2-[3-(dibenzothiophen-4-yl)phenyl]-1-phenyl-1H-benzimidazole (abbreviation: mDBT-BIm-II); heterocyclic compounds having a diazine skeleton, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 4,6-bis[3-(phenanthren-9-yl)phenyl]pyrimidine (abbreviator: 4,6mPnP2Pm), and 4,6-bis[3-(4-dibenzothienyl)phenyl]pyrimidine (abbreviation: 4,6mDBTP2Pm-II); heterocyclic compounds having a triazine skeleton such as 2-[3'-(9,9-dimethyl-9H-fluoren-2-yl)-1,1'-biphenyl-3-yl]-4,6-diphenyl-1,3,5-triazine (abbreviation: mFBPTzn), 2-[(1,1'-Biphenyl)-4-yl]-4-phenyl-6-[9,9'-spirobi(9H-fluoren)-2-yl]-1,3,5-triazine (abbreviation: BP-SFTzn), 2-{3-[3-(Benzo[b]naphtho[1,2-d]furan-8-yl)phenyl]phenyl}-4,6-diphenyl-1,3,5-triazine (abbreviation: mBnfBPTzn), and 2-{3-[3-(Benzo[b]naphtho[1,2-d]furan-6-yl)phenyl]phenyl}-4,6-diphenyl-1,3,5-triazine (abbreviation: mBnfBPTzn-02); and heterocyclic compounds having a pyridine skeleton, such as 3,5-bis[3-(9H-carbazol-9-yl)phenyl]pyridine (abbreviation: 35DCzPPy) and 1,3,5-tri[3-(3-pyridyl)phenyl]benzene (abbreviation: TmPyPB). Among the above materials, the heterocyclic compound having a diazine skeleton, the heterocyclic compound having a triazine skeleton, and the heterocyclic compound having a pyridine skeleton have high reliability and thus are preferable. In particular, the heterocyclic compound having a diazine (pyrimidine or pyrazine) skeleton has a high electron-transport property to contribute to a reduction in driving voltage.

As the TADF material that can be used as the host material, the above materials mentioned as the TADF material can also be used. When the TADF material is used as the host material, triplet excitation energy generated in the TADF material is converted into singlet excitation energy by reverse intersystem crossing and transferred to the light-emitting substance, whereby the emission efficiency of the light-emitting device can be increased. Here, the TADF material functions as an energy donor, and the light-emitting substance functions as an energy acceptor.

This is very effective in the case where the light-emitting substance is a fluorescent substance. In that case, the S1 level of the TADF material is preferably higher than that of the fluorescent substance in order that high emission efficiency be achieved. Furthermore, the T1 level of the TADF material is preferably higher than the S1 level of the fluorescent substance. Therefore, the T1 level of the TADF material is preferably higher than that of the fluorescent substance.

It is also preferable to use a TADF material that emits light whose wavelength overlaps with the wavelength on a lowest-energy-side absorption band of the fluorescent substance. This enables smooth transfer of excitation energy from the TADF material to the fluorescent substance and accordingly enables efficient light emission, which is preferable.

In addition, in order to efficiently generate singlet excitation energy from the triplet excitation energy by reverse intersystem crossing, carrier recombination preferably occurs in the TADF material. It is also preferable that the triplet excitation energy generated in the TADF material not be transferred to the triplet excitation energy of the fluorescent substance. For that reason, the fluorescent substance preferably has a protective group around a luminophore (a skeleton which causes light emission) of the fluorescent substance. As the protective group, a substituent having no π bond and a saturated hydrocarbon are preferably used. Specific examples include an alkyl group having 3 to 10 carbon atoms, a substituted or unsubstituted cycloalkyl group having 3 to carbon atoms, and a trialkylsilyl group having 3 to 10 carbon atoms. It is further preferable that the fluorescent substance have a plurality of protective groups. The substituents having no π bond are poor in carrier transport performance, whereby the TADF material and the luminophore of the fluorescent substance can be made away from each other with little influence on carrier transportation or carrier recombination. Here, the luminophore refers to an atomic group (skeleton) that causes light emission in a fluorescent substance. The luminophore is preferably a skeleton having a π bond, further preferably includes an aromatic ring, and still further preferably includes a condensed aromatic ring or a condensed heteroaromatic ring. Examples of the condensed aromatic ring or the condensed heteroaromatic ring include a phenanthrene skeleton, a stilbene skeleton, an acridone skeleton, a phenoxazine skeleton, and a phenothiazine skeleton. Specifically, a fluorescent substance having any of a naphthalene skeleton, an anthracene skeleton, a fluorene skeleton, a chrysene skeleton, a triphenylene skeleton, a tetracene skeleton, a pyrene skeleton, a perylene skeleton, a coumarin skeleton, a quinacridone skeleton, and a naphthobisbenzofuran skeleton is preferred because of its high fluorescence quantum yield.

In the case where a fluorescent substance is used as the light-emitting substance, a material having an anthracene skeleton is favorably used as the host material. The use of a substance having an anthracene skeleton as the host material for the fluorescent substance makes it possible to obtain a light-emitting layer with high emission efficiency and high durability. Among the substances having an anthracene skeleton, a substance having a diphenylanthracene skeleton, in particular, a substance having a 9,10-diphenylanthracene skeleton, is chemically stable and thus is preferably used as the host material. The host material preferably has a carbazole skeleton because the hole-injection and hole-transport properties are improved; further preferably, the host material has a benzocarbazole skeleton in which a benzene ring is further condensed to carbazole because the HOMO level thereof is shallower than that of carbazole by approximately 0.1 eV and thus holes enter the host material easily. In particular, the host material preferably has a dibenzocarbazole skeleton because the HOMO level thereof is shallower than that of carbazole by approximately 0.1 eV so that holes enter the host material easily, the hole-transport property is improved, and the heat resistance is increased. Accordingly, a substance that has both a 9,10-diphenylanthracene skeleton and a carbazole skeleton (or a benzocarbazole or dibenzocarbazole skeleton) is further preferable as the host material. Note that in terms of the hole-injection and hole-transport properties described above, instead of a carbazole skeleton, a benzofluorene skeleton or a dibenzo fluorene skeleton may be used. Examples of such a substance include 9-phenyl-3-[4-(10-phenyl-9-anthryl)phenyl]-9H-carbazole (abbreviation: PCzPA), 3-[4-(1-naphthyl)-phenyl]-9-phenyl-9H-carbazole (abbreviation: PCPN), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), 9-phenyl-10-{4-(9-phenyl-9H-fluoren-9-yl)biphenyl-4'-yl}anthracene (abbreviation: FLPPA), and 9-(1-naphthyl)-10-[4-(2-naphthyl)phenyl]anthracene (abbreviation: αN-βNPAnth). Note that CzPA, cgDBCzPA, 2mBnfPPA, and PCzPA have excellent characteristics and thus are preferably selected.

Note that the host material may be a mixture of a plurality of kinds of substances; in the case of using a mixed host material, it is preferable to mix a material having an electron-transport property with a material having a hole-transport property. By mixing the material having an electron-transport property with the material having a hole-transport property, the transport property of the light-emitting layer 113 can be easily adjusted and a recombination region can be easily controlled. The weight ratio of the content of the material having a hole-transport property to the content of the material having an electron-transport property may be 1:19 to 19:1.

Note that a phosphorescent substance can be used as part of the mixed material. When a fluorescent substance is used as the light-emitting substance, a phosphorescent substance can be used as an energy donor for supplying excitation energy to the fluorescent substance.

An exciplex may be formed of these mixed materials. When these mixed materials are selected so as to form an exciplex that exhibits light emission whose wavelength overlaps with the wavelength on a lowest-energy-side absorption band of the light-emitting substance, energy can be transferred smoothly and light emission can be obtained efficiently, which is preferable. The use of such a structure is preferable because the driving voltage can also be reduced.

Note that at least one of the materials forming an exciplex may be a phosphorescent substance. In this case, triplet excitation energy can be efficiently converted into singlet excitation energy by reverse intersystem crossing.

Combination of a material having an electron-transport property and a material having a hole-transport property whose HOMO level is higher than or equal to that of the material having an electron-transport property is preferable for forming an exciplex efficiently. In addition, the LUMO level of the material having a hole-transport property is preferably higher than or equal to the LUMO level of the material having an electron-transport property. Note that the LUMO levels and the HOMO levels of the materials can be derived from the electrochemical characteristics (the reduction potentials and the oxidation potentials) of the materials that are measured by cyclic voltammetry (CV).

The formation of an exciplex can be confirmed by a phenomenon in which the emission spectrum of the mixed film in which the material having a hole-transport property and the material having an electron-transport property are mixed is shifted to the longer wavelength side than the emission spectra of each of the materials (or has another peak on the longer wavelength side) observed by comparison of the emission spectra of the material having a hole-transport property, the material having an electron-transport property, and the mixed film of these materials, for example. Alternatively, the formation of an exciplex can be confirmed by a difference in transient response, such as a phenomenon in which the transient PL lifetime of the mixed film has more long lifetime components or has a larger proportion of delayed components than that of each of the materials, observed by comparison of transient photoluminescence (PL) of the material having a hole-transport property, the material having an electron-transport property, and the mixed film of the materials. The transient PL can be rephrased as transient electroluminescence (EL). That is, the formation of an exciplex can also be confirmed by a difference in transient response observed by comparison of the transient EL of the material having a hole-transport property, the material having an electron-transport property, and the mixed film of the materials.

An electron-transport layer 114 contains a substance having an electron-transport property. As the substance having an electron-transport property, it is possible to use any of the above-listed substances having electron-transport properties that can be used as the host material.

Note that the electron-transport layer preferably includes a material having an electron-transport property and an alkali metal, an alkaline earth metal, a compound thereof, or a complex thereof. The electron mobility of the material included in the electron-transport layer 114 in the case where the square root of the electric field strength [V/cm] is 600 is preferably higher than or equal to $1\times10^7$ cm$^2$/Vs and lower than or equal to $5\times10^5$ cm$^2$/Vs. The amount of electrons injected into the light-emitting layer can be controlled by the reduction in the electron-transport property of the electron-transport layer 114, whereby the light-emitting layer can be prevented from having excess electrons. It is particularly preferable that this structure be employed when the hole-injection layer is formed using a composite material that includes a material having a hole-transport property with a relatively deep HOMO level of −5.7 eV or higher and −5.4 eV or lower, in which case the light-emitting device can have a long lifetime. In this case, the material having an electron-transport property preferably has a HOMO level of −6.0 eV or higher. The material having an electron-transport property is preferably an organic compound having an anthracene skeleton and further preferably an organic compound having both an anthracene skeleton and a heterocyclic skeleton. The heterocyclic skeleton is preferably a nitrogen-containing five-membered ring skeleton or a nitrogen-containing six-membered ring skeleton, and particularly preferably a nitrogen-containing five-membered ring skeleton or a nitrogen-containing six-membered ring skeleton including two heteroatoms in the ring, such as a pyrazole ring, an imidazole ring, an oxazole ring, a thiazole ring, a pyrazine ring, a pyrimidine ring, or a pyridazine ring. In addition, it is preferable that the alkali metal, the alkaline earth metal, the compound thereof, or the complex thereof have a 8-hydroxyquinolinato structure. Specific examples include κ-hydroxyquinolinato-lithium (abbreviation: Liq) and 8-hydroxyquinolinato-sodium (abbreviation: Naq). In particular, a complex of a monovalent metal ion, especially a complex of lithium is preferable, and Liq is further preferable. Note that in the case where the 8-hydroxyquinolinato structure is included, a methyl-substituted product (e.g., a 2-methyl-substituted product or a 5-methyl-substituted product) of the alkali metal, the alkaline earth metal, the compound, or the complex can also be used. There is preferably a difference in the concentration (including 0) of the alkali metal, the alkaline earth metal, the compound thereof, or the complex thereof in the electron-transport layer in the thickness direction.

A layer containing an alkali metal, an alkaline earth metal, or a compound thereof such as lithium fluoride (LiF), cesium fluoride (CsF), calcium fluoride (CaF$_2$), or 8-hydroxyquinolinatolithium (Liq) may be provided as the electron-injection layer 115 between the electron-transport layer 114 and the second electrode 102. For example, an electride or a layer that is formed using a substance having an electron-transport property and that includes an alkali metal, an alkaline earth metal, or a compound thereof can be used as the electron-injection layer 115. Examples of the electride include a substance in which electrons are added at high concentration to calcium oxide-aluminum oxide.

Note that as the electron-injection layer 115, it is possible to use a layer containing a substance that has an electron-transport property (preferably an organic compound having a bipyridine skeleton) and contains a fluoride of the alkali metal or the alkaline earth metal at a concentration higher than that at which the electron-injection layer 115 becomes in a microcrystalline state (50 wt % or higher). Since the layer has a low refractive index, a light-emitting device including the layer can have high external quantum efficiency.

Figure 1B:
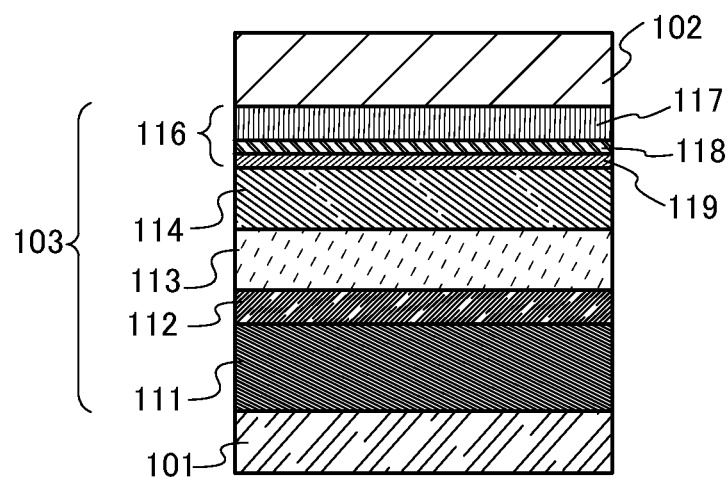

Instead of the electron-injection layer 115, a charge-generation layer 116 may be provided (FIG. 1B). The charge-generation layer 116 refers to a layer capable of injecting holes into a layer in contact with the cathode side of the charge-generation layer 116 and electrons into a layer in contact with the anode side thereof when a potential is applied. The charge-generation layer 116 includes at least a p-type layer 117. The p-type layer 117 is preferably formed using any of the composite materials given above as examples of materials that can be used for the hole-injection layer 111. The p-type layer 117 may be formed by stacking a film containing the above-described acceptor material as a material included in the composite material and a film containing a hole-transport material. When a potential is applied to the p-type layer 117, electrons are injected into the electron-transport layer 114 and holes are injected into the second electrode 102 serving as a cathode; thus, the light-emitting device operates. Since the organic compound of one embodiment of the present invention has a low refractive index, using the organic compound for the p-type layer 117 enables the light-emitting device to have high external quantum efficiency.

Note that the charge-generation layer 116 preferably includes an electron-relay layer 118 and/or an electron-injection buffer layer 119 in addition to the p-type layer 117.

The electron-relay layer 118 includes at least the substance having an electron-transport property and has a function of preventing an interaction between the electron-injection buffer layer 119 and the p-type layer 117 and smoothly transferring electrons. The LUMO level of the substance having an electron-transport property contained in the electron-relay layer 118 is preferably between the LUMO level of the acceptor substance in the p-type layer 117 and the LUMO level of a substance contained in a layer of the electron-transport layer 114 that is in contact with the charge-generation layer 116. As a specific value of the energy level, the LUMO level of the substance having an electron-transport property in the electron-relay layer 118 is preferably higher than or equal to −5.0 eV, further preferably higher than or equal to −5.0 eV and lower than or equal to −3.0 eV. Note that as the substance having an electron-transport property in the electron-relay layer 118, a phthalocyanine-based material or a metal complex having a metal-oxygen bond and an aromatic ligand is preferably used.

A substance having a high electron-injection property can be used for the electron-injection buffer layer 119. For example, an alkali metal, an alkaline earth metal, a rare earth metal, or a compound thereof (an alkali metal compound (including an oxide such as lithium oxide, a halide, and a carbonate such as lithium carbonate and cesium carbonate), an alkaline earth metal compound (including an oxide, a halide, and a carbonate), or a rare earth metal compound (including an oxide, a halide, and a carbonate)) can be used.

In the case where the electron-injection buffer layer 119 contains the substance having an electron-transport property and a donor substance, an organic compound such as tetrathianaphthacene (abbreviation: TTN), nickelocene, or decamethylnickelocene can be used as the donor substance, as well as an alkali metal, an alkaline earth metal, a rare earth metal, a compound thereof (e.g., an alkali metal compound (including an oxide such as lithium oxide, a halide, and a carbonate such as lithium carbonate and cesium carbonate), an alkaline earth metal compound (including an oxide, a halide, and a carbonate), or a rare earth metal compound (including an oxide, a halide, and a carbonate)). As the substance having an electron-transport property, a material similar to the above-described material for the electron-transport layer 114 can be used.

For the second electrode 102, a metal, an alloy, an electrically conductive compound, or a mixture thereof each having a low work function (specifically, lower than or equal to 3.8 eV) or the like can be used. Specific examples of such a cathode material are elements belonging to Groups 1 and 2 of the periodic table, such as alkali metals (e.g., lithium (Li) and cesium (Cs)), magnesium (Mg), calcium (Ca), and strontium (Sr), alloys containing these elements (e.g., MgAg and AlLi), rare earth metals such as europium (Eu) and ytterbium (Yb), and alloys containing these rare earth metals. However, when the electron-injection layer is provided between the second electrode 102 and the electron-transport layer, for the second electrode 102, a variety of conductive materials such as Al, Ag, ITO, or indium oxide-tin oxide containing silicon or silicon oxide can be used regardless of the work function. Films of these conductive materials can be formed by a dry process such as a vacuum evaporation method or a sputtering method, an ink-jet method, a spin coating method, or the like. Alternatively, a wet process using a sol-gel method or a wet process using a paste of a metal material may be employed.

Furthermore, any of a variety of methods can be used for forming the EL layer 103, regardless of a dry method or a wet method. For example, a vacuum evaporation method, a gravure printing method, an offset printing method, a screen printing method, an ink-jet method, a spin coating method, or the like may be used.

Different methods may be used to form the electrodes or the layers described above.

The structure of the layers provided between the first electrode 101 and the second electrode 102 is not limited to the above-described structure. Preferably, a light-emitting region where holes and electrons recombine is positioned away from the first electrode 101 and the second electrode 102 so as to prevent quenching due to the proximity of the light-emitting region and a metal used for electrodes and carrier-injection layers.

Furthermore, in order that transfer of energy from an exciton generated in the light-emitting layer can be suppressed, preferably, the hole-transport layer and the electron-transport layer which are in contact with the light-emitting layer 113, particularly a carrier-transport layer closer to the recombination region in the light-emitting layer 113, are formed using a substance having a wider band gap than the light-emitting material of the light-emitting layer or the light-emitting material included in the light-emitting layer.

Next, an embodiment of a light-emitting device with a structure in which a plurality of light-emitting units are stacked (this type of light-emitting device is also referred to as a stacked or tandem light-emitting device) is described with reference to FIG. 1C. This light-emitting device includes a plurality of light-emitting units between an anode and a cathode. One light-emitting unit has substantially the same structure as the EL layer 103 illustrated in FIG. 1A. In other words, the light-emitting device illustrated in FIG. 1A or 1B includes a single light-emitting unit, and the light-emitting device illustrated in FIG. 1C includes a plurality of light-emitting units.

Figure 1C:
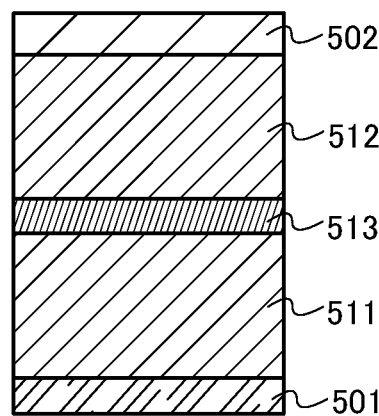

In FIG. 1C, a first light-emitting unit 511 and a second light-emitting unit 512 are stacked between an anode 501 and a cathode 502, and a charge-generation layer 513 is provided between the first light-emitting unit 511 and the second light-emitting unit 512. The anode 501 and the cathode 502 correspond, respectively, to the first electrode 101 and the second electrode 102 illustrated in FIG. 1A, and the materials given in the description for FIG. 1A can be used. Furthermore, the first light-emitting unit 511 and the second light-emitting unit 512 may have the same structure or different structures.

The charge-generation layer 513 has a function of injecting electrons into one of the light-emitting units and injecting holes into the other of the light-emitting units when a voltage is applied between the anode 501 and the cathode 502. That is, in FIG. 1C, the charge-generation layer 513 injects electrons into the first light-emitting unit 511 and holes into the second light-emitting unit 512 when a voltage is applied so that the potential of the anode becomes higher than the potential of the cathode.

The charge-generation layer 513 preferably has a structure similar to that of the charge-generation layer 116 described with reference to FIG. 1B. A composite material of an organic compound and a metal oxide has an excellent carrier-injection property and an excellent carrier-transport property; thus, low-voltage driving and low-current driving can be achieved. In the case where the anode-side surface of a light-emitting unit is in contact with the charge-generation layer 513, the charge-generation layer 513 can also function as a hole-injection layer of the light-emitting unit; therefore, a hole-injection layer is not necessarily provided in the light-emitting unit.

In the case where the charge-generation layer 513 includes the electron-injection buffer layer 119, the electron-injection buffer layer 119 functions as the electron-injection layer in the light-emitting unit on the anode side and thus, an electron-injection layer is not necessarily formed in the light-emitting unit on the anode side.

The light-emitting device having two light-emitting units is described with reference to FIG. 1C; however, one embodiment of the present invention can also be applied to a light-emitting device in which three or more light-emitting units are stacked. With a plurality of light-emitting units partitioned by the charge-generation layer 513 between a pair of electrodes as in the light-emitting device of this embodiment, it is possible to provide a long-life element which can emit light with high luminance at a low current density. A light-emitting apparatus which can be driven at a low voltage and has low power consumption can be provided.

When the emission colors of the light-emitting units are different, light emission of a desired color can be obtained from the light-emitting device as a whole. For example, in a light-emitting device having two light-emitting units, the emission colors of the first light-emitting unit may be red and green and the emission color of the second light-emitting unit may be blue, so that the light-emitting device can emit white light as the whole.

The above-described layers and electrodes such as the EL layer 103, the first light-emitting unit 511, the second light-emitting unit 512, and the charge-generation layer can be formed by a method such as an evaporation method (including a vacuum evaporation method), a droplet discharge method (also referred to as an ink-jet method), a coating method, or a gravure printing method. A low molecular material, a middle molecular material (including an oligomer and a dendrimer), or a high molecular material may be included in the layers and electrodes.

Embodiment 3

In this embodiment, a light-emitting apparatus including the light-emitting device described in Embodiment 2 is described.

In this embodiment, the light-emitting apparatus manufactured using the light-emitting device described in Embodiment 2 is described with reference to FIGS. 2A and 2B. Note that FIG. 2A is a top view of the light-emitting apparatus and FIG. 2B is a cross-sectional view taken along the lines A-B and C-D in FIG. 2A. This light-emitting apparatus includes a driver circuit (source line driver circuit) 601, a pixel portion 602, and a driver circuit portion (gate line driver circuit) 603, which are to control light emission of a light-emitting device and illustrated with dotted lines. Reference numeral 604 denotes a sealing substrate; 605, a sealing material; and 607, a space surrounded by the sealing material 605.

Reference numeral 608 denotes a lead wiring for transmitting signals to be input to the source line driver circuit 601 and the gate line driver circuit 603 and receiving signals such as a video signal, a clock signal, a start signal, and a reset signal from a flexible printed circuit (FPC) 609 serving as an external input terminal. Although only the FPC is illustrated here, a printed wiring board (PWB) may be attached to the FPC. The light-emitting apparatus in the present specification includes, in its category, not only the light-emitting apparatus itself but also the light-emitting apparatus provided with the FPC or the PWB.

Next, a cross-sectional structure is described with reference to FIG. 2B. The driver circuit portions and the pixel portion are formed over an element substrate 610; FIG. 2B shows the source line driver circuit 601, which is a driver circuit portion, and one pixel in the pixel portion 602.

The element substrate 610 may be a substrate containing glass, quartz, an organic resin, a metal, an alloy, or a semiconductor or a plastic substrate formed of fiber reinforced plastic (FRP), poly(vinyl fluoride) (PVF), polyester, or acrylic resin.

The structure of transistors used in pixels and driver circuits is not particularly limited. For example, inverted staggered transistors may be used, or staggered transistors may be used. Furthermore, top-gate transistors or bohom-gate transistors may be used. A semiconductor material used for the transistors is not particularly limited, and for example, silicon, germanium, silicon carbide, gallium nitride, or the like can be used. Alternatively, an oxide semiconductor containing at least one of indium, gallium, and zinc, such as an In—Ga—Zn-based metal oxide, may be used.

There is no particular limitation on the crystallinity of a semiconductor material used for the transistors, and an amorphous semiconductor or a semiconductor having crystallinity (a microcrystalline semiconductor, a poly crystalline semiconductor, a single crystal semiconductor, or a semiconductor partly including crystal regions) may be used. It is preferable that a semiconductor having crystallinity be used, in which case deterioration of the transistor characteristics can be suppressed.

Here, an oxide semiconductor is preferably used for semiconductor devices such as the transistors provided in the pixels and driver circuits and transistors used for touch sensors described later, and the like. In particular, an oxide semiconductor having a wider band gap than silicon is preferably used. When an oxide semiconductor having a wider band gap than silicon is used, off-state current of the transistors can be reduced.

The oxide semiconductor preferably contains at least indium (In) or zinc (Zn). Further preferably, the oxide semiconductor contains an oxide represented by an In-M-Zn-based oxide (M represents a metal such as Al, Ti, Ga, Ge, Y, Zr, Sn, La, Ce, or Hf).

As a semiconductor layer, it is particularly preferable to use an oxide semiconductor film including a plurality of crystal parts whose c-axes are aligned perpendicular to a surface on which the semiconductor layer is formed or the top surface of the semiconductor layer and in which the adjacent crystal parts have no grain boundary.

The use of such materials for the semiconductor layer makes it possible to provide a highly reliable transistor in which a change in the electrical characteristics is suppressed.

Charge accumulated in a capacitor through a transistor including the above-described semiconductor layer can be held for a long time because of the low off-state current of the transistor. When such a transistor is used in a pixel, operation of a driver circuit can be stopped while a gray scale of an image displayed in each display region is maintained. As a result, an electronic apparatus with extremely low power consumption can be obtained.

For stable characteristics of the transistor, a base film is preferably provided. The base film can be formed with a single-layer structure or a stacked-layer structure using an inorganic insulating film such as a silicon oxide film, a silicon nitride film, a silicon oxynitride film, or a silicon nitride oxide film. The base film can be formed by a sputtering method, a chemical vapor deposition (CVD) method (e.g., a plasma CVD method, a thermal CVD method, or a metal organic CVD (MOCVD) method), an atomic layer deposition (ALD) method, a coating method, a printing method, or the like. Note that the base film is not necessarily provided.

Note that an FET 623 is illustrated as a transistor formed in the driver circuit 601. In addition, the driver circuit may be formed with any of a variety of circuits such as a CMOS circuit, a PMOS circuit, or an NMOS circuit. Although a driver integrated type in which the driver circuit is formed over the substrate is illustrated in this embodiment, the driver circuit is not necessarily formed over the substrate, and the driver circuit can be formed outside, not over the substrate.

The pixel portion 602 includes a plurality of pixels including a switching FET 611, a current controlling FET 612, and a first electrode 613 electrically connected to a drain of the current controlling FET 612. One embodiment of the present invention is not limited to the structure. The pixel portion 602 may include three or more FETs and a capacitor in combination.

Note that to cover an end portion of the first electrode 613, an insulator 614 is formed, for which a positive photosensitive acrylic resin film is used here.

In order to improve coverage with an EL layer or the like which is formed later, the insulator 614 is formed to have a curved surface with curvature at its upper or lower end portion. For example, in the case where positive photosensitive acrylic resin is used as a material of the insulator 614, only the upper end portion of the insulator 614 preferably has a curved surface with a curvature radius (0.2 μm to 3 μm). As the insulator 614, either a negative photosensitive resin or a positive photosensitive resin can be used.

An EL layer 616 and a second electrode 617 are formed over the first electrode 613. Here, as a material used for the first electrode 613 functioning as an anode, a material having a high work function is preferably used. For example, a single-layer film of an ITO film, an indium tin oxide film containing silicon, an indium oxide film containing zinc oxide at 2 wt % to 20 wt %, a titanium nitride film, a chromium film, a tungsten film, a Zn film, a Pt film, or the like, a stack of a titanium nitride film and a film containing aluminum as its main component, a stack of three layers of a titanium nitride film, a film containing aluminum as its main component, and a titanium nitride film, or the like can be used. The stacked-layer structure enables low wiring resistance, favorable ohmic contact, and a function as an anode.

The EL layer 616 is formed by any of a variety of methods such as an evaporation method using an evaporation mask, an inkjet method, and a spin coating method. The EL layer 616 has the structure described in Embodiment 2. As another material included in the EL layer 616, a low molecular compound or a high molecular compound (including an oligomer or a dendrimer) may be used.

As a material used for the second electrode 617, which is formed over the EL layer 616 and functions as a cathode, a material having a low work function (e.g., Al, Mg, Li, and Ca, or an alloy or a compound thereof, such as MgAg, MgIn, and AlLi) is preferably used. In the case where light generated in the EL layer 616 is transmitted through the second electrode 617, a stack of a thin metal film and a transparent conductive film (e.g., ITO, indium oxide containing zinc oxide at 2 wt % to 20 wt %, indium tin oxide containing silicon, or zinc oxide (ZnO)) is preferably used for the second electrode 617.

Note that the light-emitting device is formed with the first electrode 613, the EL layer 616, and the second electrode 617. The light-emitting device is the light-emitting device described in Embodiment 2. In the light-emitting apparatus of this embodiment, the pixel portion, which includes a plurality of light-emitting devices, may include both the light-emitting device described in Embodiment 2 and a light-emitting device having a different structure.

The sealing substrate 604 is attached to the element substrate 610 with the sealing material 605, so that a light-emitting device 618 is provided in the space 607 surrounded by the element substrate 610, the sealing substrate 604, and the sealing material 605. The space 607 may be filled with a filler, or may be filled with an inert gas (such as nitrogen or argon), or the sealing material. It is preferable that the sealing substrate be provided with a recessed portion and a drying agent be provided in the recessed portion, in which case deterioration due to influence of moisture can be suppressed.

An epoxy-based resin or glass frit is preferably used for the sealing material 605. It is preferable that such a material not be permeable to moisture or oxygen as much as possible. As the sealing substrate 604, a glass substrate, a quartz substrate, or a plastic substrate formed of fiber reinforced plastic (FRP), poly(vinyl fluoride) (PVF), polyester, and acrylic resin can be used.

Although not illustrated in FIGS. 2A and 2B, a protective film may be provided over the second electrode. As the protective film, an organic resin film or an inorganic insulating film may be formed. The protective film may be formed so as to cover an exposed portion of the sealing material 605. The protective film may be provided so as to cover surfaces and side surfaces of the pair of substrates and exposed side surfaces of a sealing layer, an insulating layer, and the like.

The protective film can be formed using a material through which an impurity such as water does not permeate easily. Thus, diffusion of an impurity such as water from the outside into the inside can be effectively suppressed.

As a material of the protective film, an oxide, a nitride, a fluoride, a sulfide, a ternary compound, a metal, a polymer, or the like can be used. For example, the material may contain aluminum oxide, hafnium oxide, hafnium silicate, lanthanum oxide, silicon oxide, strontium titanate, tantalum oxide, titanium oxide, zinc oxide, niobium oxide, zirconium oxide, tin oxide, yttrium oxide, cerium oxide, scandium oxide, erbium oxide, vanadium oxide, indium oxide, aluminum nitride, hafnium nitride, silicon nitride, tantalum nitride, titanium nitride, niobium nitride, molybdenum nitride, zirconium nitride, gallium nitride, a nitride containing titanium and aluminum, an oxide containing titanium and aluminum, an oxide containing aluminum and zinc, a sulfide containing manganese and zinc, a sulfide containing cerium and strontium, an oxide containing erbium and aluminum, an oxide containing yttrium and zirconium, or the like.

The protective film is preferably formed using a deposition method with favorable step coverage. One such method is an atomic layer deposition (ALD) method. A material that can be deposited by an ALD method is preferably used for the protective film. A dense protective film having reduced defects such as cracks or pinholes or a uniform thickness can be formed by an ALD method. Furthermore, damage caused to a process member in forming the protective film can be reduced.

By an ALD method, a uniform protective film with few defects can be formed even on, for example, a surface with a complex uneven shape or upper, side, and lower surfaces of a touch panel.

As described above, the light-emitting apparatus manufactured using the light-emitting device described in Embodiment 2 can be obtained.

The light-emitting apparatus in this embodiment is manufactured using the light-emitting device described in Embodiment 2 and thus can have favorable characteristics. Specifically, since the light-emitting device described in Embodiment 2 has high emission efficiency, the light-emitting apparatus can achieve low power consumption.

FIGS. 3A and 3B each illustrate an example of a light-emitting apparatus in which full color display is achieved by formation of a light-emitting device exhibiting white light emission and with the use of coloring layers (color filters) and the like. In FIG. 3A, a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, first electrodes 1024W, 1024R, 1024G, and 1024B of light-emitting devices, a partition 1025, an EL layer 1028, a second electrode 1029 of the light-emitting devices, a sealing substrate 1031, a sealing material 1032, and the like are illustrated.

In FIG. 3A, coloring layers (a red coloring layer 1034R, a green coloring layer 1034G, and a blue coloring layer 1034B) are provided on a transparent base material 1033. A black matrix 1035 may be additionally provided. The transparent base material 1033 provided with the coloring layers and the black matrix is aligned and fixed to the substrate 1001. Note that the coloring layers and the black matrix 1035 are covered with an overcoat layer 1036. In FIG. 3A, light emitted from part of the light-emitting layer does not pass through the coloring layers, while light emitted from the other part of the light-emitting layer passes through the coloring layers. Since light which does not pass through the coloring layers is white and light which passes through any one of the coloring layers is red, green, or blue, an image can be displayed using pixels of the four colors.

FIG. 3B illustrates an example in which the coloring layers (the red coloring layer 1034R, the green coloring layer 1034G, and the blue coloring layer 1034B) are provided between the gate insulating film 1003 and the first interlayer insulating film 1020. As in the structure, the coloring layers may be provided between the substrate 1001 and the sealing substrate 1031.

Figure 4:
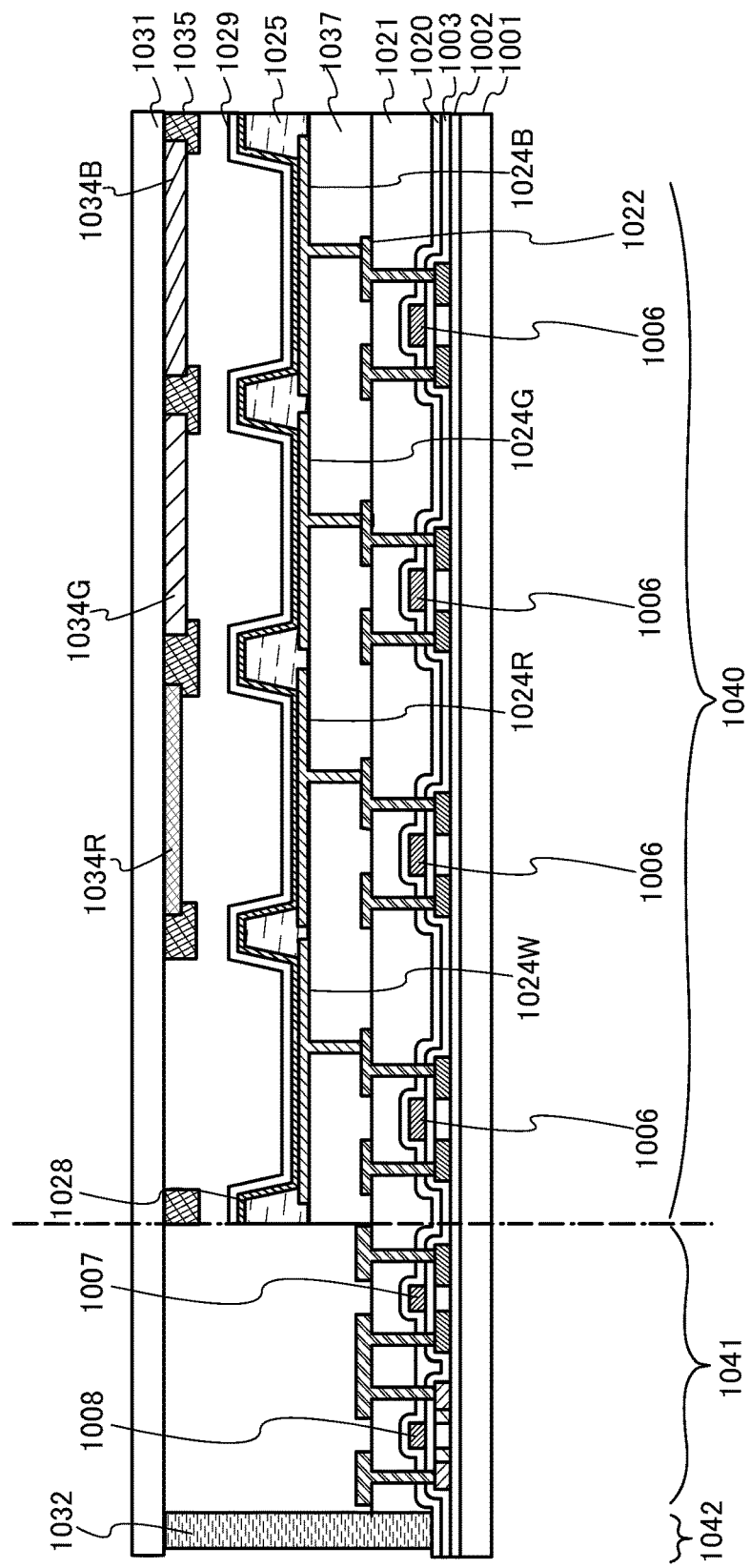
FIG. 4 is a conceptual view of an active matrix light-emitting apparatus.

The above-described light-emitting apparatus is a light-emitting apparatus having a structure in which light is extracted from the substrate 1001 side where FETs are formed (a bottom emission structure), but may be a light-emitting apparatus having a structure in which light is extracted from the sealing substrate 1031 side (a top emission structure). FIG. 4 is a cross-sectional view of a light-emitting apparatus having a top emission structure. In this case, a substrate which does not transmit light can be used as the substrate 1001. The process up to the step of forming a connection electrode which connects the FET and the anode of the light-emitting device is performed in a manner similar to that of the light-emitting apparatus having a bottom emission structure. Then, a third interlayer insulating film 1037 is formed to cover an electrode 1022. This insulating film may have a planarization function. The third interlayer insulating film 1037 can be formed using a material similar to that of the second interlayer insulating film, and can alternatively be formed using any of other known materials.

The first electrodes 1024W, 1024R, 1024G, and 1024B of the light-emitting devices each serve as an anode here, but may serve as a cathode. Furthermore, in the case of a light-emitting apparatus having a top emission structure as illustrated in FIG. 4, the first electrodes are preferably reflective electrodes. The EL layer 1028 is formed to have a structure similar to the structure of the EL layer 103, which is described in Embodiment 2, with which white light emission can be obtained.

In the case of a top emission structure as illustrated in FIG. 4, sealing can be performed with the sealing substrate 1031 on which the coloring layers (the red coloring layer 1034R, the green coloring layer 1034G, and the blue coloring layer 1034B) are provided. The sealing substrate 1031 may be provided with the black matrix 1035 which is positioned between pixels. The coloring layers (the red coloring layer 1034R, the green coloring layer 1034G, and the blue coloring layer 1034B) and the black matrix may be covered with the overcoat layer 1036. Note that a light-transmitting substrate is used as the sealing substrate 1031. Although an example in which full color display is performed using four colors of red, green, blue, and white is shown here, there is no particular limitation and full color display using four colors of red, yellow, green, and blue or three colors of red, green, and blue may be performed.

In the light-emitting apparatus having a top emission structure, a microcavity structure can be favorably employed. A light-emitting device with a microcavity structure is formed with the use of a reflective electrode as the first electrode and a semi-transmissive and semi-reflective electrode as the second electrode. The light-emitting device with a microcavity structure includes at least an EL layer between the reflective electrode and the semi-transmissive and semi-reflective electrode, which includes at least a light-emitting layer serving as a light-emitting region.

Note that the reflective electrode has a visible light reflectivity of 40% to 100%, preferably 70% to 100%, and a resistivity of $1\times10^{-2}$ Ωcm or lower. In addition, the semi-transmissive and semi-reflective electrode has a visible light reflectivity of 20% to 80%, preferably 40% to 70%, and a resistivity of $1\times10^{-2}$ Ωcm or lower.

Light emitted from the light-emitting layer included in the EL layer is reflected and resonated by the reflective electrode and the semi-transmissive and semi-reflective electrode.

In the light-emitting device, by changing thicknesses of the transparent conductive film, the composite material, the carrier-transport material, and the like, the optical path length between the reflective electrode and the semi-transmissive and semi-reflective electrode can be changed. Thus, light with a wavelength that is resonated between the reflective electrode and the semi-transmissive and semi-reflective electrode can be intensified while light with a wavelength that is not resonated therebetween can be attenuated.

Note that light that is reflected back by the reflective electrode (first reflected light) considerably interferes with light that directly enters the semi-transmissive and semi-reflective electrode from the light-emitting layer (first incident light). For this reason, the optical path length between the reflective electrode and the light-emitting layer is preferably adjusted to $(2n-1)\lambda/4$ (n is a natural number of 1 or larger and $\lambda$ is a wavelength of color to be amplified). By adjusting the optical path length, the phases of the first reflected light and the first incident light can be aligned with each other and the light emitted from the light-emitting layer can be further amplified.

Note that in the above structure, the EL layer may include a plurality of light-emitting layers or may include a single light-emitting layer. The tandem light-emitting device described above may be combined with a plurality of EL layers; for example, a light-emitting device may have a structure in which a plurality of EL layers are provided, a charge-generation layer is provided between the EL layers, and each EL layer includes a plurality of light-emitting layers or a single light-emitting layer.

With the microcavity structure, emission intensity with a specific wavelength in the front direction can be increased, whereby power consumption can be reduced. Note that in the case of a light-emitting apparatus which displays images with subpixels of four colors, red, yellow, green, and blue, the light-emitting apparatus can have favorable characteristics because the luminance can be increased owing to yellow light emission and each subpixel can employ a microcavity structure suitable for wavelengths of the corresponding color.

The light-emitting apparatus in this embodiment is manufactured using the light-emitting device described in Embodiment 2 and thus can have favorable characteristics. Specifically, since the light-emitting device described in Embodiment 2 has high emission efficiency, the light-emitting apparatus can achieve low power consumption.

Figure 5A:
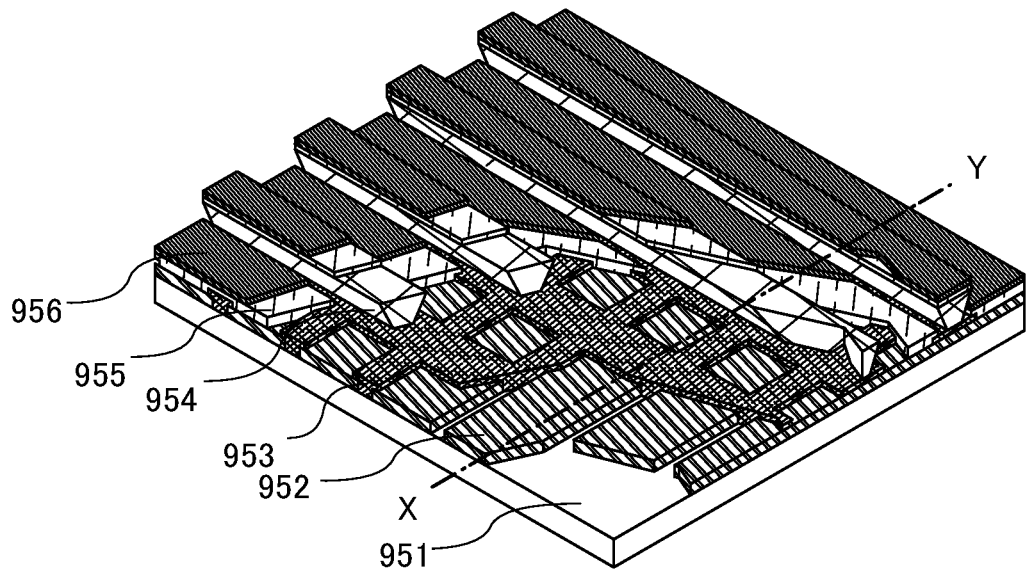
FIGS. 5A and 5B are conceptual views of a passive matrix light-emitting apparatus.
Figure 5B:
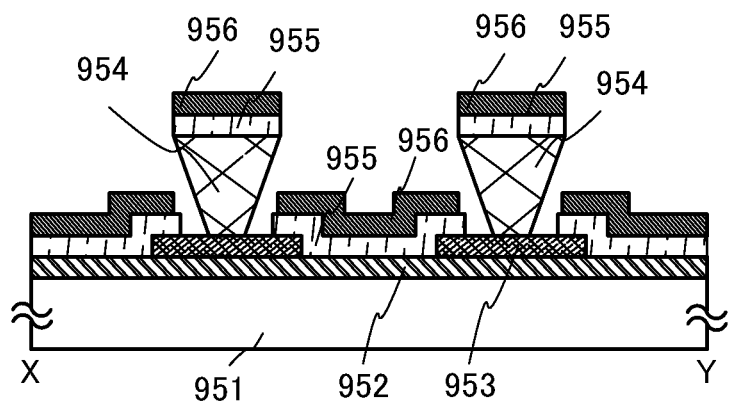

An active matrix light-emitting apparatus is described above, whereas a passive matrix light-emitting apparatus is described below. FIGS. 5A and 5B illustrate a passive matrix light-emitting apparatus manufactured using the present invention. Note that FIG. 5A is a perspective view of the light-emitting apparatus, and FIG. 5B is a cross-sectional view taken along the line X-Y in FIG. 5A. In FIGS. 5A and 5B, over a substrate 951, an EL layer 955 is provided between an electrode 952 and an electrode 956. An end portion of the electrode 952 is covered with an insulating layer 953. A partition layer 954 is provided over the insulating layer 953. The sidewalls of the partition layer 954 are aslope such that the distance between both sidewalls is gradually narrowed toward the surface of the substrate. In other words, a cross section taken along the direction of the short side of the partition layer 954 is trapezoidal, and the lower side (a side of the trapezoid which is parallel to the surface of the insulating layer 953 and is in contact with the insulating layer 953) is shorter than the upper side (a side of the trapezoid which is parallel to the surface of the insulating layer 953 and is not in contact with the insulating layer 953). The partition layer 954 thus provided can prevent defects in the light-emitting device due to static electricity or others. The passive-matrix light-emitting apparatus also includes the light-emitting device described in Embodiment 2; thus, the light-emitting apparatus can have high reliability or low power consumption.

Since many minute light-emitting devices arranged in a matrix in the light-emitting apparatus described above can each be controlled, the light-emitting apparatus can be suitably used as a display device for displaying images.

This embodiment can be freely combined with any of the other embodiments.

Embodiment 4

Figure 6A:
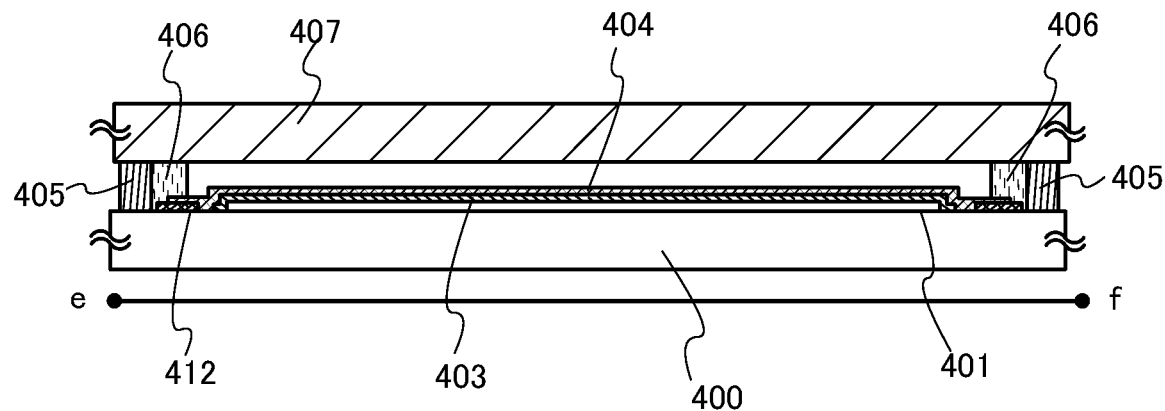
FIGS. 6A and 6B illustrate a lighting device.
Figure 6B:
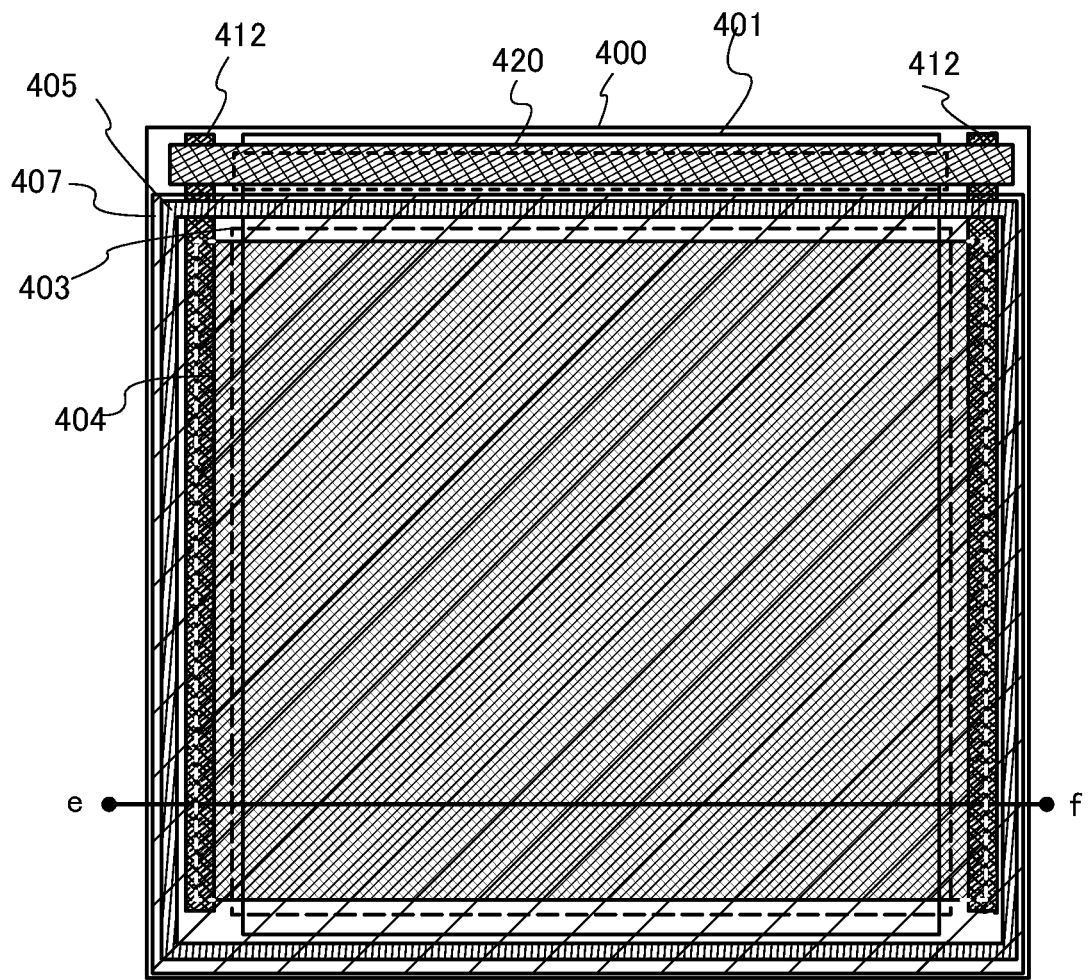

In this embodiment, an example in which the light-emitting device described in Embodiment 2 is used for a lighting device will be described with reference to FIGS. 6A and 6B. FIG. 6B is a top view of the lighting device, and FIG. 6A is a cross-sectional view taken along the line e-f in FIG. 6B.

In the lighting device in this embodiment, a first electrode 401 is formed over a substrate 400 which is a support and has a light-transmitting property. The first electrode 401 corresponds to the first electrode 101 in Embodiment 1. When light is extracted through the first electrode 401 side, the first electrode 401 is formed using a material having a light-transmitting property.

A pad 412 for applying voltage to a second electrode 404 is provided over the substrate 400.

An EL layer 403 is formed over the first electrode 401. The structure of the EL layer 403 corresponds to, for example, the structure of the EL layer 103 in Embodiment 1, or the structure in which the light-emitting units 511 and 512 and the charge-generation layer 513 are combined. Refer to the description for the structure.

The second electrode 404 is formed to cover the EL layer 403. The second electrode 404 corresponds to the second electrode 102 in Embodiment 1. The second electrode 404 is formed using a material having high reflectance when light is extracted through the first electrode 401 side. The second electrode 404 is connected to the pad 412, whereby voltage is applied.

As described above, the lighting device described in this embodiment includes a light-emitting device including the first electrode 401, the EL layer 403, and the second electrode 404. Since the light-emitting device is a light-emitting device with high emission efficiency, the lighting device in this embodiment can be a lighting device having low power consumption.

The substrate 400 provided with the light-emitting device having the above structure is fixed to a sealing substrate 407 with sealing materials 405 and 406 and sealing is performed, whereby the lighting device is completed. It is possible to use only either the sealing material 405 or the sealing material 406. The inner sealing material 406 (not shown in FIG. 6B) can be mixed with a desiccant which enables moisture to be adsorbed, increasing reliability.

When parts of the pad 412 and the first electrode 401 are extended to the outside of the sealing materials 405 and 406, the extended parts can serve as external input terminals. An IC chip 420 mounted with a converter or the like may be provided over the external input terminals.

The lighting device described in this embodiment includes as an EL element the light-emitting device described in Embodiment 2; thus, the light-emitting apparatus can consume less power.

Embodiment 5

In this embodiment, examples of electronic apparatuses each including the light-emitting device described in Embodiment 2 will be described. The light-emitting device described in Embodiment 2 has high emission efficiency and low power consumption. As a result, the electronic apparatuses described in this embodiment can each include a light-emitting portion having low power consumption.

Examples of the electronic apparatus including the above light-emitting device include television devices (also referred to as TV or television receivers), monitors for computers and the like, digital cameras, digital video cameras, digital photo frames, cellular phones (also referred to as mobile phones or mobile phone devices), portable game machines, portable information terminals, audio playback devices, and large game machines such as pachinko machines. Specific examples of these electronic apparatuses are shown below.

FIG. 7A illustrates an example of a television device. In the television device, a display portion 7103 is incorporated in a housing 7101. Here, the housing 7101 is supported by a stand 7105. Images can be displayed on the display portion 7103, and in the display portion 7103, the light-emitting devices described in Embodiment 2 are arranged in a matrix.

The television device can be operated with an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device is provided with a receiver, a modem, and the like. With the use of the receiver, a general television broadcast can be received. Moreover, when the television device is connected to a communication network with or without wires via the modem, one-way (from a sender to a receiver) or two-way (between a sender and a receiver or between receivers) data communication can be performed.

FIG. 7B1 illustrates a computer, which includes a main body 7201, a housing 7202, a display portion 7203, a keyboard 7204, an external connection port 7205, a pointing device 7206, and the like. Note that this computer is manufactured using the light-emitting devices described in Embodiment 2 and arranged in a matrix in the display portion 7203. The computer illustrated in FIG. 7B1 may have a structure illustrated in FIG. 7B2. A computer illustrated in FIG. 7B2 is provided with a second display portion 7210 instead of the keyboard 7204 and the pointing device 7206. The second display portion 7210 is a touch panel, and input operation can be performed by touching display for input on the second display portion 7210 with a finger or a dedicated pen. The second display portion 7210 can also display images other than the display for input. The display portion 7203 may also be a touch panel. Connecting the two screens with a hinge can prevent troubles; for example, the screens can be prevented from being cracked or broken while the computer is being stored or carried.

FIG. 7C illustrates an example of a portable terminal. A cellular phone is provided with a display portion 7402 incorporated in a housing 7401, operation buttons 7403, an external connection port 7404, a speaker 7405, a microphone 7406, and the like. Note that the cellular phone has the display portion 7402 including the light-emitting devices described in Embodiment 2 and arranged in a matrix.

When the display portion 7402 of the portable terminal illustrated in FIG. 7C is touched with a finger or the like, data can be input into the portable terminal. In this case, operations such as making a call and creating an e-mail can be performed by touching the display portion 7402 with a finger or the like.

The display portion 7402 has mainly three screen modes. The first mode is a display mode mainly for displaying images. The second mode is an input mode mainly for inputting information such as text. The third mode is a display-and-input mode in which the two modes, the display mode and the input mode, are combined.

For example, in the case of making a call or creating an e-mail, a text input mode mainly for inputting text is selected for the display portion 7402 so that text displayed on the screen can be input. In this case, it is preferable to display a keyboard or number buttons on almost the entire screen of the display portion 7402.

When a sensing device including a sensor such as a gyroscope sensor or an acceleration sensor for detecting inclination is provided inside the portable terminal, display on the screen of the display portion 7402 can be automatically changed in direction by determining the orientation of the portable terminal (whether the portable terminal is placed horizontally or vertically).

The screen modes are switched by touching the display portion 7402 or operating the operation buttons 7403 of the housing 7401. Alternatively, the screen modes can be switched depending on the kind of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 7402 is not performed for a certain period while a signal sensed by an optical sensor in the display portion 7402 is sensed, the screen mode may be controlled so as to be switched from the input mode to the display mode.

The display portion 7402 may also function as an image sensor. For example, an image of a palm print, a fingerprint, or the like is taken when the display portion 7402 is touched with the palm or the finger, whereby personal authentication can be performed. Furthermore, by providing a backlight or a sensing light source which emits near-infrared light in the display portion, an image of a finger vein, a palm vein, or the like can be taken.

Note that the structure described in this embodiment can be combined with any of the structures described in Embodiments 1 to 4 as appropriate.

As described above, the application range of the light-emitting apparatus having the light-emitting device described in Embodiment 2 is wide so that this light-emitting apparatus can be applied to electronic apparatuses in a variety of fields. By using the light-emitting device described in Embodiment 2, an electronic apparatus with low power consumption can be obtained.

Figure 8A:
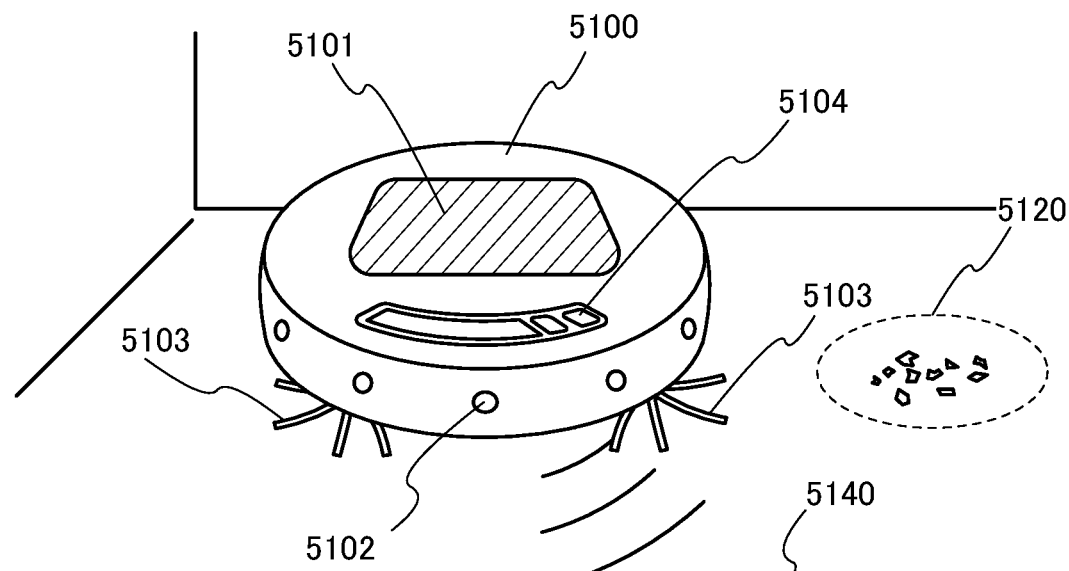
FIGS. 8A to 8C illustrate electronic apparatuses.

FIG. 8A is a schematic view illustrating an example of a cleaning robot.

A cleaning robot 5100 includes a display 5101 on its top surface, a plurality of cameras 5102 on its side surface, a brush 5103, and operation buttons 5104. Although not illustrated, the bottom surface of the cleaning robot 5100 is provided with a tire, an inlet, and the like. Furthermore, the cleaning robot 5100 includes various sensors such as an infrared sensor, an ultrasonic sensor, an acceleration sensor, a piezoelectric sensor, an optical sensor, and a gyroscope sensor. The cleaning robot 5100 has a wireless communication means.

The cleaning robot 5100 is self-propelled, detects dust 5120, and sucks up the dust through the inlet provided on the bottom surface.

The cleaning robot 5100 can determine whether there is an obstacle such as a wall, furniture, or a step by analyzing images taken by the cameras 5102. When the cleaning robot 5100 detects an object that is likely to be caught in the brush 5103 (e.g., a wire) by image analysis, the rotation of the brush 5103 can be stopped.

The display 5101 can display the remaining capacity of a battery, the amount of collected dust, and the like. The display 5101 may display a path on which the cleaning robot 5100 has run. The display 5101 may be a touch panel, and the operation buttons 5104 may be provided on the display 5101.

The cleaning robot 5100 can communicate with a portable electronic apparatus 5140 such as a smartphone. The portable electronic apparatus 5140 can display images taken by the cameras 5102. Accordingly, an owner of the cleaning robot 5100 can monitor his/her room even when the owner is not at home. The owner can also check the display on the display 5101 by the portable electronic apparatus 5140 such as a smartphone.

The light-emitting apparatus of one embodiment of the present invention can be used for the display 5101.

Figure 8B:
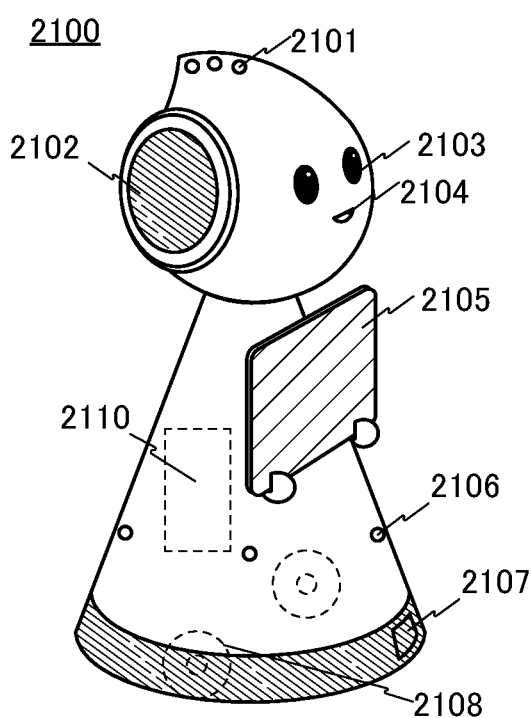

A robot 2100 illustrated in FIG. 8B includes an arithmetic device 2110, an illuminance sensor 2101, a microphone 2102, an upper camera 2103, a speaker 2104, a display 2105, a lower camera 2106, an obstacle sensor 2107, and a moving mechanism 2108.

The microphone 2102 has a function of detecting a speaking voice of a user, an environmental sound, and the like. The speaker 2104 also has a function of outputting sound. The robot 2100 can communicate with a user using the microphone 2102 and the speaker 2104.

The display 2105 has a function of displaying various kinds of information. The robot 2100 can display information desired by a user on the display 2105. The display 2105 may be provided with a touch panel. Moreover, the display 2105 may be a detachable information terminal, in which case charging and data communication can be performed when the display 2105 is set at the home position of the robot 2100.

The upper camera 2103 and the lower camera 2106 each have a function of taking an image of the surroundings of the robot 2100. The obstacle sensor 2107 can detect an obstacle in the direction where the robot 2100 advances with the moving mechanism 2108. The robot 2100 can move safely by recognizing the surroundings with the upper camera 2103, the lower camera 2106, and the obstacle sensor 2107. The light-emitting apparatus of one embodiment of the present invention can be used for the display 2105.

Figure 8C:
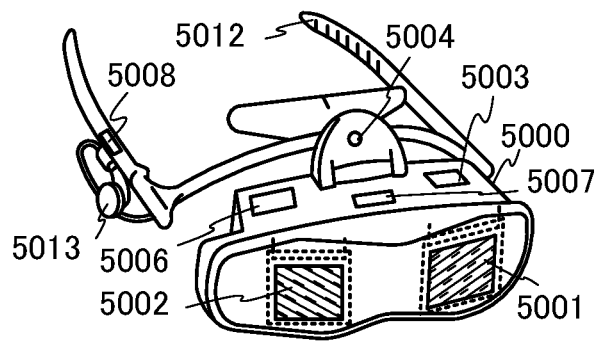

FIG. 8C illustrates an example of a goggle-type display. The goggle-type display includes, for example, a housing 5000, a display portion 5001, a speaker 5003, an LED lamp 5004, a connection terminal 5006, a sensor 5007 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared ray), a microphone 5008, a display portion 5002, a support 5012, and an earphone 5013.

The light-emitting apparatus of one embodiment of the present invention can be used for the display portion 5001 and the display portion 5002.

Figure 9:
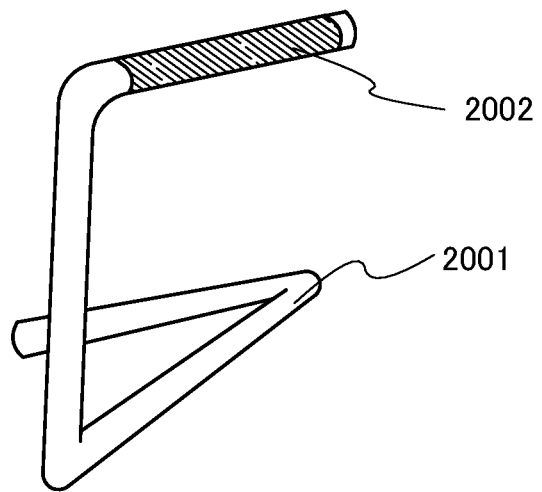
FIG. 9 illustrates a lighting device.

FIG. 9 illustrates an example in which the light-emitting device described in Embodiment 2 is used for a table lamp which is a lighting device. The table lamp illustrated in FIG. 9 includes a housing 2001 and a light source 2002, and the lighting device described in Embodiment 3 may be used for the light source 2002.

Figure 10:
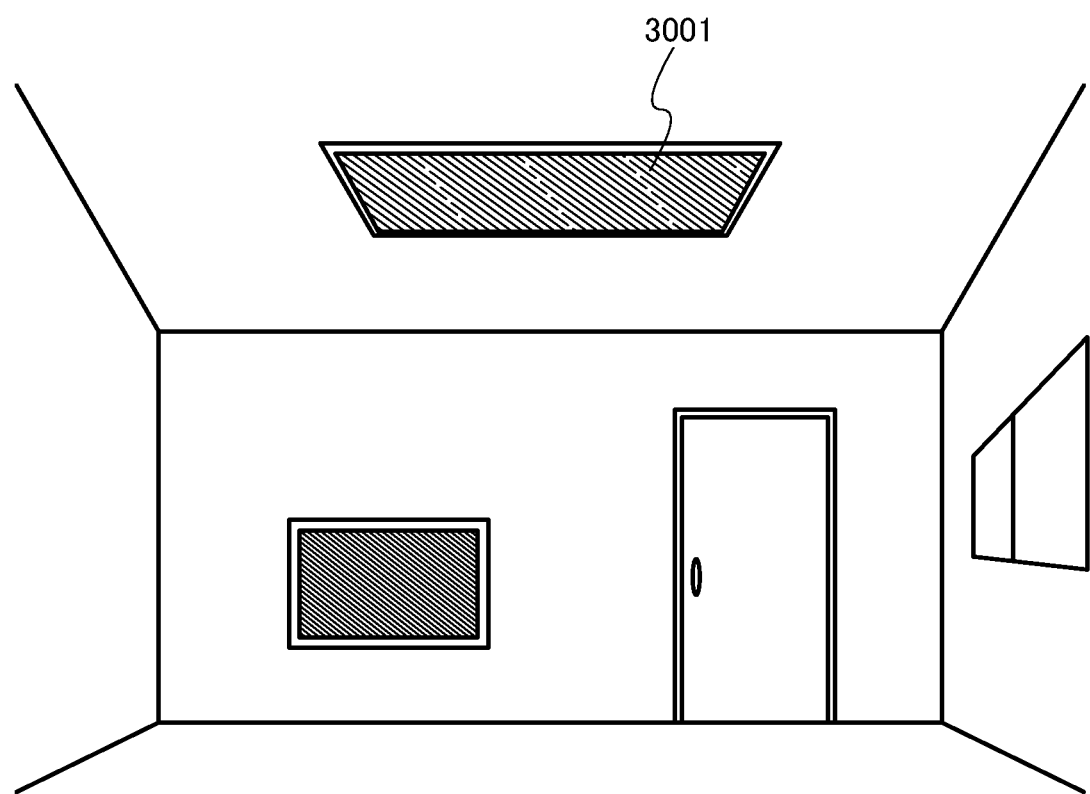
FIG. 10 illustrates alighting device.

FIG. 10 illustrates an example in which the light-emitting device described in Embodiment 2 is used for an indoor lighting device 3001. Since the light-emitting device described in Embodiment 2 has high emission efficiency, the lighting device can have low power consumption. Furthermore, since the light-emitting device described in Embodiment 2 can have a large area, the light-emitting device can be used for a large-area lighting device. Furthermore, since the light-emitting device described in Embodiment 2 is thin, the light-emitting device can be used for a lighting device having a reduced thickness.

Figure 11:
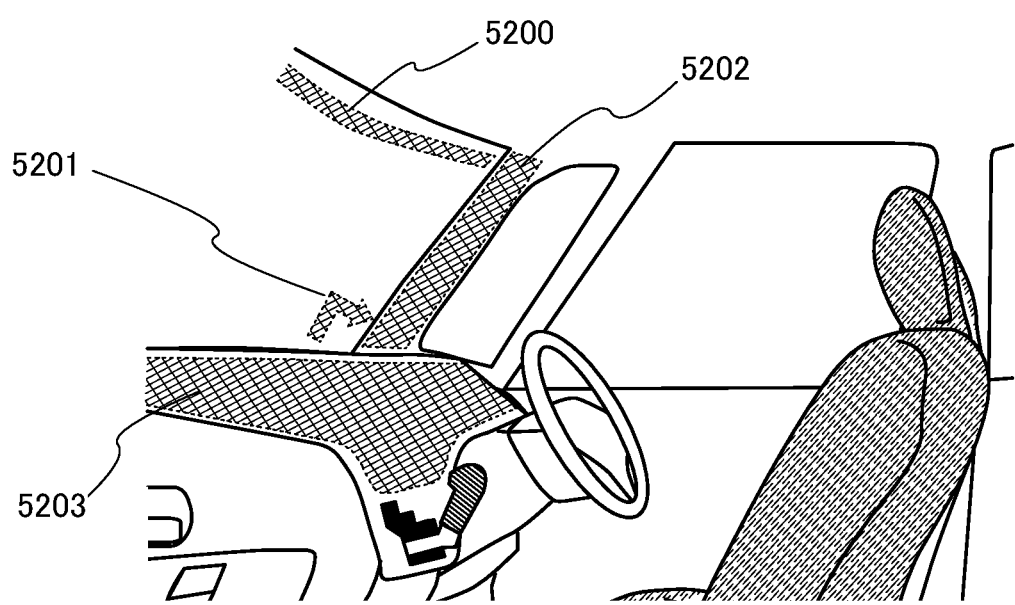
FIG. 11 illustrates in-vehicle display devices and lighting devices.

The light-emitting device described in Embodiment 2 can also be used for an automobile windshield or an automobile dashboard. FIG. 11 illustrates one mode in which the light-emitting devices described in Embodiment 2 are used for an automobile windshield and an automobile dashboard. Display regions 5200 to 5203 each include the light-emitting device described in Embodiment 2.

The display regions 5200 and 5201 are display devices which are provided in the automobile windshield and in which light-emitting devices each of which is described in Embodiment 2 are incorporated. The light-emitting devices described in Embodiment 2 can be formed into what is called a see-through display device, through which the opposite side can be seen, by including a first electrode and a second electrode formed of electrodes having a light-transmitting property. Such see-through display devices can be provided even in the automobile windshield without hindering the view. In the case where a driving transistor or the like is provided, a transistor having a light-transmitting property, such as an organic transistor including an organic semiconductor material or a transistor including an oxide semiconductor, is preferably used.

A display device incorporating the light-emitting device described in Embodiment 2 is provided in the display region 5202 in a pillar portion. The display region 5202 can compensate for the view hindered by the pillar by displaying an image taken by an imaging unit provided in the car body. Similarly, the display region 5203 provided in the dashboard portion can compensate for the view hindered by the car body by displaying an image taken by an imaging unit provided on the outside of the automobile. Thus, blind areas can be eliminated to enhance the safety. Images that compensate for the areas which a driver cannot see enable the driver to ensure safety easily and comfortably.

The display region 5203 can provide a variety of kinds of information by displaying navigation data, the speed, the number of rotations, air-condition setting, and the like. The content or layout of the display can be changed freely by a user as appropriate. Note that such information can also be displayed on the display regions 5200 to 5203. The display regions 5200 to 5203 can also be used as lighting devices.

Figure 12A:
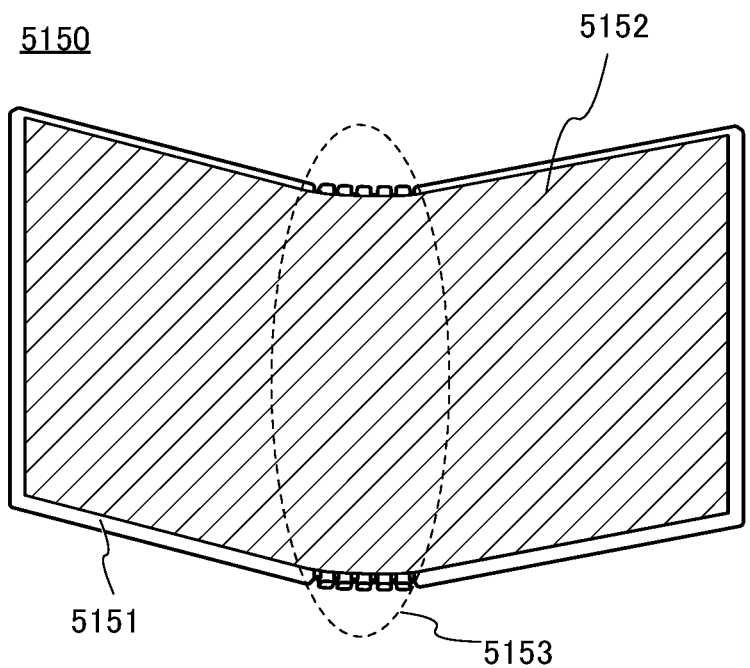
FIGS. 12A and 12B illustrate an electronic apparatus.
Figure 12B:
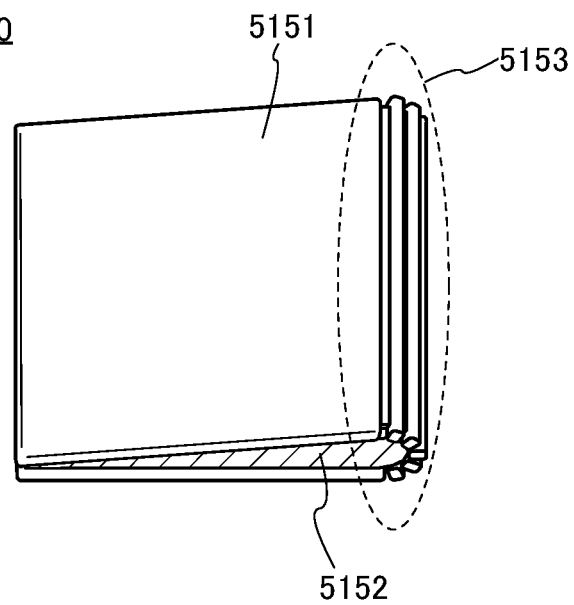

FIGS. 12A and 12B illustrate a foldable portable information terminal 5150. The foldable portable information terminal 5150 includes a housing 5151, a display region 5152, and a bend portion 5153. FIG. 12A illustrates the portable information terminal 5150 that is opened. FIG. 12B illustrates the portable information terminal 5150 that is folded. Despite its large display region 5152, the portable information terminal 5150 is compact in size and has excellent portability when folded.

The display region 5152 can be folded in half with the bend portion 5153. The bend portion 5153 includes a flexible member and a plurality of supporting members. When the display region is folded, the flexible member expands and the bend portion 5153 has a radius of curvature of greater than or equal to 2 mm, preferably greater than or equal to 3 mm.

Note that the display region 5152 may be a touch panel (an input/output device) including a touch sensor (an input device). The light-emitting apparatus of one embodiment of the present invention can be used for the display region 5152.

Figure 13A:
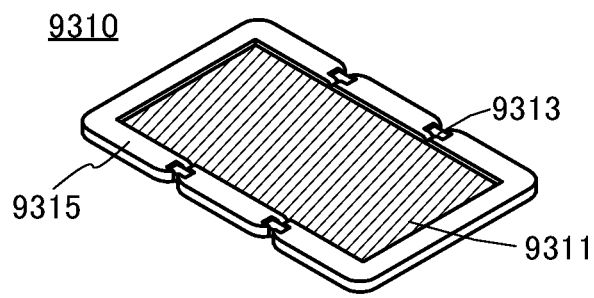
FIGS. 13A to 13C illustrate an electronic apparatus.
Figure 13B:
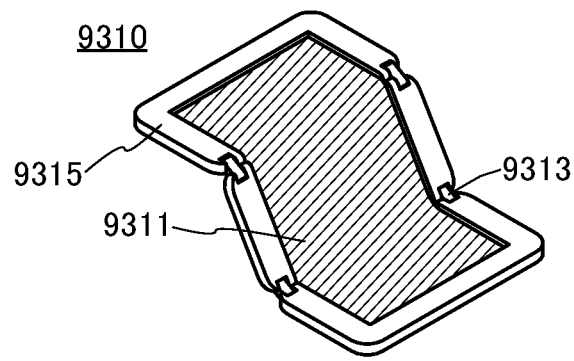
Figure 13C:
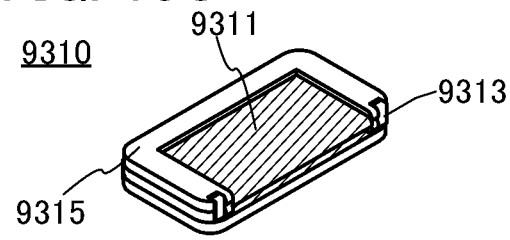

FIGS. 13A to 13C illustrate a foldable portable information terminal 9310. FIG. 13A illustrates the portable information terminal 9310 that is opened. FIG. 13B illustrates the portable information terminal 9310 that is being opened or being folded. FIG. 13C illustrates the portable information terminal 9310 that is folded. The portable information terminal 9310 is highly portable when folded. The portable information terminal 9310 is highly browsable when opened because of a seamless large display region.

A display panel 9311 is supported by three housings 9315 joined together by hinges 9313. Note that the display panel 9311 may be a touch panel (an input/output device) including a touch sensor (an input device). By folding the display panel 9311 at the hinges 9313 between two housings 9315, the portable information terminal 9310 can be reversibly changed in shape from the opened state to the folded state. The light-emitting apparatus of one embodiment of the present invention can be used for the display panel 9311.

Example 1

Synthesis Example 1

In this example, a synthesis method of N-(3,3",5',5"-tetra-t-butyl-1,1':3',1"-terphenyl-5-yl)-N-phenyl-9,9-dimethyl-9H-fluoren-2-amine (abbreviation: mmtBumTPFA-02), which is the arylamine compound of one embodiment of the present invention described in Embodiment 1, will be described. A structure of mmtBumTPFA-02 is shown below.

[Chemical Formula 39]

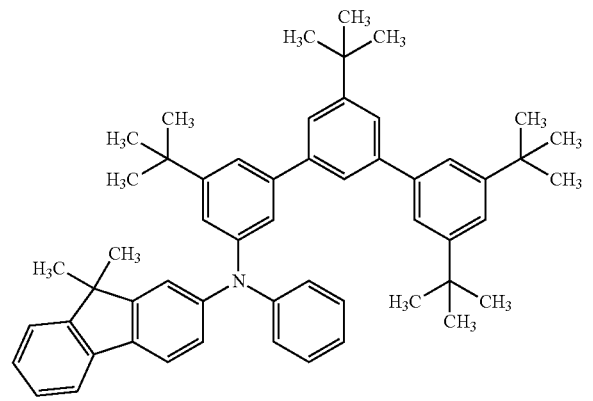

Step 1: Synthesis of 3-bromo-3',5,5'-tri-tert-butylbiphenyl

Into a three-neck flask were put 37.2 g (128 mmol) of 1,3-dibromo-5-tert-butylbenzene, 20.0 g (85 mmol) of 3,5-di-tert-butylphenylboronic acid, 35.0 g (255 mmol) of potassium carbonate, 570 mL of toluene, 170 mL of ethanol, and 130 mL of tap water. The mixture was degassed under reduced pressure, and then the air in the flask was replaced with nitrogen. Then, 382 mg (1.7 mmol) of palladium acetate and 901 mg (3.4 mmol) of triphenylphosphine were added, and the mixture was heated at 40° C. for approximately 5 hours. After that, the temperature of the flask was lowered to room temperature, and the mixture was separated into an organic layer and an aqueous layer. Magnesium sulfate was added to this organic layer to eliminate moisture, whereby the organic layer was concentrated. The obtained solution was purified by silica gel column chromatography, whereby 21.5 g of a target colorless oily substance was obtained in a yield of 63%. The synthesis scheme of Step 1 is shown below.

[Chemical Formula 40]

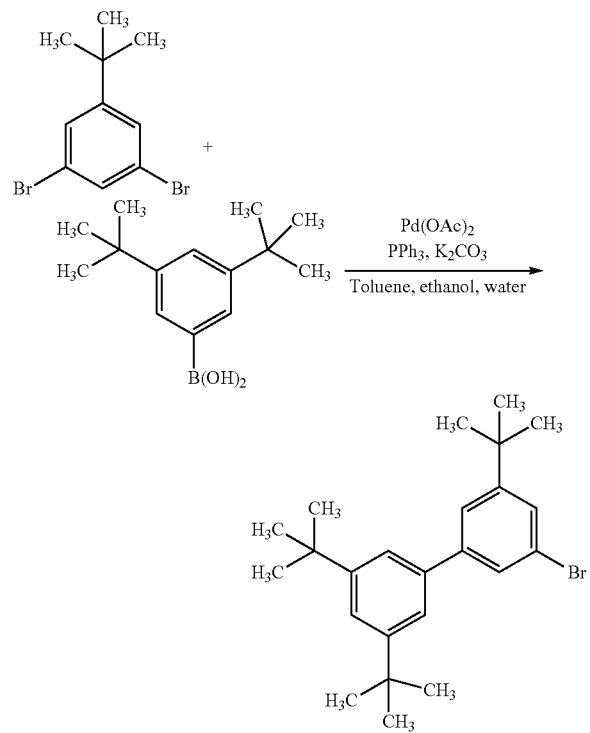

Step 2: Synthesis of 2-(3',5,5'-tri-tert-butyl[1,1'-biphenyl]-3-yl)-4,4,5,5-tetramethyl-1,3,2-dioxaborolane Into a three-neck flask were put 15.0 g (38 mmol) of 3-bromo-3',5,5'-tri-tert-butylbiphenyl obtained in Step 1, 10.5 g (41 mmol) of 4,4,4',4',5,5,5',5'-octamethyl-2,2'-bi-1,3,2-dioxaborolane, 11.0 g (113 mmol) of potassium acetate, and 125 mL of N,N-dimethylformamide. The mixture was degassed under reduced pressure, the air in the flask was replaced with nitrogen, 1.5 g (1.9 mmol) of [1,1'-bis(diphenylphosphino)ferrocene]dichloropalladium(II) was added thereto, and the mixture was heated at 100° C. for approximately three hours. Then, the temperature of the flask was lowered to room temperature, and the mixture was separated into an organic layer and an aqueous layer, and extraction was performed with ethyl acetate. Magnesium sulfate was added to the solution of the extract to eliminate moisture, whereby the solution of the extract was concentrated. A toluene solution of the obtained mixture was purified by silica gel column chromatography, and the resulting solution was concentrated to give a condensed toluene solution. Ethanol was added to this toluene solution and the toluene solution was concentrated under reduced pressure, whereby an ethanol suspension was obtained. The precipitate was filtrated at approximately 20° C., and the obtained solid was dried at approximately 80° C. under reduced pressure, whereby 13.6 g of a target white solid was obtained in a yield of 81%. The synthesis scheme of Step 2 is shown below.

[Chemical Formula 41]

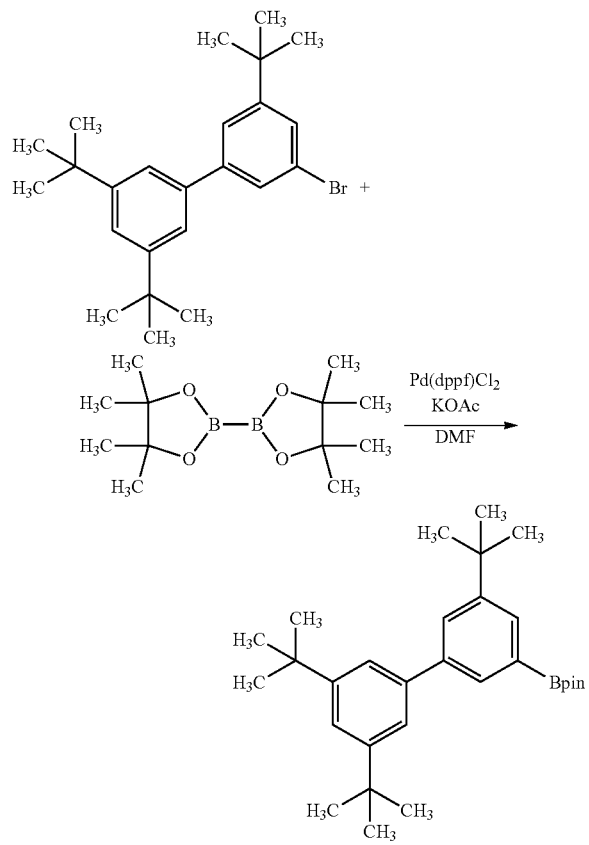

Step 3: Synthesis of 3-bromo-3",5,5',5"-tetra-tert-butyl-1,1':3',1"-terphenyl

Into a three-neck flask were put 5.0 g (11.1 mmol) of 2-(3',5,5'-tri-tert-butyl[1,1'-biphenyl]-3-yl)-4,4,5,5-tetramethyl-1,3,2-dioxaborolane, 4.8 g (16.7 mmol) of 1,3-dibromo-5-tert-butylbenzene, 4.6 g (33.3 mmol) of potassium carbonate, 56 mL of toluene, 22 mL of ethanol, and 17 mL of tap water. The mixture was degassed under reduced pressure, the air in the flask was replaced with nitrogen, 50 mg (0.22 mmol) of palladium acetate and 116 mg (0.44 mmol) of triphenylphosphine were added thereto, and the mixture was heated at 80° C. for approximately 10 hours. After that, the temperature of the flask was lowered to room temperature, and the mixture was separated into an organic layer and an aqueous layer. Magnesium sulfate was added to this solution to eliminate moisture, whereby this solution was concentrated. A hexane solution of the obtained solution was purified by silica gel column chromatography, whereby 3.0 g of a target white solid was obtained in a yield of 51.0%. The synthesis scheme of 3-bromo-3",5,5',5"-tetra-tert-butyl-1,1':3',1"-terphenyl of Step 3 is shown below.

[Chemical Formula 42]

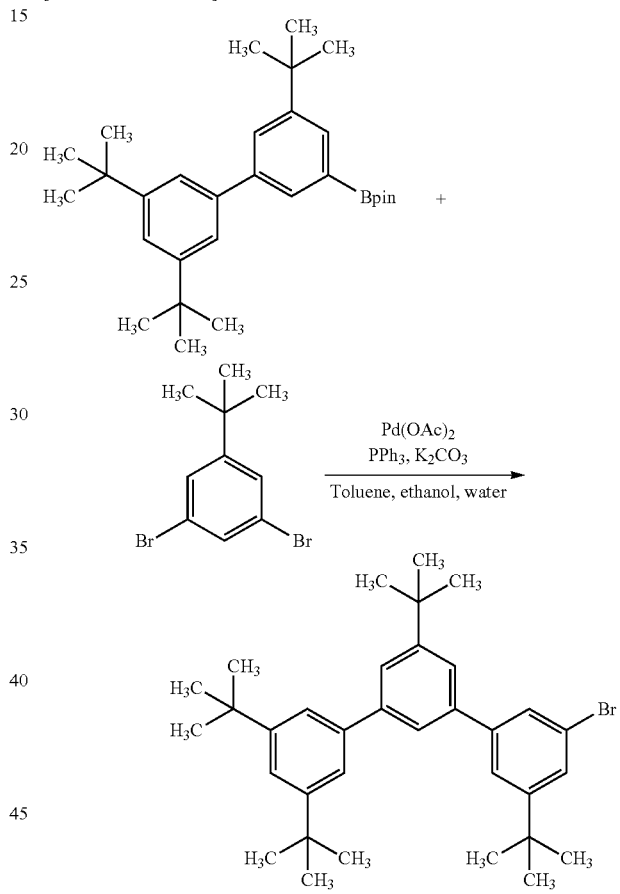

Step 4: Synthesis of mmtBumTPFA-02

Into a three-neck flask were put 3.0 g (5.6 mmol) of 3-bromo-3",5,5',5"-tetra-tert-butyl-1,1':3',1"-terphenyl, 1.6 g (5.6 mmol) of 2-anilino-9,9-dimethylfluorene, 1.6 g (16.8 mmol) of sodium tert-butoxide, and 28 mL of toluene. The mixture was degassed under reduced pressure, the air in the flask was replaced with nitrogen, 64 mg (0.11 mmol) of bis(dibenzylideneacetone)palladium(0) and 138 mg (0.34 mmol) of 2-dicyclohexylphosphino-2',6'-dimethoxybiphenyl were added thereto, and the mixture was heated at 120° C. for approximately 8 hours. After that, the temperature of the flask was lowered to approximately 60° C., approximately 1 mL of water was added, a precipitated solid was separated by filtration, and the solid was washed with toluene. The filtrate was concentrated, and the obtained toluene solution was purified by silica gel column chromatography. The obtained solution was concentrated to give a condensed toluene solution. Ethanol was added to this toluene solution and the toluene solution was concentrated under reduced pressure, whereby an ethanol suspension was obtained. The precipitate was filtrated at approximately 20° C., and ethanol was eliminated from the obtained solid by pressure reduction at approximately 80° C., whereby 3.2 g of a target white solid was obtained in a yield of 78%. The synthesis scheme of mmtBumTPFA-02 of Step 4 is shown below.

[Chemical Formula 43]

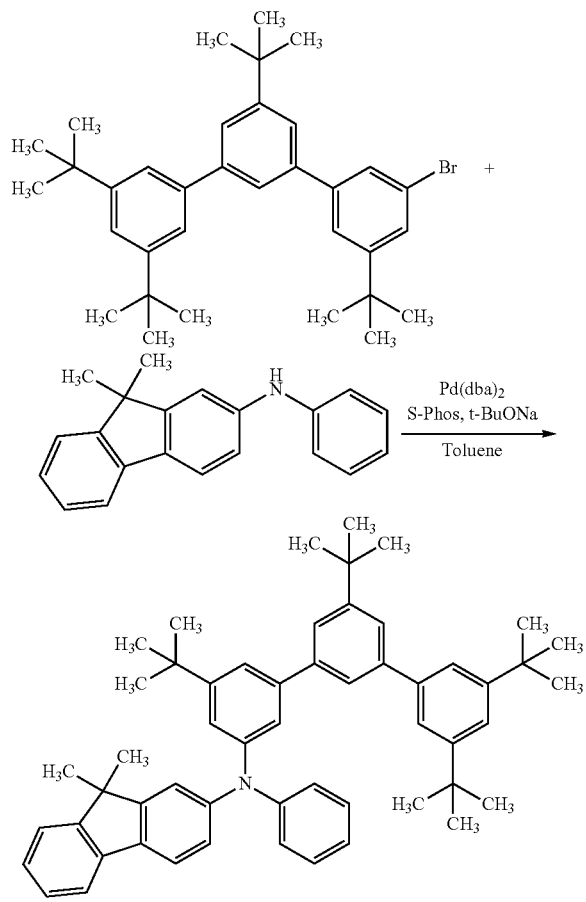

Figure 14A:
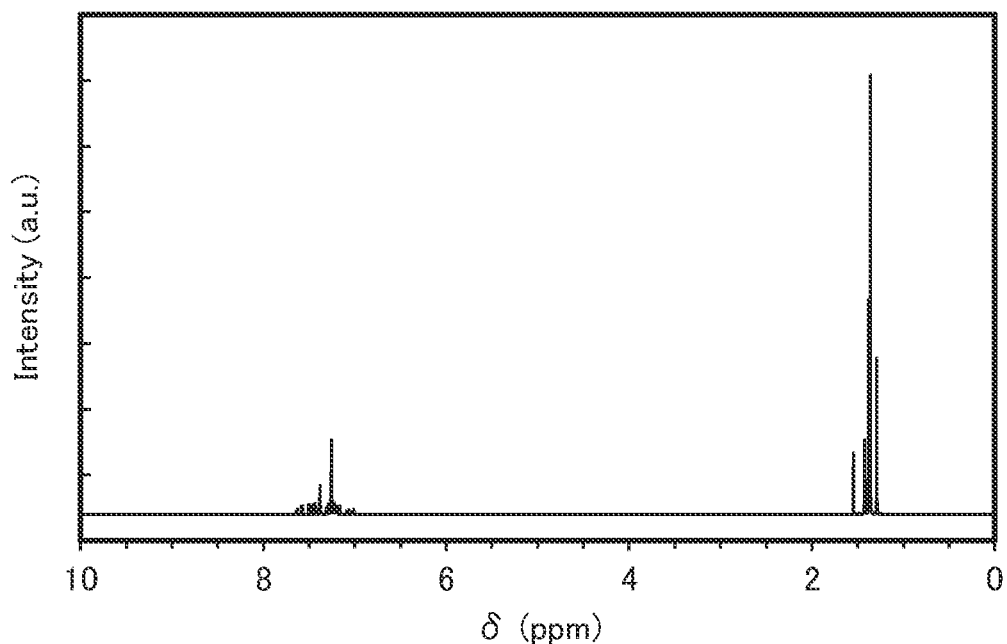
FIGS. 14A and 14B are $^1$H-NMR charts of mmtBumTPFA-02.
Figure 14B:
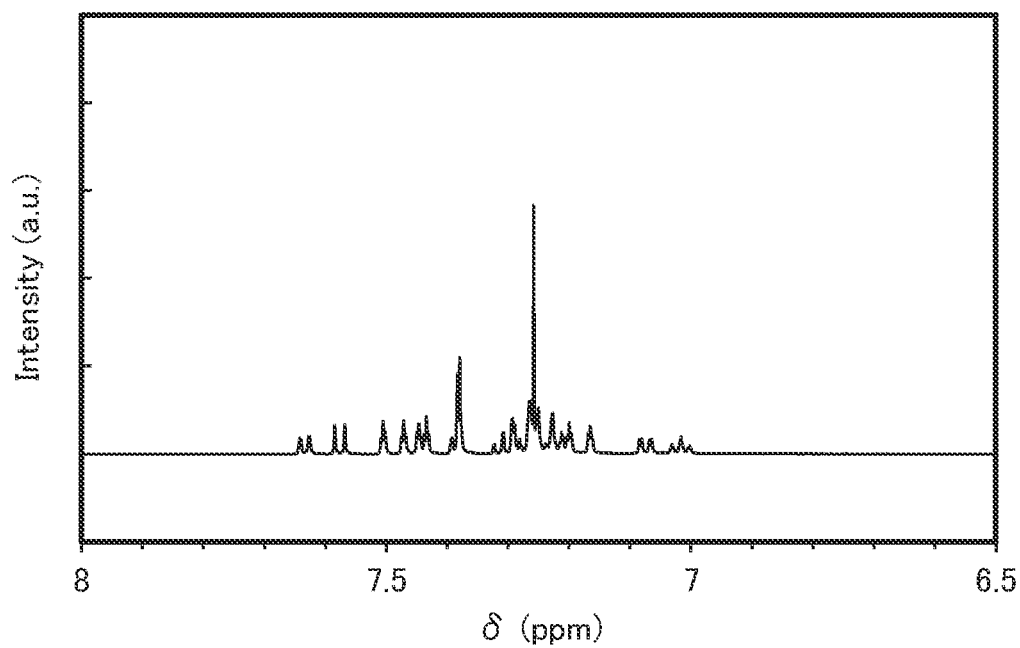

Analysis results by nuclear magnetic resonance ($^1$H-NMR) spectroscopy of the white solid obtained in Step 4 are shown in FIGS. 14A and 14B. Note that FIG. 14B is an enlarged graph of FIG. 14A in the range of 6.5 ppm to 8.0 ppm. In addition, numerical data is shown below. The results show that N-(3,3″,5′,5″-tetra-tert-butyl-1,1′:3′,1″-terphenyl-5-yl)-N-phenyl-9,9-dimethyl-9H-fluoren-2-amine was synthesized in this synthesis example.

$^1$H-NMR. δ (CDCl$_3$): 7.63 (d, 1H, J=6.9 Hz), 7.58 (d, 1H, J=8.0 Hz), 7.51 (dd, 1H, J=1.7 Hz), 7.47 (dd, 1H, J=1.7 Hz), 7.45 (dd, 1H, J=1.7 Hz), 7.43 (dd, 1H, J=1.7 Hz), 7.39 (s, 1H), 7.38 (s, 1H), 7.38 (s, 1H), 7.26-7.32 (m, 4H), 7.19-7.25 (m, 5H), 7.17 (dd, 1H, J=1.7 Hz), 7.07 (d, 1H, J=6.3 Hz), 7.02 (dd, 1H, J=7.5 Hz), 1.42 (s, 6H), 1.38 (s, 9H), 1.36 (s, 18H), 1.29 (s, 9H).

Next, 3.2 g of the obtained white solid was purified by a train sublimation method at 235° C. under a pressure of 2.9 Pa with an argon gas flow rate of 10.0 mL/min. After the purification by sublimation, 2.7 g of a pale yellowish white solid was obtained at a collection rate of 84%.

Figure 15:
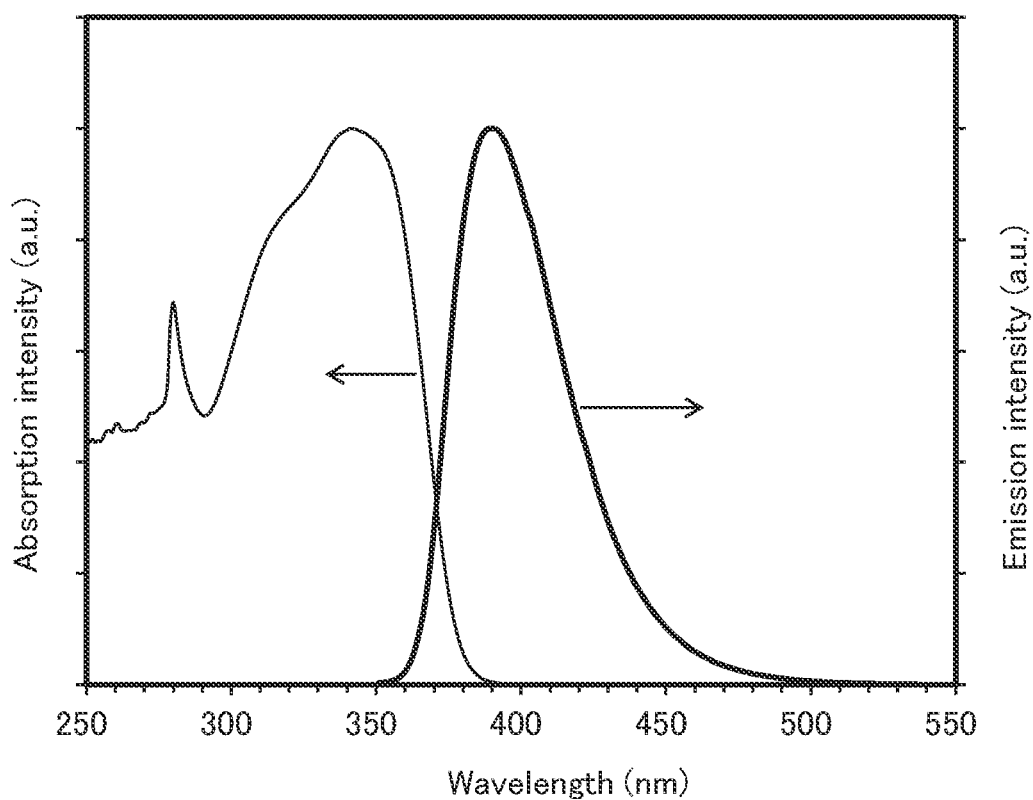
FIG. 15 shows an absorption spectrum and an emission spectrum of mmtBumTPFA-02 in a toluene solution.

Then, an ultraviolet-visible absorption spectrum (hereinafter, simply referred to as an absorption spectrum) of mmtBumTPFA-02 in a toluene solution and an emission spectrum thereof were measured. The absorption spectrum was measured at room temperature with an ultraviolet-visible light spectrophotometer (FP-8600, produced by JASCO Corporation) in a state where the toluene solution was put in a quartz cell. The emission spectrum was measured with a fluorescence spectrophotometer (FS920, produced by Hamamatsu Photonics K.K.) at room temperature in a state where the toluene solution was put in a quartz cell. FIG. 15 shows obtained measurement results of the absorption spectrum and the emission spectrum. The horizontal axis represents the wavelength and the vertical axes represent the absorbance and emission intensity. In FIG. 15, two solid lines are shown; a thin line represents the absorption spectrum, and a thick line represents the emission spectrum. The absorbance shown in FIG. 15 is a result obtained by subtraction of an absorption spectrum of only toluene in a quartz cell from the measured absorption spectrum of the toluene solution in the quartz cell.

As shown in FIG. 15, mmtBumTPFA-02 had an emission peak at 395 nm.

Next, mmtBumTPFA-02 obtained in this example was analyzed by liquid chromatography mass spectrometry (LC/MS).

In the LC/MS analysis, liquid chromatography (LC) separation was performed with UltiMate 3000 produced by Thermo Fisher Scientific K.K., and mass spectrometry (MS) was performed with Q Exactive produced by Thermo Fisher Scientific K.K.

In the LC separation, a given column was used at a column temperature of 40° C., and solution sending was performed in such a manner that an appropriate solvent was selected, the sample was prepared by dissolving mmtBumTPFA-02 in an organic solvent at a given concentration, and the injection amount was 5.0 μL.

Figure 16:
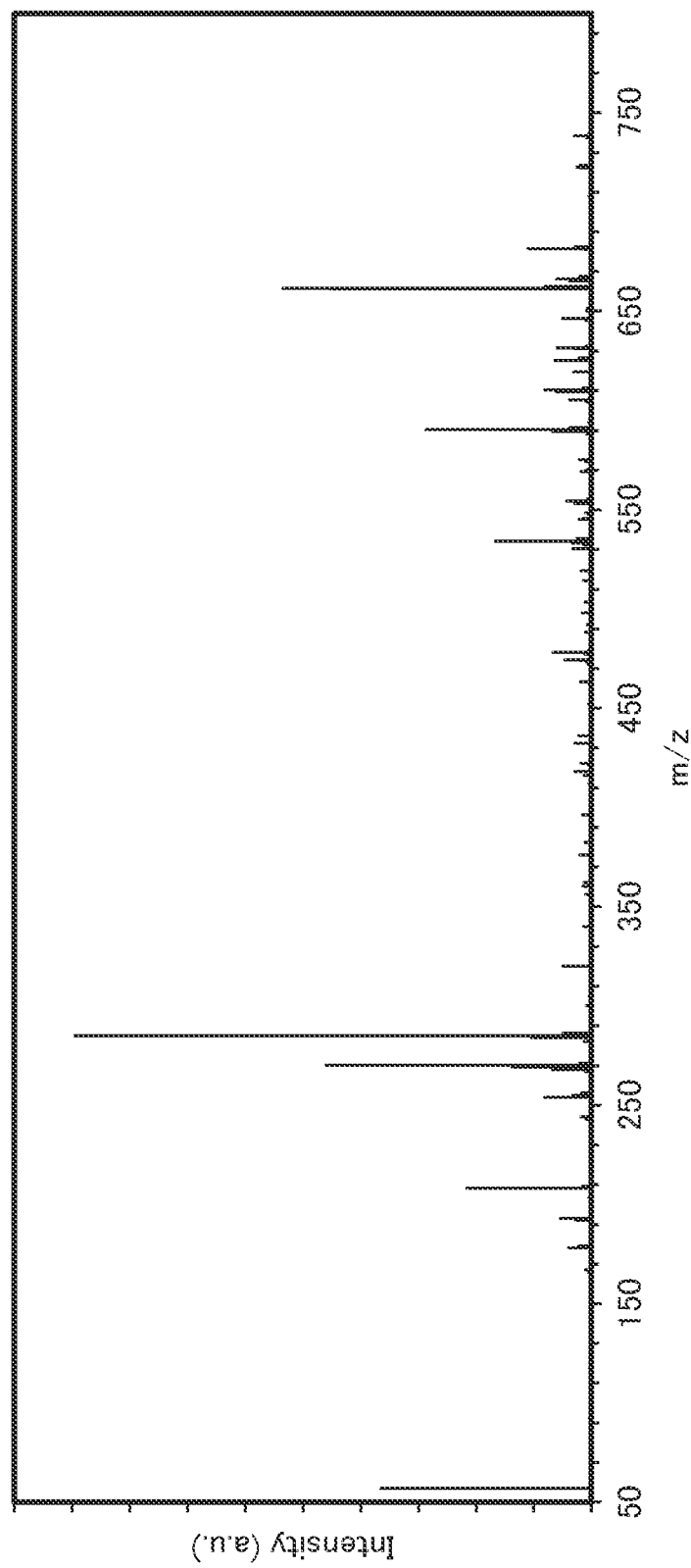
FIG. 16 shows an MS spectrum of mmtBumTPFA-02.

An ion derived from mmtBumTPFA-02, m/z=738.50, was subjected to the MS$^2$ measurement by a PRM method. For setting of the PRM, the mass range of a target ion was set to m/z=738.50±2.0 (isolation window=4) and detection was performed in a positive mode. The measurement was performed with energy (normalized collision energy: NCE) for accelerating a target ion in a collision cell set to 60. The obtained MS spectrum is shown in FIG. 16.

Figure 17:
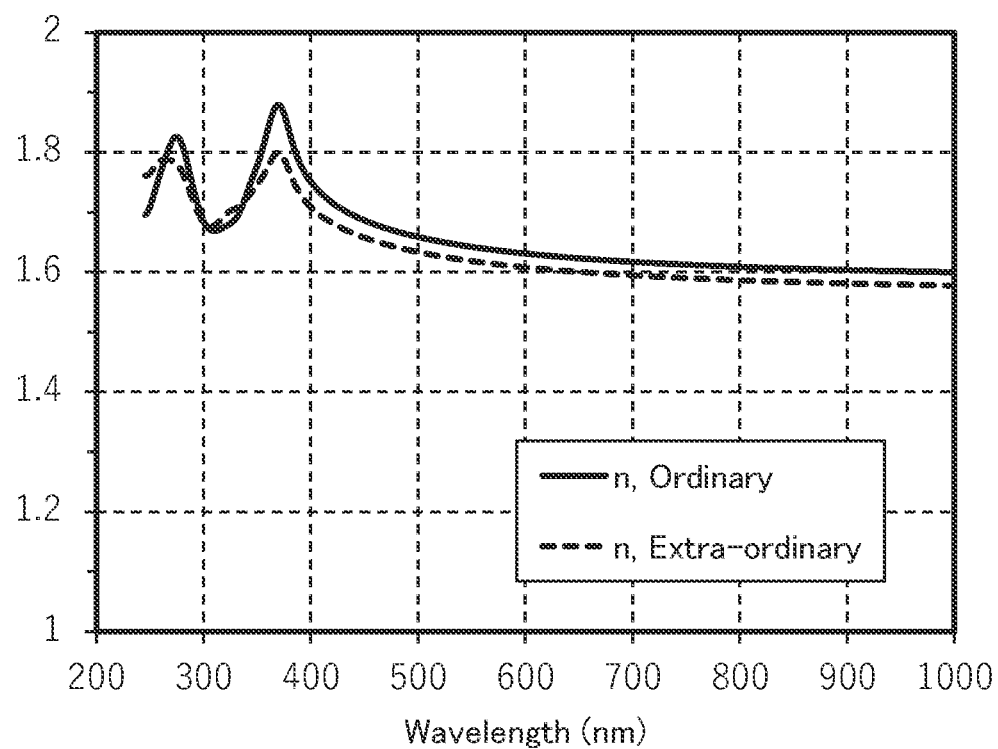
FIG. 17 shows measurement results of a refractive index of mmtBumTPFA-02.

FIG. 17 shows the results of measuring the refractive index of mmtBumTPFA-02 by a spectroscopic ellipsometer (M-2000U, produced by J.A. Woollam Japan Corp.). A film used for the measurement was formed to a thickness of approximately 50 nm with the material of each layer over a quartz substrate by a vacuum evaporation method. Note that a refractive index of an ordinary ray, n. Ordinary, and a refractive index of an extraordinary ray, n. Extra-ordinary are shown in FIG. 17.

FIG. 17 shows that mmtBumTPFA-02 is a material with a low refractive index: the ordinary refractive index with respect to light in the entire blue emission region (from 455 nm to 465 nm) is 1.68, which is within the range of 1.50 to 1.75, and the ordinary refractive index with respect to light with a wavelength of 633 nm is 1.63, which is within the range of 1.45 to 1.70.

Next, the glass transition temperature (hereinafter referred to as "Tg") of mmtBumTPFA-02 was measured. Tg was measured using a differential scanning calorimeter (Pyris 1 DSC produced by PerkinElmer Japan Co., Ltd.) in a state where a powder was put on an aluminum cell. As a result, Tg of mmtBumTPFA-02 was 109° C.

Example 2

Synthesis Example 2

In this example, a synthesis method of N-(1,1'-biphenyl-4-yl)-N-(3,3",5',5"-tetra-tert-butyl-1,1':3',1"-terphenyl-5-yl)-9,9-dimethyl-9H-fluoren-2-amine (abbreviation: mmtBumTPFBi-02), which is the arylamine compound of one embodiment of the present invention described in Embodiment 1, will be described. A structure of mmtBumTPFBi-02 is shown below.

[Chemical Formula 44]

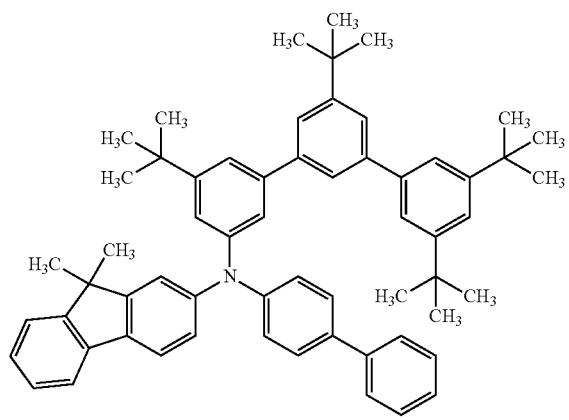

Step 1: Synthesis of 3-bromo-3',5,5'-tri-tert-butylbiphenyl

This synthesis step is similar to Step 1 in Synthesis Example 1.

Step 2: Synthesis of 2-(3',5,5'-tri-tert-butyl[1,1'-biphenyl]-3-yl)-4,4,5,5-tetramethyl-1,3,2-dioxaborolane This synthesis step is similar to Step 2 in Synthesis Example 1.

Step 3: Synthesis of 3-bromo-3",5,5',5"-tetra-tert-butyl-1,1':3',1"-terphenyl This synthesis step is similar to Step 3 in Synthesis Example 1.

Step 4: Synthesis of mmtBumTPFBi-02

Into a three-neck flask were put 3.0 g (5.6 mmol) of 3-bromo-3",5,5',5"-tetra-tert-butyl-1,1':3',1"-terphenyl obtained in Step 3, 2.0 g (5.6 mmol) of 2-(4-biphenylyl)amino-9,9-dimethylfluorene, 1.6 g (16.8 mmol) of sodium tert-butoxide, and 28 mL of toluene. The mixture was degassed under reduced pressure, the air in the flask was replaced with nitrogen, 64 mg (0.11 mmol) of bis(dibenzylideneacetone)palladium(0) and 138 mg (0.34 mmol) of 2-dicyclohexylphosphino-2',6'-dimethoxybiphenyl were added thereto, and the mixture was heated at 120° C. for approximately 8 hours. After that, the temperature of the flask was lowered to approximately 60° C., approximately 1 mL of water was added, a precipitated solid was separated by filtration, and the solid was washed with toluene. The filtrate was concentrated, and the obtained toluene solution was purified by silica gel column chromatography. The obtained solution was concentrated to give a condensed toluene solution. Ethanol was added to this toluene solution and the toluene solution was concentrated under reduced pressure, whereby an ethanol suspension was obtained. The precipitate was filtrated at approximately 20° C., and the obtained solid was dried at approximately 80° C. under reduced pressure, whereby 3.5 g of a target white solid was obtained in a yield of 77%. The synthesis scheme of Step 4 is shown below.

[Chemical Formula 45]

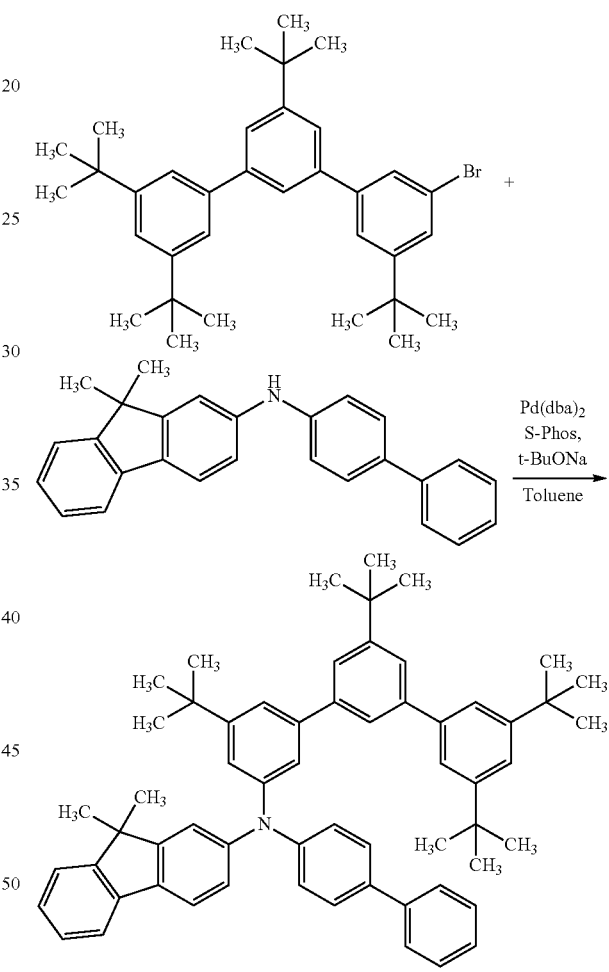

Figure 18A:
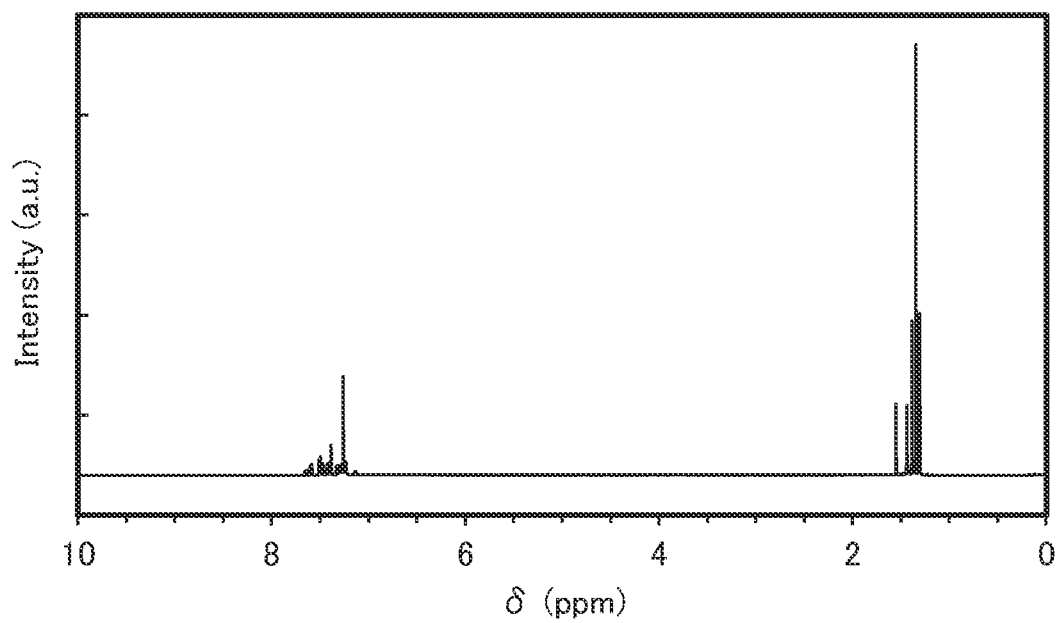
FIGS. 18A and 18B are $^1$H-NMR charts of mmtBumTPFBi-02.
Figure 18B:
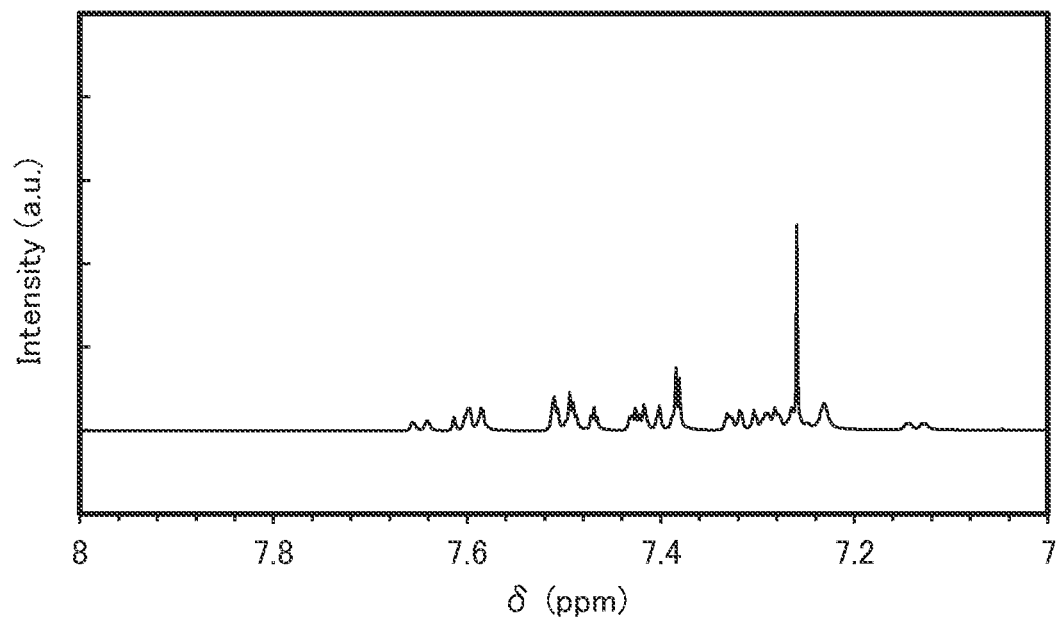

Analysis results by nuclear magnetic resonance ($^1$H-NMR) spectroscopy of the white solid obtained through the above step are shown in FIGS. 18A and 18B. Note that FIG. 18B is an enlarged graph of FIG. 18A in the range of 7.0 ppm to 8.0 ppm. In addition, numerical data is shown below. The results show that N-(1,1'-biphenyl-4-yl)-N-(3,3",5',5"-tetra-tert-butyl-1,1':3',1"-terphenyl-5-yl)-9,9-dimethyl-9H-fluoren-2-amine was synthesized in this synthesis example.

$^1$H-NMR. δ (CDCl$_3$): 7.65 (d, 1H, J=7.4 Hz), 7.61 (s, 1H), 7.58-7.60 (m, 2H), 7.49-7.51 (m, 4H), 7.47 (dd, 1H, J=1.7 Hz), 7.38-7.43 (m, 6H), 7.23-7.25 (m, 2H), 7.14 (dd, 1H, J=1.7 Hz), 1.44 (s, 6H), 1.39 (s, 9H), 1.34 (s, 18H), 1.31 (s, 9H).

Next, 3.5 g of the obtained white solid was purified by a train sublimation method at 255° C. under a pressure of 2.6 Pa with an argon gas flow rate of 10.0 mL/min. After the purification by sublimation, 2.9 g of a white solid was obtained at a collection rate of 83%.

Figure 19:
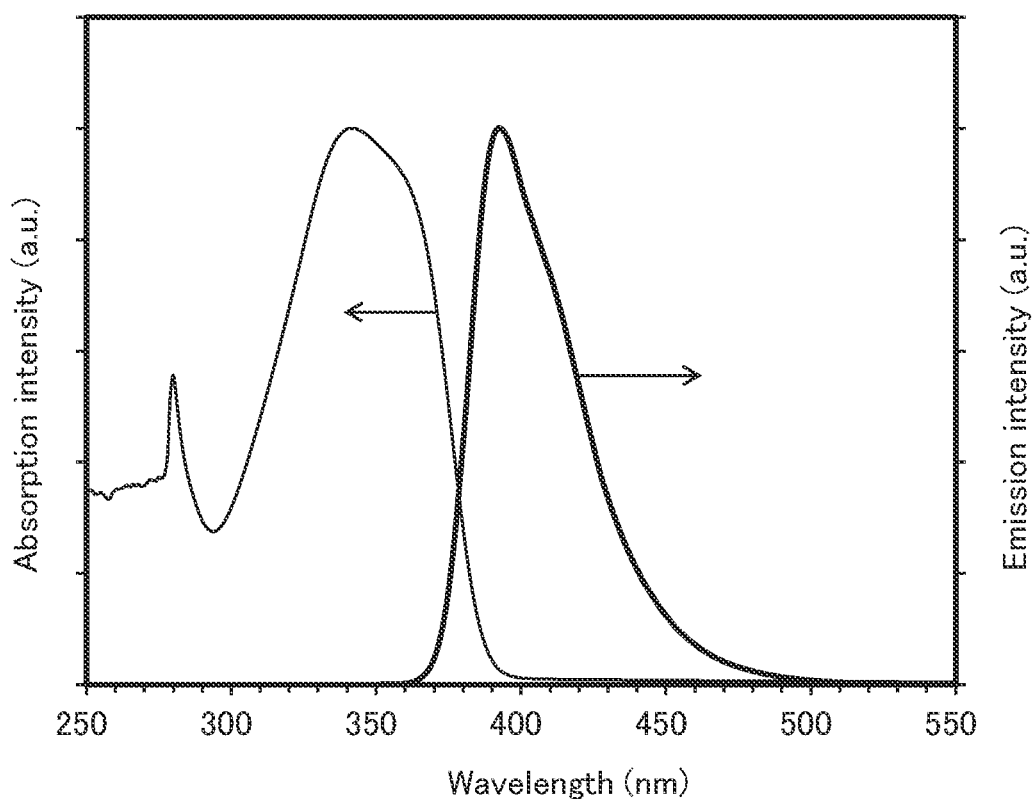
FIG. 19 shows an absorption spectrum and an emission spectrum of mmtBumTPFBi-02 in a toluene solution.

Then, an ultraviolet-visible absorption spectrum (hereinafter, simply referred to as an absorption spectrum) of mmtBumTPFBi-02 in a toluene solution and an emission spectrum thereof were measured. The absorption spectrum was measured at room temperature with an ultraviolet-visible light spectrophotometer (FP-8600, produced by JASCO Corporation) in a state where the toluene solution was put in a quartz cell. The emission spectrum was measured with a fluorescence spectrophotometer (FS920, produced by Hamamatsu Photonics K.K.) at room temperature in a state where the toluene solution was put in a quartz cell. FIG. 19 shows obtained measurement results of the absorption spectrum and the emission spectrum. The horizontal axis represents the wavelength and the vertical axes represent the absorbance and emission intensity. In FIG. 19, two solid lines are shown; a thin line represents the absorption spectrum, and a thick line represents the emission spectrum. The absorbance shown in FIG. 19 is a result obtained by subtraction of an absorption spectrum of only toluene in a quartz cell from the measured absorption spectrum of the toluene solution in the quartz cell.

As shown in FIG. 19, mmtBumTPFBi-02 had an emission peak at 392 nm.

Next, mmtBumTPFBi-02 obtained in this example was analyzed by liquid chromatography mass spectrometry (LC/MS).

In the LC/MS analysis, liquid chromatography (LC) separation was performed with UltiMate 3000 produced by Thermo Fisher Scientific K.K., and mass spectrometry (MS) was performed with Q Exactive produced by Thermo Fisher Scientific K.K.

In the LC separation, a given column was used at a column temperature of 40° C., and solution sending was performed in such a manner that an appropriate solvent was selected, the sample was prepared by dissolving mmtBumTPFBi-02 in an organic solvent at a given concentration, and the injection amount was 5.0 μL.

Figure 20:
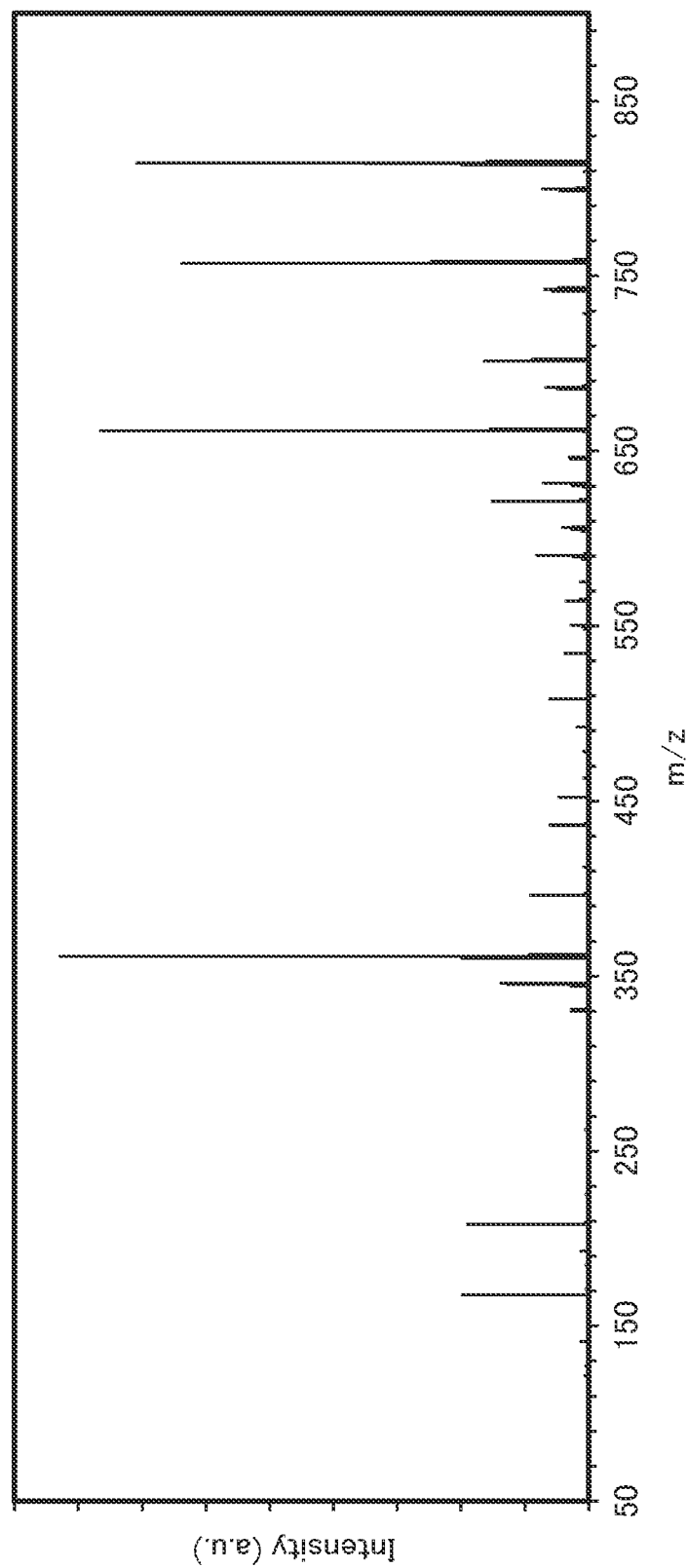
FIG. 20 shows an MS spectrum of mmtBumTPFBi-02.

An ion derived from mmtBumTPFBi-02, m/z=814.53, was subjected to the $MS^2$ measurement by a PRM method. For setting of the PRM, the mass range of a target ion was set to m/z=814.53±2.0 (isolation window=4) and detection was performed in a positive mode. The measurement was performed with energy (normalized collision energy: NCE) for accelerating a target ion in a collision cell set to 50. The obtained MS spectrum is shown in FIG. 20.

Figure 21:
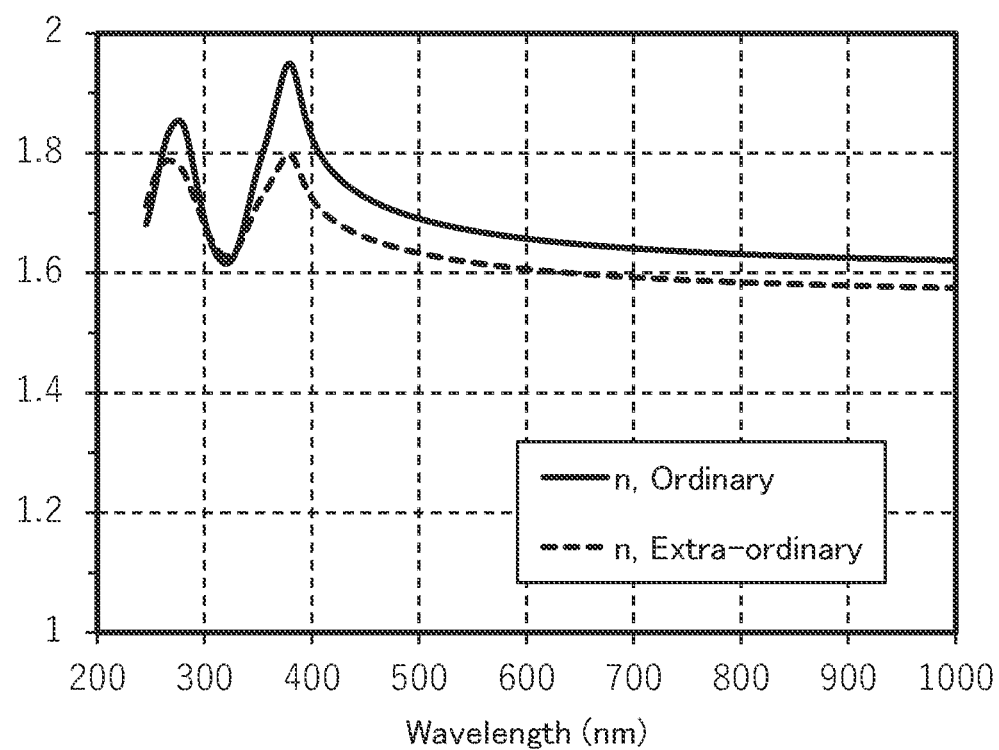
FIG. 21 shows measurement results of a refractive index of mmtBumTPFBi-02.

FIG. 21 shows the results of measuring the refractive index of mmtBumTPFBi-02 by a spectroscopic ellipsometer (M-2000U, produced by J.A. Woollam Japan Corp.). A film used for the measurement was formed to a thickness of approximately 50 nm with the material of each layer over a quartz substrate by a vacuum evaporation method. Note that a refractive index of an ordinary ray, n. Ordinary, and a refractive index of an extraordinary ray, n. Extra-ordinary are shown in FIG. 21.

FIG. 21 shows that mmtBumTPFBi-02 is a material with a low refractive index: the ordinary refractive index with respect to light in the entire blue emission region (from 455 nm to 465 nm) is 1.71 to 1.72, which is within the range of 1.50 to 1.75, and the ordinary refractive index with respect to light with a wavelength of 633 nm is 1.65, which is within the range of 1.45 to 1.70.

Next, the glass transition temperature (hereinafter referred to as "Tg") of mmtBumTPFBi-02 was measured. Tg was measured using a differential scanning calorimeter (Pyris 1 DSC produced by PerkinElmer Japan Co., Ltd.) in a state where a powder was put on an aluminum cell. As a result, Tg of mmtBumTPFBi-02 was 126° C.

Example 3

Synthesis Example 3

In this example, a synthesis method of N-(1,1'-biphenyl-2-yl)-N-(3,3'',5',5''-tetra-tert-butyl-1,1':3',1''-terphenyl-5-yl)-9,9-dimethyl-9H-fluoren-2-amine (abbreviation: mmtBumTPoFBi-02), which is the arylamine compound of one embodiment of the present invention described in Embodiment 1, will be described. A structure of mmtBumTPoFBi-02 is shown below.

[Chemical Formula 46]

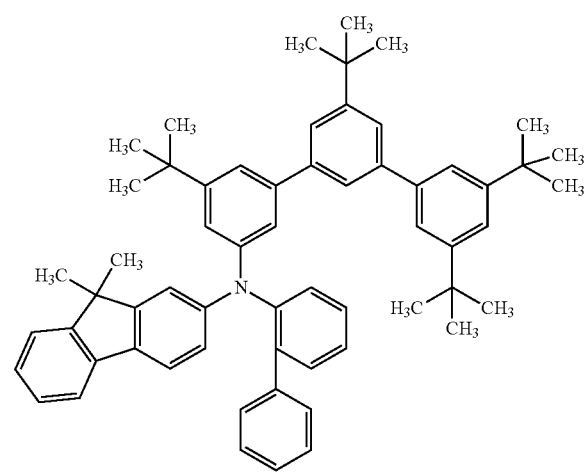

Step 1: Synthesis of 3-bromo-3',5,5'-tri-tert-butylbiphenyl

This synthesis step is similar to Step 1 in Synthesis Example 1.

Step 2: 2-(3',5,5'-tri-tert-butyl[1,1'-biphenyl]-3-yl)-4,4,5,5-tetramethyl-1,3,2-dioxaborolane This synthesis step is similar to Step 2 in Synthesis Example 1.

Step 3: Synthesis of 3-bromo-3'',5,5'',5'''-tetra-tert-butyl-1,1':3',1''-terphenyl This synthesis step is similar to Step 3 in Synthesis Example 1.

Step 4: Synthesis of mmtBumTPoFBi-02

Into a three-neck flask were put 5.8 g (10.9 mmol) of 3-bromo-3'',5,5',5''-tetra-tert-butyl-1,1':3',1''-terphenyl obtained in Step 3, 3.9 g (10.9 mmol) of N-(1,1'-biphenyl-4-yl)-N-phenyl-9,9-dimethyl-9H-fluoren-2-amine, 3.1 g (32.7 mmol) of sodium tert-butoxide, and 55 mL of toluene. The mixture was degassed under reduced pressure, the air in the flask was replaced with nitrogen, 64 mg (0.11 mmol) of bis(dibenzylideneacetone)palladium(0) and 132 mg (0.65 mmol) of tri-tert-butylphosphine were added thereto, and the mixture was heated at 80° C. for approximately two hours. After that, the temperature of the flask was lowered to approximately 60° C., approximately 1 mL of water was added, a precipitated solid was separated by filtration, and the solid was washed with toluene. The filtrate was concentrated, and the obtained toluene solution was purified by silica gel column chromatography. The obtained solution was concentrated to give a condensed toluene solution. Ethanol was added to this toluene solution and the toluene solution was concentrated under reduced pressure, whereby an ethanol suspension was obtained. The precipitate was filtrated at 20° C., and the obtained solid was dried at approximately 80° C. under reduced pressure, whereby 8.1 g of a target white solid was obtained in a yield of 91%. The synthesis scheme of mmtBumTPoFBi-02 is shown below.

[Chemical Formula 47]

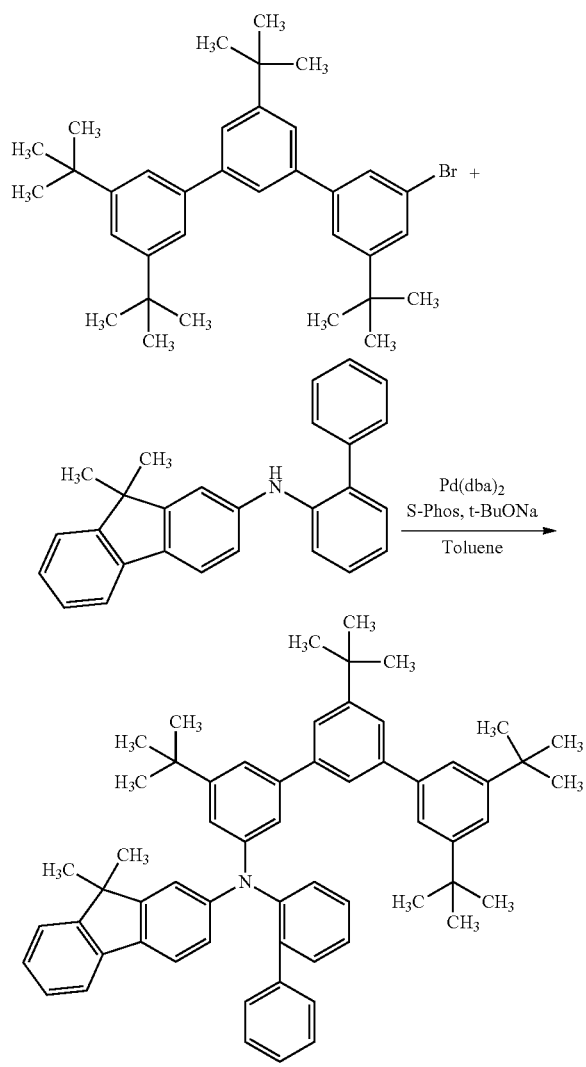

Figure 22A:
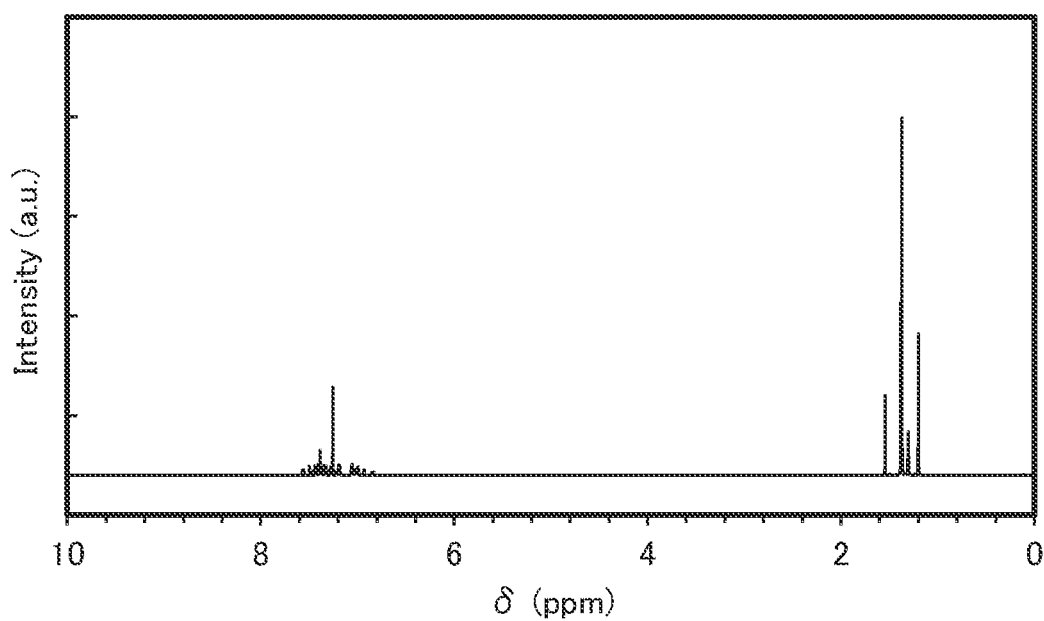
FIGS. 22A and 22B are $^1$H-NMR charts of mmtBumTPoFBi-02.
Figure 22B:
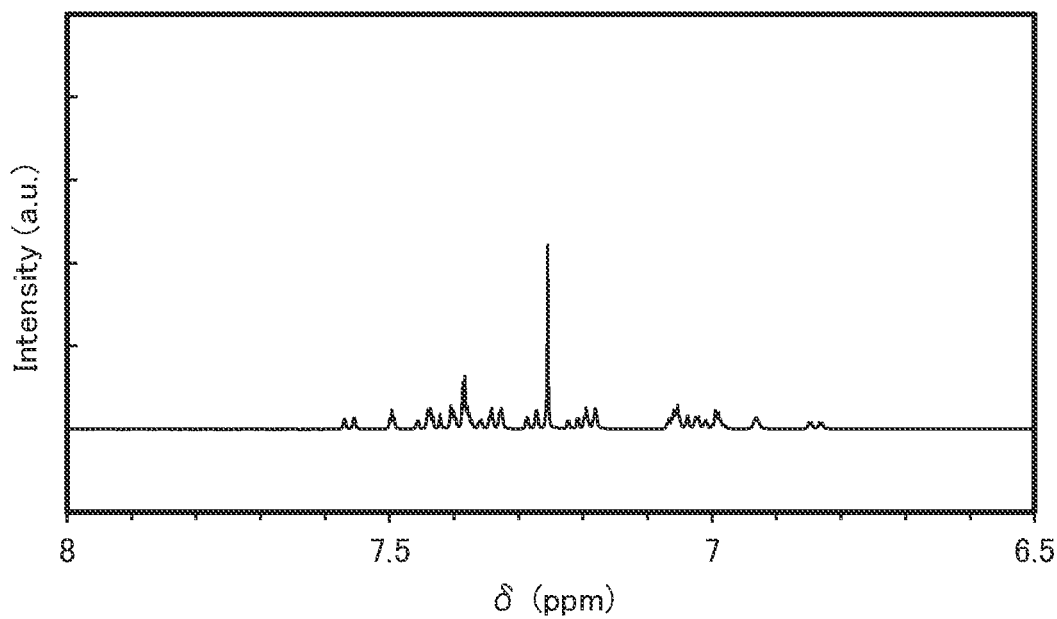

Analysis results by nuclear magnetic resonance ($^1$H-NMR) spectroscopy of the white powder obtained in the above step are shown in FIGS. 22A and 22B. Note that FIG. 22B is an enlarged graph of FIG. 22A in the range of 6.5 ppm to 8.0 ppm. In addition, numerical data is shown below. The results show that N-(1,1'-biphenyl-2-yl)-N-(3,3",5',5"-tetra-tert-butyl-1,1':3',1"-terphenyl-5-yl)-9,9-dimethyl-9H-fluoren-2-amine was synthesized.

$^1$H-NMR. δ (CDCl$_3$): 7.56 (d, 1H, J=7.4 Hz), 7.50 (dd, 1H, J=1.7 Hz), 7.33-7.46 (m, 11H), 7.27-7.29 (m, 2H), 7.22 (dd, 1H, J=2.3 Hz), 7.15 (d, 1H, J=6.9 Hz), 6.98-7.07 (m, 7H), 6.93 (s, 1H), 6.84 (d, 1H, J=6.3 Hz), 1.38 (s, 9H), 1.37 (s, 18H), 1.31 (s, 6H), 1.20 (s, 9H).

Next, 8.0 g of the obtained white solid was purified by a train sublimation method at 260° C. under a pressure of 3.4 Pa with an argon gas flow rate of 15.0 mL/min. After the purification by sublimation, 7.1 g of a pale yellowish white solid was obtained at a collection rate of 89%.

Figure 23:
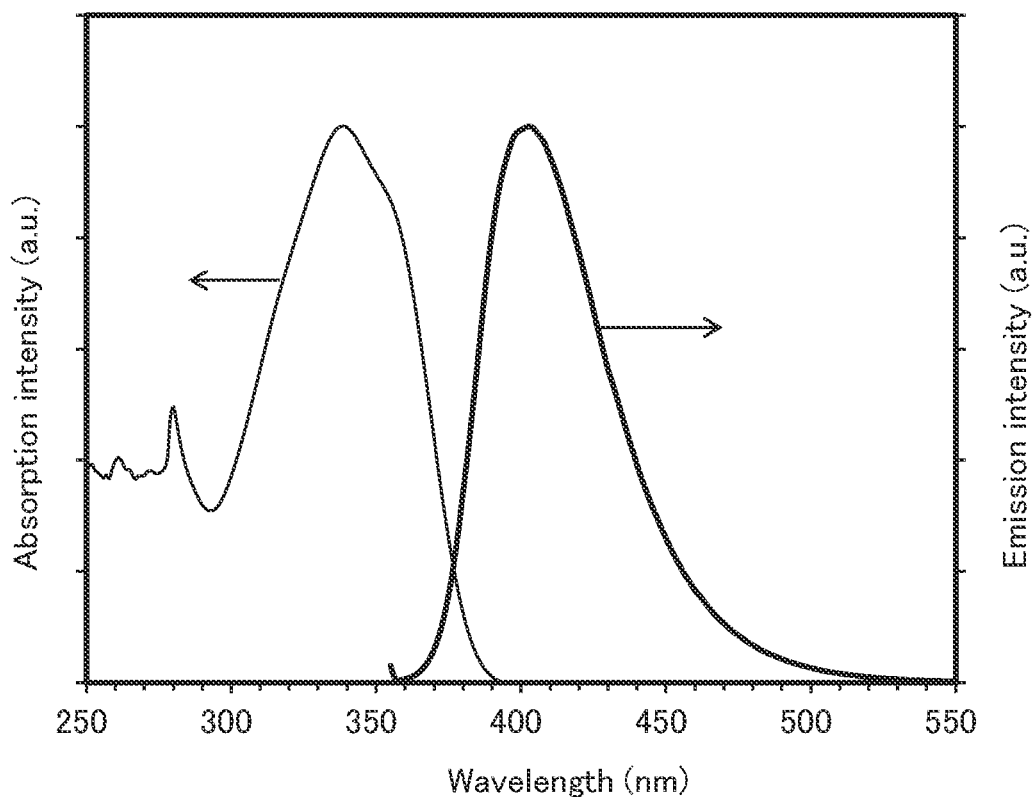
FIG. 23 shows an absorption spectrum and an emission spectrum of mmtBumTPoFBi-02 in a toluene solution.

Then, an ultraviolet-visible absorption spectrum (hereinafter, simply referred to as an absorption spectrum) of mmtBumTPoFBi-02 in a toluene solution and an emission spectrum thereof were measured. The absorption spectrum was measured at room temperature with an ultraviolet-visible light spectrophotometer (FP-8600, produced by JASCO Corporation) in a state where the toluene solution was put in a quartz cell. The emission spectrum was measured with a fluorescence spectrophotometer (FS920, produced by Hamamatsu Photonics K.K.) at room temperature in a state where the toluene solution was put in a quartz cell. FIG. 23 shows obtained measurement results of the absorption spectrum and the emission spectrum. The horizontal axis represents the wavelength and the vertical axes represent the absorbance and emission intensity. In FIG. 23, two solid lines are shown; a thin line represents the absorption spectrum, and a thick line represents the emission spectrum. The absorbance shown in FIG. 23 is a result obtained by subtraction of an absorption spectrum of only toluene in a quartz cell from the measured absorption spectrum of the toluene solution in the quartz cell.

As shown in FIG. 23, mmtBumTPoFBi-02 had an emission peak at 403 nm.

Next, mmtBumTPoFBi-02 obtained in this example was analyzed by liquid chromatography mass spectrometry (LC/MS).

In the LC/MS analysis, liquid chromatography (LC) separation was performed with UltiMate 3000 produced by Thermo Fisher Scientific K.K., and mass spectrometry (MS) was performed with Q Exactive produced by Thermo Fisher Scientific K.K.

In the LC separation, a given column was used at a column temperature of 40° C., and solution sending was performed in such a manner that an appropriate solvent was selected, the sample was prepared by dissolving mmtBumTPoFBi-02 in an organic solvent at a given concentration, and the injection amount was 5.0 μL.

Figure 24:
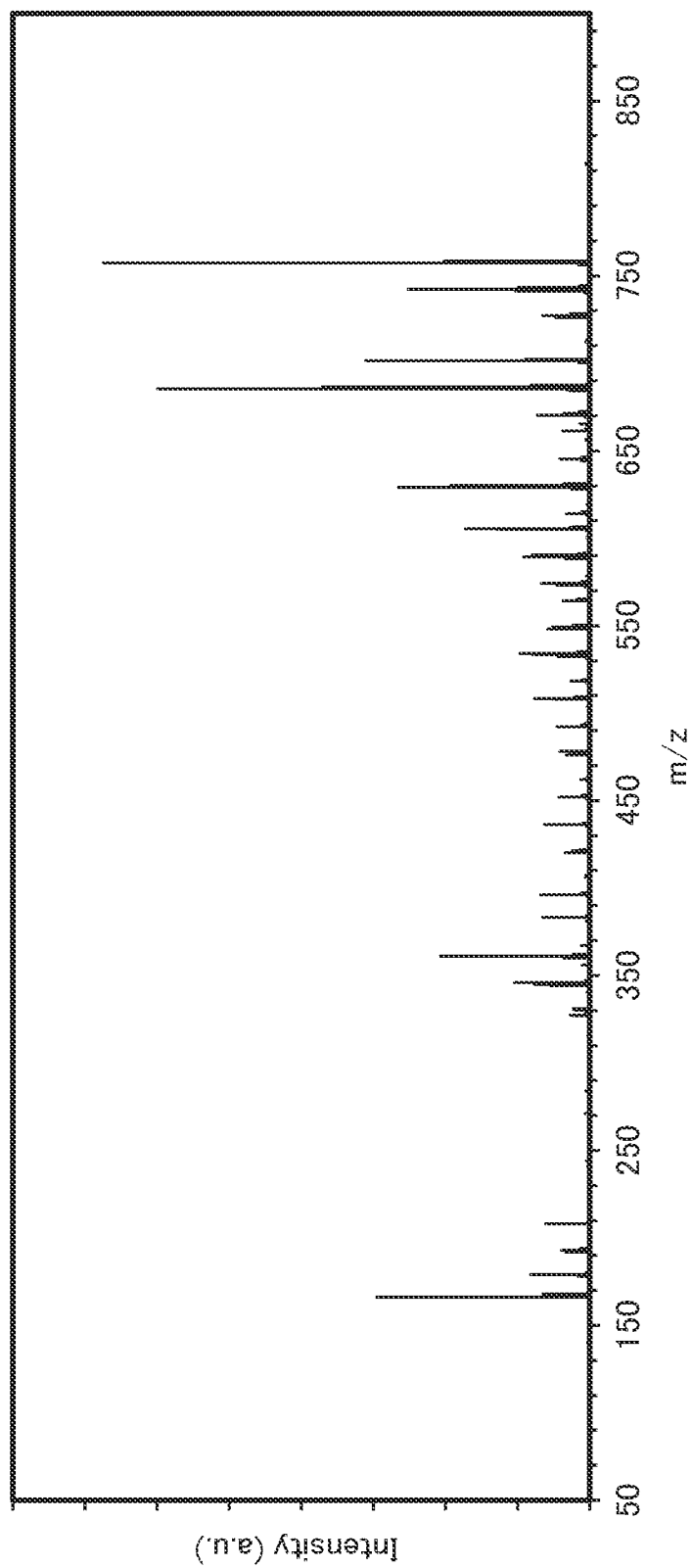
FIG. 24 shows an MS spectrum of mmtBumTPoFBi-02.

An ion derived from mmtBumTPoFBi-02, m/z=814.53, was subjected to the MS$^2$ measurement by a PRM method. For setting of the PRM, the mass range of a target ion was set to m/z=814.53±2.0 (isolation window=4) and detection was performed in a positive mode. The measurement was performed with energy (normalized collision energy: NCE) for accelerating a target ion in a collision cell set to 60. The obtained MS spectrum is shown in FIG. 24.

Figure 25:
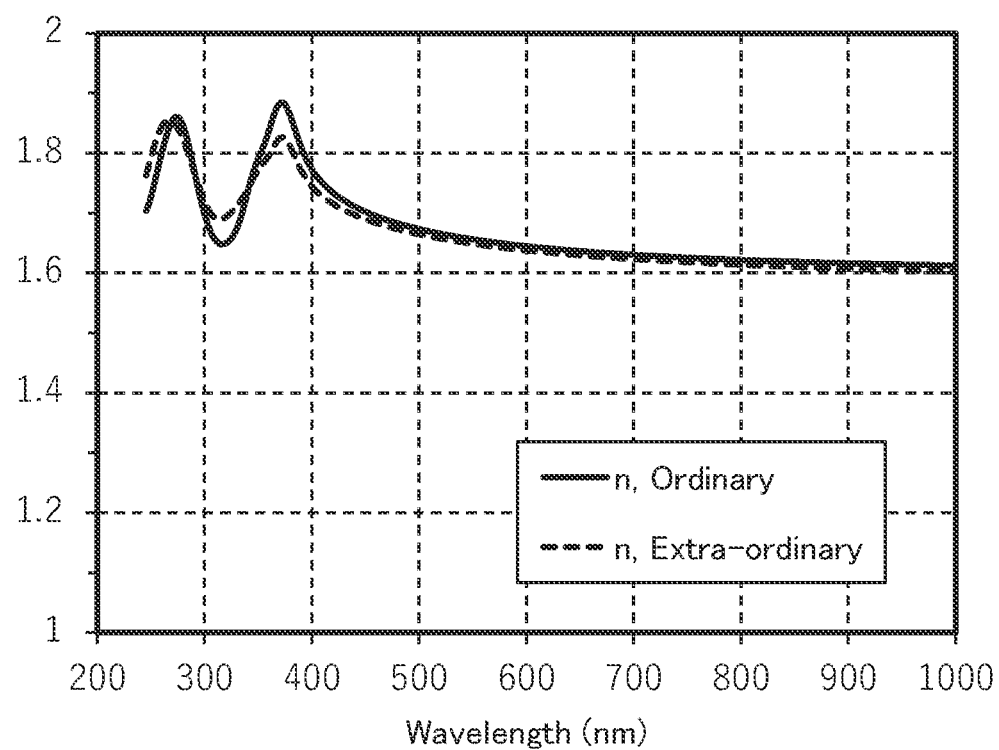
FIG. 25 shows measurement results of a refractive index of mmtBumTPoFBi-02.

FIG. 25 shows the results of measuring the refractive index of mmtBumTPoFBi-02 by a spectroscopic ellipsometer (M-2000U, produced by J.A. Woollam Japan Corp.). A film used for the measurement was formed to a thickness of approximately 50 nm with the material of each layer over a quartz substrate by a vacuum evaporation method. Note that a refractive index of an ordinary ray, n. Ordinary, and a refractive index of an extraordinary ray, n. Extra-ordinary are shown in FIG. 25.

FIG. 25 shows that mmtBumTPoFBi-02 is a material with a low refractive index: the ordinary refractive index with respect to light in the entire blue emission region (from 455 nm to 465 nm) is 1.69 to 1.70, which is within the range of 1.50 to 1.75, and the ordinary refractive index with respect to light with a wavelength of 633 nm is 1.64, which is within the range of 1.45 to 1.70.

Next, the glass transition temperature (hereinafter referred to as "Tg") of mmtBumTPoFBi-02 was measured. Tg was measured using a differential scanning calorimeter (Pyris 1 DSC produced by PerkinElmer Japan Co., Ltd.) in a state where a powder was put on an aluminum cell. As a result, Tg of mmtBumTPoFBi-02 was 126° C.

Example 4

Synthesis Example 4

In this example, a synthesis method of N-(4-cyclohexylphenyl)-N-(3,3'',5',5''-tetra-tert-butyl-1,1':3',1''-terphenyl-5-yl)-9,9-dimethyl-9H-fluoren-2-amine (abbreviation: mmtBumTPchPAF-02), which is the arylamine compound of one embodiment of the present invention described in Embodiment 1, will be described. A structure of mmtBumTPchPAF-02 is shown below.

[Chemical Formula 48]

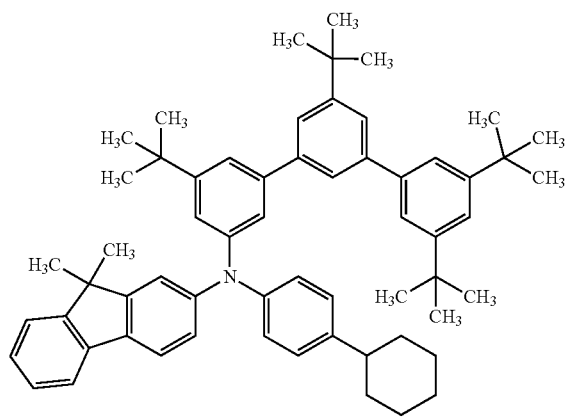

Step 1: Synthesis of 3-bromo-3',5,5'-tri-tert-butylbiphenyl

This synthesis step is similar to Step 1 in Synthesis Example 1.

Step 2: Synthesis of 2-(3',5,5'-tri-tert-butyl[1,1'-biphenyl]-3-yl)-4,4,5,5-tetramethyl-1,3,2-dioxaborolane This synthesis step is similar to Step 2 in Synthesis Example 1.

Step 3: Synthesis of 3-bromo-3'',5,5',5''-tetra-tert-butyl-1,1':3',1''-terphenyl This synthesis step is similar to Step 3 in Synthesis Example 1.

Step 4: Synthesis of mmtBumTPchPAF-02

Into a three-neck flask were put 3.0 g (5.6 mmol) of 3-bromo-3'',5,5',5''-tetra-tert-butyl-1,1':3',1''-terphenyl obtained in Step 3, 2.1 g (5.6 mmol) of N-(4-cyclohexylphenyl)-N-(9,9-dimethyl-9H-fluoren-2-yl)amine, 1.6 g (16.9 mmol) of sodium tert-butoxide, and 28 mL of toluene. The mixture was degassed under reduced pressure, the air in the flask was replaced with nitrogen, 65 mg (0.11 mmol) of bis(dibenzylideneacetone)palladium(0) and 139 mg (0.34 mmol) of 2-dicyclohexylphosphino-2',6'-dimethoxybiphenyl were added thereto, and the mixture was heated at 80° C. for approximately two hours. After that, the temperature of the flask was lowered to approximately 60° C., approximately 1 mL of water was added, a precipitated solid was separated by filtration, and the solid was washed with toluene. The filtrate was concentrated, and the obtained toluene solution was purified by silica gel column chromatography. The obtained solution was concentrated to give a condensed toluene solution. Ethanol was added to this toluene solution and the toluene solution was concentrated under reduced pressure, whereby an ethanol suspension was obtained. The precipitate was filtrated at approximately 20° C., and the obtained solid was dried at approximately 80° C. under reduced pressure, whereby 3.7 g of a target white solid was obtained in a yield of 80%. The synthesis scheme of mmtBumTPchPAF-02 is shown below.

[Chemical Formula 49]

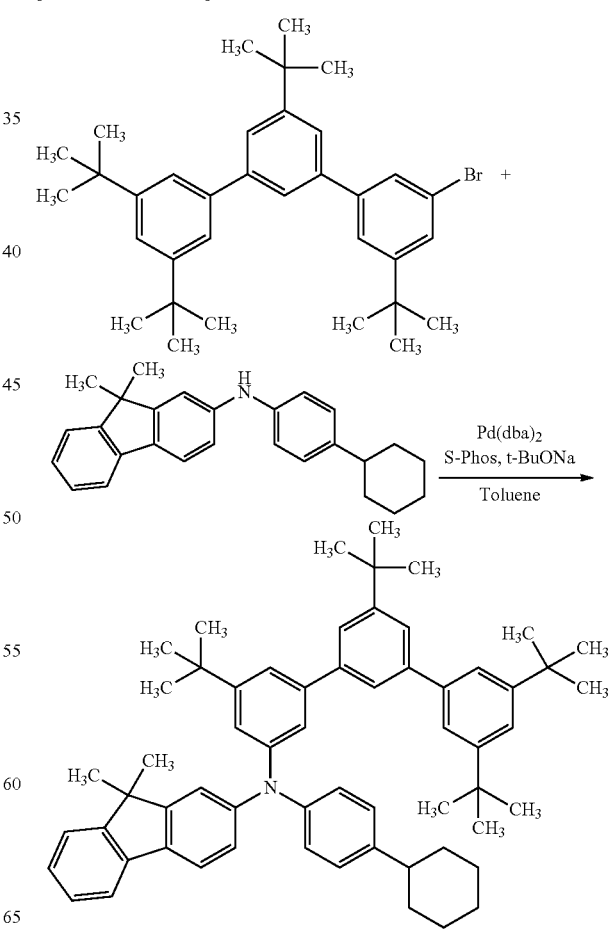

Figure 26A:
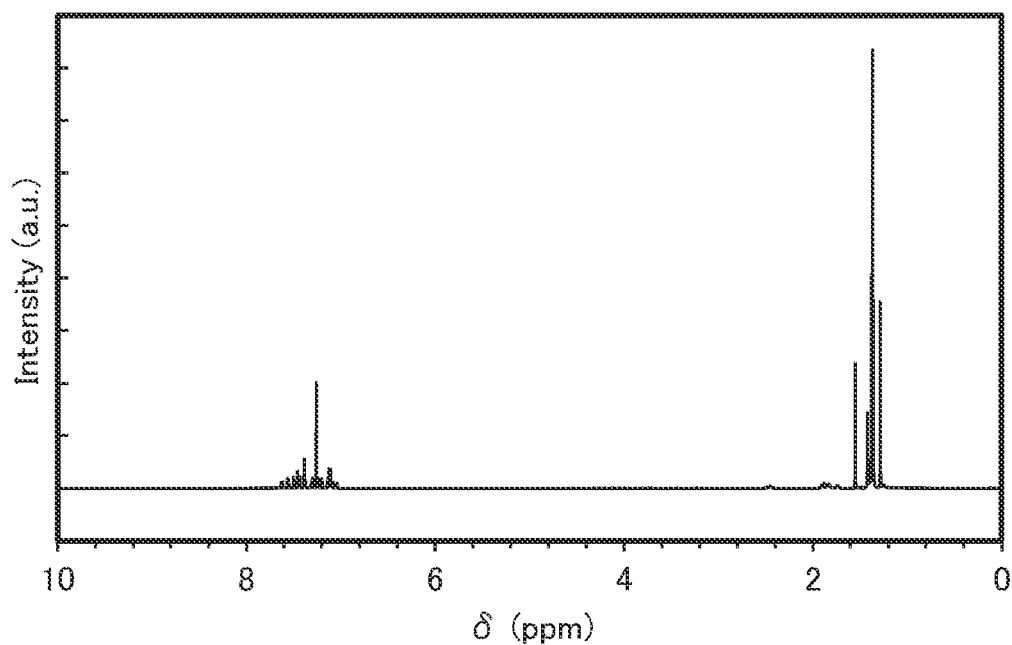
FIGS. 26A and 26B are $^1$H-NMR charts of mmtBumTPchPAF-02.
Figure 26B:
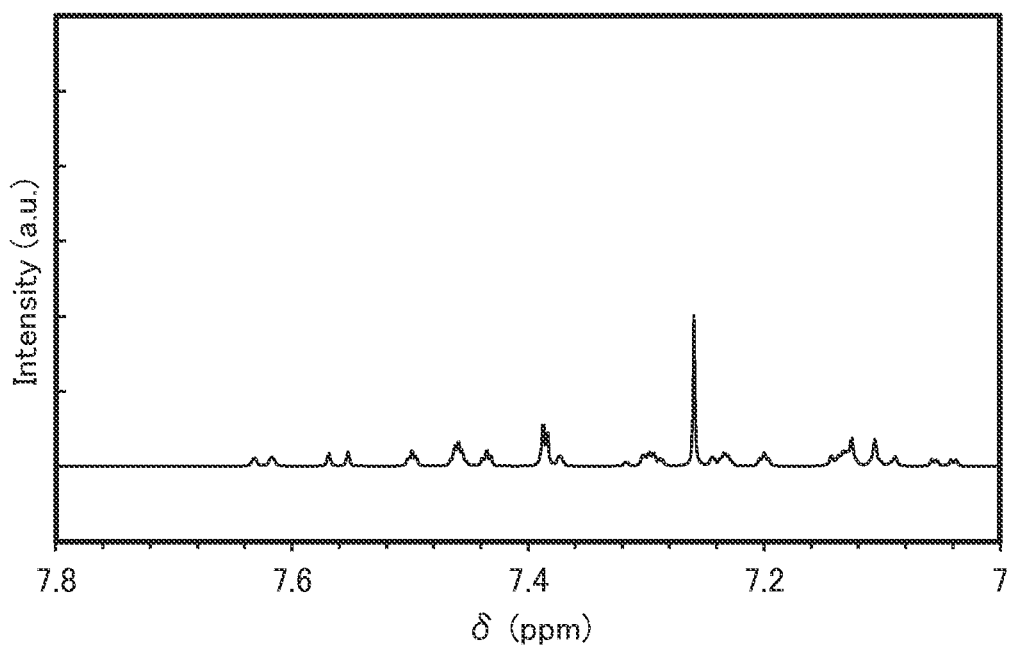

Analysis results by nuclear magnetic resonance ($^1$H-NMR) spectroscopy of the white solid obtained in the above step are shown in FIGS. 26A and 26B. Note that FIG. 26B is an enlarged graph of FIG. 26A in the range of 6.5 ppm to 8.0 ppm. In addition, numerical data is shown below. The results show that mmtBumTPchPAF-02 was synthesized in this synthesis example.

$^1$H-NMR. δ (CDCl$_3$): 7.62 (d, 1H, J=7.5 Hz), 7.56 (d, 1H, J=8.0 Hz), 7.50 (dd, 1H, J=1.7 Hz), 7.46-7.47 (m, 2H), 7.43 (dd, 1H, J=1.7 Hz), 7.37-7.39 (m, 3H), 7.29-7.32 (m, 2H), 7.23-7.25 (m, 2H), 7.20 (dd, 1H, J=1.7 Hz), 7.09-7.14 (m, 5H), 7.05 (dd, 1H, J=2.3 Hz), 2.46 (brm, 1H), 1.83-1.88 (m, 4H), 1.73-1.75 (brm, 1H), 1.42 (s, 6H), 1.38 (s, 9H), 1.36 (s, 18H), 1.29 (s, 9H).

Next, 3.5 g of the obtained white solid was purified by a train sublimation method at 265° C. under a pressure of 4.0 Pa with an argon gas flow rate of 15.0 mL/min. After the purification by sublimation, 3.1 g of a pale yellowish white solid was obtained at a collection rate of 89%.

Figure 27:
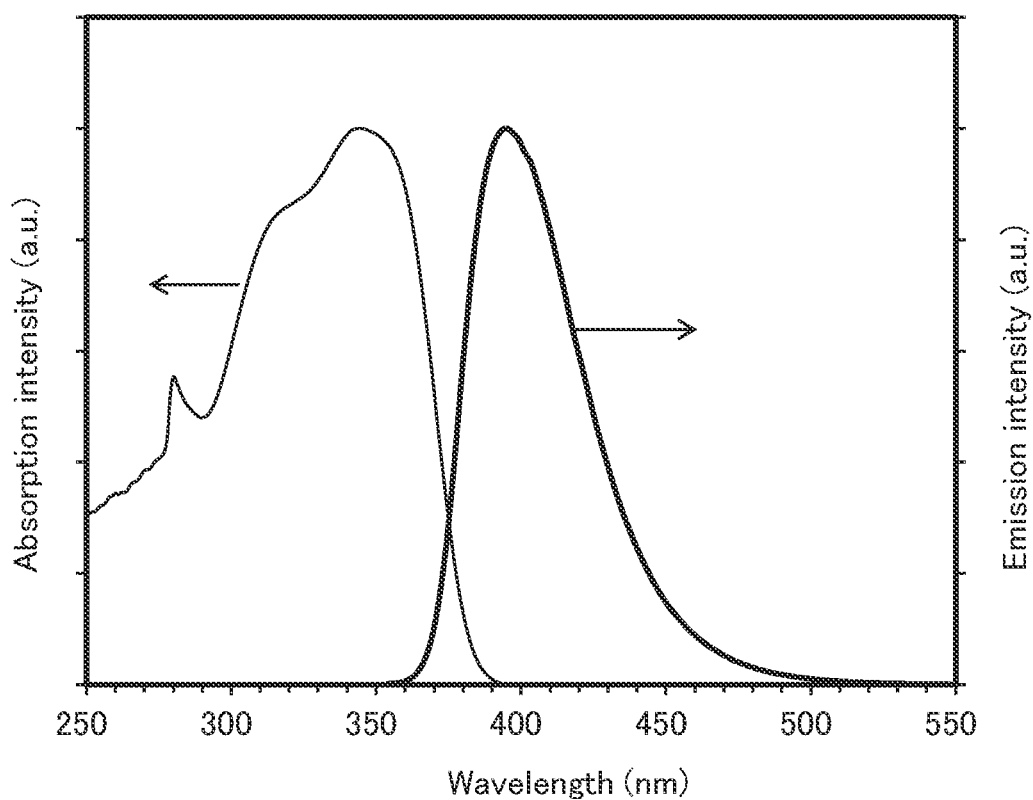
FIG. 27 shows an absorption spectrum and an emission spectrum of mmtBumTPchPAF-02 in a toluene solution.

Then, an ultraviolet-visible absorption spectrum (hereinafter, simply referred to as an absorption spectrum) of mmtBumTPchPAF-02 in a toluene solution and an emission spectrum thereof were measured. The absorption spectrum was measured at room temperature with an ultraviolet-visible light spectrophotometer (FP-8600, produced by JASCO Corporation) in a state where the toluene solution was put in a quartz cell. The emission spectrum was measured with a fluorescence spectrophotometer (FS920, produced by Hamamatsu Photonics K.K.) at room temperature in a state where the toluene solution was put in a quartz cell. FIG. 27 shows obtained measurement results of the absorption spectrum and the emission spectrum. The horizontal axis represents the wavelength and the vertical axes represent the absorbance and emission intensity. In FIG. 27, two solid lines are shown; a thin line represents the absorption spectrum, and a thick line represents the emission spectrum. The absorbance shown in FIG. 27 is a result obtained by subtraction of an absorption spectrum of only toluene in a quartz cell from the measured absorption spectrum of the toluene solution in the quartz cell.

As shown in FIG. 27, mmtBumTPchPAF-02 had an emission peak at 395 nm.

Next, mmtBumTPchPAF-02 obtained in this example was analyzed by liquid chromatography mass spectrometry (LC/MS).

In the LC/MS analysis, liquid chromatography (LC) separation was performed with UltiMate 3000 produced by Thermo Fisher Scientific K.K., and mass spectrometry (MS) was performed with Q Exactive produced by Thermo Fisher Scientific K.K.

In the LC separation, a given column was used at a column temperature of 40° C., and solution sending was performed in such a manner that an appropriate solvent was selected, the sample was prepared by dissolving mmtBumTPchPAF-02 in an organic solvent at a given concentration, and the injection amount was 5.0 μL.

Figure 28:
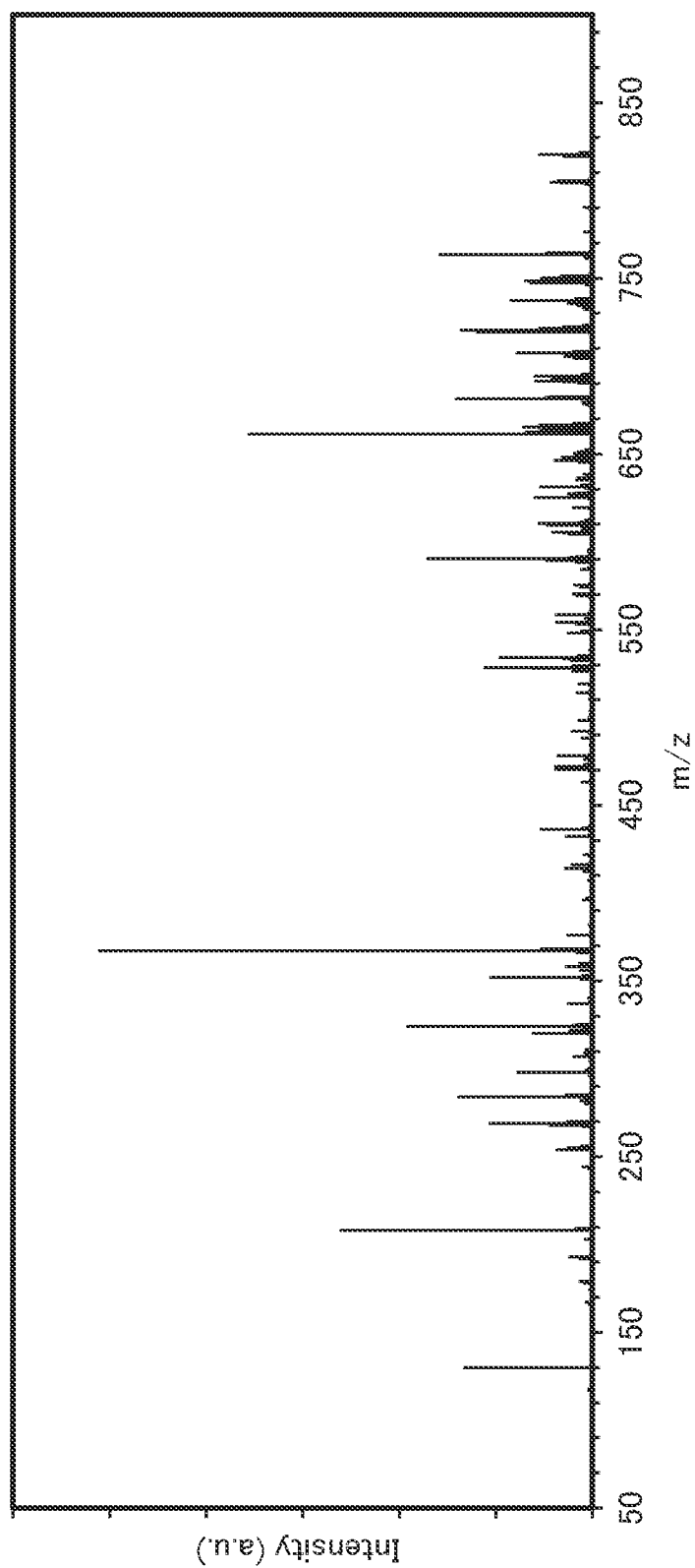
FIG. 28 shows an MS spectrum of mmtBumTPchPAF-02.

An ion derived from mmtBumTPchPAF-02, m/z=820.58, was subjected to the MS$^2$ measurement by a PRM method. For setting of the PRM, the mass range of a target ion was set to m/z=820.58±2.0 (isolation window=4) and detection was performed in a positive mode. The measurement was performed with energy (normalized collision energy: NCE) for accelerating a target ion in a collision cell set to 60. The obtained MS spectrum is shown in FIG. 28.

Figure 29:
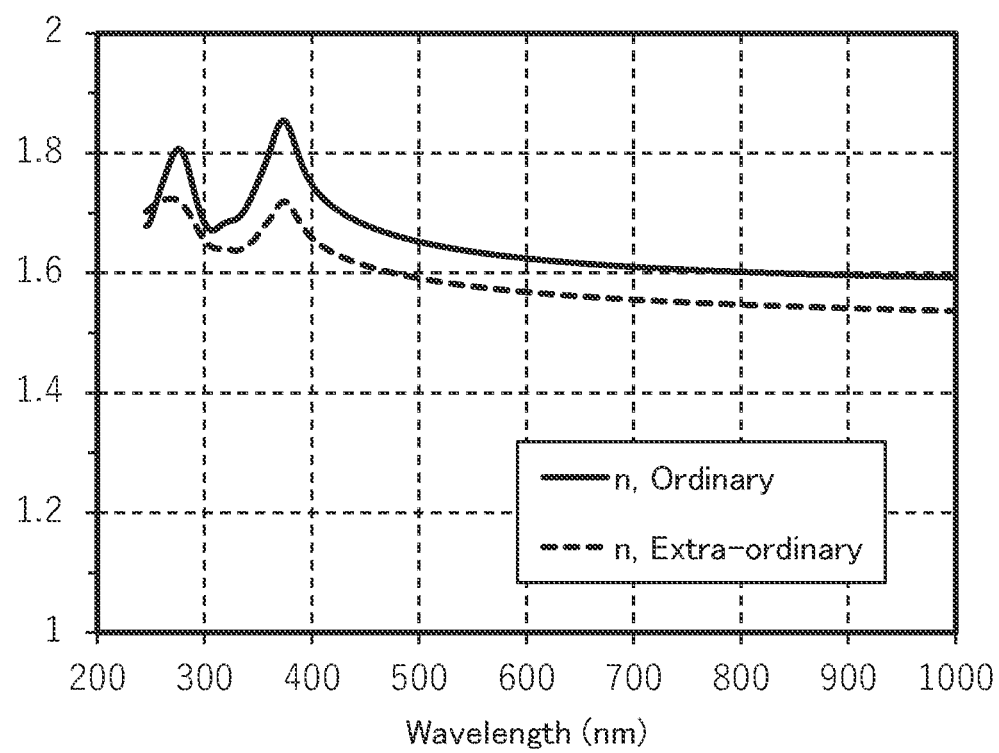
FIG. 29 shows measurement results of a refractive index of mmtBumTPchPAF-02.

FIG. 29 shows the results of measuring the refractive index of mmtBumTPchPAF-02 by a spectroscopic ellipsometer (M-2000U, produced by J.A. Woollam Japan Corp.). A film used for the measurement was formed to a thickness of approximately 50 nm with the material of each layer over a quartz substrate by a vacuum evaporation method. Note that a refractive index of an ordinary ray, n. Ordinary, and a refractive index of an extraordinary ray, n, Extra-ordinary are shown in FIG. 29.

FIG. 29 shows that mmtBumTPchPAF-02 is a material with a low refractive index: the ordinary refractive index with respect to light in the entire blue emission region (from 455 nm to 465 nm) is 1.67 to 1.68, which is within the range of 1.50 to 1.75, and the ordinary refractive index with respect to light with a wavelength of 633 nm is 1.62, which is within the range of 1.45 to 1.70.

Next, the glass transition temperature (hereinafter referred to as "Tg") of mmtBumTPchPAF-02 was measured. Tg was measured using a differential scanning calorimeter (Pyris 1 DSC produced by PerkinElmer Japan Co., Ltd.) in a state where a powder was put on an aluminum cell. As a result, Tg of mmtBumTPchPAF-02 was 127° C.

Example 5

Synthesis Example 5

In this example, a synthesis method of N-(1,1'-biphenyl-2-yl)-N-(3",5',5"-tri-tert-butyl-1,1':3',1"-terphenyl-5-yl)-9,9-dimethyl-9H-fluoren-2-amine (abbreviation: mmtBumT-PoFBi-03), which is the arylamine compound of one embodiment of the present invention described in Embodiment 1, will be described. A structure of mmtBumTPoFBi-03 is shown below.

[Chemical Formula 50]

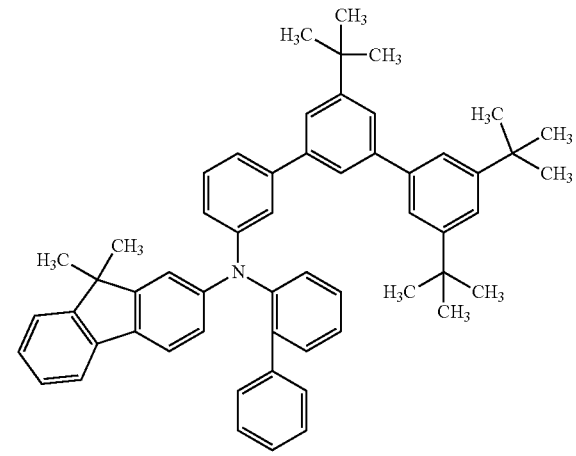

Step 1: Synthesis of
3-bromo-3',5,5'-tri-tert-butylbiphenyl

This synthesis step is similar to Step 1 in Synthesis Example 1.

Step 2: Synthesis of 2-(3',5,5'-tri-tert-butyl[1,1'-biphenyl]-3-yl)-4,4,5,5-tetramethyl-1,3,2-dioxaborolane This synthesis step is similar to Step 2 in Synthesis Example 1.

Step 3: Synthesis of 3-bromo-3″,5′,5″-tri-tert-butyl-1,1′:3′,1″-terphenyl

Into a three-neck flask were put 10.0 g (22.3 mmol) of 2-(3′,5,5′-tri-tert-butyl[1,1′-biphenyl]-3-yl)-4,4,5,5-tetramethyl-1,3,2-dioxaborolane obtained in Step 2, 12.8 g (26.8 mmol) of 1-bromo-3-iodobenzene, 9.2 g (66.9 mmol) of potassium carbonate, 112 mL of toluene, 45 mL of ethanol, and 33 mL of tap water. The mixture was degassed under reduced pressure, the air in the flask was replaced with nitrogen, 100 mg (0.44 mmol) of palladium acetate and 233 mg (0.89 mmol) of triphenyl phosphine were added thereto, and the mixture was heated at 80° C. for approximately 10 hours. After that, the temperature of the flask was lowered to room temperature, and the mixture was separated into an organic layer and an aqueous layer. Magnesium sulfate was added to this solution to eliminate moisture, whereby this solution was concentrated. A hexane solution of the obtained solution was purified by silica gel column chromatography, whereby 9.4 g of a target white solid was obtained in a yield of 89%. The synthesis scheme of Step 3 is shown below.

[Chemical Formula 51]

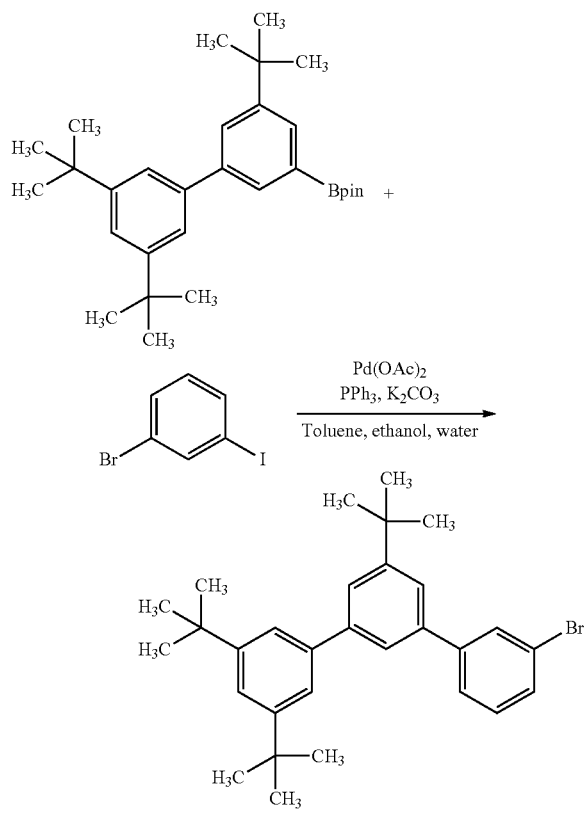

Step 4: Synthesis of mmtBumTPoFBi-03

Into a three-neck flask were put 4.0 g (8.4 mmol) of 3-bromo-3″,5′,5″-tri-tert-butyl-1,1′:3′,1″-terphenyl obtained in Step 3, 3.0 g (8.4 mmol) of N-(1,1′-biphenyl-4-yl)-N-phenyl-9,9-dimethyl-9H-fluoren-2-amine, 2.4 g (25.2 mmol) of sodium tert-butoxide, and 42 mL of toluene. The mixture was degassed under reduced pressure, the air in the flask was replaced with nitrogen, 97 mg (0.17 mmol) of bis(dibenzylideneacetone)palladium(0) and 207 mg (0.50 mmol) of 2-dicyclohexylphosphino-2′,6′-dimethoxybiphenyl were added thereto, and the mixture was heated at 80° C. for approximately two hours. After that, the temperature of the flask was lowered to approximately 60° C., approximately 1 mL of water was added, a precipitated solid was separated by filtration, and the solid was washed with toluene. The filtrate was concentrated, and the obtained toluene solution was purified by silica gel column chromatography. The obtained solution was concentrated to give a condensed toluene solution. Ethanol was added to this toluene solution and the toluene solution was concentrated under reduced pressure, whereby an ethanol suspension was obtained. The precipitate was filtrated at 20° C., and the obtained solid was dried at approximately 80° C. under reduced pressure, whereby 3.6 g of a target white solid was obtained in a yield of 56%. The synthesis scheme of Step 4 is shown below.

[Chemical Formula 52]

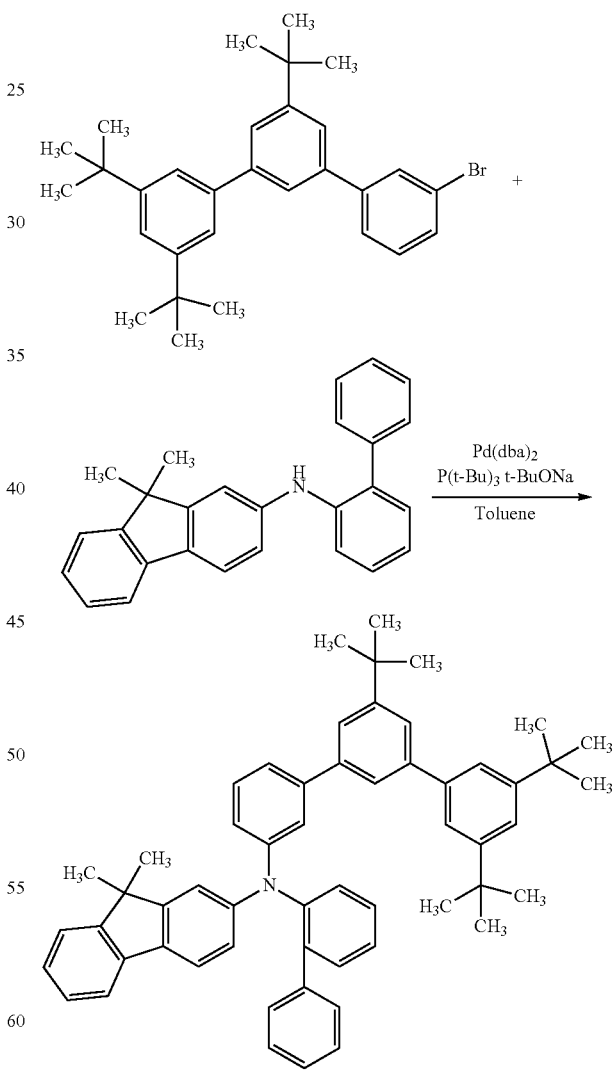

Figure 30A:
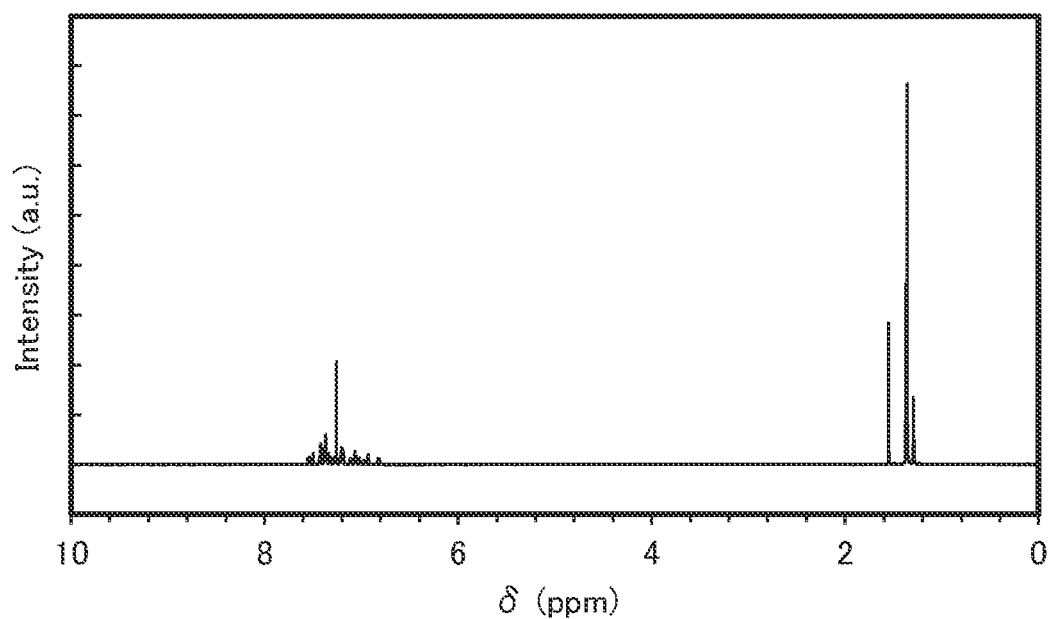
FIGS. 30A and 30B are $^1$H-NMR charts of mmtBumTPoFBi-03.
Figure 30B:
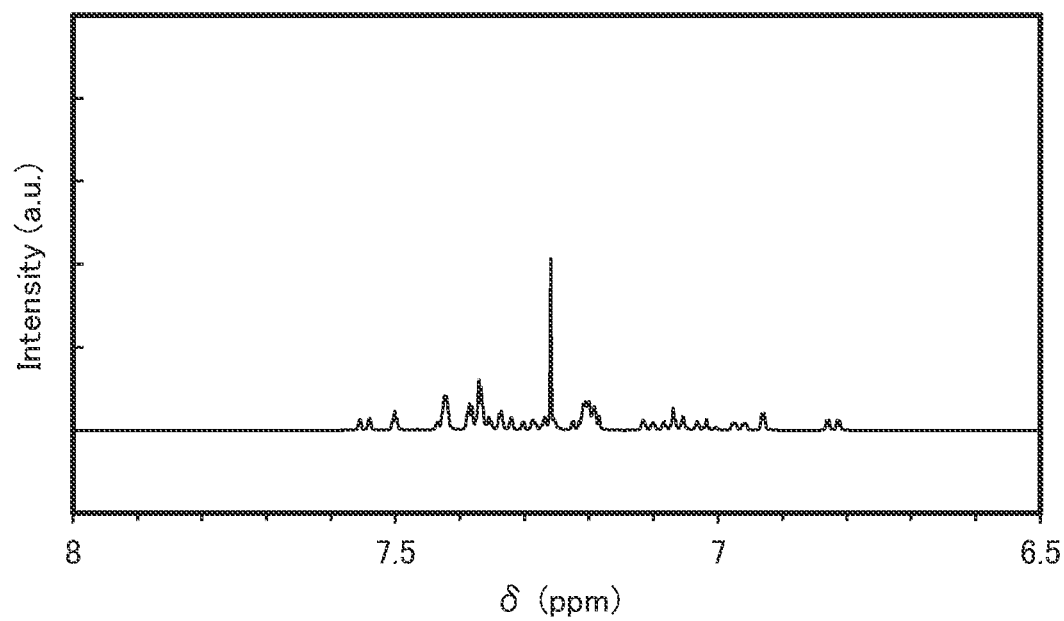

Analysis results by nuclear magnetic resonance ($^1$H-NMR) spectroscopy of the white solid obtained in the above step are shown in FIGS. 30A and 30B. Note that FIG. 30B is an enlarged graph of FIG. 30A in the range of 6.5 ppm to 8.0 ppm. In addition, numerical data is shown below. The results show that N-(1,1'-biphenyl-2-yl)-N-(3",5',5"-tri-tert-butyl-1,1':3',1"-terphenyl-5-yl)-9,9-dimethyl-9H-fluoren-2-amine was synthesized.

$^1$H-NMR. δ (CDCl$_3$): 7.55 (d, 1H, J=7.4 Hz), 7.50 (dd, 1H, J=1.7 Hz), 7.42-7.43 (m, 3H), 7.27-7.39 (m, 10H), 7.18-7.25 (m, 4H), 7.00-7.12 (m, 4H), 6.97 (dd, 1H, J=6.3 Hz, 1.7 Hz), 6.93 (d, 1H, J=1.7 Hz), 6.82 (dd, 1H, J=7.3 Hz, 2.3 Hz), 1.37 (s, 9H), 1.36 (s, 18H), 1.29 (s, 6H).

Next, 3.6 g of the obtained white solid was purified by a train sublimation method at 250° C. under a pressure of 2.3 Pa with an argon gas flow rate of 15.0 mL/min. After the purification by sublimation, 3.1 g of a pale yellowish white solid was obtained at a collection rate of 86%.

Figure 31:
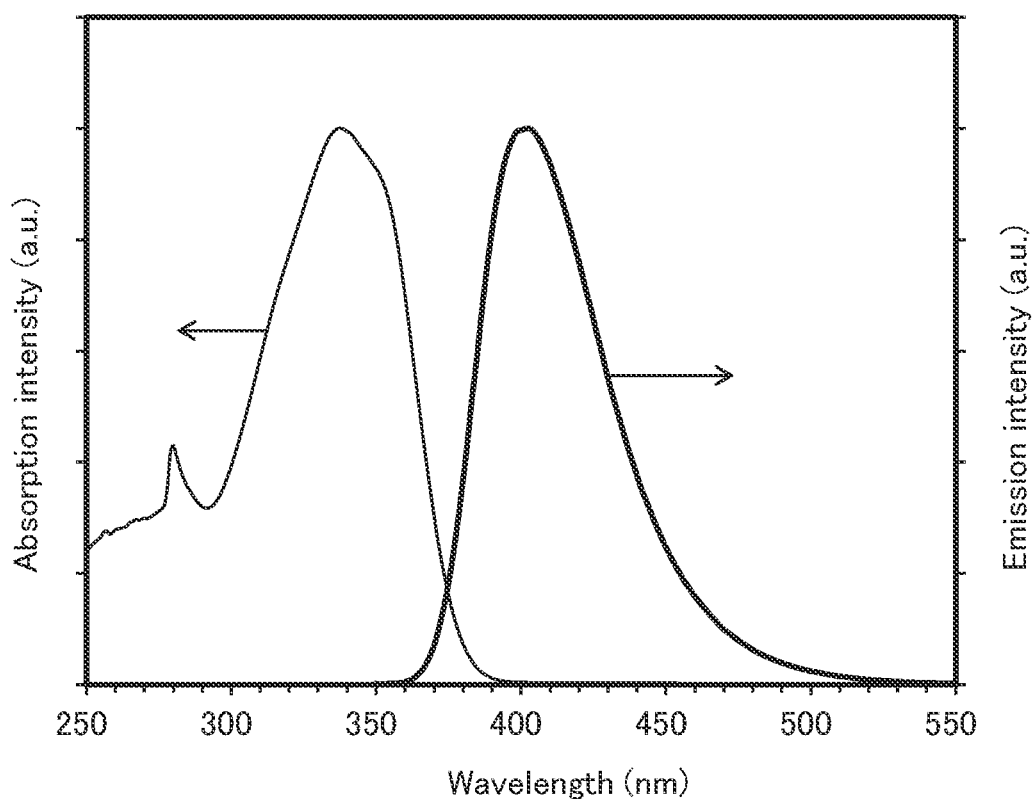
FIG. 31 shows an absorption spectrum and an emission spectrum of mmtBumTPoFBi-03 in a toluene solution.

Then, an ultraviolet-visible absorption spectrum (hereinafter, simply referred to as an absorption spectrum) of mmtBumTPoFBi-03 in a toluene solution and an emission spectrum thereof were measured. The absorption spectrum was measured at room temperature with an ultraviolet-visible light spectrophotometer (FP-8600, produced by JASCO Corporation) in a state where the toluene solution was put in a quartz cell. The emission spectrum was measured with a fluorescence spectrophotometer (FS920, produced by Hamamatsu Photonics K.K.) at room temperature in a state where the toluene solution was put in a quartz cell. FIG. 31 shows obtained measurement results of the absorption spectrum and the emission spectrum. The horizontal axis represents the wavelength and the vertical axes represent the absorbance and emission intensity. In FIG. 31, two solid lines are shown; a thin line represents the absorption spectrum, and a thick line represents the emission spectrum. The absorbance shown in FIG. 31 is a result obtained by subtraction of an absorption spectrum of only toluene in a quartz cell from the measured absorption spectrum of the toluene solution in the quartz cell.

As shown in FIG. 31, mmtBumTPoFBi-03 had an emission peak at 403 nm.

Next, mmtBumTPoFBi-03 obtained in this example was analyzed by liquid chromatography mass spectrometry (LC/MS).

In the LC/MS analysis, liquid chromatography (LC) separation was performed with UltiMate 3000 produced by Thermo Fisher Scientific K.K., and mass spectrometry (MS) was performed with Q Exactive produced by Thermo Fisher Scientific K.K.

In the LC separation, a given column was used at a column temperature of 40° C., and solution sending was performed in such a manner that an appropriate solvent was selected, the sample was prepared by dissolving mmtBumT-PoFBi-03 in an organic solvent at a given concentration, and the injection amount was 5.0 μL.

Figure 32:
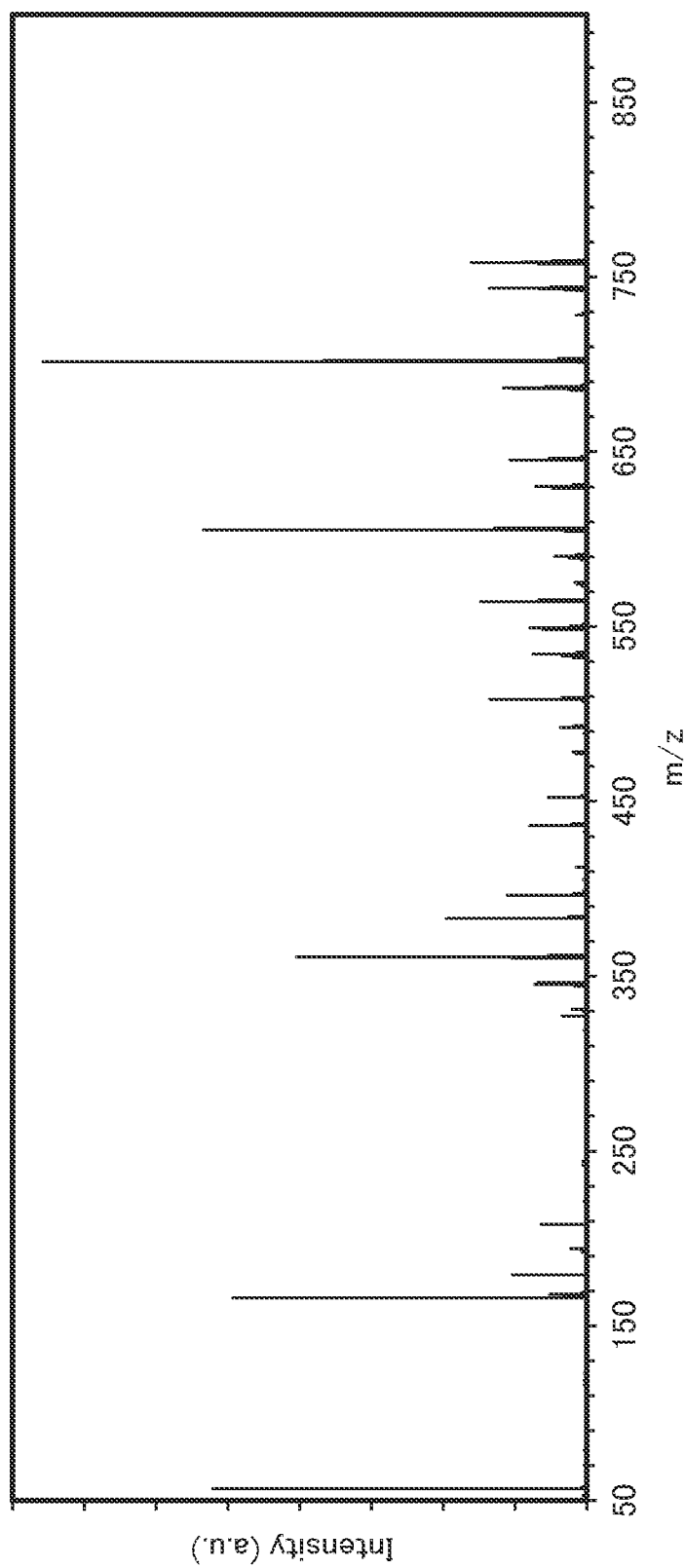
FIG. 32 shows an MS spectrum of mmtBumTPoFBi-03.

An ion derived from mmtBumTPoFBi-03, m/z=758.47, was subjected to the MS$^2$ measurement by a PRM method. For setting of the PRM, the mass range of a target ion was set to m/z=758.47±2.0 (isolation window=4) and detection was performed in a positive mode. The measurement was performed with energy (normalized collision energy: NCE) for accelerating a target ion in a collision cell set to 50. The obtained MS spectrum is shown in FIG. 32.

Figure 33:
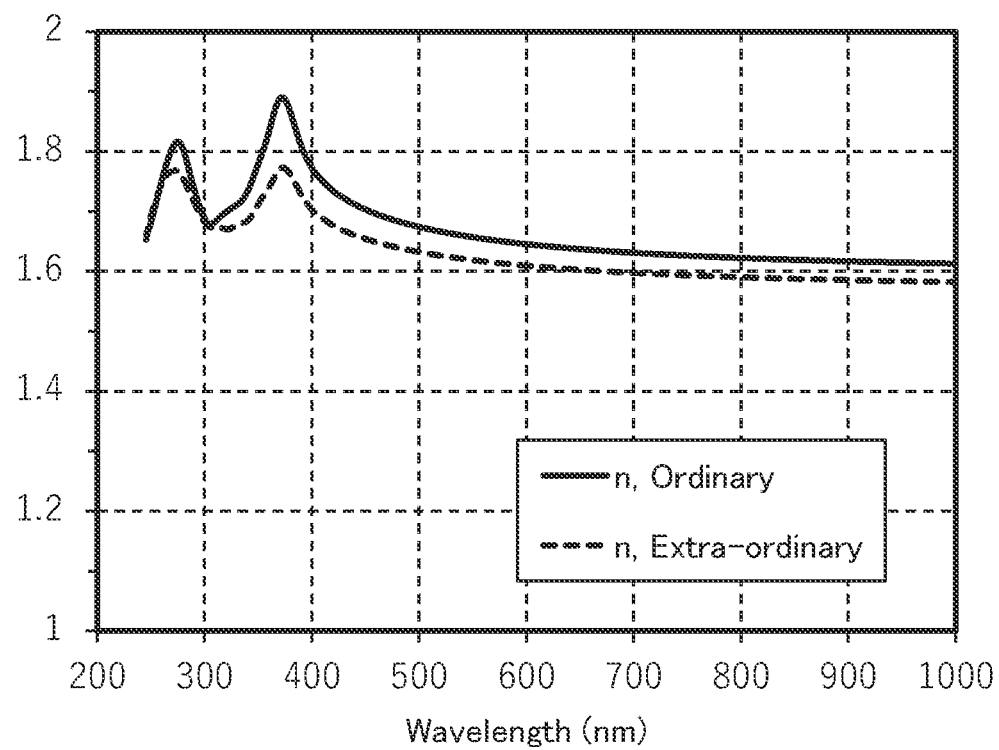
FIG. 33 shows measurement results of a refractive index of mmtBumTPoFBi-03.

FIG. 33 shows the results of measuring the refractive index of mmtBumTPoFBi-03 by a spectroscopic ellipsometer (M-2000U, produced by J.A. Woollam Japan Corp.). A film used for the measurement was formed to a thickness of approximately 50 nm with the material of each layer over a quartz substrate by a vacuum evaporation method. Note that a refractive index of an ordinary ray, n. Ordinary, and a refractive index of an extraordinary ray, n. Extra-ordinary are shown in FIG. 33.

FIG. 33 shows that mmtBumTPoFBi-03 is a material with a low refractive index: the ordinary refractive index with respect to light in the entire blue emission region (from 455 nm to 465 nm) is 1.69 to 1.70, which is within the range of 1.50 to 1.75, and the ordinary refractive index with respect to light with a wavelength of 633 nm is 1.64, which is within the range of 1.45 to 1.70.

Example 6

Synthesis Example 6

In this example, a synthesis method of N-(4-cyclohexylphenyl)-N-(3",5',5"-tri-tert-butyl-1,1':3',1"-terphenyl-5-yl)-9,9-dimethyl-9H-fluoren-2-amine (abbreviation: mmt-BumTPchPAF-03), which is the arylamine compound of one embodiment of the present invention described in Embodiment 1, will be described. A structure of mmtBumTPchPAF-03 is shown below.

[Chemical Formula 53]

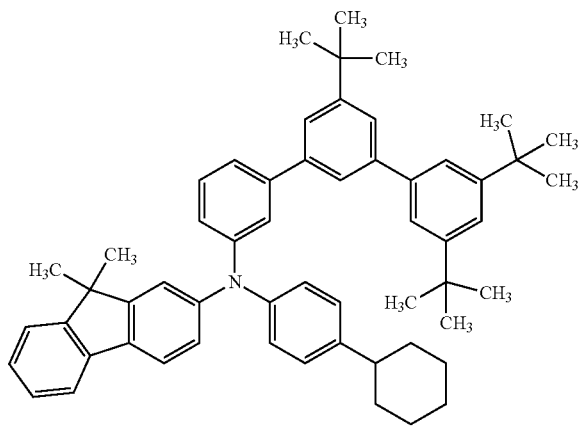

Step 1: Synthesis of 3-bromo-3',5,5'-tri-tert-butylbiphenyl

This synthesis step is similar to Step 1 in Synthesis Example 1.

Step 2: Synthesis of 2-(3',5,5'-tri-tert-butyl[1,1'-biphenyl]-3-yl)-4,4,5,5-tetramethyl-1,3,2-dioxaborolane This synthesis step is similar to Step 2 in Synthesis Example 1.

Step 3: Synthesis of 3-bromo-3",5',5"-tri-tert-butyl-1,1':3',1"-terphenyl

This synthesis step is similar to Step 3 in Synthesis Example 5.

Step 4: Synthesis of mmtBumTPchPAF-03

Into a three-neck flask were put 2.3 g (4.8 mmol) of 3-bromo-3",5',5"-tri-tert-butyl-1,1':3',1"-terphenyl obtained in Step 3, 1.8 g (4.8 mmol) of N-(4-cyclohexylphenyl)-N-(9,9-dimethyl-9H-fluoren-2-yl)amine, 1.4 g (14.4 mmol) of sodium tert-butoxide, and 24 mL of toluene. The mixture was degassed under reduced pressure, the air in the flask was replaced with nitrogen, 55 mg (0.10 mmol) of bis(dibenzylideneacetone)palladium(0) and 118 mg (0.29 mmol) of 2-dicyclohexylphosphino-2',6'-dimethoxybiphenyl were added thereto, and the mixture was heated at 80° C. for approximately two hours. After that, the temperature of the flask was lowered to approximately 60° C., approximately 1 mL of water was added, a precipitated solid was separated by filtration, and the solid was washed with toluene. The filtrate was concentrated, and the obtained toluene solution was purified by silica gel column chromatography. The obtained solution was concentrated to give a condensed toluene solution. Ethanol was added to this toluene solution and the toluene solution was concentrated under reduced pressure, whereby an ethanol suspension was obtained. The precipitate was filtrated at approximately 20° C., and the obtained solid was dried at approximately 80° C. under reduced pressure, whereby 2.9 g of a target white solid was obtained in a yield of 80%. The synthesis scheme of Step 4 is shown below.

[Chemical Formula 54]

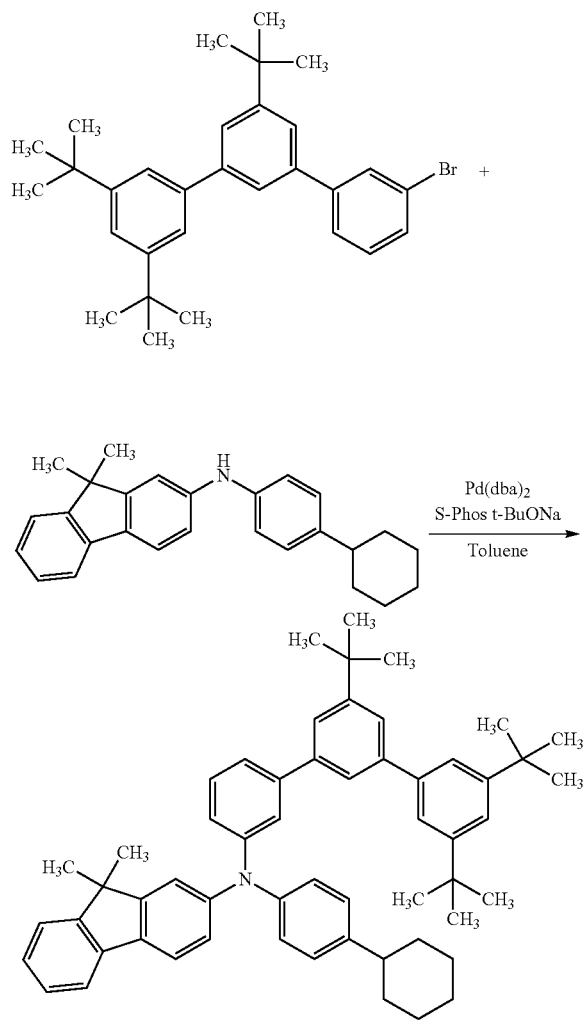

Figure 34A:
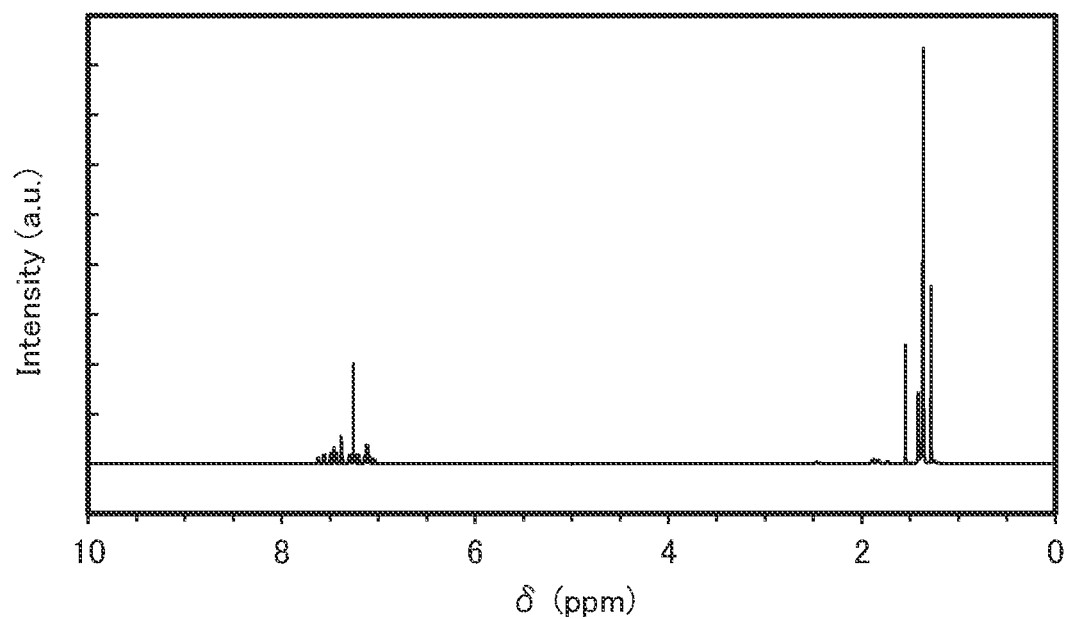
FIGS. 34A and 34B are $^1$H-NMR charts of mmtBumTPchPAF-03.
Figure 34B:
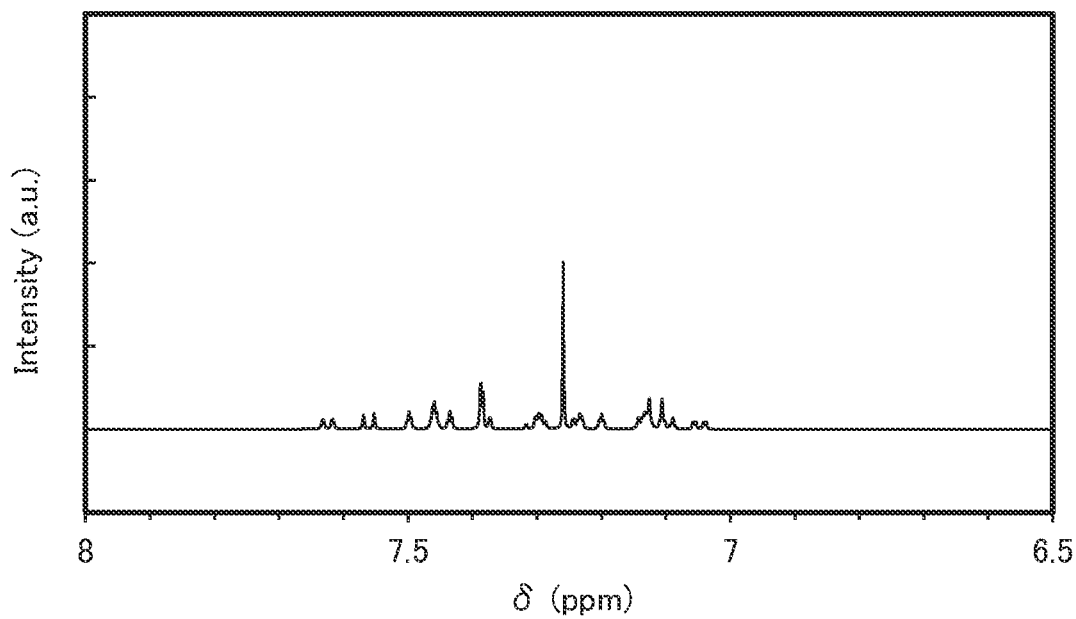

Analysis results by nuclear magnetic resonance ($^1$H-NMR) spectroscopy of the white solid obtained through the above step are shown in FIGS. 34A and 34B. Note that FIG. 34B is an enlarged graph of FIG. 34A in the range of 6.5 ppm to 8.0 ppm. In addition, numerical data is shown below. The results show that N-(4-cyclohexylphenyl)-N-(3",5',5"-tri-tert-butyl-1,1':3'1"-terphenyl-5-yl)-9,9-dimethyl-9H-fluoren-2-amine was synthesized in this synthesis example.

$^1$H-NMR. δ (CDCl$_3$): 7.62 (d, 1H, J=7.5 Hz), 7.56 (d, 1H, J=8.6 Hz), 7.51 (dd, 1H, J=1.7 Hz), 7.48 (dd, 1H, J=1.7 Hz), 7.46 (dd, 1H, J=1.7 Hz), 7.42 (dd, 1H, J=1.7 Hz), 7.37-7.39 (m, 4H), 7.27-7.33 (m, 2H), 7.23-7.25 (m, 2H), 7.05-7.13 (m, 7H), 2.46 (brm, 1H), 1.83-1.90 (m, 4H), 1.73-1.75 (brm, 1H), 1.41 (s, 6H), 1.37 (s, 9H), 1.35 (s, 18H).

Next, 2.4 g of the obtained white solid was purified by a train sublimation method at 230° C. under a pressure of 4.0 Pa with an argon gas flow rate of 15.0 mL/min. After the purification by sublimation, 1.9 g of a pale yellowish white solid was obtained at a collection rate of 79%.

Figure 35:
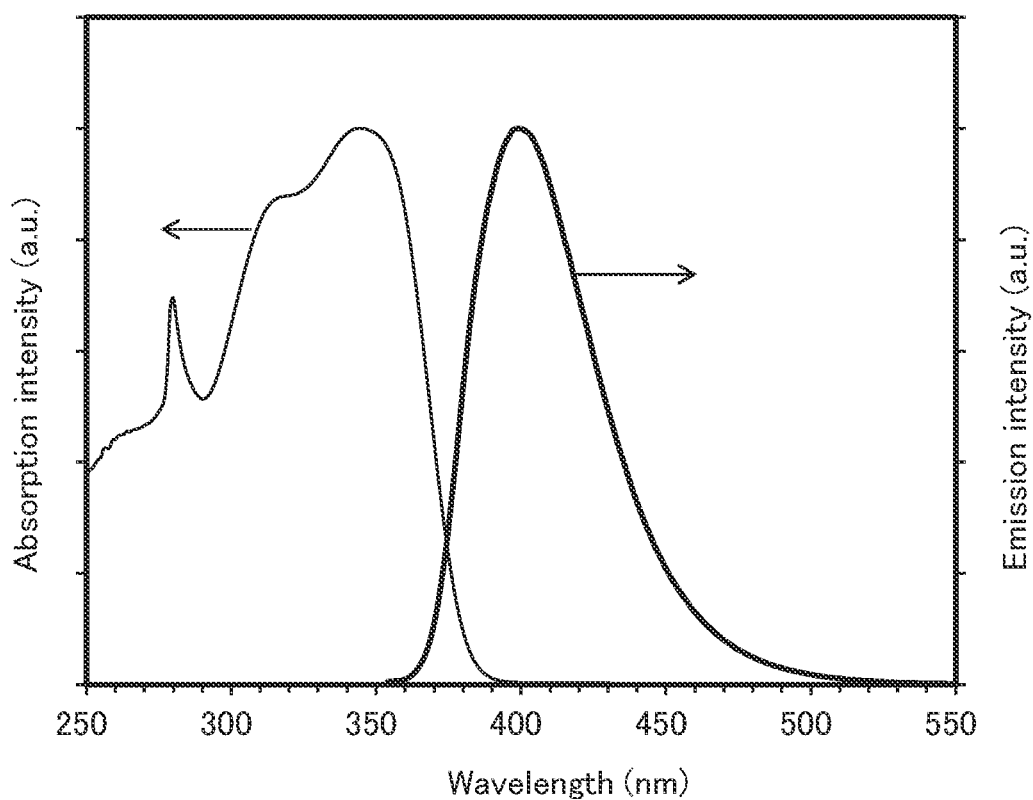
FIG. 35 shows an absorption spectrum and an emission spectrum of mmtBumTPchPAF-03 in a toluene solution.

Then, an ultraviolet-visible absorption spectrum (hereinafter, simply referred to as an absorption spectrum) of mmtBumTPchPAF-03 in a toluene solution and an emission spectrum thereof were measured. The absorption spectrum was measured at room temperature with an ultraviolet-visible light spectrophotometer (FP-8600, produced by JASCO Corporation) in a state where the toluene solution was put in a quartz cell. The emission spectrum was measured with a fluorescence spectrophotometer (FS920, produced by Hamamatsu Photonics K.K.) at room temperature in a state where the toluene solution was put in a quartz cell. FIG. 35 shows obtained measurement results of the absorption spectrum and the emission spectrum. The horizontal axis represents the wavelength and the vertical axes represent the absorbance and emission intensity. In FIG. 35, two solid lines are shown; a thin line represents the absorption spectrum, and a thick line represents the emission spectrum. The absorbance shown in FIG. 35 is a result obtained by subtraction of an absorption spectrum of only toluene in a quartz cell from the measured absorption spectrum of the toluene solution in the quartz cell.

As shown in FIG. 35, mmtBumTPchPAF-03 had an emission peak at 399 nm.

Next, mmtBumTPchPAF-03 obtained in this example was analyzed by liquid chromatography mass spectrometry (LC/MS).

In the LC/MS analysis, liquid chromatography (LC) separation was performed with UltiMate 3000 produced by Thermo Fisher Scientific K.K., and mass spectrometry (MS) was performed with Q Exactive produced by Thermo Fisher Scientific K.K.

In the LC separation, a given column was used at a column temperature of 40° C., and solution sending was performed in such a manner that an appropriate solvent was selected, the sample was prepared by dissolving mmtBumTPchPAF-03 in an organic solvent at a given concentration, and the injection amount was 5.0 μL.

Figure 36:
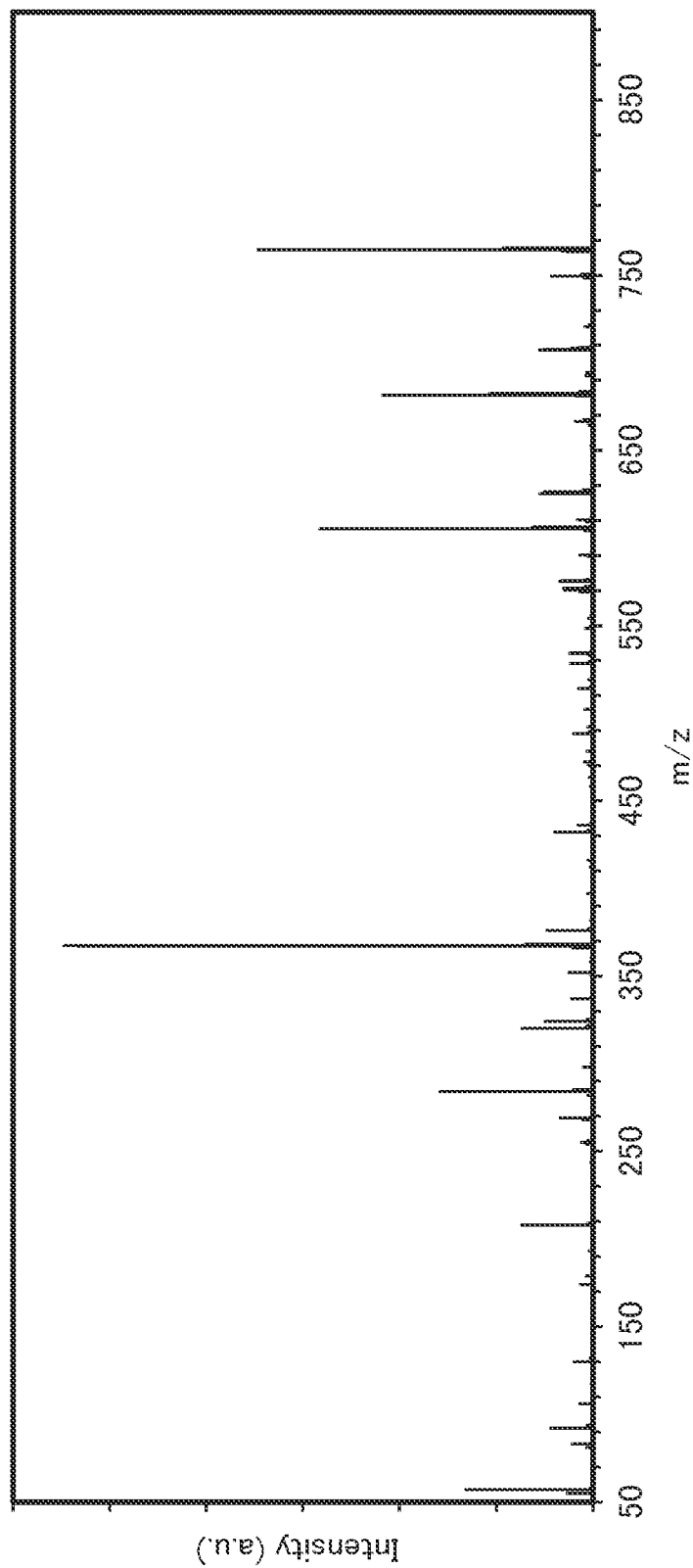
FIG. 36 shows an MS spectrum of mmtBumTPchPAF-03.

An ion derived from mmtBumTPchPAF-03, m/z=764.52, was subjected to the MS$^2$ measurement by a PRM method. For setting of the PRM, the mass range of a target ion was set to m/z=764.52±2.0 (isolation window=4) and detection was performed in a positive mode. The measurement was performed with energy (normalized collision energy: NCE) for accelerating a target ion in a collision cell set to 50. The obtained MS spectrum is shown in FIG. 36.

Figure 37:
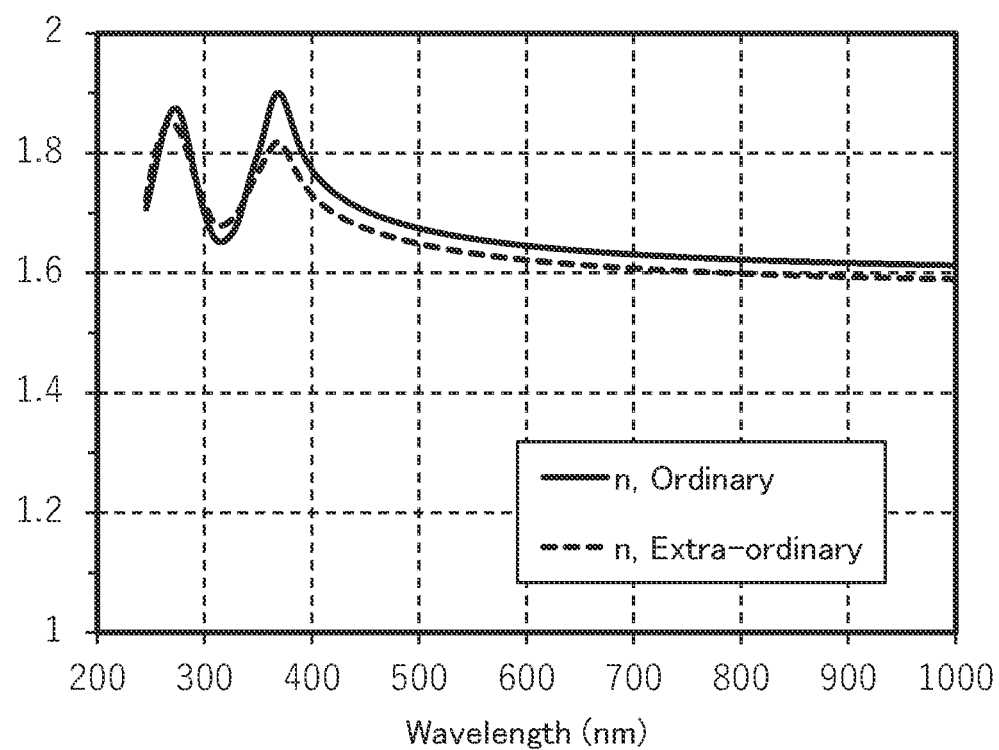
FIG. 37 shows measurement results of a refractive index of mmtBumTPchPAF-03.

FIG. 37 shows the results of measuring the refractive index of mmtBumTPchPAF-03 by a spectroscopic ellipsometer (M-2000U, produced by J.A. Woollam Japan Corp.). A film used for the measurement was formed to a thickness of approximately 50 nm with the material of each layer over a quartz substrate by a vacuum evaporation method. Note that a refractive index of an ordinary ray, n, Ordinary, and a refractive index of an extraordinary ray, n. Extra-ordinary are shown in FIG. 37.

FIG. 37 shows that mmtBumTPchPAF-03 is a material with a low refractive index: the ordinary refractive index with respect to light in the entire blue emission region (from 455 nm to 465 nm) is 1.69 to 1.70, which is within the range of 1.50 to 1.75, and the ordinary refractive index with respect to light with a wavelength of 633 nm is 1.64, which is within the range of 1.45 to 1.70.

Example 7

In this example, light-emitting devices of one embodiment of the present invention described in the above embodiments and a comparative light-emitting device are described. Structural formulae of organic compounds used in this example are shown below.

[Chemical Formula 55]

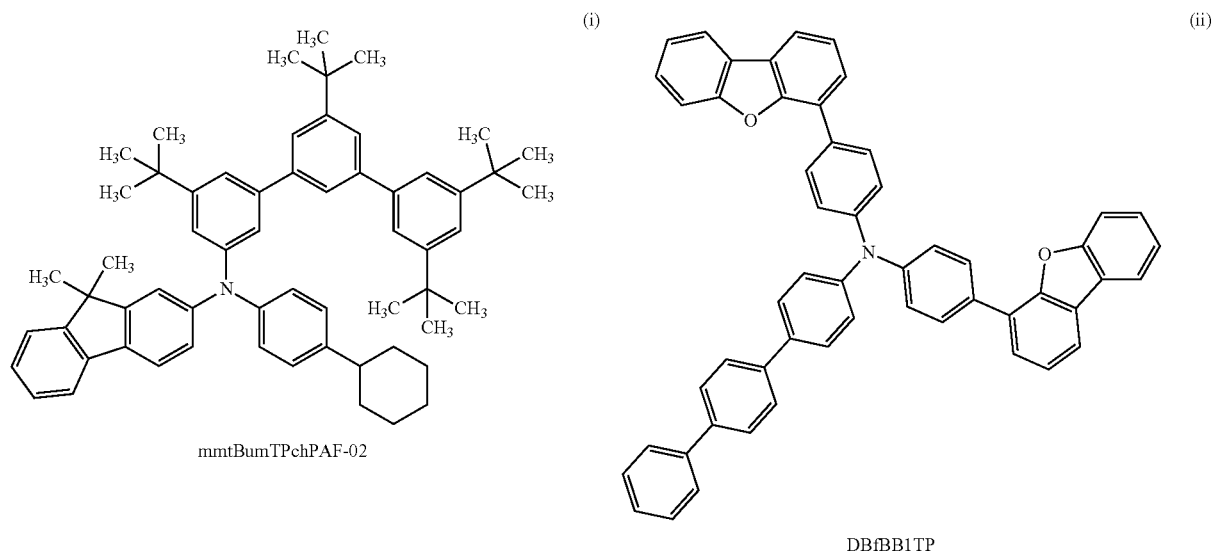

-continued

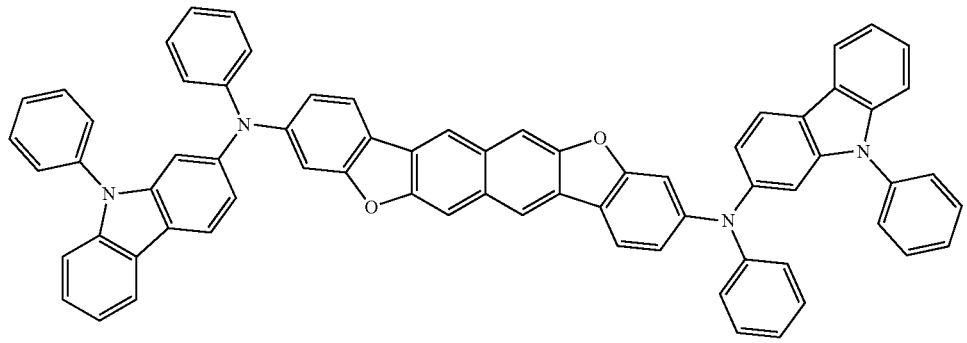
3,10PCA2Nbf(IV)-02 (iv)

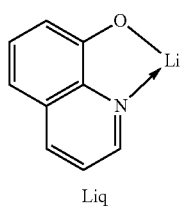
Liq (vi)

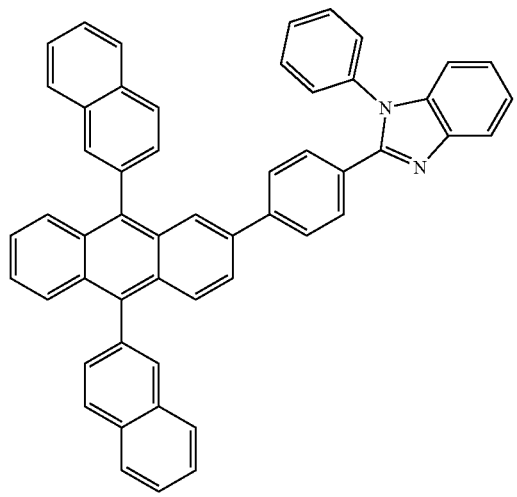
ZADN (v)

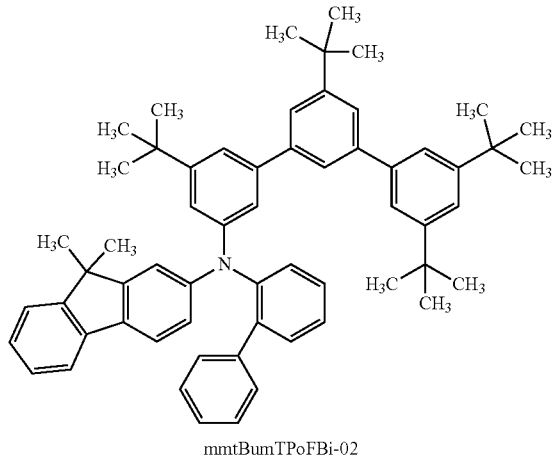
mmtBumTPoFBi-02 (vii)

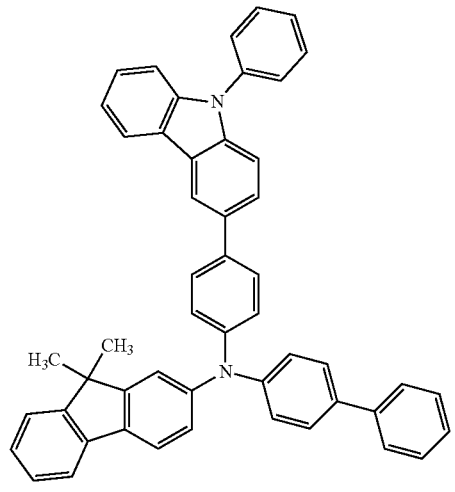
PCBBiF (viii)

(Fabrication Method of Light-Emitting Device 1)

First, indium tin oxide containing silicon oxide (ITSO) was deposited over a glass substrate by a sputtering method to form the first electrode 101. The thickness of the first electrode 101 was 55 nm and the electrode area was 2 mm×2 mm.

Next, in pretreatment for forming the light-emitting device over a substrate, a surface of the substrate was washed with water and baked at 200° C. for one hour, and then UV ozone treatment was performed for 370 seconds.

After that, the substrate was transferred into a vacuum evaporation apparatus where the pressure was reduced to approximately $10^{-4}$ Pa, vacuum baking was performed at 170° C. for 30 minutes in a heating chamber of the vacuum evaporation apparatus, and then the substrate was cooled down for approximately 30 minutes.

Next, the substrate provided with the first electrode 101 was fixed to a substrate holder provided in the vacuum evaporation apparatus such that the surface on which the first electrode 101 was formed faced downward. Then, N-(4-cyclohexylphenyl)-N-(3,3",5',5"-tetra-tert-butyl-1,1': 3',1"-terphenyl-5-yl)-9,9-dimethyl-9H-fluoren-2-amine (abbreviation: mmtBumTPchPAF-02) represented by Structural Formula (i) and an electron acceptor material (OCHD-001) were deposited by co-evaporation to a thickness of 10 nm on the first electrode 101 using a resistance-heating method such that the weight ratio of mmtBumTPchPAF-02 to OCHD-001 was 1:0.1, whereby the hole-injection layer 111 was formed.

Subsequently, over the hole-injection layer 111, mmtBumTPchPAF-02 was deposited to a thickness of 30 nm by evaporation, and then N,N-bis[4-(dibenzofuran-4-yl)phenyl]-4-amino-p-terphenyl (abbreviation: DBfBB1TP) represented by Structural Formula (ii) was deposited to a thickness of 10 nm by evaporation, whereby the hole-transport layer 112 was formed.

Then, 9-(1-naphthyl)-10-[4-(2-naphthyl)phenyl]anthracene (abbreviation: αN-βNPAnth) represented by Structural Formula (iii) and 3,10-bis[N-(9-phenyl-9H-carbazol-2-yl)-N-phenylamino]naphtho[2,3-b;6,7-b']bisbenzofuran (abbreviation: 3,10PCA2Nbf(IV)-02) represented by Structural Formula (iv) were deposited to a thickness of 25 nm by co-evaporation such that the weight ratio of αN-βNPAnth to 3,10PCA2Nbf(IV)-02 was 1:0.015, whereby the light-emitting layer 113 was formed.

After that, over the light-emitting layer 113, 2-{4-[9,10-di(naphthalen-2-yl)-2-anthryl]phenyl}-1-phenyl-1H-benzimidazole (abbreviation: ZADN) represented by Structural Formula (v) and 8-hydroxyquinolinatolithium (abbreviation: Liq) represented by Structural Formula (vi) were deposited to a thickness of 25 nm by co-evaporation such that the weight ratio of ZADN to Liq was 1:1, whereby the electron-transport layer 114 was formed.

After the formation of the electron-transport layer 114, Liq was deposited by evaporation to a thickness of 1 nm to form the electron-injection layer 115. Then, aluminum was deposited by evaporation to a thickness of 200 nm to form the second electrode 102. Thus, a light-emitting device 1 of this example was fabricated.

(Fabrication Method of Light-Emitting Device 2)

A light-emitting device 2 was fabricated in a manner similar to that for the light-emitting device 1 except that mmtBumTPchPAF-02 in the light-emitting device 1 was replaced with N-(1,1'-biphenyl-2-yl)-N-(3,3",5',5"-tetra-tert-butyl-1,1':3',1"-terphenyl-5-yl)-9,9-dimethyl-9H-fluoren-2-amine (abbreviation: mmtBumTPoFBi-02) represented by Structural Formula (vii).

(Fabrication Method of Comparative Light-Emitting Device 1)

A comparative light-emitting device 1 was fabricated in a manner similar to that for the light-emitting device 1 except that mmtBumTPchPAF-02 in the light-emitting device 1 was replaced with N-(1,1'-biphenyl-4-yl)-N-[4-(9-phenyl-9H-carbazol-3-yl)phenyl]-9,9-dimethyl-9H-fluoren-2-amine (abbreviation: PCBBiF) represented by Structural Formula (viii).

The structures of the light-emitting devices and the comparative light-emitting device are listed in the following table.

TABLE 1

| | Film thickness | Light-emitting Device 1 | Light-emitting Device 2 | Comparative Light-emitting Device 1 |
|---|---|---|---|---|
| Electron-injection layer | 1 nm | Liq | | |
| Electron-transport layer | 25 nm | ZADN:Liq (1:1) | | |
| Light-emitting layer | 25 nm | αN-βNPAnth:3,10PCA2Nbf(IV)-02 (1:0.015) | | |
| Hole-transport layer | 10 nm | DBfBB1TP | | |
| | 30 nm | mmtBumTPchPAF-02 | mmtBumTPoFBi-02 | PCBBiF |
| Hole-injection layer | 10 nm | mmtBumTPchPAF-02:OCHD-001 (1:0.1) | mmtBumTPoFBi-02:OCHD-001 (1:0.1) | PCBBiF:OCHD-001 (1:0.1) |

The refractive indices of PCBBiF as a reference and the materials with a low refractive index (mmtBumTPchPAF-02 and mmtBumTPoFBi-02) used for the hole-injection layer and part of the hole-transport layer are shown in FIG. 38, and the refractive indices at a wavelength of 458 nm are shown in the following table.

TABLE 2

| | Refractive index |
|---|---|
| mmtBumTPchPAF-02 | 1.67 |
| mmtBumTPoFBi-02 | 1.70 |
| PCBBiF | 1.94 |

The light-emitting devices and the comparative light-emitting device were sealed using a glass substrate in a glove box containing a nitrogen atmosphere so as not to be exposed to the air (a sealing material was applied to surround the device and UV treatment and heat treatment at 80° C. for 1 hour were performed at the time of sealing). Then, the initial characteristics of the light-emitting devices were measured. Note that the glass substrate over which the light-emitting device was formed was not subjected to particular treatment for improving outcoupling efficiency.

Figure 39:
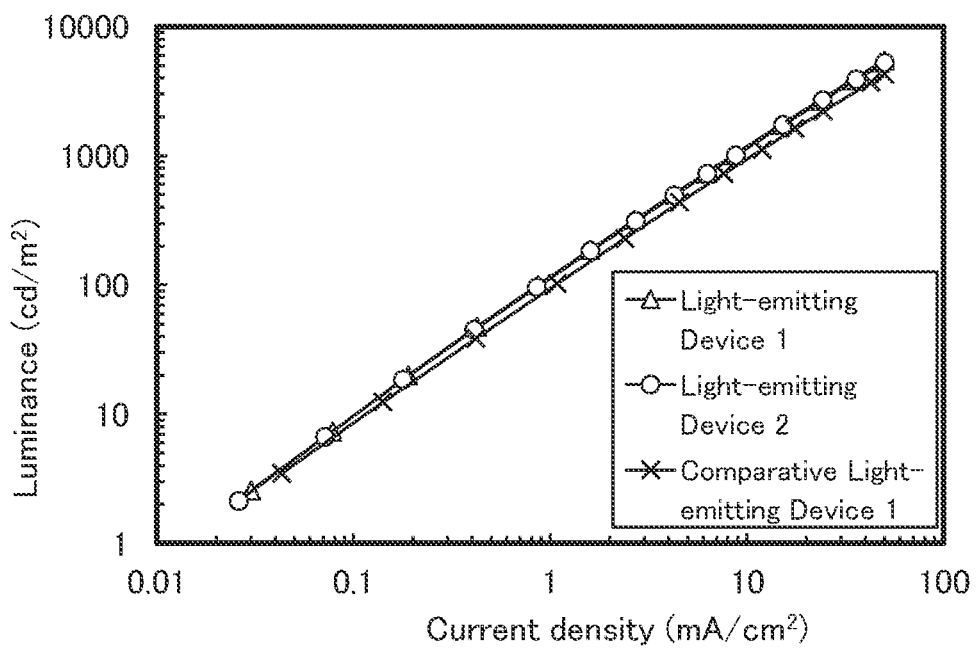
FIG. 39 shows the luminance-current density characteristics of a light-emitting device 1, a light-emitting device 2, and a comparative light-emitting device 1.
Figure 40:
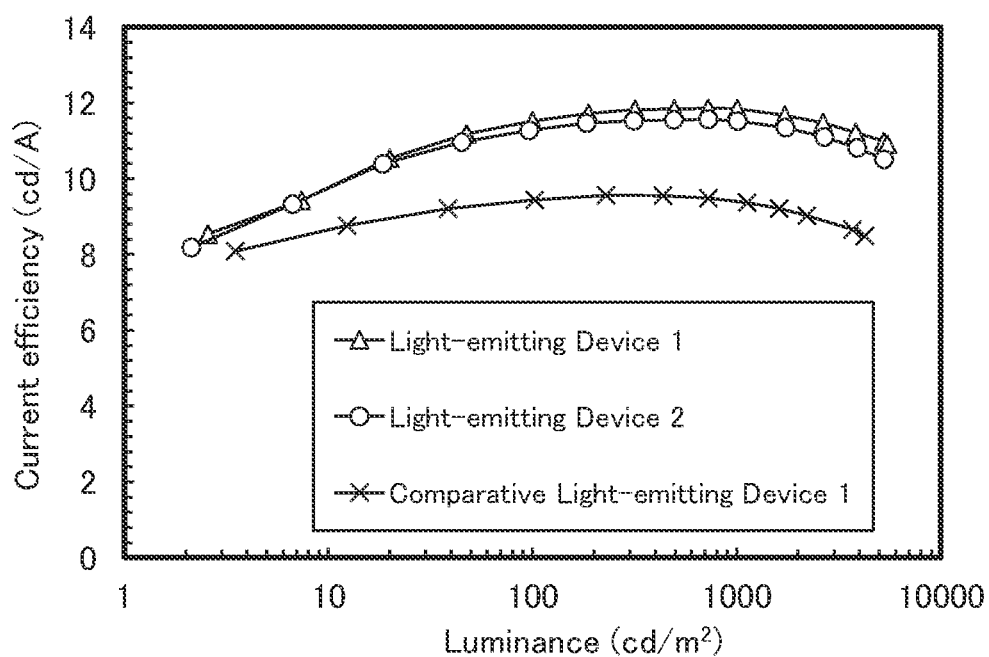
FIG. 40 shows the current efficiency-luminance characteristics of the light-emitting devices 1 and 2 and the comparative light-emitting device 1.
Figure 41:
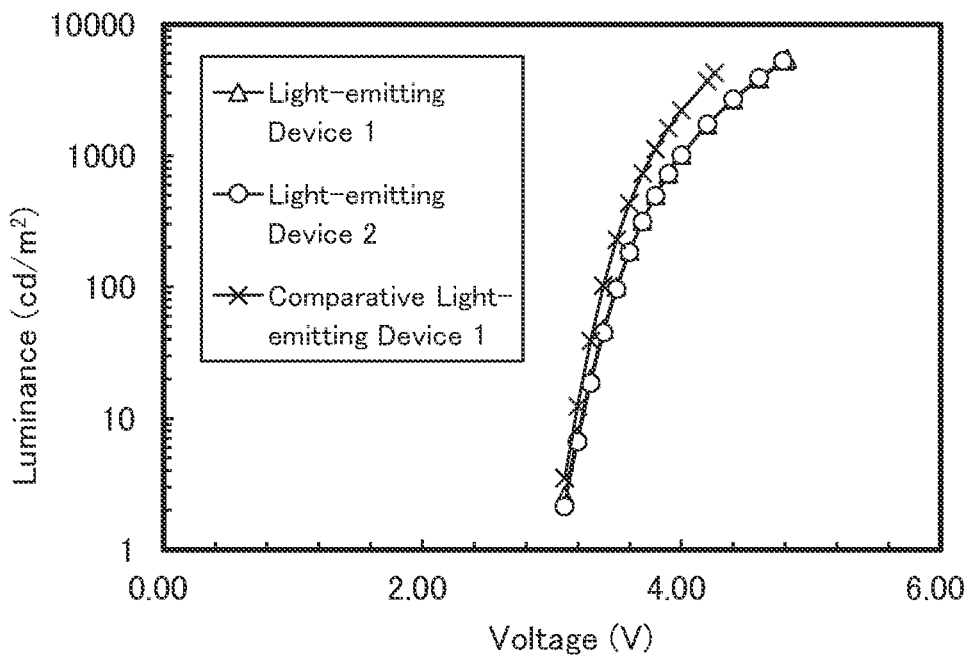
FIG. 41 shows the luminance-voltage characteristics of the light-emitting devices 1 and 2 and the comparative light-emitting device 1.
Figure 42:
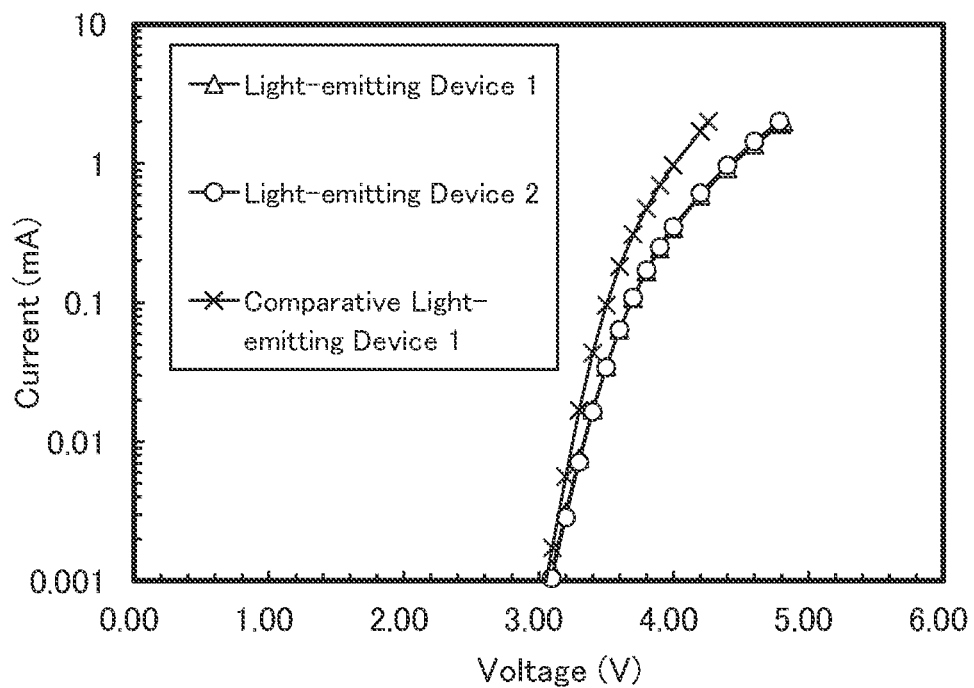
FIG. 42 shows the current-voltage characteristics of the light-emitting devices 1 and 2 and the comparative light-emitting device 1.
Figure 43:
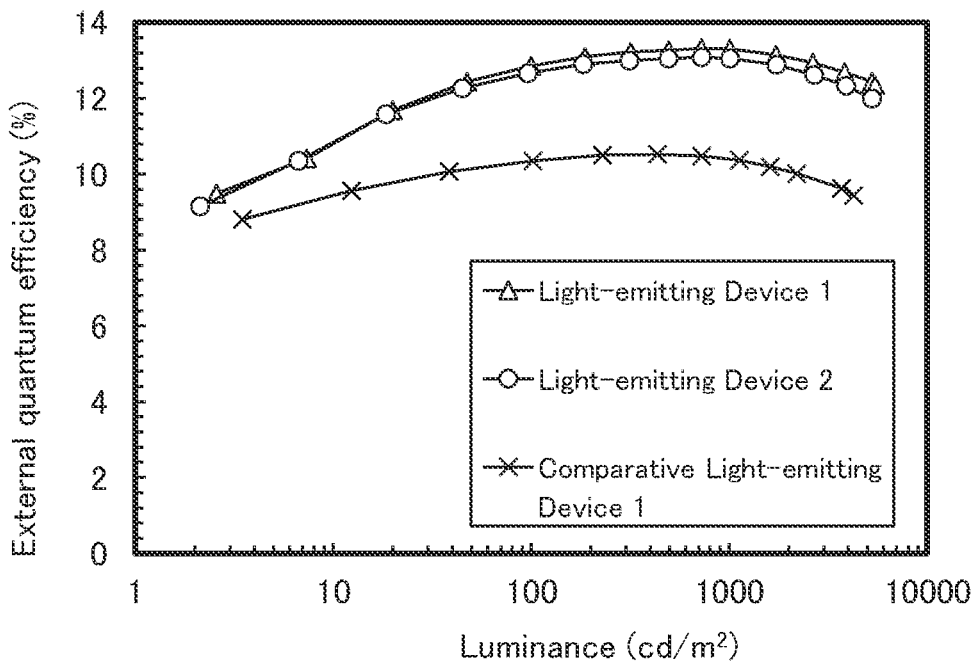
FIG. 43 shows the external quantum efficiency-luminance characteristics of the light-emitting devices 1 and 2 and the comparative light-emitting device 1.
Figure 44:
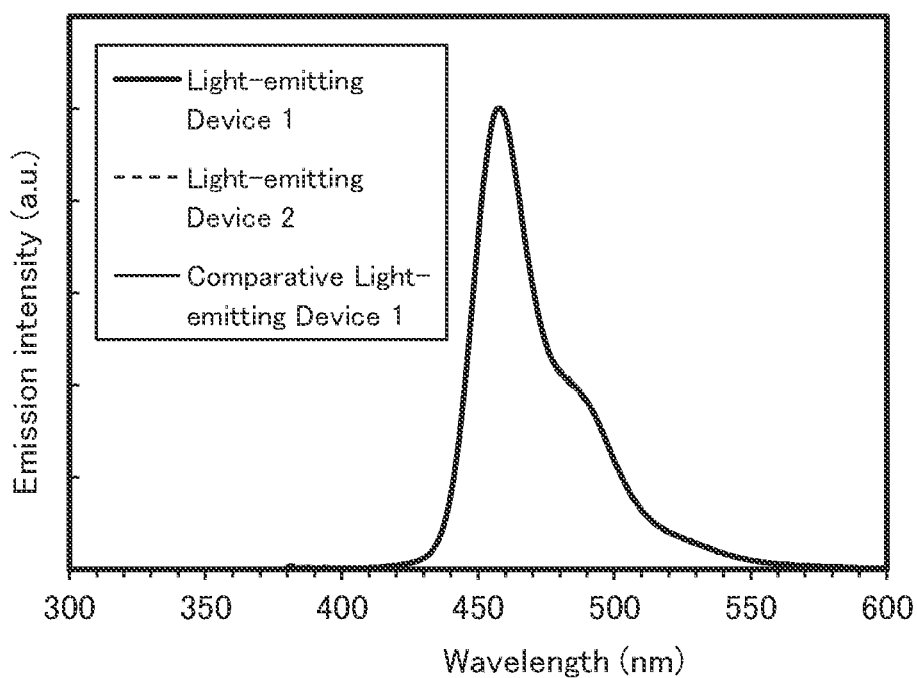
FIG. 44 shows the emission spectra of the light-emitting devices 1 and 2 and the comparative light-emitting device 1.

FIG. 39 shows the luminance-current density characteristics of the light-emitting device 1, the light-emitting device 2, and the comparative light-emitting device 1. FIG. 40 shows the current efficiency-luminance characteristics thereof. FIG. 41 shows the luminance-voltage characteristics thereof. FIG. 42 shows the current-voltage characteristics thereof. FIG. 43 shows the external quantum efficiency-luminance characteristics thereof. FIG. 44 shows the emission spectra thereof. Table 3 shows the main characteristics of the light-emitting devices at a luminance of about 1000 cd/m². Luminance, CIE chromaticity, and emission spectra were measured with a spectroradiometer (UR-UL1R produced by TOPCON TECHNOHOUSE CORPORATION). The external quantum efficiency was calculated from the luminance and emission spectra measured with the spectroradiometer, on the assumption that the light-emitting devices had Lambertian light-distribution characteristics. PGP-5I,T2

TABLE 3

| | Voltage (V) | Current (mA) | Current density (mA/cm²) | Chromaticity x | Chromaticity y | Current efficiency (cd/A) | External quantum efficiency (%) |
|---|---|---|---|---|---|---|---|
| Light-emitting Device 1 | 4.0 | 0.34 | 8.5 | 0.14 | 0.10 | 11.8 | 13.3 |
| Light-emitting Device 2 | 4.0 | 0.35 | 8.8 | 0.14 | 0.10 | 11.5 | 13.0 |
| Comparative Light-emitting Device 1 | 3.8 | 0.48 | 12.0 | 0.14 | 0.10 | 9.4 | 10.4 |

FIGS. 39 to 44 and Table 3 show that the light-emitting devices of one embodiment of the present invention, each of which includes a layer using a material with a low refractive index, are favorable EL devices having the same shape of the emission spectra as and higher emission efficiency than the comparative light-emitting device.

Figure 67:
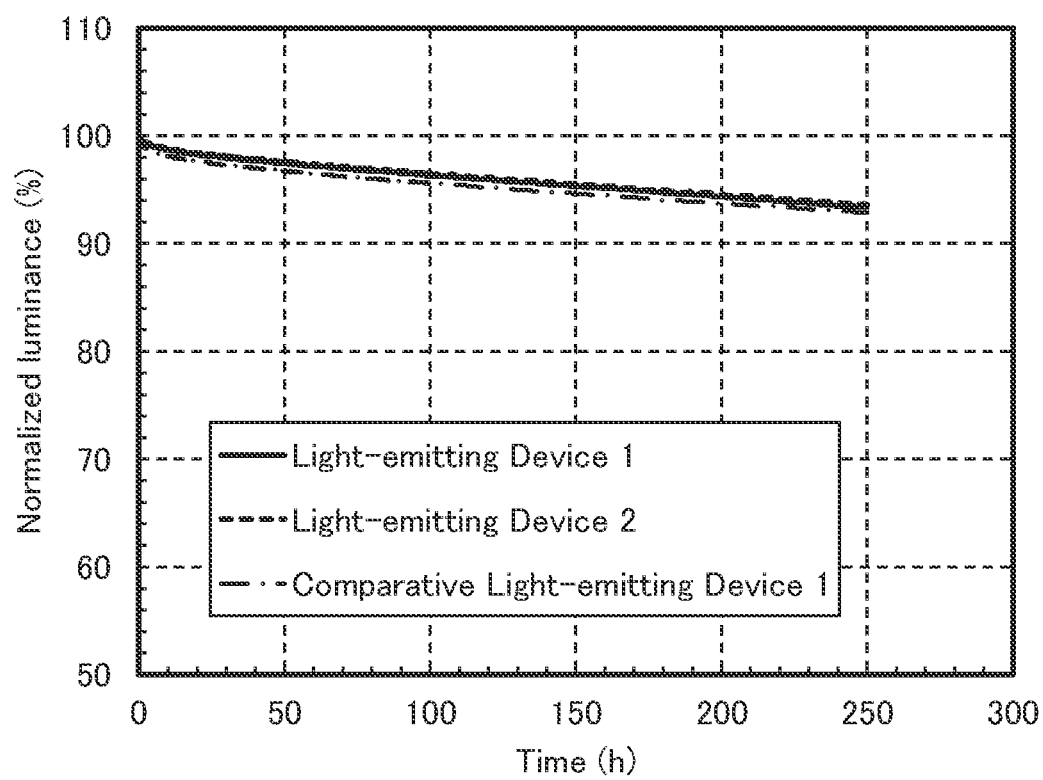
FIG. 67 shows a luminance change over driving time of the light-emitting devices 1 and 2 and the comparative light-emitting device 1.

Next, FIG. 67 shows luminance change over driving time when the light-emitting devices 1 and 2 and the comparative light-emitting device 1 are driven at a constant current with a current density of 50 mA/cm². As shown in FIG. 67, the light-emitting devices of one embodiment of the present invention have a favorable lifetime. Thus, the light-emitting devices of one embodiment of the present invention have high emission efficiency while keeping a favorable lifetime.

Example 8

In this example, light-emitting devices of one embodiment of the present invention described in the above embodiments and a comparative light-emitting device are described. Structural formulae of organic compounds used in this example are shown below.

[Chemical Formula 56]

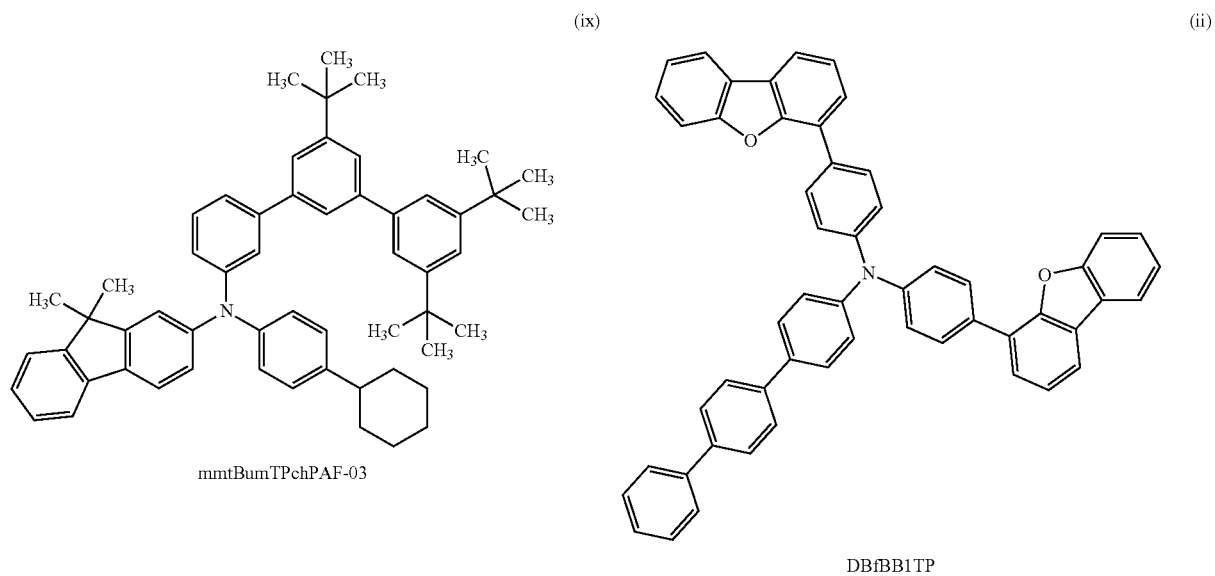

-continued
(iii)
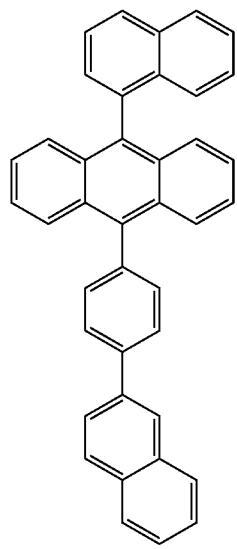
αN-βNPAnth
(iv)
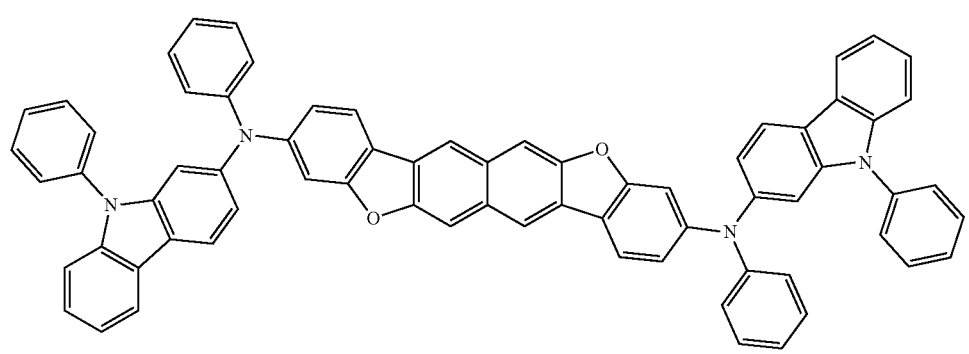
3,10PCA2Nbf(IV)-02
(vi)
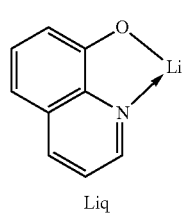
Liq
(v)
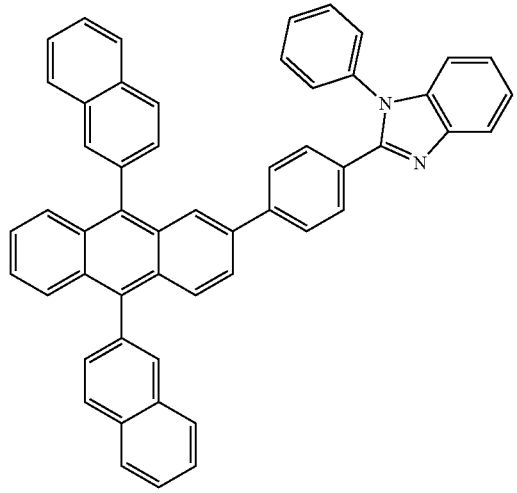
ZADN

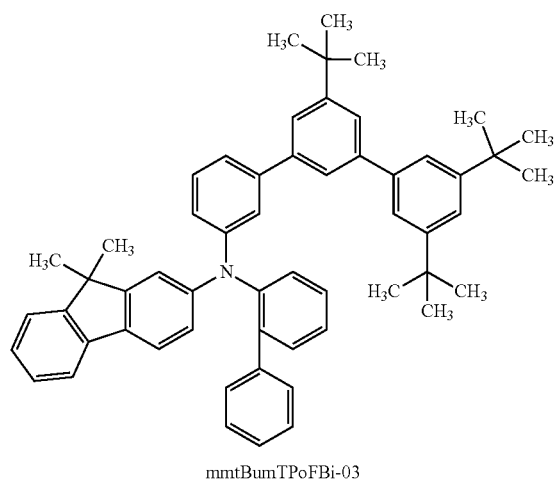

mmtBumTPoFBi-03

(x)

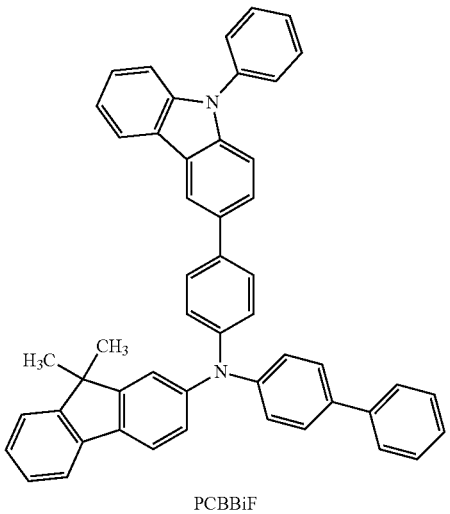

PCBBiF (viii)

(Fabrication Method of Light-Emitting Device 3)

First, indium tin oxide containing silicon oxide (ITSO) was deposited over a glass substrate by a sputtering method to form the first electrode 101. The thickness of the first electrode 101 was 55 nm and the electrode area was 2 mm×2 mm.

Next, in pretreatment for forming the light-emitting device over a substrate, a surface of the substrate was washed with water and baked at 200° C. for one hour, and then UV ozone treatment was performed for 370 seconds.

After that, the substrate was transferred into a vacuum evaporation apparatus where the pressure was reduced to approximately $10^{-4}$ Pa, vacuum baking was performed at 170° C. for 30 minutes in a heating chamber of the vacuum evaporation apparatus, and then the substrate was cooled down for approximately 30 minutes.

Next, the substrate provided with the first electrode 101 was fixed to a substrate holder provided in the vacuum evaporation apparatus such that the surface on which the first electrode 101 was formed faced downward. Then, N-(4-cyclohexylphenyl)-N-(3",5',5"-tri-tert-butyl-1,1':3',1"-terphenyl-5-yl)-9,9-dimethyl-9H-fluoren-2-amine (abbreviation: mmtBumTPchPAF-03) represented by Structural Formula (ix) and an electron acceptor material (OCHD-001) were deposited by co-evaporation to a thickness of 10 nm on the first electrode 101 using a resistance-heating method such that the weight ratio of mmtBumTPchPAF-03 to OCHD-001 was 1:0.1, whereby the hole-injection layer 111 was formed.

Subsequently, over the hole-injection layer 111, mmt-BumTPchPAF-03 was deposited to a thickness of 30 nm by evaporation, and then N,N-bis[4-(dibenzofuran-4-yl)phenyl]-4-amino-p-terphenyl (abbreviation: DBfBB1TP) represented by Structural Formula (ii) was deposited to a thickness of 10 nm by evaporation, whereby the hole-transport layer 112 was formed.

Then, 9-(1-naphthyl)-10-[4-(2-naphthyl)phenyl]anthracene (abbreviation: αN-βNPAnth) represented by Structural Formula (iii) and 3,10-bis[N-(9-phenyl-9H-carbazol-2-yl)-N-phenylamino]naphtho[2,3-b;6,7-b']bisbenzofuran (abbreviation: 3,10PCA2Nbf(IV)-02) represented by Structural Formula (iv) were deposited to a thickness of 25 nm by co-evaporation such that the weight ratio of αN-βNPAnth to 3,10PCA2Nbf(IV)-02 was 1:0.015, whereby the light-emitting layer 113 was formed.

After that, over the light-emitting layer 113, 2-{4-[9,10-di(naphthalen-2-yl)-2-anthryl]phenyl}-1-phenyl-1H-benzimidazole (abbreviation: ZADN) represented by Structural Formula (v) and 8-hydroxyquinolinatolithium (abbreviation: Liq) represented by Structural Formula (vi) were deposited to a thickness of 25 nm by co-evaporation such that the weight ratio of ZADN to Liq was 1:1, whereby the electron-transport layer 114 was formed.

After the formation of the electron-transport layer 114, Liq was deposited by evaporation to a thickness of 1 nm to form the electron-injection layer 115. Then, aluminum was deposited by evaporation to a thickness of 200 nm to form the second electrode 102. Thus, a light-emitting device 3 of this example was fabricated.

(Fabrication Method of Light-Emitting Device 4)

A light-emitting device 4 was fabricated in a manner similar to that for the light-emitting device 3 except that mmtBumTPchPAF-03 in the light-emitting device 3 was replaced with N-(1,1'-biphenyl-2-yl)-N-(3",5',5"-tri-tert-butyl-1,1':3',1"-terphenyl-5-yl)-9,9-dimethyl-9H-fluoren-2-amine (abbreviation: mmtBumTPoFBi-03) represented by Structural Formula (x).

(Fabrication Method of Comparative Light-Emitting Device 2)

A comparative light-emitting device 2 was fabricated in a manner similar to that for the light-emitting device 3 except that mmtBumTPchPAF-03 in the light-emitting device 3 was replaced with N-(1,1'-biphenyl-4-yl)-N-[4-(9-phenyl-9H-carbazol-3-yl)phenyl]-9,9-dimethyl-9H-fluoren-2-amine (abbreviation: PCBBiF) represented by Structural Formula (viii).

The structures of the light-emitting devices and the comparative light-emitting device are listed in the following table.

TABLE 4

|  | Film thickness | Light-emitting Device 3 | Light-emitting Device 4 | Comparative Light-emitting Device 2 |
|---|---|---|---|---|
| Electron-injection layer | 1 nm | Liq | | |
| Electron-transport layer | 25 nm | ZADN:Liq (1:1) | | |
| Light-emitting layer | 25 nm | αN-βNPAnth:3,10PCA2Nbf(IV)-02 (1:0.015) | | |
| Hole-transport layer | 10 nm | DBfBB1TP | | |
|  | 30 nm | mmtBumTPchPAF-03 | mmtBumTPoFBi-03 | PCBBiF |
| Hole-injection layer | 10 nm | mmtBumTPchPAF-03:OCHD-001 (1:0.1) | mmtBumTPoFBi-03:OCHD-001 (1:0.1) | PCBBiF:OCHD-001 (1:0.1) |

The refractive indices of PCBBiF as a reference and the materials with a low refractive index (mmtBumTPchPAF-03 and mmtBumTPoFBi-03) used for the hole-injection layer and part of the hole-transport layer are shown in FIG. 45, and the refractive indices at a wavelength of 457 nm are shown in the following table.

TABLE 5

|  | Refractive index |
|---|---|
| mmtBumTPchPAF-03 | 1.70 |
| mmtBumTPoFBi-03 | 1.70 |
| PCBBiF | 1.94 |

The light-emitting devices and the comparative light-emitting device were sealed using a glass substrate in a glove box containing a nitrogen atmosphere so as not to be exposed to the air (a sealing material was applied to surround the device and UV treatment and heat treatment at 80° C. for 1 hour were performed at the time of sealing). Then, the initial characteristics of the light-emitting devices were measured. Note that the glass substrate over which the light-emitting device was formed was not subjected to particular treatment for improving outcoupling efficiency.

Figure 46:
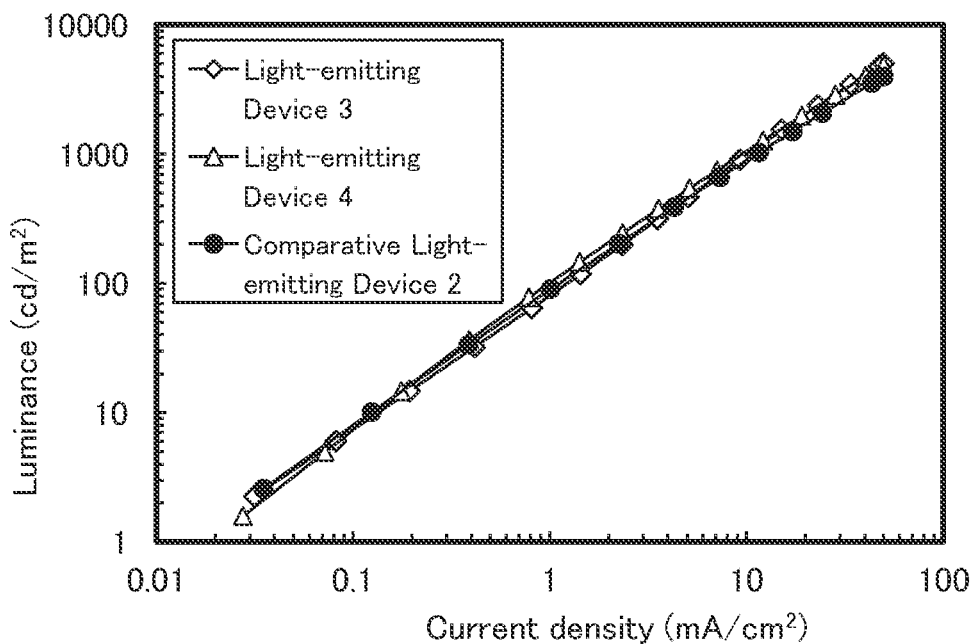
FIG. 46 shows the luminance-current density characteristics of a light-emitting device 3, a light-emitting device 4, and a comparative light-emitting device 2.
Figure 47:
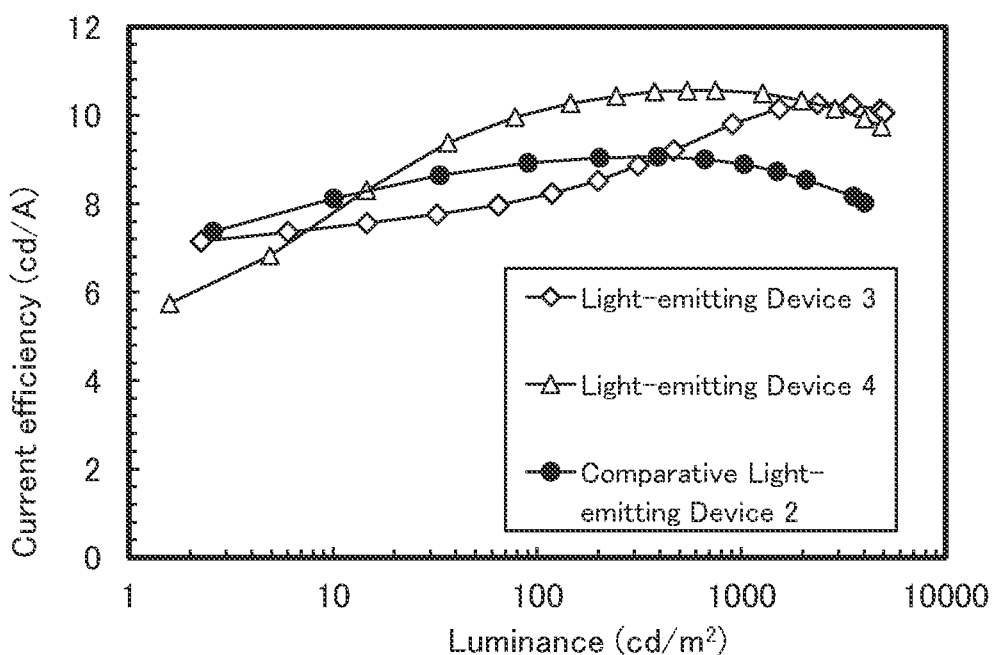
FIG. 47 shows the current efficiency-luminance characteristics of the light-emitting devices 3 and 4 and the comparative light-emitting device 2.
Figure 48:
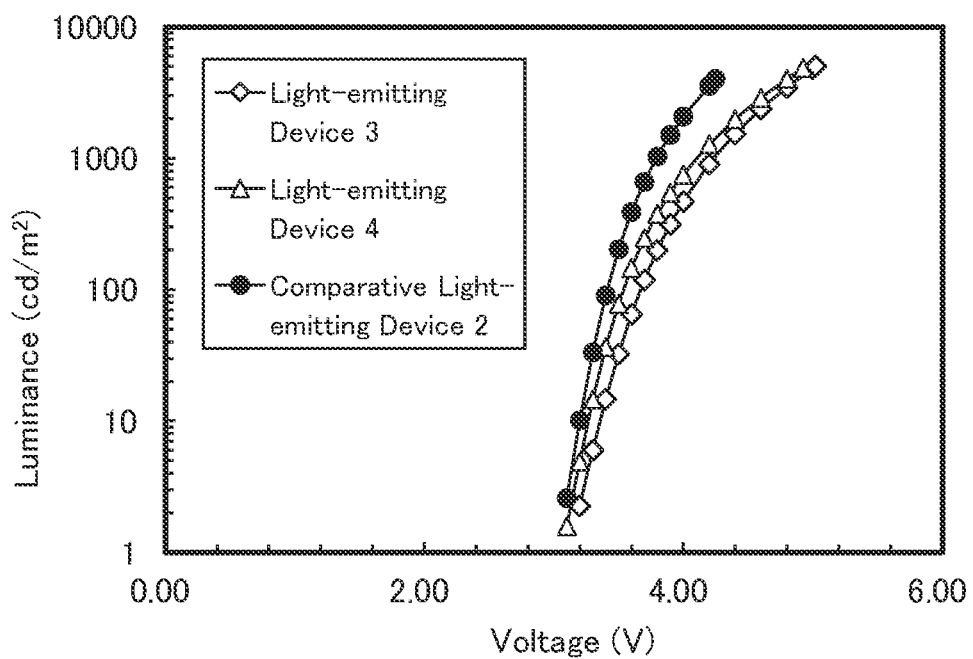
FIG. 48 shows the luminance-voltage characteristics of the light-emitting devices 3 and 4 and the comparative light-emitting device 2.
Figure 49:
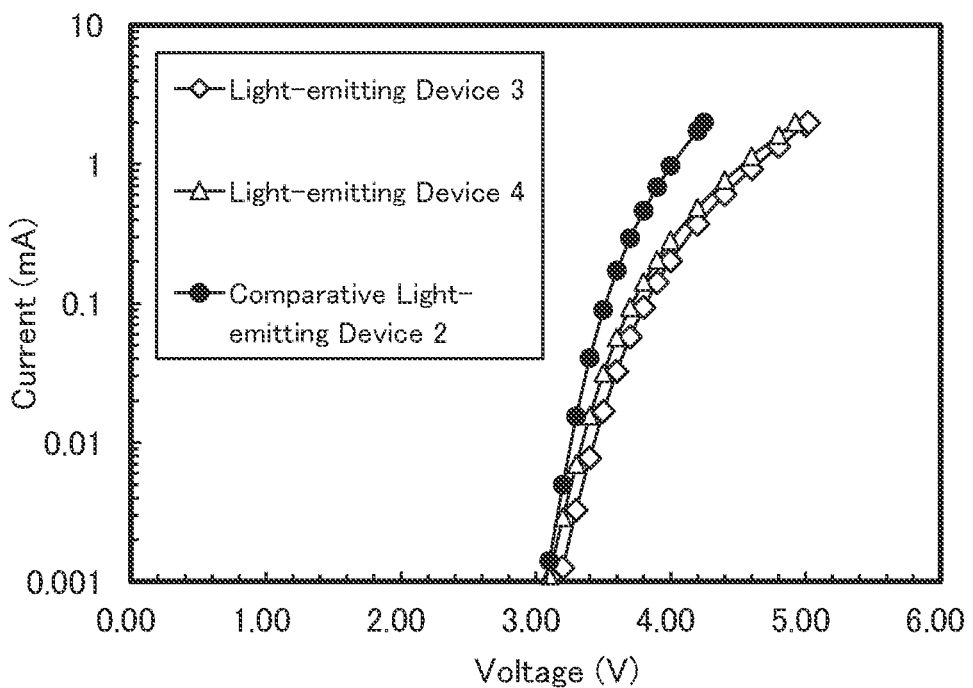
FIG. 49 shows the current-voltage characteristics of the light-emitting devices 3 and 4 and the comparative light-emitting device 2.
Figure 50:
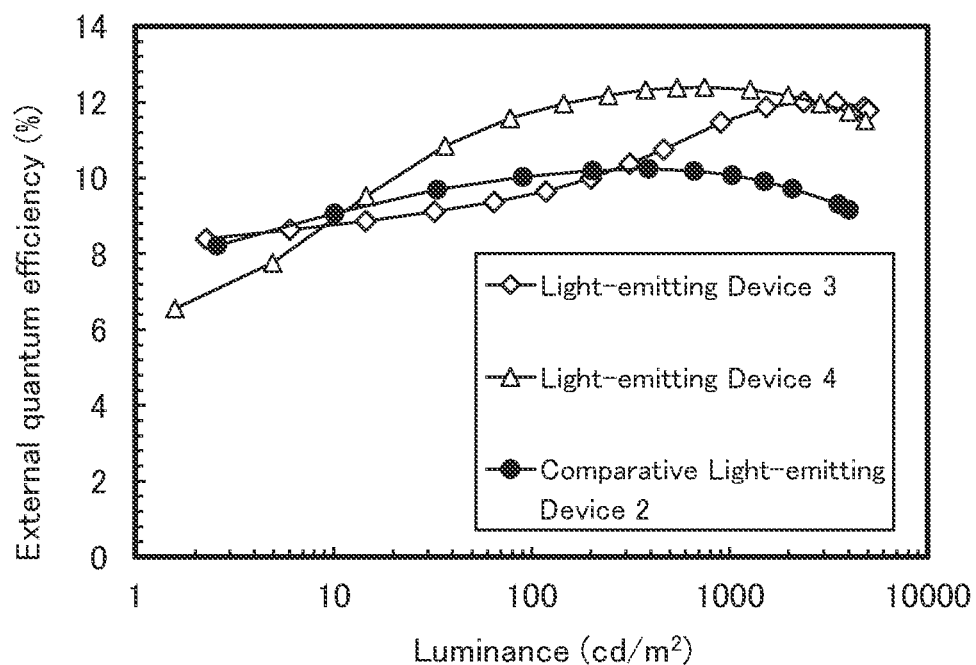
FIG. 50 shows the external quantum efficiency-luminance characteristics of the light-emitting devices 3 and 4 and the comparative light-emitting device 2.
Figure 51:
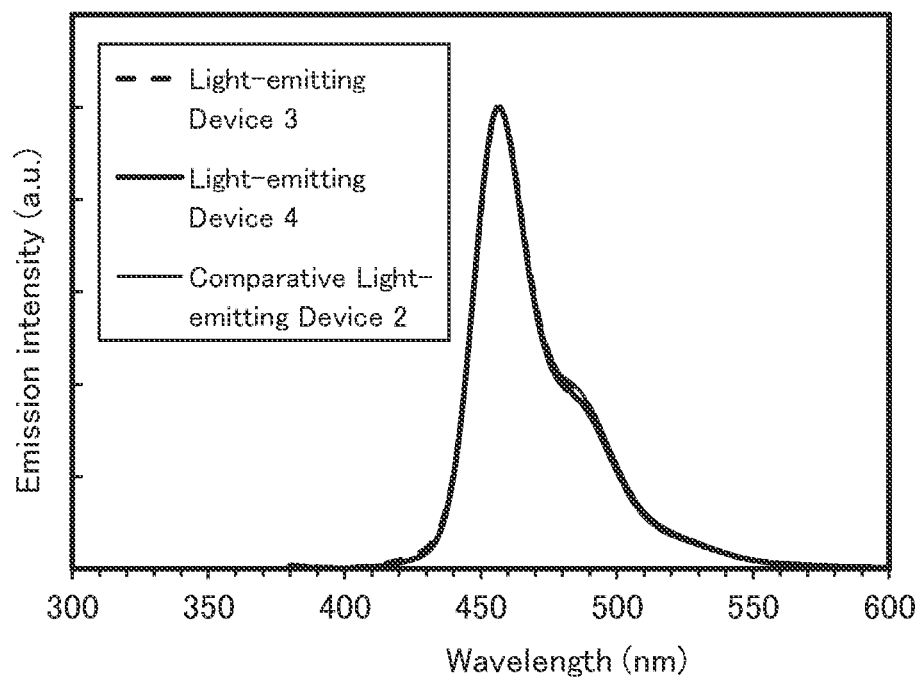
FIG. 51 shows the emission spectra of the light-emitting devices 3 and 4 and the comparative light-emitting device 2.

FIG. 46 shows the luminance-current density characteristics of the light-emitting device 3, the light-emitting device 4, and the comparative light-emitting device 2. FIG. 47 shows the current efficiency-luminance characteristics thereof. FIG. 48 shows the luminance-voltage characteristics thereof. FIG. 49 shows the current-voltage characteristics thereof. FIG. 50 shows the external quantum efficiency-luminance characteristics thereof. FIG. 51 shows the emission spectra thereof. Table 6 shows the main characteristics of the light-emitting devices at a luminance of about 1000 cd/m². Luminance, CIE chromaticity, and emission spectra were measured with a spectroradiometer (UR-UL1R produced by TOPCON TECHNOHOUSE CORPORATION). The external quantum efficiency was calculated from the luminance and emission spectra measured with the spectroradiometer, on the assumption that the light-emitting devices had Lambertian light-distribution characteristics.

TABLE 6

|  | Voltage (V) | Current (mA) | Current density (mA/cm²) | Chromaticity x | Chromaticity y | Current efficiency (cd/A) | External quantum efficiency (%) |
|---|---|---|---|---|---|---|---|
| Light-emitting Device 3 | 4.2 | 0.37 | 9.2 | 0.14 | 0.10 | 9.8 | 11.5 |
| Light-emitting Device 4 | 4.0 | 0.28 | 7.1 | 0.14 | 0.09 | 10.6 | 12.4 |
| Comparative Light-emitting Device 2 | 3.8 | 0.46 | 11.6 | 0.14 | 0.10 | 8.9 | 10.1 |

FIGS. 46 to 51 and Table 6 show that the light-emitting devices of one embodiment of the present invention, each of which includes a layer using a material with a low refractive index, are favorable EL devices having substantially the same shape of the emission spectra as and higher emission efficiency than the comparative light-emitting device.

Example 9

In this example, light-emitting devices of one embodiment of the present invention described in the above embodiments and a comparative light-emitting device are described. Structural formulae of organic compounds used in this example are shown below.

[Chemical Formula 57]
(i)
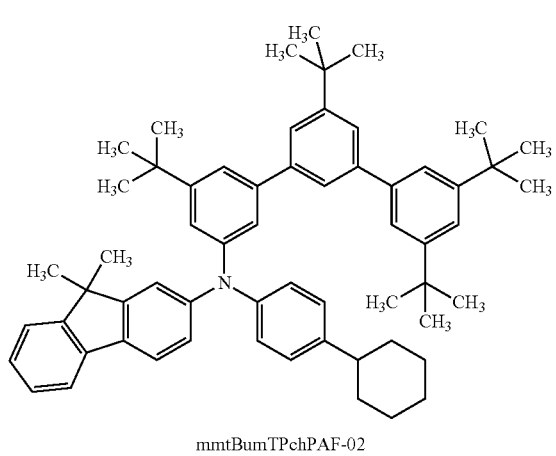
mmtBumTPchPAF-02
(x)
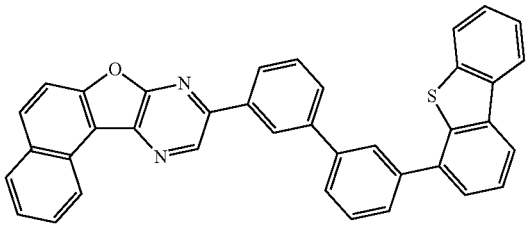
9mDBtBPNfpr
(xii)
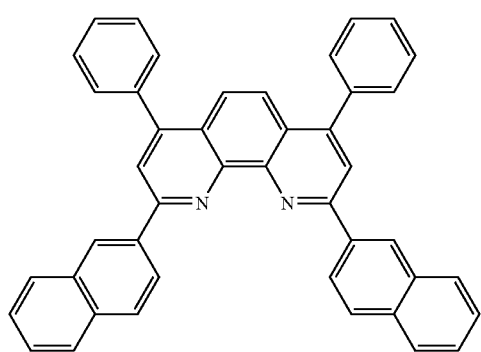
NBPhen
(vii)
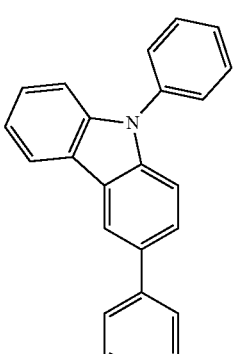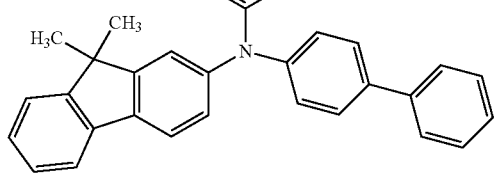
PCBBiF
(vii)
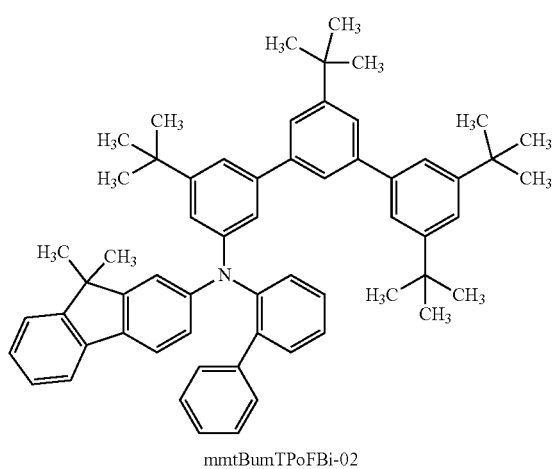
mmtBumTPoFBi-02
(ix)
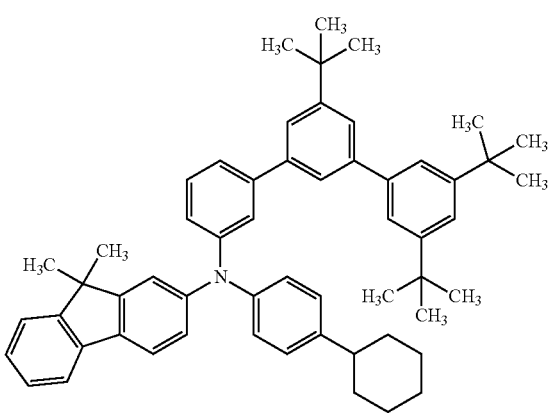
mmtBumTPchPAF-03

-continued

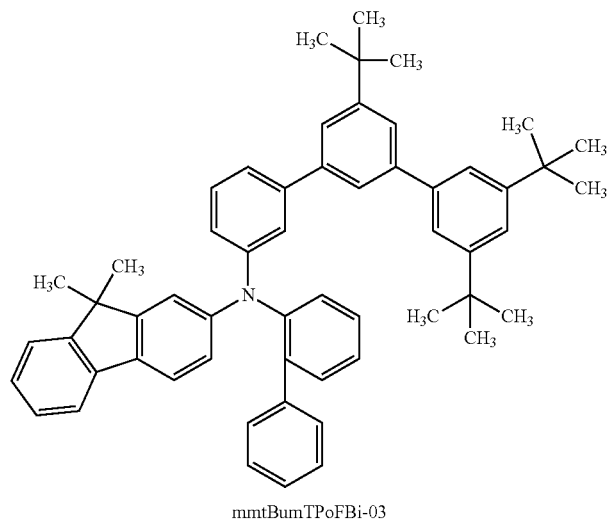

mmtBumTPoFBi-03

(x)

(Fabrication Method of Light-Emitting Device 5)

First, indium tin oxide containing silicon oxide (ITSO) was deposited over a glass substrate by a sputtering method to form the first electrode 101. The thickness of the first electrode 101 was 110 nm and the electrode area was 2 mm×2 mm.

Next, in pretreatment for forming the light-emitting device over a substrate, a surface of the substrate was washed with water and baked at 200° C. for one hour, and then UV ozone treatment was performed for 370 seconds.

After that, the substrate was transferred into a vacuum evaporation apparatus where the pressure was reduced to approximately $10^{-4}$ Pa, vacuum baking was performed at 170° C. for 30 minutes in a heating chamber of the vacuum evaporation apparatus, and then the substrate was cooled down for approximately 30 minutes.

Next, the substrate provided with the first electrode 101 was fixed to a substrate holder provided in the vacuum evaporation apparatus such that the surface on which the first electrode 101 was formed faced downward. Then, N-(4-cyclohexylphenyl)-N-(3,3″,5′,5″-tetra-tert-butyl-1,1′:3′,1″-terphenyl-5-yl)-9,9-dimethyl-9H-fluoren-2-amine (abbreviation: mmtBumTPchPAF-02) represented by Structural Formula (i) and an electron acceptor material (OCHD-001) were deposited by co-evaporation to a thickness of 10 nm on the first electrode 101 using a resistance-heating method such that the weight ratio of mmtBumTPchPAF-02 to OCHD-001 was 1:0.1, whereby the hole-injection layer 111 was formed.

Subsequently, over the hole-injection layer 111, mmtBumTPchPAF-02 was deposited by evaporation to a thickness of 50 nm to form the hole-transport layer 112.

Next, 9-[3′-(dibenzothiophen-4-yl)biphenyl-3-yl]naphtho[1′,2′:4,5]furo[2,3-b]pyrazine (abbreviation: 9mDBtBPNfpr) represented by Structural Formula (xi), N-(1,1′-biphenyl-4-yl)-N-[4-(9-phenyl-9H-carbazol-3-yl)phenyl]-9,9-dimethyl-9H-fluoren-2-amine (abbreviation: PCBBiF) represented by Structural Formula (viii), and a phosphorescent dopant OCPG-006 were deposited to a thickness of 40 nm by co-evaporation such that the weight ratio of 9mDBtBPNfpr to PCBBiF and OCPG-006 was 0.6:0.5:0.05, whereby the light-emitting layer 113 was formed.

After that, over the light-emitting layer 113, 9mDBtBPNfpr was deposited by evaporation to a thickness of 30 nm, and then 2,9-di(2-naphthyl)-4,7-diphenyl-1,10-phenanthroline (abbreviation: NBPhen) represented by Structural Formula (xii) was deposited by evaporation to a thickness of 15 nm, whereby the electron-transport layer 114 was formed.

After the formation of the electron-transport layer 114, lithium fluoride (abbreviation: LiF) was deposited by evaporation to a thickness of 1 nm to form the electron-injection layer 115. Then, aluminum was deposited by evaporation to a thickness of 200 nm to form the second electrode 102. Thus, a light-emitting device 5 of this example was fabricated.

(Fabrication Method of Light-Emitting Device 6)

A light-emitting device 6 was fabricated in a manner similar to that for the light-emitting device 5 except that mmtBumTPchPAF-02 in the light-emitting device 5 was replaced with N-(1,1′-biphenyl-2-yl)-N-(3,3″,5′,5″-tetra-tert-butyl-1,1′:3′,1″-terphenyl-5-yl)-9,9-dimethyl-9H-fluoren-2-amine (abbreviation: mmtBumTPoFBi-02) represented by Structural Formula (vii).

(Fabrication Method of Light-Emitting Device 7)

A light-emitting device 7 was fabricated in a manner similar to that for the light-emitting device 5 except that mmtBumTPchPAF-02 in the light-emitting device 5 was replaced with N-(4-cyclohexylphenyl)-N-(3″,5′,5″-tri-tert-butyl-1,1′:3′,1″-terphenyl-5-yl)-9,9-dimethyl-9H-fluoren-2-amine (abbreviation: mmtBumTPchPAF-03) represented by Structural Formula (ix).

(Fabrication Method of Light-Emitting Device 8)

A light-emitting device 8 was fabricated in a manner similar to that for the light-emitting device 5 except that mmtBumTPchPAF-02 in the light-emitting device 5 was replaced with N-(1,1′-biphenyl-2-yl)-N-(3″,5′,5″-tri-tert-butyl-1,1′:3′,1″-terphenyl-5-yl)-9,9-dimethyl-9H-fluoren-2-amine (abbreviation: mmtBumTPoFBi-03) represented by Structural Formula (x).

(Fabrication Method of Comparative Light-Emitting Device 3)

A comparative light-emitting device 3 was fabricated in a manner similar to that for the light-emitting device 5 except that mmtBumTPchPAF-02 in the light-emitting device 5 was replaced with PCBBiF.

The structures of the light-emitting devices and the comparative light-emitting device are listed in the following table.

TABLE 7

|  | Film thickness | Light-emitting Device 5 | Light-emitting Device 6 | Light-emitting Device 7 | Light-emitting Device 8 | Comparative Light-emitting Device 3 |
|---|---|---|---|---|---|---|
| Electron-injection layer | 1 nm | LiF | | | | |
| Electron-transport layer | 15 nm | NBPhen | | | | |
|  | 30 nm | 9mDBtBPNfpr | | | | |
| Light-emitting layer | 40 nm | 9mDBtBPNfpr:PCBBiF:OCPG-006 (0.6:0.4:0.05) | | | | |
| Hole-transport layer | 50 nm | *1 | | | | |
| Hole-injection layer | 10 nm | *1:OCHD-001 (1:0.1) | | | | |

*1 Light-emitting Device 5: mmtBumTPchP AF-02
Light-emitting Device 6: mmtBumTPoFBi-02
Light-emitting Device 7: mmtBumTPchP AF-03
Light-emitting Device 8: mmtBumTPoFBi-03
Comparative Light-emitting Device 3: PCBBif The refractive indices of PCBBiF as a reference and the materials with a low refractive index (mmtBumTPchPAF-02, mmtBumTPoFBi-02, mmtBumTPchPAF-03, and mmtBumTPoFBi-03) used for the hole-injection layer and part of the hole-transport layer are shown in FIG. 52, and the refractive indices at a wavelength of 629 nm are shown in the following table.

TABLE 8

|  | Refractive index |
|---|---|
| mmtBumTPchPAF-02 | 1.62 |
| mmtBumTPoFBi-02 | 1.64 |
| mmtBumTPchPAF-03 | 1.64 |
| mmtBumTPoFBi-03 | 1.64 |
| PCBBiF | 1.81 |

The light-emitting devices and the comparative light-emitting device were sealed using a glass substrate in a glove box containing a nitrogen atmosphere so as not to be exposed to the air (a sealing material was applied to surround the device and UV treatment and heat treatment at 80° C. for 1 hour were performed at the time of sealing). Then, the initial characteristics of the light-emitting devices were measured. Note that the glass substrate over which the light-emitting device was formed was not subjected to particular treatment for improving outcoupling efficiency.

Figure 53:
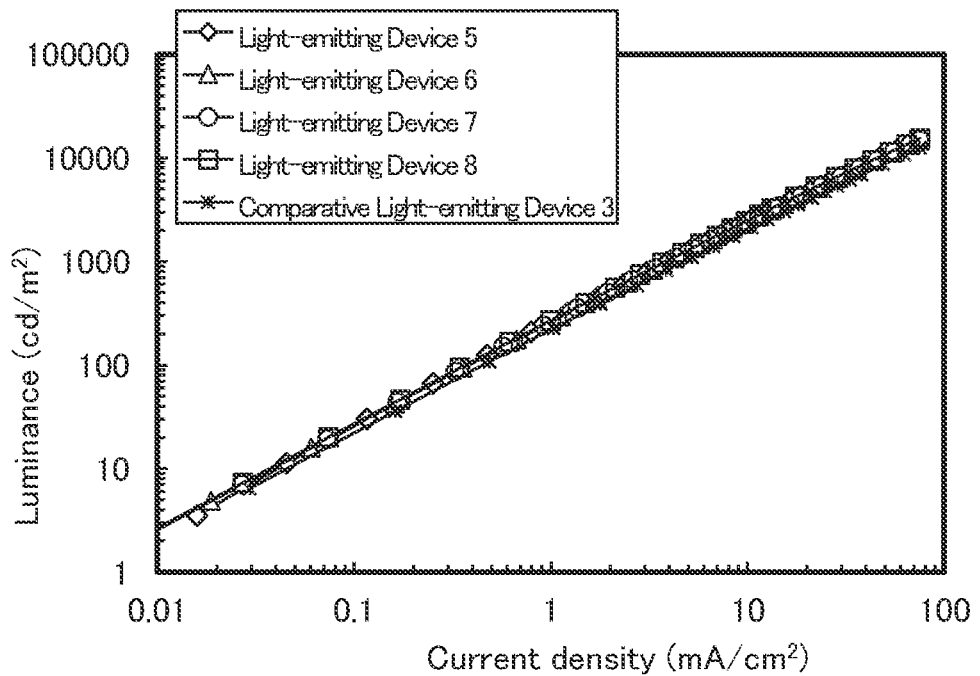
FIG. 53 shows the luminance-current density characteristics of a light-emitting device 5, a light-emitting device 6, a light-emitting device 7, a light-emitting device 8, and a comparative light-emitting device 3.
Figure 54:
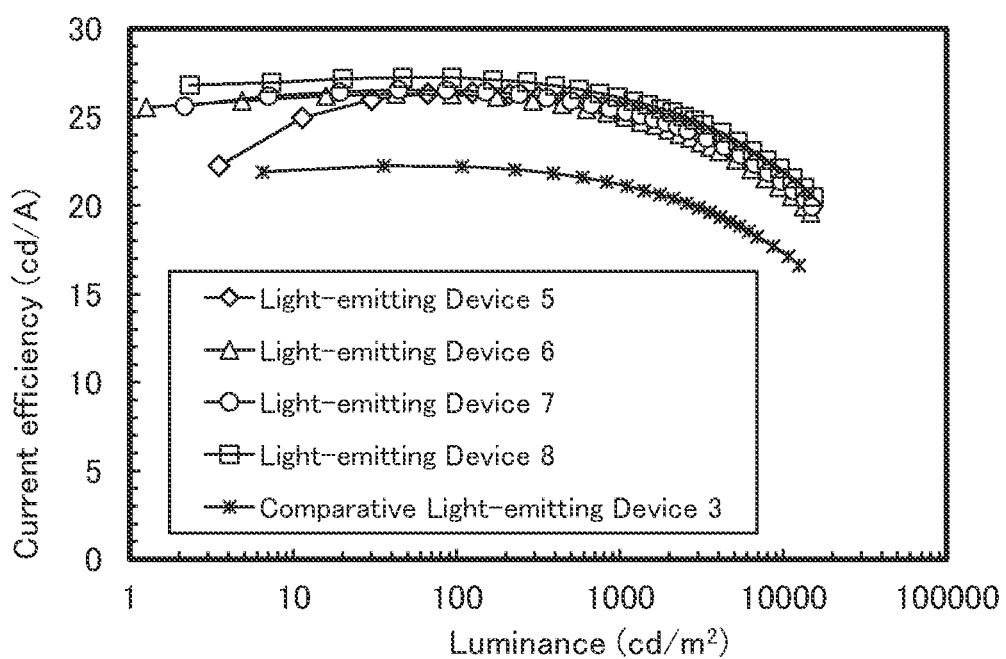
FIG. 54 shows the current efficiency-luminance characteristics of the light-emitting devices 5 to 8 and the comparative light-emitting device 3.
Figure 55:
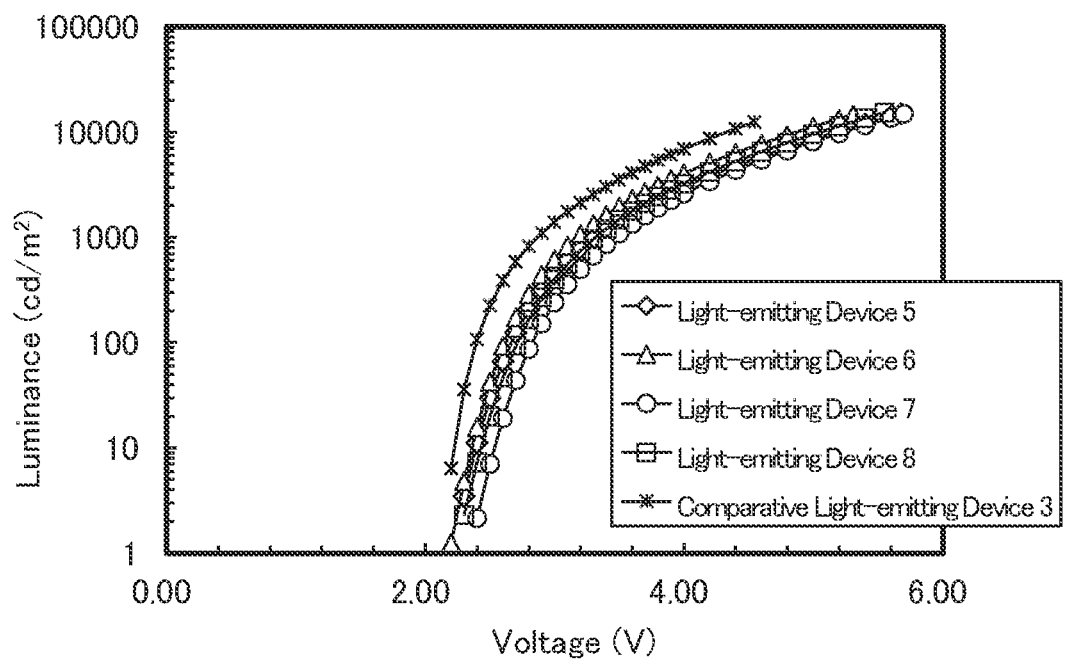
FIG. 55 shows the luminance-voltage characteristics of the light-emitting devices 5 to 8 and the comparative light-emitting device 3.
Figure 56:
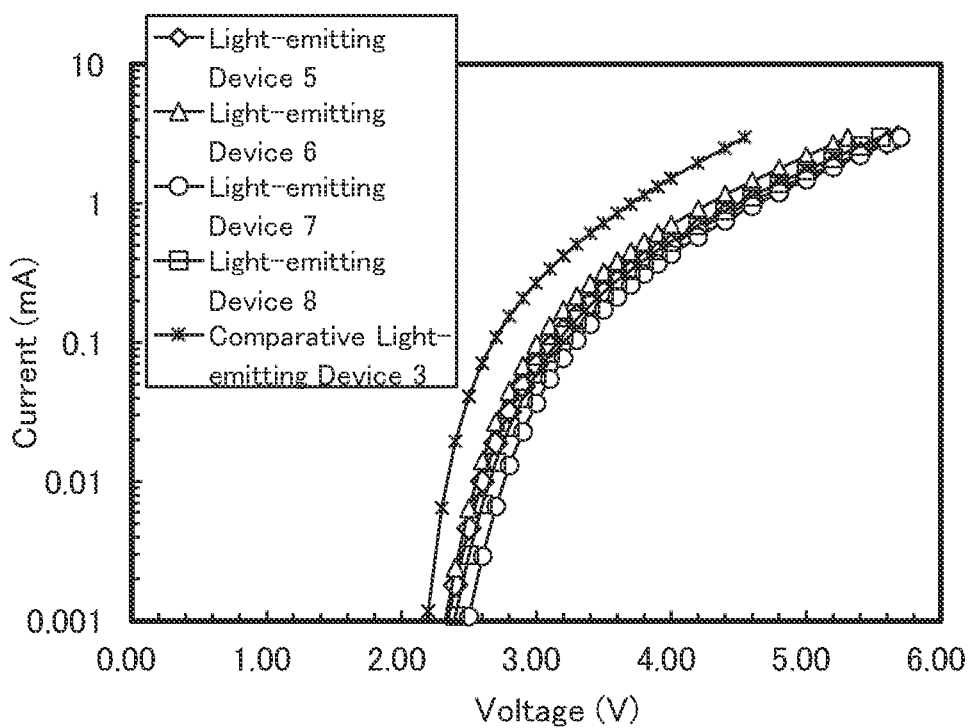
FIG. 56 shows the current-voltage characteristics of the light-emitting devices 5 to 8 and the comparative light-emitting device 3.
Figure 57:
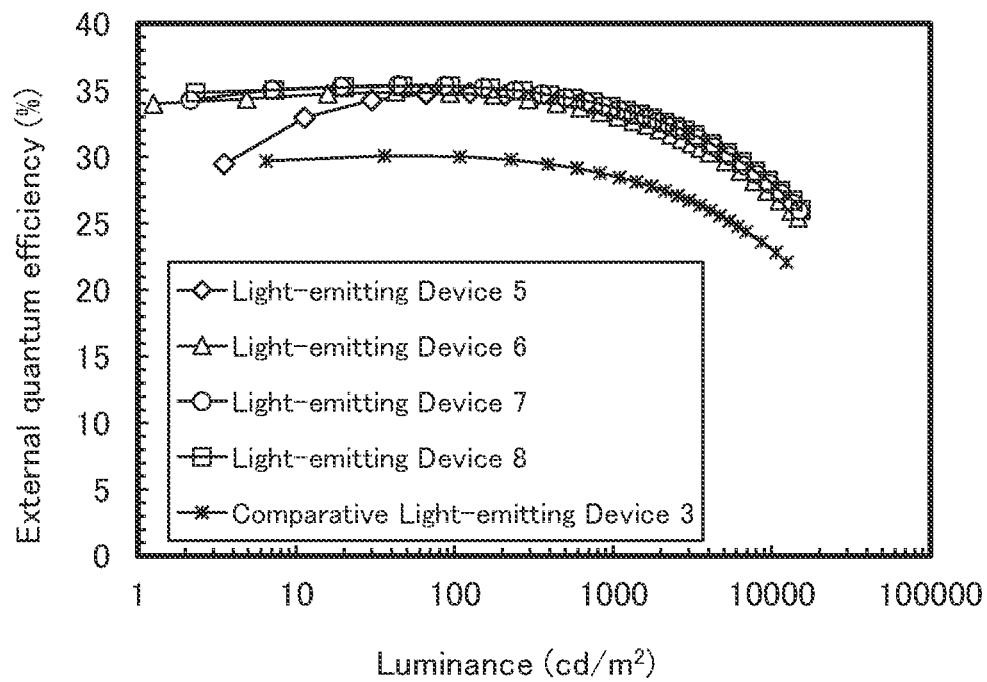
FIG. 57 shows the external quantum efficiency-luminance characteristics of the light-emitting devices 5 to 8 and the comparative light-emitting device 3.
Figure 58:
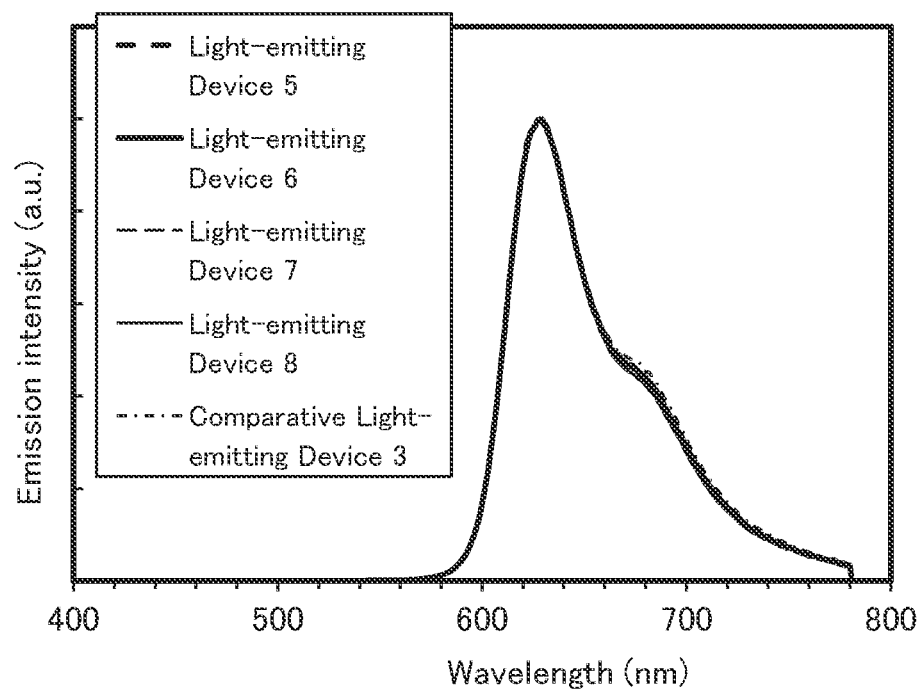
FIG. 58 shows the emission spectra of the light-emitting devices 5 to 8 and the comparative light-emitting device 3.

FIG. 53 shows the luminance-current density characteristics of the light-emitting devices 5 to 8 and the comparative light-emitting device 3. FIG. 54 shows the current efficiency-luminance characteristics thereof. FIG. 55 shows the luminance-voltage characteristics thereof. FIG. 56 shows the current-voltage characteristics thereof. FIG. 57 shows the external quantum efficiency-luminance characteristics thereof. FIG. 58 shows the emission spectra thereof. Table 9 shows the main characteristics of the light-emitting devices at a luminance of about 1000 cd/m$^2$. Luminance, CIE chromaticity, and emission spectra were measured with a spectroradiometer (UR-UL1R produced by TOPCON TECHNOHOUSE CORPORATION). The external quantum efficiency was calculated from the luminance and emission spectra measured with the spectroradiometer, on the assumption that the light-emitting devices had Lambertian light-distribution characteristics.

TABLE 9

|  | Voltage (V) | Current (mA) | Current density (mA/cm$^2$) | Chromaticity x | Chromaticity y | Current efficiency (cd/A) | External quantum efficiency (%) |
|---|---|---|---|---|---|---|---|
| Light-emitting Device 5 | 3.3 | 0.15 | 3.9 | 0.69 | 0.31 | 25.4 | 33.4 |
| Light-emitting Device 6 | 3.2 | 0.17 | 4.3 | 0.69 | 0.31 | 25.0 | 33.0 |
| Light-emitting Device 7 | 3.5 | 0.17 | 4.3 | 0.69 | 0.31 | 25.3 | 33.5 |
| Light-emitting Device 8 | 3.3 | 0.15 | 3.7 | 0.69 | 0.31 | 26.1 | 33.8 |
| Comparative Light-emitting Device 3 | 2.9 | 0.21 | 5.2 | 0.69 | 0.31 | 21.1 | 28.4 |

FIGS. 53 to 58 and Table 9 show that the light-emitting devices of one embodiment of the present invention, each of which includes a layer using a material with a low refractive index, are favorable EL devices having substantially the same shape of the emission spectra as and higher emission efficiency than the comparative light-emitting device.

Example 10

In this example, light-emitting devices of one embodiment of the present invention described in the above embodiments and a comparative light-emitting device are described. Structural formulae of organic compounds used in this example are shown below.

[Chemical Formula 58]
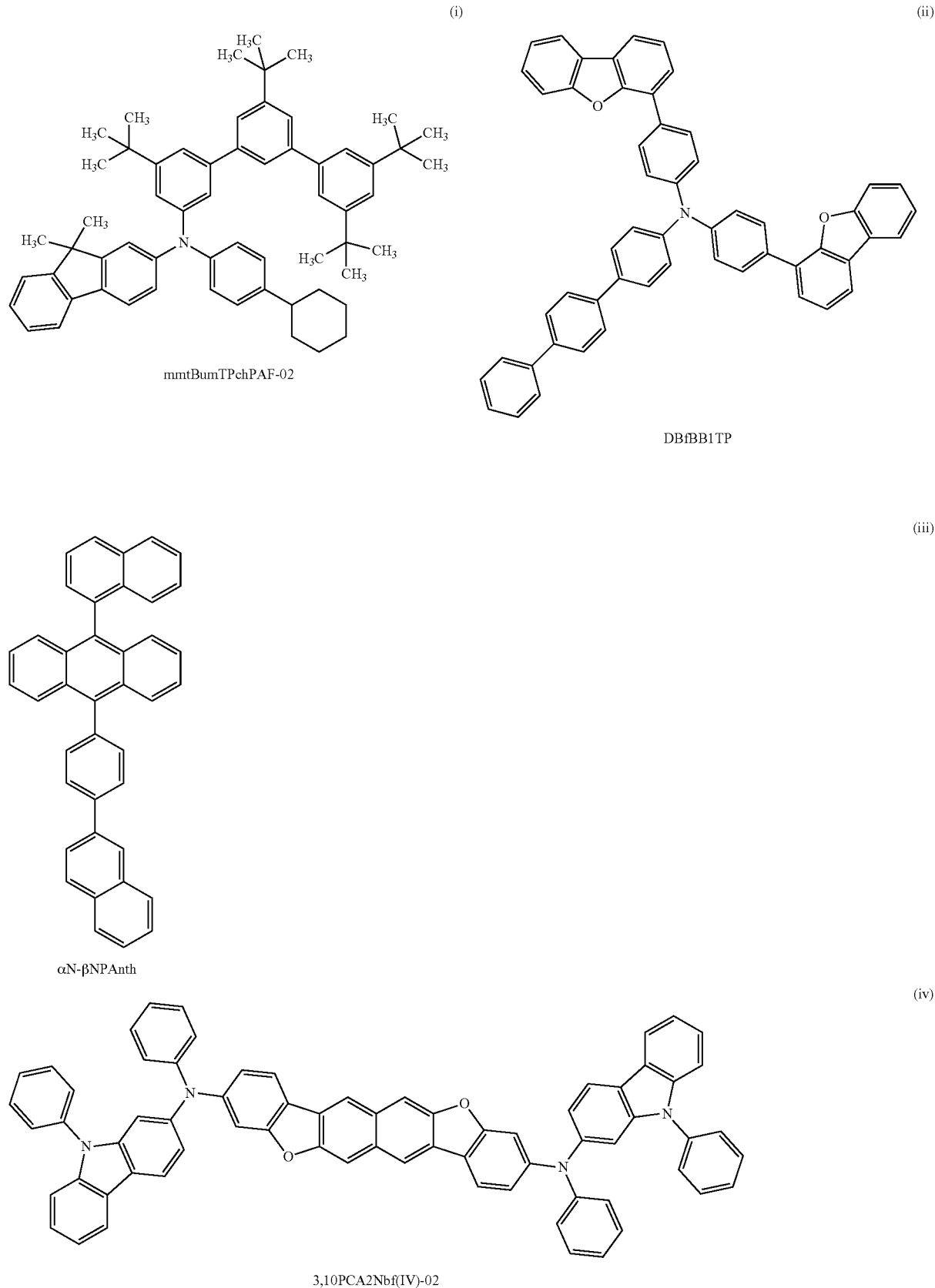

-continued
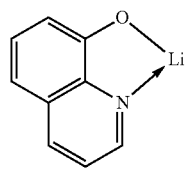
Liq
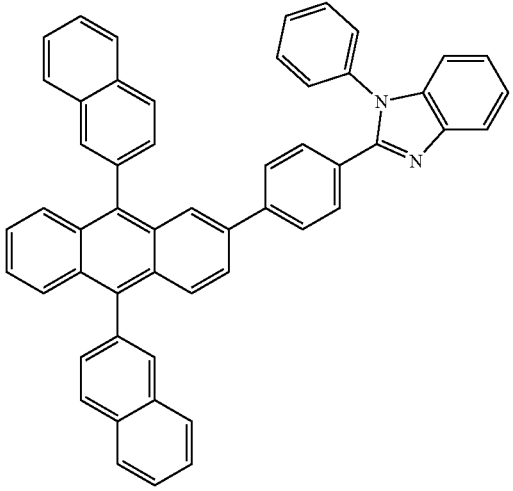
ZADN
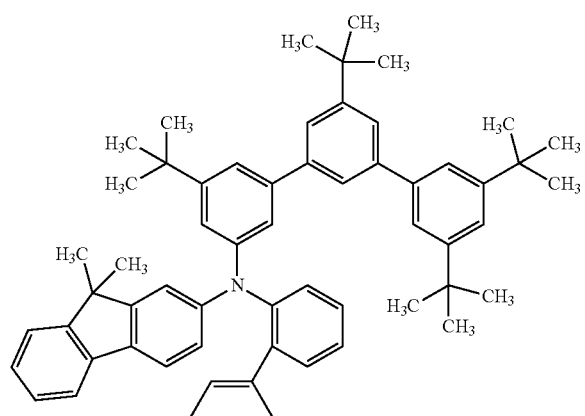
mmtBumTPoFBi-02
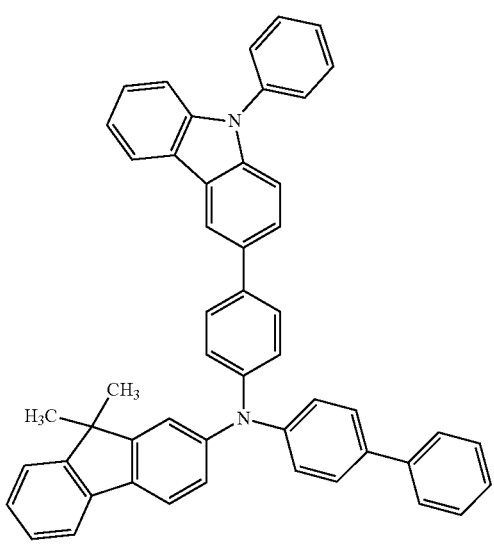
PCBBiF
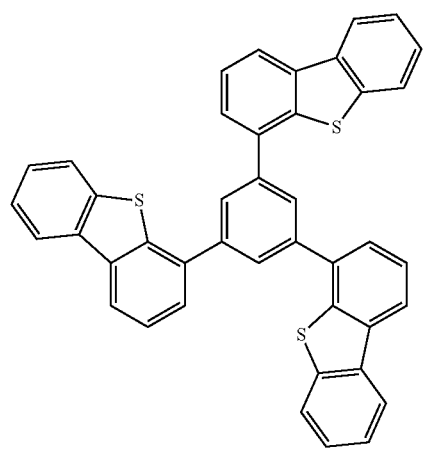
DBT3P-II (Method for Manufacturing Light-Emitting Device 9)

First, as a reflective electrode, an alloy film of silver (Ag), palladium (Pd), and copper (Cu), i.e., an Ag—Pd—Cu (APC) film, was formed over a glass substrate to a thickness of 100 nm by a sputtering method, and then, as a transparent electrode, indium tin oxide containing silicon oxide (ITSO) was formed to a thickness of 85 nm by a sputtering method, whereby the first electrode 101 was formed. The electrode area was 4 mm$^2$ (2 mm×2 mm).

Next, in pretreatment for forming the light-emitting device over a substrate, a surface of the substrate was washed with water and baked at 200° C. for one hour, and then UV ozone treatment was performed for 370 seconds.

After that, the substrate was transferred into a vacuum evaporation apparatus where the pressure was reduced to approximately 10$^{-4}$ Pa, vacuum baking was performed at 170° C. for 30 minutes in a heating chamber of the vacuum evaporation apparatus, and then the substrate was cooled down for approximately 30 minutes.

Next, the substrate provided with the first electrode 101 was fixed to a substrate holder provided in the vacuum evaporation apparatus such that the surface on which the first electrode 101 was formed faced downward. Then, N-(4-cyclohexylphenyl)-N-(3,3",5',5"-tetra-tert-butyl-1,1': 3',1"-terphenyl-5-yl)-9,9-dimethyl-9H-fluoren-2-amine (abbreviation: mmtBumTPchPAF-02) represented by Structural Formula (i) and an electron acceptor material (OCHD-001) were deposited by co-evaporation to a thickness of 10 nm on the first electrode 101 such that the weight ratio of mmtBumTPchPAF-02 to OCHD-001 was 1:0.05, whereby the hole-injection layer 111 was formed.

Over the hole-injection layer 111, mmtBumTPchPAF-02 was deposited as a first hole-transport layer to a thickness of 35 nm by evaporation, and then N,N-bis[4-(dibenzofuran-4-yl)phenyl]-4-amino-terphenyl (abbreviation: DBfBB1TP) represented by Structural Formula (ii) was deposited as a second hole-transport layer to a thickness of 10 nm by evaporation, whereby the hole-transport layer 112 was formed.

Then, 9-(1-naphthyl)-10-[4-(2-naphthyl)phenyl]anthracene (abbreviation: αN-βNPAnth) represented by Structural Formula (iii) and 3,10-bis[N-(9-phenyl-9H-carbazol-2-yl)-N-phenylamino]naphtho[2,3-b;6,7-b']bisbenzofuran (abbreviation: 3,10PCA2Nbf(IV)-02) represented by Structural Formula (iv) were deposited to a thickness of 25 nm by co-evaporation such that the weight ratio of αN-βNPAnth to 3,10PCA2Nbf(IV)-02 was 1:0.015, whereby the light-emitting layer 113 was formed.

After that, over the light-emitting layer 113, 2-{4-[9,10-di(naphthalen-2-yl)-2-anthryl]phenyl}-1-phenyl-1H-benzimidazole (abbreviation: ZADN) represented by Structural Formula (v) and 8-hydroxyquinolinatolithium (abbreviation: Liq) represented by Structural Formula (vi) were deposited to a thickness of 25 nm by co-evaporation such that the weight ratio of ZADN to Liq was 1:1, whereby the electron-transport layer 114 was formed.

After the formation of the electron-transport layer 114, Liq was deposited by evaporation to a thickness of 1 nm to form the electron-injection layer 115. Then, silver (Ag) and magnesium (Mg) were deposited by co-evaporation to a thickness of 15 nm such that the weight ratio of Ag to Mg was 10:1 to form the second electrode 102. Thus, a light-emitting device 9 was fabricated. The second electrode 102 is a transflective electrode having a function of reflecting light and a function of transmitting light; thus, the light-emitting device of this example is a top-emission device in which light is extracted through the second electrode 102. Over the second electrode 102, 1,3,5-tri(dibenzothiophen-4-yl)-benzene (abbreviation: DBT3P-II) represented by Structural Formula (xi) was deposited by evaporation to a thickness of 70 nm so that outcoupling efficiency can be improved.

(Fabrication Method of Light-Emitting Device 10)

A light-emitting device 10 was fabricated in a manner similar to that for the light-emitting device 9 except that mmtBumTPchPAF-02 in the light-emitting device 9 was replaced with N-(1,1'-biphenyl-2-yl)-N-(3,3",5',5"-tetra-tert-butyl-1,1':3',1"-terphenyl-5-yl)-9,9-dimethyl-9H-fluoren-2-amine (abbreviation: mmtBumTPoFBi-02) represented by Structural Formula (vii).

(Fabrication Method of Comparative Light-Emitting Device 4)

A comparative light-emitting device 4 was fabricated in a manner similar to that for the light-emitting device 9 except that mmtBumTPchPAF-02 in the light-emitting device 9 was replaced with N-(1,1'-biphenyl-4-yl)-N-[4-(9-phenyl-9H-carbazol-3-yl)phenyl]-9,9-dimethyl-9H-fluoren-2-amine (abbreviation: PCBBiF) represented by Structural Formula (viii) and the thickness of the first hole-transport layer was set to 30 nm.

The structures of the light-emitting devices 9 and 10 and the comparative light-emitting device 4 are listed in the following table.

TABLE 10

|  | Film thickness | Light-emitting Device 9 | Light-emitting Device 10 | Comparative Light-emitting Device 4 |
| --- | --- | --- | --- | --- |
| Electron-injection layer | 1 nm | | Liq | |
| Electron-transport layer | 25 nm | | ZADN:Liq (1:1) | |
| Light-emitting layer | 25 nm | | αN-βNPAnth:3,10PCA2Nbf(IV)-02 (1:0.015) | |
| Hole-transport layer | 10 nm *2 | mmtBumTPchPAF-02 | DBfBB1TP mmtBumTPoFBi-02 | PCBBiF |

TABLE 10-continued

|  | Film thickness | Light-emitting Device 9 | Light-emitting Device 10 | Comparative Light-emitting Device 4 |
|---|---|---|---|---|
| Hole-injection layer | 10 nm | mmtBumTPchPAF-02:OCHD-001 (1:0.1) | mmtBumTPoFBi-02:OCHD-001 (1:0.1) | PCBBiF: OCHD-001 (1:0.1) |

*2 Light-emitting Device 9, Light-emitting Device 10: 35 nm,
Comparative Light-emitting Device 4: 30 nm The refractive indices of PCBBiF as a reference and the materials with a low refractive index (mmtBumTPchPAF-02 and mmtBumTPoFBi-02) used for the hole-injection layer and part of the hole-transport layer are shown in FIG. 59, and the refractive indices at a wavelength of 458 nm are shown in the following table.

TABLE 11

|  | Refractive index |
|---|---|
| mmtBumTPchPAF-02 | 1.67 |
| mmtBumTPoFBi-02 | 1.70 |
| PCBBiF | 1.94 |

The light-emitting devices and the comparative light-emitting device were sealed using a glass substrate in a glove box containing a nitrogen atmosphere so as not to be exposed to the air (a sealing material was applied to surround the device and UV treatment and heat treatment were performed at the time of sealing). Then, the initial characteristics of the light-emitting devices were measured. Note that the sealed glass substrate was not subjected to particular treatment for improving outcoupling efficiency.

Figure 60:
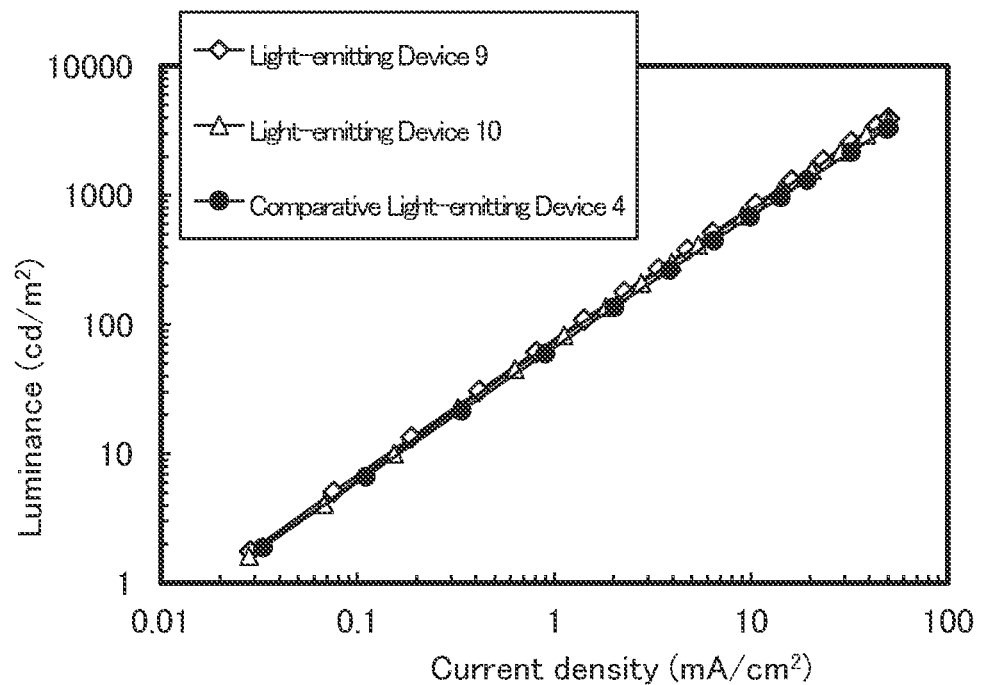
FIG. 60 shows the luminance-current density characteristics of a light-emitting device 9, a light-emitting device 10, and a comparative light-emitting device 4.
Figure 61:
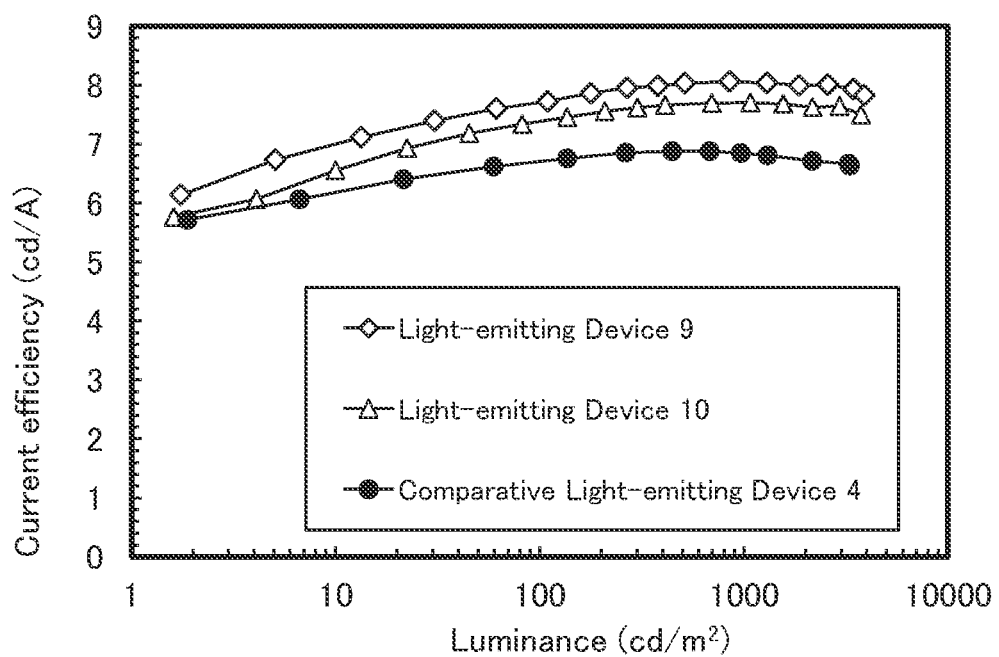
FIG. 61 shows the current efficiency-luminance characteristics of the light-emitting devices 9 and 10 and the comparative light-emitting device 4.
Figure 62:
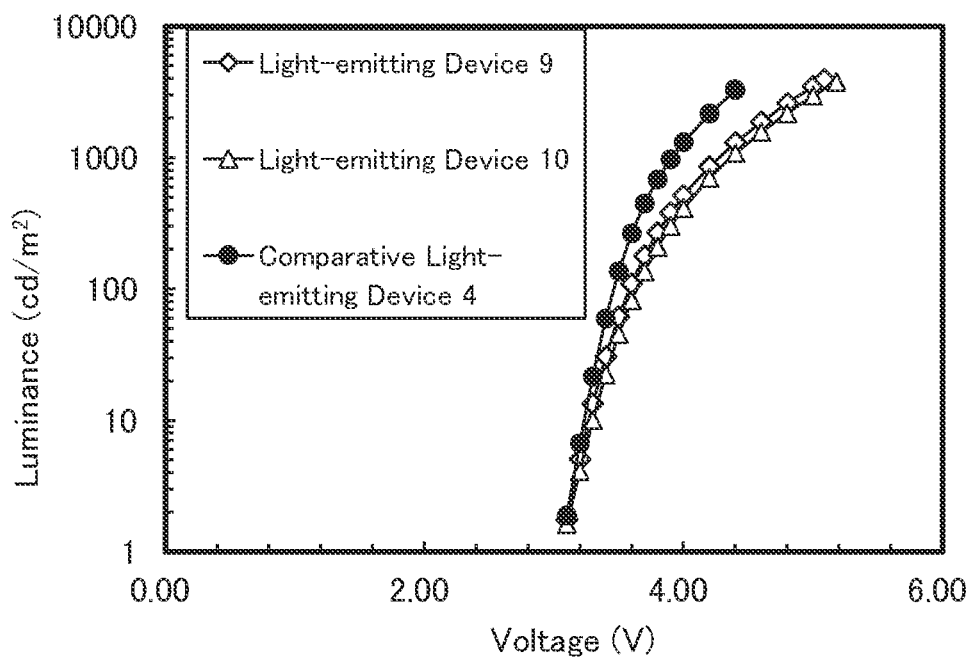
FIG. 62 shows the luminance-voltage characteristics of the light-emitting devices 9 and 10 and the comparative light-emitting device 4.
Figure 63:
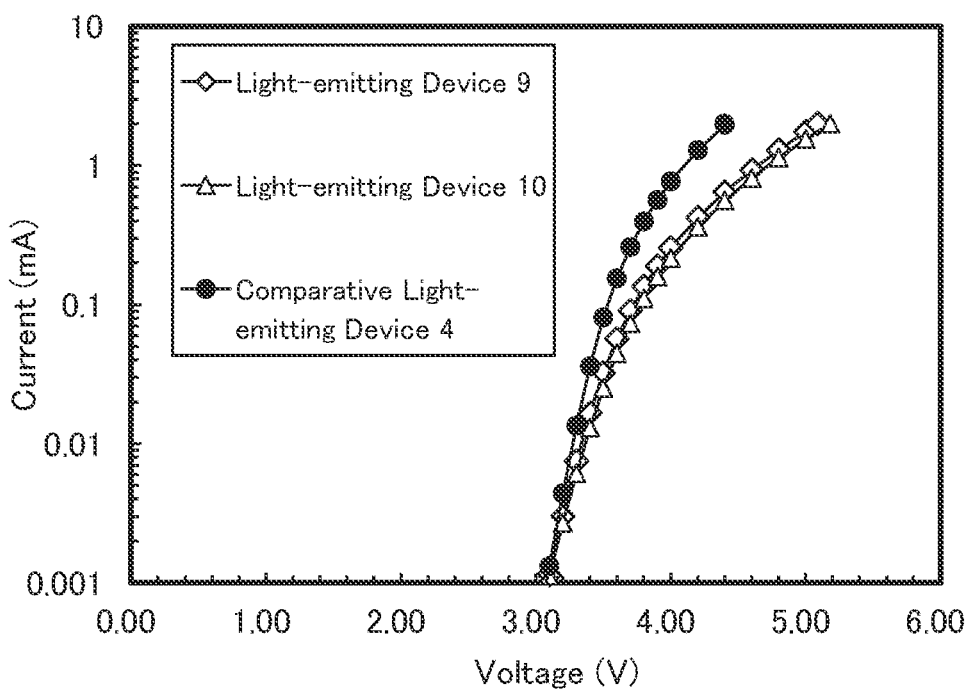
FIG. 63 shows the current-voltage characteristics of the light-emitting devices 9 and 10 and the comparative light-emitting device 4.
Figure 64:
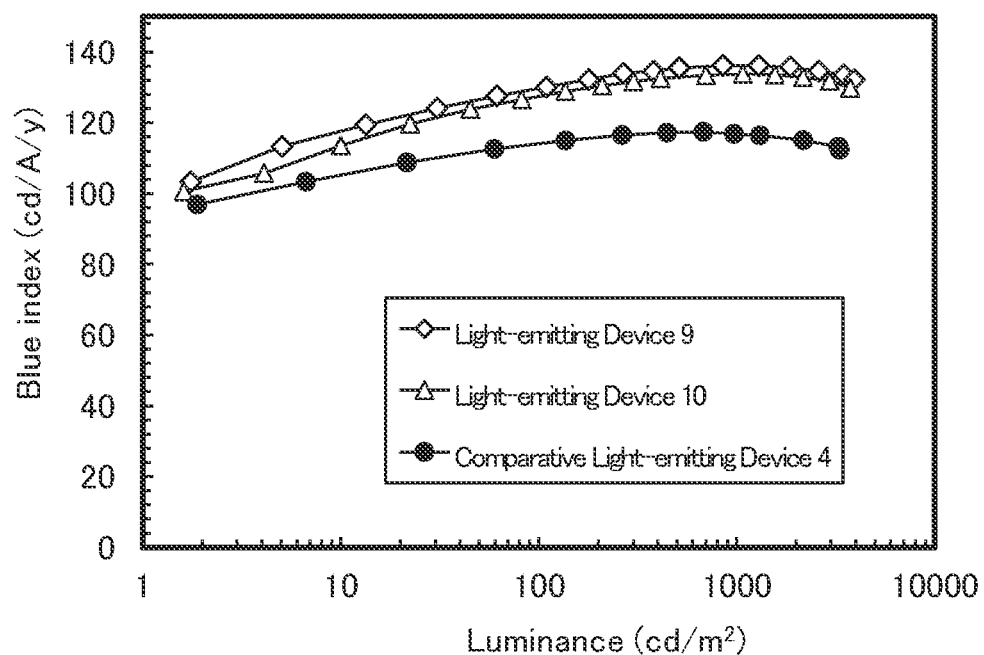
FIG. 64 shows the blue index-luminance characteristics of the light-emitting devices 9 and 10 and the comparative light-emitting device 4.
Figure 65:
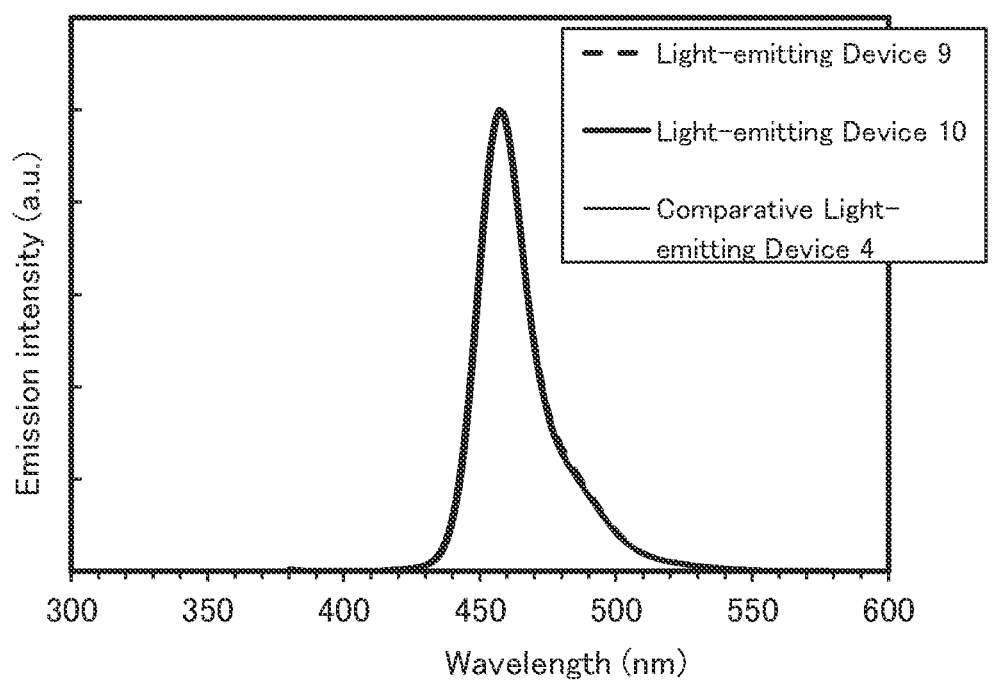
FIG. 65 shows the emission spectra of the light-emitting devices 9 and 10 and the comparative light-emitting device 4.

FIG. 60 shows the luminance-current density characteristics of the light-emitting device 9, the light-emitting device 10, and the comparative light-emitting device 4. FIG. 61 shows the current efficiency-luminance characteristics thereof. FIG. 62 shows the luminance-voltage characteristics thereof. FIG. 63 shows the current-voltage characteristics thereof. FIG. 64 shows the blue index-luminance characteristics thereof. FIG. 65 shows the emission spectra thereof. Table 12 shows the main characteristics of the light-emitting devices at a luminance of about 1000 cd/m². Luminance, CIE chromaticity, and emission spectra were measured at normal temperature with a spectroradiometer (SR-UL1R produced by TOPCON TECHNOHOUSE CORPORATION).

FIGS. 60 to 65 and Table 12 show that the light-emitting devices of one embodiment of the present invention, which use a material with a low refractive index, are EL devices with more favorable current efficiency and blue index (BI) than the comparative light-emitting device.

Note that the blue index (BI) is a value obtained by dividing current efficiency (cd/A) by chromaticity y, and is one of the indicators of characteristics of blue light emission. As the chromaticity y is smaller, the color purity of blue light emission tends to be higher. With high color purity, a wide range of blue can be expressed even with a small number of luminance components; thus, using blue light emission with high color purity reduces the luminance needed for expressing blue, leading to lower power consumption. Thus, BI that is based on chromaticity y, which is one of the indicators of color purity of blue, is suitably used as a mean for showing efficiency of blue light emission. The light-emitting device with higher BI can be regarded as a blue light emitting device having more favorable characteristics for a display.

Figure 66:
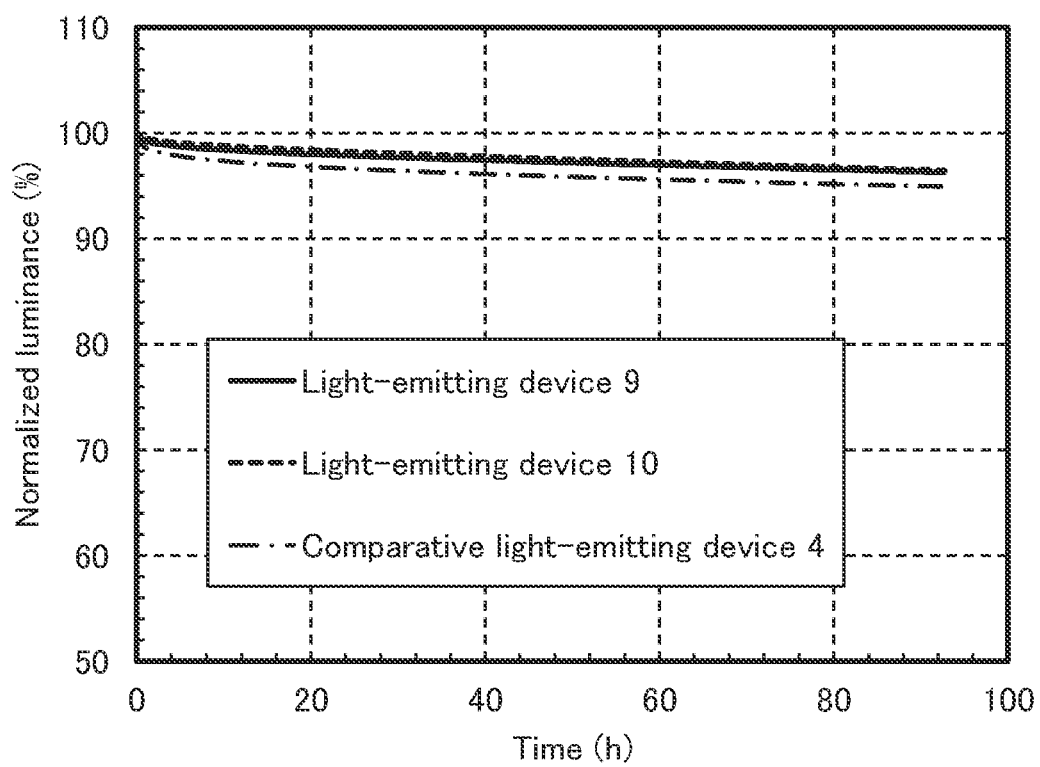
FIG. 66 shows a luminance change over driving time of the light-emitting devices 9 and 10 and the comparative light-emitting device 4.

Next, FIG. 66 shows luminance change over driving time when the light-emitting devices 9 and 10 and the comparative light-emitting device 4 are driven at a constant current with a current density of 50 mA/cm². As shown in FIG. 66, the light-emitting devices of one embodiment of the present invention have high emission efficiency while keeping a favorable lifetime.

Example 11

In this example, light-emitting devices of one embodiment of the present invention described in the above embodiments and a comparative light-emitting device are described. Structural formulae of organic compounds used in this example are shown below.

TABLE 12

|  | Voltage (V) | Current (mA) | Current density (mA/cm²) | Chromaticity x | Chromaticity y | Current efficiency (cd/A) | BI (cd/A/y) |
|---|---|---|---|---|---|---|---|
| Light-emitting Device 9 | 4.2 | 0.42 | 10.6 | 0.14 | 0.06 | 8.1 | 136 |
| Light-emitting Device 10 | 4.4 | 0.56 | 14.0 | 0.14 | 0.06 | 7.7 | 134 |
| Comparative Light-emitting Device 4 | 3.9 | 0.57 | 14.1 | 0.14 | 0.06 | 6.8 | 117 |

[Chemical Formula 59]
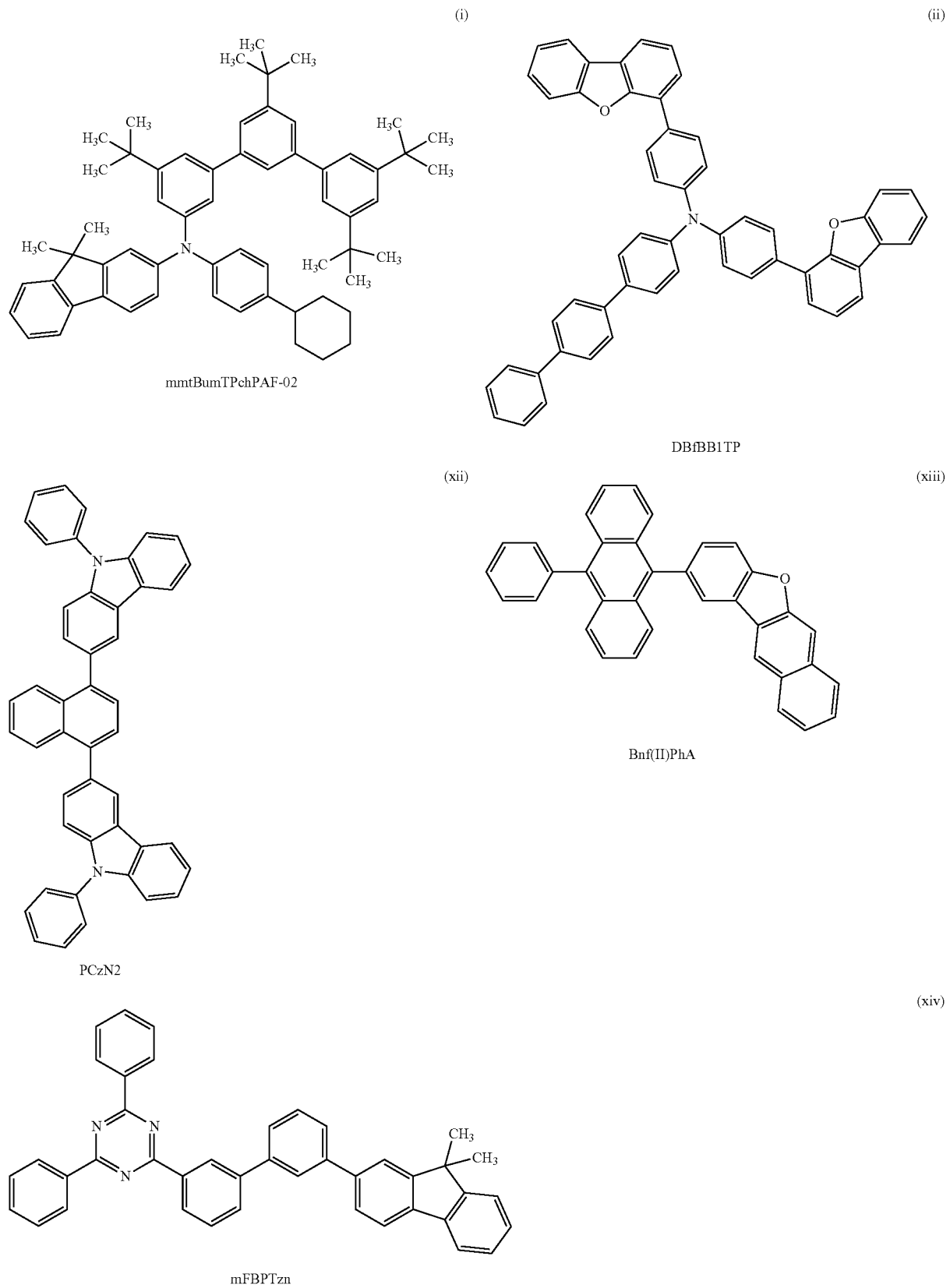

(iv)

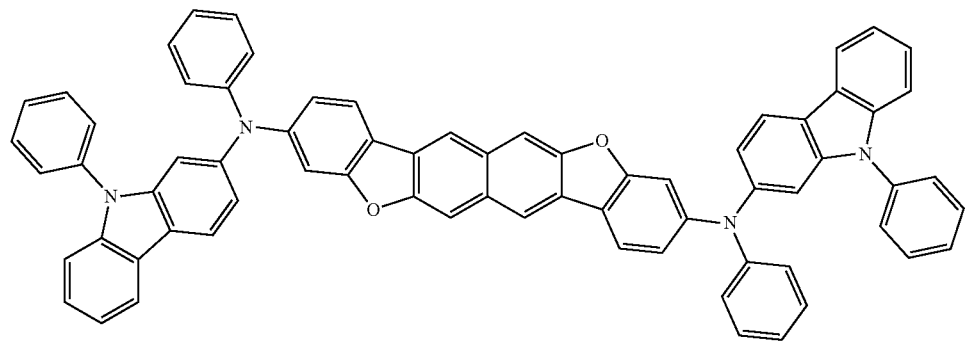

3,10PCA2Nbf(IV)-02

(vi)

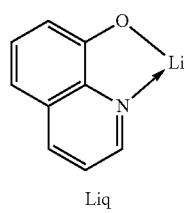

Liq (vii)

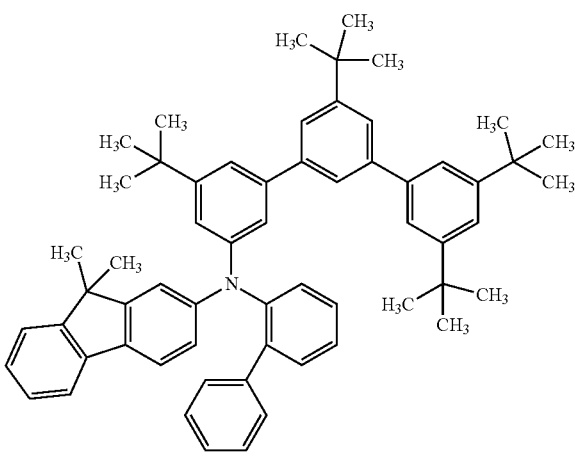

mmtBumTPoFBi-02

(viii)

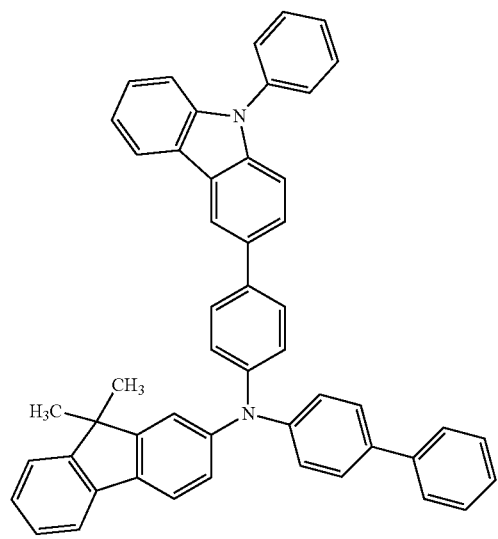

PCBBiF (xi)

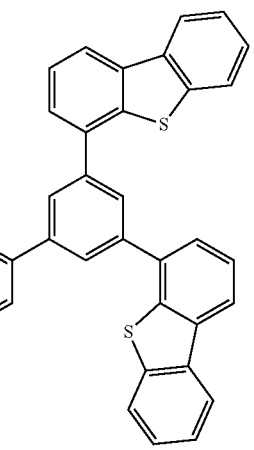

DBT3P-II (Method for Manufacturing Light-Emitting Device 11)

First, as a reflective electrode, silver (Ag) was deposited over a glass substrate to a thickness of 100 nm by a sputtering method, and then, as a transparent electrode, indium tin oxide containing silicon oxide (ITSO) was deposited to a thickness of 10 nm by a sputtering method, whereby the first electrode 101 was formed. The electrode area was 4 mm² (2 mm×2 mm).

Next, in pretreatment for forming the light-emitting device over a substrate, a surface of the substrate was washed with water and baked at 200° C. for one hour, and then UV ozone treatment was performed for 370 seconds.

After that, the substrate was transferred into a vacuum evaporation apparatus where the pressure was reduced to approximately $10^{-4}$ Pa, vacuum baking was performed at 170° C. for 30 minutes in a heating chamber of the vacuum evaporation apparatus, and then the substrate was cooled down for approximately 30 minutes.

Next, the substrate provided with the first electrode 101 was fixed to a substrate holder provided in the vacuum evaporation apparatus such that the surface on which the first electrode 101 was formed faced downward. Then, N-(4-cyclohexylphenyl)-N-(3,3",5',5"-tetra-tert-butyl-1,1': 3',1"-terphenyl-5-yl)-9,9-dimethyl-9H-fluoren-2-amine (abbreviation: mmtBumTPchPAF-02) represented by Structural Formula (i) and an electron acceptor material (OCHD-001) were deposited by co-evaporation to a thickness of 10 nm on the first electrode 101 such that the weight ratio of mmtBumTPchPAF-02 to OCHD-001 was 1:0.1, whereby the hole-injection layer 111 was formed.

Over the hole-injection layer 111, mmtBumTPchPAF-02 was deposited as a first hole-transport layer to a thickness of 125 nm by evaporation, and then N,N-bis[4-(dibenzofuran-4-yl)phenyl]-4-amino-p-terphenyl (abbreviation: DBfBB1TP) represented by Structural Formula (ii) was deposited as a second hole-transport layer to a thickness of 10 nm by evaporation, whereby the hole-transport layer 112 was formed.

Subsequently, over the hole-transport layer 112, 3,3'-(naphthalene-1,4-diyl)bis(9-phenyl-9H-carbazole) (abbreviation: PCzN2) represented by Structural Formula (xii) was deposited by evaporation to a thickness of 10 nm, whereby an electron-blocking layer was formed.

Then, 2-(10-phenyl-9-anthracenyl)-benzo[b]naphtho[2,3-d]furan (abbreviation: Bnf(II)PhA) represented by Structural Formula (xiii) and 3,10-bis[N-(9-phenyl-9H-carbazol-2-yl)-N-phenylamino]naphtho[2,3-b;6,7-b']bisbenzofuran (abbreviation: 3,10PCA2Nbf(IV)-02) represented by Structural Formula (iv) were deposited to a thickness of 25 nm by co-evaporation such that the weight ratio of Bnf(II)PhA to 3,10PCA2Nbf(IV)-02 was 1:0.015, whereby the light-emitting layer 113 was formed.

Then, over the light-emitting layer 113, 2-[3'-(9,9-dimethyl-9F7-fluoren-2-yl)-1,1'-biphenyl-3-yl]-4,6-diphenyl-1,3,5-triazine (abbreviation: mFBPTzn) represented by Structural Formula (xiv) above was deposited to a thickness of 10 nm as a hole-blocking layer, and then 2-[3-(2,6-dimethyl-3-pyridinyl)-5-(9-phenanthrenyl)phenyl]-4,6-diphenyl-1,3, 5-triazine (abbreviation: mPn-mDMePyPTzn) and 8-(quinolinolato)lithium (abbreviation: Liq) represented by Structural Formula (vi) above were deposited by co-evaporation to a thickness of 20 nm such that the weight ratio of mPn-mDMePyPTzn to Liq was 1:1, whereby the electron-transport layer 114 was formed.

After the formation of the electron-transport layer 114, lithium fluoride (LiF) was deposited by evaporation to a thickness of 1 nm to form the electron-injection layer 115. Then, silver (Ag) and magnesium (Mg) were deposited by co-evaporation to a thickness of 15 nm such that the weight ratio of Ag to Mg was 10:1 to form the second electrode 102. Thus, a light-emitting device 11 was fabricated. The second electrode 102 is a transflective electrode having a function of reflecting light and a function of transmitting light; thus, the light-emitting device of this example is a top-emission device in which light is extracted through the second electrode 102. Over the second electrode 102, 1,3,5-tri(dibenzothiophen-4-yl)-benzene (abbreviation: DBT3P-II) represented by Structural Formula (xi) was deposited by evaporation to a thickness of 70 nm so that outcoupling efficiency can be improved.

(Fabrication Method of Light-Emitting Device 12)

A light-emitting device 12 was fabricated in a manner similar to that for the light-emitting device 11 except that mmtBumTPchPAF-02 in the light-emitting device 11 was replaced with N-(1,1'-biphenyl-2-yl)-N-(3,3",5',5"-tetra-tert-butyl-1,1':3'1"-terphenyl-5-yl)-9,9-dimethyl-9H-fluoren-2-amine (abbreviation: mmtBumTPoFBi-02) represented by Structural Formula (vii) and the thickness of the first hole-transport layer was set to 130 nm.

(Fabrication Method of Comparative Light-Emitting Device 5)

A comparative light-emitting device 5 was fabricated in a manner similar to that for the light-emitting device 11 except that mmtBumTPchPAF-02 in the light-emitting device 11 was replaced with N-(1,1'-biphenyl-4-yl)-N-[4-(9-phenyl-9H-carbazol-3-yl)phenyl]-9,9-dimethyl-9H-fluoren-2-amine (abbreviation: PCBBiF) represented by Structural Formula (viii) and the thickness of the first hole-transport layer was set to 100 nm.

The structures of the light-emitting devices 11 and 12 and the comparative light-emitting device 5 are listed in the following table.

TABLE 13

| | Film thickness | Light-emitting Device 11 | Light-emitting Device 12 | Comparative Light-emitting Device 5 |
|---|---|---|---|---|
| Electron-injection layer | 1 nm | LiF | | |
| Electron-transport layer | 20 nm | mPn-mDMePyPTzn:Liq (1:1) | | |
| Hole-blocking layer | 10 nm | mFBPTzn | | |
| Light-emitting layer | 25 nm | Bnf(II)PhA:3,10PCA2Nbf(IV)-02 (1:0.015) | | |
| Electron-blocking layer | 10 nm | PCzN2 | | |
| Hole-transport | 10 nm | DBfBBYTP | | |
| | *3 | mmtBumTPchPAF-02 | mmtBumTPoFBi-02 | PCBBiF |

TABLE 13-continued

| | Film thickness | Light-emitting Device 11 | Light-emitting Device 12 | Comparative Light-emitting Device 5 |
|---|---|---|---|---|
| layer Hole-injection layer | 10 nm | mmtBumTPchPAF-02:OCHD-001 (1:0.1) | mmtBumTPoFBi-02:OCHD-001 (1:0.1) | PCBBiF: OCHD-001 (1:0.1) |

*3 Light-emitting Device 11: 125 nm,
Light-emitting Device 12: 130 nm,
Comparative Light-emitting device 5: 100 nm The refractive indices of PCBBiF as a reference and the materials with a low refractive index (mmtBumTPchPAF-02 and mmtBumTPoFBi-02) used for the hole-injection layer and part of the hole-transport layer are shown in FIG. 68, and the refractive indices at a wavelength of 458 nm are shown in the following table.

TABLE 14

| | Refractive index |
|---|---|
| mmtBumTPchPAF-02 | 1.67 |
| mmtBumTPoFBi-02 | 1.70 |
| PCBBiF | 1.94 |

The light-emitting devices and the comparative light-emitting device were sealed using a glass substrate in a glove box containing a nitrogen atmosphere so as not to be exposed to the air (a sealing material was applied to surround the device and UV treatment and heat treatment were performed at the time of sealing). Then, the initial characteristics of the light-emitting devices were measured. Note that the sealed glass substrate was not subjected to particular treatment for improving outcoupling efficiency.

Figure 69:
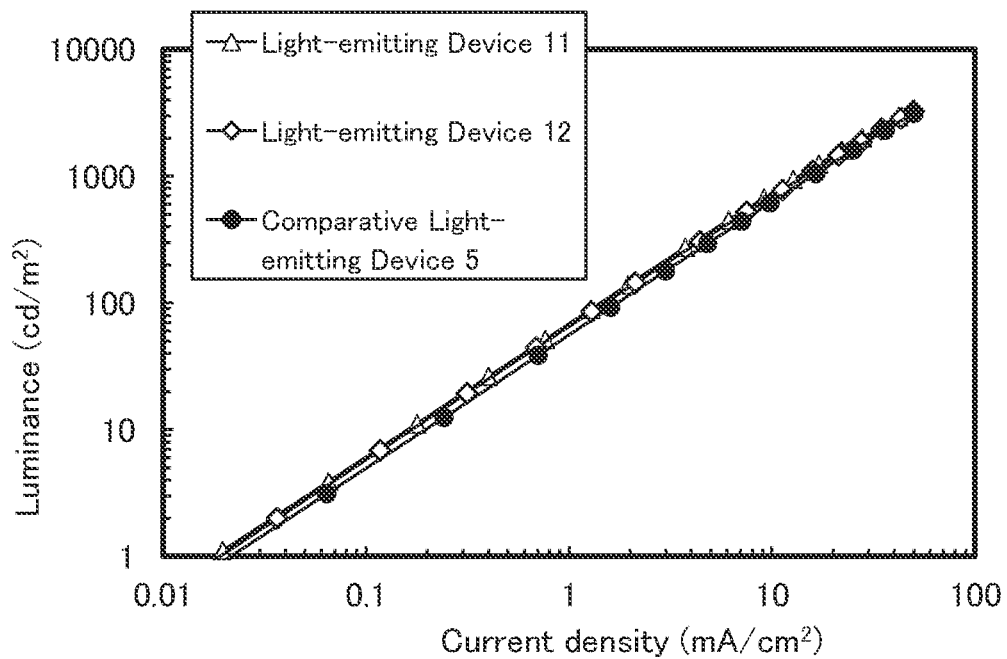
FIG. 69 shows the luminance-current density characteristics of a light-emitting device 11, a light-emitting device 12, and a comparative light-emitting device 5.
Figure 70:
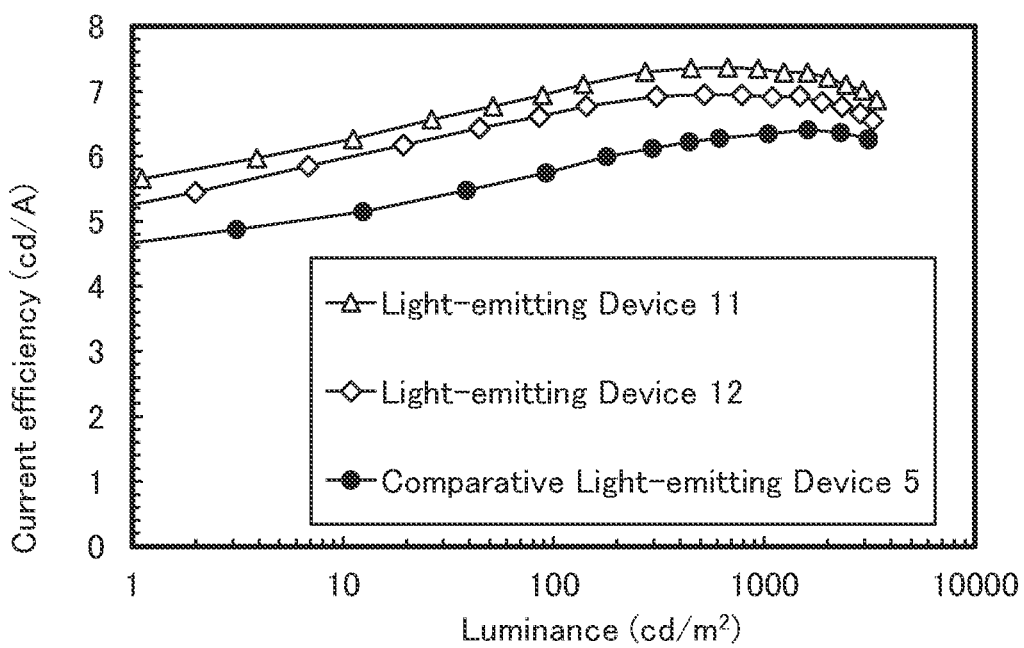
FIG. 70 shows the current efficiency-luminance characteristics of the light-emitting devices 11 and 12 and the comparative light-emitting device 5.
Figure 71:
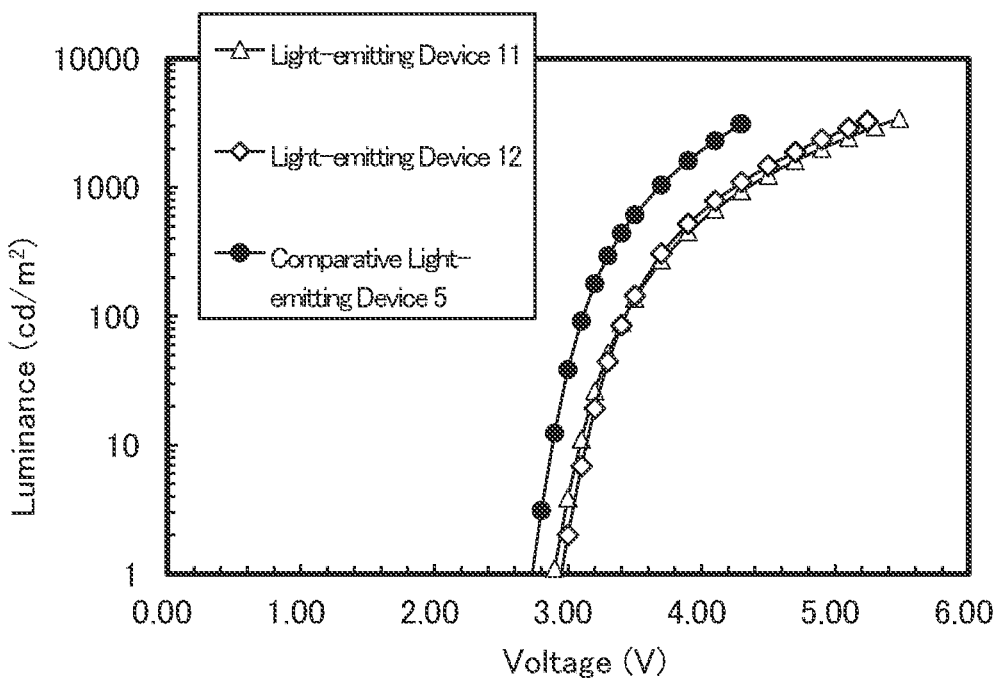
FIG. 71 shows the luminance-voltage characteristics of the light-emitting devices 11 and 12 and the comparative light-emitting device 5.
Figure 72:
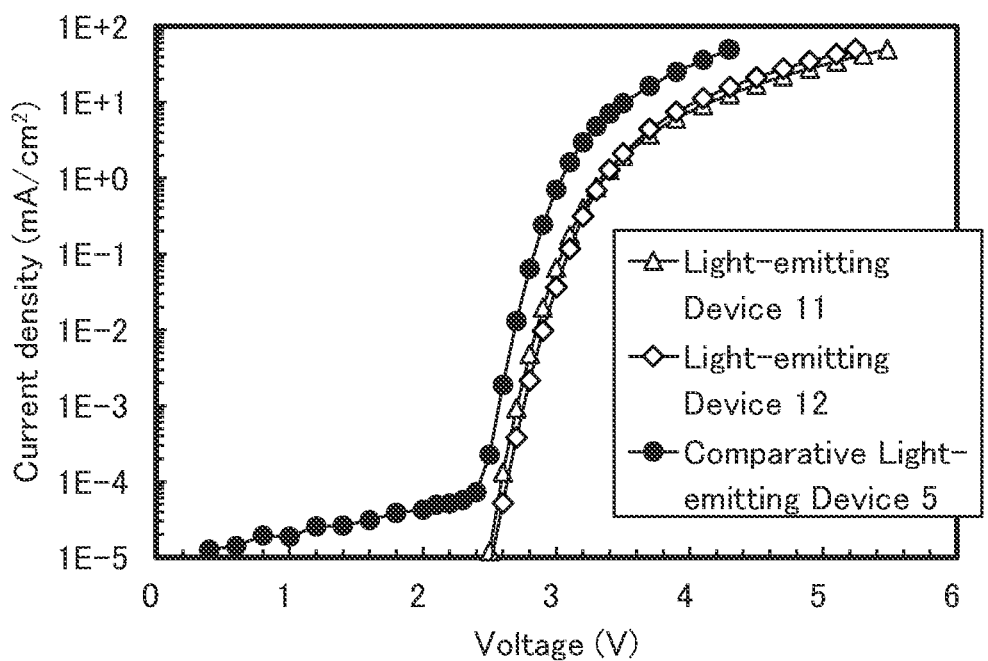
FIG. 72 shows the current-voltage characteristics of the light-emitting devices 11 and 12 and the comparative light-emitting device 5.
Figure 73:
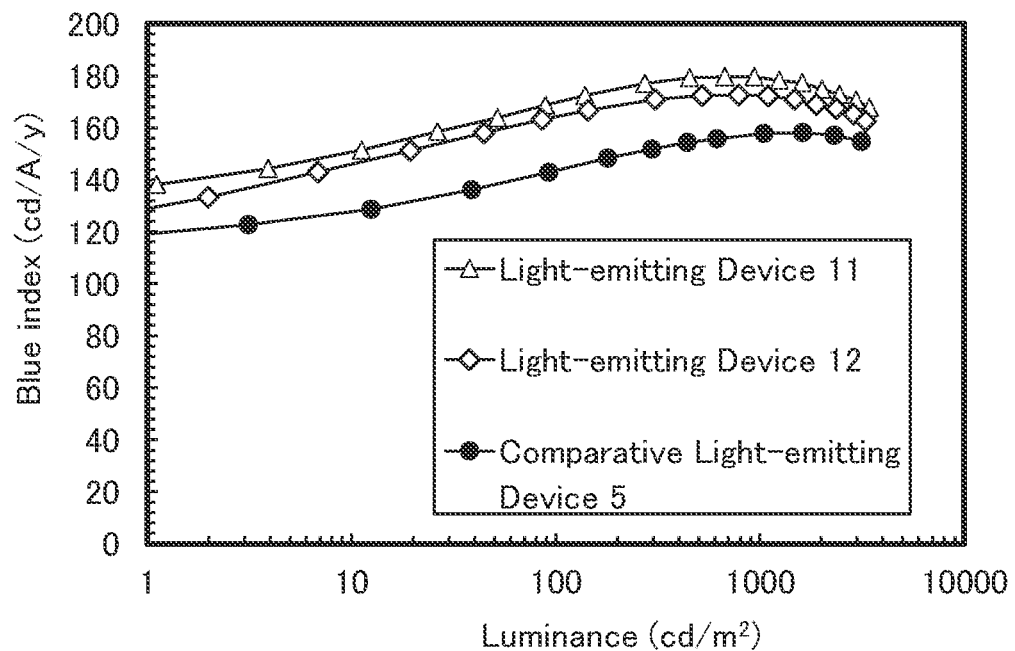
FIG. 73 shows the blue index-luminance characteristics of the light-emitting devices 11 and 12 and the comparative light-emitting device 5.
Figure 74:
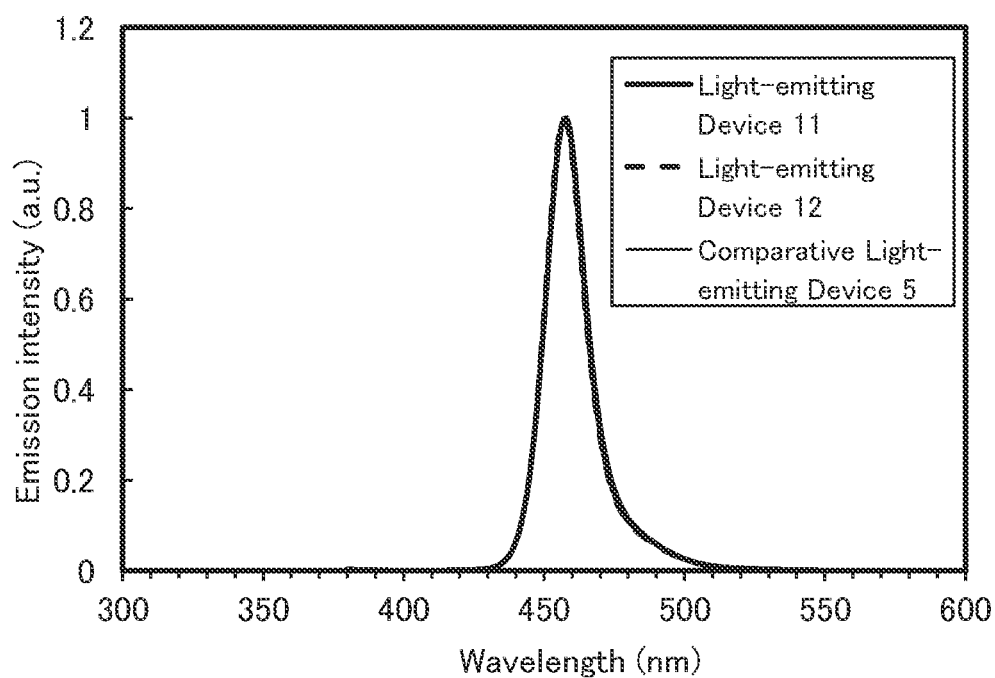
FIG. 74 shows the emission spectra of the light-emitting devices 11 and 12 and the comparative light-emitting device 5.

FIG. 69 shows the luminance-current density characteristics of the light-emitting device 11, the light-emitting device 12, and the comparative light-emitting device 5. FIG. 70 shows the current efficiency-luminance characteristics thereof. FIG. 71 shows the luminance-voltage characteristics thereof. FIG. 72 shows the current density-voltage characteristics thereof. FIG. 73 shows the blue index-luminance characteristics thereof. FIG. 74 shows the emission spectra thereof. Table 15 shows the main characteristics of the light-emitting devices at a luminance of about 1000 cd/m$^2$. Luminance, CIE chromaticity, and emission spectra were measured at normal temperature with a spectroradiometer (SR-UL1R produced by TOPCON TECHNO-HOUSE CORPORATION).

Note that the blue index (BI) is a value obtained by dividing current efficiency (cd/A) by chromaticity y, and is one of the indicators of characteristics of blue light emission. As the chromaticity y is smaller, the color purity of blue light emission tends to be higher. With high color purity, a wide range of blue can be expressed even with a small number of luminance components; thus, using blue light emission with high color purity reduces the luminance needed for expressing blue, leading to lower power consumption. Thus, BI that is based on chromaticity y, which is one of the indicators of color purity of blue, is suitably used as a mean for showing efficiency of blue light emission. The light-emitting device with higher BI can be regarded as a blue light emitting device having more favorable characteristics for a display.

Figure 75:
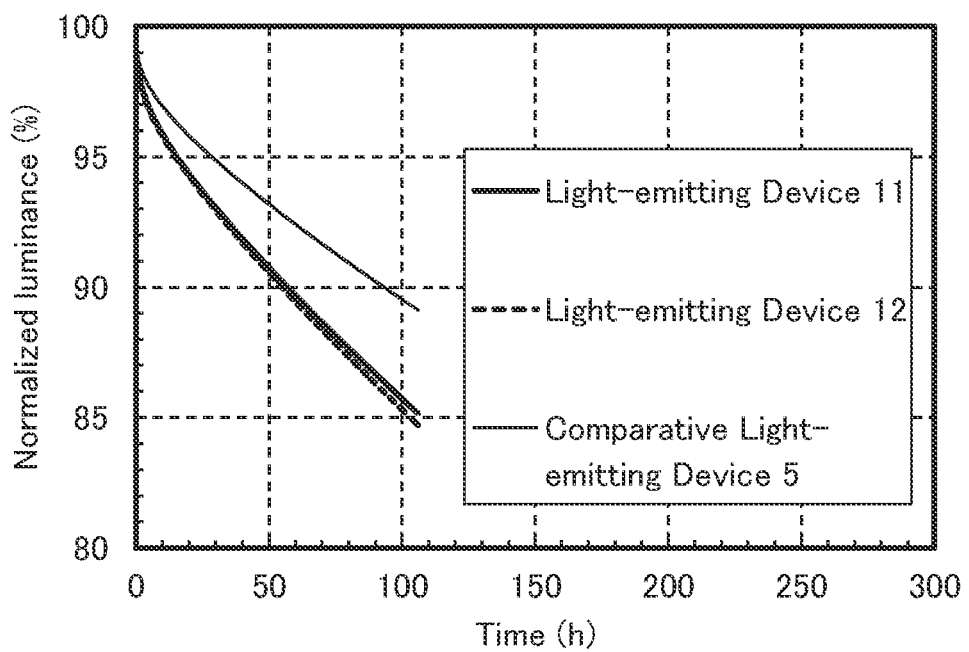
FIG. 75 shows a luminance change over driving time of the light-emitting devices 11 and 12 and the comparative light-emitting device 5.

Next, FIG. 75 shows luminance change over driving time when the light-emitting devices 11 and 12 and the comparative light-emitting device 5 are driven at a constant current with a current density of 50 mA/cm$^2$. The results show that the luminances of the light-emitting devices 11 and 12 decrease more rapidly than the luminance of the comparative light-emitting device 5. Note that the light-emitting devices 11 and 12 have higher emission efficiency than the comparative light-emitting device 5, and thus emit light with higher luminance than the comparative light-emitting device 5 when these devices are driven with the same current density.

Example 12

In this example, results of measuring the hole mobility of the organic compounds of one embodiment of the present invention are described. The hole mobility was measured with devices fabricated for the measurement. The fabrication methods of the devices are described below.
(Method for Manufacturing Device 1)

As an electrode, an alloy film of silver (Ag), palladium (Pd), and copper (Cu), i.e., an Ag—Pd—Cu (APC) film, was formed over a glass substrate to a thickness of 100 nm by a sputtering method, and then, indium tin oxide containing silicon oxide (ITSO) was formed to a thickness of 50 nm by a sputtering method, whereby the first electrode 101 was formed. The electrode area was 4 mm$^2$ (2 mm×2 mm).

TABLE 15

| | Voltage (V) | Current (mA) | Current density (mA/cm$^2$) | Chromaticity x | Chromaticity y | Current efficiency (cd/A) | BI (cd/A/y) |
|---|---|---|---|---|---|---|---|
| Light-emitting Device 11 | 4.3 | 0.51 | 12.8 | 0.14 | 0.04 | 7.3 | 180 |
| Light-emitting Device 12 | 4.1 | 0.45 | 11.3 | 0.14 | 0.04 | 6.9 | 173 |
| Comparative Light-emitting Device 5 | 3.7 | 0.66 | 16.5 | 0.14 | 0.04 | 6.3 | 158 |

FIGS. 69 to 74 and Table 15 show that the light-emitting devices of one embodiment of the present invention, which use a material with a low refractive index, are EL devices with more favorable current efficiency and blue index (BI) than the comparative light-emitting device.

Next, in pretreatment for forming the device over a substrate, a surface of the substrate was washed with water and baked at 200° C. for one hour, and then UV ozone treatment was performed for 370 seconds.

After that, the substrate was transferred into a vacuum evaporation apparatus where the pressure was reduced to approximately $10^{-4}$ Pa, vacuum baking was performed at 170° C. for 30 minutes in a heating chamber of the vacuum evaporation apparatus, and then the substrate was cooled down for approximately 30 minutes.

Next, the substrate provided with the first electrode 101 was fixed to a substrate holder provided in the vacuum evaporation apparatus such that the surface on which the first electrode 101 was formed faced downward. Then, mmtBumTPchPAF-02) and molybdenum oxide were deposited by co-evaporation to a thickness of 5 nm on the first electrode 101 such that the weight ratio of mmtBumTPch-PAF-02 to molybdenum oxide was 1:1, whereby the hole-injection layer 111 was formed.

Over the hole-injection layer 111, mmtBumTPchPAF-02 was deposited as the hole-transport layer 112 to a thickness of 520 nm by evaporation.

Then, mmtBumTPchPAF-02 and molybdenum oxide were deposited by co-evaporation to a thickness of 5 nm such that the weight ratio of mmtBumTPchPAF-02 to molybdenum oxide was 1:1, whereby a buffer layer was formed.

Then, aluminum (Al) was deposited by evaporation to a thickness of 200 nm to form the second electrode 102, whereby the device 1 through which only holes flow was fabricated.

(Method for Manufacturing Device 2)

The device 2 was fabricated in a manner similar to that for the device 1 except that mmtBumTPchPAF-02 in the device 1 was replaced with mmtBumTPoFBi-02 and the thickness of the hole-transport layer 112 was 557.5 nm.

The device structures of the devices 1 and 2 are listed below.

TABLE 16

| | Film thickness | Device 1 | Device 2 |
|---|---|---|---|
| Buffer layer | 5 nm | mmtBumTPchPAF-02:molybdenum oxide (1:1) | mmtBumTPoFBi-02:molybdenum oxide (1:1) |
| Hole-transport layer | *4 | mmtBumTPchPAF-02 | mmtBumTPoFBi-02 |
| Hole-injection layer | 5 nm | mmtBumTPchPAF-02:molybdenum oxide (1:1) | mmtBumTPoFBi-02:molybdenum oxide (1:1) |

*4 Device 1: 520 nm,
Device 2: 557.5 nm

The devices were sealed using a glass substrate in a glove box containing a nitrogen atmosphere so as not to be exposed to the air (a sealing material was applied to surround the device and UV treatment was performed at the time of sealing). Then, the devices were measured.

Figure 76:
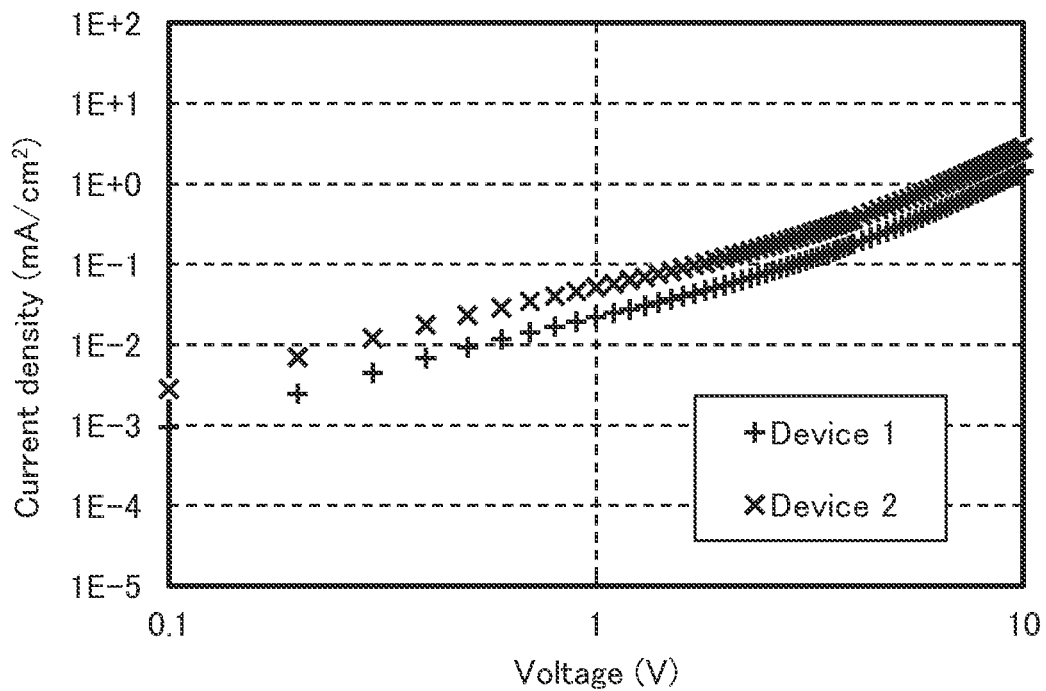
FIG. 76 shows the current density-voltage characteristics of a device 1 and a device 2.

The current density-voltage characteristics of the devices 1 and 2 are shown in FIG. 76. Note that the measurement was performed at room temperature.

The hole mobility of the organic compounds was calculated from the electrical characteristics shown in FIG. 76 using device simulation. For the simulation, Setfos (drift-diffusion module produced by CYBERNET SYSTEMS Co., Ltd.) was used. As the simulation parameters, the work function of ITSO which serves as the first electrode 101 was 5.36 eV, the work function of Al which serves as the second electrode 102 was 4.2 eV, the HOMO level of mmt-BumTPchPAF-02 was −5.39 eV, and the HOMO level of mmtBumTPoFBi-02 was −5.43 eV. The charge density of the hole-transport layer 112 was $1.0 \times 10^{18}$ cm$^3$.

The work functions of the electrodes were measured by photoelectron spectroscopy using "AC-2" produced by Riken Keiki Co., Ltd. in the air.

The HOMO levels of the organic compounds were measured by cyclic voltammetry (CV) measurement. Note that for the measurement, an electrochemical analyzer (ALS 600A or 600C, produced by BAS Inc.) was used, and the measurement was performed on a solution obtained by dissolving each compound in N,N-dimethylformamide (abbreviation: DMF). In the measurement, the potential of a working electrode with respect to a reference electrode was changed within an appropriate range, so that the oxidation peak potential and the reduction peak potential were obtained. In addition, the HOMO levels of the compounds were obtained from the estimated redox potential of the reference electrode of −4.94 eV and the obtained peak potentials.

Figure 77:
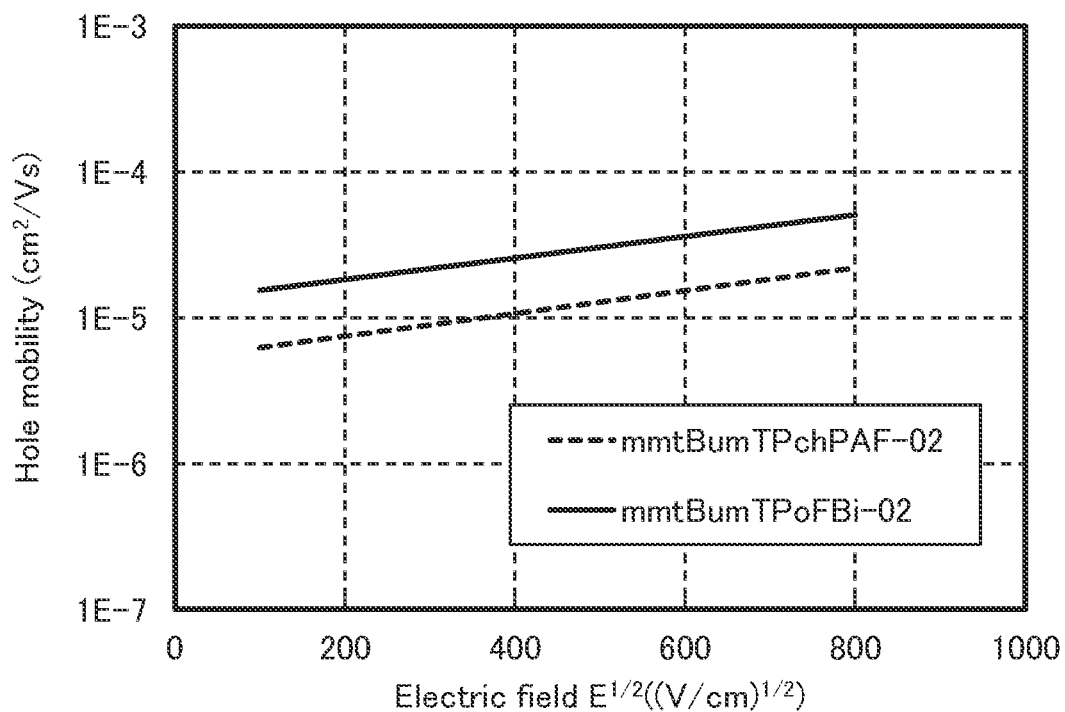
FIG. 77 shows the electric field strength dependence of the hole mobility of an organic compound of one embodiment of the present invention.

The hole mobility of the organic compounds obtained by the simulation is shown in FIG. 77. Note that the horizontal axis in FIG. 77 represents the one-half power of electric field strength calculated from voltage. In addition, the hole mobility at an electric field strength of 300 (V/cm)$^{1/2}$ is shown in the following table.

TABLE 17

| | Hole mobility*[5] (cm$^2$/Vs) |
|---|---|
| mmtBumTPchPAF-02 | $8.9 \times 10^{-6}$ |
| mmtBumTPoFBi-02 | $2.2 \times 10^{-5}$ |

*[5]intensity of an electric field: 300 (V/cm)$^{1/2}$

As described above, the organic compounds of one embodiment of the present invention are substances having hole mobility of higher than or equal to $1 \times 10^{-6}$ cm$^2$/Vs, and thus is suitable for a hole-transport layer of a light-emitting device.

Example 13

Synthesis Example 7

In this example, a synthesis method of N-(1,1'-biphenyl-2-yl)-N-(3",5',5"-tri-tert-butyl-1,1':3',1"-terphenyl-4-yl)-9,9-dimethyl-9H-fluoren-2-amine (abbreviation: mmtBumT-PoFBi-04), which is the organic compound of one embodiment of the present invention represented by Structural Formula (150) in Embodiment 1, will be described. A structure of mmtBumTPoFBi-04 is shown below.

[Chemical Formula 60]

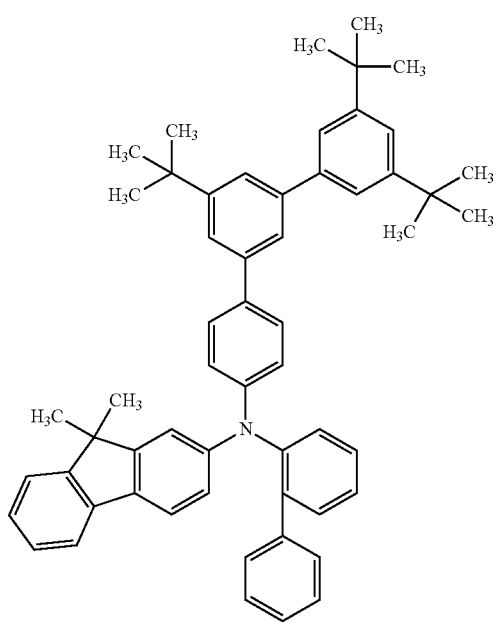

Step 1: Synthesis of 4-bromo-3",5',5"-tri-tert-butyl-1,1':3',1"-terphenyl

Into a three-neck flask were put 9.0 g (20.1 mmol) of 2-(3',5,5'-tri-tert-butyl[1,1'-biphenyl]-3-yl)-4,4,5,5-tetramethyl-1,3,2-dioxaborolane, 6.8 g (24.1 mmol) of 1-bromo-4-iodobenzene, 8.3 g (60.3 mmol) of potassium carbonate, 100 mL of toluene, 40 mL of ethanol, and 30 mL of tap water. The mixture was degassed under reduced pressure, the air in the flask was replaced with nitrogen, 91 mg (0.40 mmol) of palladium acetate and 211 mg (0.80 mmol) of triphenylphosphine were added thereto, and the mixture was heated at 80° C. for approximately four hours. After that, the temperature of the flask was lowered to room temperature, and the mixture was separated into an organic layer and an aqueous layer. Magnesium sulfate was added to this solution for drying to be concentrated. A hexane solution of the obtained solution was purified by silica gel column chromatography, whereby 6.0 g of a target white solid was obtained in a yield of 62.5%. The synthesis scheme of 4-bromo-3",5',5"-tri-tert-butyl-1,1'3',1"-terphenyl of Step 3 is shown below.

[Chemical Formula 61]

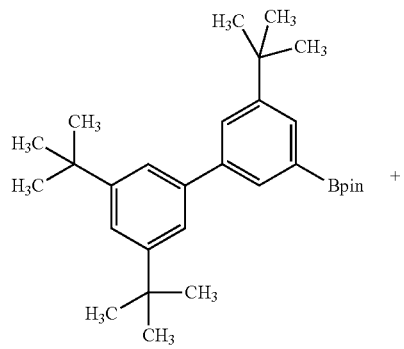

+

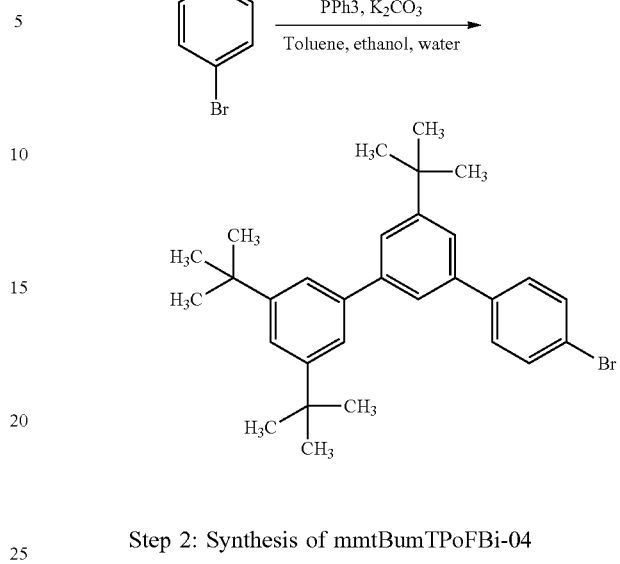

Step 2: Synthesis of mmtBumTPoFBi-04

Into a three-neck flask were put 3.0 g (6.3 mmol) of 4-bromo-3",5',5"-tri-tert-butyl-1,1':3',1"-terphenyl, 2.3 g (6.3 mmol) of N-(1,1'-biphenyl-4-yl)-N-phenyl-9,9-dimethyl-9H-fluoren-2-amine, 1.8 g (18.9 mmol) of sodium-tert-butoxide, and 32 mL of toluene. The mixture was degassed under reduced pressure, the air in the flask was replaced with nitrogen, 72 mg (0.13 mmol) of bis(dibenzylideneacetone)palladium(0) and 76 mg (0.38 mmol) of tri-tert-butylphosphine were added thereto, and the mixture was heated at 120° C. for approximately eight hours. After that, the temperature of the mixture was lowered to approximately 60° C., approximately 1 mL of water was added, a precipitated solid was separated by filtration, and the solid was washed with toluene. The filtrate was concentrated, and the obtained toluene solution was purified by silica gel column chromatography. The obtained solution was concentrated to give a condensed toluene solution. Ethanol was added to this toluene solution and the toluene solution was concentrated under reduced pressure, whereby an ethanol suspension was obtained. The precipitate was filtrated at approximately 20° C., and the obtained solid was dried at approximately 80° C. under reduced pressure, whereby 3.6 g of a target white solid was obtained in a yield of 75%. The synthesis scheme of mmtBumTPoFBi-04 of Step 4 is shown below.

[Chemical Formula 62]

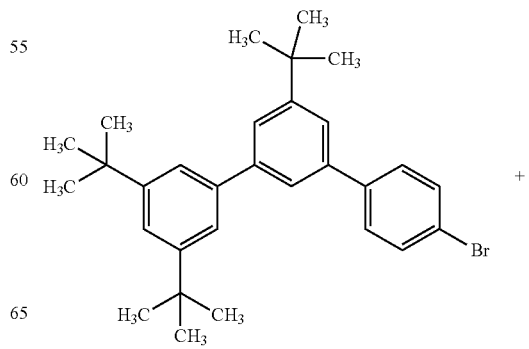

+

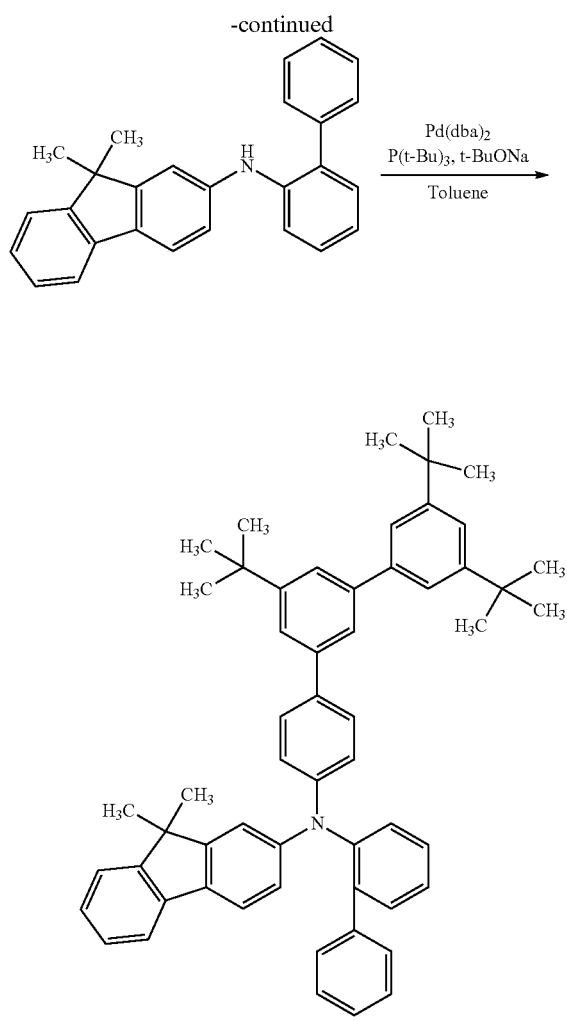

Figure 78A:
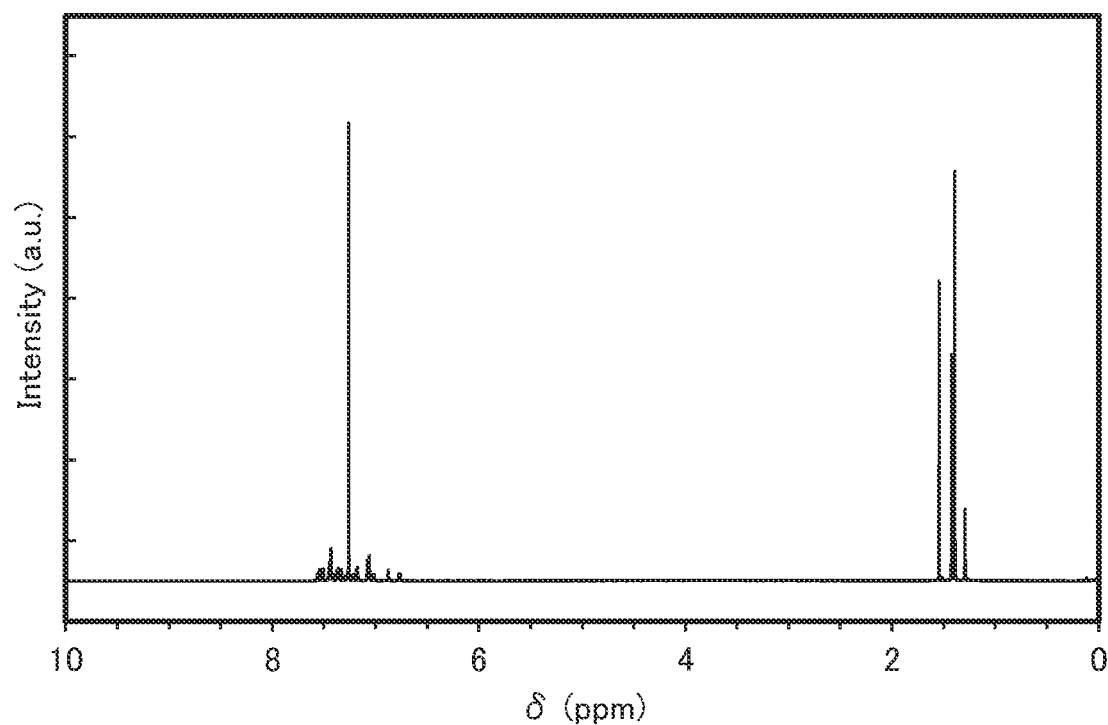
FIGS. 78A and 78B are $^1$H-NMR charts of mmtBumTPoFBi-04.
Figure 78B:
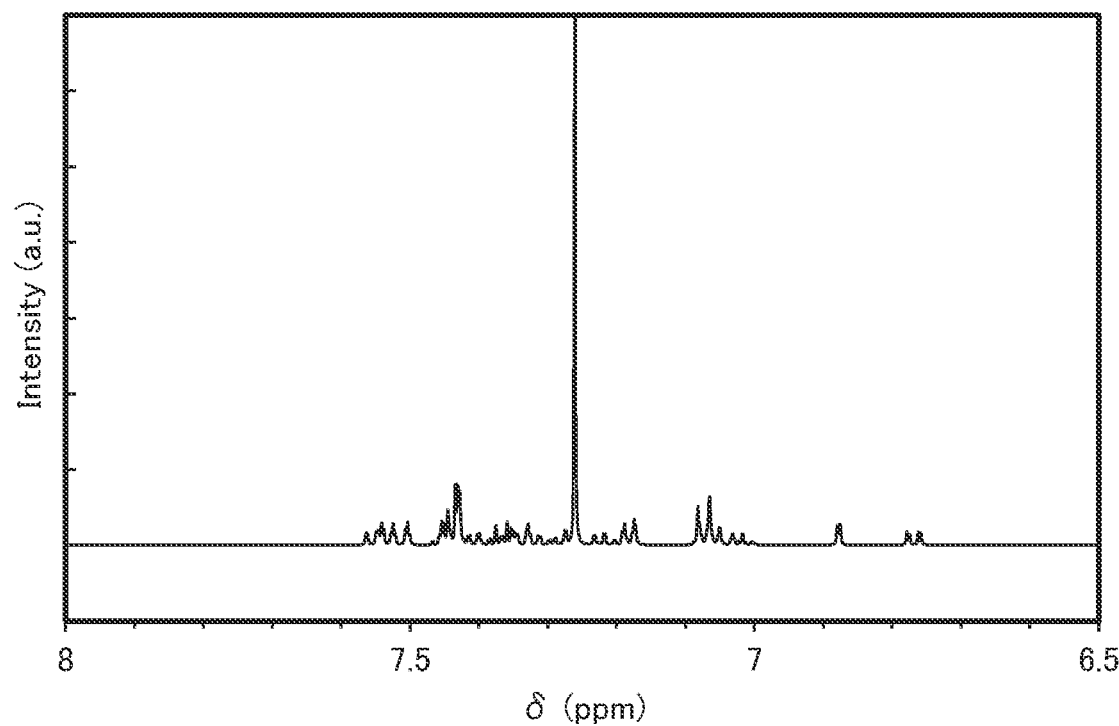

Analysis results by nuclear magnetic resonance ($^1$H-NMR) spectroscopy of the white solid obtained in Step 2 are shown in FIGS. 78A and 78B. Note that FIG. 78B is an enlarged graph of FIG. 78A in the range of 6.5 ppm to 8.0 ppm. In addition, numerical data is shown below. The results show that mmtBumTPoFBi-04 was synthesized in this synthesis example.

$^1$H-NMR. δ (CDCl$_3$): 7.54-7.56 (m, 1H), 7.53 (dd, 1H, J=1.7 Hz), 7.50 (dd, 1H, J=1.7 Hz), 7.27-7.47 (m, 13H), 7.23 (dd, 1H, J=6.3 Hz, 1.2 Hz), 7.18-7.19 (m, 2H), 7.08-7.00 (m, 5H), 6.88 (d, 1H, J=1.7 Hz) 6.77 (dd, 1H, J=8.0 Hz, 2.3 Hz), 1.42 (s, 9H), 1.39 (s, 18H), 1.29 (s, 6H).

Then, 3.6 g of the obtained white solid was purified by a train sublimation method. The purification by sublimation was conducted by heating at 255° C. under a pressure of 3.9 Pa with a flow rate of an argon gas of 15.0 mL/min. After the purification by sublimation, 2.1 g of a pale yellowish white solid was obtained at a collection rate of 58%.

Figure 79:
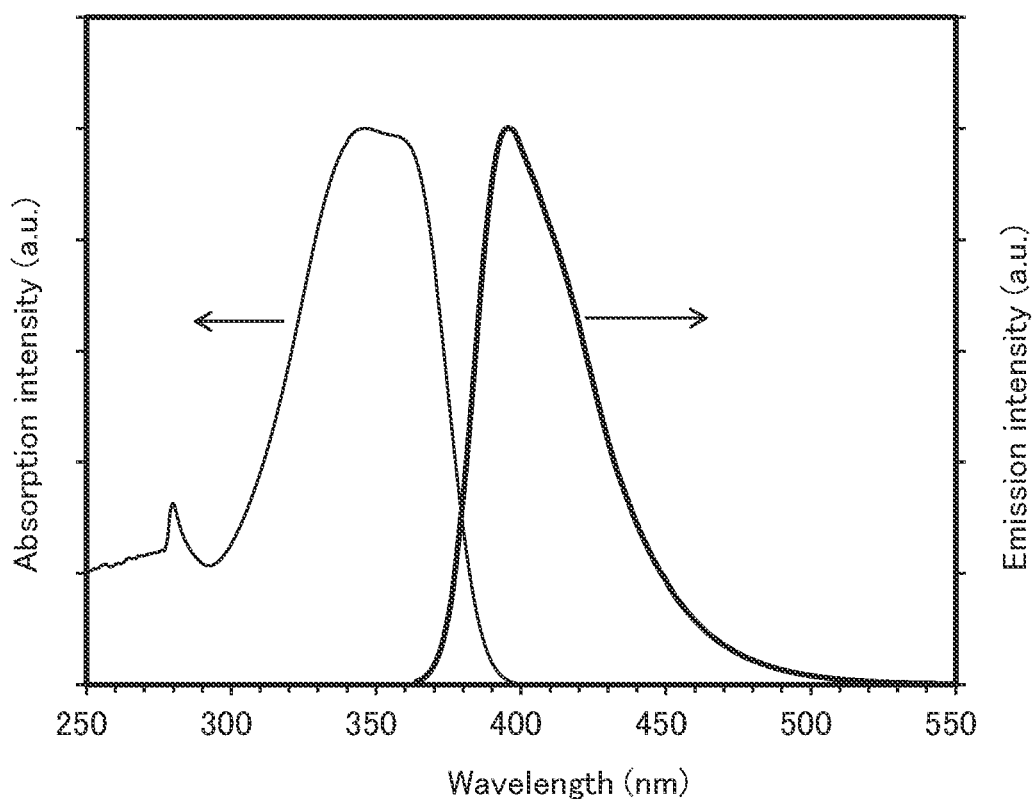
FIG. 79 shows an absorption spectrum and an emission spectrum of mmtBumTPoFBi-04 in a toluene solution.

Then, an ultraviolet-visible absorption spectrum (hereinafter, simply referred to as an absorption spectrum) of mmtBumTPoFBi-04 in a toluene solution and an emission spectrum thereof were measured. The absorption spectrum was measured at room temperature with an ultraviolet-visible light spectrophotometer (V-550, produced by JASCO Corporation) in a state where the toluene solution was put in a quartz cell. The emission spectrum was measured with a fluorescence spectrophotometer (FP-8600, produced by JASCO Corporation) at room temperature in a state where the toluene solution was put in a quartz cell. FIG. 79 shows obtained measurement results of the absorption spectrum and the emission spectrum. The horizontal axis represents the wavelength and the vertical axes represent the absorbance and emission intensity. In FIG. 79, two solid lines are shown; a thin line represents the absorption spectrum, and a thick line represents the emission spectrum. The absorbance shown in FIG. 79 is a result obtained by subtraction of an absorption spectrum of only toluene in a quartz cell from the measured absorption spectrum of the toluene solution in the quartz cell.

As shown in FIG. 79, the organic compound, mmtBumTPoFBi-04 had an emission peak at 396 nm.

Next, mmtBumTPoFBi-04 obtained in this example was analyzed by liquid chromatography mass spectrometry (LC/MS).

In the LC/MS analysis, liquid chromatography (LC) separation was performed with UltiMate 3000 produced by Thermo Fisher Scientific K.K., and mass spectrometry (MS) was performed with Q Exactive produced by Thermo Fisher Scientific K.K.

In the LC separation, a given column was used at a column temperature of 40° C., and solution sending was performed in such a manner that an appropriate solvent was selected, the sample was prepared by dissolving mmtBumTPoFBi-04 in an organic solvent at a given concentration, and the injection amount was 5.0 μL.

Figure 80:
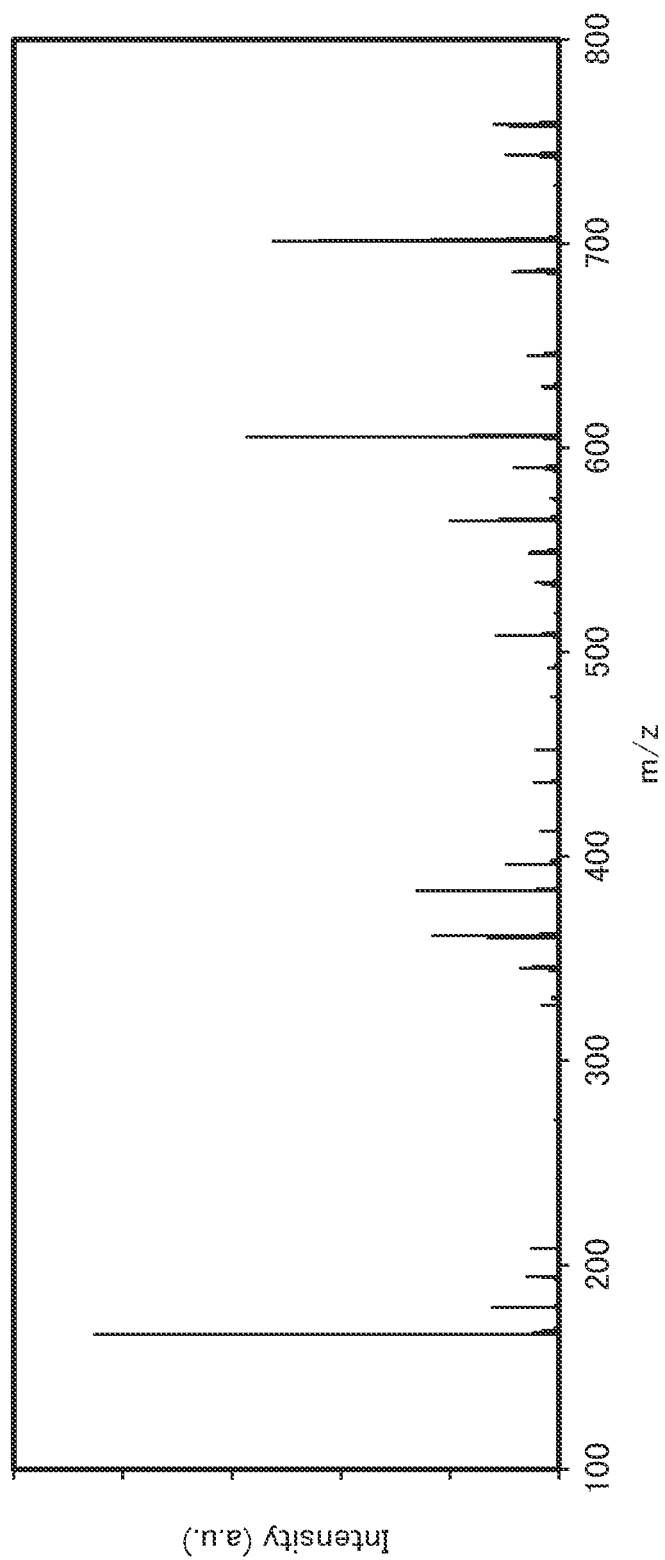
FIG. 80 shows an MS spectrum of mmtBumTPoFBi-04.

An ion derived from mmtBumTPoFBi-04, m/z=757.46, was subjected to the MS$^2$ measurement by a PRM method. F or setting of the PRM, the mass range of a target ion was set to m/z=757.46±2.0 (isolation window=4) and detection was performed in a positive mode. The measurement was performed with energy (normalized collision energy: NCE) for accelerating a target ion in a collision cell set to 50. The obtained MS spectrum is shown in FIG. 80.

Next, the glass transition temperature (hereinafter referred to as "Tg") of mmtBumTPoFBi-04 was measured. Tg was measured using a differential scanning calorimeter (Pyris 1 DSC produced by PerkinElmer Japan Co., Ltd.) in a state where a powder was put on an aluminum cell. As a result, Tg of mmtBumTPoFBi-04 was 123° C.

Example 14

Synthesis Example 8

In this example, a synthesis method of N-(3",5',5"-tri-tert-butyl-1,1':3',1"-terphenyl-4-yl)-N-(4-cyclohexylphenyl)-9,9-dimethyl-9H-fluoren-2-amine (abbreviation: mmtBumTPchPAF-04), which is the organic compound of one embodiment of the present invention represented by Structural Formula (151) in Embodiment 1, will be described. A structure of mmtBumTPchPAF-04 is shown below.

[Chemical Formula 63]

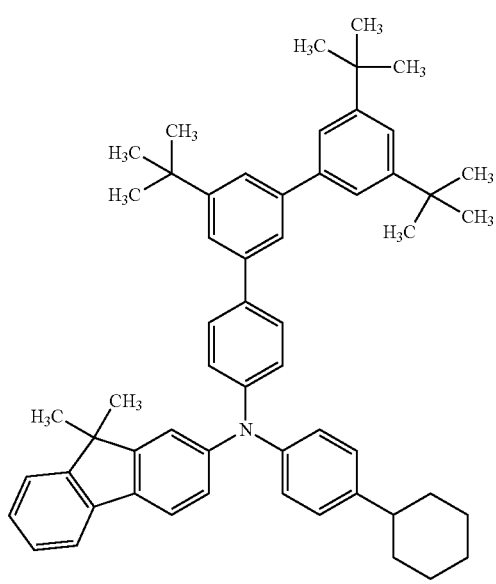

Step 1: Synthesis of 4-bromo-3",5',5"-tri-tert-butyl-1,1':3',1"-terphenyl

This synthesis step is similar to Step 1 in Synthesis Example 7.

Step 2: Synthesis of mmtBumTPchPAF-04

Into a three-neck flask were put 3.0 g (6.3 mmol) of 4-bromo-3",5',5"-tri-tert-butyl-1,1':3',1"-terphenyl obtained in Step 1,2,3 g (6.3 mmol) of N-(4-cyclohexylphenyl)-9,9-dimethyl-9H-fluoren-2-yl)amine, 1.8 g (18.9 mmol) of sodium tert-butoxide, and 32 mL of toluene. The mixture was degassed under reduced pressure, the air in the flask was replaced with nitrogen, 72 mg (0.13 mmol) of bis(dibenzylideneacetone)palladium(0) and 76 mg (0.38 mmol) of tri-tert-butylphosphine were added thereto, and the mixture was heated at 80° C. for approximately two hours. After that, the temperature of the flask was lowered to approximately 60° C., approximately 1 mL of water was added, a precipitated solid was separated by filtration, and the solid was washed with toluene. The filtrate was concentrated, and the obtained toluene solution was purified by silica gel column chromatography. The obtained solution was concentrated to give a condensed toluene solution. Ethanol was added to this toluene solution and the toluene solution was concentrated under reduced pressure, whereby an ethanol suspension was obtained. The precipitate in the ethanol suspension was filtrated at approximately 20° C., and the obtained solid was dried at approximately 80° C. under reduced pressure, whereby 4.1 g of a target white solid was obtained in a yield of 85%. The synthesis scheme of mmtBumTPchPAF-04 is shown below.

[Chemical Formula 64]

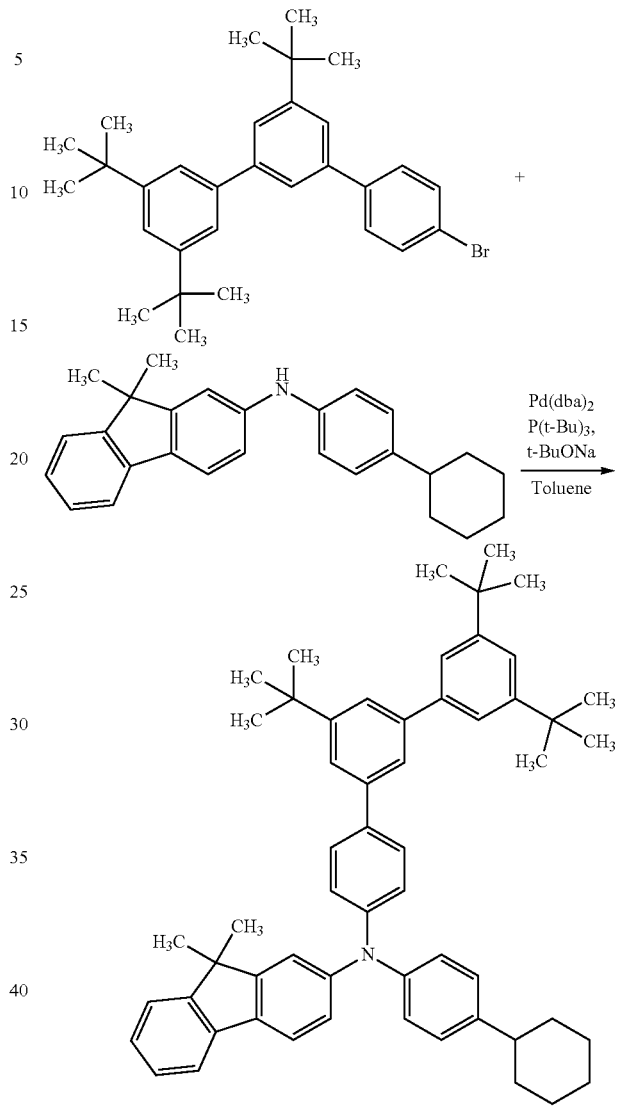

Figure 81A:
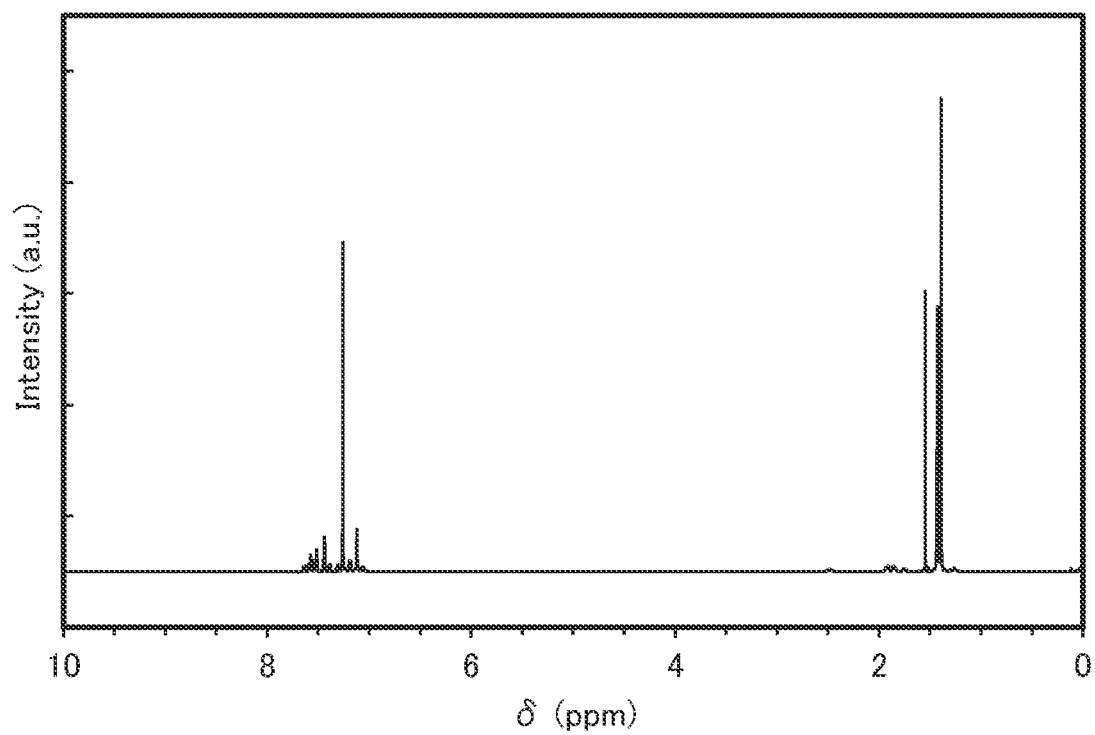
FIGS. 81A and 81B are $^1$H-NMR charts of mmtBumTPchPAF-04.
Figure 81B:
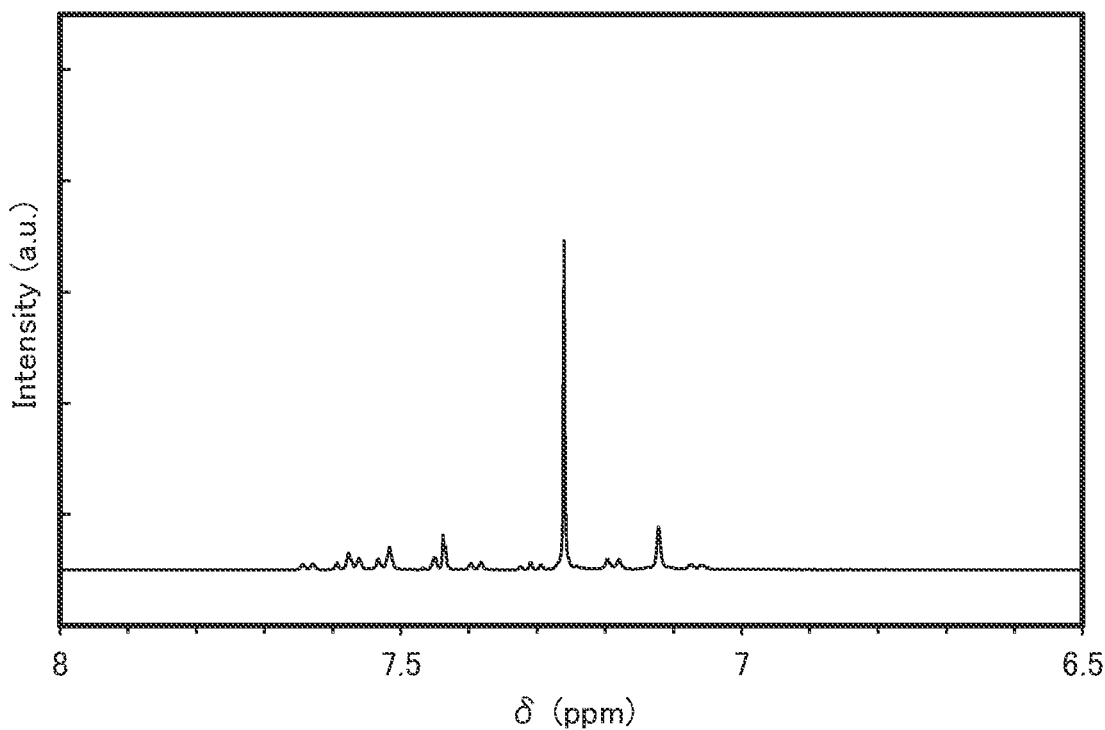

Analysis results by nuclear magnetic resonance ($^1$H-NMR) spectroscopy of the white solid obtained in Step 2 are shown in FIGS. 81A and 81B. Note that FIG. 81B is an enlarged graph of FIG. 81A in the range of 6.5 ppm to 8.0 ppm. In addition, numerical data is shown below. The results show that mmtBumTPchPAF-04 was synthesized in this synthesis example.

$^1$H-NMR. δ (CDCl$_3$): 7.63 (d, 1H, J=7.5 Hz), 7.52-7.59 (m, 7H), 7.44-7.45 (m, 4H), 7.39 (d, 1H, J=7.4 Hz), 7.31 (dd, 1H, J=7.4 Hz), 7.19 (d, 2H, J=6.6 Hz), 7.12 (m, 4H), 7.07 (d, 1H, J=9.7 Hz), 2.48 (brm, 1H), 1.84-1.93 (brm, 4H), 1.74-1.76 (brm, 1H), 1.43 (s, 18H), 1.39 (brm, 19H), 1.24-1.30 (brm, 1H).

Then, 4.1 g of the obtained white solid was purified by a train sublimation method. The purification by sublimation was conducted by heating at 255° C. under a pressure of 4.3 Pa with a flow rate of an argon gas of 15.0 mL/min. After the purification by sublimation, 3.0 g of a pale yellowish white solid was obtained at a collection rate of 73%.

Figure 82:
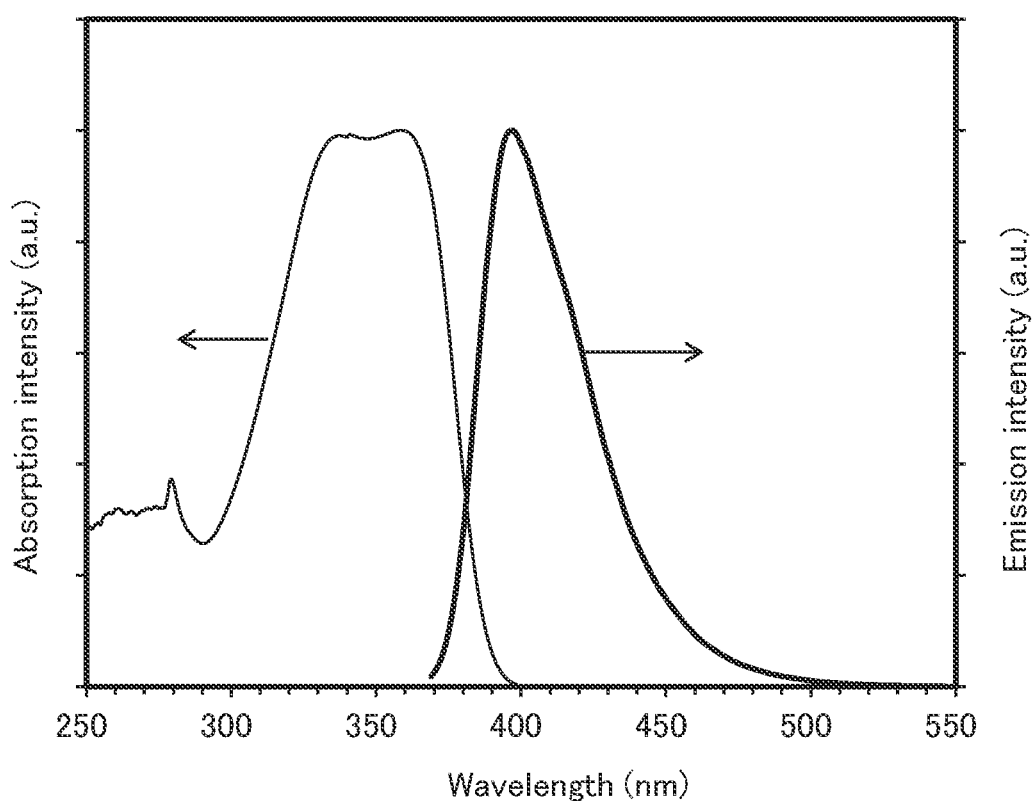
FIG. 82 shows an absorption spectrum and an emission spectrum of mmtBumTPchPAF-04 in a toluene solution.

Then, an ultraviolet-visible absorption spectrum (hereinafter, simply referred to as an absorption spectrum) of mmtBumTPchPAF-04 in a toluene solution and an emission spectrum thereof were measured. The absorption spectrum was measured at room temperature with an ultraviolet-visible light spectrophotometer (V-550, produced by JASCO Corporation) in a state where the toluene solution was put in a quartz cell. The emission spectrum was measured with a fluorescence spectrophotometer (FP-8600, produced by JASCO Corporation) at room temperature in a state where the toluene solution was put in a quartz cell. FIG. 82 shows obtained measurement results of the absorption spectrum and the emission spectrum. The horizontal axis represents the wavelength and the vertical axes represent the absorbance and emission intensity. In FIG. 82, two solid lines are shown; a thin line represents the absorption spectrum, and a thick line represents the emission spectrum. The absorbance shown in FIG. 82 is a result obtained by subtraction of an absorption spectrum of only toluene in a quartz cell from the measured absorption spectrum of the toluene solution in the quartz cell.

As shown in FIG. 82, the organic compound, mmtBumTPchPAF-04 had an emission peak at 397 nm.

Next, mmtBumTPchPAF-04 obtained in this example was analyzed by liquid chromatography mass spectrometry (LC/MS).

In the LC/MS analysis, liquid chromatography (LC) separation was performed with UltiMate 3000 produced by Thermo Fisher Scientific K.K., and mass spectrometry (MS) was performed with Q Exactive produced by Thermo Fisher Scientific K.K.

In the LC separation, a given column was used at a column temperature of 40° C., and solution sending was performed in such a manner that an appropriate solvent was selected, the sample was prepared by dissolving mmtBumTPchPAF-04 in an organic solvent at a given concentration, and the injection amount was 5.0 µL.

Figure 83:
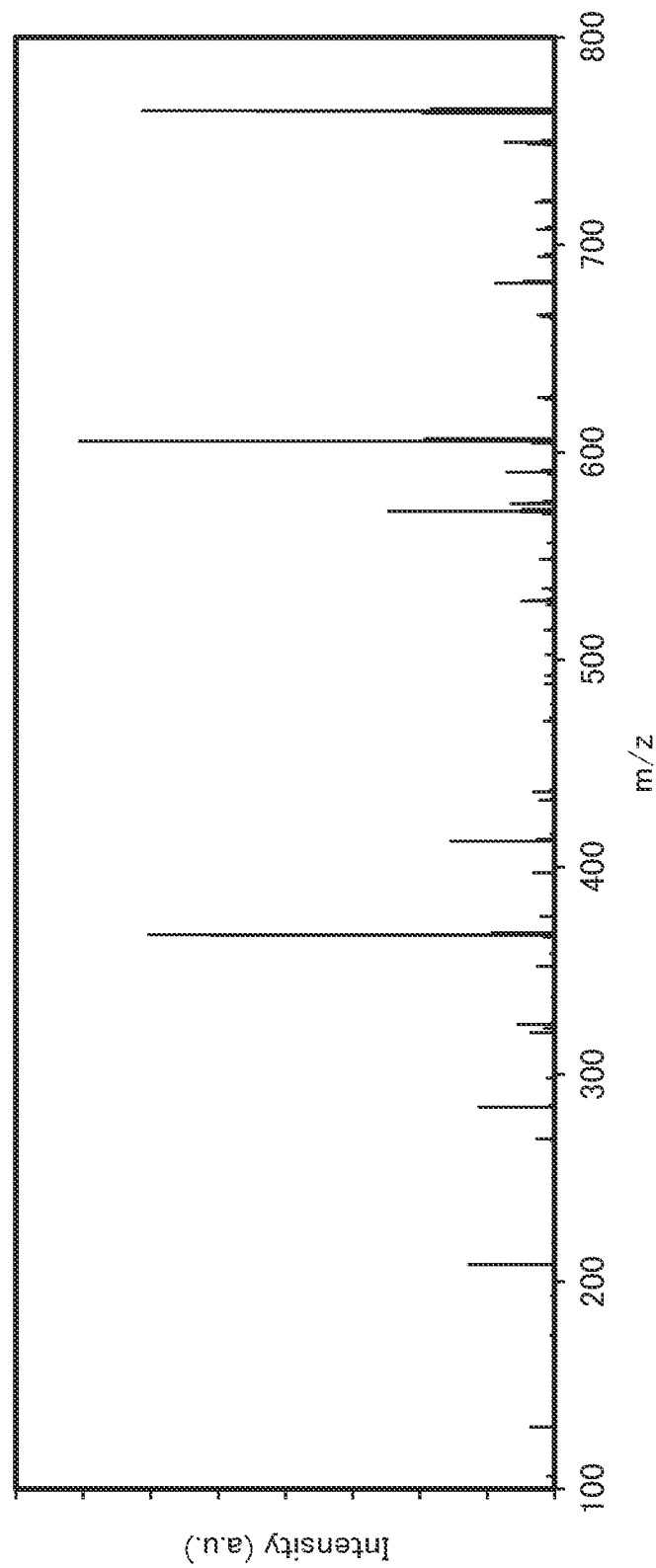
FIG. 83 shows an MS spectrum of mmtBumTPchPAF-04.

An ion derived from mmtBumTPchPAF-04, m/z=764.52, was subjected to the $MS^2$ measurement by a PRM method. F or setting of the PRM, the mass range of a target ion was set to m/z=764.52±2.0 (isolation window=4) and detection was performed in a positive mode. The measurement was performed with energy (normalized collision energy: NCE) for accelerating a target ion in a collision cell set to 50. The obtained MS spectrum is shown in FIG. 83.

Next, the glass transition temperature (hereinafter referred to as "Tg") of mmtBumTPchPAF-04 was measured. Tg was measured using a differential scanning calorimeter (Pyris 1 DSC produced by PerkinElmer Japan Co., Ltd.) in a state where a powder was put on an aluminum cell. As a result, Tg of mmtBumTPchPAF-04 was 122° C.

Example 15

Synthesis Example 9

In this example, a synthesis method of N-(1,1'-biphenyl-2-yl)-N-(3,3'',5''-tri-tert-butyl-1,1':4',1''-terphenyl-5-yl)-9,9-dimethyl-9H-fluoren-2-amine (abbreviation: mmtBumTPoFBi-05), which is the organic compound of one embodiment of the present invention represented by Structural Formula (175) in Embodiment 1, will be described. A structure of mmtBumTPoFBi-05 is shown below.

[Chemical Formula 65]

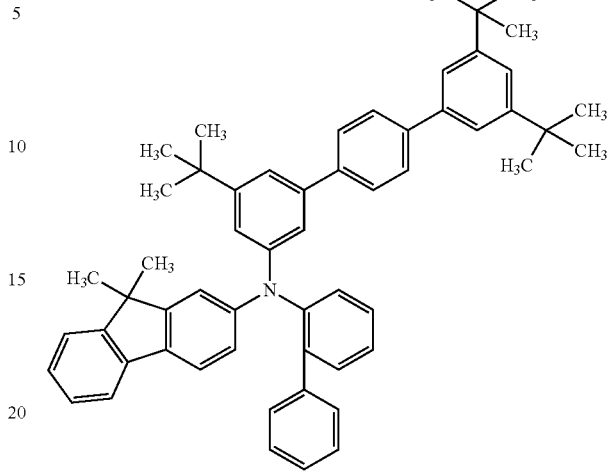

Step 1: Synthesis of 4-bromo-3',5'-di-tert-butylbiphenyl

Into a three-neck flask were put 12.0 g (43 mmol) of 1-bromo-4-iodobenzene, 10.0 g (43 mmol) of 3,5-di-tert-butylphenylboronic acid, 17.7 g (128 mmol) of potassium carbonate, 285 mL of toluene, 85 mL of ethanol, and 60 mL of tap water. The mixture was degassed under reduced pressure, the air in the flask was replaced with nitrogen, and 2.5 g (2.1 mmol) of tetrakis(triphenylphosphine)palladium (0) was added thereto. This mixture was heated at 40° C. for approximately five hours. After that, the temperature of the flask was lowered to room temperature, and the mixture was separated into an organic layer and an aqueous layer. Magnesium sulfate was added to this solution for drying to be concentrated. A hexane solution of the obtained solution was purified by silica gel column chromatography, whereby 11.1 g of a target colorless oily substance was obtained in a yield of 76%. The synthesis scheme of 3-bromo-3',5,5'-tri-tert-butylbiphenyl of Step 1 is shown below.

[Chemical Formula 66]

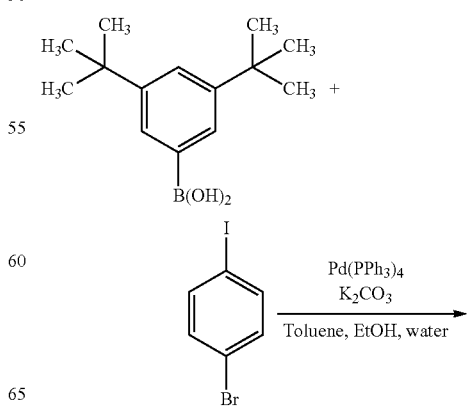

-continued

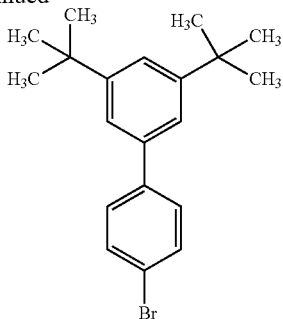

Step 2: Synthesis of 2-(3',5'-di-tert-butyl[1,1'-biphenyl]-4-yl)-4,4,5,5-tetramethyl-1,3,2-dioxaborolane Into a three-neck flask were put 11.1 g (32 mmol) of 4-bromo-3',5'-di-tert-butylbiphenyl obtained in Step 1, 9.0 g (35 mmol) of 4,4,4',4',5,5,5',5'-octamethyl-2,2'-bi-1,3,2-dioxaborolane, 9.5 g (96 mmol) of potassium acetate, and 214 mL of N,N-dimethylformamide. The mixture was degassed under reduced pressure, the air in the flask was replaced with nitrogen, 1.3 g (1.6 mmol) of [1,1'-bis(diphenylphosphino)ferrocene]dichloropalladium(II) was added thereto, and the mixture was heated at 100° C. for approximately three hours. Then, the temperature of the flask was lowered to room temperature, and the mixture was separated into an organic layer and an aqueous layer, and the aqueous layer was subjected to extraction with ethyl acetate. Magnesium sulfate was added to this solution to eliminate moisture, whereby the solution was concentrated. A toluene solution of the obtained mixture was purified by silica gel column chromatography, and the resulting solution was concentrated to give a condensed toluene solution. Ethanol was added to this toluene solution and the toluene solution was concentrated under reduced pressure, whereby an ethanol suspension was obtained. The precipitate was filtrated at approximately 20° C., and the obtained solid was dried at approximately 80° C. under reduced pressure, whereby 11.6 g of a target white solid was obtained in a yield of 92%. The synthesis scheme of Step 2 is shown below.

[Chemical Formula 67]

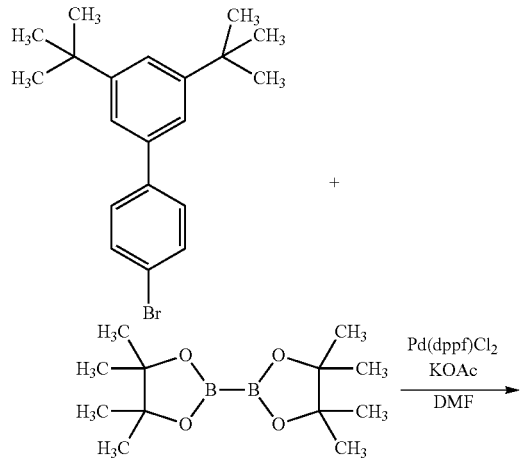

Step 3: Synthesis of 3-bromo-3",5,5"-tri-tert-butyl-1,1':3',1"-terphenyl

Into a three-neck flask were put 11.6 g (38.2 mmol) of 2-(3',5'-di-tert-butyl[1,1'-biphenyl]-4-yl)-4,4,5,5-tetramethyl-1,3,2-dioxaborolane, 16.6 g (57.3 mmol) of 1,3-dibromo-5-tert-butylbenzene, 15.8 g (115 mmol) of potassium carbonate, 255 mL of toluene, 76 mL of ethanol, and 57 mL of tap water. The mixture was degassed under reduced pressure, the air in the flask was replaced with nitrogen, 2.2 g (1.9 mmol) of tetrakis(triphenylphosphine)palladium(0) was added thereto, and the mixture was heated at 80° C. for approximately 10 hours. After that, the temperature of the flask was lowered to room temperature, and the mixture was separated into an organic layer and an aqueous layer. Magnesium sulfate was added to this solution for drying to be concentrated. A hexane solution of the obtained solution was purified by silica gel column chromatography, whereby 4.4 g of a target white solid was obtained in a yield of 24.4%. The synthesis scheme of 3-bromo-3",5,5"-tri-tert-butyl-1,1':3',1"-terphenyl of Step 3 is shown below.

[Chemical Formula 68]

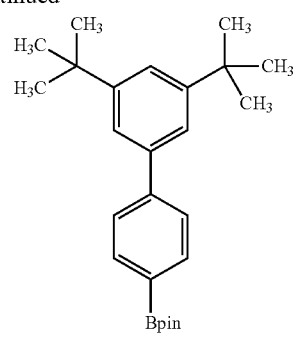

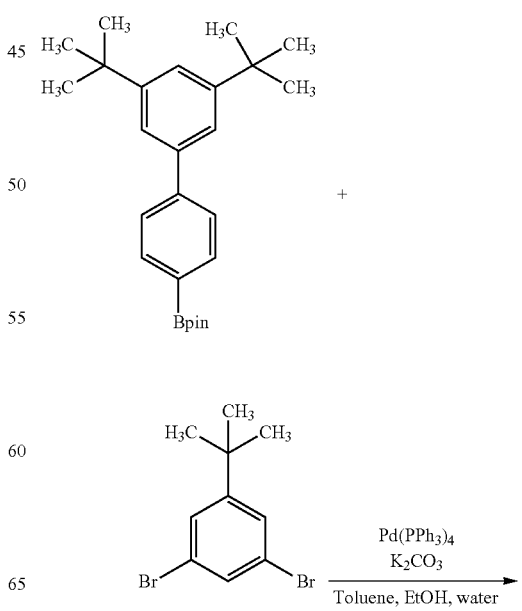

-continued

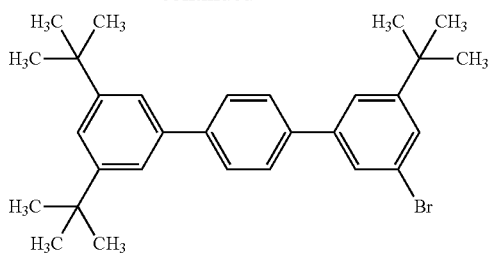

Step 4: Synthesis of mmtBumTPoFBi-05

Into a three-neck flask were put 2.2 g (4.6 mmol) of 3-bromo-3",5,5"-tri-tert-butyl-1,1':3',1"-terphenyl, 1.7 g (4.6 mmol) of N-(1,1'-biphenyl-4-yl)-N-phenyl-9,9-dimethyl-9H-fluoren-2-amine, 1.3 g (13.8 mol) of sodium tert-butoxide, and 23 mL of toluene. The mixture was degassed under reduced pressure, the air in the flask was replaced with nitrogen, 53 mg (0.10 mmol) of bis(dibenzylideneacetone)palladium(0) and 56 mg (0.28 mmol) of tri-tert-butylphosphine were added thereto, and the mixture was heated at 120° C. for approximately eight hours. After that, the temperature of the flask was lowered to approximately 60° C., approximately 1 mL of water was added, a precipitated solid was separated by filtration, and the solid was washed with toluene. The filtrate was concentrated, and the obtained toluene solution was purified by silica gel column chromatography. The obtained solution was concentrated to give a condensed toluene solution. Ethanol was added to this toluene solution and the toluene solution was concentrated under reduced pressure, whereby an ethanol suspension was obtained. The precipitate in the ethanol suspension was filtrated at approximately 20° C., and the obtained solid was dried at approximately 80° C. under reduced pressure, whereby 2.7 g of a target white solid was obtained in a yield of 77%. The synthesis scheme of Step 4 is shown below.

[Chemical Formula 69]

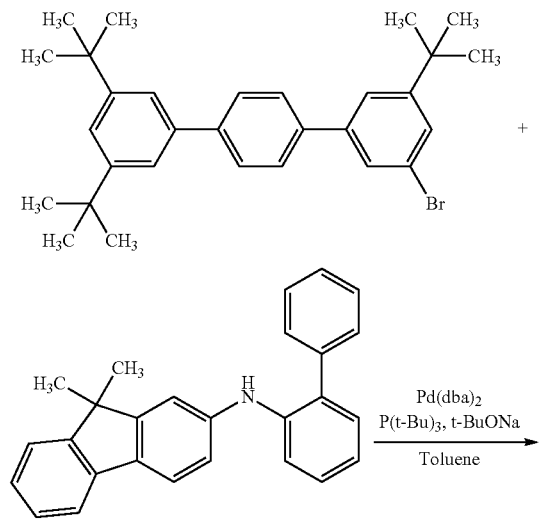

-continued

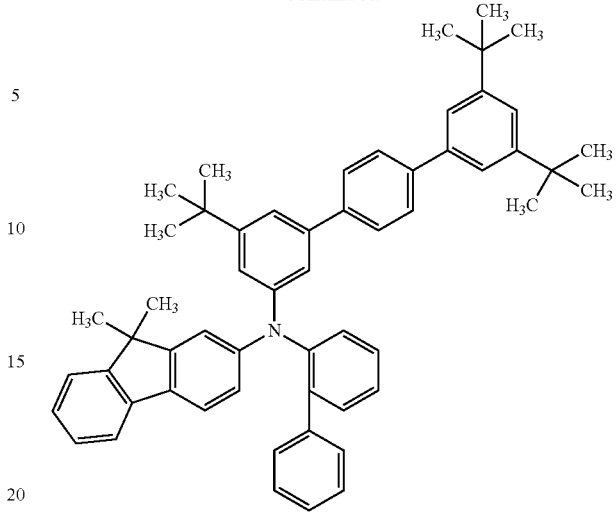

Figure 84A:
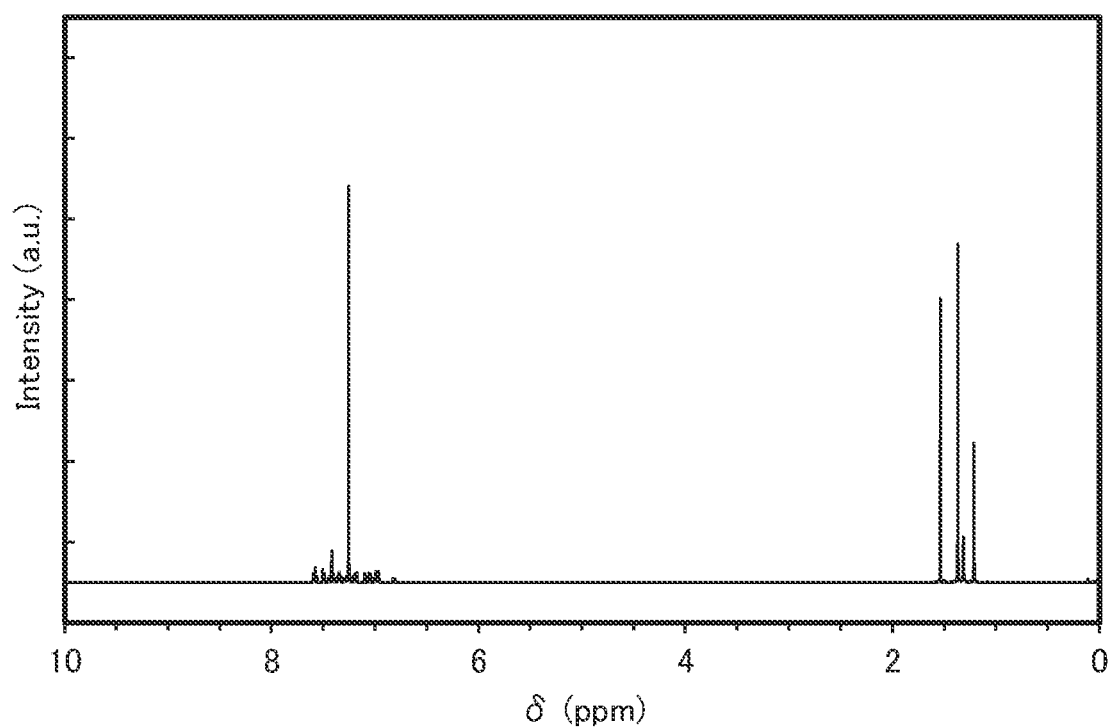
FIGS. 84A and 84B are $^1$H-NMR charts of mmtBumTPoFBi-05.
Figure 84B:
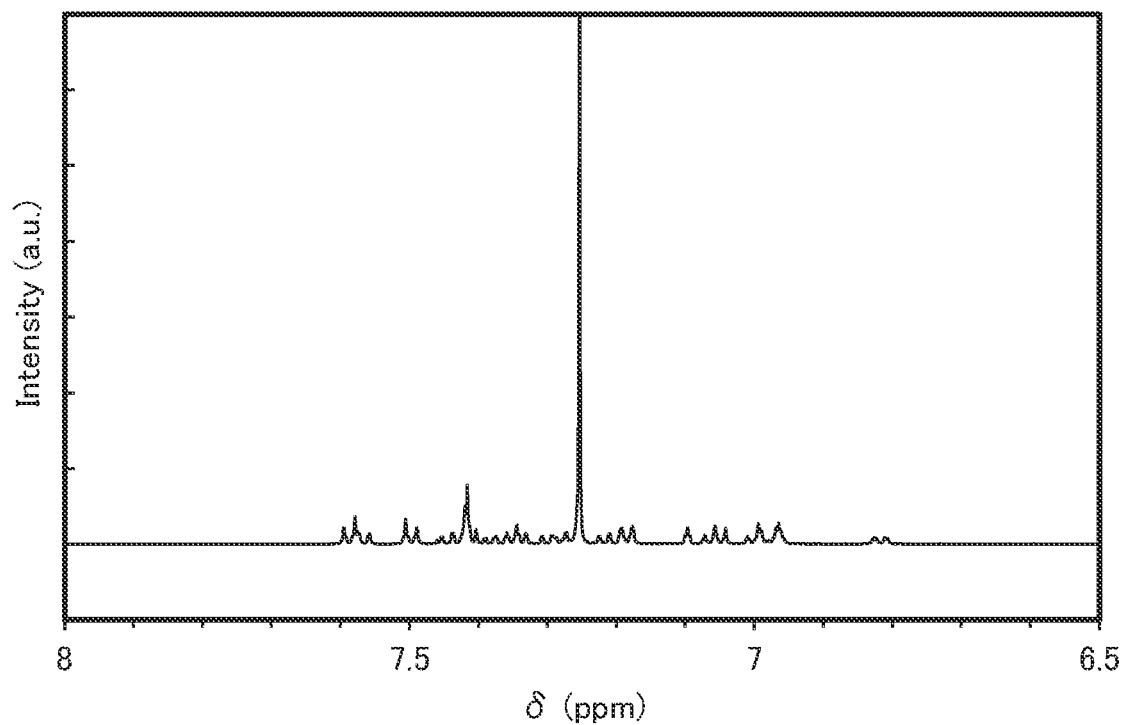

Analysis results by nuclear magnetic resonance ($^1$H-NMR) spectroscopy of the white solid obtained in Step 4 are shown in FIGS. 84A and 84B. Note that FIG. 84B is an enlarged graph of FIG. 84A in the range of 6.5 ppm to 8.0 ppm. In addition, numerical data is shown below. The results show that mmtBumTPoFBi-05 was synthesized in this synthesis example.

$^1$H-NMR. δ (CDCl$_3$): 7.56-7.60 (m, 3H), 7.49 (d, 2H, J=8.0 Hz), 7.27-7.46 (m, 10H), 7.22 (dd, 1H, J=7.5 Hz, 1.2 Hz), 7.18 (dd, 2H, J=8.0 Hz, 1.2 Hz), 7.10 (dd, 1H, J=1.7 Hz), 7.04-7.07 (m, 2H), 6.97-7.01 (m, 4H), 6.82 (dd, 1H, J=8.0 Hz, 2.3 Hz), 1.37 (s, 18H), 1.31 (s, 6H), 1.21 (s, 9H).

Then, 2.7 g of the obtained white solid was purified by a train sublimation method. The purification by sublimation was conducted by heating at 255° C. under a pressure of 2.9 Pa with a flow rate of an argon gas of 15.0 mL/min. After the purification by sublimation, 2.0 g of a pale yellowish white solid was obtained at a collection rate of 74%.

Figure 85:
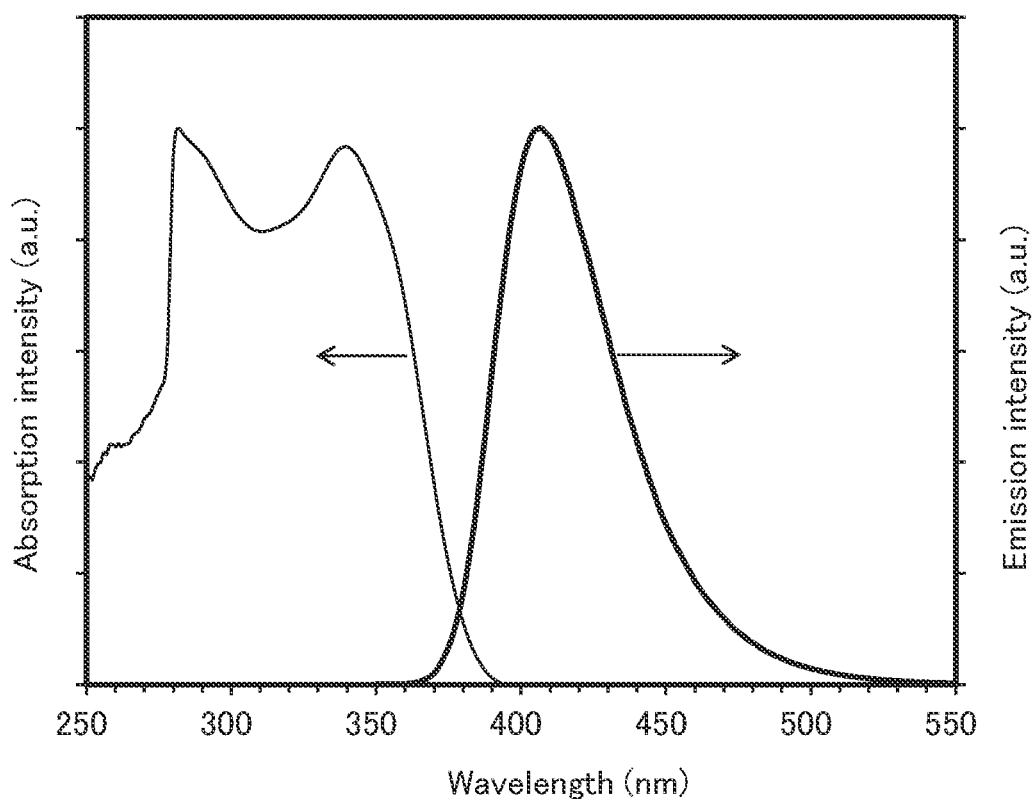
FIG. 85 shows an absorption spectrum and an emission spectrum of mmtBumTPoFBi-05 in a toluene solution.

Then, an ultraviolet-visible absorption spectrum (hereinafter, simply referred to as an absorption spectrum) of mmtBumTPoFBi-05 in a toluene solution and an emission spectrum thereof were measured. The absorption spectrum was measured at room temperature with an ultraviolet-visible light spectrophotometer (V-550, produced by JASCO Corporation) in a state where the toluene solution was put in a quartz cell. The emission spectrum was measured with a fluorescence spectrophotometer (FP-8600, produced by JASCO Corporation) at room temperature in a state where the toluene solution was put in a quartz cell. FIG. 85 shows obtained measurement results of the absorption spectrum and the emission spectrum. The horizontal axis represents the wavelength and the vertical axes represent the absorbance and emission intensity. In FIG. 85, two solid lines are shown; a thin line represents the absorption spectrum, and a thick line represents the emission spectrum. The absorbance shown in FIG. 85 is a result obtained by subtraction of an absorption spectrum of only toluene in a quartz cell from the measured absorption spectrum of the toluene solution in the quartz cell.

As shown in FIG. 85, the organic compound, mmtBumTPoFBi-05 had an emission peak at 407 nm.

Next, the glass transition temperature (hereinafter referred to as "Tg") of mmtBumTPoFBi-05 was measured. Tg was measured using a differential scanning calorimeter (Pyris 1 DSC produced by PerkinElmer Japan Co., Ltd.) in a state where a powder was put on an aluminum cell. As a result, Tg of mmtBumTPoFBi-05 was 118° C.

Example 16

Synthesis Example 10

In this example, a synthesis method of N-(4-cyclohexylphenyl)-N-(3,3",5"-tri-tert-butyl-1,1':4',1"-terphenyl-5-yl)-9,9-dimethyl-9H-fluoren-2-amine (abbreviation: mmtBumTPchPAF-05), which is the organic compound of one embodiment of the present invention represented by Structural Formula (176) in Embodiment 1, will be described. A structure of mmtBumTPchPAF-05 is shown below.

[Chemical Formula 70]

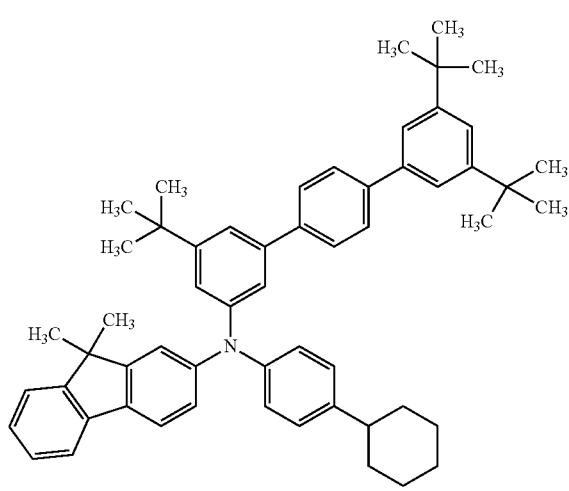

Step 1: Synthesis of 4-bromo-3',5'-di-tert-butylbiphenyl

This synthesis step is similar to Step 1 in Synthesis Example 9.

Step 2: Synthesis of 2-(3',5'-di-tert-butyl[1,1'-biphenyl]-4-yl)-4,4,5,5-tetramethyl-1,3,2-dioxaborolane This synthesis step is similar to Step 2 in Synthesis Example 9.

Step 3: Synthesis of 3-bromo-3",5,5"-tri-tert-butyl-1,1':3',1"-terphenyl

This synthesis step is similar to Step 3 in Synthesis Example 9.

Step 4: Synthesis of mmtBumTPchPAF-05

Into a three-neck flask were put 2.2 g (4.6 mmol) of 3-bromo-3",5,5"-tri-tert-butyl-1,1':3',1"-terphenyl obtained in Step 3, 1.7 g of (4.6 mmol) of N-(4-cyclohexylphenyl)-N-(9,9-dimethyl-9H-fluoren-2-yl)amine, 1.3 g (13.8 mmol) of sodium-tert-butoxide, and 23 mL of toluene. The mixture was degassed under reduced pressure, the air in the flask was replaced with nitrogen, 53 mg (0.10 mmol) of bis(dibenzylideneacetone)palladium(0) and 56 mg (0.28 mmol) of tri-tert-butylphosphine were added thereto, and the mixture was heated at 80° C. for approximately two hours. After that, the temperature of the flask was lowered to approximately 60° C., approximately 1 mL of water was added, a precipitated solid was separated by filtration, and the solid was washed with toluene. The filtrate was concentrated, and the obtained toluene solution was purified by silica gel column chromatography. The obtained solution was concentrated to give a condensed toluene solution. Ethanol was added to this toluene solution and the toluene solution was concentrated under reduced pressure, whereby an ethanol suspension was obtained. The precipitate in the ethanol suspension was filtrated at approximately 20° C., and the obtained solid was dried at approximately 80° C. under reduced pressure, whereby 3.2 g of a target white solid was obtained in a yield of 91%. The synthesis scheme of mmtBumTPchPAF-05 is shown below.

[Chemical Formula 71]

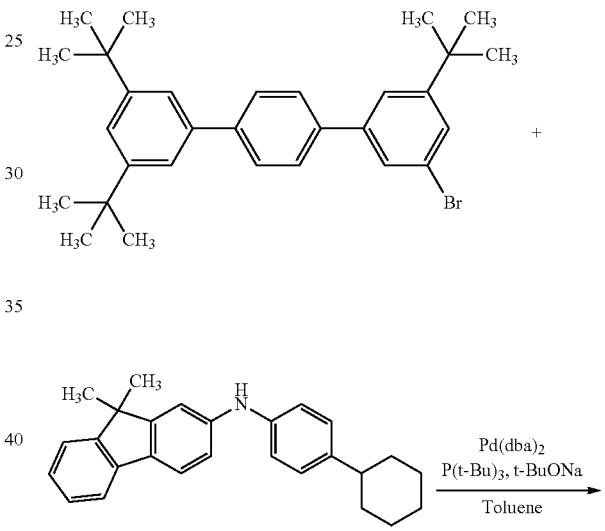

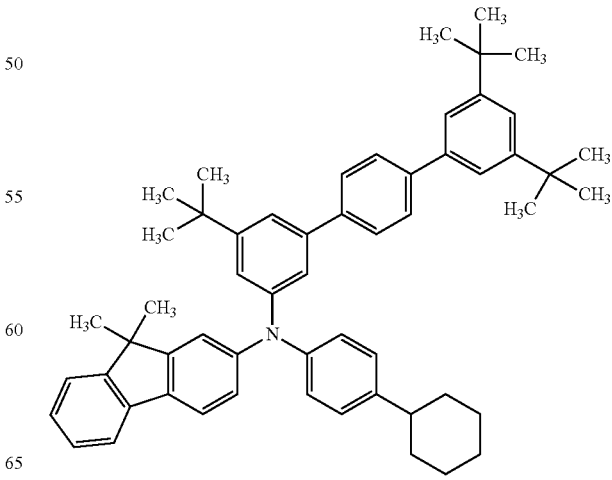

Figure 86A:
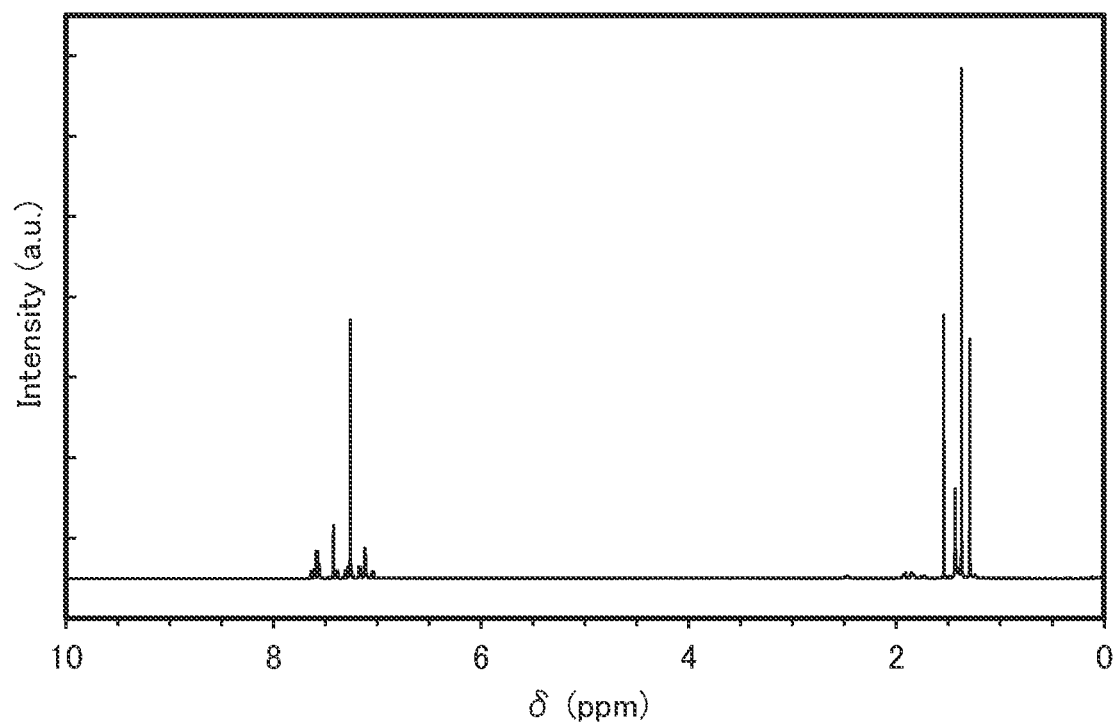
FIGS. 86A and 86B are $^1$H-NMR charts of mmtBumTPchPAF-05.
Figure 86B:
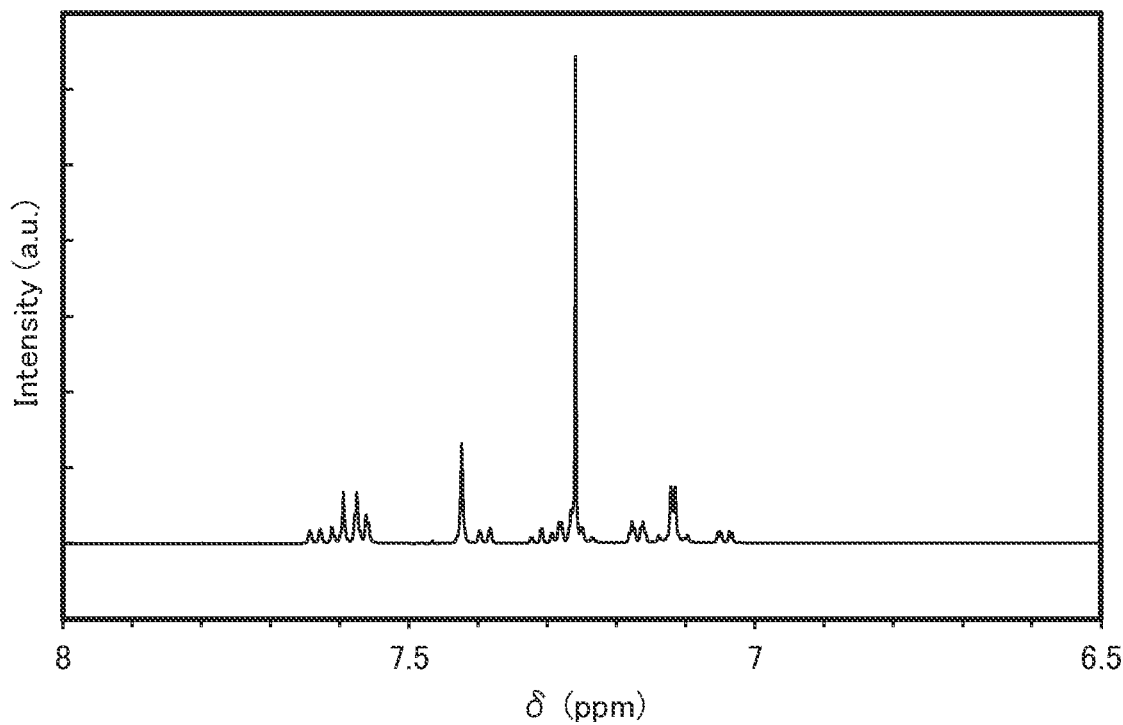

Analysis results by nuclear magnetic resonance ($^1$H-NMR) spectroscopy of the white solid obtained in Step 4 are shown in FIGS. 86A and 86B. Note that FIG. 86B is an enlarged graph of FIG. 86A in the range of 6.5 ppm to 8.0 ppm. The results show that mmtBumTPchPAF-05 was synthesized in this synthesis example.

$^1$H-NMR. δ (CDCl$_3$): 7.64 (d, 1H, J=7.4 Hz), 7.56-7.61 (m, 6H), 7.42 (s, 3H), 7.39 (d, 1H, J=7.4 Hz), 7.23-7.32 (m, 5H), 7.12 (dd, 4H, J=3.4 Hz, 6.3 Hz, 2.3 Hz), 7.04 (dd, 1H, J=7.9 Hz, 1.7 Hz), 2.48-2.50 (brm, 1H), 1.84-1.93 (brm, 4H), 1.73-1.76 (brm, 1H), 1.43 (s, 6H), 1.40-1.42 (m, 4H), 1.37 (s, 18H), 1.29 (s, 9H), 1.24-1.26 (m, 1H).

Then, 3.2 g of the obtained white solid was purified by a train sublimation method. The purification by sublimation was conducted by heating at 255° C. under a pressure of 2.9 Pa with a flow rate of an argon gas of 15.0 mL/min. After the purification by sublimation, 2.1 g of a pale yellowish white solid was obtained at a collection rate of 66%.

Figure 87:
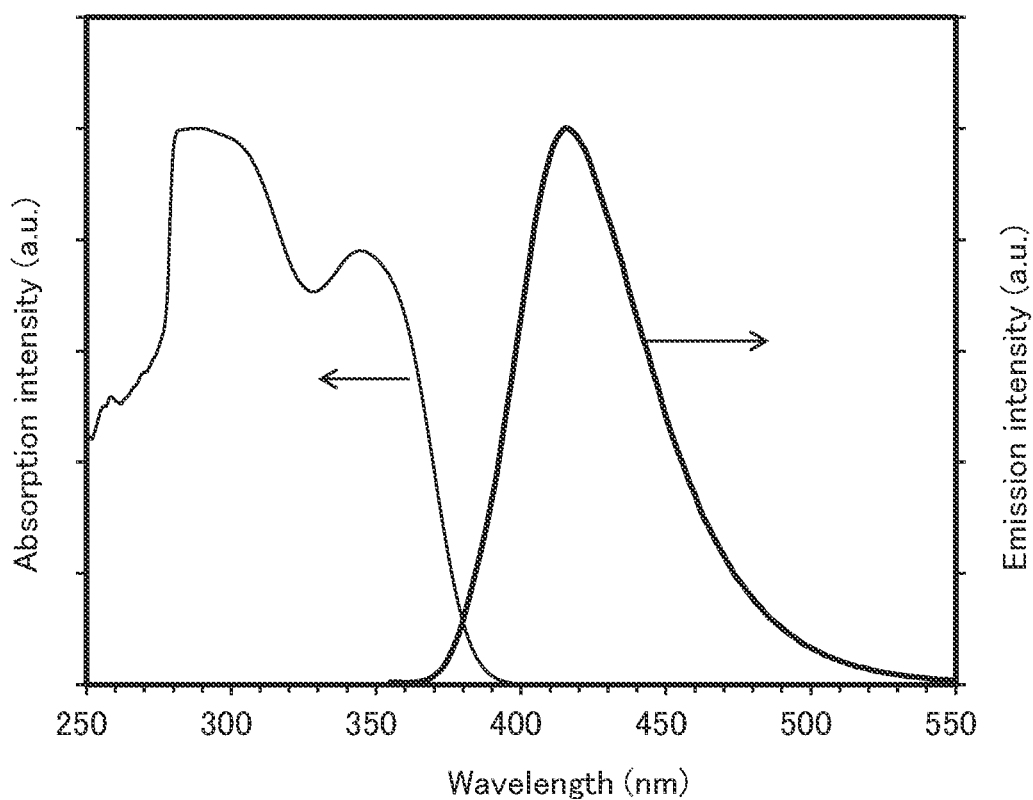
FIG. 87 shows an absorption spectrum and an emission spectrum of mmtBumTPchPAF-05 in a toluene solution.

Then, an ultraviolet-visible absorption spectrum (hereinafter, simply referred to as an absorption spectrum) of mmtBumTPchPAF-05 in a toluene solution and an emission spectrum thereof were measured. The absorption spectrum was measured at room temperature with an ultraviolet-visible light spectrophotometer (V-550, produced by JASCO Corporation) in a state where the toluene solution was put in a quartz cell. The emission spectrum was measured with a fluorescence spectrophotometer (FP-8600, produced by JASCO Corporation) at room temperature in a state where the toluene solution was put in a quartz cell. FIG. 87 shows obtained measurement results of the absorption spectrum and the emission spectrum. The horizontal axis represents the wavelength and the vertical axes represent the absorbance and emission intensity. In FIG. 87, two solid lines are shown; a thin line represents the absorption spectrum, and a thick line represents the emission spectrum. The absorbance shown in FIG. 87 is a result obtained by subtraction of an absorption spectrum of only toluene in a quartz cell from the measured absorption spectrum of the toluene solution in the quartz cell.

As shown in FIG. 87, the organic compound, mmtBumTPchPAF-05 had an emission peak at 416 nm.

Next, the glass transition temperature (hereinafter referred to as "Tg") of mmtBumTPchAPF-05 was measured. Tg was measured using a differential scanning calorimeter (Pyris 1 DSC produced by PerkinElmer Japan Co., Ltd.) in a state where a powder was put on an aluminum cell. As a result, Tg of mmtBumTPchAPF-05 was 121° C.

Example 17

Synthesis Example 11

In this example, a synthesis method of N-(1,1'-biphenyl-2-yl)-N-(3',3''',5'',5'''-tetra-t-butyl-1,1':3',1'':5',1'''-quaterphenyl-4-yl)-9,9-dimethyl-9H-fluoren-2-amine (abbreviation: mmtBumQPoFBi), which is the organic compound of one embodiment of the present invention, will be described. A structure of mmtBumQPoFBi is shown below.

[Chemical Formula 72]

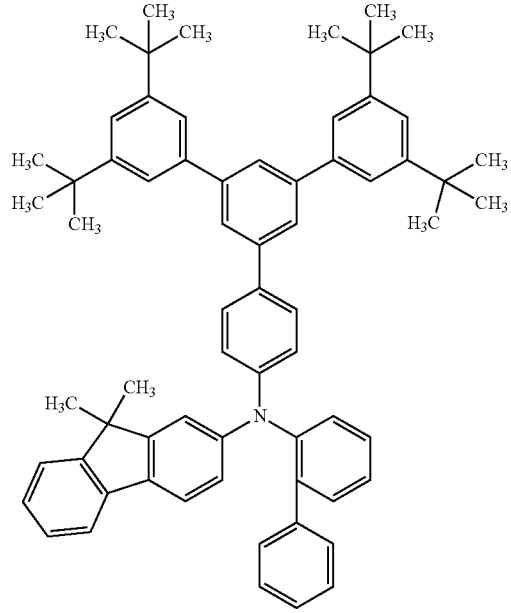

Step 1: Synthesis of N-(1,1'-biphenyl-2-yl)-N-(1-bromophenyl-4-yl)-9,9-dimethyl-9H-fluoren-2-amine Into a three-neck flask were put 10 g (28 mmol) of 2-(2-biphenylyl)amino-9,9-dimethylfluorene, 17 g (55 mmol) of 1-bromo-4-iodobenzene, 4.0 g (42 mmol) of sodium tert-butoxide, and 92 mL of toluene. The mixture was degassed under reduced pressure, and then the air in the flask was replaced with nitrogen. Then, 1.3 g (1.4 mmol) of bis(dibenzylideneacetone)palladium(0) and 0.28 g (1.4 mmol) of tri-tert-butylphosphine were added thereto, and the mixture was heated at 80° C. for approximately four hours. After that, the temperature of the flask was lowered to approximately 60° C., approximately 1 mL of water was added, a precipitated solid was separated by filtration, and the solid was washed with toluene. The filtrate was concentrated, and the obtained toluene solution was purified by silica gel column chromatography. The obtained solution was concentrated to give a condensed toluene solution. Ethanol was added to this toluene solution and the toluene solution was concentrated under reduced pressure, whereby an ethanol suspension was obtained. The precipitate was filtrated at approximately 20° C., and the obtained solid was dried at approximately 80° C. under reduced pressure, whereby 9.4 g of a target white solid was obtained in a yield of 66%. The synthesis scheme of Step 1 is shown below.

[Chemical Formula 73]

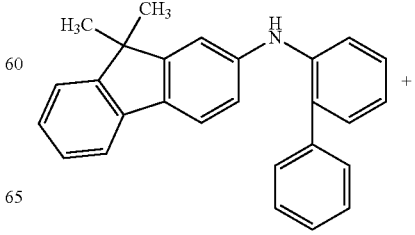

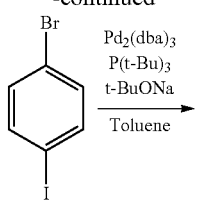

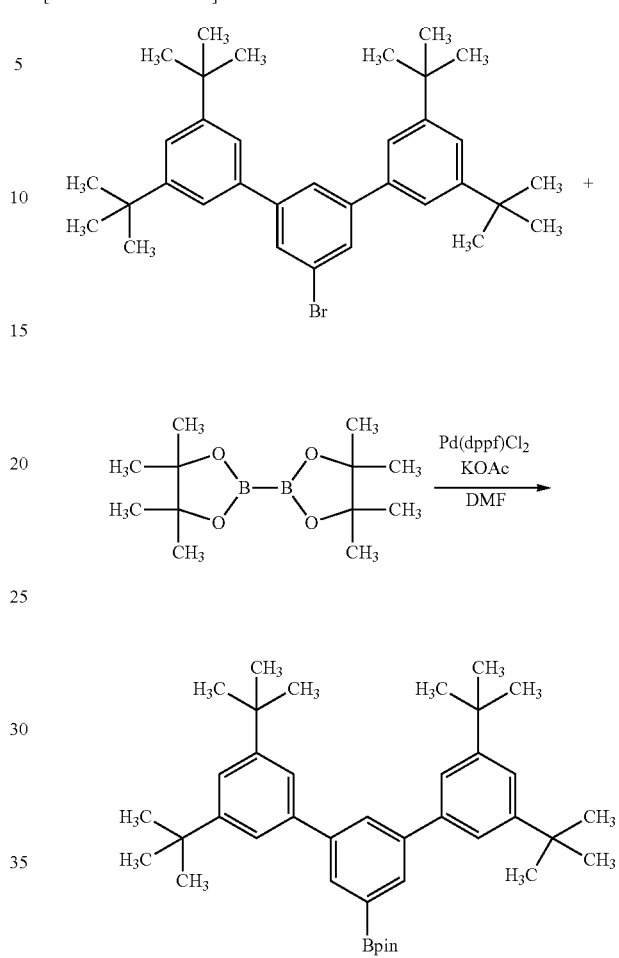

[Chemical Formula 74]

Step 2: Synthesis of 2-(3',3'',5',5''-tetra-tert-butyl[1,1':3,1''-terphenyl]-5-yl)-4,4,5,5-tetramethyl-1,3,2-dioxaborolane Into a three-neck flask were put 7.0 g (13 mmol) of 5-bromo-3',3'',5',5''-tetra-tert-butyl-1,1':3,1''-terphenyl, 3.7 g (14 mmol) of 4,4,4',4',5,5,5',5'-octamethyl-2,2'-bi-1,3,2-dioxaborolane, 3.9 g (39 mmol) of potassium acetate, and 87 mL of N,N-dimethylformamide. The mixture was degassed under reduced pressure, and then the air in the flask was replaced with nitrogen. Then, 0.53 g (0.66 mmol) of [1,1'-bis(diphenylphosphino)ferrocene]dichloropalladium(II) was added thereto, and the mixture was heated at 100° C. for approximately three hours. Then, the temperature of the flask was lowered to room temperature, and the mixture was separated into an organic layer and an aqueous layer, and the aqueous layer was subjected to extraction with ethyl acetate. Magnesium sulfate was added to this solution for drying to be concentrated. A toluene solution of the obtained mixture was purified by silica gel column chromatography, and the resulting solution was concentrated to give a condensed toluene solution. Ethanol was added to this toluene solution and the toluene solution was concentrated under reduced pressure, whereby an ethanol suspension was obtained. The precipitate was filtrated at approximately 20° C., and the obtained solid was dried at approximately 80° C. under reduced pressure, whereby 5.2 g of a target white solid was obtained in a yield of 68%. The synthesis scheme of Step 2 is shown below.

Step 3: Synthesis of mmtBumQPoFBi

Into a three-neck flask were put 1.7 g (3.4 mmol) of N-(1,1'-biphenyl-2-yl)-N-(1-bromophenyl-4-yl)-9,9-dimethyl-9H-fluoren-2-amine synthesized in Step 1, 2.0 g (3.4 mmol) of 2-(3',3'',5',5''-tetra-tert-butyl[1,1':3,1''-terphenyl]-5-yl)-4,4,5,5-tetramethyl-1,3,2-dioxaborolane synthesized in Step 2, 1.4 g (10 mmol) of potassium carbonate, 23 mL of toluene, 7.0 mL of ethanol, and 5.0 mL of tap water. The mixture was degassed under reduced pressure, the air in the flask was replaced with nitrogen, 15 mg (0.068 mmol) of palladium acetate and 41 mg (0.14 mmol) of tris(2-methylphenyl)phosphine were added thereto, and the mixture was heated at 80° C. for approximately five hours. After that, the temperature of the flask was lowered to room temperature, and the mixture was separated into an organic layer and an aqueous layer. Magnesium sulfate was added to the organic layer for drying to be concentrated. A hexane solution of the obtained solution was purified by silica gel column chromatography, whereby 2.2 g of a target colorless oily substance was obtained in a yield of 73%. The synthesis scheme of Step 3 is shown below.

249

[Chemical Formula 75]

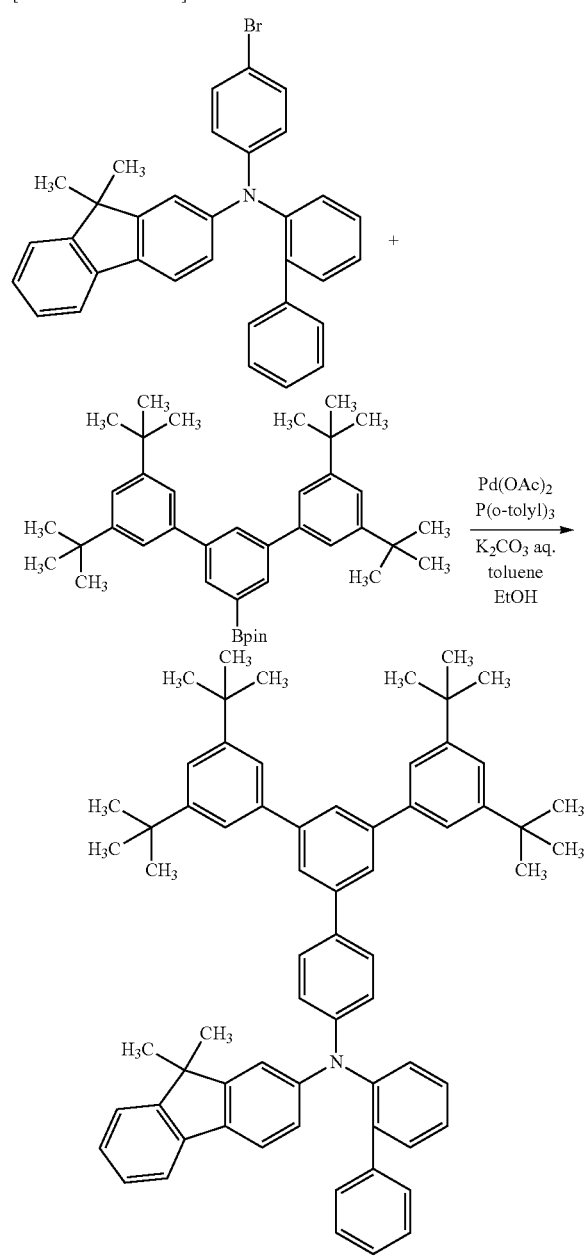

Figure 88A:
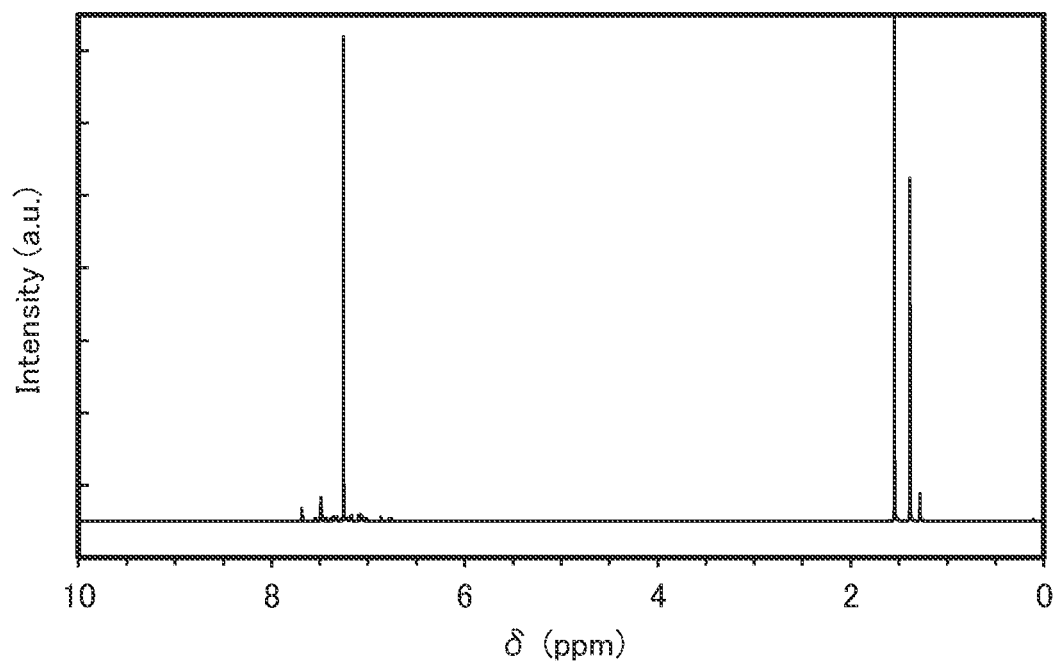
FIGS. 88A and 88B are $^1$H-NMR charts of mmtBumQPoFBi.
Figure 88B:
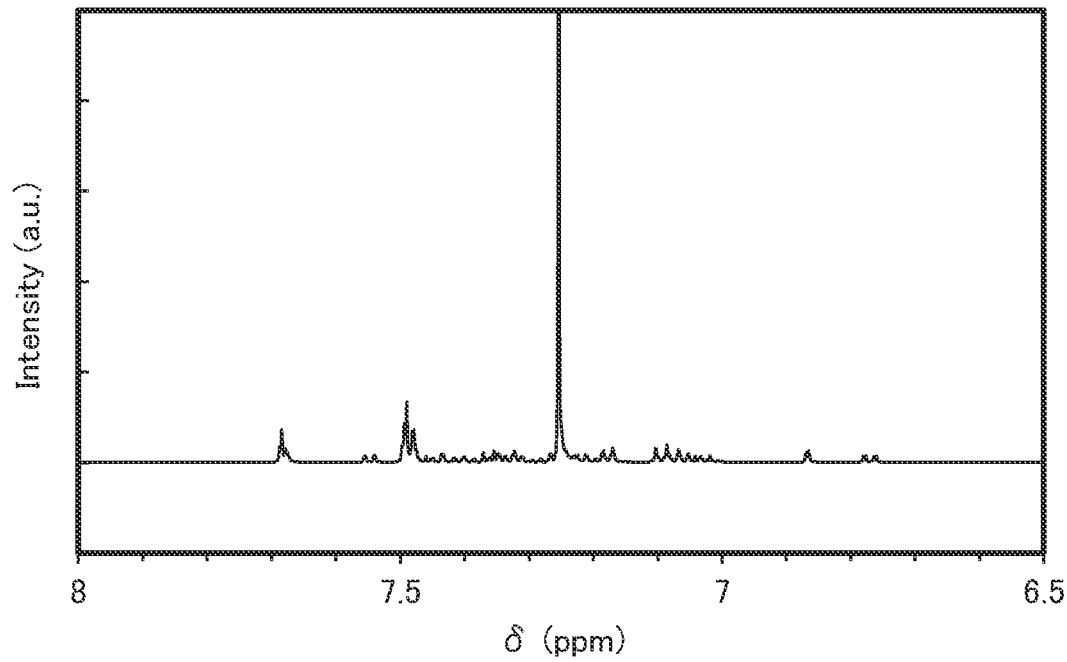

Analysis results by nuclear magnetic resonance ($^1$H-NMR) spectroscopy of the white solid obtained in Step 3 are shown in FIGS. 88A and 88B and below. The results show that mmtBumQPoFBi was synthesized in this synthesis example.

$^1$H-NMR. δ (CDCl$_3$): 7.68-7.69 (m, 3H), 7.55 (d, 1H, J=7.4 Hz), 7.48-7.50 (m, 8H), 7.27-7.46 (m, 6H), 7.18-7.23 (m, 4H), 7.01-7.11 (m, 5H), 6.87 (d, 1H, J=1.7 Hz), 6.78 (dd, 1H, J=5.2 Hz, 2.3 Hz), 1.39 (s, 36H), 1.29 (s, 6H).

Then, 2.2 g of the obtained white solid was purified by a train sublimation method. The purification by sublimation was conducted by heating at 260° C. under a pressure of 2.9 Pa with a flow rate of an argon gas of 10 mL/min. After the purification by sublimation, 1.5 g of a pale yellowish white solid was obtained at a collection rate of 68%.

250

Example 18

Synthesis Example 12

In this example, a synthesis method of N-(4-cyclohexylphenyl)-N-(3",3"',5",5"'-tetra-t-butyl-1,1':3',1":5',1"'-quaterphenyl-4-yl)-9,9-dimethyl-9H-fluoren-2-amine (abbreviation: mmtBumQPchPAF), which is the organic compound of one embodiment of the present invention, will be described. A structure of mmtBumQPchPAF is shown below.

[Chemical Formula 76]

Step 1: Synthesis of N-(4-cyclohexylphenyl)-N-(1-bromophenyl-4-yl)-9,9-dimethyl-9H-fluoren-2-amine Into a three-neck flask were put 11 g (30 mmol) of N-(4-cyclohexylphenyl)-N-(9,9-dimethyl-9H-fluoren-2-yl) amine, 17 g (60 mmol) of 1-bromo-4-iodobenzene, 4.3 g (45 mmol) of sodium tert-butoxide, and 0.10 L of toluene. The mixture was degassed under reduced pressure, the air in the flask was replaced with nitrogen, 1.4 g (1.5 mmol) of bis(dibenzylideneacetone)palladium(0) and 0.30 g (1.5 mmol) of tri-tert-butylphosphine were added thereto, and the mixture was heated at 80° C. for approximately four hours. After that, the temperature of the flask was lowered to approximately 60° C., approximately 1.0 mL of water was added, a precipitated solid was separated by filtration, and the solid was washed with toluene. The filtrate was concentrated, and the obtained toluene solution was purified by silica gel column chromatography. The obtained solution was concentrated to give a condensed toluene solution. Ethanol was added to this toluene solution and the toluene solution was concentrated under reduced pressure, whereby an ethanol suspension was obtained. The precipitate was filtrated at approximately 20° C., and the obtained solid was dried at approximately 80° C. under reduced pressure, whereby 6.6 g of a target white solid was obtained in a yield of 42%. The synthesis scheme of Step 1 is shown below.

[Chemical Formula 77]

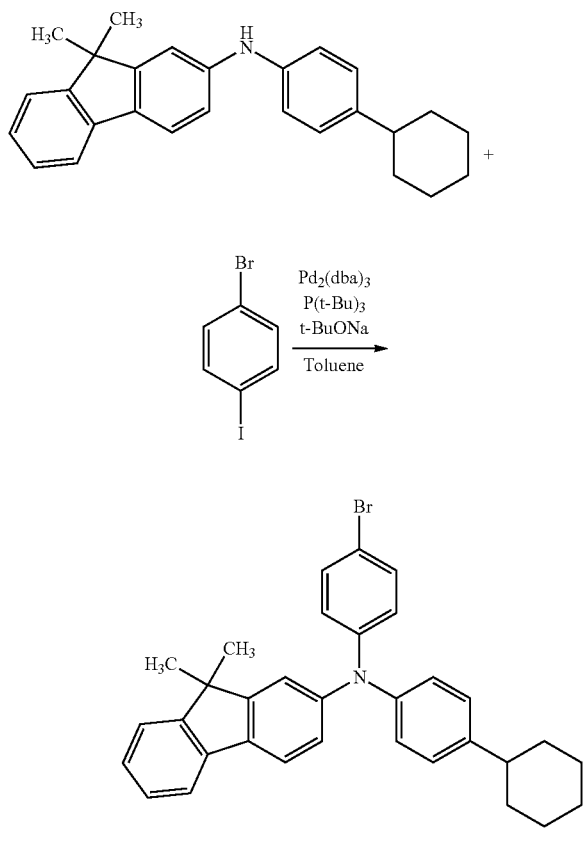

Step 2: Synthesis of 2-(3',3'',5',5''-tetra-tert-butyl[1,1':3,1''-terphenyl]-5-yl)-4,4,5,5-tetramethyl-1,3,2-dioxaborolane This synthesis step is similar to Step 2 in Synthesis Example 11 in Example 17.

Step 3: Synthesis of mmtBumQPchPAF

Into a three-neck flask were put 1.8 g (3.4 mmol) of N-(4-cyclohexylphenyl)-N-(1-bromophenyl-4-yl)-9,9-dimethyl-9H-fluoren-2-amine, 2.0 g (3.4 mmol) of 2-(3',3'',5',5''-tetra-tert-butyl[1,1':3,1''-terphenyl]-5-yl)-4,4,5,5-tetramethyl-1,3,2-dioxaborolane, 1.4 g (10 mmol) of potassium carbonate, 23 mL of toluene, 7.0 mL of ethanol, and 5.0 mL of tap water. The mixture was degassed under reduced pressure, the air in the flask was replaced with nitrogen, 15 mg (0.068 mmol) of palladium acetate and 41 mg (0.14 mmol) of tris(2-methylphenyl)phosphine were added thereto, and the mixture was heated at 80° C. for approximately five hours. After that, the temperature of the flask was lowered to room temperature, and the mixture was separated into an organic layer and an aqueous layer. Magnesium sulfate was added to the organic layer for drying to be concentrated. A hexane solution of the obtained solution was purified by silica gel column chromatography, whereby 2.1 g of a target colorless oily substance was obtained in a yield of 70%. The synthesis scheme of Step 3 is shown below.

[Chemical Formula 78]

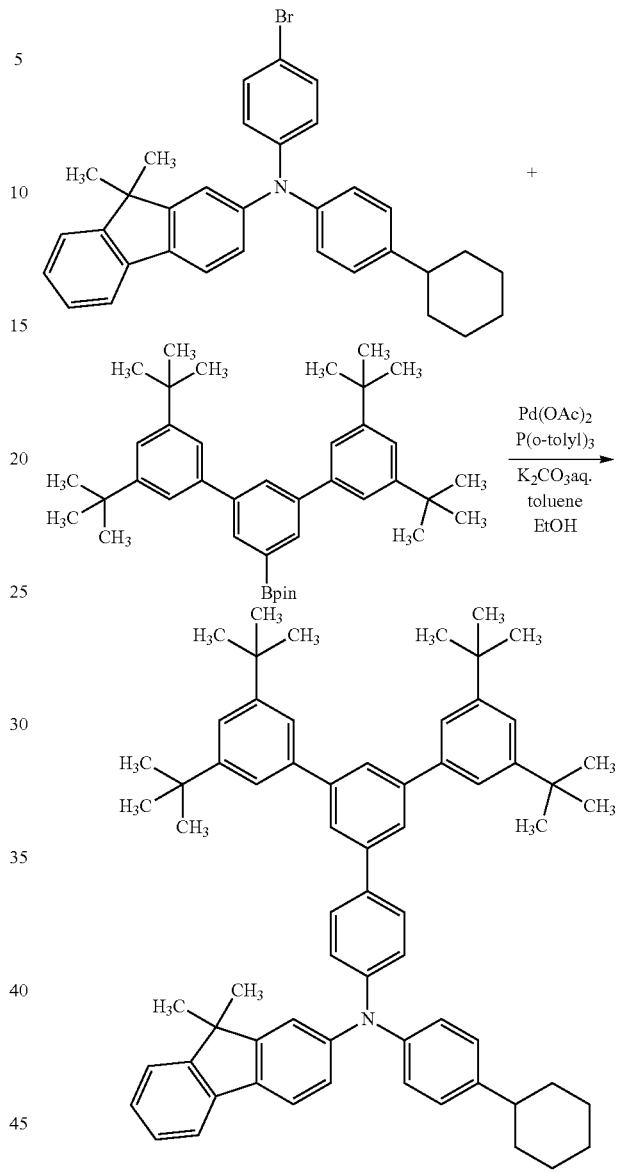

Figure 89A:
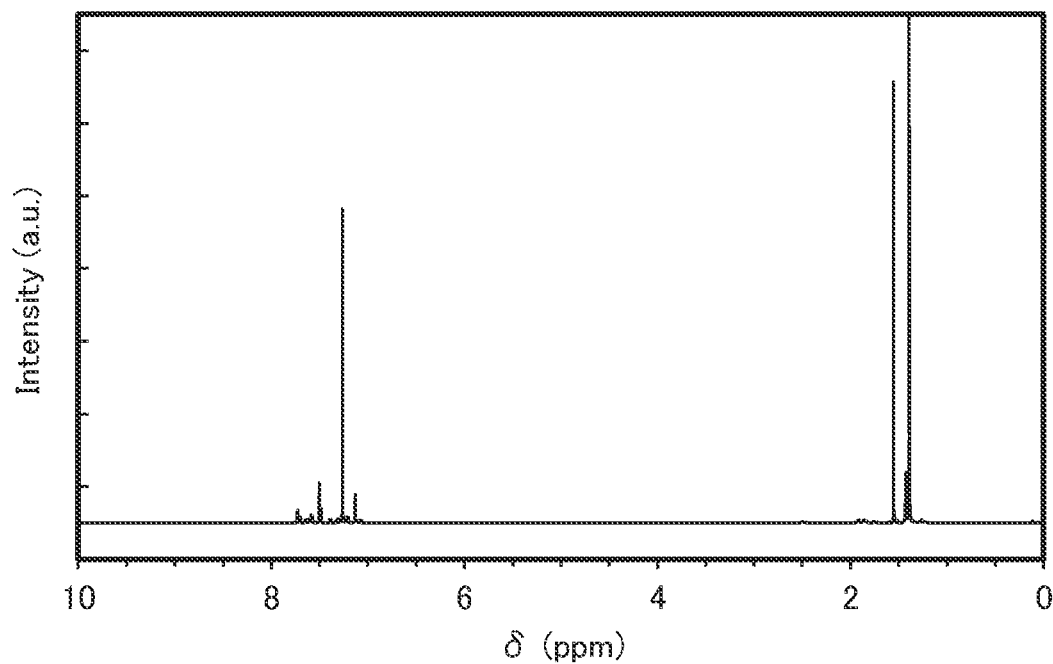
FIGS. 89A and 89B are $^1$H-NMR charts of mmtBumQPchPAF.
Figure 89B:
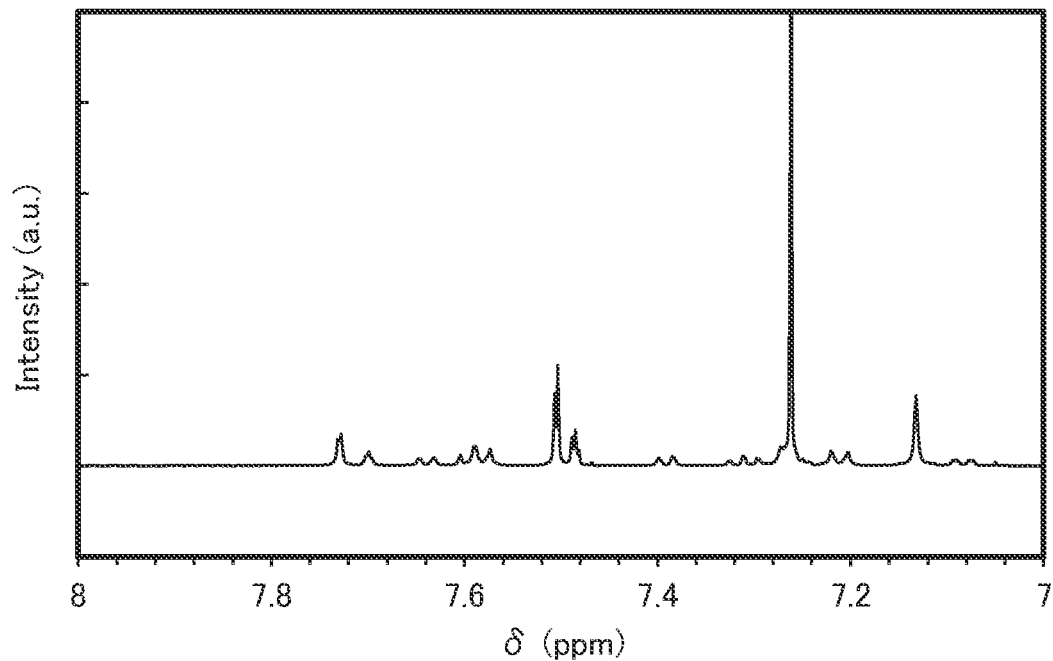

Analysis results by nuclear magnetic resonance ($^1$H-NMR) spectroscopy of the white solid obtained in Step 3 are shown in FIGS. 89A and 89B and below. The results show that mmtBumQPchPAF was synthesized in this synthesis example.

$^1$H-NMR. δ (CDCl$_3$): 7.73 (d, 1H, J=1.7 Hz), 7.70 (s, 1H), 7.64 (d, 1H, J=7.4 Hz), 7.57-7.60 (m, 3H), 7.48-7.51 (m, 7H), 7.39 (d, 1H, J=7.4 Hz), 7.27-7.32 (m, 1H), 7.20-7.22 (m, 2H), 7.13 (m, 4H), 7.08 (d, 1H, J=8.0 Hz), 2.48-2.51 (brm, 1H), 1.84-1.93 (m, 4H), 1.74-1.76 (brm, 1H), 1.56 (brm, 9H), 1.39 (brm, 40H).

Then, 2.1 g of the obtained white solid was purified by a train sublimation method. The purification by sublimation was conducted by heating at 265° C. under a pressure of 2.9 Pa with a flow rate of an argon gas of 10 mL/min. After the purification by sublimation, 1.4 g of a pale yellowish white solid was obtained at a collection rate of 67%.

This application is based on Japanese Patent Application Serial No. 2020-067217 filed with Japan Patent Office on Apr. 3, 2020, Japanese Patent Application Serial No. 2020-

078772 filed with Japan Patent Office on Apr. 28, 2020, and Japanese Patent Application Serial No. 2020-129665 filed with Japan Patent Office on Jul. 30, 2020, the entire contents of which are hereby incorporated by reference.

What is claimed is:
1. An arylamine compound represented by General Formula (G1):

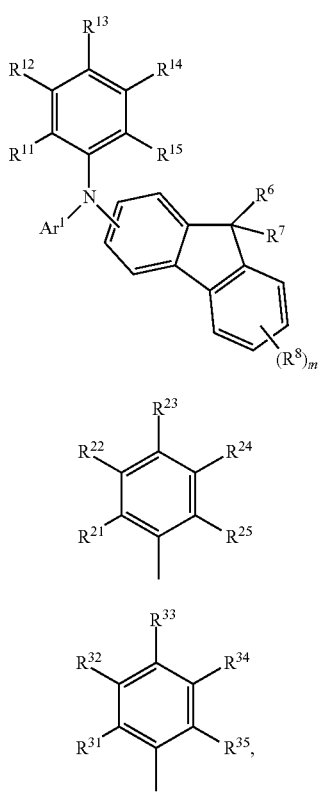

wherein:
Ar$^1$ represents a substituted or unsubstituted phenyl group, a substituted or unsubstituted biphenyl group, a substituted or unsubstituted terphenyl group, and a substituted or unsubstituted naphthylphenyl group,
each of R$^6$, R$^7$, and R$^8$ independently represents an alkyl group having 1 to 4 carbon atoms,
m represents an integer of 0 to 4,
when m is greater than or equal to 2, a plurality of R$^8$ represents the same alkyl group or different alkyl groups,
one of R$^{11}$ to R$^{15}$ represents a substituent represented by General Formula (g1), each of the others of R$^{11}$ to R$^{15}$ independently represents any one of hydrogen, an alkyl group having 1 to 6 carbon atoms, an unsubstituted phenyl group, and a phenyl group substituted with an alkyl group having 1 to 6 carbon atoms,
one of R$^{21}$ to R$^{25}$ represents a substituent represented by General Formula (g2), each of the others of R$^{21}$ to R$^{25}$ independently represents any one of hydrogen, an alkyl group having 1 to 6 carbon atoms, and a phenyl group substituted with an alkyl group having 1 to 6 carbon atoms,
each of R$^{31}$ to R$^{35}$ independently represents any one of hydrogen, an alkyl group having 1 to 6 carbon atoms, and a phenyl group substituted with an alkyl group having 1 to 6 carbon atoms,
at least three of R$^{11}$ to R$^{15}$, R$^{21}$ to R$^{25}$, and R$^{31}$ to R$^{35}$ represent an alkyl group having 1 to 6 carbon atoms,
none or one of R$^{11}$ to R$^{15}$ represents the unsubstituted phenyl group or the phenyl group substituted with an alkyl group having 1 to 6 carbon atoms,
none or one of R$^{21}$ to R$^{25}$ and R$^{31}$ to R$^{35}$ represents the phenyl group substituted with an alkyl group having 1 to 6 carbon atoms, and
in at least two combinations of the three combinations R$^{12}$ and R$^{14}$, R$^{22}$ and R$^{24}$, and R$^{32}$ and R$^{34}$, at least one of R$^{12}$ and R$^{14}$, R$^{22}$ and R$^{24}$, and R$^{32}$ and R$^{34}$ represents any of the substituents other than hydrogen.

2. An arylamine compound represented by General Formula (G2):

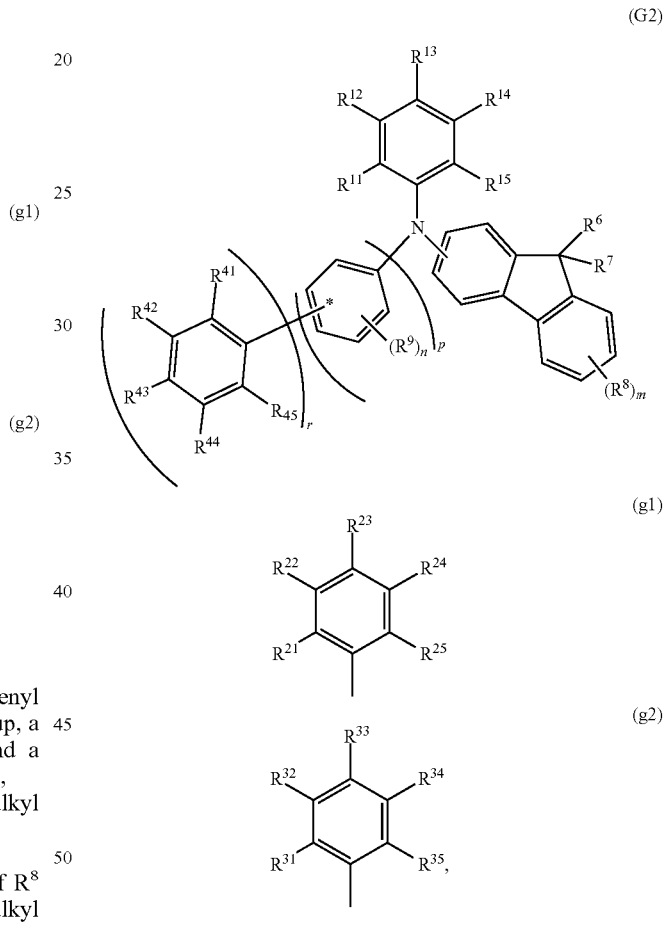

wherein:
each of p and r independently represents 1 or 2,
p+r is 2 or 3,
each of R$^6$ to R$^9$ independently represents an alkyl group having 1 to 4 carbon atoms,
each of m and n independently represents an integer of 0 to 4,
each of R$^{41}$ to R$^{45}$ independently represents any one of hydrogen, an alkyl group having 1 to 6 carbon atoms, and a cycloalkyl group having 5 to 12 carbon atoms,
one of R$^{11}$ to R$^{15}$ represents a substituent represented by General Formula (g1),
each of the others of R$^{11}$ to R$^{15}$ independently represents any one of hydrogen, an alkyl group having 1 to 6 carbon atoms, an unsubstituted phenyl group, and a phenyl group substituted with an alkyl group having 1 to 6 carbon atoms, one of $R^{21}$ to $R^{25}$ represents a substituent represented by General Formula each of the others of $R^{21}$ to $R^{25}$ independently represents any one of hydrogen, an alkyl group having 1 to 6 carbon atoms, and a phenyl group substituted with an alkyl group having 1 to 6 carbon atoms, each of $R^{31}$ to $R^{35}$ independently represents any one of hydrogen, an alkyl group having 1 to 6 carbon atoms, and a phenyl group substituted with an alkyl group having 1 to 6 carbon atoms, at least three of $R^{11}$ to $R^{15}$, $R^{21}$ to $R^{25}$, and $R^{31}$ to $R^{35}$ represent the alkyl group having 1 to 6 carbon atoms, none or one of $R^{11}$ to $R^{15}$ represents the unsubstituted phenyl group or the phenyl group substituted with an alkyl group having 1 to 6 carbon atoms, none or one of $R^{21}$ to $R^{25}$ and $R^{31}$ to $R^{35}$ represents the phenyl group substituted with an alkyl group having 1 to 6 carbon atoms, and in at least two combinations of the three combinations $R^{12}$ and $R^{14}$, $R^{22}$ and $R^{24}$, and $R^{32}$ and $R^{34}$, at least one of $R^{12}$ and $R^{14}$, $R^{22}$ and $R^{24}$, and $R^{32}$ and $R^{34}$ represents any of the substituents other than hydrogen.

3. The arylamine compound according to claim 2, wherein n represents 0.

4. The arylamine compound according to claim 2, wherein p represents 1 and r represents 1.

5. An arylamine compound represented by General Formula (G3):

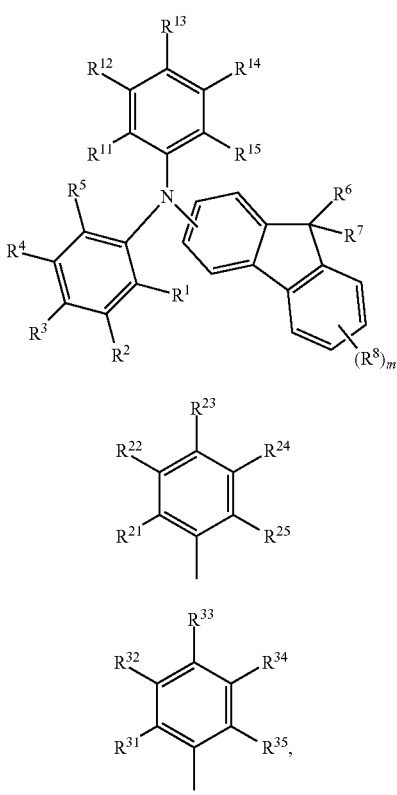

wherein:

each of $R^1$ to $R^4$ independently represents any one of hydrogen, an alkyl group having 1 to 6 carbon atoms, a cycloalkyl group having 5 to 12 carbon atoms, an unsubstituted phenyl group, and a phenyl group substituted with an alkyl group having 1 to 6 carbon atoms, each of $R^6$, $R^7$, and $R^8$ independently represents an alkyl group having 1 to 4 carbon atoms, m represents an integer of 0 to 4, when m is greater than or equal to 2, a plurality of $R^8$ represents the same alkyl group or different alkyl groups, one of $R^{11}$ to $R^{15}$ represents a substituent represented by General Formula (g1), each of the others of $R^{11}$ to $R^{15}$ independently represents any one of hydrogen, an alkyl group having 1 to 6 carbon atoms, an unsubstituted phenyl group, and a phenyl group substituted with an alkyl group having 1 to 6 carbon atoms, one of $R^{21}$ to $R^{25}$ represents a substituent represented by General Formula (g2), each of the others of $R^{21}$ to $R^{25}$ independently represents any one of hydrogen, an alkyl group having 1 to 6 carbon atoms, and a phenyl group substituted with an alkyl group having 1 to 6 carbon atoms, each of $R^{31}$ to $R^{35}$ independently represents any one of hydrogen, an alkyl group having 1 to 6 carbon atoms, and a phenyl group substituted with an alkyl group having 1 to 6 carbon atoms, at least three of $R^{11}$ to $R^{15}$, $R^{21}$ to $R^{25}$, and $R^{31}$ to $R^{35}$ represent an alkyl group having 1 to 6 carbon atoms, none or one of $R^{11}$ to $R^{15}$ represents the unsubstituted phenyl group or the phenyl group substituted with an alkyl group having 1 to 6 carbon atoms, none or one of $R^{21}$ to $R^{25}$ and $R^{31}$ to $R^{35}$ represents the phenyl group substituted with an alkyl group having 1 to 6 carbon atoms, and in at least two combinations of the three combinations $R^{12}$ and $R^{14}$, $R^{22}$ and $R^{24}$, and $R^{32}$ and $R^{34}$, at least one of $R^{12}$ and $R^{14}$, $R^{22}$ and $R^{24}$, and $R^{32}$ and $R^{34}$ represents any of the substituents other than hydrogen.

6. The arylamine compound according to claim 5, wherein $R^3$ represents a cyclohexyl group and each of $R^1$, $R^2$, $R^4$, and $R^5$ represents hydrogen.

7. The arylamine compound according to claim 5, wherein $R^1$ represents an unsubstituted phenyl group and each of $R^2$ to $R^5$ represents hydrogen.

8. The arylamine compound according to claim 1, wherein at least one of $R^{12}$, $R^{14}$, $R^{22}$, and $R^{24}$ represents any of the substituents other than hydrogen, and wherein at least one of $R^{32}$ and $R^{34}$ represents any of the substituents other than hydrogen.

9. The arylamine compound according to claim 1, wherein m represents 0.

10. The arylamine compound according to claim 1, wherein the alkyl group having 1 to 6 carbon atoms is a chain alkyl group having 2 to 5 carbon atoms.

11. The arylamine compound according to claim 1, wherein the alkyl group having 1 to 6 carbon atoms is a chain alkyl group having a branch formed of 3 to 5 carbon atoms.

12. The arylamine compound according to claim 1, wherein the alkyl group having 1 to 6 carbon atoms is a tert-butyl group.

13. The arylamine compound according to claim 2, wherein each of $R^{12}$, $R^{14}$, $R^{22}$, $R^{32}$, and $R^{34}$ among $R^{11}$ to $R^{15}$, $R^{21}$ to $R^{25}$, and $R^{31}$ to $R^{35}$ represents any of the substituents other than hydrogen, and each of the others represents hydrogen.

14. The arylamine compound according to claim 1, wherein each of $R^6$ and $R^7$ represents a methyl group.

15. The arylamine compound according to claim 1, wherein an ordinary refractive index of a layer formed of the arylamine compound with respect to light with a wavelength greater than or equal to 455 nm and less than or equal to 465 nm is greater than or equal to 1.50 and less than or equal to 1.75.

16. The arylamine compound according to claim 1, wherein an ordinary refractive index of a layer formed of the arylamine compound with respect to an ordinary light with a wavelength of 633 nm is greater than or equal to 1.45 and less than or equal to 1.70.

17. A material for a hole-transport layer, comprising the arylamine compound according to claim 1.

18. A material for a hole-injection layer, comprising the arylamine compound according to claim 1.

19. A material for a hole-injection layer, comprising:
the arylamine compound according to claim 1, and
an organic compound comprising a cyano group or a fluorine atom.

20. A light-emitting device comprising the arylamine compound according to claim 1.

21. An electronic apparatus comprising:
the light-emitting device according to claim 20; and
at least one of a sensor, an operation button, a speaker, and a microphone.

22. A light-emitting apparatus comprising:
the light-emitting device according to claim 20; and
at least one of a transistor and a substrate.

23. A lighting device comprising:
the light-emitting device according to claim 20; and
a housing.

* * * * *